US012528819B2

(12) United States Patent
Mekonnen et al.

(10) Patent No.: US 12,528,819 B2
(45) Date of Patent: Jan. 20, 2026

(54) BENZODIAZEPINE DERIVATIVES, COMPOSITIONS, AND METHODS FOR TREATING COGNITIVE IMPAIRMENT

(71) Applicant: AGENEBIO, INC., Baltimore, MD (US)

(72) Inventors: Belew Mekonnen, Gilbertsville, PA (US); John A. Butera, Clarksburg, NJ (US); Jianxing Huang, Bethlehem, PA (US); Hemantbhai Patel, Piscataway, NJ (US)

(73) Assignee: AGENEBIO, INC., Baltimore, MD (US)

( * ) Notice: Subject to any disclaimer, the term of this patent is extended or adjusted under 35 U.S.C. 154(b) by 522 days.

(21) Appl. No.: 17/902,374

(22) Filed: Sep. 2, 2022

(65) Prior Publication Data

US 2023/0134844 A1 May 4, 2023

Related U.S. Application Data

(60) Division of application No. 16/471,237, filed as application No. PCT/IB2017/001762 on Dec. 20, 2017, now Pat. No. 11,505,555, which is a continuation of application No. PCT/IB2017/001763, filed on Dec. 19, 2017.

(60) Provisional application No. 62/436,272, filed on Dec. 19, 2016.

(51) Int. Cl.

| | |
|---|---|
| ***C07D 487/14*** | (2006.01) |
| ***A61K 31/13*** | (2006.01) |
| ***A61K 31/5517*** | (2006.01) |
| ***A61K 45/06*** | (2006.01) |
| ***A61P 25/00*** | (2006.01) |
| ***A61P 25/28*** | (2006.01) |
| ***A61P 35/00*** | (2006.01) |

(52) U.S. Cl.

CPC ............ *C07D 487/14* (2013.01); *A61K 31/13* (2013.01); *A61K 31/5517* (2013.01); *A61K 45/06* (2013.01); *A61P 25/00* (2018.01); *A61P 25/28* (2018.01); *A61P 35/00* (2018.01)

(58) Field of Classification Search

None

See application file for complete search history.

(56) References Cited

U.S. PATENT DOCUMENTS

| | | | |
|---|---|---|---|
| 3,391,142 | A | 7/1968 | Jack et al. |
| 3,539,573 | A | 11/1970 | Schmutz et al. |
| 4,122,193 | A | 10/1978 | Scherm et al. |
| 4,145,434 | A | 3/1979 | Van der Burg |
| 4,273,774 | A | 6/1981 | Scherm |
| 4,710,500 | A | 12/1987 | Perregaard |
| 4,734,416 | A | 3/1988 | Banno et al. |
| 4,804,663 | A | 2/1989 | Kennis et al. |
| 4,816,456 | A | 3/1989 | Summers |
| 4,831,031 | A | 5/1989 | Lowe et al. |
| 4,879,288 | A | 11/1989 | Warawa et al. |

(Continued)

FOREIGN PATENT DOCUMENTS

| | | |
|---|---|---|
| CN | 108567786 A | 9/2018 |
| CN | 108567787 A | 9/2018 |

(Continued)

OTHER PUBLICATIONS

Manoj. International Journal of Pharma and Bio Sciences, 2011, 2(1), pp. 468-477 (Year: 2011).*

Black. Journal of Chemical Education, 1990, 2, 141-142 (Year: 1990).*

NGUYEN. Organic Letters, 2013, 15(17), 4492-4495 (Year: 2013).*

Wang et al., "Magnetic resonance imaging of hippocampal subfields in posttraumatic stress disorder," Arch Gen Psychiatry, vol. 67, 2010, pp. 296-303.

Whitehouse et al., "Alzheimer's disease and senile dementia: loss of neurons in the basal forebrain," Science, 215:1237-39 (1982).

Wilson et al. "Age associated alterations of hippocampal place cells are subregion specific," J. Neuroscience (2005) 25(29): 6877-6886.

Wilson et al., "Cognitive Aging and the Hippocampus: How Old Rats Represent New Environments," J. Neurosci., 2004, 24(15): 3870-3878.

(Continued)

*Primary Examiner* — Noble E Jarrell

(74) *Attorney, Agent, or Firm* — HALEY GUILIANO LLP; James F. Haley, Jr.; Marcus Jellen

(57) ABSTRACT

This invention relates to benzodiazepine derivatives, compositions comprising therapeutically effective amounts of those benzodiazepine derivatives and methods of using those derivatives or compositions in treating cognitive impairment associated with central nervous system (CNS) disorders. In particular, it relates to the use of a α5-containing $GABA_A$ receptor agonist (e.g., a α5-containing $GABA_A$ receptor positive allosteric modulator) as described herein in treating cognitive impairment associated with central nervous system (CNS) disorders in a subject in need or at risk thereof, including, without limitation, subjects having or at risk for age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction. It also relates to the use of a α5-containing $GABA_A$ receptor agonist (e.g., a α5-containing $GABA_A$ receptor positive allosteric modulator) as described herein in treating brain cancers (including brain tumors, e.g., medulloblastomas), and cognitive impairment associated therewith.

11 Claims, 10 Drawing Sheets

(56) References Cited

U.S. PATENT DOCUMENTS

Figure 1:
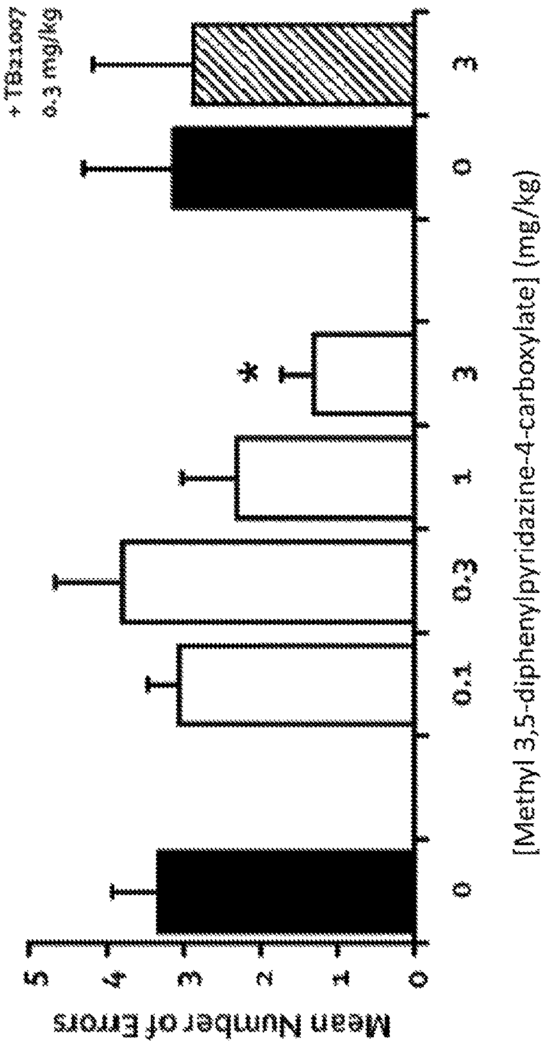

| | | | |
|---|---|---|---|
| 4,895,841 A | 1/1990 | Sugimoto et al. | |
| 5,006,528 A | 4/1991 | Oshiro et al. | |
| 5,041,455 A | 8/1991 | Sauerberg et al. | |
| 5,061,703 A | 10/1991 | Bormann et al. | |
| 5,106,856 A | 4/1992 | Kosley et al. | |
| 5,229,382 A | 7/1993 | Chakrabarti et al. | |
| 5,312,925 A | 5/1994 | Allen et al. | |
| 5,387,585 A | 2/1995 | Borer et al. | |
| 5,500,438 A | 3/1996 | Barnette et al. | |
| 5,532,372 A | 7/1996 | Saji et al. | |
| 5,552,409 A | 9/1996 | Michelotti et al. | |
| 5,602,176 A | 2/1997 | Enz | |
| 5,763,476 A | 6/1998 | Delbressine et al. | |
| 6,677,330 B1 | 1/2004 | Imura et al. | |
| 6,689,816 B2 | 2/2004 | Fogel | |
| 6,743,789 B2 | 6/2004 | Masciadri et al. | |
| 7,340,299 B2 | 3/2008 | Puskas | |
| 7,381,725 B2 | 6/2008 | Fletcher et al. | |
| 7,498,361 B2 | 3/2009 | Fogel | |
| 7,507,728 B2 | 3/2009 | Knust et al. | |
| 7,635,709 B2 | 12/2009 | Korsten et al. | |
| 7,642,267 B2 | 1/2010 | Li et al. | |
| 8,058,268 B2 | 11/2011 | Kovach | |
| 8,510,055 B2 | 8/2013 | Gallagher et al. | |
| 8,741,808 B2 | 6/2014 | Li et al. | |
| 8,853,219 B2 | 10/2014 | Hendrickson et al. | |
| 9,145,372 B2 | 9/2015 | Lowe, III | |
| 9,801,879 B2 | 10/2017 | Lowe, III | |
| 10,329,301 B2 | 6/2019 | Mekonnen et al. | |
| 10,815,242 B2 | 10/2020 | Mekonnen et al. | |
| 11,142,529 B2 | 10/2021 | Mekonnen et al. | |
| 11,312,721 B2 | 4/2022 | Mekonnen et al. | |
| 12,291,535 B2 * | 5/2025 | Mekonnen ............. | A61K 45/06 |
| 2003/0125333 A1 | 7/2003 | Bryant et al. | |
| 2004/0087658 A1 | 5/2004 | Moebius | |
| 2005/0113458 A1 | 5/2005 | Gupta et al. | |
| 2006/0079507 A1 | 4/2006 | Knust et al. | |
| 2006/0084642 A1 | 4/2006 | Knust et al. | |
| 2006/0128691 A1 | 6/2006 | Buettelmann et al. | |
| 2006/0167032 A1 | 7/2006 | Galer et al. | |
| 2006/0205822 A1 | 9/2006 | Jonas et al. | |
| 2006/0235021 A1 | 10/2006 | Blackaby et al. | |
| 2007/0112017 A1 | 5/2007 | Barlow et al. | |
| 2008/0269236 A1 | 10/2008 | Ji et al. | |
| 2009/0081259 A1 | 3/2009 | Jonas et al. | |
| 2009/0124659 A1 | 5/2009 | Moebius | |
| 2009/0143385 A1 | 6/2009 | Buettelmann et al. | |
| 2010/0075954 A1 | 3/2010 | Knust et al. | |
| 2010/0081723 A1 | 4/2010 | Jonas et al. | |
| 2010/0227852 A1 | 9/2010 | Moebius | |
| 2012/0035139 A9 | 2/2012 | Xu et al. | |
| 2013/0237530 A1 | 9/2013 | Lowe, III | |
| 2014/0057903 A1 | 2/2014 | Gallagher et al. | |
| 2015/0374705 A1 | 12/2015 | Zhang et al. | |
| 2016/0008357 A1 | 1/2016 | Lowe, III | |
| 2018/0170941 A1 | 6/2018 | Mekonnen et al. | |
| 2020/0048268 A1 | 2/2020 | Mekonnen et al. | |
| 2022/0274996 A1 | 9/2022 | Mekonnen et al. | |
| 2023/0098667 A1 * | 3/2023 | Mekonnen .............. | A61P 35/00 514/220 |
| 2023/0107032 A1 * | 4/2023 | Mekonnen .............. | A61P 25/28 514/220 |

FOREIGN PATENT DOCUMENTS

| | | |
|---|---|---|
| EP | 0368388 A2 | 5/1990 |
| EP | 0402644 A1 | 12/1990 |
| EP | 0468187 A2 | 1/1992 |
| EP | 0481429 A2 | 4/1992 |
| EP | 1682109 B1 | 10/2008 |
| EP | 2260839 A2 | 12/2010 |
| GB | 2352630 A | 2/2001 |
| GB | 2352631 A | 2/2001 |
| GB | 2352632 A | 2/2001 |
| WO | 99/25353 A1 | 5/1999 |
| WO | 00/27849 A2 | 5/2000 |
| WO | 01/62726 A2 | 8/2001 |
| WO | 02/32412 A2 | 4/2002 |
| WO | 02/40487 A2 | 5/2002 |
| WO | 02/69948 A1 | 9/2002 |
| WO | 02/94834 A1 | 11/2002 |
| WO | 03/25122 A2 | 3/2003 |
| WO | 2004/014865 A1 | 2/2004 |
| WO | 2004/014891 A1 | 2/2004 |
| WO | 2004/048551 A2 | 6/2004 |
| WO | 2005/079779 A1 | 9/2005 |
| WO | 2006/045429 A1 | 5/2006 |
| WO | 2006/063708 A1 | 6/2006 |
| WO | 2007/018660 A2 | 2/2007 |
| WO | 2007/019312 A2 | 2/2007 |
| WO | 2007/042421 A1 | 4/2007 |
| WO | 2009/071477 A1 | 6/2009 |
| WO | 2010/036553 A1 | 4/2010 |
| WO | 2012/059482 A1 | 5/2012 |
| WO | 2012/068149 A1 | 5/2012 |
| WO | 2012/068161 A1 | 5/2012 |
| WO | 2012/161133 A1 | 11/2012 |
| WO | 2014/039920 A1 | 3/2014 |
| WO | 2015/095783 A1 | 6/2015 |
| WO | 2016/191288 A1 | 12/2016 |
| WO | 2016/205739 A1 | 12/2016 |
| WO | 2018/130868 A1 | 7/2018 |
| WO | 2019/246300 A1 | 12/2019 |

OTHER PUBLICATIONS

Wilson et al., "Place cell rigidity correlates with impaired spatial learning in aged rats," Neurobiology of Aging, 2003, 24: 297-305.

Winblad et al., "Mild cognitive impairment—beyond controversies, towards a consensus: report of the International Working Group on Mild Cognitive Impairment," Journal of Internal Medicine, 2004, 256: 240-246.

Wisden et al., "The Distribution of 13 GABA.sub.A Receptor Subunit mRNAs in the Rat Brain. I. Telencephalon, Diencephalon, Mesencephalon," The Journal of Neuroscience, Mar. 1992, 12(3): 1040-1062.

Wishart et al., "Increased Brain Activation During Working Memory in Cognitively Intact Adults With the APOE c:4 Allele," Am J Psychiatry, 2006, 163: 1603-1610.

Wood et al., "Hippocampal pathology in individuals at ultra-high risk for psychosis: a multi-modal magnetic resonance study," NeuroImage 52(1):62-68 (2010).

Woon et al., "Hippocampal volume deficits associated with exposure to psychological trauma and posttraumatic stress disorder in adults: A meta-analysis," Progress in Neuro-Psychopharmacology & Biological Psychiatry 34 (2010) 1181-1188.

Wu et al., "A Model Based Background Adjustment for Oligonucleotide Expression Arrays," Journal of American Statistical Association, 99:909-917 (2004).

Xiang et al., "Stereochemistry as a Tool in Deciphering the Processes of a Tandem Iminium Cyclization and Smiles Rearrangement," Journal of Organic Chemistry, 75(23), 8147-8154 (2010).

Yaffe et al., "Posttraumatic Stress Disorder and Risk of Dementia Among US Veterans," Arch. Gen. Psvchiatrv, 67(6):608-613, 2010.

Yang et al., "Cyclophosphamide impairs hippocampus-dependent learning and memory in adult mice: Possible involvement of hippocampal neurogenesis in chemotherapy-induced memory deficits," Neurobiology of Learning and Memory, vol. 93, Issue 4, May 2010, pp. 487-494.

Yassa et al., "Ultrahigh-resolution microstructural diffusion tensor imaging reveals perforant path degradation in aged humans in vivo," PNAS, 107(28):12687-12691 (2010).

Yehuda et al., "Longitudinal assessment of cognitive performance in Holocaust survivors with and without PTSD," Biological Psychiatry, 60(7):714-721 (2006).

Yoon et al., "GABA Concentration Is Reduced in Visual Cortex in Schizophrenia and Correlates with Orientation-Specific Surround Suppression," J. Neurosci., 2010, 30(10): 3777-3781.

(56) References Cited

OTHER PUBLICATIONS

Young et al., “Using the MATRICS to guide development of a preclinical cognitive test battery for research in schizophrenia,” Pharmacol Ther., 2009, 122(2): 150-202.
Youngjohn et al., “Stability of everyday memory in age-associated impairment: A longitudinal study,” Neuropsychology, 7(3);406-416 (1993).
Zierhut et al., “The role of hippocampus dysfunction in deficient memory encoding and positive symptoms in schizophrenia,” Psychiatry Res., 183:187-194 (2010).
Zoran et al., “Specific muscle contacts induce increased transmitter release and neuritic arborization in motoneuronal cultures,” Dev Biol., 179:212-22 (1996).
U.S. Appl. No. 15/104,494 U.S. Pat. No. 10,329,301, filed Jun. 14, 2016 Jun. 25, 2019, Belew Mekonnen et al., Issued.
U.S. Appl. No. 16/428,394 U.S. Pat. No. 11,142,529, filed May 31, 2019 Oct. 12, 2021, Belew Mekonnen et al., Issued.
U.S. Appl. No. 15/736,697 U.S. Pat. No. 10,815,242, filed Dec. 14, 2017 Oct. 27, 2020, Belew Mekonnen et al., Issued.
U.S. Appl. No. 17/028,917 U.S. Pat. No. 11,312,721, filed Sep. 22, 2020 Apr. 26, 2022, Belew Mekonnen et al., Issued.
U.S. Appl. No. 17/592,679, filed Feb. 4, 2022, Belew Mekonnen et al., Pending.
U.S. Appl. No. 15/847,906, filed Dec. 19, 2017, Belew Mekonnen et al., Abandoned.
U.S. Appl. No. 15/848,835, filed Dec. 20, 2017, Belew Mekonnen et al., Abandoned.
U.S. Appl. No. 16/471,237 U.S. Pat. No. 11,505,555, filed Jun. 19, 2019 Nov. 22, 2022, Belew Mekonnen et al., Issued.
U.S. Appl. No. 16/445,854 U.S. Pat. No. 11,414,425, filed Jun. 19, 2019 Aug. 16, 2022, Belew Mekonnen et al., Issued.
U.S. Appl. No. 17/850,144, filed Jun. 27, 2022, Belew Mekonnen et al., Pending.
U.S. Appl. No. 17/786,175, filed Jun. 16, 2022, Belew Mekonnen et al., Pending.
U.S. Appl. No. 17/372,405, filed Jul. 9, 2021, Michela Gallagher et al., Pending.
U.S. Appl. No. 18/015,439, filed Jan. 10, 2023, Michela Gallagher et al., Pending.
U.S. Appl. No. 18/015,445, filed Jan. 10, 2023, Deepa Gandla et al., Pending.
U.S. Appl. No. 18/235,753, filed Aug. 18, 2023, Belew Mekonnen et al., Pending.
Koh et al., “664.17/YY12-BPN-27473: a novel GABAaa5 positive allosteric modulator that improves memory performance of rats with conditions of hippocampal hyperactivity,” Neuorscience, 2022 (https://www.abstractsonline.com/pp8/#!/10619/presentation/79719) (2 pages).
Ronald et al., “Mild cognitive impairment: Aging to Alzheimer’s Disease,” New England Journal of Medicine, 349(14):1393 (2003) (1 page).
U.S. Appl. No. 15/104,494 (U.S. Pat. No. 10,329,301).
U.S. Appl. No. 16/428,394 (U.S. Pat. No. 11,142,529).
U.S. Appl. No. 15/736,697 (U.S. Pat. No. 10,815,242).
U.S. Appl. No. 17/028,917 (U.S. Pat. No. 11,312,721).
U.S. Appl. No. 17/592,679 (Pending).
U.S. Appl. No. 15/847,906 (abandoned).
U.S. Appl. No. 15/848,835 (abandoned).
U.S. Appl. No. 16/471,237 (U.S. Pat. No. 11,505,555).
U.S. Appl. No. 16/445,854 (U.S. Pat. No. 11,414,425).
U.S. Appl. No. 17/786,175 (Pending).
Mendez et al., “The brain GABA-benzodiazepine receptor alpha-5 subtype in autism spectrum disorder: a pilot [.sup.11-C]R015-4513 position emission tomography study,” Neuropharmacology (2013), 68:195-201.
Meyers et al., “Neurocognitive Function,” Symptoms Secondary to Cancer and its Treatment, pp. 557-571, (2002).
Miller et al., “Hippocampal activation in adults with mild cognitive impairment predicts subsequent cognitive decline,” J. Neurol. Neurosurg. Psychiatry 79: 630-635 (2008).
Mirza et al., “NS11394 [3'-[5-(1-hydroxy-1-methyl-ethyl)-benzoimidazol-1-y1]-biphenyl-2-carbonitrile], a unique subtype-selective GABAA receptor positive allosteric modulator: in vitro actions, pharmacokinetic properties and in vivo anxiolytic efficacy,” J Pharmacol Exp Ther 327(3): 954-68, 2008.
Mondadori et al., “Enhanced brain activity may precede the diagnosis of Alzheimer’s disease by 30 years,” Brain. 129:2908-22, 2006.
Morris, “Spatial Localization Does Not Require the Presence of Local Cues,” Learning and Motivation 12:239-260 (1981).
Munro et al., “Comparison of the Novel Subtype-Selective GABA.sub.A Receptor-Positive Allosteric Modulator NS11394 [3'-[5-(1-Hydroxy-1-methyl-ethyl)-benzoimidazol-1-yl]-bipheny1-2-carbonitrile] with Diazepam, Zolpidem, Bretazenil, and Gaboxadol in Rat Models of Inflammatory and Neuropathic Pain,” J Pharmacol. Exp. Ther. 327(3):969-81 (2008).
Nguyen et al., “Facile one-pot assembly of imidazotriazolobenzodiazepines via indium(III)-catalyzed multicomponent reactions,” Organic Letters, 15(17):4492-4495 (2013).
Nicolle et al., “In vitro autoradiography of ionotropic glutamate receptors in hippocampus and striatum of aged Long-Evans rats: relationship to spatial learning,” Neuroscience, vol. 74, 1996, pp. 741-756.
Nicolle et al., “Metabotropic glutamate receptor-mediated hippocampal phosphoinositide turnover is blunted in spatial learning-impaired aged rats,” J. Neurosci, vol. 19, 1999, pp. 9604-9610.
Nishio et al., “A Mouse Model Characterizing Features of Vascular Dementia With Hippocampal Atrophy,” Stroke vol. 41, pp. 1278-1284 (2010).
Nyberg, “Cognitive Impairments in Drug Addicts,” Chapter 9 from the book Brain Damage—Bridging Between Basic Research and Clinics, 221-245 (2012).
Oler et al., “Age-Related Deficits in the Ability to Encode Contextual Change: A Place Cell Analysis,” Hiooocampus, 2000, 10: 338-350.
Palop et al., “Aberrant excitatory neuronal activity and compensatory remodeling of inhibitory hippocampal circuits in mouse models of Alzheimer’s disease,” Neuron 55: 697-711 (2007).
Patani et al., “Bioisosterism: A Rational Approach in Drug Design,” Chemical Reviews vol. 96, pp. 3147-3176 (1996)*.sup.4.
Pepeu et al., “Mild cognitive impairment: animal models,” Dialogs Clin. Neurosci., vol. 6 pp. 369-377 (2004).
Petersen et al., “Mild cognitive impairment: clinical characterization and outcome,” Archives in Neurology, 56(3):303-308 (1999).
Petersen, “Mild Cognitive Impairment: Current Research and Clinical Implications.” Seminars in Neurology, 2007, 27(1): 22-31.
Petersen. et al., “Mild Cognitive Impairment: An Overview,” CNS spectrum, vol. 13, 2008, pp. 45-53.
Platt et al., “Contribution of .alpha..sub.1GABA.sub.A and .alpha..sub.5GABA.sub.A receptor subtypes to the discriminative stimulus effects of ethanol in squirrel monkeys,” J. Pharmacol. & Exp. Ther., 313(2):658-667 (2005).
Pym et al., “Selective labelling of diazepam-insensitive GABA.sub.A receptors in vivo using [.sup.3H]Ro 15-4513,” British Journal of Pharmacology, 2005, 146: 817-825.
Qin et al., “Evaluation of methods for oligonucleotide array data via quantitative real-time PCR,” BMC Bioinformatics, 7:23: 1-12 (2006).
Rapp . et al., “Preserved neuron No. in the hippocampus of aged rats with spatial learning deficits,” Proc. Natl. Acad. Sci, vol. 93, 1996, pp. 9926-9930.
Rapp et al., “An Evaluation of Spatial Information Processing in Aged Rats,” Behavioral Neuroscience, 1987, 101(1):3-12.
Rapp et al., “Memory systems in normal and pathological aging,” Curr. Opin. Neurol., 7:294-298 (1994).
Reilly et al., “Effects of Acamprosate on Neuronal Receptors and Ion Channels Expressed in Xenopus Oocytes,” Alcohol Clin Exp Res, Feb. 2008, 32(2): 188-196.
Ried et al., “Syntheses of new 1,3-diazepines,” Chemiker-Zeitung, 111(5):179-180 (1987).
Rinaldi et al., “Hyper-connectivity and hyper-plasticity in the medial prefrontal cortex in the valproic acid animal model of autism,” (2008), Frontiers in Neural Circuits, 2, 1-7.

(56) References Cited

OTHER PUBLICATIONS

Robbins et al. "Cambridge Neuropsychological Test Automated Battery (CANTAB): a factor analytic study of a large sample of normal elderly volunteers," Dementia and geriatric cognitive disorders, vol. 5, Issue 5, 1994, pp. 266-281.
Rodier et al., "Linking etiologies in humans and animal models: studies of autism," (1997) Reprod. Toxicol. 11, 417-422.
Rosenzweig-Lipson et al., "Antidepressant-like effects of the novel, selective, 5-HT.sub.2C receptor agonist WAY-163909 in rodents," (2007) Psychopharmacology 192:159-170.
Sankaranarayanan., "Genetically modified mice models for Alzheimer's disease," Curr. Top. Medicinal Chem., vol. 6, 2006, pp. 609-627.
Sengupta et al., "a5-GABAA receptors negatively regulate MYC-amplified medulloblastoma growth.," Acta Neuropathologica, 127(4): 593--603 (2014).
Silverman et al., "Negative Allosteric Modulation of the mGluR5 Receptor Reduces Repetitive Behaviors and Rescues Social Deficits in Mouse Models of Autism," Sci Transl. Med., Apr. 25, 2012, 4(131) 1-9.
Small et al., "Imaging correlates of brain function in monkeys and rats isolates a hippocampal subregion differentially vulnerable to aging," Proc. Natl. Acad. Sci. USA., 101(18):7181-7186 (2004).
Smith et al., "Age-associated memory impairment diagnoses: problems of reliability and concerns for terminology," 6(4):551-558 (1991).
Smith et al., "Circuit-specific alterations in hippocampal synaptophysin immunoreactivity predict spatial learning impairment in aged rats," J. Neuroscience, 20(17):6587-6593 (2000).
Soussain et al., "CNS complications of radiotherapy and chemotherapy," Lancet vol. 374, 2009, pp. 1639-1651.
Steele et al., "Delay-dependent impairment of a matching-to-place task with chronic and intrahippocampal infusion of the NMDA-antagonist D-AP5," Hippocampus 9(2):118-36 (1999).
Sternfeld et al., "Selective, orally active .gamma.-aminobutyric acid.sub.A .alpha.5 receptor inverse agonists as cognitition enhancers," J. Med. Chem., 47:2176-2179 (2004).
Sur et al., "Rat and Human Hippocampal .alpha.5 Subunit-Containing .gamma.—Aminobutyric Acid.sub.A Receptors Have .alpha.5.beta.3.gamma.2 Pharmacological Characteristics." Molecular Pharmacology, 1998, 54: 928-933.
Szekeres et al., "3,4-Dihydronaphthalen-1(2H)-ones: novel ligands for the benzodiazepine site of .alpha.5-containing GABA.sub.A receptors," Bioorg. Med. Chem. Lett., 14:2871-2875 (2004).
Tanila et al., "Discordance of Spatial Representation in Ensembles of Hiooocampal Place Cells," Hiooocampus, 1997, 7: 613-623.
Thomaes et al., "Increased activation of the left hippocampus region in Complex PTSD during encoding and recognition of emotional words: A pilot study," Psvchiatrv Research: Neuroimagi.ng 171 (2009) 44-53.
Tremolizzo et al., "An epigenetic mouse model for molecular and behavioral neuropathologies related to schizophrenia vulnerability," PNAS, 2002, 99(26): 17095-17100.
Van Niel et al., "A new pyridazine series of GABA.sub.A .alpha.5 ligands", J. Med. Chem., 48: 6004-6011 (2005).
Van Spronsen et al., "Synapse Pathology in Psychiatric and Neurologic Disease," Curr. Neurol. Neurosci. Rep., (2010) 10, 207-214.
Vinkers et al, "The inhibitory GABA system as a therapeutic target for cognitive symptoms in schizophrenia: investigational agents in the pipeline," Expert Opin. Investig. Drugs (2010) 19(10):1217-1233.
Volk et al., "Decreased Glutamic Acid Decarboxylase.sub.67 Messenger RNA Expression in a Subset of Prefrontal Cortical .gamma.-Aminobutyric Acid Neurons in Subjects With Schizophrenia," Arch Gen Psychiatry, 2000, 57:237-245.
Walsh et al., "Ionic currents in cultured rat suprachiasmatic neurons," Neuroscience, 69:915-929 (1995).
Gallagher et al., "Relationship of age-related decline across several behavioral domains," Neurobiology of Aging, 10(6):691-708 (1989).
Gallagher et al., "Severity of spatial learning impairment in aging: development of a learning index for performance in the Morris water maze," Behavioral Neuroscience, 107(4):618-626 (1993).
Gallagher, "Animal models of memory impairment," Phil. Trans. R. Soc. Lond. B., 352:1711-1717 (1997).
Gerecke. M, et al, "New tetracyclic Derivatives oflmidazo-[I,5-a [I,4]benzodiazepines and oflmidazo[I,5-a]thieno[3,2-f][I,4]diazepines", Heterocycles (1994), vol. 39(2), p. 693-721 Schemes 2-4 and Experimental section, Compounds 22-28, 31-33, 35-48, p. 697.
Gharaghani S. et al., "A Structure-based QSAR and Docking Study on Imidazo[1,5-a][1,2,4]-triazolo[1,5-d][1,4,]benzodiazepines as Selective GABAAa5 Inverse Agonists", Chemical Biology & Drug Design, vol. 78, No. 4, 2011, pp. 612-621.
Gill et al., "A novel a5GABA(A)R-positive allosteric modulator reverses hyperactivation of the dopamine system in the MAM model of schizophrenia," Neuropsychopharmacology, 36:1903-1911 (2011).
Giusti et al., "Imidazenil: A New Partial Positive Allosteric Modulator of .gamma.-Aminobutyric Acid (GABA) Action at GABA. sub.A Receptors.sup.1," The Journal of Pharmacology and Experimental Therapeutics, 1993, 266(2):1018-1028.
Goldin et al., "Maintenance of Xenopus laevis and oocyte injection," Methods in Enzymology, 207: 266-279 (1992).
Goodacre et al., "Imidazo[1,2-.alpha.]pyrimidines as Functionally Selective and Orally Bioavailable GABA.sub.A.alpha.2/.alpha.3 Binding Site Agonists for the Treatment of Anxiety Disorders," J. Med. Chem., 2006, 49:35-38.
Gotz et al., "Animal models of Alzheimer's disease and frontotemporal dementia," Nature Review vol. 9, pp. 532-544 (2008).
Gourevitch et al., "Working memory deficits in adult rats after prenatal disruption of neurogenesis," Behavioral Pharmacology, 15:287-292 (2004).
Grauer et al., "WAY-163909, a 5-HT2C agonist, enhances the preclinical potency of current antipsychotics," Psychopharmacology, 204(1):37-48 (2004).
Guidotti et al., "GABAergic dysfunction in schizophrenia: new treatment strategies on the horizon" Psychopharmacology, 180:191-205, 2005.
Haberman et al., "Rapid encoding of new information alters the profile of plasticity-related mRNA transcripts in the hippocampal CA3 region," PNAS, 105(30): 10601-10606 (2008).
Harvey et al., "Stress-restress evokes sustained iNOS activity and altered GABA levels and NMDA receptors in rat hippocampus," Psychopharmacology, 175: 494-502 (2004).
Hashimoto et al., "Alterations in GABA-related transcriptome in the dorsolateral prefrontal cortex of subjects with schizophrenia," Molecular Psychiatry, 13: 147-161 (2008).
Hashimoto et al., "Gene Expression Deficits in a Subclass of GABA Neurons in the Prefrontal Cortex of Subjects with Schizophrenia," J. Neurosc1, 2003, 23(15): 6315-6326.
Helm et al., "GABAB receptor antagonist SGS742 improves spatial memory and reduces protein binding to the CAMP response element (CRE) in the hippocampus," Neuropharmacology, 2005, 48: 956-964.
Herholz et al., "Discrimination between Alzheimer dementia and controls by automated analysis of multicenter FDG PET," Neuroimage, 17(1):302-316 (2002).
Hill et al., "First Occurrence of Hippocampal Spatial Firing in a New Environment," Experimental Neurology, 1978, 62:282-297.
Hines. Current Opinion in Neurobiology, 2012, 22, 552-558 (Year: 2012).
Hughes et al., "Physiochemical drug properties associated with in vivo toxicological outcomes," Bioorganic & Medicinal Chemistry Letters, 18: 4872-4875 (2008).
Hussain, M.K., et al. "Tandem C-2 Functionalization-Intramolecular Azide-Alkyne 1,3-Dipolar Cycloaddition Reaction: A Convenient Route to Highly Diversified 9H-Benzo[b ]pyrrolo[ 1,2-g]triazolo[ 1,5-d] [1,4 ]diazepines", Organic Letters (2014), vol. 16, p. 560-563.
International Union of Pure and Applied Chemistry—Organic Chemistry Division—Commission on Nomenclature of Organic Chemistry, "Rules for the Nomenclature of Organic Chemistry—SectionE: Stereochemistry," Pure & Appl. Chem., 1976, 45: 11-30.

(56) References Cited

OTHER PUBLICATIONS

Jarrard, "On the role of the hippocampus in learning and memory in the rat," Behav. Neural. Biol. 60(1):9-26 (1993).
Jonas et al., "First in vivo testing of compounds targeting group 3 medulloblastomas using an implantable microdevice as a new paradigm for drug development," Journal of Biomedical Nanotechnology, vol. 12, Issue 6, 2016, pp. 1297-1302.
Kamenetz et al. "APP processing and synaptic function," Neuron (2003) 37: 925-37.
Kauer et al., "Synaptic plasticity and addiction," Nat. Rev. Neurosci. (2007), 8, 844-858.
Khan et al., "Topiramate attenuates exaggerated acoustic startle in an animal model of PTSD," Psychopharmacology 172(2):225-229 (2004).
Kim et al., "Transient impairment of hippocampus-dependent learning and memory in relatively low-dose of acute radiation syndrome is associated with inhibition of hippocampal neurogenesis," Journal of Radiation Research, 49:517-526 (2008).
Kluger et al., "Neuropsychological Prediction of Decline to Dementia in Nondemented Elderly," Journal of Geriatric Psychiatry and Neurology, 12:168-179 (1999).
Knust H. et al., "The discovery and unique pharmacological profile of RO4938581 and RO4882224 as potent and selective GABA (Alfa5) inverse agonists for the treatment of cognitive dysfunction", Bioorganic & Medical Chemistry Letters, vol. 19, 2009, pp. 5940-5944.
Kobayashi et al. "Behavioral phenotypes of amyloid-based genetically modified mouse models of Alzheimer's disease," Genes Brain Behav., 4:173-196 (2005).
Koh et al., "Treatment with selective GABA.sub.A .alpha.5 receptor agonists improves cognitive function in aged rats with memory impairment," Society for Neuroscience meeting, Nov. 16, 2010, Handout, 1 page.
Korakas et al., "Synthesis of the novel pyrrolo[2,1-d][1,2,5]benzotriazepine, pyrrolo[2,1-e][1,3,6]benzotriazocine and pyrrolo[1,2-a]tetrazolo[1,5-d][1,4]benzodiazepine ring systems. A new route to pyrrolo[1,2-a]quinoxaline via transamination of in situ generated 1-(2-aminophenyl)-2-iminomethylpyrroles", Tetrahedron, vol. 52, No. 32, 1996, pp. 10751-10760.
Larrabee, "Age-associated memory impairment: Definition and psychometric characteristics," Aging, Neuropsychology, and Cognition, 3(2):118-131 (1996).
Lein et al., "Defining a molecular atlas of the hippocampus using DNA microarrays and high-throughput in situ hybridization," J Neurosci., 24(15):3879-3889 (2004).
Leutgeb. et al., "Independent Codes for Spatial and Episodic Memory in Hippocampal Neuronal Ensembles," Science, 2005, 309: 619-623.
Leutgeb. et al., "Pattern Separation in the Dentate Gyrus and CA3 of the Hippocampus," Science, 2007, 315: 961-966.
Liberzon et al., "Stress-Restress: Effects on ACTH And Fast Feedback," Psvchoneuroendocrinology, 1997, 22(6): 443-453.
Lingford-Hughes et al., "Imaging the GABA-Benzodiazepine Receptor Subtype Containing the a5-Subunit In Vivo with [11C]Ro15 4513 Positron Emission Tomography," J. Cereb. Blood Flow Metab, vol. 22, 2002, pp. 878-889.
Lippa et al., "Selective anxiolysis produced by ocinaplon, a GABA. sub.A receptor modulator," PNAS 102(20):7380-7385, 2005.
Liu et al., "Synthesis and Pharmacological Properties of Novel 8-Substituted Imidazobenzodiazepines: High-Affinity, Selective Probes for .alpha.5-Containing GABA.sub.A Receptors.sup.1," J. Med. Chem., 1996, 39: 1928-1934.
Lodge et al., "A Loss of Parvalbumin-Containing Interneurons Is Associated with Diminished Oscillatory Activity in an Animal Model of Schizophrenia," J. Neurosci., 29(8):2344-2354, 2009.
Lodge et al., "Aberrant Hippocampal Activity Underlies the Dopamine Dysregulation in an Animal Model of Schizophrenia," J. Neurosci. (2007), 27(42), 11424-11430.
Lupien et al., "Effects of stress throughout the lifespan on the brain, behaviour and coe.nition," Nature Review/Neuroscience, Jun. 2009, vol. 10, 434-445.
Maeda et al., "Visualization of .alpha.5 Subunit of GABA.sub.A/ Benzodiazepine Receptor by [.sup.11C]Ro15-4513 Using Positron Emission Tomography," Synapse, 2003, 47: 200-208.
Marquis et al., "Independent predictors of cognitive decline in healthy elderly persons," Archives of Neurology, 59:601-606 (2002).
Masur et al., "Neuropsychological prediction of dementia and the absence of dementia in healthy elderly persons ," Neurology, vol. 44, Issue 8, 1994, pp. 1427-1432.
Meguro K. "Subjective memory complaints are not sine qua non as diagnostic criteria for MCI: the Tajiri project," Acta Neurologica Taiwanica, vol. 15, 2006, pp. 55-57.
Achermann et al., "Discovery of the imidazo [1,5-.alpha.][1,2,4]-triazolo[1,5-d][1,4] benzodiazepine scaffold as a novel, potent and selective GABA.sub.A .alpha.5 inverse agonist series," Aug. 2009, Bioorganic & Medicinal Chemistry Letters, vol. 19, pp. 5746-5752*. sup. 16.
Adams et al., "Hippocampal dependent learning ability correlates with N-methyl-D-aspartate (NMDA) receptor levels in CA3 neurons of young and aged rats," J. Comp. Neural., 432:230-243 (2001).
Aisen et al., "Clinical Core of the Alzheimer's Disease Neuroimaging Initiative: progress and plans," Alzheimer's & Dementia, 6(3):239-246 (2010).
Akbarian et al., "Gene Expression for Glutamic Acid Decarboxylase Is Reduced Without Loss of Neurons in Prefrontal Cortex of Schizophrenics," Arch. Gen. Psychiatry 52:258-266, 1995.
Alajarin et al., "A new modular and flexible approach to [1,2,3]triazolo[1,5-a][1,4]benzodiazepines", Tetrahedron Letters. Vol. 48, No. 20, 2007, pp. 3495-3499.
Albert, "The ageing brain: normal and abnormal memory," Philos. Trans. R. Soc. Lond. B. Biol. Sci., 352:1703-1709 (1997).
Ashe et al., "Probing the biology of Alzheimer's disease in mice," Neuron., 2010, 66(5): 631-645.
Auta et al., "Imidazenil: A Low Efficacy Agonist at .alpha.1—but High Efficacy at .alpha.5-GABA.sub.A Receptors Fail to Show Anticonvulsant Cross Tolerance to Diazepam or Zolpidem," Neuropharmacology, 2008, 55(2): 148-153.
Bakker et al., "Pattern separation in the human hippocampal CA3 and dentate gyms," Science, 319: 1640-1642 (2008).
Baldessarini et al., "Drugs and the Treatment of Psychiatric Disorders," (2001) Goodman & Gilman's the Pharmacological Basis of Therapeutics 10 Edition, 485-520.
Ballard et al., "RO4938581, a novel cognitive enhancer acting at GABA.sub.A .alpha.5 subunit-containing receptors," Psychopharmacology, 2009, 202: 207-223.
Barker et al., "A Prevalence Study of Age-Associated Memory Impairment," British Journal of Psychiatry, 167:642-648 (1995).
Barnes et al., "Region-specific age effects on AMP A sensitivity: electrophysiological evidence for loss of synaptic contacts in hippocampal field CA1," Hippocampus, 2:457-468 (1992).
Bartus et al., "The cholinergic hypothesis of geriatric memory dysfunction," Science, 217:408-417 (1982).
Bassett et al., "Familial risk for Alzheimer's disease alters fMRI activation patterns," Brain., 2006, 129(5):1229-1239.
Baxter et al., "Neurobiological substrates of behavioral decline: models and data analytic strategies for individual differences in aging," Neurobiol. Of Aging, 17:491-495 (1996).
Becker et al., "Why Do So Many Drugs for Alzheimer's Disease Fail in Development? Time for New Methods and New Practices?" J. Alzheimers Disease vol. 15 (2): 303-325 (2008).
Berezhnoy et al., "Pharmacological Properties of DOV 315,090, an ocinaplon metabolite," BMC Pharmacology, 2008, 8:11: 1-10.
Berntsen, "The Unbidden Past: Involuntary Autobiographical Memories as a Basic Mode of Remembering," Current Directions in Psychological Science 19(3) 138-142, 2010.
Berton et al., "Acamprosate Enhances N-Methyl-D-Apartate Receptor-Mediated Neurotransmission But Inhibits Presynaptic GABAB Receptors in Nucleus Accumbens Neurons," Alcohol Clin Exp Res, Feb. 1998, 22(1):183-191.

(56) References Cited

OTHER PUBLICATIONS

Betarbet et al., "Animal models of Parkinson's disease," BioEssays (2002), 24:308-318.
Blalock et al., Gene Microarrays in Hippocampal Aging: Statistical Profiling Identifies Novel Processes Correlated with Cognitive Impairment, J. Neurosci., 2003, 23(9): 3807-3819.
Bontekoe et al. "Knockout mouse model for Fxr2: a model for mental retardation," Hum. Mol. Genet., vol. 11, 2002, pp. 487-498.
Bookheimer et al., "Patterns of Brain Activation in People at Risk for Alzheimer's Disease", N Engl J Med., 2000, 343(7): 450-456.
Braccio et al., "1,5-Benzodiazepines XIV. Synthesis of new substituted 9H-bis-[1,2,4]triazolo[4,3-a:3',4'-d][1,5]benzodiazepines and relate compounds endowed with in vitro cytotoxic properties", Farmaco, vol. 60, No. 2, 2005, pp. 113-125.
Brewer et al., "Optimized survival of hippocampal neurons in B27-supplemented Neurobasal, a new serum-free medium combination," J. Neuroscience Res. 35:567-576 (1993).
Buchanan et al., "The FDA-NIMH-MATRICS guidelines for clinical trial design of cognitive-enchanceing drugs: what do we know 5 years later?" Schizophr. Bull. Nov. 2011;. 37(6):1209-1217.
Buettelmann B. et al., "Imidazo[1,5-a][1,2,4]-triazolo[1,5-d][1,4]benzodiazepines as potent and highly selective GABA (Alfa5) inverse agonists with potential for the treatment of congnitive dysfunction", Bioorganic & Medicinal Chemistry Letters, vol. 19, 2009, pp. 5958-5961.
Busche et al., "Clusters of Hyperactive Neurons Near Amyloid Plaques in a Mouse Model of Alzheimer's Disease," Science, 2008, 321: 1686-1689.
Buschke et al., "Evaluating storage, retention, and retrieval in disordered memory and learning," Neurology, 24:1019-1025 (1974).
Carling et al., "7-(1,1-Dimethylethyl)-6-(2-ethyl-2H-1,2,4-triazol-3-ylmethoxy)-3-(2-fluorophenyl)-1,2,4-triazolo[4,3-b]pyridazine: A Functionally Selective .gamma.-Aminobutyric Acid.sub.A (GABA.sub.A) .alpha.2/.alpha 3-Subtype Selective Agonist That Exhibits Potent Anxiolytic Activity but Is Not Sedating in Animal Models", Journal of Medicinal Chemistry, 2005, 48(23): 7089-7092.
Celone et al., "Alterations in Memory Networks in Mild Cognitive Impairment and Alzheimer's Disease: An Independent Component Analysis," J. Neurosci., 2006, 26(40): 10222-10231.
Chambers "An Orally Bioavailable, Functionally Selective Inverse Agonist at the Benzodiazepine Site of GABA.sub.A.alpha.5 Receptors with Cognition Enhancing Properties," J. Med. Chem., 47:5829-5832 (2004).
Chambers et al. "Identification of a Novel, Selective GABAA a5 Receptor Inverse Agonist Which Enhances Cognition," J. Med. Chem., vol. 46, 2003, pp. 2227-2240.
Chappell et al., "A re-examination of the role of basal forebrain cholinergic neurons in spatial working memory," Neuropharmacology, 37(4-5):481-487 (1998).
Ciccocioppo et al., "Genetically selected Marchigian Sardinian alcohol-preferring (msP) rats: an animal model to study the neurobiology of alcoholism," Addiction Biology, 11(3-4):339-355 (2006).
Colombo et al., "Spatial memory is related to hippocampal subcellular concentrations of calcium-dependent protein kinase C isoforms in young and aged rats," Proc. Natl. Acad. Sci, vol. 94, 1997, pp. 14195-14199.
Costa et al., "GABA.sub.A receptors and benzodiazepines: a role for dendritic resident subunit mRNAs," Neuropharmacology 43: 925-937 (2002).
Crook et al., "Age-Associated Memory Impairment: Proposed Diagnostic Criteria and Measures of Clinical Change—Report of a National Institute of Mental Health Work Group," Developmental Neuropsychology, 1986, 2(4), 261-276.
Cross et al., "Rules for the Nomenclature of Organic Chemistry: Section E: Stereochemistry," Pure & Appl. Chem. (1976), 45, 11-30.
De Hoz et al., "Spatial learning with unilateral and bilateral hippocampal networks," Eur. J. Neurosci., 22:745-754 (2005).
Dickerson BC et al., "Medial temporal lobe function and structure in mild cognitive impairment," Ann. Neurol. 56:27-35 (2004).
Dickerson et al., "Increased hippocampal activation in mild cognitive impairment compared to normal aging and AD," Neurology, 2005, 65: 404-411.
Dietrich et al., "Clinical patterns and biological correlates of cognitive dysfunction associated with cancer therapy," Oncologist, vol. 13, 2008, pp. 1285-1295.
Donald et al., "Application of a sequential multicomponent assembly process/huisgen cycloaddition strategy to the preparation of libraries of 1,2,3-triazole-fused 1,4-benzodiazepines," ACS Combinatorial Science, 14(2):135-143 (2012).
El Youssoufi et al., "Glycosylated benzocycloheptadipyrazoles: a new class of water-soluble heterocyclic compounds," Bulletin de la Societe Chimique de France, 134(6):571-581 (1997).
Ellison et al., "Beyond the "C" in MCI: Noncognitive Symptoms in Amnestic and Non-amnestic Mild Co!mi.tive Impairment," CNS Spectr. 13(1):66-72, 2008.
Enomoto et al., "Disruptions in spatial working memory, but not short-term memory, induced by repeated ketamine exposure," Progress in Neuro-Psychopharmacology & Biological Psychiatry 33 (2009) 668-675.
Essassi et al., "Recherches En Série Benzodiazepine-1,5: Synthèses Des Ditriazolo-[4,3-a;3,4-d]-Benzodiazepines-1,5", Wiley Online Library, vol. 100, No. 3, 1991, pp. 277-286.
Folstein et al., ""Mini-mental state". A practical method for grading the cognitive state of patients for the clinician," Journal of Psychiatric Research, 12(3):189-198 (1975).
Plassman et al., "Prevalence of cognitive impairment without dementia in the United States," Annals oflnternal Medicine, 148(6):427-434 (2008).
Zahodne et al., "Pathophysiology and treatment of psychosis in Parkinson's disease," Drugs Aging. Vol. 25, Issue 8, 2008, pp. 665-682.
Bustamante et al., "A Modification of the Extended Hildebrand Approach to Predict the Solubility of Structurally Related Drugs in Solvent Mixtures," Journal of Pharmacy and Pharmacology, 45:253-257 (1993).
Owens et al, "Alternative Routes of Insulin Delivery," Diabetic Medicine, 20:886-898 (2003).

* cited by examiner

BENZODIAZEPINE DERIVATIVES, COMPOSITIONS, AND METHODS FOR TREATING COGNITIVE IMPAIRMENT

RELATED APPLICATIONS

This application is a divisional application of U.S. patent application Ser. No. 16/471,237 (allowed), filed Jun. 19, 2019, which is a United States National Phase Application filed under 35 U.S.C. § 371 of International Patent Application No. PCT/IB2017/001762 (formerly International Patent Application No. PCT/US2017/067729), filed Dec. 20, 2017, which claims the benefit of and priority from U.S. Provisional Application No. 62/436,272, filed Dec. 19, 2016, and is a continuation of International Application No. PCT/IB2017/001763 (formerly International Application No. PCT/US2017/067448), filed Dec. 19, 2017. Each of these applications is incorporated herein by reference in their entireties.

STATEMENT OF GOVERNMENT SUPPORT

This invention was made with government support under Grant No. U01 AG041140 and Grant No. UH2NS101856 awarded by the National Institutes of Health (NIH), and in particular, its National Institute on Aging (NIA) division, an agency of the United States Government. The United States Government has certain rights in the invention.

FIELD OF THE INVENTION

The invention relates to compounds, compositions and methods for treating cognitive impairment associated with central nervous system (CNS) disorders, cognitive impairment associated with brain cancers, and brain cancers in a subject in need thereof.

BACKGROUND OF THE INVENTION

Cognitive ability may decline as a normal consequence of aging or as a consequence of a central nervous disorder.

For example, a significant population of elderly adults experiences a decline in cognitive ability that exceeds what is typical in normal aging. Such age-related loss of cognitive function is characterized clinically by progressive loss of memory, cognition, reasoning, and judgment. Mild Cognitive Impairment (MCI), Age-Associated Memory Impairment (AAMI), Age-Related Cognitive Decline (ARCD) or similar clinical groupings are among those related to such age-related loss of cognitive function. According to some estimates, there are more than 16 million people with AAMI in the U.S. alone (Barker et al., 1995), and MCI is estimated to affect 5.5-7 million in the U.S. over the age of 65 (Plassman et al., 2008).

Cognitive impairment is also associated with other central nervous system (CNS) disorders, such as dementia, Alzheimer's Disease (AD), prodromal AD, post traumatic stress disorder (PTSD), schizophrenia, bipolar disorder (in particular, mania), amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction.

There is, therefore, a need for effective treatment of cognitive impairment associated with central nervous system (CNS) disorders and to improve cognitive function in patients diagnosed with, for example, age-related cognitive impairment, MCI, amnestic MCI, AAMI, ARCD, dementia, AD, prodromal AD, PTSD, schizophrenia or bipolar disorder (in particular, mania), amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction and similar central nervous system (CNS) disorders with cognitive impairment or at risk of developing them.

$GABA_A$ receptors ($GABA_A$ R) are pentameric assemblies from a pool of different subunits (α1-6, β1-3, γ1-3, δ, ε, π, θ) that form a Cl-permeable channel that is gated by the neurotransmitter γ-aminobutyric acid (GABA). Various pharmacological effects, including anxiety disorders, epilepsy, insomnia, pre-anesthetic sedation, and muscle relaxation, are mediated by different $GABA_A$ subtypes.

Various studies have demonstrated that reduced GABA signaling is linked to various CNS disorders with cognitive impairment. In particular, the α5-containing $GABA_A$ Rs, which are relatively sparse in the mammalian brain, play a role in modifying learning and memory. Previous studies demonstrated a reduction of hippocampal expression of the α5 subunit of the $GABA_A$ receptor in rats with age-related cognitive decline (see International Patent Publication WO 2007/019312). Such results suggest that upregulation of α5-containing $GABA_A$ R function may be effective in the treatment of cognitive impairment associated with said CNS disorders.

Thus, there is a need for positive allosteric modulators of α5-containing $GABA_A$ R that are useful in therapeutic preparations for the treatment of cognitive impairment associated with said CNS disorders.

SUMMARY OF THE INVENTION

The present invention addresses the aforementioned need by providing a compound of formula I:

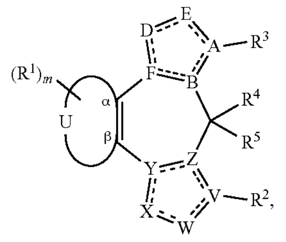

I or a pharmaceutically acceptable salt, hydrate, solvate, polymorph, isomer, or combination thereof, wherein:

U and the two carbon atoms designated by α and β together form a 5- or 6-membered aromatic ring having 0-2 nitrogen atoms;

A is C, $CR^6$, or N;

B and F are each independently selected from C, $CR^6$, and N, wherein B and F cannot both be N;

D is N, $NR^7$, O, $CR^6$ or $C(R^6)_2$;

E is N, $NR^7$, $CR^6$ or $C(R^6)_2$;

W is N, $NR^7$, $CR^6$ or $C(R^6)_2$;

X is N, $NR^7$, O, $CR^6$ or $C(R^6)_2$;

Y and Z are each independently selected from C, $CR^6$, and N, wherein Y and Z cannot both be N;

V is C or $CR^6$, or when Z is C or $CR^6$, V is C, $CR^6$, or N;

wherein when the ring formed by X, Y, Z, V and W is

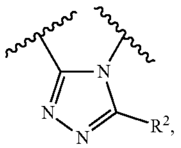

then $R^2$ is —$OR^8$, —$SR^8$, —$(CH_2)_nOR^8$, —$(CH_2)_nO(CH_2)_nR^8$, —$(CH_2)_pR^8$ and —$(CH_2)_nN(R'')R^{10}$; and wherein $R^2$ is independently substituted with 0-5 R';

m and n are independently integers selected from 0-4;

p is an integer selected from 2-4;

each occurrence of the bond "---" is either a single bond or a double bond;

each occurrence of $R^1$, $R^2$, $R^4$, and $R^8$ are each independently selected from:

halogen, —R, —OR, —$NO_2$, —NCS, —CN, —$CF_3$, —$OCF_3$, —$SiR_3$, —$N(R)_2$, —SR, —SOR, —$SO_2R$, —$SO_2N(R)_2$, —$SO_3R$, —$(CR_2)_{1-3}R$, —$(CR_2)_{1-3}$—OR, —$(CR_2)_{0-3}$—C(O)NR$(CR_2)_{0-3}$R, —$(CR_2)_{0-3}$—C(O)NR$(CR_2)_{0-3}$OR, —C(O)R, —C(O)C(O)R, —C(O)$CH_2$C(O)R, —C(S)R, —C(S)OR, —C(O)OR, —C(O)C(O)OR, —C(O)C(O)$N(R)_2$, —OC(O)R, —C(O)$N(R)_2$, —OC(O)$N(R)_2$, —C(S)$N(R)_2$, —$(CR_2)_{0-3}$NHC(O)R, —N(R)N(R)COR, —N(R)N(R)C(O)OR, —N(R)N(R)CON$(R)_2$, —N(R)$SO_2$R, —N(R)$SO_2N(R)_2$, —N(R)C(O)OR, —N(R)C(O)R, —N(R)C(S)R, —N(R)C(O)$N(R)_2$, —N(R)C(S)$N(R)_2$, —N(COR)COR, —N(OR)R, —C(=NH)$N(R)_2$, —C(O)N(OR)R, —C(=NOR)R, —OP(O)$(OR)_2$, —P(O)$(R)_2$, —P(O)$(OR)_2$, and —P(O)(H)(OR);

$R^3$ is absent or is selected from:

halogen, —R, —OR, —$NO_2$, —NCS, —CN, —$CF_3$, —$OCF_3$, —$SiR_3$, —$N(R)_2$, —SR, —SOR, —$SO_2R$, —$SO_2N(R)_2$, —$SO_3R$, —$(CR_2)_{1-3}R$, —$(CR_2)_{1-3}$—OR, —$(CR_2)_{0-3}$—C(O)NR$(CR_2)_{0-3}$R, —$(CR_2)_{0-3}$—C(O)NR$(CR_2)_{0-3}$OR, —C(O)R, —C(O)C(O)R, —C(O)$CH_2$C(O)R, —C(S)R, —C(S)OR, —C(O)OR, —C(O)C(O)OR, —C(O)C(O)$N(R)_2$, —OC(O)R, —C(O)$N(R)_2$, —OC(O)$N(R)_2$, —C(S)$N(R)_2$, —$(CR_2)_{0-3}$NHC(O)R, —N(R)N(R)COR, —N(R)N(R)C(O)OR, —N(R)N(R)CON$(R)_2$, —N(R)$SO_2$R, —N(R)$SO_2N(R)_2$, —N(R)C(O)OR, —N(R)C(O)R, —N(R)C(S)R, —N(R)C(O)$N(R)_2$, —N(R)C(S)$N(R)_2$, —N(COR)COR, —N(OR)R, —C(—NH)$N(R)_2$, —C(O)N(OR)R, —C(—NOR)R, —OP(O)$(OR)_2$, —P(O)$(R)_2$, —P(O)$(OR)_2$, and —P(O)(H)(OR);

each $R^6$ is independently —H or —(C1-C6)alkyl;

each $R^7$ is independently —H or —(C1-C6)alkyl;

each $R^8$ is independently —(C1-C6)alkyl, —(C3-C10)-cycloalkyl, (C6-C10)-aryl, or 5- to 10-membered heteroaryl, wherein each occurrence of $R^8$ is independently substituted with 0-5 R';

each $R^{10}$ is independently —(C3-C10)-cycloalkyl, 3- to 10-membered heterocyclyl-, (C6-C10)-aryl, or 5- to 10-membered heteroaryl, wherein each occurrence of $R^{10}$ is independently substituted with 0-5 R';

each R is independently selected from:

H—,
(C1-C12)-aliphatic-,
(C3-C10)-cycloalkyl-,
(C3-C10)-cycloalkenyl-,
[(C3-C10)-cycloalkyl]-(C1-C12)-aliphatic-,
[(C3-C10)-cycloalkenyl]-(C1-C12)-aliphatic-,
[(C3-C10)-cycloalkyl]-O—(C1-C12)-aliphatic-,
[(C3-C10)-cycloalkenyl]-O—(C1-C12)-aliphatic-,
(C6-C10)-aryl-,
(C6-C10)-aryl-(C1-C12)aliphatic-,
(C6-C10)-aryl-O—(C1-C12)aliphatic-,
(C6-C10)-aryl-N(R")—(C1-C12)aliphatic-,
3- to 10-membered heterocyclyl-,
(3- to 10-membered heterocyclyl)-(C1-C12)aliphatic-,
(3- to 10-membered heterocyclyl)-O—(C1-C12)aliphatic-,
(3- to 10-membered heterocyclyl)-N(R")—(C1-C12)aliphatic-,
5- to 10-membered heteroaryl-,
(5- to 10-membered heteroaryl)-(C1-C12)-aliphatic-,
(5- to 10-membered heteroaryl)-O—(C1-C12)-aliphatic-; and
(5- to 10-membered heteroaryl)-N(R")—(C1-C12)-aliphatic-;

wherein said heterocyclyl has 1-4 heteroatoms independently selected from N, NH, O, S, SO, and $SO_2$, and said heteroaryl has 1-4 heteroatoms independently selected from N, NH, O, and S;

wherein each occurrence of R is independently substituted with 0-5 R';

or when two R groups bound to the same atom, the two R groups may be taken together with the atom to which they are bound to form a 3- to 10-membered aromatic or non-aromatic ring having 0-4 heteroatoms independently selected from N, NH, O, S, SO, and $SO_2$, wherein said ring is optionally substituted with 0-5 R', and wherein said ring is optionally fused to a (C6-C10) aryl, 5- to 10-membered heteroaryl, (C3-C10)cycloalkyl, or a 3- to 10-membered heterocyclyl;

wherein each occurrence of R' is independently selected from halogen, —R", —OR", oxo, —$CH_2$OR", —$CH_2NR''_2$, —C(O)N$(R'')_2$, —C(O)OR", —$NO_2$, —NCS, —CN, —$CF_3$, —$OCF_3$ and —N$(R'')_2$;

wherein each occurrence of R" is independently selected from H, —(C1-C6)-alkyl, —(C1-C6)-aliphatic, (C3-C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, and (C6-C10)-aryl-O—(C1-C6)-alkyl-, wherein each occurrence of R" is independently substituted with 0-3 substituents selected from: halogen, —$R^\circ$, —$OR^\circ$, oxo, —$CH_2OR^\circ$, —$CH_2NR^\circ_2$, —C(O)N$(R^\circ)_2$, —C(O)$OR^\circ$, —$NO_2$, —NCS, —CN, —$CF_3$, —$OCF_3$ and —N$(R^\circ)_2$, wherein each occurrence of $R^\circ$ is independently selected from: —(C1-C6)-aliphatic, (C3-C6)-cycloalkyl, 3- to 6-membered heterocyclyl, 5- to 10-membered heteroaryl-, and (C6-C10)-aryl-.

Some embodiments of this application provide a compound of formula I:

I

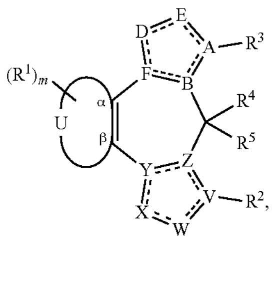

or a pharmaceutically acceptable salt, hydrate, solvate, polymorph, isomer, or combination thereof, wherein:

U and the two carbon atoms designated by α and β together form a 5- or 6-membered aromatic ring having 0-2 nitrogen atoms;

A is C, $CR^6$, or N;

B and F are each independently selected from C, $CR^6$, and N, wherein B and F cannot both be N;

D is N, $NR^7$, O, $CR^6$ or $C(R^6)_2$;

E is N, $NR^7$, $CR^6$ or $C(R^6)_2$;

W is N, $NR^7$, $CR^6$ or $C(R^6)_2$;

X is N, $NR^7$, O, $CR^6$ or $C(R^6)_2$;

Y and Z are each independently selected from C, $CR^6$, and N, wherein Y and Z cannot both be N;

V is C or $CR^6$, or when Z is C or $CR^6$, V is C, $CR^6$, or N;

wherein when the ring formed by X, Y, Z, V and W is

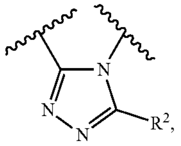

then $R^2$ is —$OR^8$, —$SR^8$, —$(CH_2)_nOR^8$, —$(CH_2)_nO(CH_2)_pR^8$, —$(CH_2)_pR^8$ and —$(CH_2)_nN(R'')R^{10}$; and wherein $R^2$ is independently substituted with 0-5 R';

m and n are independently integers selected from 0-4;

p is an integer selected from 2-4;

each occurrence of the bond "$\overset{---}{—}$" is either a single bond or a double bond;

each occurrence of $R^1$, $R^2$, $R^4$, and $R^5$ are each independently selected from:

halogen, —R, —OR, —$NO_2$, —NCS, —CN, —$CF_3$, —$OCF_3$, —$SiR_3$, —$N(R)_2$, —SR, —SOR, —$SO_2R$, —$SO_2N(R)_2$, —$SO_3R$, —$(CR_2)_{1-3}R$, —$(CR_2)_{1-3}$—OR, —$(CR_2)_{0-3}$—C(O)NR$(CR_2)_{0-3}R$, —$(CR_2)_{0-3}$—C(O)NR$(CR_2)_{0-3}OR$, —C(O)R, —C(O)C(O)R, —C(O)$CH_2$C(O)R, —C(S)R, —C(S)OR, —C(O)OR, —C(O)C(O)OR, —C(O)C(O)$N(R)_2$, —OC(O)R, —C(O)$N(R)_2$, —OC(O)$N(R)_2$, —C(S)$N(R)_2$, —$(CR_2)_{0-3}$NHC(O)R, —N(R)N(R)COR, —N(R)N(R)C(O)OR, —N(R)N(R)CON$(R)_2$, —N(R)$SO_2R$, —N(R)$SO_2N(R)_2$, —N(R)C(O)OR, —N(R)C(O)R, —N(R)C(S)R, —N(R)C(O)$N(R)_2$, —N(R)C(S)$N(R)_2$, —N(COR)COR, —N(OR)R, —C(=NH)$N(R)_2$, —C(O)N(OR)R, —C(=NOR)R, —OP(O)$(OR)_2$, —P(O)$(R)_2$, —P(O)$(OR)_2$, and —P(O)(H)(OR);

$R^3$ is absent or is selected from:

halogen, —R, —OR, —$NO_2$, —NCS, —CN, —$CF_3$, —$OCF_3$, —$SiR_3$, —$N(R)_2$, —SR, —SOR, —$SO_2R$, —$SO_2N(R)_2$, —$SO_3R$, —$(CR_2)_{1-3}R$, —$(CR_2)_{1-3}$—OR, —$(CR_2)_{0-3}$—C(O)NR$(CR_2)_{0-3}R$, —$(CR_2)_{0-3}$—C(O)NR$(CR_2)_{0-3}OR$, —C(O)R, —C(O)C(O)R, —C(O)$CH_2$C(O)R, —C(S)R, —C(S)OR, —C(O)OR, —C(O)C(O)OR, —C(O)C(O)$N(R)_2$, —OC(O)R, —C(O)$N(R)_2$, —OC(O)$N(R)_2$, —C(S)$N(R)_2$, —$(CR_2)_{0-3}$NHC(O)R, —N(R)N(R)COR, —N(R)N(R)C(O)OR, —N(R)N(R)CON$(R)_2$, —N(R)$SO_2R$, —N(R)$SO_2N(R)_2$, —N(R)C(O)OR, —N(R)C(O)R, —N(R)C(S)R, —N(R)C(O)$N(R)_2$, —N(R)C(S)$N(R)_2$, —N(COR)COR, —N(OR)R, —C(—NH)$N(R)_2$, —C(O)N(OR)R, —C(—NOR)R, —OP(O)$(OR)_2$, —P(O)$(R)_2$, —P(O)$(OR)_2$, and —P(O)(H)(OR);

each $R^6$ is independently —H or —(C1-C6)alkyl;

each $R^7$ is independently —H or —(C1-C6)alkyl;

each $R^8$ is independently —(C1-C6)alkyl, —(C3-C10)-cycloalkyl, (C6-C10)-aryl, or 5- to 10-membered heteroaryl, wherein each occurrence of $R^8$ is independently substituted with 0-5 R';

each $R^{10}$ is independently —(C3-C10)-cycloalkyl, 3- to 10-membered heterocyclyl-, (C6-C10)-aryl, or 5- to 10-membered heteroaryl, wherein each occurrence of $R^{10}$ is independently substituted with 0-5 R';

each R is independently selected from:

H—,
(C1-C12)-aliphatic-,
(C3-C10)-cycloalkyl-,
(C3-C10)-cycloalkenyl-,
[(C3-C10)-cycloalkyl]-(C1-C12)-aliphatic-,
[(C3-C10)-cycloalkenyl]-(C1-C12)-aliphatic-,
[(C3-C10)-cycloalkyl]-O—(C1-C12)-aliphatic-,
[(C3-C10)-cycloalkenyl]-O—(C1-C12)-aliphatic-,
(C6-C10)-aryl-,
(C6-C10)-aryl-(C1-C12)aliphatic-,
(C6-C10)-aryl-O—(C1-C12)aliphatic-,
(C6-C10)-aryl-N(R")—(C1-C12)aliphatic-,
3- to 10-membered heterocyclyl-,
(3- to 10-membered heterocyclyl)-(C1-C12)aliphatic-,
(3- to 10-membered heterocyclyl)-O—(C1-C12)aliphatic-,
(3- to 10-membered heterocyclyl)-N(R")—(C1-C12)aliphatic-,
5- to 10-membered heteroaryl-,
(5- to 10-membered heteroaryl)-(C1-C12)-aliphatic-,
(5- to 10-membered heteroaryl)-O—(C1-C12)-aliphatic-; and
(5- to 10-membered heteroaryl)-N(R")—(C1-C12)-aliphatic-;

wherein said heterocyclyl has 1-4 heteroatoms independently selected from N, NH, O, S, SO, and $SO_2$, and said heteroaryl has 1-4 heteroatoms independently selected from N, NH, O, and S;

wherein each occurrence of R is independently substituted with 0-5 R';

or when two R groups bound to the same atom, the two R groups may be taken together with the atom to which they are bound to form a 3- to 10-membered aromatic or non-aromatic ring having 0-4 heteroatoms independently selected from N, NH, O, S, SO, and $SO_2$, wherein said ring is optionally substituted with 0-5 R', and wherein said ring is optionally fused to a (C6-C10)aryl, 5- to 10-membered heteroaryl, (C3-C10)cycloalkyl, or a 3- to 10-membered heterocyclyl;

wherein each occurrence of R' is independently selected from halogen, —R", —OR", oxo, —$CH_2OR''$, —$CH_2NR''_2$, —C(O)$N(R'')_2$, —C(O)OR", —$NO_2$, —NCS, —CN, —$CF_3$, —$OCF_3$ and —$N(R'')_2$;

wherein each occurrence of R" is independently selected from H, —(C1-C6)-alkyl, (C3-C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, and (C6-C10)-aryl-O—(C1-C6)-alkyl-.

Some embodiments of this application provide a compound of formula I:

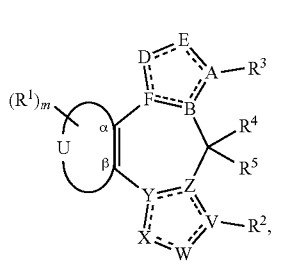

I or a pharmaceutically acceptable salt, hydrate, solvate, polymorph, isomer, or combination thereof, wherein:

U and the two carbon atoms designated by α and β together form a 5- or 6-membered aromatic ring having 0-2 nitrogen atoms;

A is C, $CR^6$, or N;

B and F are each independently selected from C, $CR^6$, and N, wherein B and F cannot both be N;

D is N, $NR^7$, O, $CR^6$ or $C(R^6)_2$;

E is N, $NR^7$, $CR^6$ or $C(R^6)_2$;

W is N, $NR^7$, $CR^6$ or $C(R^6)_2$;

X is N, $NR^7$, O, $CR^6$ or $C(R^6)_2$;

Y and Z are each independently selected from C, $CR^6$, and N, wherein Y and Z cannot both be N;

V is C or $CR^6$, or when Z is C or $CR^6$, V is C, $CR^6$, or N;

wherein when the ring formed by X, Y, Z, V and W is

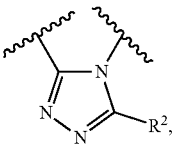

then $R^2$ is —$OR^8$, —$SR^8$, or —$(CH_2)_nOR^8$;

m and n are each independently an integer selected from 0-4;

each occurrence of the bond "$\overline{---}$" is either a single bond or a double bond;

each occurrence of $R^1$, $R^2$, $R^4$, and $R^5$ are each independently selected from:

halogen, —R, —OR, —$NO_2$, —NCS, —CN, —$CF_3$, —$OCF_3$, —$SiR_3$, —$N(R)_2$, —SR, —SOR, —$SO_2R$, —$SO_2N(R)_2$, —$SO_3R$, —$(CR_2)_{1-3}R$, —$(CR_2)_{1-3}$—OR, —$(CR_2)_{0-3}$—$C(O)NR(CR_2)_{0-3}R$, —$(CR_2)_{0-3}$—$C(O)NR(CR_2)_{0-3}OR$, —C(O)R, —C(O)C(O)R, —$C(O)CH_2C(O)R$, —C(S)R, —C(S)OR, —C(O)OR, —C(O)C(O)OR, —$C(O)C(O)N(R)_2$, —OC(O)R, —$C(O)N(R)_2$, —$OC(O)N(R)_2$, —$C(S)N(R)_2$, —$(CR_2)_{0-3}NHC(O)R$, —N(R)N(R)COR, —N(R)N(R)C(O)OR, —$N(R)N(R)CON(R)_2$, —$N(R)SO_2R$, —$N(R)SO_2N(R)_2$, —N(R)C(O)OR, —N(R)C(O)R, —N(R)C(S)R, —$N(R)C(O)N(R)_2$, —$N(R)C(S)N(R)_2$, —N(COR)COR, —N(OR)R, —C(—NH)$N(R)_2$, —C(O)N(OR)R, —C(—NOR)R, —$OP(O)(OR)_2$, —$P(O)(R)_2$, —$P(O)(OR)_2$, and —P(O)(H)(OR);

$R^3$ is absent or is selected from:

halogen, —R, —OR, —$NO_2$, —NCS, —CN, —$CF_3$, —$OCF_3$, —$SiR_3$, —$N(R)_2$, —SR, —SOR, —$SO_2R$, —$SO_2N(R)_2$, —$SO_3R$, —$(CR_2)_{1-3}R$, —$(CR_2)_{1-3}$—OR, —$(CR_2)_{0-3}$—$C(O)NR(CR_2)_{0-3}R$, —$(CR_2)_{0-3}$—$C(O)NR(CR_2)_{0-3}OR$, —C(O)R, —C(O)C(O)R, —$C(O)CH_2C(O)R$, —C(S)R, —C(S)OR, —C(O)OR, —C(O)C(O)OR, —$C(O)C(O)N(R)_2$, —OC(O)R, —$C(O)N(R)_2$, —$OC(O)N(R)_2$, —$C(S)N(R)_2$, —$(CR_2)_{0-3}NHC(O)R$, —N(R)N(R)COR, —N(R)N(R)C(O)OR, —$N(R)N(R)CON(R)_2$, —$N(R)SO_2R$, —$N(R)SO_2N(R)_2$, —N(R)C(O)OR, —N(R)C(O)R, —N(R)C(S)R, —$N(R)C(O)N(R)_2$, —$N(R)C(S)N(R)_2$, —N(COR)COR, —N(OR)R, —C(=NH)$N(R)_2$, —C(O)N(OR)R, —C(=NOR)R, —$OP(O)(OR)_2$, —$P(O)(R)_2$, —$P(O)(OR)_2$, and —P(O)(H)(OR);

each $R^6$ is independently —H or —(C1-C6)alkyl;

each $R^7$ is independently —H or —(C1-C6)alkyl;

each $R^8$ is independently —(C1-C6)alkyl, —(C3-C10)-cycloalkyl, —(C6-C10)-aryl, or 5- to 10-membered heteroaryl, wherein each occurrence of $R^8$ is independently substituted with 0-5 R';

each R is independently selected from:

H—,
(C1-C12)-aliphatic-,
(C3-C10)-cycloalkyl-,
(C3-C10)-cycloalkenyl-,
[(C3-C10)-cycloalkyl]-(C1-C12)-aliphatic-,
[(C3-C10)-cycloalkenyl]-(C1-C12)-aliphatic-,
[(C3-C10)-cycloalkyl]-O—(C1-C12)-aliphatic-,
[(C3-C10)-cycloalkenyl]-O—(C1-C12)-aliphatic-,
(C6-C10)-aryl-,
(C6-C10)-aryl-(C1-C12)aliphatic-,
(C6-C10)-aryl-O—(C1-C12)aliphatic-,
3- to 10-membered heterocyclyl-,
(3- to 10-membered heterocyclyl)-(C1-C12)aliphatic-,
(3- to 10-membered heterocyclyl)-O—(C1-C12)aliphatic-,
5- to 10-membered heteroaryl-,
(5- to 10-membered heteroaryl)-(C1-C12)-aliphatic-, and
(5- to 10-membered heteroaryl)-O—(C1-C12)-aliphatic-;

wherein said heterocyclyl has 1-4 heteroatoms independently selected from N, NH, O, S, SO, and $SO_2$, and said heteroaryl has 1-4 heteroatoms independently selected from N, NH, O, and S;

wherein each occurrence of R is independently substituted with 0-5 R';

or when two R groups bound to the same atom, the two R groups may be taken together with the atom to which they are bound to form a 3- to 10-membered aromatic or non-aromatic ring having 0-4 heteroatoms independently selected from N, NH, O, S, SO, and $SO_2$, wherein said ring is optionally substituted with 0-5 R', and wherein said ring is optionally fused to a (C6-C10) aryl, 5- to 10-membered heteroaryl, (C3—C10)cycloalkyl, or a 3- to 10-membered heterocyclyl;

wherein each occurrence of R' is independently selected from halogen, —R", —OR", oxo, —$CH_2OR"$, —$CH_2NR"_2$, —$C(O)N(R")_2$, —C(O)OR", —$NO_2$, —NCS, —CN, —$CF_3$, —$OCF_3$ and —$N(R")_2$;

wherein each occurrence of R" is independently selected from H, —(C1-C6)-alkyl, (C3-C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, and (C6-C10)-aryl-O—(C1-C6)-alkyl-.

In another aspect, the present invention provides a compound of formula II:

II

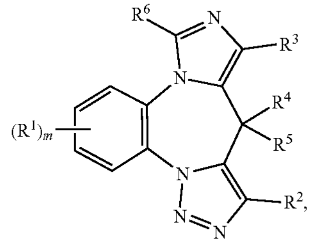

or a pharmaceutically acceptable salt, hydrate, solvate, polymorph, isomer, or combination thereof, wherein m, $R^1$, $R^2$, $R^3$, $R^4$, $R^5$ and $R^6$ are as defined in formula I.

In another aspect, the present invention provides a compound of formula III:

III

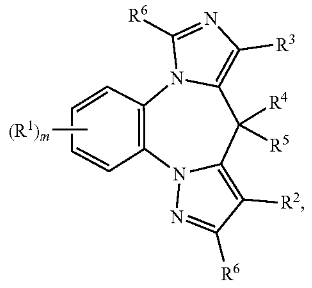

or a pharmaceutically acceptable salt, hydrate, solvate, polymorph, isomer, or combination thereof, wherein m, $R^1$, $R^2$, $R^3$, $R^4$, $R^5$ and $R^6$ are as defined in formula I.

In another aspect, the present invention provides a compound of formula IV:

IV

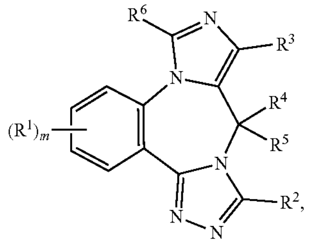

or a pharmaceutically acceptable salt, hydrate, solvate, polymorph, isomer, or combination thereof, wherein $R^2$ is —$OR^8$, —$SR^8$, or —$(CH_2)_nOR^8$, wherein $R^2$ is independently substituted with 0-5 R' and wherein m, n, $R^1$, $R^3$, $R^4$, $R^5$, $R^6$, and $R^8$ are as defined in formula I.

In another aspect, the present invention provides a compound of formula IV:

IV

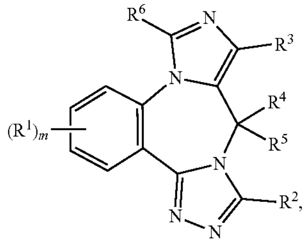

or a pharmaceutically acceptable salt, hydrate, solvate, polymorph, isomer, or combination thereof, wherein $R^2$ is —$(CH_2)_nO(CH_2)_nR^8$, —$(CH_2)_pR^8$ or —$(CH_2)_nN(R'')R^{10}$, wherein $R^2$ is independently substituted with 0-5 R' and wherein m, n, p, $R^1$, $R^3$, $R^4$, $R^5$, $R^6$, $R^8$, $R^{10}$, and R'' are as defined herein.

In another aspect, the present invention provides a compound of formula V:

V

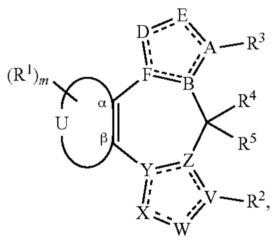

or a pharmaceutically acceptable salt, hydrate, solvate, polymorph, isomer, or combination thereof, wherein:

U and the two carbon atoms designated by α and β together form a 5- or 6-membered aromatic ring having 0-2 nitrogen atoms;

A is C, $CR^6$, or N;

B and F are each independently selected from C, $CR^6$, and N, wherein B and F cannot both be N;

D is N, $NR^7$, O, $CR^6$ or $C(R^6)_2$;

E is N, $NR^7$, $CR^6$ or $C(R^6)_2$;

W is N, $NR^7$, $CR^6$ or $C(R^6)_2$;

X is N, $NR^7$, O, $CR^6$ or $C(R^6)_2$;

Y and Z are each independently selected from C, $CR^6$, and N, wherein Y and Z cannot both be N;

V is C or $CR^6$, or when Z is C or $CR^6$, V is C, $CR^6$, or N;

wherein when the ring formed by X, Y, Z, V and W is

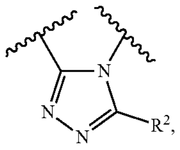

then $R^2$ is —$OR^8$, —$SR^8$, —$(CH_2)_nOR^8$, —$(CH_2)_nO(CH_2)_nR^8$, —$(CH_2)_pR^8$ and —$(CH_2)_nN(R'')R^{10}$; and wherein $R^2$ is independently substituted with 0-5 R';

m and n are independently integers selected from 0-4;

p is an integer selected from 2-4;

each occurrence of the bond "$\overline{---}$" is either a single bond or a double bond;

each occurrence of $R^1$, $R^2$, $R^4$, and $R^5$ are each independently selected from:

halogen, —R, —OR, —$NO_2$, —NCS, —CN, —$CF_3$, —$OCF_3$, —$SiR_3$, —$N(R)_2$, —SR, —SOR, —$SO_2R$, —$SO_2N(R)_2$, —$SO_3R$, —$(CR_2)_{1-3}R$, —$(CR_2)_{1-3}$—OR, —$(CR_2)_{1-3}$—$O(CR_2)_{1-3}$—R, —$(CR_2)_{0-3}$—C(O)NR$(CR_2)_{0-3}$R, —$(CR_2)_{0-3}$—C(O)NR$(CR_2)_{0-3}$OR, —C(O)R, —C(O)C(O)R, —C(O)$CH_2$C(O)R, —C(S)R, —C(S)OR, —C(O)OR, —C(O)C(O)OR, —C(O)C(O)$N(R)_2$, —OC(O)R, —C(O)$N(R)_2$, —OC(O)$N(R)_2$, —C(S)$N(R)_2$, —$(CR_2)_{0-3}$NHC(O)R, —N(R)N(R)COR, —N(R)N(R)C(O)OR, —N(R)N(R)CON$(R)_2$, —N(R)$SO_2$R, —N(R)$SO_2$N$(R)_2$, —N(R)C(O)OR, —N(R)C(O)R, —N(R)C(S)R, —N(R)C(O)N$(R)_2$, —N(R)C(S)N$(R)_2$, —N(COR)COR, —N(OR)R, —C(=NH)N$(R)_2$, —C(O)N(OR)R, —C(=NOR)R, —OP(O)$(OR)_2$, —P(O)$(R)_2$, —P(O)$(OR)_2$, —P(O)(H)(OR), C≡C—$R^8$, $CH_2CF_3$, and $CHF_3$;

each occurrence of $R^8$ is —H, —(C1-C6) alkyl, —(C3-C6) cycloalkyl, —(C1-C6) alkyl-(C3-C6) cycloalkyl, —(C1-C6) alkyl-(C6-C10) aryl, —(C6-C10) aryl, -5-10 membered heteroaryl, or —(C1-C6) alkyl-5-10 membered heteroaryl;

wherein each $R^8$ excluding —H and —(C1-C6) alkyl is independently substituted by 0-5 of -halogen, —(C1-C6) alkyl, —$CF_3$, —$OCF_3$, or O—(C1-C6) alkyl;

$R^3$ is absent or is selected from:

halogen, —R, —OR, —$NO_2$, —NCS, —CN, —$CF_3$, —$OCF_3$, —$SiR_3$, —$N(R)_2$, —SR, —SOR, —$SO_2R$, —$SO_2N(R)_2$, —$SO_3R$, —$(CR_2)_{1-3}R$, —$(CR_2)_{1-3}$—OR, —$(CR_2)_{0-3}$—C(O)NR$(CR_2)_{0-3}$R, —$(CR_2)_{0-3}$—C(O)NR$(CR_2)_{0-3}$OR, —C(O)R, —C(O)C(O)R, —C(O)$CH_2$C(O)R, —C(S)R, —C(S)OR, —C(O)OR, —C(O)C(O)OR, —C(O)C(O)$N(R)_2$, —OC(O)R, —C(O)$N(R)_2$, —OC(O)$N(R)_2$, —C(S)$N(R)_2$, —$(CR_2)_{0-3}$NHC(O)R, —N(R)N(R)COR, —N(R)N(R)C(O)OR, —N(R)N(R)CON$(R)_2$, —N(R)$SO_2$R, —N(R)$SO_2$N$(R)_2$, —N(R)C(O)OR, —N(R)C(O)R, —N(R)C(S)R, —N(R)C(O)N$(R)_2$, —N(R)C(S)N$(R)_2$, —N(COR)COR, —N(OR)R, —C(=NH)N$(R)_2$, —C(O)N(OR)R, —C(=NOR)R, —OP(O)$(OR)_2$, —P(O)$(R)_2$, —P(O)$(OR)_2$, —P(O)(H)(OR), C≡C—$R^9$, COOMe, COOEt, —(C1-C6)alkyl-C≡C—$R^{10}$, $CH_2$—$OR^{10}$, and $CH_2$—O—$CH_2$—$R^{10}$;

wherein each of $R^9$ is selected from —H, —(C1-C6) alkyl, —(C6-C10) aryl, -5-10 membered heteroaryl, —(C1-C6) alkyl-(C6-C10) aryl, —(C1-C6) alkyl-5-10 membered heteroaryl, —(C3-C6) cycloalkyl, —(C1-C6) alkyl-(C3-C6) cycloalkyl, —C(O)—(C6-C10) aryl,

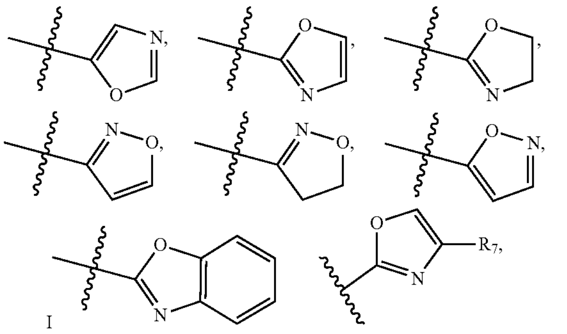

I

-continued

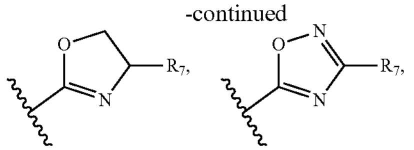

and

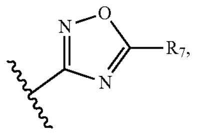

wherein each $R^9$ is independently substituted with 0-5 $R^{11}$;

wherein each occurrence of $R^{11}$ is independently selected from -halogen, —$CF_3$, —$OCF_3$, —OMe, —(C6-C10) aryl, —(C1-C6)alkyl, and -5 to 10 membered heteroaryl, wherein $R^{10}$ is selected from —H, —(C1-C6) alkyl, —(C6-C10) aryl, -5-10 membered heteroaryl, —(C3-C6) cycloalkyl, —$CH_2$—(C3-C6) cycloalkyl, —$CH_2$—(C6-C10) aryl, and —$CH_2$-5-10-membered heteroaryl, wherein each $R^{10}$ is independently substituted with 0-5 R';

wherein $R_7$ is selected from —(C1-C6)alkyl, —(C3-C6)cycloalkyl, -5 to 10 membered heteroaryl, —(C6-C10) aryl, —(C6-C10)aryl-(C1-C6)alkyl, and -5 to 10 membered heteroaryl-(C1-C6)alkyl, and -5-10 membered heteroaryl, wherein each $R_7$ is independently substituted with 0-5 R';

each $R^6$ is independently —H or —(C1-C6)alkyl;

each $R^7$ is independently —H or —(C1-C6)alkyl;

each $R^8$ is independently —(C1-C6)alkyl, —(C3-C10)-cycloalkyl, (C6-C10)-aryl, or 5- to 10-membered heteroaryl, wherein each occurrence of $R^8$ is independently substituted with 0-5 R';

each $R^{10}$ is independently —(C3-C10)-cycloalkyl, 3- to 10-membered heterocyclyl-, (C6-C10)-aryl, or 5- to 10-membered heteroaryl, wherein each occurrence of $R^{10}$ is independently substituted with 0-5 R';

each R is independently selected from:

H—,
(C1-C12)-aliphatic-,
(C3-C10)-cycloalkyl-,
(C3-C10)-cycloalkenyl-,
[(C3-C10)-cycloalkyl]-(C1-C12)-aliphatic-,
[(C3-C10)-cycloalkenyl]-(C1-C12)-aliphatic-,
[(C3-C10)-cycloalkyl]-O—(C1-C12)-aliphatic-,
[(C3-C10)-cycloalkenyl]-O—(C1-C12)-aliphatic-,
(C6-C10)-aryl-,
(C6-C10)-aryl-(C1-C12)aliphatic-,
(C6-C10)-aryl-O—(C1-C12)aliphatic-,
(C6-C10)-aryl-N(R")—(C1-C12)aliphatic-,
3- to 10-membered heterocyclyl-,
(3- to 10-membered heterocyclyl)-(C1-C12)aliphatic-,
(3- to 10-membered heterocyclyl)-O—(C1-C12)aliphatic-,
(3- to 10-membered heterocyclyl)-N(R")—(C1-C12) aliphatic-,
5- to 10-membered heteroaryl-,
(5- to 10-membered heteroaryl)-(C1-C12)-aliphatic-,
(5- to 10-membered heteroaryl)-O—(C1-C12)-aliphatic-; and
(5- to 10-membered heteroaryl)-N(R")—(C1-C12)-aliphatic-;

wherein said heterocyclyl has 1-4 heteroatoms independently selected from N, NH, O, S, SO, and $SO_2$, and said heteroaryl has 1-4 heteroatoms independently selected from N, NH, O, and S;

wherein each occurrence of R is independently substituted with 0-5 R';

or when two R groups bound to the same atom, the two R groups may be taken together with the atom to which they are bound to form a 3- to 10-membered aromatic or non-aromatic ring having 0-4 heteroatoms independently selected from N, NH, O, S, SO, and $SO_2$, wherein said ring is optionally substituted with 0-5 R', and wherein said ring is optionally fused to a (C6-C10) aryl, 5- to 10-membered heteroaryl, (C3-C10)cycloalkyl, or a 3- to 10-membered heterocyclyl;

wherein each occurrence of R' is independently selected from halogen, —R", —OR", oxo, —$CH_2$OR", —$CH_2$NR"$_2$, —C(O)N(R")$_2$, —C(O)OR", —$NO_2$, —NCS, —CN, —$CF_3$, —$OCF_3$ and —N(R")$_2$;

wherein each occurrence of R" is independently selected from H, —(C1-C6)-alkyl, —(C1-C6)-aliphatic, (C3-C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, and (C6-C10)-aryl-O—(C1-C6)-alkyl-, wherein each occurrence of R" is independently substituted with 0-3 substituents selected from: halogen, —R°, —OR°, oxo, —$CH_2$OR°, —$CH_2$N(R°)$_2$, —C(O)N(R°)$_2$, —C(O)OR°, —$NO_2$, —NCS, —CN, —$CF_3$, —$OCF_3$ and —N(R°)$_2$, wherein each occurrence of R° is independently selected from: —(C1-C6)-aliphatic, (C3-C6)-cycloalkyl, 3- to 6-membered heterocyclyl, 5- to 10-membered heteroaryl-, and (C6-C10)-aryl-.

In another aspect, the present invention provides a compound of formula VI:

VI

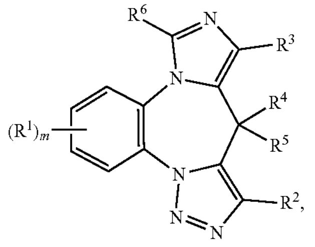

or a pharmaceutically acceptable salt, hydrate, solvate, polymorph, isomer, or combination thereof, wherein:

m is 0-3;

each $R^1$ is independently selected from: -halogen, —OMe, —C≡C—$R^8$, —CN, —$CHF_2$, —$CH_2CF_3$, —$CF_3$, —$OCF_3$, —(C1-C6) alkyl, —(C6-C10) aryl, —(C1-C6) alkyl-(C6-C10) aryl, -5-10 membered heteroaryl, —(C1-C6) alkyl-5-10 membered heteroaryl, and —(C3-C6) cycloalkyl;

wherein $R^8$ is —H, —(C1-C6) alkyl, —(C3-C6) cycloalkyl, —(C1-C6) alkyl-(C3-C6) cycloalkyl, —(C1-C6) alkyl-(C6-C10) aryl, —(C6-C10) aryl, -5-10 membered heteroaryl, or —(C1-C6) alkyl-5-10 membered heteroaryl;

wherein each $R^8$ excluding —H and —(C1-C6) alkyl is independently substituted by 0-5 of -halogen, —(C1-C6) alkyl, —$CF_3$, —$OCF_3$, or O—(C1-C6) alkyl;

$R^2$ is -halogen, —$(CR_2)_{1-3}$—OR, —$(CR_2)_{1-3}$—O$(CR_2)_{1-3}$—R, —H, —(C1-C6) alkyl, —(C6-C10) aryl, (C6-C10) aryl-(C1-C6) alkyl-, -5-10 membered heteroaryl, 5-10 membered heteroaryl-(C1-C6) alkyl-, or —$OR^9$;

wherein each occurrence of R is independently selected from —H, —(C1-C6) alkyl, (C6—C10) aryl-, -5- to 10-membered heteroaryl, (C6-C10)-aryl-(C1-C12) aliphatic-, 5-10 membered heteroaryl-(C6-C10) alkyl-, or —(C3-C6) cycloalkyl;

wherein each R excluding —H and —(C1-C6) alkyl is independently substituted by 0-5 of -halogen, —(C1-C6) alkyl, —$CF_3$, —$OCF_3$, or —O—(C1-C6) alkyl, wherein $R^9$ is selected from —H, —(C1-C6) alkyl, —(C6-C10) aryl, -5-10 membered heteroaryl, —(C1-C6) alkyl-(C6-C10) aryl, —(C1-C6) alkyl-5-10 membered heteroaryl, —(C3-C6) cycloalkyl, and —(C1-C6) alkyl-(C3-C6) cycloalkyl;

wherein each $R^9$ is independently substituted with 0-5 $R^{11}$;

wherein each occurrence of $R^{11}$ is independently selected from -halogen, —$CF_3$, —$OCF_3$, —OMe, —(C6-C10) aryl, —(C1-C6)alkyl, and -5 to 10 membered heteroaryl, $R^3$ is selected from: -halogen, —CN, —C≡C$R^9$, COOMe, —COOEt, —(C1-C6) alkyl-C≡C—$R^{10}$, —$CH_2$—O—$R^{10}$, —$CH_2$O—$CH_2$—$R^{10}$

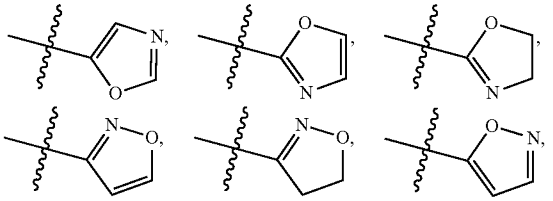

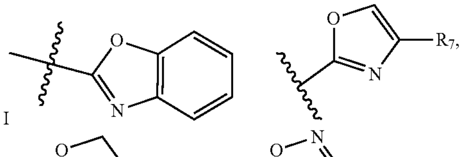

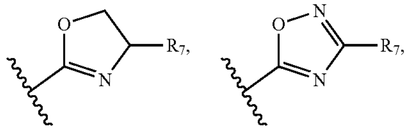

and

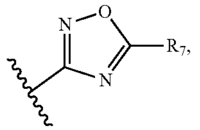

wherein $R^9$ is selected from —H, —(C1-C6) alkyl, —(C6-C10) aryl, -5-10 membered heteroaryl, —(C1-C6) alkyl-(C6-C10) aryl, —(C1-C6) alkyl-5-10 membered heteroaryl, —(C3-C6) cycloalkyl, —(C1-C6) alkyl-(C3-C6) cycloalkyl, and —C(O)—(C6-C10) aryl;

wherein each $R^9$ is independently substituted with 0-5 $R^{11}$;

wherein each occurrence of $R^{11}$ is independently selected from -halogen, —$CF_3$, —$OCF_3$, —OMe, —(C6-C10) aryl, —(C1-C6)alkyl, and -5 to 10 membered heteroaryl, wherein $R^{10}$ is selected from —H, —(C1-C6) alkyl, —(C6-C10) aryl, -5-0 membered heteroaryl, —(C3-

C6) cycloalkyl, —$CH_2$—(C3-C6) cycloalkyl, —$CH_2$—(C6-C10) aryl, and —$CH_2$-5-10-membered heteroaryl, wherein each $R^{10}$ is independently substituted with 0-5 R';

wherein $R_7$ is selected from —(C1-C6)alkyl, —(C3-C6) cycloalkyl, -5 to 10 membered heteroaryl, —(C6-C10) aryl, —(C6-C10)aryl-(C1-C6)alkyl, and -5 to 10 membered heteroaryl-(C1-C6)alkyl, and -5-10 membered heteroaryl; wherein each $R_7$ is independently substituted with 0-5 R';

wherein $R^3$ is substituted with 0-5 R';

each occurrence of $R^4$ and $R^5$ is independently —H, —(C1-C6)alkyl, or —(C1-C6) alkyl-(C6-C10) aryl; the (C6-C10) aryl being independently substituted with 0-5 -halogen;

each $R^6$ is independently —H or —(C1-C6)alkyl;

wherein each occurrence of R' is independently selected from halogen, —R", —OR", oxo, —$CH_2$OR", —$CH_2NR"_2$, —C(O)N(R")$_2$, —C(O)OR", —$NO_2$, —NCS, —CN, —$CF_3$, —$OCF_3$ and —N(R")$_2$;

wherein each occurrence of R" is independently selected from H, —(C1-C6)-alkyl, —(C1-C6)-aliphatic, (C3-C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, or (C6-C10)-aryl-O—(C1-C6)-alkyl-, wherein each occurrence of R" is independently substituted with 0-5 substituents selected from: halogen, —R°, —OR°, oxo, —$CH_2$OR°, —$CH_2$N(R°)$_2$, —C(O)N(R°)$_2$, —C(O)OR°, —$NO_2$, —NCS, —CN, —$CF_3$, —$OCF_3$ and —N(R°)$_2$, wherein each occurrence of R° is independently selected from: —(C1-C6)-aliphatic, (C3-C6)-cycloalkyl, 3- to 6-membered heterocyclyl, 5- to 10-membered heteroaryl-, and (C6-C10)-aryl.

In another aspect, the present invention provides a compound of formula VII:

VII

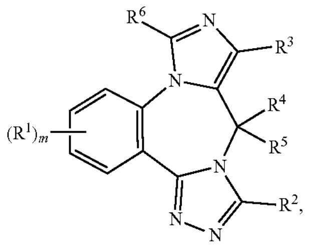

or a pharmaceutically acceptable salt, hydrate, solvate, polymorph, isomer, or combination thereof, wherein:

m is 0-3;

each $R^1$ is independently selected from: -halogen, —OMe, —C≡C—$R^9$, —CN, —$CHF_2$, —$CH_2CF_3$, —$CF_3$, —$OCF_3$, —(C1-C6) alkyl, —(C6-C10) aryl, —(C1-C6) alkyl-(C6-C10) aryl, -5-10 membered heteroaryl, —(C1-C6) alkyl-5-10 membered heteroaryl, and —(C3-C6) cycloalkyl;

wherein $R^9$ is —H, —(C1-C6) alkyl, —(C3-C6) cycloalkyl, —(C1-C6) alkyl-(C3-C6) cycloalkyl, —(C1-C6) alkyl-(C6-C10) aryl, —(C6-C10) aryl, -5-10 membered heteroaryl, or —(C1-C6) alkyl-5-10 membered heteroaryl;

wherein each $R^9$ excluding —H and —(C1-C6) alkyl is independently substituted by 0-5 of -halogen, —(C1-C6) alkyl, —$CF_3$, —$OCF_3$, or O—(C1-C6) alkyl;

$R^2$ is —$(CH_2)_n OR^8$, or —$(CH_2)_n O(CH_2)_n R^8$, wherein each occurrence of $R^8$ is independently —H, —(C1-C6)alkyl, —(C6-C10)-aryl, 5- to 10-membered heteroaryl-, 5-10 membered heteroaryl-(C1-C6) alkyl-, —(C3-C6)cycloalkyl, —(C1-C6) alkyl-(C6-C10) aryl, or —(C1-C6) alkyl-(C3-C6) cycloalkyl;

wherein each $R^8$ excluding —H and —(C1-C6) alkyl is independently substituted by 0-5 of -halogen, —(C1-C6) alkyl, —$CF_3$, —$OCF_3$, or —O—(C1-C6) alkyl;

wherein n is an integer from 0-4;

wherein $R^2$ is independently substituted with 0-5 R';

$R^3$ is selected from: -halogen, —CN, —C≡C$R^9$, COOMe, —COOEt, —(C1-C6)alkyl-C≡C—$R^{10}$, —$CH_2$—O—$R^{10}$, —$CH_2$—O—$CH_2$—$R^{10}$

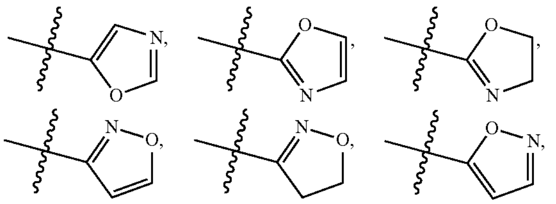

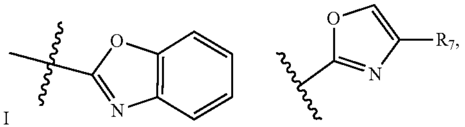

I

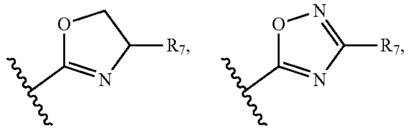

and

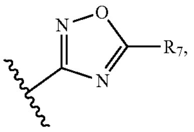

wherein $R^9$ is selected from —H, —(C1-C6) alkyl, —(C6-C10) aryl, -5-10 membered heteroaryl, —(C1-C6) alkyl-(C6-C10) aryl, —(C1-C6) alkyl-5-10 membered heteroaryl, —(C3-C6) cycloalkyl, —(C1-C6) alkyl-(C3-C6) cycloalkyl, and —C(O)—(C6-C10) aryl;

wherein each $R^9$ is independently substituted with 0-5 $R^{11}$;

wherein $R^{10}$ is selected from —H, —(C1-C6) alkyl, —(C6-C10) aryl, -5-10 membered heteroaryl, —(C3-C6) cycloalkyl, —$CH_2$—(C3-C6) cycloalkyl, —$CH_2$—(C6-C10) aryl, and —$CH_2$-5-10-membered heteroaryl, wherein each $R^{10}$ is independently substituted with 0-5 R';

wherein each occurrence of $R^{11}$ is independently selected from -halogen, —$CF_3$, —$OCF_3$, —OMe, —(C6-C10) aryl, —(C1-C6)alkyl, and -5 to 10 membered heteroaryl, wherein $R_7$ is selected from —(C1-C6)alkyl, —(C3-C6) cycloalkyl, -5 to 10 membered heteroaryl, —(C6-C10) aryl, —(C6-C10)aryl-(C1-C6)alkyl, and -5 to 10 membered heteroaryl-(C1-C6)alkyl, and -5-10 membered heteroaryl;

wherein each $R_7$ is independently substituted with 0-5 R';

wherein $R^3$ is substituted with 0-5 R';

each occurrence of $R^4$ and $R^5$ is independently —H or —(C1-C6)alkyl;

each $R^6$ is independently —H or —(C1-C6)alkyl;

wherein each occurrence of R' is independently selected from halogen, —R", —OR", oxo, —$CH_2$OR", —$CH_2NR"_2$, —C(O)N(R")$_2$, —C(O)OR", —$NO_2$, —NCS, —CN, —$CF_3$, —$OCF_3$ and —N(R")$_2$, —OMe;

wherein each occurrence of R" is independently selected from H, —(C1-C6)-alkyl, —(C1-C6)-aliphatic, (C3-C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, and (C6-C10)-aryl-O—(C1-C6)-alkyl-, wherein each occurrence of R" is independently substituted with 0-5 $R^{t}$ independently selected from: halogen, —R°, —OR°, oxo, —$CH_2$OR°, —$CH_2$N(R°)$_2$, —C(O)N(R°)$_2$, —C(O)OR°, —$NO_2$, —NCS, —CN, —$CF_3$, —$OCF_3$ and —N(R°)$_2$, wherein each occurrence of R° is independently selected from:

—(C1-C6)-aliphatic, (C3-C6)-cycloalkyl, 3- to 6-membered heterocyclyl, 5- to 10-membered heteroaryl-, and (C6-C10)-aryl-.

In another aspect, the present invention provides a compound of formula VIII:

VIII

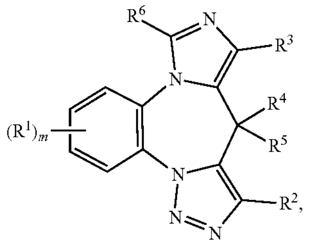

or a pharmaceutically acceptable salt, hydrate, solvate, polymorph, isomer, or combination thereof, wherein:

m is 0-3;

each $R^1$ is independently selected from: -halogen, —OMe, —C≡C—$R^8$, —$CHF_2$, —$CF_3$, —$OCF_3$, wherein $R^8$ is —H, —(C1-C6) alkyl, —(C3-C6) cycloalkyl, —(C1-C6) alkyl-(C3-C6) cycloalkyl, —(C1-C6) alkyl-(C6-C10) aryl, —(C6-C10) aryl, -5-10 membered heteroaryl, or —(C1-C6) alkyl-5-10 membered heteroaryl;

wherein each $R^8$ excluding —H and —(C1-C6) alkyl is independently substituted by 0-5 of -halogen, —(C1-C6) alkyl, —$CF_3$, —$OCF_3$, or O—(C1-C6) alkyl;

$R^2$ is —H, —$CH_2$—OR, $CH_3$, $CH_2$-phenyl;

wherein each occurrence of R is independently selected from —(C1-C6) alkyl, (C6-C10) aryl-, -5- to 10-membered heteroaryl, (C6-C10)-aryl-(C1-C12) aliphatic-, 5-10 membered heteroaryl-(C6-C10) alkyl-, or —(C3-C6) cycloalkyl;

wherein each R excluding —H and —(C1-C6) alkyl is independently substituted by 0-5 of -halogen, —(C1-C6) alkyl, —$CF_3$, —$OCF_3$, or —O—(C1-C6) alkyl, wherein each occurrence of $R^{11}$ is independently selected from -halogen, —$CF_3$, —$OCF_3$, —OMe, —(C6-C10) aryl, —(C1-C6)alkyl, and -5 to 10 membered heteroaryl, $R^3$ is selected from: —C≡C$R^9$, —(C1-C6) alkyl-C≡C—$R^{10}$, —$CH_2$—O—$R^{10}$,

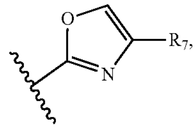

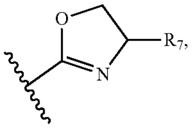

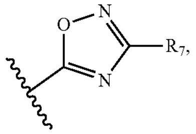

and

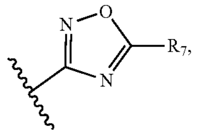

wherein R is selected from —H, —(C1-C6) alkyl, —(C6-C10) aryl, -5-10 membered heteroaryl, —(C1-C6) alkyl-(C6-C10) aryl, —(C1-C6) alkyl-5-10 membered heteroaryl, —(C3-C6) cycloalkyl, —(C1-C6) alkyl-(C3-C6) cycloalkyl, and —C(O)—(C6-C10) aryl;

wherein each $R^9$ is independently substituted with 0-5 $R^{11}$;

wherein each occurrence of $R^{11}$ is independently selected from -halogen, —$CF_3$, —$OCF_3$, —OMe, —(C6-C10) aryl, —(C1-C6)alkyl, and -5 to 10 membered heteroaryl, wherein $R^{10}$ is selected from —H, —(C1-C6) alkyl, —(C6-C10) aryl, -5-10 membered heteroaryl, —(C3-C6) cycloalkyl, —$CH_2$—(C3-C6) cycloalkyl, —$CH_2$—(C6-C10) aryl, and —$CH_2$-5-10-membered heteroaryl, wherein each $R^{10}$ is independently substituted with 0-5 R';

wherein $R_7$ is selected from —(C1-C6)alkyl, —(C3-C6) cycloalkyl, -5 to 10 membered heteroaryl, —(C6-C10) aryl, —(C6-C10)aryl-(C1-C6)alkyl, and -5 to 10 membered heteroaryl-(C1-C6)alkyl, and -5-10 membered heteroaryl; wherein each $R_7$ is independently substituted with 0-5 R';

each occurrence of $R^4$ and $R^5$ is independently —H, —(C1-C6)alkyl, or —(C1-C6) alkyl-(C6-C10) aryl; the (C6-C10) aryl being independently substituted with 0-5 -halogen;

each $R^6$ is independently —H or —(C1-C6)alkyl.

In another aspect, the present invention provides a compound of formula IX:

IX

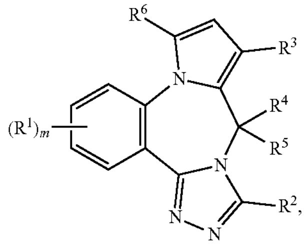

or a pharmaceutically acceptable salt, hydrate, solvate, polymorph, isomer, or combination thereof, wherein:

each $R^1$ is independently selected from: —Cl, —OMe, —C≡C—$R^9$, —$CHF_2$, —$CF_3$, and —$OCF_3$;

wherein $R^9$ is —H, —(C1-C6) alkyl, —(C3-C6) cycloalkyl, —(C1-C6) alkyl-(C3-C6) cycloalkyl, —(C1-C6) alkyl-(C6-C10) aryl, —(C6-C10) aryl, -5-10 membered heteroaryl, or —(C1-C6) alkyl-5-10 membered heteroaryl;

wherein each $R^9$ excluding —H and —(C1-C6) alkyl is independently substituted by 0-5 of -halogen, —(C1-C6) alkyl, —$CF_3$, —$OCF_3$, or O—(C1-C6) alkyl;

$R^2$ is —H, $CH_2OR^8$, $CH_3$, $CH_2$-phenyl, wherein each occurrence of $R^8$ is independently —H, —(C1-C6) alkyl, —(C6-C10)-aryl, 5- to 10-membered heteroaryl-, 5-10 membered heteroaryl-(C1-C6) alkyl-, —(C3-C6)cycloalkyl, —(C1-C6) alkyl-(C6-C10) aryl, or (C1-C6) alkyl-(C3-C6) cycloalkyl;

wherein each $R^8$ excluding —H and —(C1-C6) alkyl is independently substituted by 0-5 of -halogen, —(C1-C6) alkyl, —$CF_3$, —$OCF_3$, or —O—(C1-C6) alkyl;

$R^3$ is selected from: —C≡$CR^9$, —(C1-C6)alkyl-C≡C—$R^{10}$,

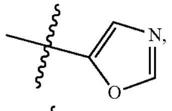
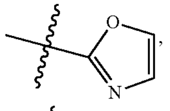
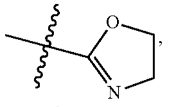
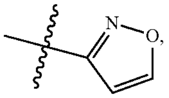
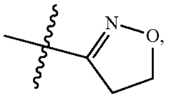
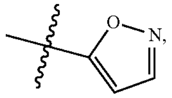
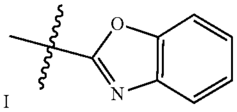
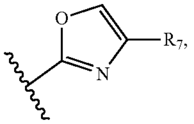

I

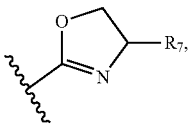
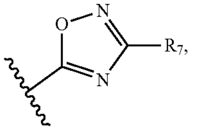
and

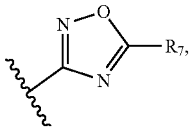

wherein $R^9$ is selected from —H, —(C1-C6) alkyl, —(C6-C10) aryl, -5-10 membered heteroaryl, —(C1-C6) alkyl-(C6-C10) aryl, —(C1-C6) alkyl-5-10 membered heteroaryl, —(C3-C6) cycloalkyl, —(C1-C6) alkyl-(C3-C6) cycloalkyl, and —C(O)—(C6-C10) aryl;

wherein each $R^9$ is independently substituted with 0-5 $R^{11}$;

wherein $R^{10}$ is selected from —H, —(C1-C6) alkyl, —(C6-C10) aryl, -5-10 membered heteroaryl, —(C3-C6) cycloalkyl, —$CH_2$—(C3-C6) cycloalkyl, —$CH_2$—(C6-C10) aryl, and —$CH_2$-5-10-membered heteroaryl, wherein each $R^{10}$ is independently substituted with 0-5 R';

wherein each occurrence of $R^{11}$ is independently selected from -halogen, —$CF_3$, —$OCF_3$, —OMe, —(C6-C10) aryl, —(C1-C6)alkyl, and -5 to 10 membered heteroaryl, wherein $R_7$ is selected from —(C1-C6)alkyl, —(C3-C6) cycloalkyl, -5 to 10 membered heteroaryl, —(C6-C10) aryl, —(C6-C10)aryl-(C1-C6)alkyl, and -5 to 10 membered heteroaryl-(C1-C6)alkyl, and -5-10 membered heteroaryl;

wherein each $R_7$ is independently substituted with 0-5 R';

wherein $R^3$ is substituted with 0-5 R';

each occurrence of $R^4$ and $R^5$ is independently —H or —(C1-C6)alkyl;

each $R^6$ is independently —H or —(C1-C6)alkyl.

The present invention also provides pharmaceutical compositions that comprise a compound of formulae I, II, III, IV, V, VI, VII, VIII or IX or a pharmaceutically acceptable salt, hydrate, solvate, polymorph, isomer, or combination thereof.

In some embodiments, compounds of formula I are $GABA_A$ α5 receptor positive allosteric modulators. In some embodiments, compounds of formula II are $GABA_A$ α5 receptor positive allosteric modulators. In some embodiments, compounds of formula III are $GABA_A$ α5 receptor positive allosteric modulators. In some embodiments, compounds of formula IV are $GABA_A$ α5 receptor positive allosteric modulators. In some embodiments, compounds of formula V are $GABA_A$ α5 receptor positive allosteric modulators. In some embodiments, compounds of formula VI are $GABA_A$ α5 receptor positive allosteric modulators. Compounds of formula I, II, III, IV, V, VI, VII, VIII, or IX can be used to treat the conditions described herein, such as through activity as $GABA_A$ α5 receptor positive allosteric modulators.

In another aspect of the invention, there is provided a method for treating cognitive impairment associated with a CNS disorder in a subject in need of treatment or at risk of said cognitive impairment, the method comprising the step of administering to said subject a therapeutically effective amount of a compound of the invention or a pharmaceutically acceptable salt, hydrate, solvate, polymorph, isomer, or combination thereof. In some embodiments, the CNS disorder with cognitive impairment includes, without limitation, age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction. In another aspect of the invention, there is provided a method of preserving or improving cognitive function in a subject in need thereof, the method comprising the step of administering to said subject a therapeutically effective amount of a compound of the invention or a pharmaceutically acceptable salt, hydrate, solvate, polymorph, isomer, or combination thereof. In certain embodiments of the invention, a compound of the invention or a pharmaceutically acceptable salt, hydrate, solvate, polymorph, isomer, or combination thereof is administered every 12 or 24 hours.

In another aspect of the invention, there is provided a method for treating brain cancers (including brain tumors, e.g., medulloblastomas), the method comprising the step of administering to said subject a therapeutically effective amount of a compound of the invention or a pharmaceutically acceptable salt, hydrate, solvate, polymorph, isomer, or combination thereof. In another aspect of the invention, there is provided a method of preserving or improving cognitive function in a subject suffering from brain cancers (including brain tumors, e.g., medulloblastomas), the method comprising the step of administering to said subject a therapeutically effective amount of a compound of the invention or a pharmaceutically acceptable salt, hydrate, solvate, polymorph, isomer, or combination thereof. In certain embodiments of the invention, a compound of the invention or a pharmaceutically acceptable salt, hydrate, solvate, polymorph, isomer, or combination thereof is administered every 12 or 24 hours.

In some embodiments, the compounds and compositions of the present invention are for use as a medicament. In some embodiments, the compounds and compositions of the present invention are for use in treating cognitive impairment associated with a CNS disorder in a subject in need of treatment or at risk of said cognitive impairment. In some embodiments, the CNS disorder with cognitive impairment includes, without limitation, age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction. In some embodiments, the compounds and compositions of the present invention are for use as a medicament in treating brain cancers (including brain tumors, e.g., medulloblastomas). In some embodiments, the compounds and compositions of the present invention are for use as a medicament in treating cognitive impairment associated with brain cancers (including brain tumors, e.g., medulloblastomas).

In some embodiments, this application provides the use of a compound or composition described herein in the preparation of a medicament for the treatment of cognitive impairment associated with a CNS disorder in a subject in need of treatment or at risk of said cognitive impairment. In some embodiments, the CNS disorder with cognitive impairment includes, without limitation, age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction. In some embodiments, the compounds and compositions of the present invention are for use in the preparation of a medicament for the treatment of brain cancers (including brain tumors, e.g., medulloblastomas). In some embodiments, the compounds and compositions of the present invention are for use in the preparation of a medicament for the treatment of cognitive impairment associated with brain cancers (including brain tumors, e.g., medulloblastomas).

DETAILED DESCRIPTION OF THE FIGURES

FIG. 1 is a graph depicting the effects of administering methyl 3,5-diphenylpyridazine-4-carboxylate on the spatial memory retention of ten aged-impaired (AI) rats in an eight-arm Radial Arm Maze (RAM) test. The black bars refer to rats treated with vehicle alone; open bars refer to rats treated with methyl 3,5-diphenylpyridazine-4-carboxylate at different doses; hatched bar refers to rats treated with the combination of TB21007 and methyl 3,5-diphenylpyridazine-4-carboxylate.

Figure 2:
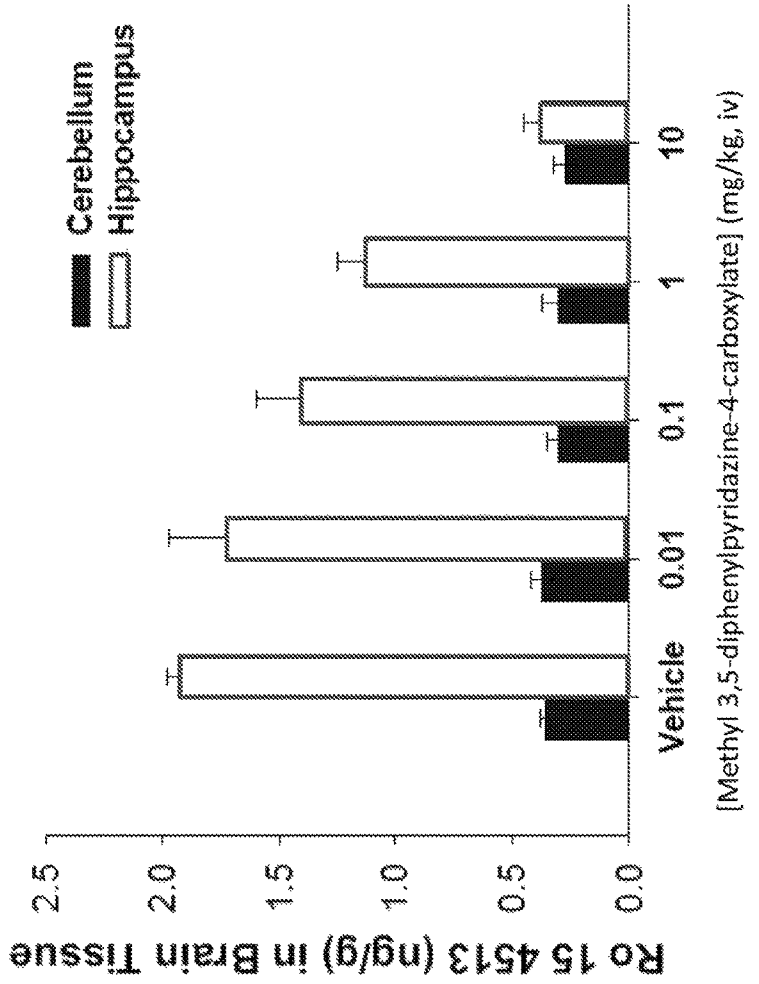

FIG. 2 is a graph showing the effect of methyl 3,5-diphenylpyridazine-4-carboxylate (administered intravenously) on the binding of Ro154513 in the hippocampus and cerebellum. Methyl 3,5-diphenylpyridazine-4-carboxylate blocked the binding of Ro154513 in the hippocampus but did not affect binding of Ro15413 in the cerebellum.

Figure 3:
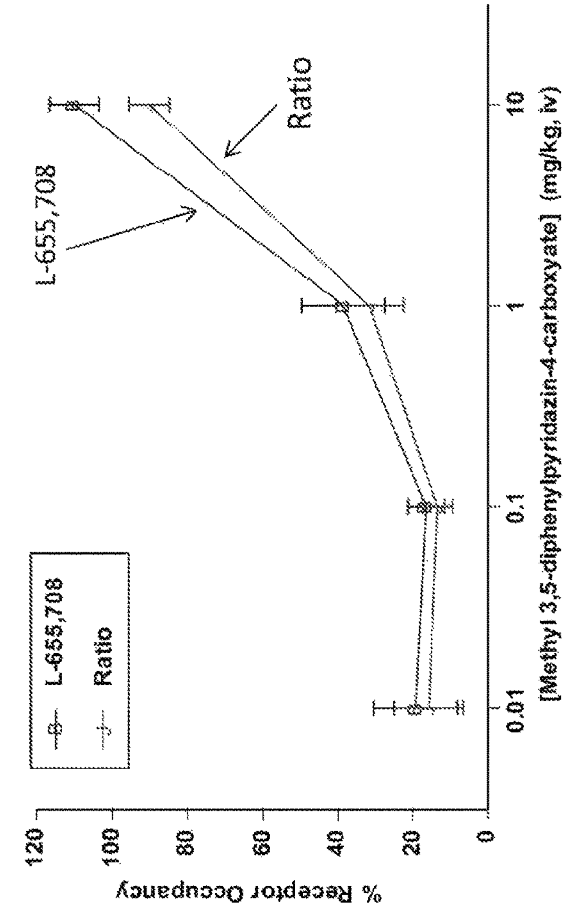

FIG. 3 is a graph showing dose-dependent $GABA_A$ α5 receptor occupancy by methyl 3,5-diphenylpyridazine-4-carboxylate administered intravenously, with receptor occupancy determined either by the ratio between hippocampus (a region of high $GABA_A$ α5 receptor density) exposure of RO 15-4513 and cerebellum (a region with low $GABA_A$α5 receptor density) exposure of RO 15-4513, or by using the $GABA_A$ α5 selective compound L-655,708 (10 mg/kg, i.v.) to define full occupancy.

Figure 4:
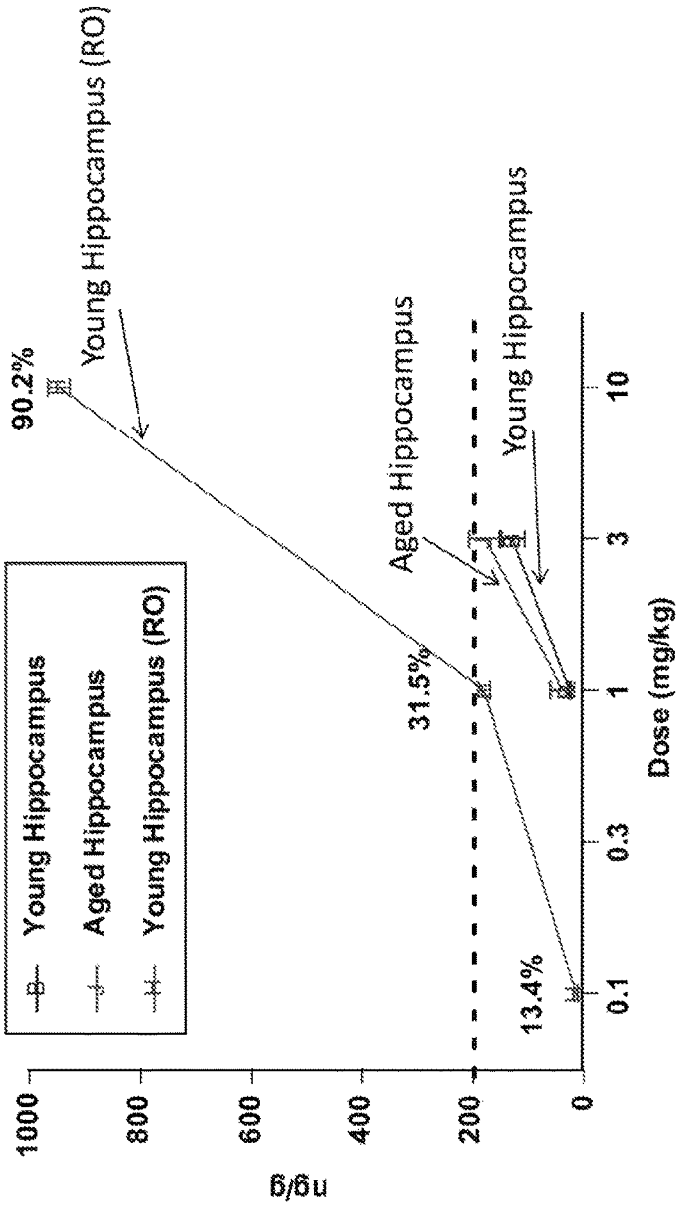

FIG. 4 is a graph showing exposure occupancy relationships for methyl 3,5-diphenylpyridazine-4-carboxylate in hippocampus. Methyl 3,5-diphenylpyridazine-4-carboxylate occupies about 32% of $GABA_A$ α5 receptors at exposures which are behaviorally active in aged-impaired rats.

Figure 5:
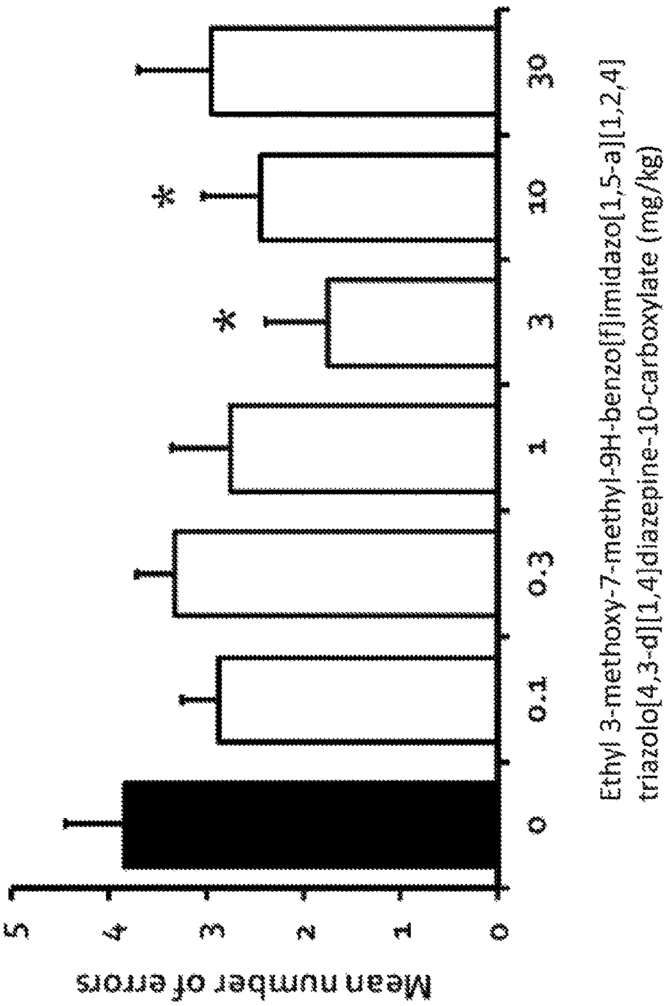

FIG. 5 is a graph depicting the effect of ethyl 3-methoxy-7-methyl-9H-benzo[f]imidazo[1,5-a][1,2,4]triazolo[4,3-d][1,4]diazepine-10-carboxylate on the spatial memory retention of ten aged-impaired (AI) rats in an eight-arm Radial Arm Maze (RAM) test. FIG. 5 shows the effect of ethyl 3-methoxy-7-methyl-9H-benzo[f]imidazo[1,5-a][1,2,4]triazolo[4,3-d][1,4]diazepine-10-carboxylate on the spatial memory retention of ten aged-impaired (AI) rats in the RAM test, where the vehicle control was tested 3 times, and the different doses of ethyl 3-methoxy-7-methyl-9H-benzo[f]imidazo[1,5-a][1,2,4]triazolo[4,3-d][1,4]diazepine-10-carboxylate were tested twice; In FIG. 5, black bars refer to rats treated with vehicle alone and open bars refer to rats treated with ethyl 3-methoxy-7-methyl-9H-benzo[f]imidazo[1,5-a][1,2,4]triazolo[4,3-d][1,4]diazepine-10-carboxylate at different doses.

Figure 6:
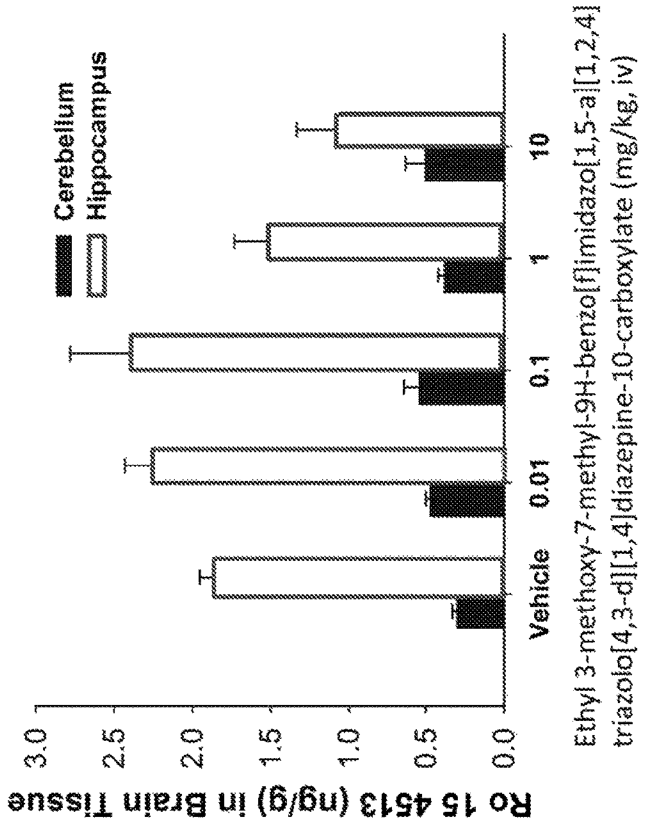

FIG. 6 is a graph showing the effect of ethyl 3-methoxy-7-methyl-9H-benzo[f]imidazo[1,5-a][1,2,4]triazolo[4,3-d][1,4]diazepine-10-carboxylate (administered intravenously) on the binding of Ro154513 in the hippocampus and cerebellum. Ethyl 3-methoxy-7-methyl-9H-benzo[f]imidazo[1,5-a][1,2,4]triazolo[4,3-d][1,4]diazepine-10-carboxylate blocked the binding of Ro154513 in the hippocampus but did not affect binding of Ro15413 in the cerebellum.

Figure 7:
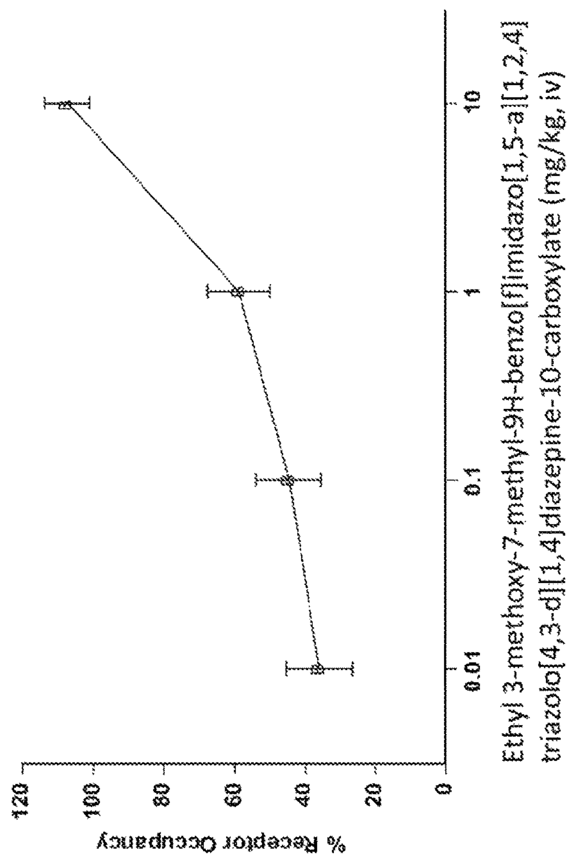

FIG. 7 is a graph showing dose-dependent $GABA_A$ α5 receptor occupancy by ethyl 3-methoxy-7-methyl-9H-benzo[f]imidazo[1,5-a][1,2,4]triazolo[4,3-d][1,4]diazepine-10-carboxylate administered intravenously, as calculated by the ratio between hippocampus (a region of high $GABA_A$α5 receptor density) exposure of RO 15-4513 and cerebellum (a region with low $GABA_A$α5 receptor density) exposure of RO 15-4513 to define full occupancy.

Figure 8A:
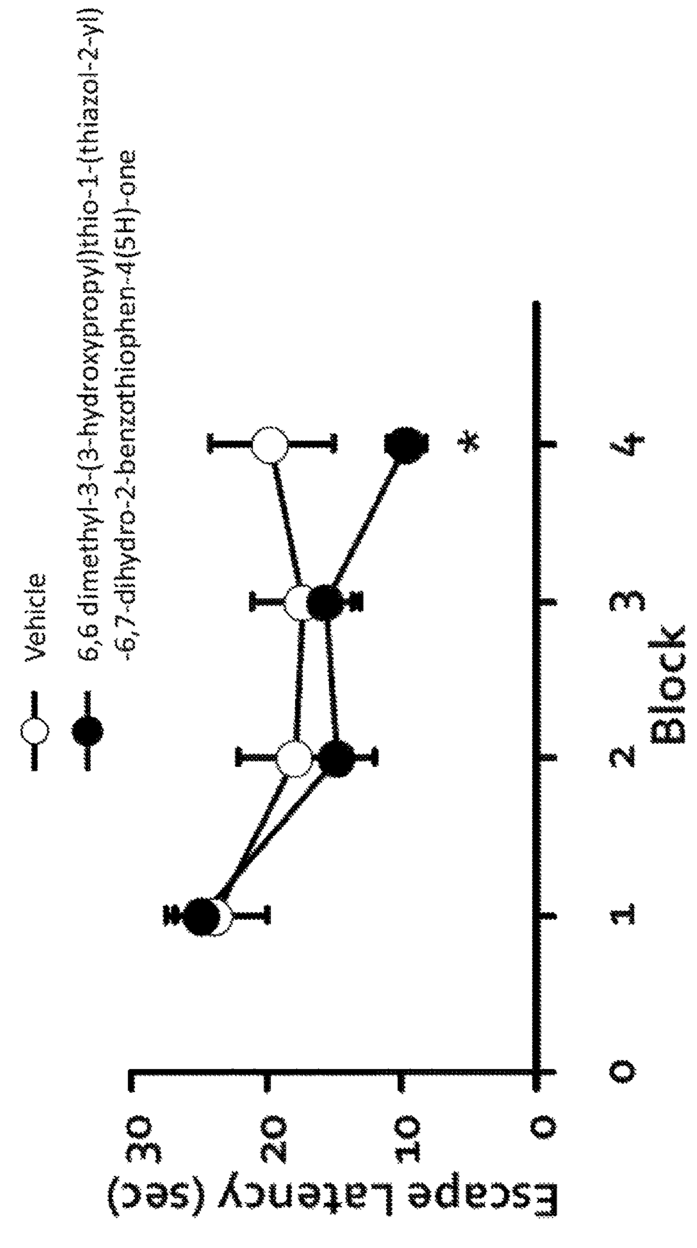
Figure 8B:
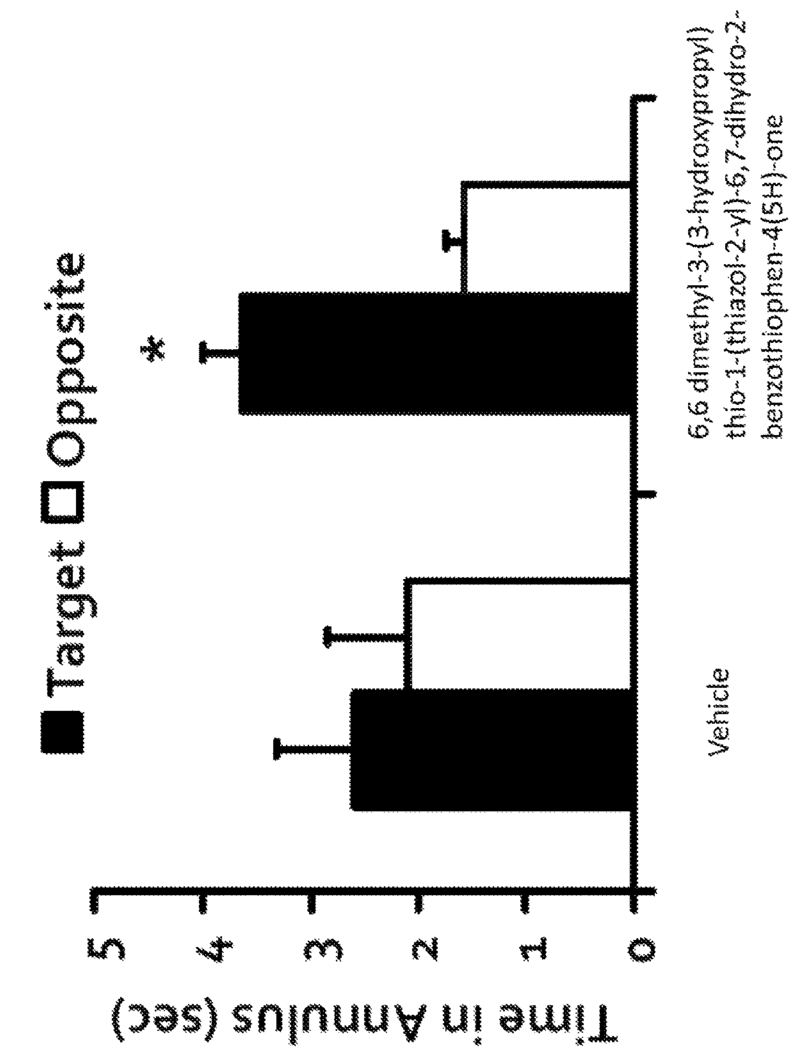
Figure 8C:
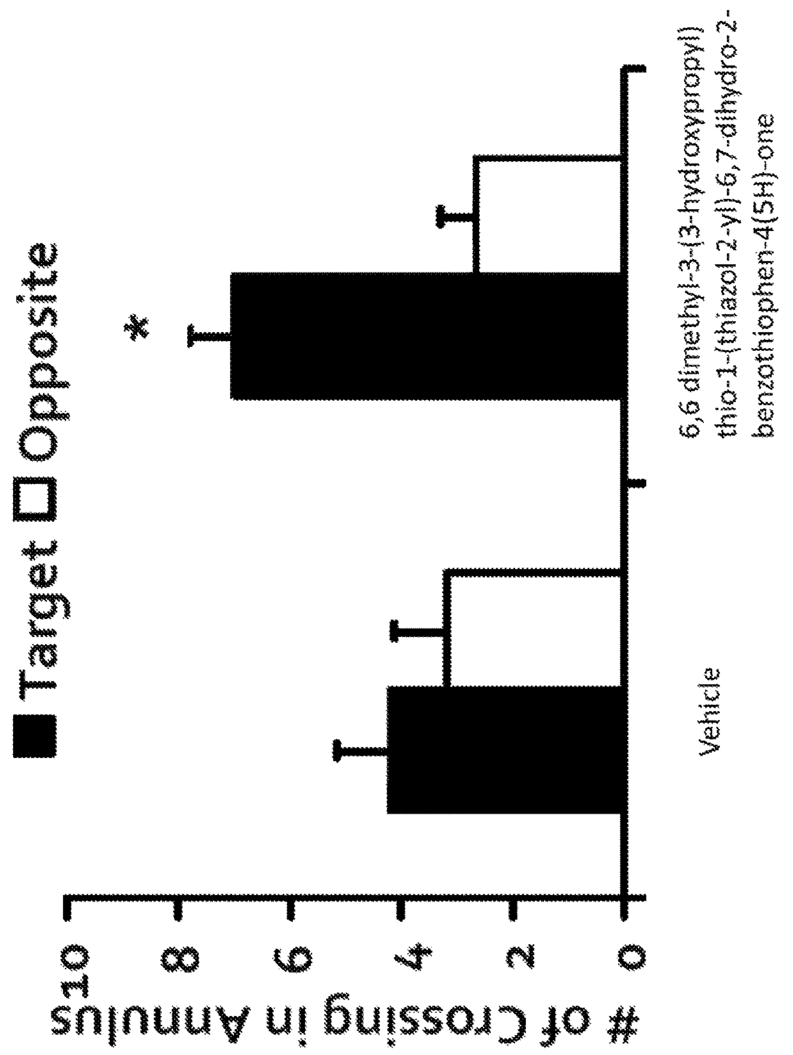

FIG. 8(A)-(C) are graphs showing the effect of 6,6 dimethyl-3-(3-hydroxypropyl)thio-1-(thiazol-2-yl)-6,7-dihydro-2-benzothiophen-4(5H)-one, as compared to vehicle dimethyl sulfoxide (DMSO), in aged-impaired rats using a Morris water maze behavioral task. FIG. 8(A) shows the escape latency (i.e., the average time in seconds rats took to find the hidden platform in the water pool) during training in rats received 6,6 dimethyl-3-(3-hydroxypropyl)thio-1-(thiazol-2-yl)-6,7-dihydro-2-benzothiophen-4(5H)-one and rats received vehicle DMSO; FIG. 8(B) shows the amount of time spent in target annulus and opposite annulus by rats received 6,6 dimethyl-3-(3-hydroxypropyl)thio-1-(thiazol-2-yl)-6,7-dihydro-2-benzothiophen-4(5H)-one and rats received vehicle DMSO; FIG. 8(C) shows number of crossing in target annulus and opposite annulus by rats received 6,6 dimethyl-3-(3-hydroxypropyl)thio-1-(thiazol-2-yl)-6,7-dihydro-2-benzothiophen-4(5H)-one and rats received vehicle DMSO.

DETAILED DESCRIPTION OF THE INVENTION

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present invention are generally performed, unless otherwise indicated, according to conventional methods well known in the art and as described in various general and more specific references that are cited and discussed throughout this specification. See, e.g. "Principles of Neural Science," McGraw-Hill Medical, New York, N.Y. (2000); Motulsky, "Intuitive Biostatistics," Oxford University Press, Inc. (1995); Lodish et al., "Molecular Cell Biology, 4th ed.," W. H. Freeman & Co., New York (2000); Griffiths et al., "Introduction to Genetic Analysis, 7th ed.," W. H. Freeman & Co., N.Y. (1999); and Gilbert et al., "Developmental Biology, 6th ed.," Sinauer Associates, Inc., Sunderland, MA (2000).

Chemistry terms used herein are used according to conventional usage in the art, as exemplified by "The McGraw-Hill Dictionary of Chemical Terms," Parker S., Ed., McGraw-Hill, San Francisco, C.A. (1985).

All of the publications, patents and published patent applications referred to in this application are specifically incorporated by reference herein. In case of conflict, the present specification, including its specific definitions, will control.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to". "Including" and "including but not limited to" are used interchangeably.

The term "agent" is used herein to denote a chemical compound (such as an organic or inorganic compound (including, such as, a compound of the present invention), a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents which are known with respect to structure, and those which are not known with respect to structure. The α5-containing $GABA_A$ receptor agonist activity of such agents may render them suitable as "therapeutic agents" in the methods and compositions of this invention.

A "patient," "subject," or "individual" are used interchangeably and refer to either a human or a non-human animal. These terms include mammals, such as humans, primates, livestock animals (including bovine, porcine, etc.), companion animals (e.g., canine, feline, etc.) and rodents (e.g., mice and rats).

"Cognitive function" or "cognitive status" refers to any higher order intellectual brain process or brain state, respectively, involved in learning and/or memory including, but not limited to, attention, information acquisition, information processing, working memory, short-term memory, long-term memory, anterograde memory, retrograde memory, memory retrieval, discrimination learning, decision-making, inhibitory response control, attentional set-shifting, delayed reinforcement learning, reversal learning, the temporal integration of voluntary behavior, expressing an interest in one's surroundings and self-care, speed of processing, reasoning and problem solving and social cognition.

In humans, cognitive function may be measured, for example and without limitation, by the clinical global impression of change scale (CIBIC-plus scale); the Mini Mental State Exam (MMSE); the Neuropsychiatric Inventory (NPI); the Clinical Dementia Rating Scale (CDR); the Cambridge Neuropsychological Test Automated Battery (CANTAB); the Sandoz Clinical Assessment-Geriatric (SCAG), the Buschke Selective Reminding Test (Buschke and Fuld, 1974); the Verbal Paired Associates subtest; the Logical Memory subtest; the Visual Reproduction subtest of the Wechsler Memory Scale-Revised (WMS-R) (Wechsler, 1997); the Benton Visual Retention Test, or the explicit 3-alternative forced choice task, or MATRICS consensus neuropsychological test battery. See Folstein et al., *J Psychiatric Res* 12: 189-98, (1975); Robbins et al., Dementia 5: 266-81, (1994); Rey, L'examen clinique en psychologie, (1964); kluger et al., *J Geriatr Psychiatry Neurol* 12:168-79, (1999); Marquis et al., 2002 and Masur et al., 1994. Also see Buchanan, R. W., Keefe, R. S. E., Umbricht, D., Green, M. F., Laughren, T., and Marder, S. R. (2011), The FDA-NIMH-MATRICS guidelines for clinical trial design of cognitive-enhancing drugs: what do we know 5 years later? Schizophr. Bull. 37, 1209-1217.

In animal model systems, cognitive function may be measured in various conventional ways known in the art, including using a Morris Water Maze (MWM), Barnes circular maze, elevated radial arm maze, T maze or any other mazes in which the animals use spatial information. Cognitive function can be assessed by reversal learning, extradimensional set shifting, conditional discrimination learning and assessments of reward expectancy. Other tests known in the art may also be used to assess cognitive function, such as novel object recognition and odor recognition tasks.

Cognitive function may also be measured using imaging techniques such as Positron Emission Tomography (PET), functional magnetic resonance imaging (fMRI), Single Photon Emission Computed Tomography (SPECT), or any other imaging technique that allows one to measure brain function. In animals, cognitive function may also be measured with electrophysiological techniques.

"Promoting" cognitive function refers to affecting impaired cognitive function so that it more closely resembles the function of a normal, unimpaired subject. Cognitive function may be promoted to any detectable degree, but in humans preferably is promoted sufficiently to allow an impaired subject to carry out daily activities of normal life at a level of proficiency as close as possible to a normal, unimpaired subject or an age-matched normal, unimpaired subject.

In some cases, "promoting" cognitive function in a subject affected by age-related cognitive refers to affecting impaired cognitive function so that it more closely resembles the function of an aged-matched normal, unimpaired subject, or the function of a young adult subject. Cognitive function of that subject may be promoted to any detectable degree, but in humans preferably is promoted sufficiently to allow an impaired subject to carry out daily activities of normal life at a level of proficiency close as possible to a normal, unimpaired subject or a young adult subject or an age-matched normal unimpaired subject.

"Preserving" cognitive function refers to affecting normal or impaired cognitive function such that it does not decline or does not fall below that observed in the subject upon first presentation or diagnosis, or delays such decline.

"Improving" cognitive function includes promoting cognitive function and/or preserving cognitive function in a subject.

"Cognitive impairment" refers to cognitive function in subjects that is not as robust as that expected in a normal, unimpaired subject. In some cases, cognitive function is reduced by about 5%, about 10%, about 30%, or more, compared to cognitive function expected in a normal, unimpaired subject. In some cases, "cognitive impairment" in subjects affected by aged-related cognitive impairment refers to cognitive function in subjects that is not as robust as that expected in an aged-matched normal, unimpaired subject, or the function of a young adult subject (i.e. subjects with mean scores for a given age in a cognitive test).

"Age-related cognitive impairment" refers to cognitive impairment in aged subjects, wherein their cognitive function is not as robust as that expected in an age-matched normal subject or as that expected in young adult subjects. In some cases, cognitive function is reduced by about 5%, about 10%, about 30%, or more, compared to cognitive function expected in an age-matched normal subject. In some cases, cognitive function is as expected in an age-matched normal subject, but reduced by about 5%, about 10%, about 30%, about 50% or more, compared to cognitive function expected in a young adult subject. Age-related impaired cognitive function may be associated with Mild Cognitive Impairment (MCI) (including amnestic MCI and non-amnestic MCI), Age-Associated Memory Impairment (AAMI), and Age-related Cognitive Decline (ARCD).

"Cognitive impairment" associated with AD or related to AD or in AD refers to cognitive function in subjects that is not as robust as that expected in subjects who have not been diagnosed AD using conventional methodologies and standards.

"Mild Cognitive Impairment" or "MCI" refers to a condition characterized by isolated memory impairment unaccompanied other cognitive abnormalities and relatively normal functional abilities. One set of criteria for a clinical characterization of MCI specifics the following characteristics: (1) memory complaint (as reported by patient, informant, or physician), (2) normal activities of daily living (ADLs), (3) normal global cognitive function, (4) abnormal memory for age (defined as scoring more than 1.5 standard deviations below the mean for a given age), and (5) absence of indicators of dementia (as defined by DSM-IV guidelines). Petersen et al., *Srch. Neurol.* 56: 303-308 (1999); Petersen, "Mild cognitive impairment: Aging to Alzheimer's Disease." Oxford University Press, N.Y. (2003). The cognitive deficit in subjects with MCI may involve any cognition area or mental process including memory, language, association, attention, perception, problem solving, executive function and visuospatial skills. See, e.g., Winbald et al., *J. Intern. Med.* 256:240-240, 2004; Meguro, *Acta. Neurol. Taiwan.* 15:55-57, 2008; Ellison et al., *CNS Spectr.* 13:66-72, 2008, Petersen, *Semin. Neurol.* 27:22-31, 2007. MCI is further subdivided into amnestic MCI (aMCI) and non-amnestic MCI, characterized by the impairment (or lack thereof) of memory in particular. MCI is defined as aMCI if memory is found to be impaired given the age and education level of the subject. If, on the other hand, the memory of the subject is found to be intact for age and education, but other non-memory cognitive domains are impaired, such as language, executive function, or visuospatial skills, MCI is defines an non-amnestic MCI. aMCI and non-amnestic MCI can both be further subdivided into single or multiple domain MCI. aMCI-single domain refers to a condition where memory, but not other cognitive areas are impaired. aMCI-multiple domain refers to a condition where memory and at least one other cognitive area are impaired. Non-amnestic MCI is single domain or multiple domain dependent on whether nor not more than one non-memory cognitive area is impaired. See, e.g., Peterson and Negash, *CNS Speectr.* 13:45-53, 2008.

Diagnosis of MCI usually entails an objective assessment of cognitive impairment, which can be garnered through the use of well-established neuropsychological tests, including the Mini Mental State Examination (MMSE), the Cambridge Neuropsychological Test Automated Battery (CANTAB) and individual tests such as Rey Auditory Verbal Learning Test (AVLT), Logical Memory Subtest of the revised Wechsler Memory Scale (WMS-R) and the New York University (NYU) Paragraph Recall Test. See Folstein et al., *J Psychiatric Res* 12: 189-98 (1975); Robbins et al., *Dementia* 5: 266-81 (1994); Kluger et al., *J Geriatric Psychiatry Neurol* 12:168-79 (1999).

"Age-Associate Memory Impairment (AAMI)" refers to a decline in memory due to aging. A patient may be considered to have AAMI if he or she is at least 50 years old and meets all of the following criteria: a) The patient has noticed a decline in memory performance, b) The patient performs worse on a standard test of memory compared to young adults, c) All other obvious causes of memory decline, except normal aging, have been ruled out (in other words, the memory decline cannot be attributed to other causes such as a recent heart attack or head injury, depression, adverse reactions to medication, Alzheimer's disease, etc.).

"Age-Related Cognitive Decline (ARCD)" refers to declines in memory and cognitive abilities that are a normal consequence of aging in humans (e.g., Craik & Salthouse, 1992). This is also true in virtually all mammalian species. Age-Associated Memory Impairment refers to older persons with objective memory declines relative to their younger years, but cognitive functioning that is normal relative to their age peers (Crook et al., 1986). Age-Consistent Memory Decline is a less pejorative label which emphasizes that these are normal developmental changes (Crook, 1993; Larrabee, 1996), are not pathophysiological (Smith et al., 1991), and rarely progress to overt dementia (Youngjohn & Crook, 1993). The DSM-IV (1994) has codified the diagnostic classification of ARCD.

"Dementia" refers to a condition characterized by severe cognitive deficit that interferes in normal activities of daily living. Subjects with dementia also display other symptoms such as impaired judgment, changes in personality, disorientation, confusion, behavior changes, trouble speaking, and motor deficits. There are different types of dementias, such as Alzheimer's disease (AD), vascular dementia, dementia with Lewy bodies, and frontotemporal dementia.

Alzheimer's disease (AD) is characterized by memory deficits in its early phase. Later symptoms include impaired judgment, disorientation, confusion, behavior changes, trouble speaking, and motor deficits. Histologically, AD is characterized by beta-amyloid plaques and tangles of protein tau.

Vascular dementia is caused by strokes. Symptoms overlap with those of AD, but without the focus on memory impairment.

Dementia with Lewy bodies is characterized by abnormal deposits of alpha-synuclein that form inside neurons in the brain. Cognitive impairment may be similar to AD, including impairments in memory and judgment and behavior changes.

Frontotemporal dementia is characterized by gliosis, neuronal loss, superficial spongiform degeneration in the frontal cortex and/or anterior temporal lobes, and Picks' bodies. Symptoms include changes in personality and behavior, including a decline in social skills and language expression/comprehension.

"Post traumatic stress disorder (PTSD)" refers to an anxiety disorder characterized by an immediate or delayed response to a catastrophic event, characterized by re-experiencing the trauma, psychic numbing or avoidance of stimuli associated with the trauma, and increased arousal. Re-experiencing phenomena include intrusive memories, flashbacks, nightmares, and psychological or physiological distress in response to trauma reminders. Such responses produce anxiety and can have significant impact, both chronic and acute, on a patient's quality of life and physical and emotional health. PTSD is also associated with impaired cognitive performance, and older individuals with PTSD have greater decline in cognitive performance relative to control patients.

"Schizophrenia" refers to a chronic debilitating disorder, characterized by a spectrum of psychopathology, including positive symptoms such as aberrant or distorted mental representations (e.g., hallucinations, delusions), negative symptoms characterized by diminution of motivation and adaptive goal-directed action (e.g., anhedonia, affective flattening, avolition), and cognitive impairment. While abnormalities in the brain are proposed to underlie the full spectrum of psychopathology in schizophrenia, currently available antipsychotics are largely ineffective in treating cognitive impairments in patients.

"Bipolar disorder" or "BP" or "manic depressive disorder" or "manic depressive illness" refers to a chronic psychological/mood disorder which can be characterized by significant mood changes including periods of depression and euphoric manic periods. BP may be diagnosed by a skilled physician based on personal and medical history, interview consultation and physical examinations. The term "mania" or "manic periods" or other variants refers to periods where an individual exhibits some or all of the following characteristics: racing thoughts, rapid speech, elevated levels of activity and agitation as well as an inflated sense of self-esteem, euphoria, poor judgment, insomnia, impaired concentration and aggression.

"Amyotrophic lateral sclerosis," also known as ALS, refers to a progressive, fatal, neurodegenerative disease characterized by a degeneration of motor neurons, the nerve cells in the central nervous system that control voluntary muscle movement. ALS is also characterized by neuronal degeneration in the entorhinal cortex and hippocampus, memory deficits, and neuronal hyperexcitability in different brain areas such as the cortex.

"Cancer-therapy-related cognitive impairment" refers to cognitive impairment that develops in subjects that are treated with cancer therapies such as chemotherapy (e.g., chemobrain) and radiation. Cytotoxicity and other adverse side-effects on the brain of cancer therapies result in cognitive impairment in such functions as memory, learning and attention.

Parkinson's disease (PD) is a neurological disorder characterized by a decrease of voluntary movements. The afflicted patient has reduction of motor activity and slower voluntary movements compared to the normal individual. The patient has characteristic "mask" face, a tendency to hurry while walking, bent over posture and generalized weakness of the muscles. There is a typical "lead-pipe" rigidity of passive movements. Another important feature of the disease is the tremor of the extremities occurring at rest and decreasing during movements.

"Autism," as used herein, refers to an autism spectrum disorder characterized by a neural development disorder leading to impaired social interaction and communication by restricted and repetitive behavior. "Autism Spectrum Disorder" refers to a group of developmental disabilities that includes: autism; Asperger syndrome; pervasive developmental disorder not otherwise specified (PDD-NOS or atypical autism); Rett syndrome; and childhood disintegrative disorder.

Mental retardation is a generalized disorder characterized by significantly impaired cognitive function and deficits in adaptive behaviors. Mental retardation is often defined as an Intelligence Quotient (IQ) score of less than 70. Inborn causes are among many underlying causes for mental retardation. The dysfunction in neuronal communication is also considered one of the underlying causes for mental retardation (Myrrhe van Spronsen and Casper C. Hoogenraad, *Curr. Neurol. Neurosci. Rep.* 2010, 10, 207-214).

In some instances, mental retardation includes, but are not limited to, Down syndrome, velocariofacial syndrome, fetal alcohol syndrome, Fragile X syndrome, Klinefelter's syndrome, neurofibromatosis, congenital hypothyroidism, Williams syndrome, phenylketonuria (PKU), Smith-Lemli-Opitz syndrome, Prader-Willi syndrome, Phelan-McDermid syndrome, Mowat-Wilson syndrome, ciliopathy, Lowe syndrome and siderium type X-linked mental retardation. Down syndrome is a disorder that includes a combination of birth defects, including some degree of mental retardation, characteristic facial features and, often, heart defects, increased infections, problems with vision and hearing, and other health problems. Fragile X syndrome is a prevalent form of inherited mental retardation, occurring with a frequency of 1 in 4,000 males and 1 in 8,000 females. The syndrome is also characterized by developmental delay, hyperactivity, attention deficit disorder, and autistic-like behavior. There is no effective treatment for fragile X syndrome.

Obsessive compulsive disorder ("OCD") is a mental condition that is most commonly characterized by intrusive, repetitive unwanted thoughts (obsessions) resulting in compulsive behaviors and mental acts that an individual feels driven to perform (compulsion). Current epidemiological data indicates that OCD is the fourth most common mental disorder in the United States. Some studies suggest the prevalence of OCD is between one and three percent, although the prevalence of clinically recognized OCD is much lower, suggesting that many individuals with the disorder may not be diagnosed. Patients with OCD are often diagnosed by a psychologist, psychiatrist, or psychoanalyst according to the Diagnostic and Statistical Manual of Mental Disorders, 4th edition text revision (DSM-IV-TR) (2000) diagnostic criteria that include characteristics of obsessions and compulsions.

Substance addiction (e.g., drug addiction, alcohol addiction) is a mental disorder. The addiction is not triggered instantaneously upon exposure to substance of abuse. Rather, it involves multiple, complex neural adaptations that develop with different time courses ranging from hours to days to months (Kauer J. A. *Nat. Rev. Neurosci.* 2007, 8, 844-858). The path to addiction generally begins with the voluntary use of one or more controlled substances, such as narcotics, barbiturates, methamphetamines, alcohol, nicotine, and any of a variety of other such controlled substances. Over time, with extended use of the controlled substance(s), the voluntary ability to abstain from the controlled substance(s) is compromised due to the effects of prolonged use on brain function, and thus on behavior. As such, substance addiction generally is characterized by compulsive substance craving, seeking and use that persist even in the face of negative consequences. The cravings may represent changes in the underlying neurobiology of the patient which likely must be addressed in a meaningful way if recovery is to be obtained. Substance addiction is also characterized in many cases by withdrawal symptoms, which for some substances are life threatening (e.g., alcohol, barbiturates) and in others can result in substantial morbidity (which may include nausea, vomiting, fever, dizziness, and profuse sweating), distress, and decreased ability to obtain recovery. For example, alcoholism, also known as alcohol dependence, is one such substance addiction. Alcoholism is primarily characterized by four symptoms, which include cravings, loss of control, physical dependence and tolerance. These symptoms also may characterize addictions to other controlled substances. The craving for alcohol, as well as other controlled substances, often is as strong as the need for food or water. Thus, an alcoholic may continue to drink despite serious family, health and/or legal ramifications.

"Treating" a condition or patient refers to taking steps to obtain beneficial or desired results, including clinical results. Beneficial or desired clinical results include, but are not limited to, preventing or slowing the progression of the disease or disorder, or alleviation, amelioration, or slowing the progression, of one or more symptoms of cognitive impairment associated with CNS disorders, such as age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction. In some embodiments, treatment comprises preventing or slowing the progression, of a CNS disorder (such as one as described herein). In certain embodiments, treatment comprises alleviation, amelioration, or slowing the progression of one or more symptoms associated with that CNS disorder. In certain embodiments, the symptom to be treated is cognitive impairment or cognitive deficit. Treating age-related cognitive impairment further comprises slowing the conversion of age-related cognitive impairment (including, but not limited to MCI, ARCD and AAMI) into dementia (e.g., AD).

"Treating cognitive impairment" refers to taking steps to improve cognitive function in a subject with cognitive impairment so that the subject's performance in one or more cognitive tests is improved to any detectable degree, or is prevented from further decline. Preferably, that subject's cognitive function, after treatment of cognitive impairment, more closely resembles the function of a normal, unimpaired subject. Treatment of cognitive impairment in humans may improve cognitive function to any detectable degree, but is preferably improved sufficiently to allow the impaired subject to carry out daily activities of normal life at the same level of proficiency as a normal, unimpaired subject. In some cases, "treating cognitive impairment" refers to taking steps to improve cognitive function in a subject with cognitive impairment so that the subject's performance in one or more cognitive tests is improved to any detectable degree, or is prevented from further decline. Preferably, that subject's cognitive function, after treatment of cognitive impairment, more closely resembles the function of a normal, unimpaired subject. In some cases, "treating cognitive impairment" in a subject affecting by age-related cognitive impairment refers to takings steps to improve cognitive function in the subject so that the subject's cognitive function, after treatment of cognitive impairment, more closely resembles the function of an age-matched normal, unimpaired subject, or the function of a young adult subject.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, intravenously, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow, or controlled release of the compound or agent. Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

Appropriate methods of administering a substance, a compound or an agent to a subject will also depend, for example, on the age of the subject, whether the subject is active or inactive at the time of administering, whether the subject is cognitively impaired at the time of administering, the extent of the impairment, and the chemical and biological properties of the compound or agent (e.g. solubility, digestibility, bioavailability, stability and toxicity). In some embodiments, a compound or an agent is administered orally, e.g., to a subject by ingestion, or intravenously, e.g., to a subject by injection. In some embodiments, the orally administered compound or agent is in an extended release or slow release formulation, or administered using a device for such slow or extended release.

As used herein, a "α5-containing $GABA_A$ receptor agonist," "α5-containing $GABA_A$ R agonist" or a "$GABA_A$ α5 receptor agonist" and other variations as used herein refer to a compound that enhances the function of α5-containing $GABA_A$ receptor ($GABA_A$ R), i.e., a compound that increase GABA-gated $Cl^-$ currents. In some embodiments, α5-containing $GABA_A$ R agonist as used herein refers to a positive allosteric modulator, which potentiates the activity of GABA. α5-containing $GABA_A$ receptor agonists, suitable for use in the present invention, include the α5-containing $GABA_A$ receptor agonists of all formulas and specific α5-containing $GABA_A$ receptor agonists described herein, and their hydrates, solvates, polymorphs, salts (e.g., pharmaceutically acceptable salts), isomers (e.g., stereoisomers, E/Z isomers, and tautomers), and combinations thereof.

"Antipsychotic", "antipsychotic agent", "antipsychotic drug", or "antipsychotic compound" refers to (1) a typical or an atypical antipsychotic; (2) an agent that is selected from dopaminergic agents, glutamatergic agents, NMDA receptor positive allosteric modulators, glycine reuptake inhibitors, glutamate reuptake inhibitor, metabotropic glutamate receptors (mGluRs) agonists or positive allosteric modulators (PAMs) (e.g., mGluR2/3 agonists or PAMs), glutamate receptor glur5 positive allosteric modulators (PAMs), M1 muscarinic acetylcholine receptor (mAChR) positive allosteric modulators (PAMs), histamine 113 receptor antagonists, AMPA/kainate receptor antagonists, ampakines (CX-516), glutathione prodrugs, noradrenergic agents, serotonin receptor modulators, cholinergic agents, cannabinoid CBI antagonists, neurokinin 3 antagonists, neurotensin agonists, MAO B inhibitors, PDE10 inhibitors, nNOS inhibits, neurosteroids, and neurotrophic factors, alpha-7 agonists or positive allosteric modulators (PAMs)PAMs, serotonin 2C agonists; and/or (3) an agent that is useful in treating one or more signs or symptoms of schizophrenia or bipolar disorder (in particular, mania).

"Typical antipsychotics", as used herein, refer to conventional antipsychotics, which produce antipsychotic effects as well as movement related adverse effects related to disturbances in the nigrostriatal dopamine system. These extrapyramidal side effects (EPS) include Parkinsonism, akathisia, tardive dyskinesia and dystonia. See Baldessarini and Tarazi in Goodman & Gilman's The Pharmacological Basis of Therapeutics 10 Edition, 2001, pp. 485-520.

"Atypical antipsychotics", as used herein, refer to antipsychotic drugs that produce antipsychotic effects with little or no EPS and include, but are not limited to, aripiprazole, asenapine, clozapine, iloperidone, olanzapine, lurasidone, paliperidone, quetiapine, risperidone and ziprasidone. "Atypical" antipsychotics differ from conventional antipsychotics in their pharmacological profiles. While conventional antipsychotics are characterized principally by $D_2$ dopamine receptor blockade, atypical antipsychotics show antagonist effects on multiple receptors including the $5HT_a$ and $5HT_c$ serotonin receptors and varying degrees of receptor affinities. Atypical antipsychotic drugs are commonly referred to as serotonin/dopamine antagonists, reflecting the influential hypothesis that greater affinity for the $5HT_2$ receptor than for the $D_2$ receptor underlies "atypical" antipsychotic drug action or "second generation" antipsychotic drugs. However, the atypical antipsychotics often display side effects, including, but not limited to, weight gain, diabetes (e.g., type II diabetes mellitus), hyperlipidemia, QTc interval prolongation, myocarditis, sexual side effects, extrapyramidal side effects and cataract. Thus, atypical antipsychotics do not represent a homogeneous class, given their differences in the context of both alleviation of clinical symptoms and their potential for inducing side effects such as the ones listed above. Further, the common side effects of the atypical antipsychotics as described above often limit the antipsychotic doses that can be used for these agents.

Memantine is chemically known as 3,5-dimethyladamantan-1-amine or 3,5-dimethyltricyclo[3.3.1.1$^{3,7}$]decan-1-amine, which is an uncompetitive N-methyl-D-aspartate (NMDA) receptor antagonist with moderate affinity. The proprietary names for memantine include: Axura® and Akatinol® (Merz), Namenda® (Forest Laboratories), Ebixa® and Abixa® (Lundbeck), and Memox® (Unipharm). Memantine is approved for the treatment of moderate to severe Alzheimer's disease (AD) in the United States at a dose of up to 28 mg/day. Derivatives or analogs of memantine, which include compounds that structurally or chemically resemble memantine, are also useful in the present invention. Such derivatives or analogs of memantine include, but are not limited to those compounds disclosed in U.S. Pat. Nos. 3,391,142; 4,122,193; 4,273,774; and 5,061,703; U.S. Patent Application Publication US20040087658, US20050113458, US20060205822, US20090081259, US20090124659, and US20100227852; EP Patent Application Publication EP2260839A2; EP Patent EP1682109B1; and PCT Application Publication WO2005079779, all of which are incorporated herein by reference. Memantine, as used in the present invention, includes memantine and its derivatives and analogs, as well as hydrates, polymorphs, prodrugs, salts, and solvates thereof. Memantine, as used herein, also includes a composition comprising memantine or a derivative or an analog or a pharmaceutically acceptable salt, hydrate, solvate, polymorph, or prodrug thereof, wherein the composition optionally further comprises at least one additional therapeutic agent (such as a therapeutic agent useful for treating a CNS disorder or cognitive impairments associated thereof). In some embodiments, the memantine composition suitable for use in the present invention comprises memantine and a second therapeutic agent that is donepezil (under the trade name Aricept).

"Acetylcholinesterase inhibitor" or "AChE-I" as used herein refers to an agent that inhibits the ability of the cholinesterase enzyme to break down the neurotransmitter acetylcholine, thereby increasing the concentration and duration of acetylcholine, mainly in brain synapses or neuromuscular junctions. AChE-Is suitable for use in this application may include, for example, the subcategories of (i) reversible non-competitive inhibitors or reversible competitive inhibitors, (ii) irreversible, and (iii) quasi-irreversible inhibitors.

The term "simultaneous administration," as used herein, means that a α5-containing $GABA_A$ receptor agonist (e.g., a α5-containing $GABA_A$ receptor positive allosteric modulator) and a second therapeutic agent (e.g., an antipsychotic, memantine or an AChE-I), or their pharmaceutically acceptable salts, hydrates, solvates, or polymorphs, are administered with a time separation of no more than about 15 minutes, and in some embodiments no more than about 10 minutes. When the drugs are administered simultaneously, the α5-containing $GABA_A$ receptor agonist (e.g., an α5-containing $GABA_A$ receptor positive allosteric modulator) and a second therapeutic agent (e.g., an antipsychotic, memantine or an AChE-I), or their salts, hydrates, solvates, or polymorphs, may be contained in the same dosage (e.g., a unit dosage form comprising both the α5-containing $GABA_A$ receptor agonist (e.g., an α5-containing $GABA_A$ receptor positive allosteric modulator) and a second therapeutic agent (e.g., an antipsychotic, memantine or an AChE-I) or in discrete dosages (e.g., the α5-containing $GABA_A$ receptor agonist (e.g., an α5-containing $GABA_A$ receptor positive allosteric modulator) or its salt, hydrate, solvate, or polymorph is contained in one dosage form and a second therapeutic agent (e.g., an antipsychotic, memantine or an AChE-I), or its salt, hydrate, solvate, or polymorph is contained in another dosage form).

The term "sequential administration" as used herein means that the α5-containing $GABA_A$ receptor agonist (e.g., a α5-containing $GABA_A$ receptor positive allosteric modulator) and a second therapeutic agent (e.g., an antipsychotic, memantine or an AChE-I), or their pharmaceutically acceptable salts, hydrates, solvates, polymorphs, are administered with a time separation of more than about 15 minutes, and in some embodiments more than about one hour, or up to 12-24 hours. Either the α5-containing $GABA_A$ receptor agonist (e.g., a α5-containing $GABA_A$ receptor positive allosteric modulator) or a second therapeutic agent (e.g., an antipsychotic, memantine or an AChE-I) may be administered first. The α5-containing $GABA_A$ receptor agonist (e.g., a α5-containing $GABA_A$ receptor positive allosteric modulator) and a second therapeutic agent (e.g., an antipsychotic, memantine or an AChE-I), or their salts, hydrates, solvents, or polymorphs, for sequential administration may be contained in discrete dosage forms, optionally contained in the same container or package.

A "therapeutically effective amount" of a drug or agent is an amount of a drug or an agent that, when administered to a subject will have the intended therapeutic effect, e.g. improving cognitive function in a subject, e.g., a patient having cognitive impairment associated with a CNS disorder. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, the nature and extent of the cognitive impairment or other symptoms of the CNS disorder (such as age-related cognitive impairment, Mild Cognitive Impairment (MCI), dementia, Alzheimer's Disease (AD), prodromal AD, post traumatic stress disorder (PTSD), schizophrenia, bipolar, ALS, cancer-therapy-related cognitive impairment, mental retardation, Parkinson's disease (PD), autism spectrum disorders, fragile X disorder, Rett syndrome, compulsive behavior, and substance addiction), and the therapeutics or combination of therapeutics selected for administration, and the mode of administration. The skilled worker can readily determine the effective amount for a given situation by routine experimentation.

The compounds of the present invention also include prodrugs, analogs or derivatives. The term "prodrug" is art-recognized and is intended to encompass compounds or agents which, under physiological conditions, are converted into α5-containing $GABA_A$ R positive allosteric modulators. A common method for making a prodrug is to select moieties which are hydrolyzed or metabolized under physiological conditions to provide the desired compound or agent. In other embodiments, the prodrug is converted by an enzymatic activity of the host animal to a $GABA_A$ α5 receptor positive allosteric modulator.

"Analog" is used herein to refer to a compound which functionally resembles another chemical entity, but does not share the identical chemical structure. For example, an analog is sufficiently similar to a base or parent compound such that it can substitute for the base compound in therapeutic applications, despite minor structural differences.

"Derivative" is used herein to refer to the chemical modification of a compound. Chemical modifications of a compound can include, for example, replacement of hydrogen by an alkyl, acyl, or amino group. Many other modifications are also possible.

The term "aliphatic" as used herein refers to a straight chained or branched alkyl, alkenyl or alkynyl. It is understood that alkenyl or alkynyl embodiments need at least two carbon atoms in the aliphatic chain. Aliphatic groups typically contain from 1 (or 2) to 12 carbons, such as from 1 (or 2) to 4 carbons.

The term "aryl" as used herein refers to a monocyclic or bicyclic carbocyclic aromatic ring system. Aryl as used herein includes a (C6-C12)-aryl-. For example, aryl as used herein can be a C6-C10 monocyclic or C8-C12 bicyclic carbocyclic aromatic ring system. In some embodiments, aryl as used herein can be a (C6-C10)-aryl-. Phenyl (or Ph) is an example of a monocyclic aromatic ring system. Bicyclic aromatic ring systems include systems wherein both rings are aromatic, e.g., naphthyl, and systems wherein only one of the two rings is aromatic, e.g., tetralin.

The term "heterocyclic" as used herein refers to a monocyclic or bicyclic non-aromatic ring system having 1 to 4 heteroatom or heteroatom groups selected from O, N, NH, S, SO, or $SO_2$ in a chemically stable arrangement. Heterocyclic as used herein includes a 3- to 12-membered heterocyclyl- having 1-4 heteroatoms independently selected from O, N, NH, S, SO, or $SO_2$. For example, heterocyclic as used herein can be a 3- to 10-membered monocyclic or 8- to 12-membered bicyclic non-aromatic ring system having 1 to 4 heteroatom or heteroatom groups selected from O, N, NH, S, SO, or $SO_2$ in a chemically stable arrangement. In some embodiments, heterocyclic as used herein can be a 3- to 10-membered heterocyclyl- having 1-4 heteroatoms independently selected from O, N, NH, S, SO, or $SO_2$. In a bicyclic non-aromatic ring system embodiment of "heterocyclyl," one or both rings may contain said heteroatom or heteroatom groups. In another bicyclic "heterocyclyl" embodiment, one of the two rings may be aromatic. In yet another heterocyclic ring system embodiment, a non-aromatic heterocyclic ring may optionally be fused to an aromatic carbocycle.

Examples of heterocyclic rings include 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

The term "heteroaryl" as used herein refers to a monocyclic or bicyclic aromatic ring system having 1 to 4 heteroatom or heteroatom groups selected from O, N, NH or S in a chemically stable arrangement. Heteroaryl as used herein includes a 5- to 12-membered heteroaryl having 1-4 heteroatoms independently selected from O, N, NH or S. In some embodiments, heteroaryl as used herein can be a 5- to 10-membered heteroaryl having 1-4 heteroatoms independently selected from O, N, Nil or S. For example, heteroaryl as used herein can be a 5- to 10-membered monocyclic or 8- to 12-membered bicyclic aromatic ring system having 1 to 4 heteroatom or heteroatom groups selected from O, N, NH or S in one or both rings in a chemically stable arrangement. In such a bicyclic aromatic ring system embodiment of "heteroaryl":

both rings are aromatic; and one or both rings may contain said heteroatom or heteroatom groups.

Examples of heteroaryl rings include 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "cycloalkyl or cycloalkenyl" refers to a monocyclic or fused or bridged bicyclic carbocyclic ring system that is not aromatic. For example, cycloalkyl or cycloalkenyl as used herein can be a C3-C10 monocyclic or fused or bridged C8-C12 bicyclic carbocyclic ring system that is not aromatic. Cycloalkenyl rings have one or more units of unsaturation. Preferred cycloalkyl or cycloalkenyl groups include cyclopropyl, cyclobutyl, cyclopentyl, cyclohexyl, cyclohexenyl, cycloheptyl, cycloheptenyl, norbornyl, adamantyl and decalinyl.

The term "heretoaralkyl" refers to an alkyl in which a heteroaryl group is substituted for an alkyl H atom. For example, ??? [[[heteroaryl=heterocyclic and aromatic]]]

As used herein, the carbon atom designations may have the indicated integer and any intervening integer. For example, the number of carbon atoms in a (C1-C4)-alkyl group is 1, 2, 3, or 4. It should be understood that these designations refer to the total number of atoms in the appropriate group. For example, in a (C3-C10)-heterocyclyl the total number of carbon atoms and heteroatoms is 3 (as in aziridine), 4, 5, 6 (as in morpholine), 7, 8, 9, or 10.

"Pharmaceutically acceptable salt" is used herein to refer to an agent or a compound according to the invention that is a therapeutically active, non-toxic base and acid salt form of the compounds. The acid addition salt form of a compound that occurs in its free form as a base can be obtained by treating said free base form with an appropriate acid such as an inorganic acid, for example, a hydrohalic such as hydrochloric or hydrobromic, sulfuric, nitric, phosphoric and the like; or an organic acid, such as, for example, acetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclic, salicylic, p-aminosalicylic, pamoic and the like. See, e.g., WO 01/062726.

Compounds containing acidic protons may be converted into their therapeutically active, non-toxic base addition salt form, e.g. metal or amine salts, by treatment with appropriate organic and inorganic bases. Appropriate base salt forms include, for example, ammonium salts, alkali and earth alkaline metal salts, e.g., lithium, sodium, potassium, magnesium, calcium salts and the like, salts with organic bases, e.g. N-methyl-D-glucamine, hydrabamine salts, and salts with amino acids such as, for example, arginine, lysine and the like. Conversely, said salt forms can be converted into the free forms by treatment with an appropriate base or acid.

Compounds and their salts can be in the form of a solvate, which is included within the scope of the present invention. Such solvates include for example hydrates, alcoholates and the like. See, e.g., WO 01/062726.

As used herein, the term "hydrate" refers to a combination of water with a compound wherein the water retains its molecular state as water and is either absorbed, adsorbed or contained within a crystal lattice of the substrate compound.

As used herein, the term "polymorph" refers to different crystalline forms of the same compound and other solid state molecular forms including pseudo-polymorphs, such as hydrates (e.g., bound water present in the crystalline structure) and solvates (e.g., bound solvents other than water) of the same compound. Different crystalline polymorphs have different crystal structures due to a different packing of the molecules in the lattice. This results in a different crystal symmetry and/or unit cell parameters which directly influences its physical properties such the X-ray diffraction characteristics of crystals or powders. A different polymorph, for example, will in general diffract at a different set of angles and will give different values for the intensities. Therefore X-ray powder diffraction can be used to identify different polymorphs, or a solid form that comprises more than one polymorph, in a reproducible and reliable way. Crystalline polymorphic forms are of interest to the pharmaceutical industry and especially to those involved in the development of suitable dosage forms. If the polymorphic form is not held constant during clinical or stability studies, the exact dosage form used or studied may not be comparable from one lot to another. It is also desirable to have processes for producing a compound with the selected polymorphic form in high purity when the compound is used in clinical studies or commercial products since Impurities present may produce undesired toxicological effects. Certain polymorphic forms may exhibit enhanced thermodynamic stability or may be more readily manufactured in high purity in large quantities, and thus are more suitable for inclusion in pharmaceutical formulations. Certain polymorphs may display other advantageous physical properties such as lack of hygroscopic tendencies, improved solubility, and enhanced rates of dissolution due to different lattice energies.

This application contemplates all the isomers of the compounds of formulae I-IV. "Isomer" as used herein includes optical isomers (such as stereoisomers, e.g., enantiomers and diastereoisomers), Z (zusammen) or E (entgegen) isomers, and tautomers. Many of the compounds useful in the methods and compositions of this invention have at least one stereogenic center in their structure. This stereogenic center may be present in a R or a S configuration, said R and S notation is used in correspondence with the rules described in Pure Appl. Chem. (1976), 45, 11-30. The invention also relates to all stereoisomeric forms such as enantiomeric and diastereoisomeric forms of the compounds or mixtures thereof (including all possible mixtures of stereoisomers). See, e.g., WO 01/062726. Furthermore, certain compounds which contain alkenyl groups may exist as Z (zusammen) or E (entgegen) isomers. In each instance, the invention includes both mixture and separate individual isomers. Multiple substituents on a piperidinyl or the azepanyl ring can also stand in either cis or trans relationship to each other with respect to the plane of the piperidinyl or the azepanyl ring. Some of the compounds may also exist in tautomeric forms. Such forms, although not explicitly indicated in the formulae described herein, are intended to be included within the scope of the present invention. With respect to the methods and compositions of the present invention, reference to a compound or compounds is intended to encompass that compound in each of its possible isomeric forms and mixtures thereof unless the particular isomeric form is referred to specifically. See, e.g., WO 01/062726.

The compounds of the invention enhance the function of α5-containing $GABA_AR$, i.e., they are α5-containing $GABA_A$ R agonists (e.g., α5-containing $GABA_A$ receptor positive allosteric modulators) and are capable of increasing GABA-gated $Cl^-$ currents.

The invention further provides pharmaceutical compositions comprising one or more compounds of the invention together with a pharmaceutically acceptable carrier or excipient. In some embodiments, the pharmaceutical compositions of this application may further comprise a second therapeutic agent, such as an antipsychotic, memantine or an AChE-I.

The invention further provides methods for treating cognitive impairment associated with said CNS disorders that are responsive to positive allosteric modulators of α5-containing $GABA_A$ receptor, e.g., age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction. In certain embodiments, the method is a method of treating the age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction. In certain embodiments, treatment comprises preventing or slowing the progression of a CNS disorder as described herein (such as those described herein). In certain embodiments, treatment comprises alleviation, amelioration, or slowing the progression of one or more symptoms associated with the CNS disorder. In certain embodiments, the symptom to be treated is cognitive impairment or cognitive deficit. In another aspect of the invention, there is provided a method of preserving or improving cognitive function in a subject in need thereof, the method comprising the step of administering to said subject a therapeutically effective amount of a compound of the invention or a pharmaceutically acceptable salt, hydrate, solvate, polymorph, isomer, or combination thereof.

The various CNS disorders with cognitive impairment (e.g., age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction) may have a variety of etiologies. However, the symptom of cognitive impairment in each of the above-mentioned disorders may have overlapping causes. Thus, a composition or method of treatment that treats cognitive impairment in one CNS disorder may also treat cognitive impairment in another.

Benzodiazepine Derivatives

The present invention provides a compound of formula I:

I

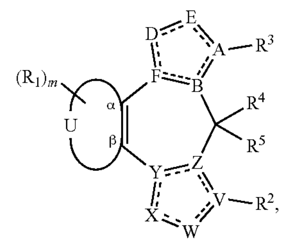

or a pharmaceutically acceptable salt, hydrate, solvate, polymorph, isomer, or combination thereof, wherein:

U and the two carbon atoms designated by α and β together form a 5- or 6-membered aromatic ring having 0-2 nitrogen atoms;

A is C, $CR^6$, or N;

B and F are each independently selected from C, $CR^6$, and N, wherein B and F cannot both be N;

D is N, $NR^7$, O, $CR^6$ or $C(R^6)_2$;

E is N, $NR^7$, $CR^6$ or $C(R^6)_2$;

W is N, $NR^7$, $CR^6$ or $C(R^6)_2$;

X is N, $NR^7$, O, $CR^6$ or $C(R^6)_2$;

Y and Z are each independently selected from C, $CR^6$, and N, wherein Y and Z cannot both be N;

V is C or $CR^6$, or when Z is C or $CR^6$, V is C, $CR^6$, or N;

wherein when the ring formed by X, Y, Z, V and W is

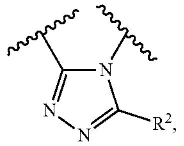

then $R^2$ is —$OR^8$, —$SR^8$, —$(CH_2)_nOR^8$, —$(CH_2)_nO(CH_2)_nR^8$, —$(CH_2)_pR^8$ and —$(CH_2)_nN(R'')R^{10}$; and wherein $R^2$ is independently substituted with 0-5 R';

m and n are independently integers selected from 0-4;

p is an integer selected from 2-4;

each occurrence of the bond "$\overline{---}$" is either a single bond or a double bond;

each occurrence of $R^1$, $R^2$, $R^4$, and $R^5$ are each independently selected from:

halogen, —R, —OR, —$NO_2$, —NCS, —CN, —$CF_3$, —$OCF_3$, —$SiR_3$, —$N(R)_2$, —SR, —SOR, —$SO_2R$, —$SO_2N(R)_2$, —$SO_3R$, —$(CR_2)_{1-3}R$, —$(CR_2)_{1-3}$—OR, —$(CR_2)_{0-3}$—C(O)NR$(CR_2)_{0-3}$R, —$(CR_2)_{0-3}$—C(O)NR$(CR_2)_{0-3}$OR, —C(O)R, —C(O)C(O)R, —C(O)$CH_2$C(O)R, —C(S)R, —C(S)OR, —C(O)OR, —C(O)C(O)OR, —C(O)C(O)$N(R)_2$, —OC(O)R, —C(O)$N(R)_2$, —OC(O)$N(R)_2$, —C(S)$N(R)_2$, —$(CR_2)_{0-3}$NHC(O)R, —N(R)N(R)COR, —N(R)N(R)C(O)OR, —N(R)N(R)CON$(R)_2$, —N(R)$SO_2$R, —N(R)$SO_2$N$(R)_2$, —N(R)C(O)OR, —N(R)C(O)R, —N(R)C(S)R, —N(R)C(O)N$(R)_2$, —N(R)C(S)N$(R)_2$, —N(COR)COR, —N(OR)R, —C(—NH)N$(R)_2$, —C(O)N(OR)R, —C(—NOR)R, —OP(O)$(OR)_2$, —P(O)$(R)_2$, —P(O)$(OR)_2$, and —P(O)(H)(OR);

$R^3$ is absent or is selected from:

halogen, —R, —OR, —$NO_2$, —NCS, —CN, —$CF_3$, —$OCF_3$, —$SiR_3$, —$N(R)_2$, —SR, —SOR, —$SO_2R$, —$SO_2N(R)_2$, —$SO_3R$, —$(CR_2)_{1-3}R$, —$(CR_2)_{1-3}$—OR, —$(CR_2)_{0-3}$—C(O)NR$(CR_2)_{0-3}$R, —$(CR_2)_{0-3}$—C(O)NR$(CR_2)_{0-3}$OR, —C(O)R, —C(O)C(O)R, —C(O)$CH_2$C(O)R, —C(S)R, —C(S)OR, —C(O)OR, —C(O)C(O)OR, —C(O)C(O)$N(R)_2$, —OC(O)R, —C(O)$N(R)_2$, —OC(O)$N(R)_2$, —C(S)$N(R)_2$, —$(CR_2)_{0-3}$NHC(O)R, —N(R)N(R)COR, —N(R)N(R)C(O)OR, —N(R)N(R)CON$(R)_2$, —N(R)$SO_2$R, —N(R)$SO_2N(R)_2$, —N(R)C(O)OR, —N(R)C(O)R, —N(R)C(S)R, —N(R)C(O)$N(R)_2$, —N(R)C(S)$N(R)_2$, —N(COR)COR, —N(OR)R, —C(=NH)$N(R)_2$, —C(O)N(OR)R, —C(=NOR)R, —OP(O)$(OR)_2$, —P(O)$(R)_2$, —P(O)$(OR)_2$, and —P(O)(H)(OR);

each $R^6$ is independently —H or —(C1-C6)alkyl;

each $R^7$ is independently —H or —(C1-C6)alkyl;

each $R^8$ is independently —(C1-C6)alkyl, —(C3-C10)-cycloalkyl, (C6-C10)-aryl, or 5- to 10-membered heteroaryl, wherein each occurrence of $R^8$ is independently substituted with 0-5 R';

each $R^{10}$ is independently —(C3-C10)-cycloalkyl, 3- to 10-membered heterocyclyl-, (C6-C10)-aryl, or 5- to 10-membered heteroaryl, wherein each occurrence of $R^{10}$ is independently substituted with 0-5 R';

each R is independently selected from:

H—,
(C1-C12)-aliphatic-,
(C3-C10)-cycloalkyl-,
(C3-C10)-cycloalkenyl-,
[(C3-C10)-cycloalkyl]-(C1-C12)-aliphatic-,
[(C3-C10)-cycloalkenyl]-(C1-C12)-aliphatic-,
[(C3-C10)-cycloalkyl]-O—(C1-C12)-aliphatic-,
[(C3-C10)-cycloalkenyl]-O—(C1-C12)-aliphatic-,
(C6-C10)-aryl-,
(C6-C10)-aryl-(C1-C12)aliphatic-,
(C6-C10)-aryl-O—(C1-C12)aliphatic-,
(C6-C10)-aryl-N(R")—(C1-C12)aliphatic-,
3- to 10-membered heterocyclyl-,
(3- to 10-membered heterocyclyl)-(C1-C12)aliphatic-,
(3- to 10-membered heterocyclyl)-O—(C1-C12)aliphatic-,
(3- to 10-membered heterocyclyl)-N(R")—(C1-C12)aliphatic-,
5- to 10-membered heteroaryl-,
(5- to 10-membered heteroaryl)-(C1-C12)-aliphatic-,
(5- to 10-membered heteroaryl)-O—(C1-C12)-aliphatic-; and
(5- to 10-membered heteroaryl)-N(R")—(C1-C12)-aliphatic-;

wherein said heterocyclyl has 1-4 heteroatoms independently selected from N, NH, O, S, SO, and $SO_2$, and said heteroaryl has 1-4 heteroatoms independently selected from N, NH, O, and S;

wherein each occurrence of R is independently substituted with 0-5 R';

or when two R groups bound to the same atom, the two R groups may be taken together with the atom to which they are bound to form a 3- to 10-membered aromatic or non-aromatic ring having 0-4 heteroatoms independently selected from N, NH, O, S, SO, and $SO_2$, wherein said ring is optionally substituted with 0-5 R', and wherein said ring is optionally fused to a (C6-C10)aryl, 5- to 10-membered heteroaryl, (C3-C10)cycloalkyl, or a 3- to 10-membered heterocyclyl;

wherein each occurrence of R' is independently selected from halogen, —R", —OR", oxo, —$CH_2$OR", —$CH_2NR"_2$, —C(O)N$(R")_2$, —C(O)OR", —$NO_2$, —NCS, —CN, —$CF_3$, —$OCF_3$ and —N$(R")_2$;

wherein each occurrence of R" is independently selected from H, —(C1-C6)-alkyl, —(C1-C6)-aliphatic, (C3-C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, and (C6-C10)-aryl-O—(C1-C6)-alkyl-, wherein each occurrence of R" is independently substituted with 0-3 substituents selected from: halogen, —R", —OR", oxo, —$CH_2$OR", —$CH_2NR^{\circ}_2$, —C(O)N$(R^{\circ})_2$, —C(O)$OR^{\circ}$, —$NO_2$, —NCS, —CN, —$CF_3$, —$OCF_3$ and —N$(R^{\circ})_2$, wherein each occurrence of $R^{\circ}$ is independently selected from: —(C1-C6)-aliphatic, (C3-C6)-cycloalkyl, 3- to 6-membered heterocyclyl, 5- to 10-membered heteroaryl-, and (C6-C10)-aryl-.

In some embodiments, the present invention provides a compound of formula I:

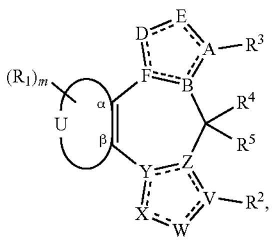
I or a pharmaceutically acceptable salt, hydrate, solvate, polymorph, isomer, or combination thereof, wherein:

U and the two carbon atoms designated by α and β together form a 5- or 6-membered aromatic ring having 0-2 nitrogen atoms;

A is C, $CR^6$, or N;

B and F are each independently selected from C, $CR^6$, and N, wherein B and F cannot both be N;

D is N, $NR^7$, O, $CR^6$ or $C(R^6)_2$;

E is N, $NR^7$, $CR^6$ or $C(R^6)_2$;

W is N, $NR^7$, $CR^6$ or $C(R^6)_2$;

X is N, $NR^7$, O, $CR^6$ or $C(R^6)_2$;

Y and Z are each independently selected from C, $CR^6$, and N, wherein Y and Z cannot both be N;

V is C or $CR^6$, or when Z is C or $CR^6$, V is C, $CR^6$, or N;

wherein when the ring formed by X, Y, Z, V and W is

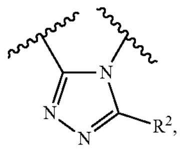

then $R^2$ is —$OR^8$, —$SR^8$, —$(CH_2)_nOR^8$, —$(CH_2)_nO(CH_2)_nR^8$, —$(CH_2)_pR^8$ and —$(CH_2)_nN(R")R^{10}$; and wherein $R^2$ is independently substituted with 0-5 R';

m and n are independently integers selected from 0-4;

p is an integer selected from 2-4; each occurrence of the bond "---" is either a single bond or a double bond;

each occurrence of $R^1$, $R^2$, $R^4$, and $R^5$ are each independently selected from:

halogen, —R, —OR, —$NO_2$, —NCS, —CN, —$CF_3$, —$OCF_3$, —$SiR_3$, —$N(R)_2$, —SR, —SOR, —$SO_2R$, —$SO_2N(R)_2$, —SOR, —$(CR_2)_{1-3}R$, —$(CR_2)_{1-3}$—OR, —$(CR_2)_{0-3}$—C(O)NR$(CR_2)_{0-3}$R, —$(CR_2)_{0-3}$—C(O)NR$(CR_2)_{0-3}$OR, —C(O)R, —C(O)C(O)R, —C(O)$CH_2$C(O)R, —C(S)R, —C(S)OR, —C(O)OR, —C(O)C(O)OR, —C(O)C(O)N$(R)_2$, —OC(O)R, —C(O)N$(R)_2$, —OC(O)N$(R)_2$, —C(S)N$(R)_2$, —$(CR_2)_{0-3}$NHC(O)R, —N(R)N(R)COR, —N(R)N(R)C(O)OR, —N(R)N(R)CON$(R)_2$, —N(R)$SO_2$R, —N(R)$SO_2$N$(R)_2$, —N(R)C(O)OR, —N(R)C(O)R, —N(R)C(S)R, —N(R)C(O)N$(R)_2$, —N(R)C(S)N$(R)_2$, —N(COR)COR, —N(OR)R, —C(=NH)N$(R)_2$, —C(O)N(OR)R, —C(=NOR)R, —OP(O)$(OR)_2$, —P(O)$(R)_2$, —P(O)$(OR)_2$, and —P(O)(H)(OR);

$R^3$ is absent or is selected from:

halogen, —R, —OR, —$NO_2$, —NCS, —CN, —$CF_3$, —$OCF_3$, —$SiR_3$, —$N(R)_2$, —SR, —SOR, —$SO_2R$, —$SO_2N(R)_2$, —$SO_3R$, —$(CR_2)_{1-3}R$, —$(CR_2)_{1-3}$—OR, —$(CR_2)_{0-3}$—C(O)NR$(CR_2)_{0-3}$R, —$(CR_2)_{0-3}$—C(O)NR$(CR_2)_{0-3}$OR, —C(O)R, —C(O)C(O)R, —C(O)$CH_2$C(O)R, —C(S)R, —C(S)OR, —C(O)OR, —C(O)C(O)OR, —C(O)C(O)N$(R)_2$, —OC(O)R, —C(O)N$(R)_2$, —OC(O)N$(R)_2$, —C(S)N$(R)_2$, —$(CR_2)_{0-3}$NHC(O)R, —N(R)N(R)COR, —N(R)N(R)C(O)OR, —N(R)N(R)CON$(R)_2$, —N(R)$SO_2$R, —N(R)$SO_2$N$(R)_2$, —N(R)C(O)OR, —N(R)C(O)R, —N(R)C(S)R, —N(R)C(O)N$(R)_2$, —N(R)C(S)N$(R)_2$, —N(COR)COR, —N(OR)R, —C(=NH)N$(R)_2$, —C(O)N(OR)R, —C(=NOR)R, —OP(O)$(OR)_2$, —P(O)$(R)_2$, —P(O)$(OR)_2$, and —P(O)(H)(OR);

each $R^6$ is independently —H or —(C1-C6)alkyl;

each $R^7$ is independently —H or —(C1-C6)alkyl;

each $R^8$ is independently —(C1-C6)alkyl, —(C3-C10)-cycloalkyl, (C6-C10)-aryl, or 5- to 10-membered heteroaryl, wherein each occurrence of $R^8$ is independently substituted with 0-5 R';

each $R^{10}$ is independently —(C3-C10)-cycloalkyl, 3- to 10-membered heterocyclyl-, (C6-C10)-aryl, or 5- to 10-membered heteroaryl, wherein each occurrence of $R^{10}$ is independently substituted with 0-5 R';

each R is independently selected from:

H—,
(C1-C12)-aliphatic-,
(C3-C10)-cycloalkyl-,
(C3-C10)-cycloalkenyl-,
[(C3-C10)-cycloalkyl]-(C1-C12)-aliphatic-,
[(C3-C10)-cycloalkenyl]-(C1-C12)-aliphatic-,
[(C3-C10)-cycloalkyl]-O—(C1-C12)-aliphatic-,
[(C3-C10)-cycloalkenyl]-O—(C1-C12)-aliphatic-,
(C6-C10)-aryl-,
(C6-C10)-aryl-(C1-C12)aliphatic-,
(C6-C10)-aryl-O—(C1-C12)aliphatic-,
(C6-C10)-aryl-N(R")—(C1-C12)aliphatic-,
3- to 10-membered heterocyclyl-,
(3- to 10-membered heterocyclyl)-(C1-C12)aliphatic-,
(3- to 10-membered heterocyclyl)-O—(C1-C12)aliphatic-,
(3- to 10-membered heterocyclyl)-N(R")—(C1-C12) aliphatic-,
5- to 10-membered heteroaryl-,
(5- to 10-membered heteroaryl)-(C1-C12)-aliphatic-,
(5- to 10-membered heteroaryl)-O—(C1-C12)-aliphatic-; and
(5- to 10-membered heteroaryl)-N(R")—(C1-C12)-aliphatic-;

wherein said heterocyclyl has 1-4 heteroatoms independently selected from N, NH, O, S, SO, and $SO_2$, and said heteroaryl has 1-4 heteroatoms independently selected from N, NH, O, and S;

wherein each occurrence of R is independently substituted with 0-5 R';

or when two R groups bound to the same atom, the two R groups may be taken together with the atom to which they are bound to form a 3- to 10-membered aromatic or non-aromatic ring having 0-4 heteroatoms independently selected from N, NH, O, S, SO, and $SO_2$, wherein said ring is optionally substituted with 0-5 R', and wherein said ring is optionally fused to a (C6-C10) aryl, 5- to 10-membered heteroaryl, (C3-C10)cycloalkyl, or a 3- to 10-membered heterocyclyl;

wherein each occurrence of R' is independently selected from halogen, —R", —OR", oxo, —$CH_2$OR", —$CH_2$NR"$_2$, —C(O)N(R")$_2$, —C(O)OR", —$NO_2$, —NCS, —CN, —$CF_3$, —$OCF_3$ and —N(R")$_2$;

wherein each occurrence of R" is independently selected from H, —(C1-C6)-alkyl, (C3-C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, and (C6-C10)-aryl-O—(C1-C6)-alkyl-.

Some embodiments provide a compound of formula I:

I

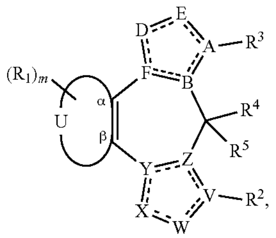

or a pharmaceutically acceptable salt, hydrate, solvate, polymorph, isomer, or combination thereof, wherein:

U and the two carbon atoms designated by α and β together form a 5- or 6-membered aromatic ring having 0-2 nitrogen atoms;

A is C, $CR^6$, or N;

B and F are each independently selected from C, $CR^6$, and N, wherein B and F cannot both be N;

D is N, $NR^7$, O, $CR^6$ or $C(R^6)_2$;

E is N, $NR^7$, $CR^6$ or $C(R^6)_2$;

W is N, $NR^7$, $CR^6$ or $C(R^6)_2$;

X is N, $NR^7$, O, $CR^6$ or $C(R^6)_2$;

Y and Z are each independently selected from C, $CR^6$, and N, wherein Y and Z cannot both be N;

V is C or $CR^6$, or when Z is C or $CR^6$, V is C, $CR^6$, or N;

wherein when the ring formed by X, Y, Z, V and W is

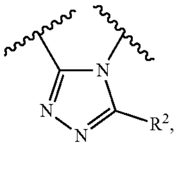

then $R^2$ is —$OR^8$, —$SR^8$, or —$(CH_2)_nOR^8$;

m and n are each independently an integer selected from 0-4;

each occurrence of the bond "$\overline{---}$" is either a single bond or a double bond;

each occurrence of $R^1$, $R^2$, $R^4$, and $R^5$ are each independently selected from: halogen, —R, —OR, —$NO_2$, —NCS, —CN, —$CF_3$, —$OCF_3$, —$SiR_3$, —$N(R)_2$, —SR, —SOR, —$SO_2R$, —$SO_2N(R)_2$, —$SO_3R$, —$(CR_2)_{1-3}R$, —$(CR_2)_{1-3}$—OR, —$(CR_2)_{0-3}$—C(O)NR$(CR_2)_{0-3}$R, —$(CR_2)_{0-3}$—C(O)NR$(CR_2)_{0-3}$OR, —C(O)R, —C(O)C(O)R, —C(O)$CH_2$C(O)R, —C(S)R, —C(S)OR, —C(O)OR, —C(O)C(O)OR, —C(O)C(O)$N(R)_2$, —OC(O)R, —C(O)$N(R)_2$, —OC(O)$N(R)_2$, —C(S)$N(R)_2$, —$(CR_2)_{0-3}$NHC(O)R, —N(R)N(R)COR, —N(R)N(R)C(O)OR, —N(R)N(R)CON$(R)_2$, —N(R)$SO_2$R, —N(R)$SO_2N(R)_2$, —N(R)C(O)OR, —N(R)C(O)R, —N(R)C(S)R, —N(R)C(O)N$(R)_2$, —N(R)C(S)N$(R)_2$, —N(COR)COR, —N(OR)R, —C(═NH)N$(R)_2$, —C(O)N(OR)R, —C(═NOR)R, —OP(O)$(OR)_2$, —P(O)$(R)_2$, —P(O)$(OR)_2$, and —P(O)(H)(OR);

$R^3$ is absent or is selected from:

halogen, —R, —OR, —$NO_2$, —NCS, —CN, —$CF_3$, —$OCF_3$, —$SiR_3$, —$N(R)_2$, —SR, —SOR, —$SO_2R$, —$SO_2N(R)_2$, —$SO_3R$, —$(CR_2)_{1-3}R$, —$(CR_2)_{1-3}$—OR, —$(CR_2)_{0-3}$—C(O)NR$(CR_2)_{0-3}$R, —$(CR_2)_{0-3}$C(O)NR$(CR_2)_{0-3}$OR, —C(O)R, —C(O)C(O)R, —C(O)$CH_2$C(O)R, —C(S)R, —C(S)OR, —C(O)OR, —C(O)C(O)OR, —C(O)C(O)N$(R)_2$, —OC(O)R, —C(O)N$(R)_2$, —OC(O)N$(R)_2$, —C(S)N$(R)_2$, —$(CR_2)_{0-3}$NHC(O)R, —N(R)N(R)COR, —N(R)N(R)C(O)OR, —N(R)N(R)CON$(R)_2$, —N(R)$SO_2$R, —N(R)$SO_2N(R)_2$, —N(R)C(O)OR, —N(R)C(O)R, —N(R)C(S)R, —N(R)C(O)N$(R)_2$, —N(R)C(S)N$(R)_2$, —N(COR)COR, —N(OR)R, —C(—NH)N$(R)_2$, —C(O)N(OR)R, —C(—NOR)R, —OP(O)$(OR)_2$, —P(O)$(R)_2$, —P(O)$(OR)_2$, and —P(O)(H)(OR);

each $R^6$ is independently —H or —(C1-C6)alkyl;

each $R^7$ is independently —H or —(C1-C6)alkyl;

each $R^8$ is independently —(C1-C6)alkyl, —(C3-C10)-cycloalkyl, (C6-C10)-aryl, or 5- to 10-membered heteroaryl, wherein each occurrence of $R^8$ is independently substituted with 0-5 R';

each R is independently selected from:

H—,
(C1-C12)-aliphatic-,
(C3-C10)-cycloalkyl-,
(C3-C10)-cycloalkenyl-,
[(C3-C10)-cycloalkyl]-(C1-C12)-aliphatic-,
[(C3-C10)-cycloalkenyl]-(C1-C12)-aliphatic-,
[(C3-C10)-cycloalkyl]-O—(C1-C12)-aliphatic-,
[(C3-C10)-cycloalkenyl]-O—(C1-C12)-aliphatic-,
(C6-C10)-aryl-,
(C6-C10)-aryl-(C1-C12)aliphatic-,
(C6-C10)-aryl-O—(C1-C12)aliphatic-,
3- to 10-membered heterocyclyl-,
(3- to 10-membered heterocyclyl)-(C1-C12)aliphatic-,
(3- to 10-membered heterocyclyl)-O—(C1-C12)aliphatic-,
5- to 10-membered heteroaryl-,
(5- to 10-membered heteroaryl)-(C1-C12)-aliphatic-, and
(5- to 10-membered heteroaryl)-O—(C1-C12)-aliphatic-;

wherein said heterocyclyl has 1-4 heteroatoms independently selected from N, NH, O, S, SO, and $SO_2$, and said heteroaryl has 1-4 heteroatoms independently selected from N, NH, O, and S;

wherein each occurrence of R is independently substituted with 0-5 R';

or when two R groups bound to the same atom, the two R groups may be taken together with the atom to which they are bound to form a 3- to 10-membered aromatic or non-aromatic ring having 0-4 heteroatoms independently selected from N, NH, O, S, SO, and $SO_2$, wherein said ring is optionally substituted with 0-5 R', and wherein said ring is optionally fused to a (C6-C10) aryl, 5- to 10-membered heteroaryl, (C3-C10)cycloalkyl, or a 3- to 10-membered heterocyclyl;

wherein each occurrence of R' is independently selected from halogen, —R", —OR", oxo, —$CH_2$OR", —$CH_2$NR"$_2$, —C(O)N(R")$_2$, —C(O)OR", —$NO_2$, —NCS, —CN, —$CF_3$, —$OCF_3$ and —N(R")$_2$;

wherein each occurrence of R" is independently selected from H, —(C1-C6)-alkyl, (C3-C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, and (C6-C10)-aryl-O—(C1-C6)-alkyl-.

The present invention provides a compound of formula I:

I

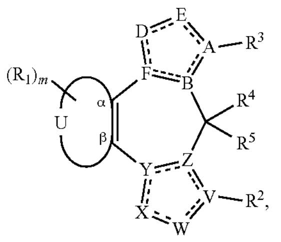

or a pharmaceutically acceptable salt, hydrate, solvate, polymorph, isomer, or combination thereof, wherein:

U and the two carbon atoms designated by α and β together form a 5- or 6-membered aromatic ring having 0-2 nitrogen atoms;

A is C, $CR^6$, or N;

B and F are each independently selected from C, $CR^6$, and N, wherein B and F cannot both be N;

D is N, $NR^7$, O, $CR^6$ or $C(R^6)_2$;

E is N, $NR^7$, $CR^6$ or $C(R^6)_2$;

W is N, $NR^7$, $CR^6$ or $C(R^6)_2$;

X is N, $NR^7$, O, $CR^6$ or $C(R^6)_2$;

Y and Z are each independently selected from C, $CR^6$, and N, wherein Y and Z cannot both be N;

V is C or $CR^6$, or when Z is C or $CR^6$, V is C, $CR^6$, or N;

wherein when the ring formed by X, Y, Z, V and W is

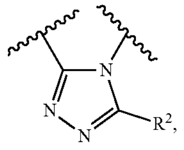

then $R^2$ is $—(CH_2)_nOR^8$ or $—(CH_2)_nO(CH_2)_nR^8$; and wherein $R^2$ is independently substituted with 0-5 R';

m and n are independently integers selected from 0-4;

p is an integer selected from 2-4;

each occurrence of the bond “- - -” is either a single bond or a double bond;

each $R^1$ is independently selected from: halogen, —R, and —OR;

$R^2$ is selected from: halogen, —R and $—(CR_2)_{1-3}—OR$;

$R^3$ is selected from: —R and —CN;

$R^4$ and $R^5$ are each independently —H or —(C1-C6)alkyl;

each $R^6$ is independently —H or —(C1-C6)alkyl;

each $R^7$ is independently —H or —(C1-C6)alkyl;

each $R^8$ is independently —(C1-C6)alkyl, —(C3-C10)-cycloalkyl, (C6-C10)-aryl, or 5- to 10-membered heteroaryl, wherein each occurrence of $R^8$ is independently substituted with 0-5 R';

each R is independently selected from:

H—,
(C1-C12)-aliphatic-,
(C3-C10)-cycloalkyl-,
(C3-C10)-cycloalkenyl-,
[(C3-C10)-cycloalkyl]-(C1-C12)-aliphatic-,
[(C3-C10)-cycloalkenyl]-(C1-C12)-aliphatic-,
[(C3-C10)-cycloalkyl]-O—(C1-C12)-aliphatic-,
[(C3-C10)-cycloalkenyl]-O—(C1-C12)-aliphatic-,
(C6-C10)-aryl-,
(C6-C10)-aryl-(C1-C12)aliphatic-,
(C6-C10)-aryl-O—(C1-C12)aliphatic-,
(C6-C10)-aryl-N(R")—(C1-C12)aliphatic-,
3- to 10-membered heterocyclyl-,
(3- to 10-membered heterocyclyl)-(C1-C12)aliphatic-,
(3- to 10-membered heterocyclyl)-O—(C1-C12)aliphatic-,
(3- to 10-membered heterocyclyl)-N(R")—(C1-C12) aliphatic-,
5- to 10-membered heteroaryl-,
(5- to 10-membered heteroaryl)-(C1-C12)-aliphatic-,
(5- to 10-membered heteroaryl)-O—(C1-C12)-aliphatic-; and
(5- to 10-membered heteroaryl)-N(R")—(C1-C12)-aliphatic-;

wherein said heterocyclyl has 1-4 heteroatoms independently selected from N, NH, O, S, SO, and $SO_2$, and said heteroaryl has 1-4 heteroatoms independently selected from N, NH, O, and S;

wherein each occurrence of R is independently substituted with 0-5 R';

or when two R groups bound to the same atom, the two R groups may be taken together with the atom to which they are bound to form a 3- to 10-membered aromatic or non-aromatic ring having 0-4 heteroatoms independently selected from N, NH, O, S, SO, and $SO_2$, wherein said ring is optionally substituted with 0-5 R', and wherein said ring is optionally fused to a (C6-C10) aryl, 5- to 10-membered heteroaryl, (C3-C10)cycloalkyl, or a 3- to 10-membered heterocyclyl;

wherein each occurrence of R' is independently selected from halogen, —R", —OR", oxo, $—CH_2OR"$, $—CH_2NR"_2$, $—C(O)N(R")_2$, —C(O)OR", $—NO_2$, —NCS, —CN, $—CF_3$, $—OCF_3$ and $—N(R")_2$;

wherein each occurrence of R" is independently selected from H, —(C1-C6)-alkyl, —(C1-C6)-aliphatic, (C3-C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, and (C6-C10)-aryl-O—(C1-C6)-alkyl-, wherein each occurrence of R" is independently substituted with 0-5 substituents selected from: halogen, $—R^\circ$, $—OR^\circ$, oxo, $—CH_2OR^\circ$, $—CH_2N(R^\circ)_2$, $—C(O)N(R^\circ)_2$, $—C(O)OR^\circ$, $—NO_2$, —NCS, —CN, $—CF_3$, $—OCF_3$ and $—N(R^\circ)_2$, wherein each occurrence of $R^\circ$ is independently selected from: —(C1-C6)-aliphatic, (C3-C6)-cycloalkyl, 3- to 6-membered heterocyclyl, 5- to 10-membered heteroaryl-, and (C6-C10)-aryl-.

The present invention provides a compound of formula I:

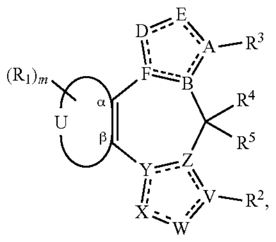

I or a pharmaceutically acceptable salt, hydrate, solvate, polymorph, isomer, or combination thereof, wherein:

U and the two carbon atoms designated by α and β together form a 5- or 6-membered aromatic ring having 0-2 nitrogen atoms;

A is C, $CR^6$, or N;

B and F are each independently selected from C, $CR^6$, and N, wherein B and F cannot both be N;

D is N, $NR^7$, O, $CR^6$ or $C(R^6)_2$;

E is N, $NR^7$, $CR^6$ or $C(R^6)_2$;

W is N, $NR^7$, $CR^6$ or $C(R^6)_2$;

X is N, $NR^7$, O, $CR^6$ or $C(R^6)_2$;

Y and Z are each independently selected from C, $CR^6$, and N, wherein Y and Z cannot both be N;

V is C or $CR^6$, or when Z is C or $CR^6$, V is C, $CR^6$, or N;

wherein when the ring formed by X, Y, Z, V and W is

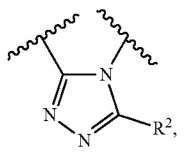

then $R^2$ is $—(CH_2)_nOR^8$ or $—(CH_2)_nO(CH_2)_nR^8$, wherein each occurrence of $R^8$ is independently —(C1-C6)alkyl or (C6-C10)-aryl (e.g., phenyl), and wherein $R^2$ is independently substituted with 0-5 R';

m and n are independently integers selected from 0-4 (in some embodiments, m is 1);

p is an integer selected from 2-4;

each occurrence of the bond “- - -” is either a single bond or a double bond;

each $R^1$ is independently selected from: —Cl, —F, —OMe, and —C≡CH;

$R^2$ is halogen, $—(CR_2)_{1-3}—OR$, wherein each occurrence of R is independently selected from —H, —(C1-C6) alkyl, (C6-C10)-aryl- (e.g., phenyl), and (C6-C10)-aryl-(C1-C12)aliphatic- (e.g., phenyl-(C1-C6)alkyl-), and wherein each occurrence of R is independently substituted with 0-5 R';

$R^3$ is selected from: —CN, —C≡CH, —C≡C—(C1-C6) alkyl, —C≡C-phenyl,

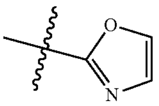
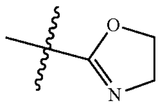
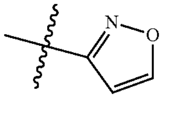
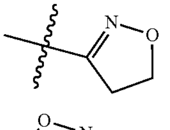
and
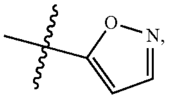

wherein $R^3$ is substituted with 0-5 R';

each occurrence of $R^4$ and $R^5$ is independently —H or —(C1-C6)alkyl;

each $R^6$ is independently —H or —(C1-C6)alkyl;

each $R^7$ is independently —H or —(C1-C6)alkyl;

wherein each occurrence of R' is independently selected from halogen, —R", —OR", oxo, —$CH_2$OR", —$CH_2$NR"$_2$, —C(O)N(R")$_2$, —C(O)OR", —$NO_2$, —NCS, —CN, —$CF_3$, —$OCF_3$ and —N(R")$_2$;

wherein each occurrence of R" is independently selected from H, —(C1-C6)-alkyl, —(C1-C6)-aliphatic, (C3-C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, and (C6-C10)-aryl-O—(C1-C6)-alkyl-, wherein each occurrence of R" is independently substituted with 0-5 substituents selected from: halogen, —R°, —OR°, oxo, —$CH_2$OR", —$CH_2$NR°$_2$, —C(O)N(R°)$_2$, —C(O)OR°, —$NO_2$, —NCS, —CN, —$CF_3$, —$OCF_3$ and —N(R°)$_2$, wherein each occurrence of R° is independently selected from: —(C1-C6)-aliphatic, (C3-C6)-cycloalkyl, 3- to 6-membered heterocyclyl, 5- to 10-membered heteroaryl-, and (C6-C10)-aryl-.

In some of the above embodiments, $R^3$ is selected from:

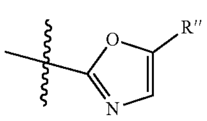
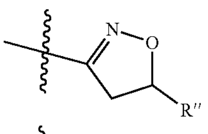
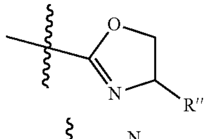
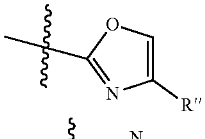
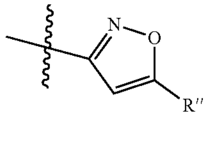
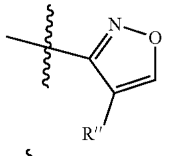
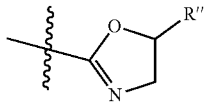
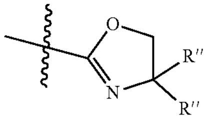

-continued

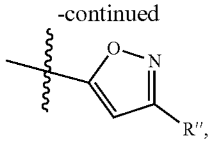

wherein each occurrence of R" is independently selected from —(C1-C6)-alkyl (e.g., linear or branched), —C≡CH, phenyl, thiophene, (5- to 10-membered heteroaryl)-(C1-C6)-alkyl-, (C6-C10)-aryl-(C1-C6)-alkyl-, wherein each R" is independently substituted with 0-3 substituents selected from: halogen, —R°, —OR°, oxo, —$CH_2$OR°, —$CH_2$NR°2, —C(O)N(R°)$_2$, —C(O)OR°, —$NO_2$, —NCS, —CN, —$CF_3$, —$OCF_3$ and —N(R°)$_2$, wherein each occurrence of R° is independently selected from: —(C1-C6)-aliphatic, (C3-C6)-cycloalkyl, 3- to 6-membered heterocyclyl, 5- to 10-membered heteroaryl-, and (C6-C10)-aryl-.

In some embodiments of a compound of formula I, X, Y, Z, V and W together form a 5-membered aromatic or non-aromatic ring having 1-4 nitrogen atoms, wherein said ring is substituted with 0-3 $R^6$ and 0-2 $R^7$. In some embodiments, X, Y, Z, V and W together form a 5-membered aromatic ring having 1-3 nitrogen atoms, wherein said ring is substituted with 0-2 $R^6$ and 0-1 $R^7$.

In certain embodiments, X, Y, Z, V and W form a ring that is selected from:

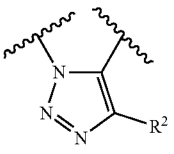
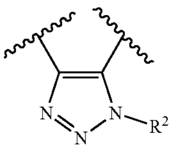
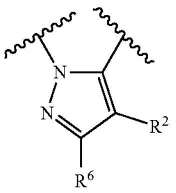
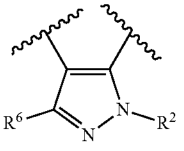
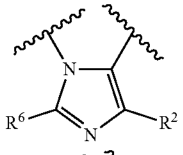
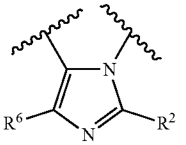
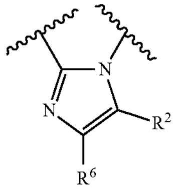
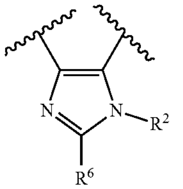
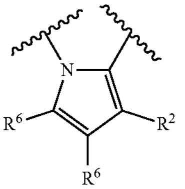
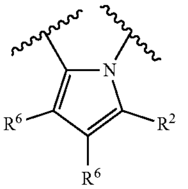
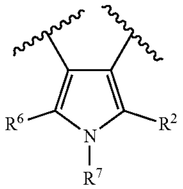

-continued
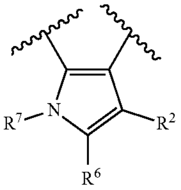
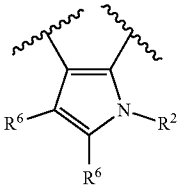
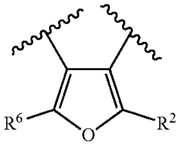
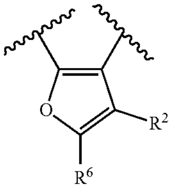
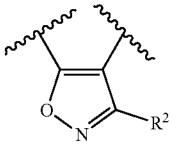
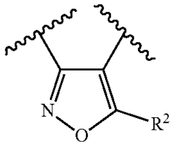
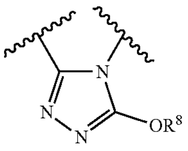
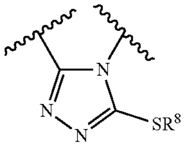
and
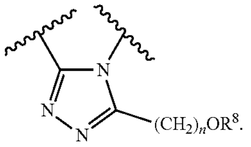
In some embodiments, X, Y, Z, V and W form a ring that is selected from:
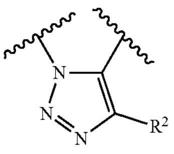
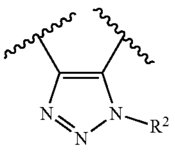
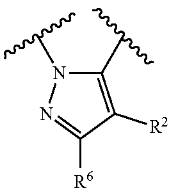
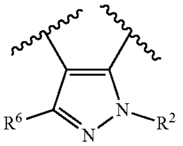
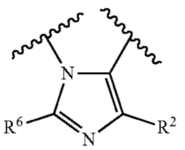
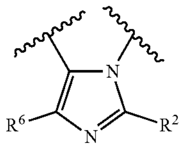
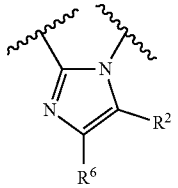
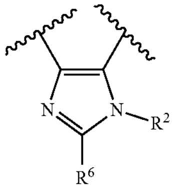
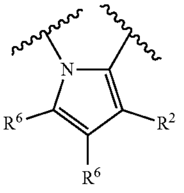
-continued
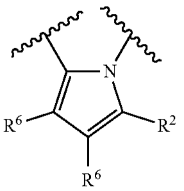
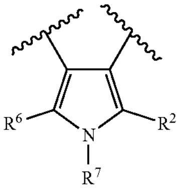
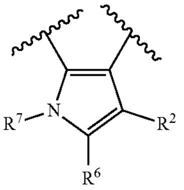
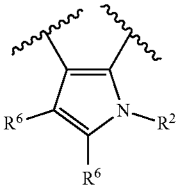
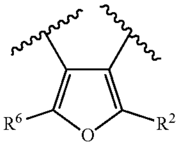
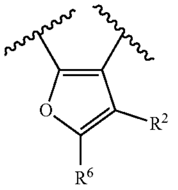
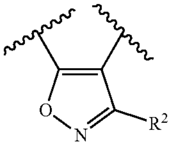
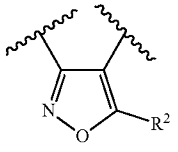
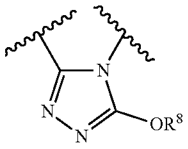
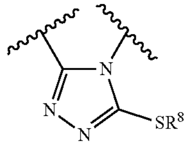
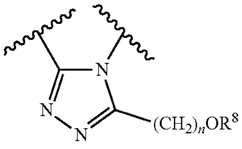
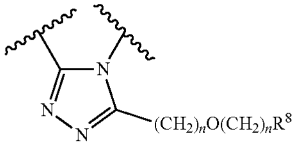
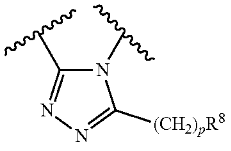
and
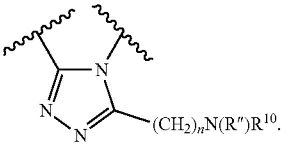
In some embodiments of a compound of formula I, W is N. In some embodiments, W is N, and X, Y, Z, V and W form a ring that is selected from:
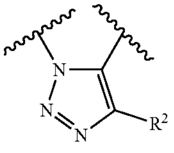
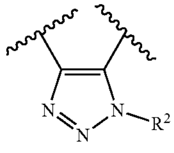

-continued
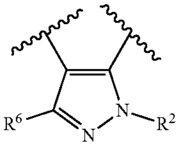
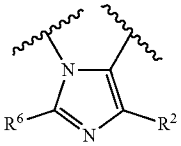
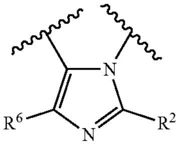
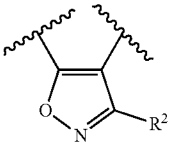
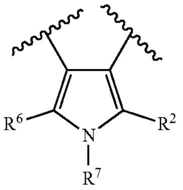
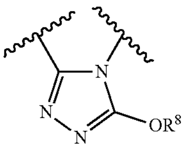
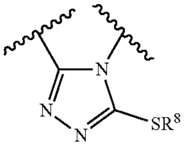
and
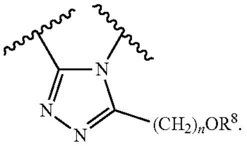
In some embodiments, W is N, and X, Y, Z, V and W form a ring that is selected from:
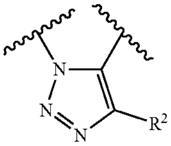
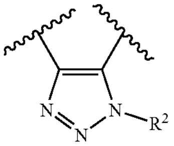
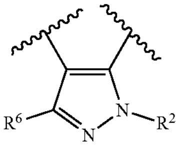
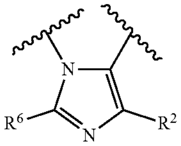
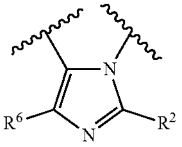
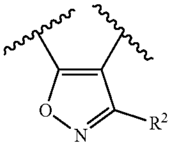
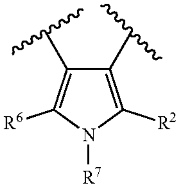
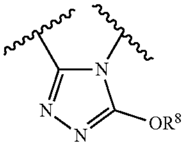
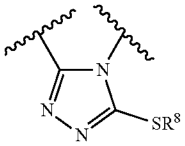
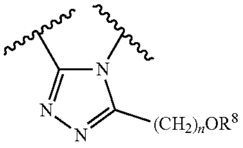
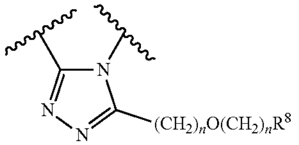
-continued
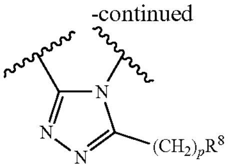
and
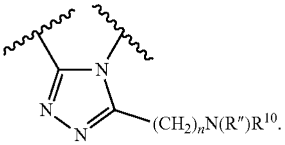
In certain embodiments of a compound of formula I, the ring formed by X, Y, Z, V and W is:
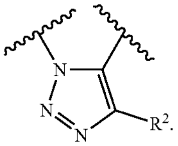
In certain embodiments of a compound of formula I, the ring formed by X, Y, Z,
V and W is:
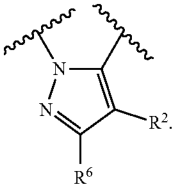
In certain embodiments of a compound of formula I, the ring formed by X, Y, Z, V and W is selected from:
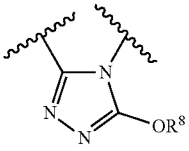
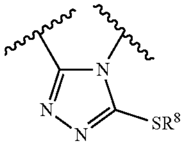
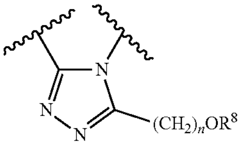
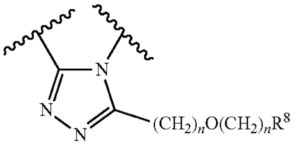
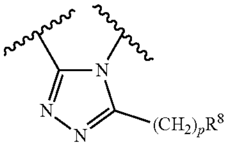
and
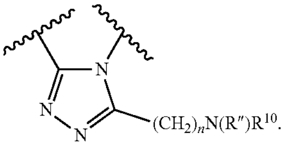

In certain embodiments of a compound of formula I, the ring formed by X, Y, Z, V and W is selected from:

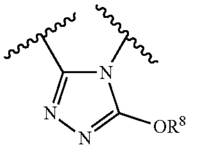 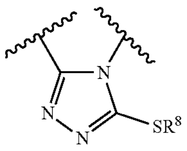 and

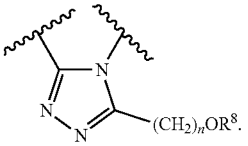

In some embodiments, the ring formed by X, Y, Z V and W is:

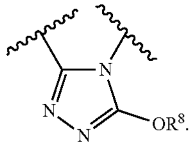

In some embodiments, the ring formed by X, Y, Z, V and W is:

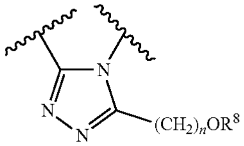 or

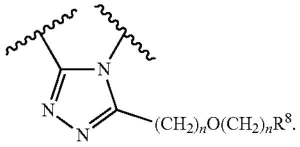

In some embodiments of a compound of formula I, A, B, D, E and F together form a 5-membered aromatic or non-aromatic ring having 1-4 nitrogen atoms, wherein said ring is substituted with 0-3 $R^6$ and 0-2 $R^7$. In certain embodiments, A, B, D, E and F together form a 5-membered aromatic ring having 1-3 nitrogen atoms, wherein said ring is substituted with 0-2 $R^6$ and 0-1 $R^7$.

In some embodiments of a compound of formula I, A, B, D, E and F form a ring that is selected from:

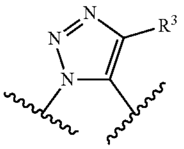 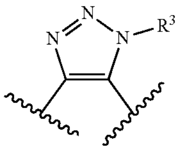

-continued

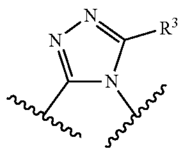 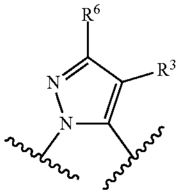

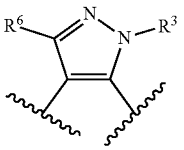 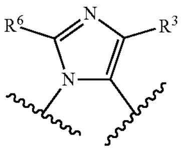

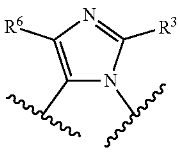 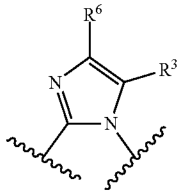

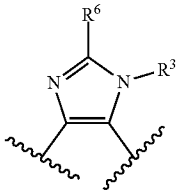 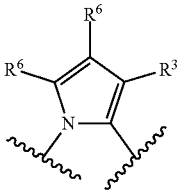

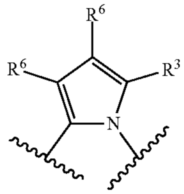 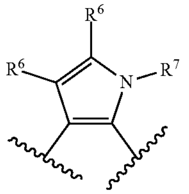

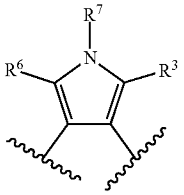 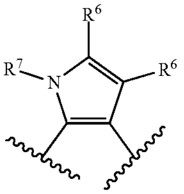

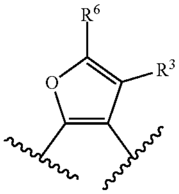 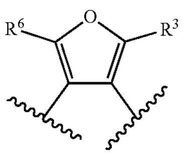

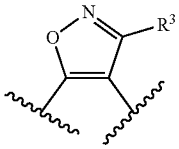 and 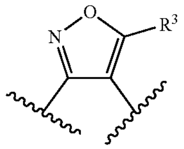

In certain embodiments of a compound of formula I, the ring formed by A, B, D, F and E is:

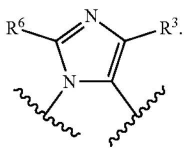

In some embodiments of a compound of formula I, the compound has a structure of formula II:

II

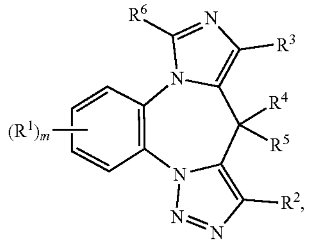

or a pharmaceutically acceptable salt, hydrate, solvate, polymorph, isomer, or combination thereof, wherein m, $R^1$, $R^2$, $R^3$, $R^4$, $R^5$ and $R^6$ are as defined in formula I.

In some embodiments of a compound of formula I, the compound has a structure of formula III:

III

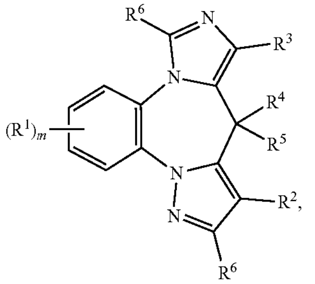

or a pharmaceutically acceptable salt, hydrate, solvate, polymorph, isomer, or combination thereof, wherein m, $R^1$, $R^2$, $R^3$, $R^4$, $R^5$ and $R^6$ are as defined in formula I.

In some embodiments of a compound of formula I, the compound has a structure of formula IV:

IV

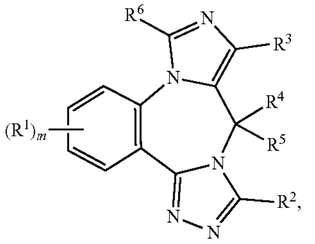

or a pharmaceutically acceptable salt, hydrate, solvate, polymorph, isomer, or combination thereof, wherein $R^2$ is —$OR^8$, —$SR^8$, or —$(CH_2)_nOR^8$, wherein $R^2$ is independently substituted with 0-5 R' and wherein m, n, $R^1$, $R^3$, $R^4$, $R^5$, $R^6$, and $R^8$ are as defined in formula I. In some embodiments, $R^2$ is —$OR^8$. In some embodiments, $R^2$ is —$(CH_2)_nOR^8$.

In some embodiments of a compound of formula I, the compound has a structure of formula IV:

IV

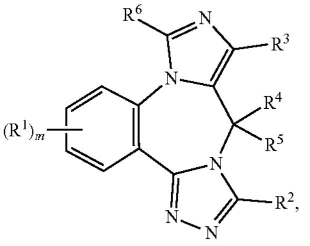

or a pharmaceutically acceptable salt, hydrate, solvate, polymorph, isomer, or combination thereof, wherein $R^2$ is —$(CH_2)_nO(CH_2)_nR^8$, —$(CH_2)_pR^8$ or —$(CH_2)_nN(R'')R^{10}$, wherein $R^2$ is independently substituted with 0-5 R' and wherein m, n, p, $R^1$, $R^3$, $R^4$, $R^5$, $R^6$, $R^8$, $R^{10}$, and R'' are as defined herein. In some embodiments, $R^2$ is —$(CH)_nO(CH_2)_nR^8$.

In some embodiments of a compound of formula I, II, III, or IV, each occurrence of $R^1$ is selected from: halogen, —R, —OR, —$NO_2$, —CN, —$CF_3$, —$OCF_3$, —$N(R)_2$, and —$N(R)SO_2R$, wherein each occurrence of R is independently substituted with 0-5 R'. In some embodiments, each occurrence of $R^1$ is independently selected from: halogen, —H, —(C1-C6)alkyl, —OH, —O((C1-C6)alkyl), —$NO_2$, —CN, —$CF_3$, —$OCF_3$, —$NH_2$, —N((C1-C6)alkyl)$_2$, —N((C1-C6)alkyl)$SO_2$((C1-C6)alkyl), and —$NHSO_2$((C1-C6)alkyl), wherein said alkyl is independently substituted with 0-5 R'. In certain embodiments, each occurrence of $R^1$ is independently selected from: —H, —F, —Cl, —Br, —OH, -Me, -Et, —OMe, —OEt, —$NO_2$, —CN, —$CF_3$, —$OCF_3$, —$NH_2$, —$NMe_2$, —$NEt_2$, —$NHSO_2Me$, and —$NHSO_2Et$. In certain embodiments of a compound of any one of formulae I-IV, at least one $R^1$ is —OR. In some embodiments, the at least one $R^1$ is —O((C1-C6)alkyl), such as —OMe.

In some embodiments of a compound of formula I, II or III, $R^2$ is selected from: halogen, —R, —OR, —$NO_2$, —$(CR_2)_{1-3}R$, —$(CR_2)_{1-3}$—OR, —CN, —$CF_3$, —$C(O)NR_2$, —C(O)OR, and —$OCF_3$, wherein each occurrence of R is independently substituted with 0-5 R'. In some embodiments, $R^2$ is selected from:

—H, —(C1-C6)alkyl, —$CH_2$—O((C1-C6)alkyl), —(C((C1-C6)alkyl)$_2$)$_{1-3}$—O((C1-C6)alkyl), —OH,
—O((C1-C6)alkyl), —$NO_2$, —CN, —$CF_3$, —$OCF_3$, (C3-C10)-cycloalkyl-,
—C(O)N((C1-C6)alkyl)$_2$, —C(O)O((C1-C6)alkyl), 3- to 10-membered heterocyclyl-,
(C6-C10)aryl-, 5- to 10-membered heteroaryl-,
(C6-C10)aryl-(C1-C12)aliphatic-,
(C6-C10)aryl-O—(C1-C12)aliphatic-,
(C6-C10)aryl-N(R'')—(C1-C12)aliphatic-,(C6-C10)aryl-(C1-C12)aliphatic-O—,
(5- to 10-membered heteroaryl)-(C1-C12)-aliphatic-,
(5- to 10-membered heteroaryl)-O—(C1-C12)-aliphatic-,
(5- to 10-membered heteroaryl)-N(R'')—(C1-C12)-aliphatic-,
(5- to 10-membered heteroaryl)-(C1-C12)-aliphatic-O—,
(3- to 10-membered heterocyclyl)-(C1-C12)aliphatic-, (3- to 10-membered heterocyclyl)-O—(C1-C12)aliphatic-, (3- to 10-membered heterocyclyl)-N(R")—(C1-C12)aliphatic-, and (3- to 10-membered heterocyclyl)-(C1-C12)aliphatic-O—, wherein $R^2$ is independently substituted with 0-5 R'.

In some embodiments of a compound of formula I, II or III, $R^2$ is selected from: —H, -Me, -Et, propyl, isopropyl, butyl, tert-butyl, cyclopropyl, cyclobutyl, cyclopentyl, cyclohexyl, —$CF_3$, —C(O)OMe, —C(O)OEt, —OMe, —$CH_2$OMe, —$CH_2$OEt, —$CH_2$OPh, —$CH_2$-pyrrolidine, —$CH_2$-morpholine, —$CH_2$-pyridine, and —$CH_2$Ph, wherein said $R^2$ is substituted with 0-3 R'. In some embodiments of a compound of formula I, II or III, $R^2$ is -Me substituted with 0-3 R' selected from —R", —OR", oxo, —$CH_2$OR", —$CH_2$NR"$_2$, —C(O)N(R")$_2$, —C(O)OR", —$NO_2$, —NCS, —CN, —$CF_3$, —$OCF_3$ and —N(R")$_2$, wherein R" is independently selected from H, —(C1-C6)-alkyl, (C6-C10)-aryl-, and (C6-C10)-aryl-(C1-C6)-alkyl-. In some embodiment, $R^2$ is -Me that is independently substituted with 0-3 R' selected from —N(Me)$_2$, —N(Et)$_2$ and —N(Me)($CH_2$Ph).

In some embodiments of a compound of formula I, II or III, $R^2$ is selected from: —$CH_2$Ph, —$CH_2CH_2$Ph, -Ph, —$OCH_2$Ph, —$CH_2$OPh, —$OCH_2CH_2$Ph, —$CH_2CH_2$OPh, —$CH_2$-pyrrolidine, —$CH_2$-morpholine, —$CH_2$-pyridine, and —$CH_2$Ph wherein said Ph, pyrrolidine, pyridine or morpholine is substituted with 0-5 R'. In some embodiments of a compound of formula I, II or III, $R^2$ is selected from: —$CH_2$Ph, —$CH_2CH_2$Ph, -Ph, —$OCH_2$Ph, —$CH_2$OPh, —$OCH_2CH_2$Ph, —$CH_2CH_2$OPh, —$CH_2$-pyrrolidine, —$CH_2$-morpholine, —$CH_2$-pyridine, and —$CH_2$Ph, wherein said Ph, pyrrolidine, pyridine or morpholine is substituted with 0-5 R' independently selected from halogen, (C1-C6)-alkyl, —OH, —O((C1-C6)-alkyl), —$CH_2$OH, —$CH_2$O(C1-C6)-alkyl), —$CH_2$N(C1-C6)-alkyl)$_2$, —C(O)O(C1-C6)-alkyl), —C(O)N(C1-C6)-alkyl)$_2$, —$NO_2$, —CN, —$CF_3$, —$OCF_3$ and —N(C1-C6)-alkyl)$_2$. In some of the above embodiments, the -Ph, pyrrolidine, pyridine or morpholine of $R^2$ is substituted with 0-5 R' independently selected from —F, —Cl, —CN, -Me, -Et, —OMe, and —OEt. In some embodiments of a compound of formula I, II or III, $R^2$ is —$CH_2$Ph, —$CH_2$OPh, —$CH_2$-pyridine, —$CH_2$-pyrrolidine, or —$CH_2$-morpholine wherein said -Ph, pyrrolidine, pyridine or morpholine is substituted with 0-3 R' independently selected from —F, —Cl, —CN, -Me, and —OMe.

In some embodiments of a compound of formula IV, $R^2$ is —$OR^8$, —$SR^8$, —$(CH_2)_nOR^8$, —$(CH_2)_nO(CH_2)_nR^8$, —$(CH_2)_pR^8$ or —$(CH_2)_nN(R")R^{10}$, wherein each $R^8$ is independently —(C1-C6)alkyl, —(C3-C10)-cycloalkyl, (C6-C10)-aryl, or 5- to 10-membered heteroaryl, wherein each occurrence of $R^8$ is independently substituted with 0-5 R'; n is an integer selected from 0-4; p is an integer selected from 2-4; and each $R^{10}$ is independently —(C3-C10)-cycloalkyl, 3- to 10-membered heterocyclyl-, (C6-C10)-aryl, or 5- to 10-membered heteroaryl, wherein each occurrence of $R^{10}$ is independently substituted with 0-5 R'. In some embodiments, $R^2$ is $OR^8$. In some embodiments, $R^2$ is $OR^8$, wherein $R^8$ is (C6-C10)-aryl, substituted with 0-5 R'. In some embodiments, $R^2$ is $OR^8$, wherein $R^8$ is (C6-C10)-aryl, substituted with 0-3 halogen (such as —F). In some embodiments, $R^2$ is —$(CH_2)_nOR^8$ or —$(CH_2)_nO(CH_2)_nR^8$. In some embodiments, $R^2$ is —$(CH_2)_nOR^8$ or —$(CH_2)_nO(CH_2)_nR^8$, wherein $R^8$ is —(C1-C6)alkyl, (C6-C10)-aryl, or 5- to 10-membered heteroaryl, wherein each occurrence of $R^8$ is independently substituted with 0-5 R'.

In some embodiments of a compound of formula I, II, III, or IV, $R^3$ is selected from: halogen, —R, —CN, —$CF_3$, —$SO_2$R, —C(O)N(R)$_2$, —C(O)R and —C(O)OR, wherein each occurrence of R is independently substituted with 0-5 R'. In some embodiments, $R^3$ is selected from: —F, —Br, —Cl, —(C1-C6)alkyl, —CN, —C≡C, —$CF_3$, —$SO_2$((C1-C6)alkyl), —C(O)N((C1-C6)alkyl)$_2$, —C(O)$NH_2$, —C(O)((C1-C6)alkyl), —$SO_2$((C6-C10)-aryl), —C(O)O((C1-C6)alkyl), —(C2-C6)-alkenyl, —(C2-C6)-alkynyl, —(C6-C10)-aryl, 5- to 10-membered heteroaryl-, and 3- to 10-membered heterocyclyl-, wherein said alkyl, alkenyl, alkynyl, aryl, heteroaryl or heterocyclyl- is independently substituted with 0-5 R'. In some embodiments of a compound of formula I, II, III, or IV, $R^3$ is selected from: —H, —C(O)OMe, —C(O)Et, —C(O)$NMe_2$, —C(O)$NH_2$, —C(O)OEt, —C(O)$OCH_2$(tert-butyl), —C(O)$OCH_2CF_3$, —C(O)O(isopropyl), —C(O)$NEt_2$, —$CHF_2$, —CN, —C≡C, —$SO_2$Me, —$SO_2$Et, —$SO_2$Ph(Me), —$CF_3$, —$CHF_2$, -Me, -Et, —Br, —Cl, —$CH_2$Ph,

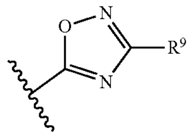
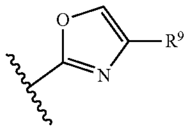
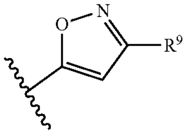
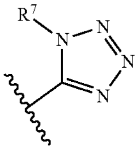
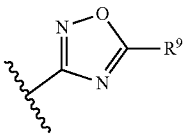
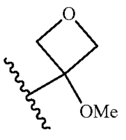
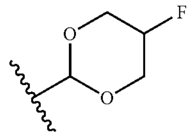
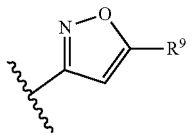
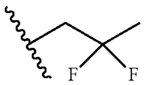
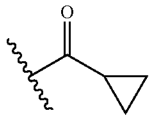
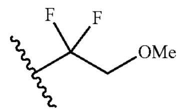
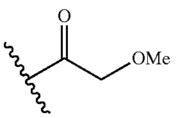
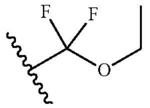
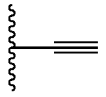
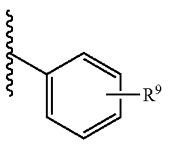
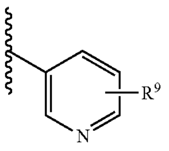
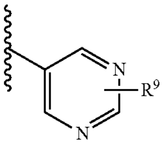

-continued

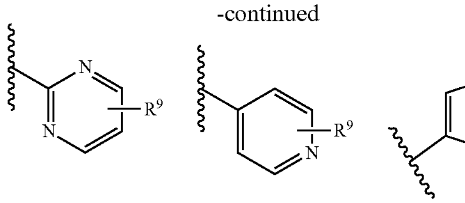

wherein $R^9$ is selected from —H, -Me, -Et, —$CF_3$, isopropyl, —OMe, —OEt, —O-isopropyl, —$CH_2NMe_2$, -tert-butyl and cyclopropyl.

In certain embodiments of a compound of formula I, II, III, or IV, $R^3$ is —C(O)OMe or —C(O)OEt. In certain embodiments of a compound of formula I, II, III, or IV, $R^3$ is

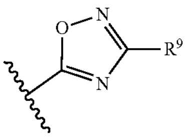

or

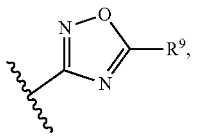

wherein $R^9$ is selected from —H, -Me, -Et, —$CF_3$, isopropyl, —OMe, —OEt, —O-isopropyl, —$CH_2NMe_2$, -tert-butyl and cyclopropyl.

In some embodiments of a compound of formula I, II, III, or IV, $R^4$ and $R^5$ are each independently selected from —H, halogen and —R, wherein each occurrence of R is independently substituted with 0-5 R', or $R^4$ and $R^5$ may be taken together with the carbon atom to which they are bound to form a 3- to 10-membered aromatic or non-aromatic ring having 0-3 additional heteroatoms independently selected from N, O, S, SO, and $SO_2$, wherein said ring is substituted with 0-5 R'. In some embodiments, $R^4$ and $R^5$ are each independently selected from —H, -Me, -Et, —F, or $R^4$ and $R^5$ are taken together with the carbon atom to which they are bound to form a 3- to 8-membered aliphatic ring. In certain embodiments, both $R^4$ and $R^5$ are —H.

In some embodiments, the present invention provides a compound of formula II:

II

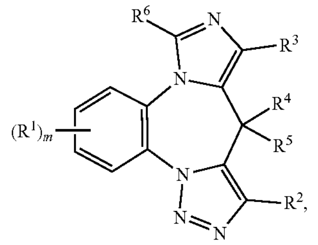

or a pharmaceutically acceptable salt, hydrate, solvate, polymorph, isomer, or combination thereof, wherein:

m is 0-3 (e.g., m is 1);

each $R^1$ is independently selected from: —Cl, —F, —OMe, and —C≡CH;

$R^2$ is halogen, —$(CR_2)_{1-3}$—OR, or —$(CR_2)_{1-3}$—O$(CR_2)_{1-3}$—R, wherein each occurrence of R is independently selected from —H, —(C1-C6)alkyl, (C6-C10)-aryl- (e.g., phenyl), or 5- to 10-membered heteroaryl- (e.g., pyridyl) and (C6-C10)-aryl-(C1-C12)aliphatic- (e.g., phenyl-(C1-C6)alkyl-), and wherein each occurrence of R is independently substituted with 0-5 R';

$R^3$ is selected from: —CN, —C≡CH, —C≡C—(C1-C6) alkyl, —C≡C-phenyl, —COOMe, —COOEt, —(C1-C6)alkyl,

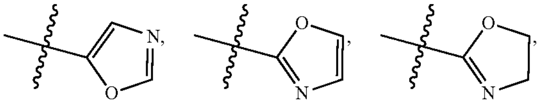

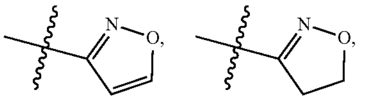

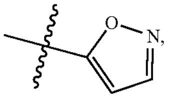

and

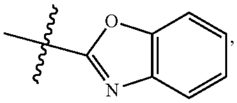

wherein $R^3$ is substituted with 0-5 R';

each occurrence of $R^4$ and $R^5$ is independently —H or —(C1-C6)alkyl;

each $R^6$ is independently —H or —(C1-C6)alkyl;

wherein each occurrence of R' is independently selected from halogen, —R", —OR", oxo, —$CH_2OR$", —$CH_2NR"_2$, —C(O)N$(R")_2$, —C(O)OR", —$NO_2$, —NCS, —CN, —$CF_3$, —$OCF_3$ and —N$(R")_2$;

wherein each occurrence of R" is independently selected from H, —(C1-C6)-alkyl, —(C1-C6)-aliphatic, (C3-C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, or (C6-C10)-aryl-O—(C1-C6)-alkyl-, wherein each occurrence of R" is independently substituted with 0-5 substituents selected from: halogen, —R°, —OR°, oxo, —$CH_2OR$", —$CH_2N(R°)_2$, —C(O)N$(R°)_2$, —C(O)OR°, —$NO_2$, —NCS, —CN, —$CF_3$, —$OCF_3$ and —N$(R°)_2$, wherein each occurrence of R° is independently selected from: —(C1-C6)-aliphatic, (C3-C6)-cycloalkyl, 3- to 6-membered heterocyclyl, 5- to 10-membered heteroaryl-, and (C6-C10)-aryl-.

In some of the above embodiments, $R^1$ is —Cl.

In some of the above embodiments, $R^3$ is selected from:

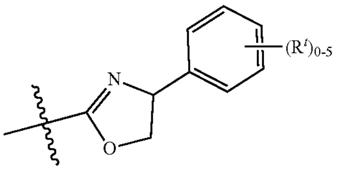

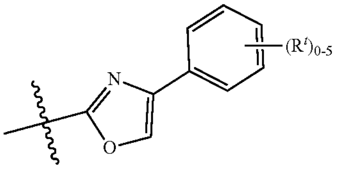

-continued

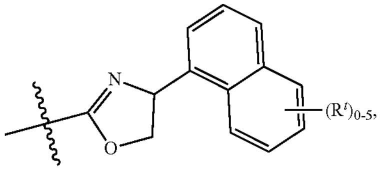

wherein each occurrence of $R^t$ is independently selected from: halogen, —$R^\circ$, —$OR^\circ$, oxo, —$CH_2OR^\circ$, —$CH_2N(R^\circ)_2$, —$C(O)N(R^\circ)_2$, —$C(O)OR^\circ$, —$NO_2$, —NCS, —CN, —$CF_3$, —$OCF_3$ and —$N(R^\circ)_2$, wherein each occurrence of $R^\circ$ is independently selected from: —(C1-C6)-aliphatic, (C3-C6)-cycloalkyl, 3- to 6-membered heterocyclyl, 5- to 10-membered heteroaryl-, and (C6-C10)-aryl-. In some embodiments, $R^3$ is selected from:

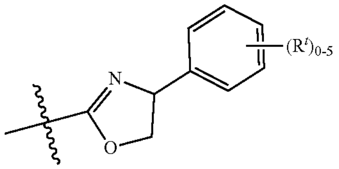

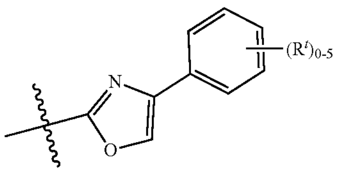

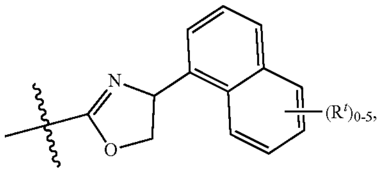

wherein each occurrence of $R^t$ is independently selected from: halogen, —$R^\circ$, —$OR^\circ$, oxo, —$CH_2OR^\circ$, —$CH_2N(R^\circ)_2$, —$C(O)N(R^\circ)_2$, —$C(O)OR^\circ$, —$NO_2$, —NCS, —CN, —$CF_3$, —$OCF_3$ and —$N(R^\circ)_2$, wherein each occurrence of $R^\circ$ is independently selected from: —(C1-C6)-aliphatic, (C3-C6)-cycloalkyl, 3- to 6-membered heterocyclyl, 5- to 10-membered heteroaryl-, and (C6-C10)-aryl-, and $R^2$ is —$(CH_2)_nOR^8$, wherein $R^8$ is —(C1-C6)alkyl (e.g., -Me, -Et, -propyl, or -isopropyl) wherein $R^2$ is independently substituted with 0-5 R'.

In some of the above embodiments, $R^3$ is selected from:

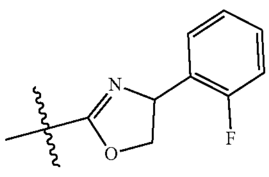

-continued

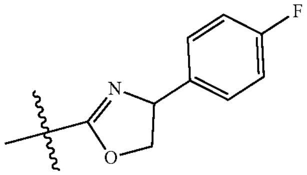

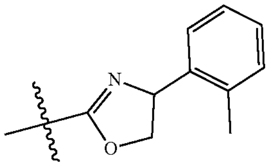

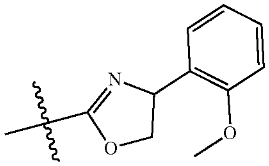

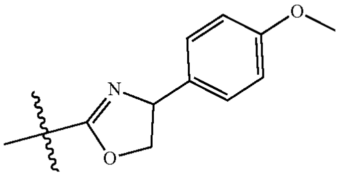

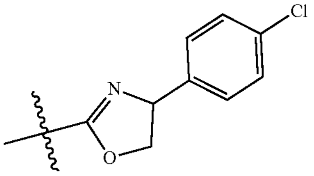

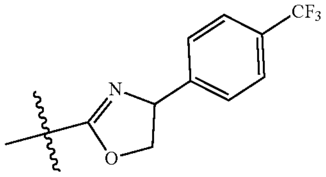

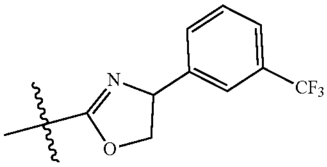

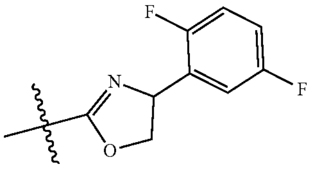

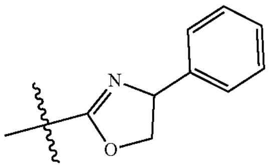

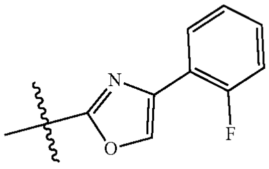

-continued
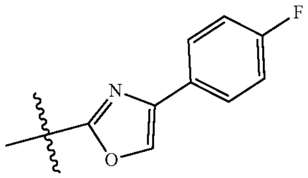
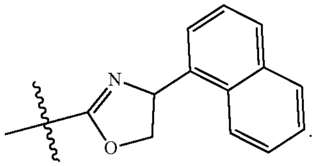
In some of the above embodiments, $R^3$ is selected from:
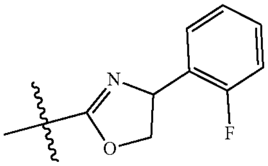
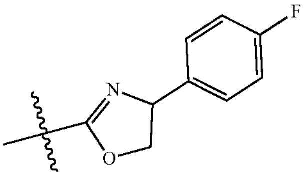
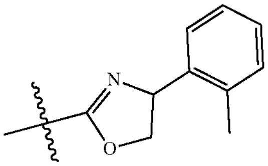
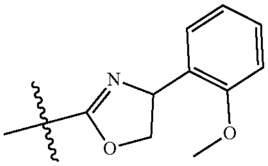
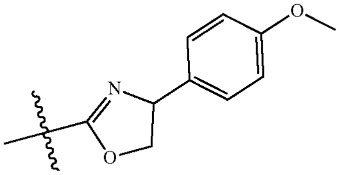
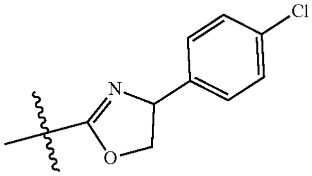
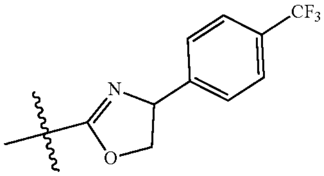
-continued
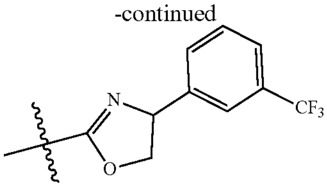
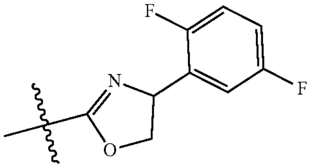
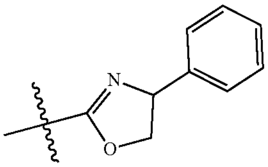
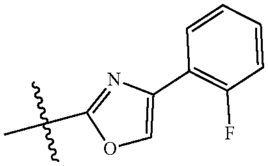
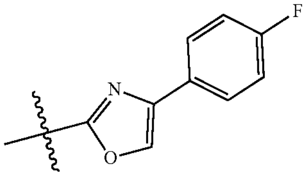
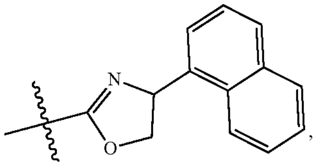
and $R^2$ is —$(CH_2)_nOR^8$, wherein $R^8$ is —(C1-C6)alkyl (e.g., -Me, -Et, -propyl, or -isopropyl).
In some of the above embodiments $R^3$ is selected from:
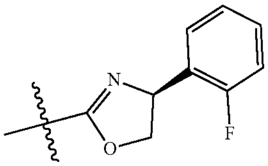
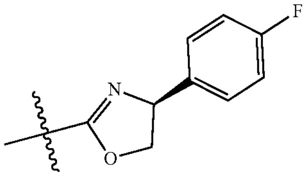
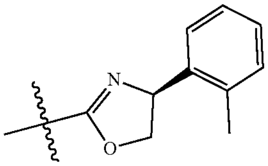

-continued
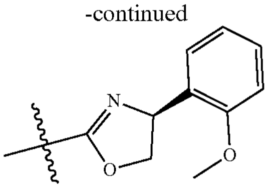
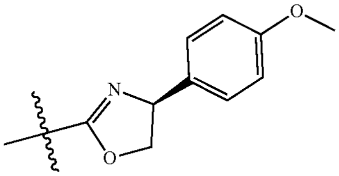
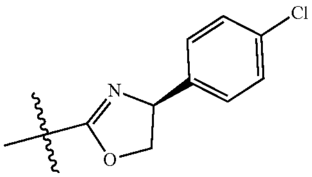
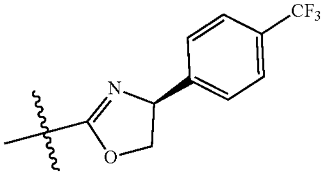
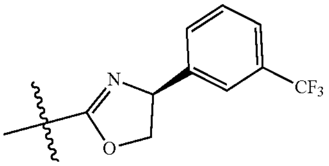
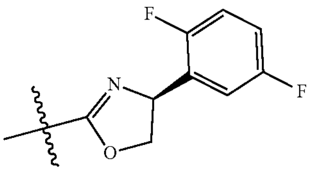
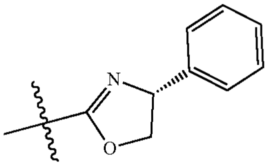
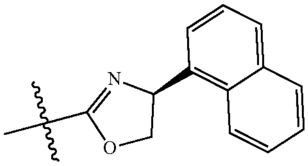
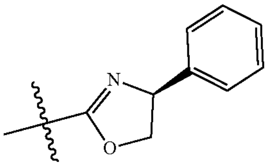
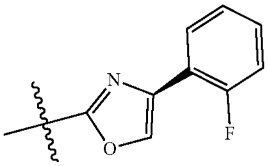
-continued
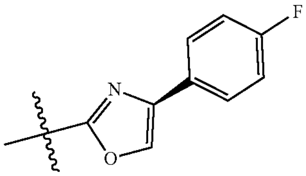
In some embodiments, $R^3$ is selected from:
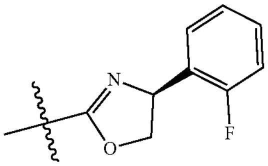
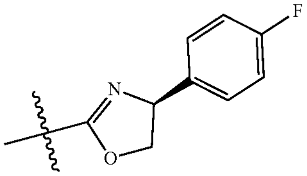
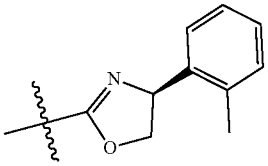
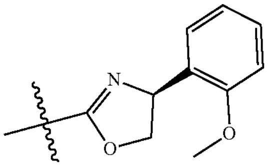
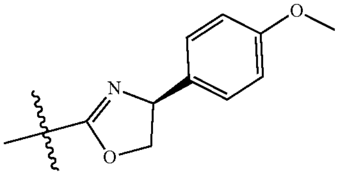
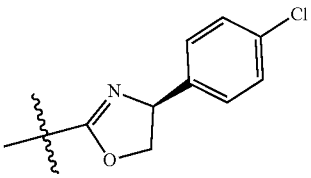
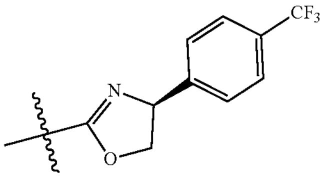
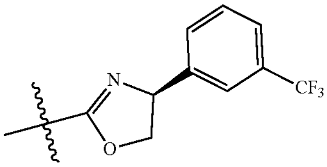

-continued

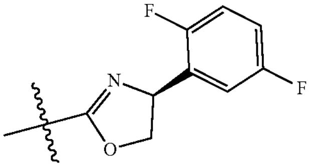

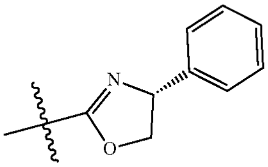

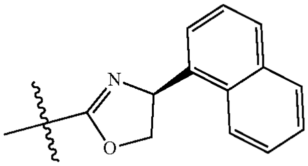

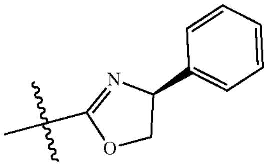

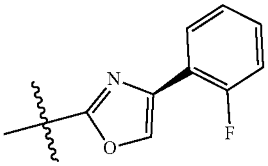

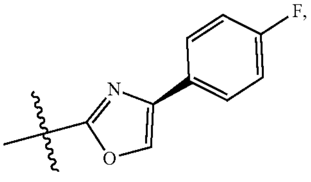

and $R^2$ is —$(CH_2)_nOR^8$, wherein $R^8$ is —(C1-C6)alkyl (e.g., -Me, -Et, -propyl, or -isopropyl).

In some embodiments, $R^2$ is —$(CH_2)_nOR^8$ or —$(CH_2)_nO(CH_2)_nR^8$, wherein each occurrence of $R^8$ is independently (C6-C10)-aryl (e.g., phenyl) or 5- to 10-membered heteroaryl- (e.g., pyridyl) and wherein $R^2$ is independently substituted with 0-5 R'. In some embodiments, $R^2$ is —$(CH_2)_nOR^8$ or —$(CH_2)_nO(CH_2)_nR^8$, wherein each occurrence of $R^8$ is independently (C6-C10)-aryl (e.g., phenyl) or 5- to 10-membered heteroaryl- (e.g., pyridyl) and wherein $R^2$ is independently substituted with 0-5 R', and $R^3$ is selected from: —CN, —C≡CH, —C≡C—(C1-C6)alkyl, —COOMe, —COOEt, —(C1-C6)alkyl,

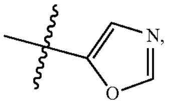
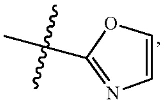
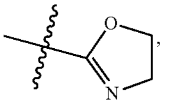
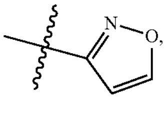
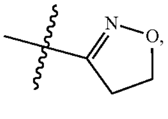
and

-continued

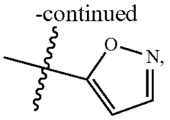

wherein $R^3$ is substituted with 0-3 R'.

In some embodiments, $R^2$ is —$CH_2OR^8$ or —$CH_2OCH_2R^8$, wherein each occurrence of $R^8$ is independently (C6-C10)-aryl (e.g., phenyl) or 5- to 10-membered heteroaryl- (e.g., pyridyl) and wherein $R^2$ is independently substituted with 0-5 R'; and $R^3$ is selected from: —C≡CH, —C≡C—(C1-C6)alkyl,

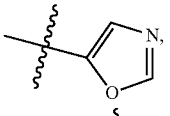
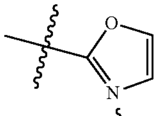
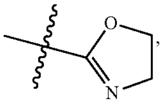
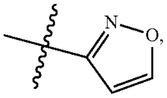
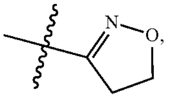
and
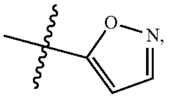

wherein $R^3$ is substituted with 0-2 R' (e.g., $R^3$ is unsubstituted).

In some embodiments, the present invention provides a compound of formula II:

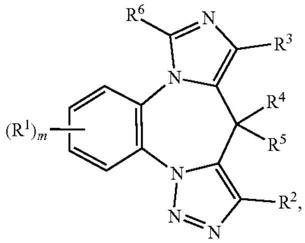

II or a pharmaceutically acceptable salt, hydrate, solvate, polymorph, isomer, or combination thereof, wherein:

m is 0-3 (e.g., m is 1);

each $R^1$ is independently selected from: —Cl, —F, —OMe, and —C═CH;

$R^2$ is halogen or —$(CR)_{1-3}$—OR, wherein each occurrence of R is independently selected from —H, —(C1-C6)alkyl, (C6-C10)-aryl- (e.g., phenyl), and (C6-C10)-aryl-(C1-C12)aliphatic- (e.g., phenyl-(C1-C6)alkyl-), and wherein each occurrence of R is independently substituted with 0-5 R'

$R^3$ is selected from: —CN, —C≡CH, —C≡C—(C1-C6) alkyl, —C≡C-phenyl,

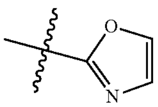
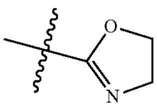

-continued

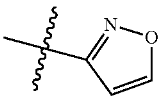 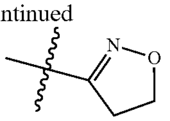 and

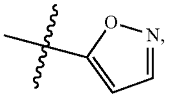

wherein $R^3$ is substituted with 0-5 R';

each occurrence of $R^4$ and $R^5$ is independently —H or —(C1-C6)alkyl;

each $R^6$ is independently —H or —(C1-C6)alkyl;

wherein each occurrence of R' is independently selected from halogen, —R", —OR", oxo, —$CH_2$OR", —$CH_2$NR"$_2$, —C(O)N(R")$_2$, —C(O)OR", —$NO_2$, —NCS, —CN, —$CF_3$, —$OCF_3$ and —N(R")$_2$;

wherein each occurrence of R" is independently selected from H, —(C1-C6)-alkyl, —(C1-C6)-aliphatic, (C3-C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, or (C6-C10)-aryl-O—(C1-C6)-alkyl-, wherein each occurrence of R" is independently substituted with 0-5 substituents selected from: halogen, —$R^\circ$, —$OR^\circ$, oxo, —$CH_2OR^\circ$, —$CH_2N(R^\circ)_2$, —$C(O)N(R^\circ)_2$, —$C(O)OR^\circ$, —$NO_2$, —NCS, —CN, —$CF_3$, —$OCF_3$ and —$N(R^\circ)_2$, wherein each occurrence of $R^\circ$ is independently selected from: —(C1-C6)-aliphatic, (C3-C6)-cycloalkyl, 3- to 6-membered heterocyclyl, 5- to 10-membered heteroaryl-, and (C6-C10)-aryl-.

In some of the above embodiments, $R^3$ is selected from:

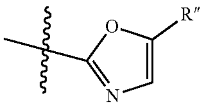 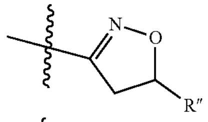

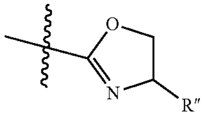 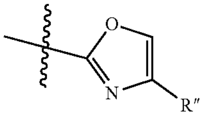

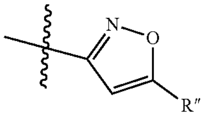 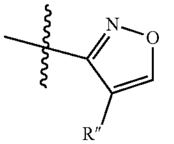

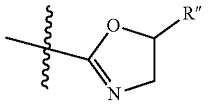 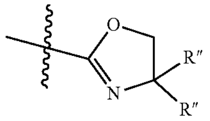

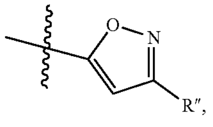

wherein each occurrence of R" is independently selected from —(C1-C6)-alkyl (e.g., linear or branched), —C≡CH, phenyl, thiophene, (5- to 10-membered heteroaryl)-(C1-C6)-alkyl-, and (C6-C10)-aryl-(C1-C6)-alkyl-, wherein each R" is independently substituted with 0-3 substituents selected from: halogen, —$R^\circ$, —$OR^\circ$, oxo, —$CH_2OR^\circ$, —$CH_2N(R^\circ)_2$, —$C(O)N(R^\circ)_2$, —$C(O)OR^\circ$, —$NO_2$, —NCS, —CN, —$CF_3$, —$OCF_3$ and —$N(R^\circ)_2$, wherein each occurrence of $R^\circ$ is independently selected from: —(C1-C6)-aliphatic, (C3-C6)-cycloalkyl, 3- to 6-membered heterocyclyl, 5- to 10-membered heteroaryl-, and (C6-C10)-aryl-.

In some embodiments, the present invention provides a compound of formula II:

II

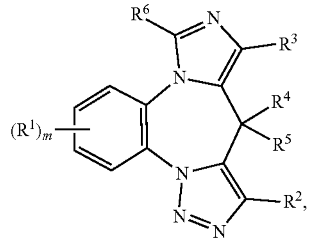

or a pharmaceutically acceptable salt, hydrate, solvate, polymorph, isomer, or combination thereof, wherein:

m is 0-3;

each $R^1$ is independently selected from: halogen (e.g., Cl, F), —H, —(C1-C6)alkyl, —OH, —O((C1-C6)alkyl) (e.g., —OMe), —$NO_2$, —CN, —$CF_3$, and —$OCF_3$, wherein $R^1$ is independently substituted with 0-5 R';

$R^2$ is selected from:

—H, halogen, —(C1-C6)alkyl, —OH, —O((C1-C6) alkyl), —C(O)O((C1-C6)alkyl), —C(O)$NR^2$, (C6-C10)-aryl- (e.g., phenyl), (C6-C10)-aryl-(C1-C12)aliphatic-, (C6-C10)-aryl-O—(C1-C12)aliphatic-, (C6-C10)-aryl-N(R")—(C1-C12)aliphatic-, (5- to 10-membered heteroaryl)-(C1-C12)aliphatic-, (5- to 10-membered heteroaryl)-O—(C1-C12)aliphatic-, (5- to 10-membered heteroaryl)-N(R")—(C1-C12)aliphatic-, (3- to 10-membered heterocyclyl)-(C1-C12)aliphatic-, (3- to 10-membered heterocyclyl)-O—(C1-C12)aliphatic-, and (3- to 10-membered heterocyclyl)-N(R")—(C1-C12) aliphatic-, wherein $R^2$ is independently substituted with 0-5 R';

$R^3$ is selected from:

—(C1-C6)alkyl, —(C2-C6)alkenyl (e.g., —CH≡$CH_2$), —C≡CH, —CN, halogen (e.g., Br), —$SO_2$((C6-C10)-aryl), —$SO_2$((C1-C6)alkyl), —C(O)N((C1-C6)alkyl)$_2$, —C(O)$NH_2$, —C(O)O((C1-C6)alkyl), —C(O)((C1-C6)alkyl), —(C6-C10)aryl, 5- to 10-membered heteroaryl (e.g., 5-membered heteroaryl such as an optionally substituted

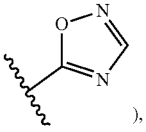 [SMILES: *c1ncno1] ), and 5- to 10-membered heterocyclyl (e.g., 5-membered heterocyclyl such as an optionally substituted

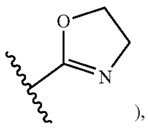 [SMILES: *C1=NCCO1]

), wherein $R^3$ is independently substituted with 0-5 R';

$R^4$ and $R^5$ are each independently selected from —H, halogen and —(C1-C6)alkyl;

$R^6$ is selected from —H and —(C1-C6)alkyl;

each R is independently selected from:

H—, (C1-C12)-aliphatic-, (C3-C10)-cycloalkyl-, (C3-C10)-cycloalkenyl-,

[(C3-C10)-cycloalkyl]-(C1-C12)-aliphatic-,

[(C3-C10)-cycloalkenyl]-(C1-C12)-aliphatic-,

[(C3-C10)-cycloalkyl]-O—(C1-C12)-aliphatic-,

[(C3-C10)-cycloalkenyl]-O—(C1-C12)-aliphatic-, (C6-C10)-aryl-, (C6-C10)-aryl-(C1-C12)aliphatic-, (C6-C10)-aryl-O—(C1-C12)aliphatic-, (C6-C10)-aryl-N(R")—(C1-C12)aliphatic-, 3- to 10-membered heterocyclyl-, (3- to 10-membered heterocyclyl)-(C1-C12)aliphatic-, (3- to 10-membered heterocyclyl)-O—(C1-C12)aliphatic-, (3- to 10-membered heterocyclyl)-N(R")—(C1-C12) aliphatic-, 5- to 10-membered heteroaryl-, (5- to 10-membered heteroaryl)-(C1-C12)-aliphatic-, (5- to 10-membered heteroaryl)-O—(C1-C12)-aliphatic-; and (5- to 10-membered heteroaryl)-N(R")—(C1-C12)-aliphatic-;

wherein said heterocyclyl has 1-4 heteroatoms independently selected from N, NH, O, S, SO, and $SO_2$, and said heteroaryl has 1-4 heteroatoms independently selected from N, NH, O, and S;

wherein each occurrence of R is independently substituted with 0-5 R';

or when two R groups bound to the same atom, the two R groups may be taken together with the atom to which they are bound to form a 3- to 10-membered aromatic or non-aromatic ring having 0-4 heteroatoms independently selected from N, NH, O, S, SO, and $SO_2$, wherein said ring is optionally substituted with 0-5 R', and wherein said ring is optionally fused to a (C6-C10) aryl, 5- to 10-membered heteroaryl, (C3-C10)cycloalkyl, or a 3- to 10-membered heterocyclyl;

wherein each occurrence of R' is independently selected from halogen, —R", —OR", oxo, —$CH_2$OR", —$CH_2$NR"$_2$, —C(O)N(R")$_2$, —C(O)OR", —$NO_2$, —NCS, —CN, —$CF_3$, —$OCF_3$ and —N(R")$_2$;

wherein each occurrence of R" is independently selected from H, —(C1-C6)-alkyl, (C3—C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, and (C6-C10)-aryl-O—(C1-C6)-alkyl-.

In some embodiments, the present invention provides a compound of formula II:

II

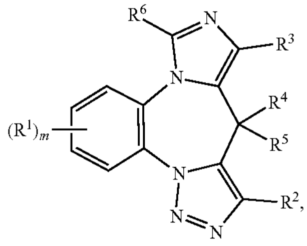

or a pharmaceutically acceptable salt, hydrate, solvate polymorph, isomer, or combination thereof, wherein:

m is 0-3;

each $R^1$ is independently selected from: halogen (e.g., Cl, F), —H, —(C1-C6)alkyl, —OH, —O((C1-C6)alkyl) (e.g., —OMe), —$NO_2$, —CN, —$CF_3$, and —$OCF_3$, wherein $R^1$ is independently substituted with 0-5 R';

$R^2$ is selected from:

—H, —C(O)$NR^2$, and (C6-C10)-aryl- (e.g., phenyl);

$R^3$ is selected from:

—(C1-C6)alkyl, —(C2-C6)alkenyl (e.g., —CH≡$CH_2$), —C≡CH, —CN, halogen (e.g., Br), —$SO_2$((C6-C10)-aryl), —$SO_2$((C1-C6)alkyl), —C(O)N((C1-C6)alkyl)$_2$, —C(O)$NH_2$, —C(O)O((C1-C6)alkyl), —C(O)((C1-C6)alkyl), —(C6-C10)aryl, 5- to 10-membered heteroaryl (e.g., 5-membered heteroaryl such as an optionally substituted

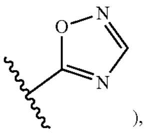 [SMILES: *c1ncno1]

), and 5- to 10-membered heterocyclyl (e.g., 5-membered heterocyclyl such as an optionally substituted

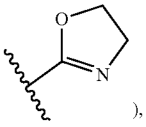

), wherein $R^3$ is independently substituted with 0-5 R';

$R^4$ and $R^5$ are each —H, halogen and —(C1-C6)alkyl;

$R^6$ is selected from —H and —(C1-C6)alkyl;

each R is independently selected from:

H—, (C1-C12)-aliphatic-, (C3-C10)-cycloalkyl-, (C3-C10)-cycloalkenyl-,

[(C3-C10)-cycloalkyl]-(C1-C12)-aliphatic-,

[(C3-C10)-cycloalkenyl]-(C1-C12)-aliphatic-,

[(C3-C10)-cycloalkyl]-O—(C1-C12)-aliphatic-,

[(C3-C10)-cycloalkenyl]-O—(C1-C12)-aliphatic-, (C6-C10)-aryl-, (C6-C10)-aryl-(C1-C12)aliphatic-, (C6-C10)-aryl-O—(C1-C12)aliphatic-, (C6-C10)-aryl-N(R")—(C1-C12)aliphatic-, 3- to 10-membered heterocyclyl-, (3- to 10-membered heterocyclyl)-(C1-C12)aliphatic-, (3- to 10-membered heterocyclyl)-O—(C1-C12)aliphatic-, (3- to 10-membered heterocyclyl)-N(R")—(C1-C12) aliphatic-, 5- to 10-membered heteroaryl-, (5- to 10-membered heteroaryl)-(C1-C12)-aliphatic-, (5- to 10-membered heteroaryl)-O—(C1-C12)-aliphatic-; and (5- to 10-membered heteroaryl)-N(R")—(C1-C12)-aliphatic-;

wherein said heterocyclyl has 1-4 heteroatoms independently selected from N, NH, O, S, SO, and $SO_2$, and said heteroaryl has 1-4 heteroatoms independently selected from N, NH, O, and S;

wherein each occurrence of R is independently substituted with 0-5 R';

or when two R groups bound to the same atom, the two R groups may be taken together with the atom to which they are bound to form a 3- to 10-membered aromatic or non-aromatic ring having 0-4 heteroatoms independently selected from N, NH, O, S, SO, and $SO_2$, wherein said ring is optionally substituted with 0-5 R', and wherein said ring is optionally fused to a (C6-C10) aryl, 5- to 10-membered heteroaryl, (C3-C10)cycloalkyl, or a 3- to 10-membered heterocyclyl;

wherein each occurrence of R' is independently selected from halogen, —R", —OR", oxo, —$CH_2$OR", —$CH_2$NR"$_2$, —C(O)N(R")$_2$, —C(O)OR", —$NO_2$, —NCS, —CN, —$CF_3$, —$OCF_3$ and —N(R")$_2$;

wherein each occurrence of R" is independently selected from H, —(C1-C6)-alkyl, (C3-C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, and (C6-C10)-aryl-O—(C1-C6)-alkyl-.

In some embodiments, the present invention provides a compound of formula II:

II

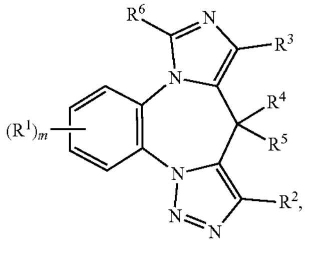

or a pharmaceutically acceptable salt, hydrate, solvate, polymorph, isomer, or combination thereof, wherein:

m is 0-3;

each $R^1$ is independently selected from: halogen (e.g., Cl, F) and —O((C1-C6)alkyl) (e.g., —OMe), wherein $R^1$ is independently substituted with 0-5 R';

$R^2$ is selected from:

—H, —C(O)$NR_2$, and (C6-C10)-aryl- (e.g., phenyl);

$R^3$ is selected from:

halogen (e.g., Br), 5- to 10-membered heteroaryl (e.g., 5-membered heteroaryl such as an optionally substituted

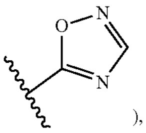 [SMILES: *c1ncno1]

), and 5- to 10-membered heterocyclyl (e.g., 5-membered heterocyclyl such as an optionally substituted

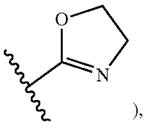 [SMILES: *C1=NCCO1]

), wherein $R^3$ is independently substituted with 0-5 R';

$R^4$ and $R^5$ are each —H;

$R^6$ is —H;

each R is independently selected from:

H—, (C1-C12)-aliphatic-, (C3-C10)-cycloalkyl-, (C3-C10)-cycloalkenyl-,

[(C3-C10)-cycloalkyl]-(C1-C12)-aliphatic-,

[(C3-C10)-cycloalkenyl]-(C1-C12)-aliphatic-,

[(C3-C10)-cycloalkyl]-O—(C1-C12)-aliphatic-,

[(C3-C10)-cycloalkenyl]-O—(C1-C12)-aliphatic-, (C6-C10)-aryl-, (C6-C10)-aryl-(C1-C12)aliphatic-, (C6-C10)-aryl-O—(C1-C12)aliphatic-, (C6-C10)-aryl-N(R")—(C1-C12)aliphatic-, 3- to 10-membered heterocyclyl-, (3- to 10-membered heterocyclyl)-(C1-C12)aliphatic-, (3- to 10-membered heterocyclyl)-O—(C1-C12)aliphatic-, (3- to 10-membered heterocyclyl)-N(R")—(C1-C12) aliphatic-, 5- to 10-membered heteroaryl-, (5- to 10-membered heteroaryl)-(C1-C12)-aliphatic-, (5- to 10-membered heteroaryl)-O—(C1-C12)-aliphatic-; and (5- to 10-membered heteroaryl)-N(R")—(C1-C12)-aliphatic-;

wherein said heterocyclyl has 1-4 heteroatoms independently selected from N, NH, O, S, SO, and $SO_2$, and said heteroaryl has 1-4 heteroatoms independently selected from N, NH, O, and S;

wherein each occurrence of R is independently substituted with 0-5 R';

or when two R groups bound to the same atom, the two R groups may be taken together with the atom to which they are bound to form a 3- to 10-membered aromatic or non-aromatic ring having 0-4 heteroatoms independently selected from N, Nil, O, S, SO, and $SO_2$, wherein said ring is optionally substituted with 0-5 R', and wherein said ring is optionally fused to a (C6-C10) aryl, 5- to 10-membered heteroaryl, (C3—C10)cycloalkyl, or a 3- to 10-membered heterocyclyl;

wherein each occurrence of R' is independently selected from halogen, —R", —OR", oxo, —$CH_2$OR", —$CH_2$NR"$_2$, —C(O)N(R")$_2$, —C(O)OR", —$NO_2$, —NCS, —CN, —$CF_3$, —$OCF_3$ and —N(R")$_2$;

wherein each occurrence of R" is independently selected from H, —(C1-C6)-alkyl, (C3-C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, and (C6-C10)-aryl-O—(C1-C6)-alkyl-.

In some embodiments, the present invention provides a compound of formula II:

II

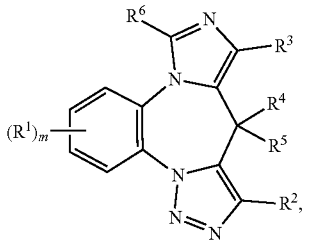

or a pharmaceutically acceptable salt, hydrate, solvate, polymorph, isomer, or combination thereof, wherein:

m is 0-3;

each $R^1$ is independently selected from: halogen (e.g., Cl, F), —H, —(C1-C6)alkyl, —OH, —O((C1-C6)alkyl) (e.g., —OMe), $-NO_2$, —CN, $-CF_3$, and $-OCF_3$, wherein $R^1$ is independently substituted with 0-5 R";

$R^2$ is selected from:

—H, —(C1-C6)alkyl, —OH, —O((C1-C6)alkyl), —C(O)O((C1-C6)alkyl), $-C(O)NR_2$, (C6-C10)-aryl- (C6-C10)-aryl-(C1-C12)aliphatic-, (C6-C10)-aryl-O—(C1-C12)aliphatic-, (C6-C10)-aryl-N(R")—(C1-C12)aliphatic-, (5- to 10-membered heteroaryl)-(C1-C12)aliphatic-, (5- to 10-membered heteroaryl)-O—(C1-C12)aliphatic-, (5- to 10-membered heteroaryl)-N(R")—(C1-C12)aliphatic-, (3- to 10-membered heterocyclyl)-(C1-C12)aliphatic-, (3- to 10-membered heterocyclyl)-O—(C1-C12)aliphatic-, and (3- to 10-membered heterocyclyl)-N(R")—(C1-C12) aliphatic-, wherein $R^2$ is independently substituted with 0-5 R';

$R^3$ is selected from:

—(C2-C6)alkenyl (e.g., $-CH{\equiv}CH_2$) and 5- to 10-membered heterocyclyl (e.g., 5-membered heterocyclyl such as an optionally substituted

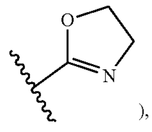 [SMILES: *C1=NCCO1]

), wherein $R^3$ is independently substituted with 0-5 R';

$R^4$ and $R^5$ are each independently selected from —H, halogen and —(C1-C6)alkyl;

$R^6$ is selected from —H and —(C1-C6)alkyl;

each R is independently selected from:

H—, (C1-C12)-aliphatic-, (C3-C10)-cycloalkyl-, (C3-C10)-cycloalkenyl-,

[(C3-C10)-cycloalkyl]-(C1-C12)-aliphatic-,

[(C3-C10)-cycloalkenyl]-(C1-C12)-aliphatic-,

[(C3-C10)-cycloalkyl]-O—(C1-C12)-aliphatic-,

[(C3-C10)-cycloalkenyl]-O—(C1-C12)-aliphatic-, (C6-C10)-aryl-, (C6-C10)-aryl-(C1-C12)aliphatic-, (C6-C10)-aryl-O—(C1-C12)aliphatic-, (C6-C10)-aryl-N(R")—(C1-C12)aliphatic-, 3- to 10-membered heterocyclyl-, (3- to 10-membered heterocyclyl)-(C1-C12)aliphatic-, (3- to 10-membered heterocyclyl)-O—(C1-C12)aliphatic-, (3- to 10-membered heterocyclyl)-N(R")—(C1-C12) aliphatic-, 5- to 10-membered heteroaryl-, (5- to 10-membered heteroaryl)-(C1-C12)-aliphatic-, (5- to 10-membered heteroaryl)-O—(C1-C12)-aliphatic-; and (5- to 10-membered heteroaryl)-N(R")—(C1-C12)-aliphatic-;

wherein said heterocyclyl has 1-4 heteroatoms independently selected from N, NH, O, S, SO, and $SO_2$, and said heteroaryl has 1-4 heteroatoms independently selected from N, NH, O, and S;

wherein each occurrence of R is independently substituted with 0-5 R';

or when two R groups bound to the same atom, the two R groups may be taken together with the atom to which they are bound to form a 3- to 10-membered aromatic or non-aromatic ring having 0-4 heteroatoms independently selected from N, NH, O, S, SO, and $SO_2$, wherein said ring is optionally substituted with 0-5 R', and wherein said ring is optionally fused to a (C6-C10) aryl, 5- to 10-membered heteroaryl, (C3-C10)cycloalkyl, or a 3- to 10-membered heterocyclyl;

wherein each occurrence of R' is independently selected from halogen, —R", —OR", oxo, $-CH_2OR"$, $-CH_2N(R")_2$, $-C(O)N(R")_2$, —C(O)OR", $-NO_2$, —NCS, —CN, $-CF_3$, $-OCF_3$ and $-N(R")_2$;

wherein each occurrence of R" is independently selected from H, —(C1-C6)-alkyl, (C3-C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, and (C6-C10)-aryl-O—(C1-C6)-alkyl-.

In some embodiments, the present invention provides a compound of formula II:

II

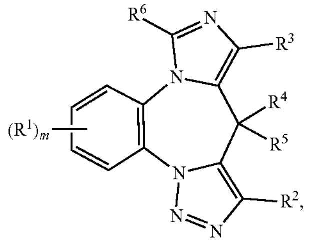

or a pharmaceutically acceptable salt, hydrate, solvate, polymorph, isomer, or combination thereof, wherein:

m is 0-3;

each $R^1$ is independently selected from: halogen (e.g., Cl, F) and —O((C1-C6)alkyl) (e.g., —OMe), wherein $R^1$ is independently substituted with 0-5 R';

$R^2$ is selected from:

—H, —(C1-C6)alkyl, (C6-C10)-aryl- (e.g., phenyl), and (C6-C10)-aryl-(C1-C12)aliphatic-, wherein $R^2$ is independently substituted with 0-5 R';

$R^3$ is selected from:

—(C2-C6)alkenyl (e.g., —CH═CH$_2$) and 5- to 10-membered heterocyclyl (e.g., 5-membered heterocyclyl such as an optionally substituted

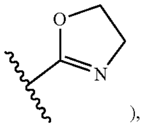 [SMILES: *C1=NCCO1]

), wherein $R^3$ is independently substituted with 0-5 R';

$R^4$ and $R^5$ are each —H;

$R^6$ is —H;

wherein each occurrence of R' is independently selected from halogen, —R", —OR", oxo, —CH$_2$OR", —CH$_2$N(R")$_2$, —C(O)N(R")$_2$, —C(O)OR", —NO$_2$, —NCS, —CN, —CF$_3$, —OCF$_3$ and —N(R")$_2$;

wherein each occurrence of R" is independently selected from H, —(C1-C6)-alkyl, (C3-C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, and (C6-C10)-aryl-O—(C1-C6)-alkyl-.

In some embodiments, the present invention provides a compound of formula II:

II

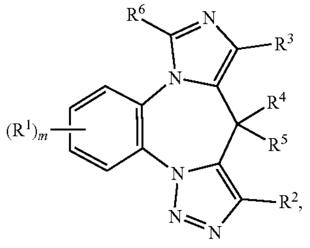

or a pharmaceutically acceptable salt, hydrate, solvate, polymorph, isomer, or combination thereof, wherein:

m is 0-3;

each $R^1$ is independently selected from: halogen, —H, —(C1-C6)alkyl, —OH, —O((C1-C6)alkyl), —NO$_2$, —CN, —CF$_3$, and —OCF$_3$, wherein said alkyl is independently substituted with 0-5 R';

$R^2$ is selected from: —(C1-C6)alkyl, —OH, —O((C1-C6)alkyl), —C(O)O((C1-C6)alkyl), (C6-C10)-aryl-(C1-C12)aliphatic-, (C6-C10)-aryl-O—(C1-C12)aliphatic-, (C6-C10)-aryl-(C1-C12)aliphatic-O—, (3- to 10-membered heterocyclyl)-(C1-C12)aliphatic-, (5- to 10-membered heteroaryl)-(C1-C12)-aliphatic-, (5- to 10-membered heteroaryl)-O—(C1-C12)-aliphatic-, and (5- to 10-membered heteroaryl)-(C1-C12)-aliphatic-O—, wherein said alkyl, aryl or heteroaryl is independently substituted with 0-5 R';

$R^3$ is selected from: —(C1-C6)alkyl, —SO$_2$((C1-C6)alkyl), —C(O)N((C1-C6)alkyl)$_2$, and —C(O)O((C1-C6) alkyl), wherein said alkyl is independently substituted with 0-5 R';

R' is as defined herein;

$R^4$ and $R^5$ are each independently selected from —H, halogen and —(C1-C6)alkyl; and $R^6$ is selected from —H and —(C1-C6)alkyl.

In some of the embodiments of a compound of formula II, m is 0, 1 or 2;

when m is 1 or 2, at least one occurrence of $R^1$ is halogen or —O((C1-C6)alkyl) (such as —F and —OMe);

$R^2$ is selected from: —(C1-C6)alkyl (e.g., -Me), (C6-C10)-aryl-(C1-C12)aliphatic- (e.g., —CH$_2$Ph), (C6-C10)-aryl-O—(C1-C12)aliphatic- (e.g., —CH$_2$OPh) and (3- to 10-membered heterocyclyl)-(C1-C12)aliphatic- (e.g., —CH$_2$-pyrrolidine and —CH$_2$-morpholine), wherein said aryl (e.g., -Ph) or heterocyclyl (e.g., pyrrolidine or morpholine) is independently substituted with 0-5 R' independently selected from —F, -Me, and —OMe, and wherein said alkyl (e.g., -Me) is independently substituted with 0-3 R' selected from —N(Et)$_2$ and —N(Me)(CH$_2$Ph).

$R^3$ is —C(O)O((C1-C6)alkyl) (e.g., —COOEt);

$R^4$ and $R^5$ are both —H; and $R^6$ is —H.

In some embodiments, the present invention provides a compound of formula II:

II

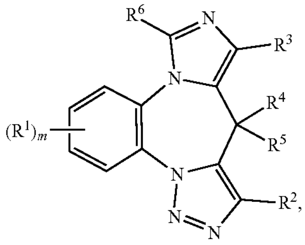

or a pharmaceutically acceptable salt, hydrate, solvate, polymorph, isomer, or combination thereof, wherein:

m is 0-3;

each $R^1$ is independently selected from: halogen, —H, —(C1-C6)alkyl, —OH, —O((C1-C6)alkyl), —NO$_2$, —CN, —CF$_3$, and —OCF$_3$, wherein $R^1$ is independently substituted with 0-5 R';

$R^2$ is selected from:

—(C1-C6)alkyl, —OH, —O((C1-C6)alkyl), —C(O)O((C1-C6)alkyl), (C6-C10)-aryl-(C1-C12)aliphatic-, (C6-C10)-aryl-O—(C1-C12)aliphatic-, (C6-C10)-aryl-N(R")—(C1-C12)aliphatic-, (5- to 10-membered heteroaryl)-(C1-C12)aliphatic-, (5- to 10-membered heteroaryl)-O—(C1-C12)aliphatic-, (5- to 10-membered heteroaryl)-N(R")—(C1-C12)aliphatic-, (3- to 10-membered heterocyclyl)-(C1-C12)aliphatic-, (3- to 10-membered heterocyclyl)-O—(C1-C12)aliphatic-, and (3- to 10-membered heterocyclyl)-N(R")—(C1-C12) aliphatic-, wherein $R^2$ is independently substituted with 0-5 R';

$R^3$ is selected from:

—(C1-C6)alkyl, —C═C, —CN, halogen, —SO$_2$((C6-C10)-aryl), —SO$_2$((C1-C6)alkyl), —C(O)N((C1-C6)alkyl)$_2$, —C(O)NH$_2$, —C(O)O((C1-C6)alkyl), —C(O)((C1-C6)alkyl), —(C6-C10)aryl, and 5- to 10-membered heteroaryl, wherein $R^3$ is independently substituted with 0-5 R';

$R^4$ and $R^5$ are each independently selected from —H, halogen and —(C1-C6)alkyl;

$R^6$ is selected from —H and —(C1-C6)alkyl; and

R' and R" are as defined herein.

In some embodiments of a compound of formula II:

m is 0, 1 or 2;

when m is 1 or 2, at least one occurrence of $R^1$ is halogen or —O((C1-C6)alkyl);

$R^2$ is selected from:

—(C1-C6)alkyl, (C6-C10)-aryl-(C1-C12)aliphatic-, (C6-C10)aryl-O—(C1-C12)aliphatic-, (5- to 10-membered heteroaryl)-(C1-C12)aliphatic-, and (3- to 10-membered heterocyclyl)-(C1-C12)aliphatic-, wherein $R^2$ is independently substituted with 0-3 R';

$R^3$ is halogen, —CN, —C≡C, —C(O)$NH_2$, —(C1-C6) alkyl, —C(O)((C1-C6)alkyl), —C(O)O((C1-C6)alkyl), —$SO_2$(Ph(Me)),

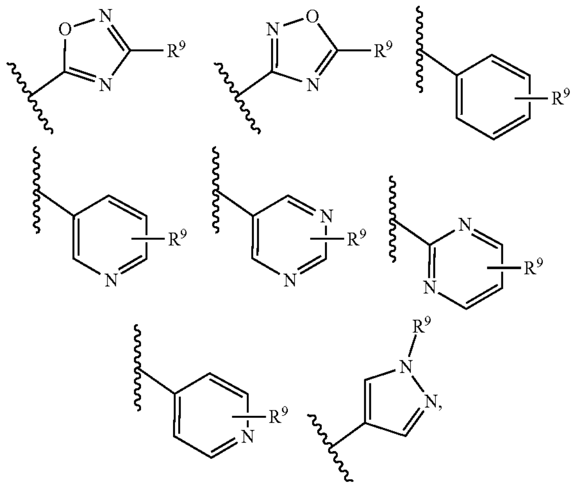

wherein $R^3$ is independently substituted with 0-3 R', and wherein $R^9$ is selected from —H, -Me, -Et, —$CF_3$, isopropyl, —OMe, -tert-butyl, and cyclopropyl;

$R^4$ and $R^5$ are both —H;

$R^6$ is —H; and

R' is as defined herein.

In some embodiments of a compound of formula II, $R^3$ is:

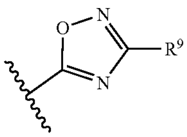

or

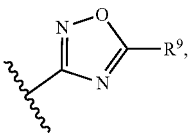

wherein $R^9$ is selected from —H, -Me, -Et, —$CF_3$, isopropyl, —OMe, and -tert-butyl.

In some embodiments, the present invention provides a compound of formula

III

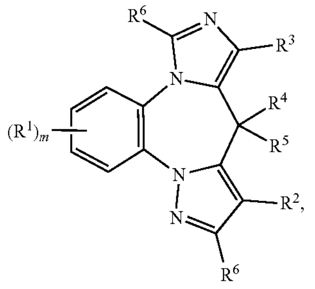

or a pharmaceutically acceptable salt, hydrate, solvate, polymorph, isomer, or combination thereof, wherein:

m is 0, 1, or 2, and when m is 1 or 2, at least one occurrence of $R^1$ is —O((C1-C6)alkyl) (such as —OMe);

$R^2$ is selected from: —(C1-C6)alkyl (e.g., -Me) and (C6-C10)-aryl-(C1-C12)aliphatic- (e.g., —$CH_2$Ph);

$R^3$ is —C(O)O((C1-C6)alkyl) (e.g., —COOEt);

$R^4$ and $R^5$ are both —H; and $R^6$ is —H.

In another aspect, the present invention provides a compound of formula IV:

IV

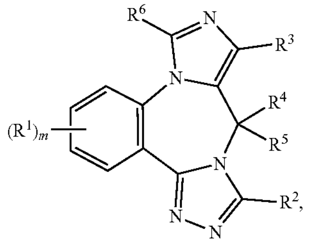

or a pharmaceutically acceptable salt, hydrate, solvate, polymorph, isomer, or combination thereof, wherein:

m is 0-3 (e.g., m is 1);

each $R^1$ is independently selected from: —Cl, —F, —OMe, and —C≡CH;

$R^2$ is —$(CH_2)_n OR^8$ or —$(CH_2)_n O(CH_2)_n R^8$, wherein each occurrence of $R^8$ is independently —(C1-C6) alkyl, (C6-C10)-aryl (e.g., phenyl), or 5- to 10-membered heteroaryl- (e.g., pyridyl) and wherein $R^2$ is independently substituted with 0-5 R';

$R^3$ is selected from: —CN, —C≡CH, —C≡C—(C1-C6) alkyl, —C≡C-phenyl, —COOMe, —COOEt, —(C1-C6)alkyl,

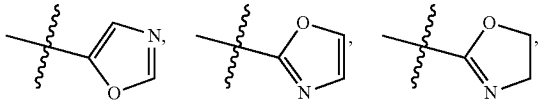

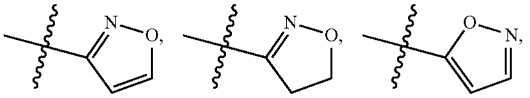

and

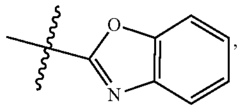

wherein $R^3$ is substituted with 0-5 R';

each occurrence of $R^4$ and $R^5$ is independently —H or —(C1-C6)alkyl;

each $R^6$ is independently —H or —(C1-C6)alkyl;

wherein each occurrence of R' is independently selected from halogen, —R", —OR", oxo, —$CH_2$OR", —$CH_2$NR"$_2$, —C(O)N(R")$_2$, —C(O)OR", —$NO_2$, —NCS, —CN, —$CF_3$, —$OCF_3$ and —N(R")$_2$;

wherein each occurrence of R" is independently selected from H, —(C1-C6)-alkyl, —(C1-C6)-aliphatic, (C3-C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, and (C6-C10)-aryl-O—(C1-C6)-alkyl-, wherein each occurrence of R" is independently substituted with 0-5 $R^1$ independently selected from: halogen, —R°, —OR°, oxo, —$CH_2$OR°, —$CH_2$N(R°)$_2$, —C(O)N(R°)$_2$, —C(O)OR°, —$NO_2$, —NCS, —CN, —$CF_3$, —$OCF_3$ and —N(R°)$_2$, wherein each occurrence of R° is independently selected from:

—(C1-C6)-aliphatic, (C3-C6)-cycloalkyl, 3- to 6-membered heterocyclyl, 5- to 10-membered heteroaryl-, and (C6-C10)-aryl-.

In some of the above embodiments, $R^1$ is —Cl.

In some of the above embodiments, $R^3$ is selected from:

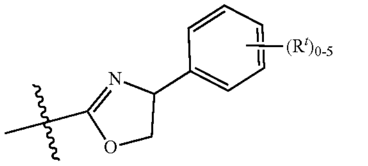

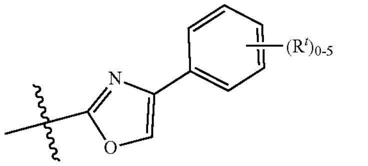

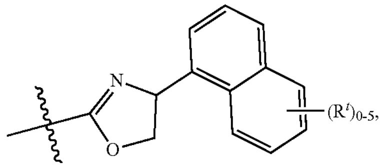

wherein each occurrence of $R^t$ is independently selected from: halogen, —R°, —OR°, oxo, —$CH_2$OR°, —$CH_2$N(R°) 2, —C(O)N(R°)$_2$, —C(O)OR°, —$NO_2$, —NCS, —CN, —$CF_3$, —$OCF_3$ and —N(R°)$_2$, wherein each occurrence of R° is independently selected from: —(C1-C6)-aliphatic, (C3-C6)-cycloalkyl, 3- to 6-membered heterocyclyl, 5- to 10-membered heteroaryl-, and (C6-C10)-aryl-. In some embodiments, $R^3$ is selected from:

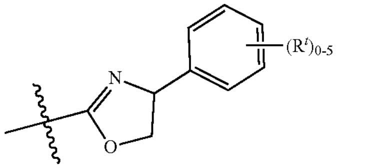

-continued

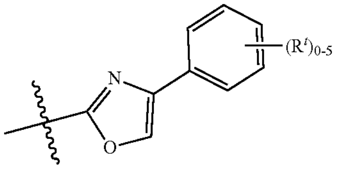

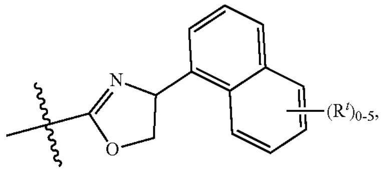

wherein each occurrence of $R^t$ is independently selected from: halogen, —R°, —OR°, oxo, —$CH_2$OR°, —$CH_2$N(R°)$_2$, —C(O)N(R°)$_2$, —C(O)OR°, —$NO_2$, —NCS, —CN, —$CF_3$, —$OCF_3$ and —N(R°)$_2$, wherein each occurrence of R° is independently selected from: —(C1-C6)-aliphatic, (C3-C6)-cycloalkyl, 3- to 6-membered heterocyclyl, 5- to 10-membered heteroaryl-, and (C6-C10)-aryl-, and $R^2$ is —$(CH_2)_n$O$R^8$, wherein $R^8$ is —(C1-C6)alkyl (e.g., -Me, -Et, -propyl, or -isopropyl), wherein $R^2$ is independently substituted with 0-5 R'.

In some of the above embodiments, $R^3$ is selected from:

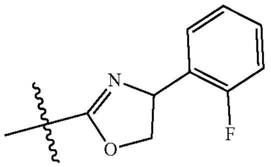

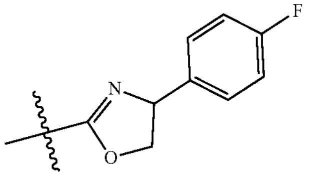

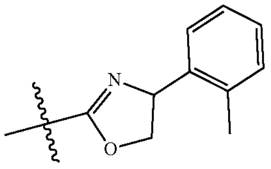

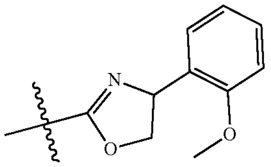

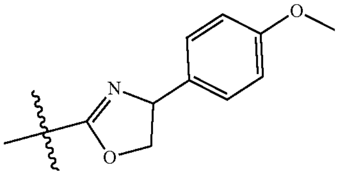

-continued
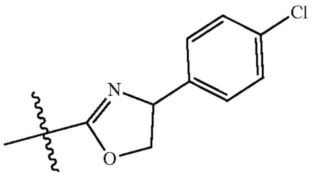
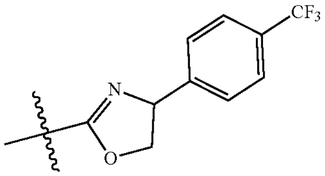
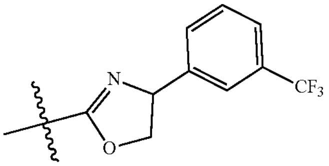
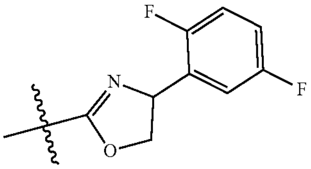
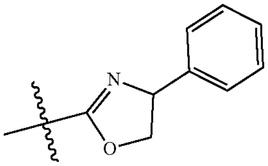
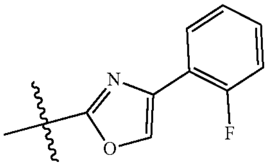
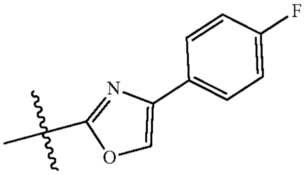
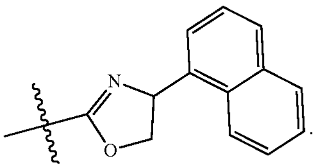
In some embodiments, $R^3$ is selected from:
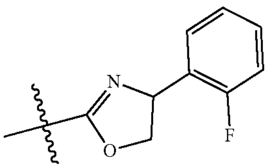
-continued
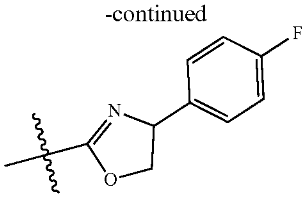
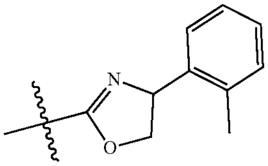
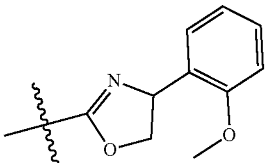
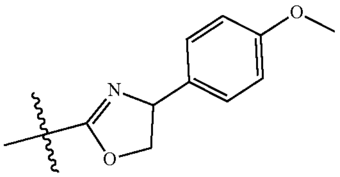
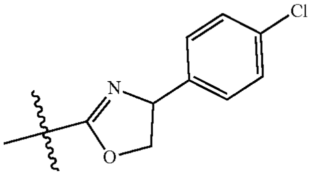
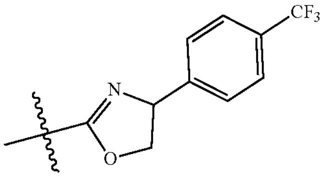
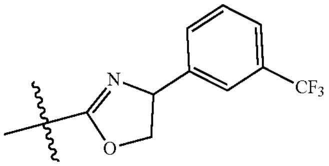
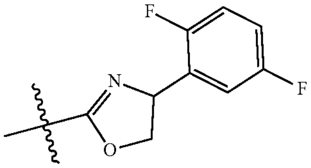
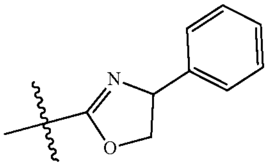
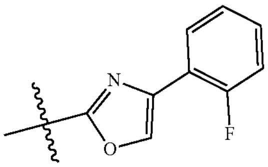

-continued
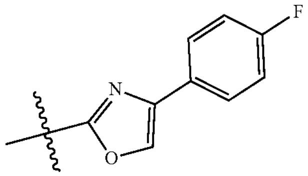
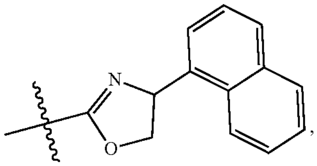,
and
$R^2$ is —$(CH_2)_n OR^8$, wherein $R^8$ is —(C1-C6)alkyl (e.g., -Me, -Et, -propyl, or -isopropyl).
In some of the above embodiments, $R^3$ is selected from:
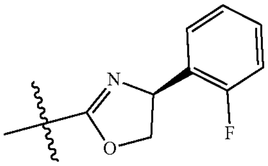
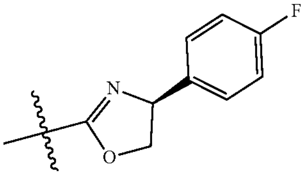
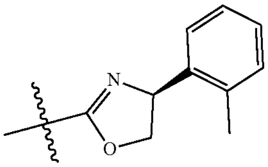
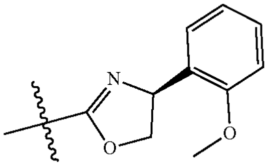
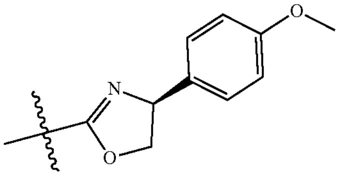
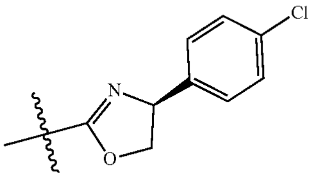
-continued
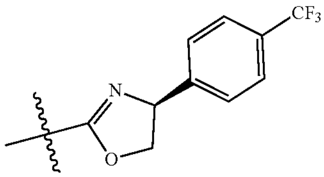
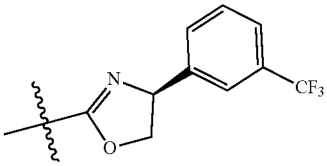
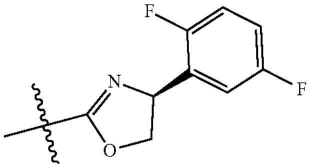
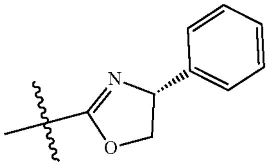
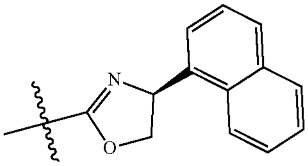
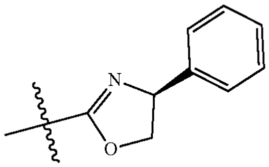
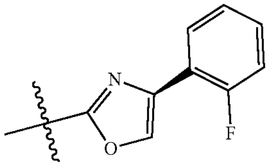
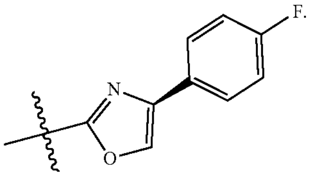
In some embodiments, $R^3$ is selected from:
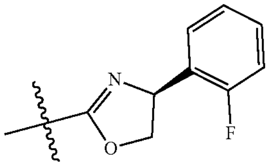

-continued

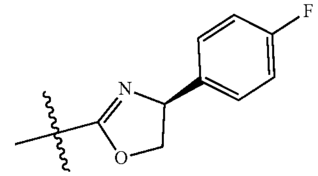

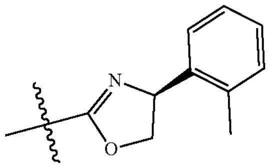

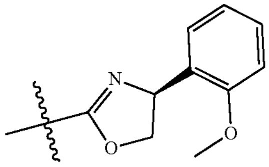

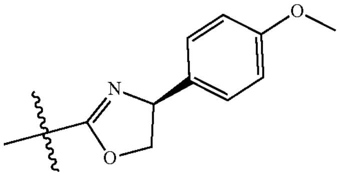

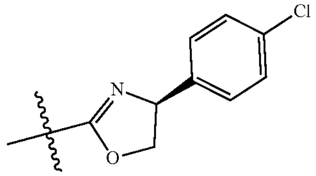

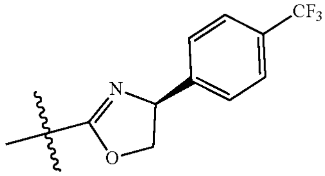

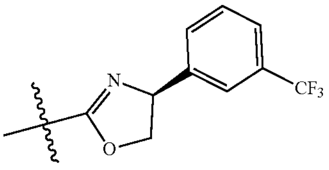

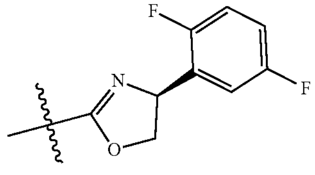

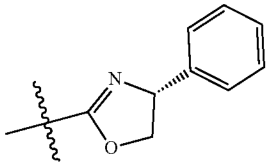

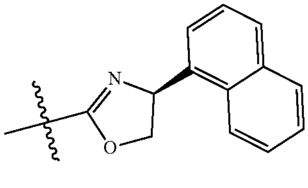

-continued

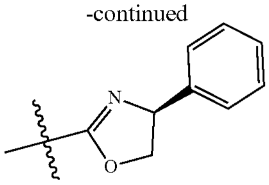

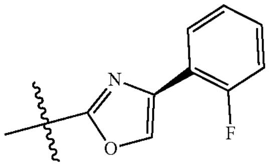

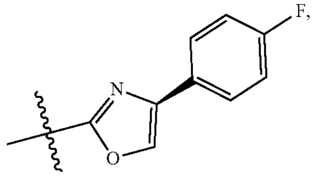

and $R^2$ is —$(CH_2)_nOR^8$, wherein $R^8$ is —(C1-C6)alkyl (e.g., -Me, -Et, -propyl, or -isopropyl).

In some embodiments, $R^8$ is —$(CH_2)_nOR^8$ or —$(CH_2)_nO(CH_2)_nR^8$, wherein each occurrence of $R^8$ is independently (C6-C10)-aryl (e.g., phenyl) or 5- to 10-membered heteroaryl- (e.g., pyridyl) and wherein $R^2$ is independently substituted with 0-5 R'. In some embodiments, $R^2$ is —$(CH_2)_nOR^8$ or —$(CH_2)_nO(CH_2)_nR^8$, wherein each occurrence of $R^8$ is independently (C6-C10)-aryl (e.g., phenyl) or 5- to 10-membered heteroaryl- (e.g., pyridyl) and wherein $R^2$ is independently substituted with 0-5 R', and $R^3$ is selected from: —CN, —C≡CH, —C≡C—(C1-C6)alkyl, —COOMe, —COOEt, —(C1-C6)alkyl,

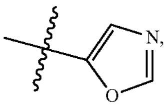
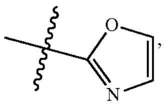
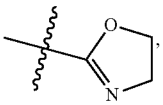
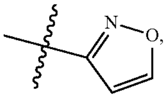
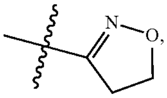
and
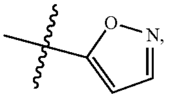

wherein $R^3$ is substituted with 0-3 R'.

In some embodiments, $R^2$ is —$CH_2OR^8$ or —$CH_2OCH_2R^8$, wherein each occurrence of $R^8$ is independently (C6-C10)-aryl (e.g., phenyl) or 5- to 10-membered heteroaryl- (e.g., pyridyl) and wherein $R^2$ is independently substituted with 0-5 R'; and $R^3$ is selected from: —C≡CH, —C≡C—(C1-C6)alkyl,

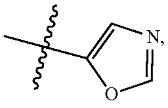
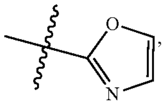
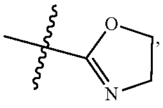
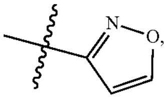
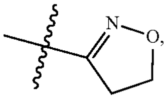
and

-continued

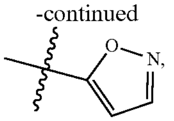

wherein $R^3$ is substituted with 0-2 R' (e.g., $R^3$ is unsubstituted).

In another aspect, the present invention provides a compound of formula IV:

IV

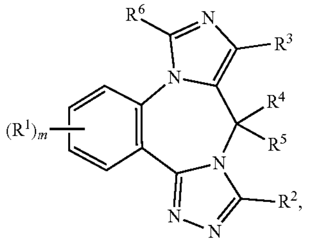

or a pharmaceutically acceptable salt, hydrate, solvate, polymorph, isomer, or combination thereof, wherein:

m is 0-3 (e.g., m is 1);

each $R^1$ is independently selected from: —Cl, —F, —OMe, and —C≡CH;

$R^2$ is —$(CH_2)_nOR^8$ or —$(CH_2)_nO(CH_2)_nR^8$, wherein each occurrence of $R^8$ is independently —(C1-C6)alkyl or (C6-C10)-aryl (e.g., phenyl), and wherein $R^2$ is independently substituted with 0-5 R';

$R^3$ is selected from: —CN, —C≡CH, —C≡C—(C1-C6) alkyl, —C≡C-phenyl,

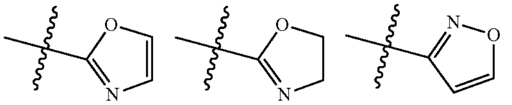

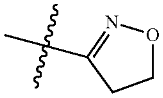

and

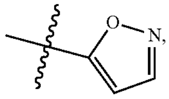

wherein $R^3$ is substituted with 0-5 R';

each occurrence of $R^4$ and $R^5$ is independently —H or —(C1-C6)alkyl;

each $R^6$ is independently —H or —(C1-C6)alkyl;

wherein each occurrence of R' is independently selected from halogen, —R", —OR", oxo, —$CH_2$OR", —$CH_2$NR"$_2$, —C(O)N(R")$_2$, —C(O)OR", —$NO_2$, —NCS, —CN, —$CF_3$, —$OCF_3$ and —N(R")$_2$;

wherein each occurrence of R" is independently selected from H, —(C1-C6)-alkyl, —(C1-C6)-aliphatic, (C3-C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, and (C6-C10)-aryl-O—(C1-C6)-alkyl-, wherein each occurrence of R" is independently substituted with 0-5 substituents selected from: halogen, —R°, —OR°, oxo, —$CH_2$OR°, —$CH_2$N(R°)$_2$, —C(O)N(R°)$_2$, —C(O)OR°, —$NO_2$, —NCS, —CN, —$CF_3$, —$OCF_3$ and —N(R°)$_2$, wherein each occurrence of R° is independently selected from: —(C1-C6)-aliphatic, (C3-C6)-cycloalkyl, 3- to 6-membered heterocyclyl, 5- to 10-membered heteroaryl-, and (C6-C10)-aryl-.

In some of the above embodiments, $R^3$ is selected from:

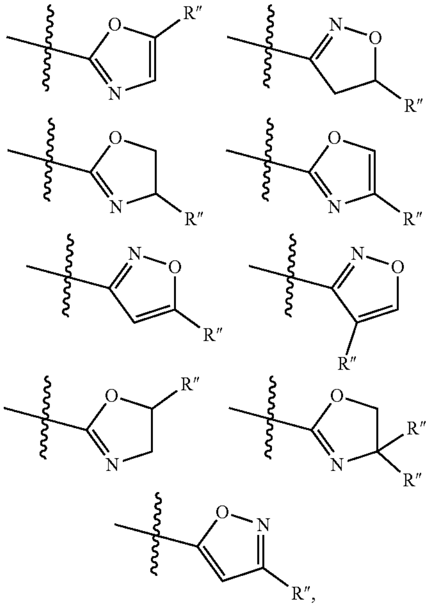

wherein each occurrence of R" is independently selected from —(C1-C6)-alkyl (e.g., linear or branched), —C≡CH, phenyl, thiophene, (5- to 10-membered heteroaryl)-(C1-C6)-alkyl-, and (C6-C10)-aryl-(C1-C6)-alkyl-, wherein each R" is independently substituted with 0-3 substituents selected from: halogen, —R°, —OR°, oxo, —$CH_2$OR°, —$CH_2$N(R°)$_2$, —C(O)N(R°)$_2$, —C(O)OR°, —$NO_2$, —NCS, —CN, —$CF_3$, —$OCF_3$ and —N(R°)$_2$, wherein each occurrence of R is independently selected from: —(C1-C6)-aliphatic, (C3-C6)-cycloalkyl, 3- to 6-membered heterocyclyl, 5- to 10-membered heteroaryl-, and (C6-C10)-aryl-.

In another aspect, the present invention provides a compound of formula IV:

IV

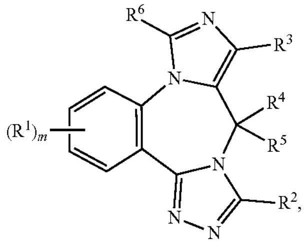

or a pharmaceutically acceptable salt, hydrate, solvate, polymorph, isomer, or combination thereof, wherein:

m is 0-3;

each $R^1$ is independently selected from: halogen (e.g., Cl), —H, —(C1-C6)alkyl, —C≡CH, —OH, —O((C1-C6) alkyl) (e.g., OMe), —$NO_2$, —CN, —$CF_3$, and —$OCF_3$, wherein $R^1$ is independently substituted with 0-5 R';

$R^2$ is selected from —$OR^8$, —$SR^8$, —$(CH_2)_nOR^8$ (e.g., —$CH_2$OMe, —$CH_2$OEt, —$CH_2$Oisopropyl, —$CH_2$Opyridyl), —$(CH_2)_nO(CH_2)_nR^8$, —$(CH_2)_pR^8$ and —$(CH_2)_nN(R'')R^{10}$, wherein n is an integer selected from 0-4; p is an integer selected from 2-4; each $R^8$ is independently —(C1-C6)alkyl, —(C3-C10)-cycloalkyl, (C6-C10)-aryl, or 5- to 10-membered heteroaryl, wherein each occurrence of $R^8$ is independently substituted with 0-5 R'; each $R^{10}$ is independently —(C3-C10)-cycloalkyl, 3- to 10-membered heterocyclyl-, (C6-C10)-aryl, or 5- to 10-membered heteroaryl, wherein each occurrence of $R^{10}$ is independently substituted with 0-5 R'; and wherein $R^2$ is independently substituted with 0-5 R';

$R^3$ is selected from:

—H, —CN, halogen (e.g., Br), —(C1-C6)alkyl, —C≡CH, —$SO_2$((C1-C6)alkyl), —C(O)N((C1-C6) alkyl)$_2$, —C(O)NH((C1-C6)aliphatic)$_2$ (e.g., —C(O) NH((C2-C6)alkynyl)$_2$), (C6-C10)-aryl-(C1-C12)aliphatic-, —C(O)((C1-C6)alkyl), —C(O)O((C1-C6) alkyl), 5- or 6-membered heterocyclyl- (e.g., optionally substituted

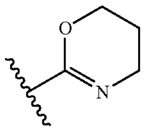 [SMILES: *C1=NCCCO1]

or optionally substituted

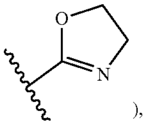 [SMILES: *C1=NCCO1]
), and 5- or 6-membered heteroaryl (e.g., optionally substituted

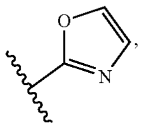 [SMILES: *c1ncco1]
, optionally substituted

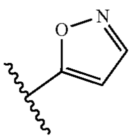
, 
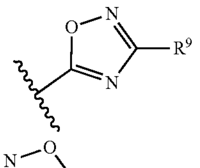
or
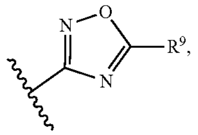
, wherein $R^9$ is selected from -Me, -Et, isopropyl, —$CF_3$, —OMe, —OEt, —O-isopropyl, —$CH_2NMe_2$, and cyclopropyl; and wherein $R^3$ is independently substituted with 0-5 R';

$R^4$ and $R^5$ are each independently selected from —H, halogen and —(C1-C6)alkyl;

$R^6$ is selected from —H and —(C1-C6)alkyl;

wherein each occurrence of R' is independently selected from halogen, —R'', —OR'', oxo, —$CH_2$OR'', —$CH_2N(R'')_2$, —C(O)N(R'')$_2$, —C(O)OR'', —$NO_2$, —NCS, —CN, —$CF_3$, —$OCF_3$ and —N(R'')$_2$;

wherein each occurrence of R'' is independently selected from H, —(C1-C6)-alkyl, (C3—C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, and (C6-C10)-aryl-O—(C1-C6)-alkyl-.

In another aspect, the present invention provides a compound of formula IV:

IV

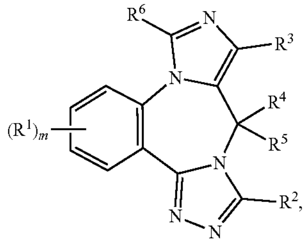

or a pharmaceutically acceptable salt, hydrate, solvate, polymorph, isomer, or combination thereof, wherein:

m is 1;

$R^1$ is —C≡CH, optionally substituted with a R';

$R^2$ is selected from —$OR^8$, —$SR^8$, —$(CH_2)_nOR^8$ (e.g., —$CH_2$OMe, —$CH_2$OEt, —$CH_2$Oisopropyl, —$CH_2$Opyridyl), —$(CH_2)_nO(CH_2)_nR^8$, —$(CH_2)_pR^8$ and —$(CH_2)_nN(R'')R^{10}$, wherein n is an integer selected from 0-4; p is an integer selected from 2-4; each $R^8$ is independently —(C1-C6)alkyl, —(C3-C10)-cycloalkyl, (C6-C10)-aryl, or 5- to 10-membered heteroaryl, wherein each occurrence of $R^8$ is independently substituted with 0-5 R'; each $R^{10}$ is independently —(C3-C10)-cycloalkyl, 3- to 10-membered heterocyclyl-, (C6-C10)-aryl, or 5- to 10-membered heteroaryl, wherein each occurrence of $R^{10}$ is independently substituted with 0-5 R'; and wherein $R^2$ is independently substituted with 0-5 R';

$R^3$ is selected from:

—H, —CN, halogen (e.g., Br), —(C1-C6)alkyl, —C≡CH, —$SO_2$((C1-C6)alkyl), —C(O)N((C1-C6) alkyl)$_2$, —C(O)NH((C1-C6)aliphatic)$_2$ (e.g., —C(O) NH((C1-C6)alkynyl)$_2$), (C6-C10)-aryl-(C1-C12)aliphatic-, —C(O)((C1-C6)alkyl), —C(O)O((C1-C6) alkyl), 5- or 6-membered heterocyclyl- (e.g., optionally substituted

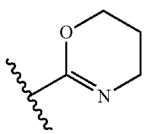 [SMILES: *C1=NCCCO1]

or optionally substituted

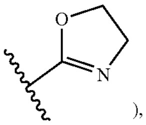 [SMILES: *C1=NCCO1]

), and 5- or 6-membered heteroaryl (e.g., optionally substituted

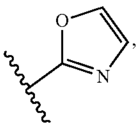

optionally substituted

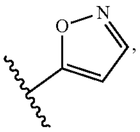 [SMILES: *c1ccno1]

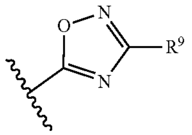

or

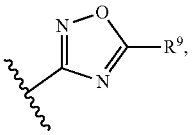

wherein $R^9$ is selected from -Me, -Et, isopropyl, —$CF_3$, —OMe, —OEt, —O-isopropyl, —$CH_2NMe_2$, and cyclopropyl; and wherein $R^3$ is independently substituted with 0-5 R';

$R^4$ and $R^5$ are each independently selected from —H, halogen and —(C1-C6)alkyl;

$R^6$ is selected from —H and —(C1-C6)alkyl;

wherein each occurrence of R' is independently selected from halogen, —R", —OR", oxo, —$CH_2OR$", —$CH_2NR"_2$, —C(O)N(R")$_2$, —C(O)OR", —$NO_2$, —NCS, —CN, —$CF_3$, —$OCF_3$ and —N(R")$_2$;

wherein each occurrence of R" is independently selected from H, —(C1-C6)-alkyl, (C3-C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, and (C6-C10)-aryl-O—(C1-C6)-alkyl-.

In another aspect, the present invention provides a compound of formula IV:

IV

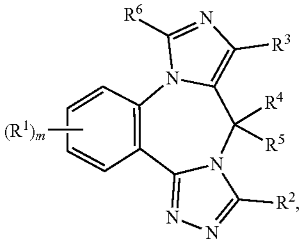

or a pharmaceutically acceptable salt, hydrate, solvate, polymorph, isomer, or combination thereof, wherein:

m is 1;

each $R^1$ is —C≡CH, optionally substituted with a R';

$R^2$ is —$(CH_2)_nOR^8$ (e.g., —$CH_2OMe$, —$CH_2OEt$, —$CH_2$Oisopropyl, —$CH_2$Opyridyl); and wherein $R^2$ is independently substituted with 0-5 R';

$R^3$ is selected from:

5- or 6-membered heterocyclyl- (e.g., optionally substituted

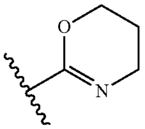 [SMILES: *C1=NCCCO1]

or optionally substituted

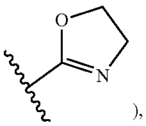 [SMILES: *C1=NCCO1]

), and 5- or 6-membered heteroaryl (e.g., optionally substituted

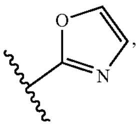 [SMILES: *c1ncco1]

or optionally substituted

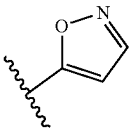

);

and wherein $R^3$ is independently substituted with 0-5 R;

$R^4$ and $R^5$ are each —H;

$R^6$ is —H; and wherein each occurrence of R' is independently selected from halogen, —R", —OR", oxo, —$CH_2OR$", —$CH_2NR"_2$, —C(O)N(R")$_2$, —C(O)OR", —$NO_2$, —NCS, —CN, —$CF_3$, —$OCF_3$ and —N(R")$_2$;

wherein each occurrence of R" is independently selected from H, —(C1-C6)-alkyl, (C3-C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, and (C6-C10)-aryl-O—(C1-C6)-alkyl-.

In another aspect, the present invention provides a compound of formula IV:

IV

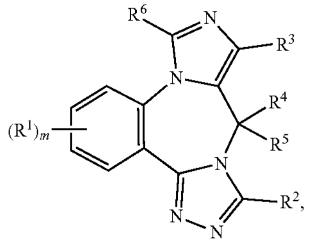

or a pharmaceutically acceptable salt, hydrate, solvate, polymorph, isomer, or combination thereof, wherein:

m is 0-3;

when m is 1 or 2, at least one occurrence of $R^1$ is -halogen or —O((C1-C6)alkyl);

each $R^1$ is independently selected from: halogen (e.g., Cl), —H, —(C1-C6)alkyl, —C≡CH, —OH, —O((C1-C6) alkyl) (e.g., OMe), —$NO_2$, —CN, —$CF_3$, and —$OCF_3$, wherein $R^1$ is independently substituted with 0-5 R';

$R^2$ is selected from —$OR^8$, —$SR^8$, —$(CH_2)_nOR^8$ (e.g., —$CH_2OMe$, —$CH_2OEt$, —$CH_2$Oisopropyl, —$CH_2$Opyridyl), —$(CH_2)_nO(CH_2)_nR^8$, —$(CH_2)_pR^8$ and —$(CH_2)_nN(R'')R^{10}$, wherein n is an integer selected from 0-4; p is an integer selected from 2-4; each $R^8$ is independently —(C1-C6)alkyl, —(C3-C10)-cycloalkyl, (C6-C10)-aryl, or 5- to 10-membered heteroaryl, wherein each occurrence of $R^8$ is independently substituted with 0-5 R'; each $R^{10}$ is independently —(C3-C10)-cycloalkyl, 3- to 10-membered heterocyclyl-, (C6-C10)-aryl, or 5- to 10-membered heteroaryl, wherein each occurrence of $R^{10}$ is independently substituted with 0-5 R'; and wherein $R^2$ is independently substituted with 0-5 R';

$R^3$ is selected from:

—C≡CH, —C(O)NH((C1-C6)aliphatic)$_2$ (e.g., —C(O) NH((C1-C6)alkynyl)$_2$), (C6-C10)-aryl-(C1-C12)aliphatic-, 5- or 6-membered heterocyclyl- (e.g., optionally substituted

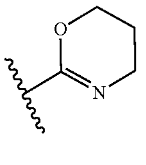 [SMILES: *C1=NCCCO1]

or optionally substituted

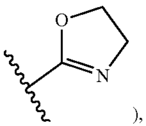 [SMILES: *C1=NCCO1]

), optionally substituted

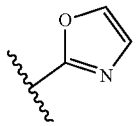

, and optionally substituted

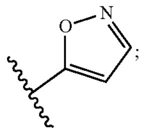 [SMILES: *c1ccno1]

;

and wherein $R^3$ is independently substituted with 0-5 R';

$R^4$ and $R^5$ are each independently selected from —H, halogen and —(C1-C6)alkyl;

$R^6$ is selected from —H and —(C1-C6)alkyl; and wherein each occurrence of R' is independently selected from halogen, —R", —OR", oxo, —$CH_2OR''$, —$CH_2NR''_2$, —C(O)N(R")$_2$, —C(O)OR", —$NO_2$, —NCS, —CN, —$CF_3$, —$OCF_3$ and —N(R")$_2$;

wherein each occurrence of R" is independently selected from H, —(C1-C6)-alkyl, (C3-C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, and (C6-C10)-aryl-O—(C1-C6)-alkyl-.

In another aspect, the present invention provides a compound of formula IV:

IV

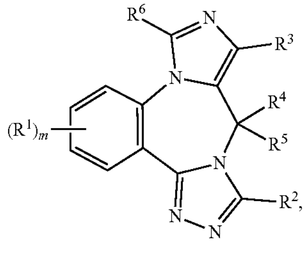

or a pharmaceutically acceptable salt, hydrate, solvate, polymorph, isomer, or combination thereof, wherein:

m is 0-3;

each $R^1$ is independently selected from: halogen (e.g., Cl), —C≡CH, and —O((C1-C6)alkyl) (e.g., OMe), wherein $R^1$ is independently substituted with 0-5 R';

$R^2$ is —$(CH_2)_nOR^8$ (e.g., —$CH_2OMe$, —$CH_2OEt$, —$CH_2$O-isopropyl, —$CH_2$O-pyridyl), wherein n is an integer selected from 0-4; $R^8$ is —(C1-C6)alkyl, —(C3-C10)-cycloalkyl, (C6-C10)-aryl, or 5- to 10-membered heteroaryl, wherein each occurrence of $R^8$ is independently substituted with 0-5 R'; and wherein $R^2$ is independently substituted with 0-5 R';

$R^3$ is selected from:

—C≡CH, —C(O)NH((C1-C6)aliphatic)$_2$ (e.g., —C(O)NH((C1-C6)alkynyl)$_2$)), (C6-C10)-aryl-(C1-C12) aliphatic-, 5- or 6-membered heterocyclyl- (e.g., optionally substituted

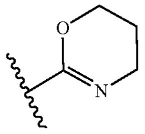 [SMILES: *C1=NCCCO1]

or optionally substituted

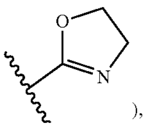 [SMILES: *C1=NCCO1]

), optionally substituted

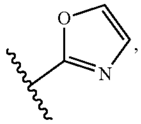 [SMILES: *c1ncco1]

, and optionally substituted

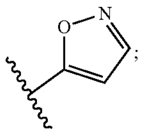 [SMILES: *c1ccno1]

;

and wherein $R^3$ is independently substituted with 0-5 R';

$R^4$ and $R^5$ are each —H;

$R^6$ is —H or —(C1-C6)alkyl; and wherein each occurrence of R' is independently selected from halogen, —R", —OR", oxo, —CH$_2$OR", —CH$_2$NR"$_2$, —C(O)N(R")$_2$, —C(O)OR", —NO$_2$, —NCS, —CN, —CF$_3$, —OCF$_3$ and —N(R")$_2$;

wherein each occurrence of R" is independently selected from H, —(C1-C6)-alkyl, (C3-C6)-cycloalkyl, 3- to 6-membered heterocyclyl, 5- to 10-membered heteroaryl-, (C6-C10)-aryl-, (5- to 10-membered heteroaryl)-(C1-C6)-alkyl-, (C6-C10)-aryl-(C1-C6)-alkyl-, (5- to 10-membered heteroaryl)-O—(C1-C6)-alkyl-, and (C6-C10)-aryl-O—(C1-C6)-alkyl-.

In another aspect, the present invention provides a compound of formula IV:

IV

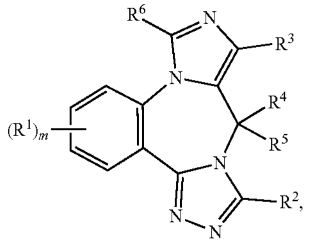

or a pharmaceutically acceptable salt, hydrate, solvate, polymorph, isomer, or combination thereof, wherein:

m is 0, 1, or 2, and when m is 1 or 2, at least one occurrence of $R^1$ is —O((C1-C6)alkyl) (such as —OMe);

$R^2$ is $OR^8$, wherein $R^8$ is (C6-C10)-aryl (such as phenyl), substituted with 0-3 halogen (such as —F);

$R^3$ is —C(O)O((C1-C6)alkyl) (e.g., —COOEt);

$R^4$ and $R^5$ are both —H; and $R^6$ is —H.

In another aspect, the present invention provides a compound of formula IV:

IV

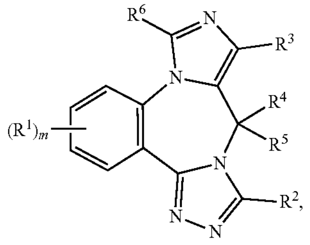

or a pharmaceutically acceptable salt, hydrate, solvate, polymorph, isomer, or combination thereof, wherein:

m is 0-3;

when m is 1 or 2, at least one occurrence of $R^1$ is -halogen or —O((C1-C6)alkyl);

each $R^1$ is independently selected from: halogen, —H, —(C1-C6)alkyl, —OH, —O((C1-C6)alkyl), —NO$_2$, —CN, —CF$_3$, and —OCF$_3$, wherein $R^1$ is independently substituted with 0-5 R';

$R^2$ is selected from —OR$^8$, —SR$^8$, —(CH$_2$)$_n$OR$^8$, —(CH$_2$)$_n$O(CH$_2$)$_n$R$^8$, —(CH$_2$)$_p$R$^8$ and —(CH$_2$)$_n$N(R")R$^{10}$, wherein n is an integer selected from 0-4; p is an integer selected from 2-4; each $R^8$ is independently —(C1-C6)alkyl, —(C3-C10)-cycloalkyl, (C6-C10)-aryl, or 5- to 10-membered heteroaryl, wherein each occurrence of $R^8$ is independently substituted with 0-5 R'; each $R^{10}$ is independently —(C3-C10)-cycloalkyl, 3- to 10-membered heterocyclyl-, (C6-C10)-aryl, or 5- to 10-membered heteroaryl, wherein each occurrence of $R^{10}$ is independently substituted with 0-5 R'; and wherein $R^2$ is independently substituted with 0-5 R'

$R^3$ is selected from:

—H, —CN, halogen, —(C1-C6)alkyl, —SO$_2$((C1-C6)alkyl), —C(O)N((C1-C6)alkyl)$_2$, —C(O)((C1-C6)alkyl), —C(O)O((C1-C6)alkyl),

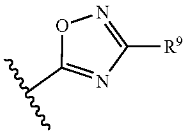 and 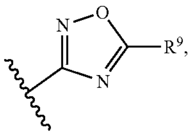

wherein $R^9$ is selected from -Me, -Et, isopropyl, —$CF_3$, —OMe, —OEt, —O-isopropyl, —$CH_2NMe_2$, and cyclopropyl; and wherein $R^3$ is independently substituted with 0-5 R';

$R^4$ and $R^5$ are each independently selected from —H, halogen and —(C1-C6)alkyl;

$R^6$ is selected from —H and —(C1-C6)alkyl; and

R' and R" are as defined herein.

In some embodiments of a compound of formula IV:

m is 0, 1, or 2;

$R^2$ is —$OR^8$, —$(CH_2)_nOR^8$, —$(CH_2)_nO(CH_2)_nR^8$, wherein n is 1, and wherein $R^8$ is —(C1-C6)alkyl, (C6-C10)-aryl or 5- to 10-membered heteroaryl, wherein $R^8$ is independently substituted with 0-3 R';

$R^3$ is halogen, —H, —CN, —(C1-C6)alkyl, —C(O)((C1-C6)alkyl), —C(O)O((C1-C6)alkyl),

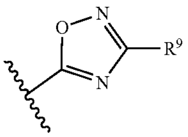 or 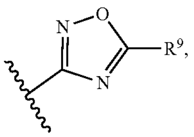

wherein said alkyl is independently substituted with 0-3 R'; $R^9$ is selected from -Me, -Et, isopropyl, and —$CF_3$;

$R^4$ and $R^5$ are both —H;

$R^6$ is —H; and

R' is as defined herein.

Examples of particular compounds of the present application include:

| Compound | Structure |
|---|---|
| 1 | 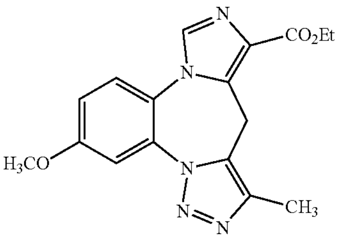 [SMILES: CCOC(=O)c1ncn2c1Cc1c(C)nnn1-c1cc(OC)ccc1-2] |
| 2 | 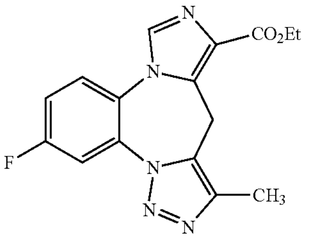 [SMILES: CCOC(=O)c1ncn2c1Cc1c(C)nnn1-c1cc(F)ccc1-2] |

-continued

| Compound | Structure |
|---|---|
| 3 | 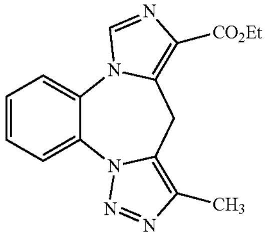 [SMILES: CCOC(=O)c1ncn2c1Cc1c(C)nnn1-c1ccccc1-2] |
| 4 | 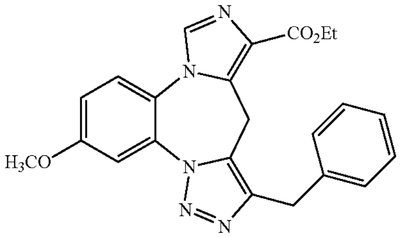 [SMILES: CCOC(=O)c1ncn2c1Cc1c(Cc3ccccc3)nnn1-c1cc(OC)ccc1-2] |
| 5 | 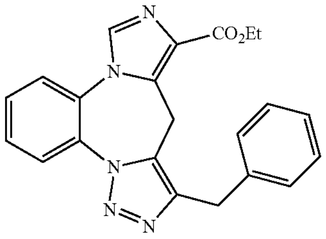 [SMILES: CCOC(=O)c1ncn2c1Cc1c(Cc3ccccc3)nnn1-c1ccccc1-2] |
| 6 | 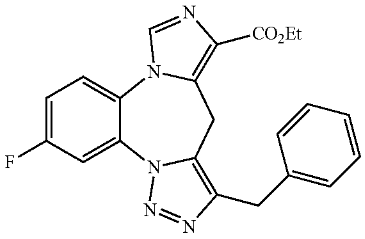 [SMILES: CCOC(=O)c1ncn2c1Cc1c(Cc3ccccc3)nnn1-c1cc(F)ccc1-2] |
| 7 | 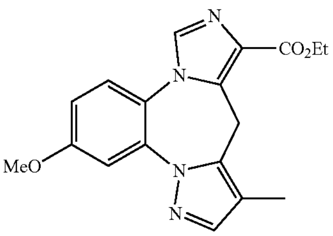 [SMILES: CCOC(=O)c1ncn2c1Cc1c(C)cnn1-c1cc(OC)ccc1-2] |
| 8 | 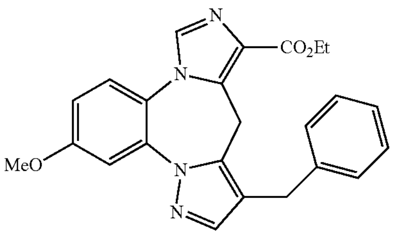 [SMILES: CCOC(=O)c1ncn2c1Cc1c(Cc3ccccc3)cnn1-c1cc(OC)ccc1-2] |

-continued
| Compound | Structure |
| --- | --- |
| 9 | 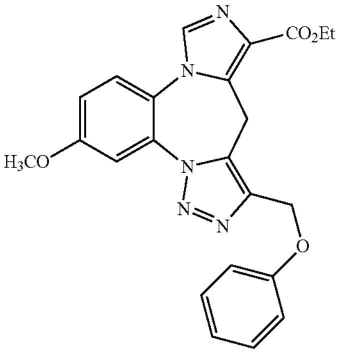 [SMILES: CCOC(=O)c1ncn2c1Cc1c(COc3ccccc3)nnn1-c1cc(OC)ccc1-2] |
| 10 | 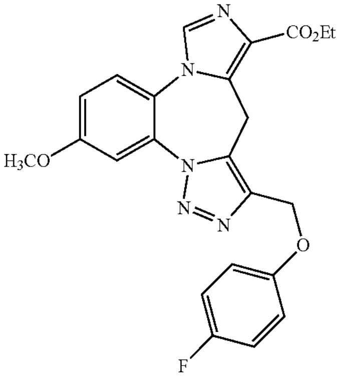 [SMILES: CCOC(=O)c1ncn2c1Cc1c(COc3ccc(F)cc3)nnn1-c1cc(OC)ccc1-2] |
| 11 | 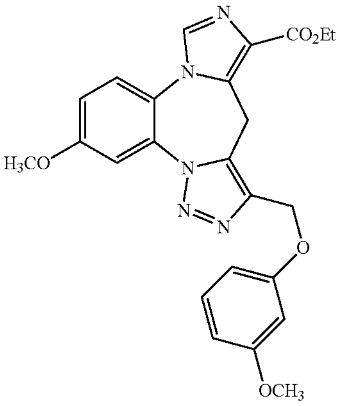 [SMILES: CCOC(=O)c1ncn2c1Cc1c(COc3cccc(OC)c3)nnn1-c1cc(OC)ccc1-2] |
| 12 | 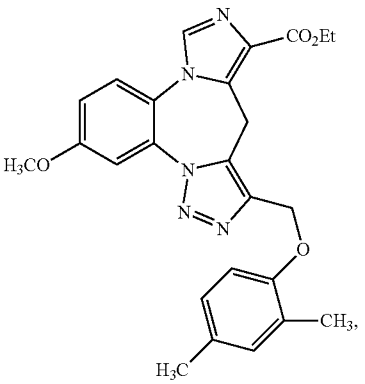 [SMILES: CCOC(=O)c1ncn2c1Cc1c(COc3ccc(C)cc3C)nnn1-c1cc(OC)ccc1-2] |
-continued
| Compound | Structure |
| --- | --- |
| 44 | 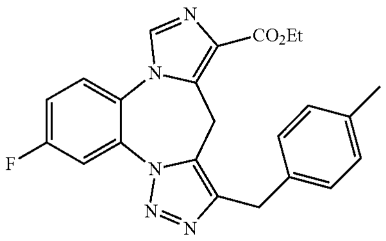 [SMILES: CCOC(=O)c1ncn2c1Cc1c(Cc3ccc(C)cc3)nnn1-c1cc(F)ccc1-2] |
| 45 | 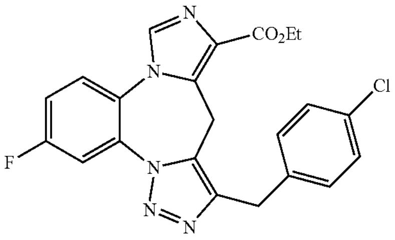 [SMILES: CCOC(=O)c1ncn2c1Cc1c(Cc3ccc(Cl)cc3)nnn1-c1cc(F)ccc1-2] |
| 46 | 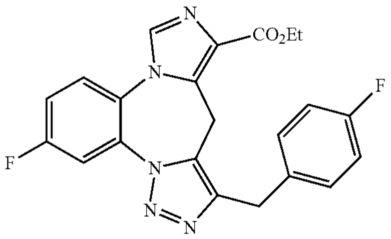 [SMILES: CCOC(=O)c1ncn2c1Cc1c(Cc3ccc(F)cc3)nnn1-c1cc(F)ccc1-2] |
| 47 | 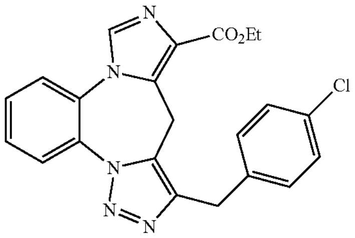 [SMILES: CCOC(=O)c1ncn2c1Cc1c(Cc3ccc(Cl)cc3)nnn1-c1ccccc1-2] |
| 48 | 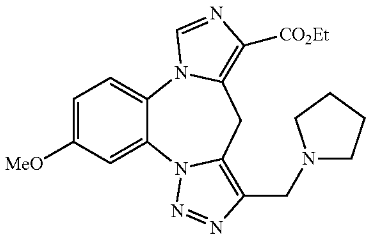 [SMILES: CCOC(=O)c1ncn2c1Cc1c(CN3CCCC3)nnn1-c1cc(OC)ccc1-2] |
| 49 | 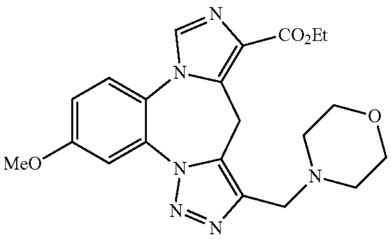 [SMILES: CCOC(=O)c1ncn2c1Cc1c(CN3CCOCC3)nnn1-c1cc(OC)ccc1-2] |

-continued
| Compound | Structure |
|---|---|
| 50 | 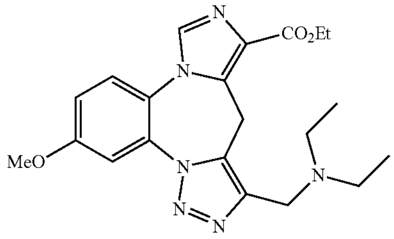 [SMILES: CCOC(=O)c1ncn2c1Cc1c(CN(CC)CC)nnn1-c1cc(OC)ccc1-2] |
| 51 | 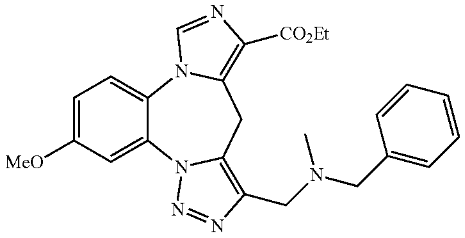 [SMILES: CCOC(=O)c1ncn2c1Cc1c(CN(C)Cc3ccccc3)nnn1-c1cc(OC)ccc1-2] |
| 52 | 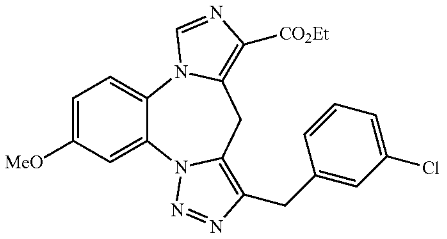 [SMILES: CCOC(=O)c1ncn2c1Cc1c(Cc3cccc(Cl)c3)nnn1-c1cc(OC)ccc1-2] |
| 53 | 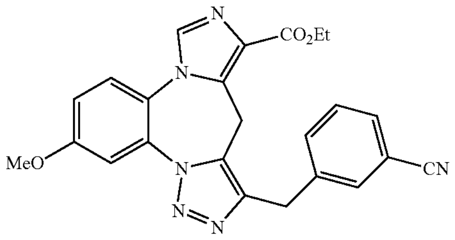 [SMILES: CCOC(=O)c1ncn2c1Cc1c(Cc3cccc(C#N)c3)nnn1-c1cc(OC)ccc1-2] |
| 54 | 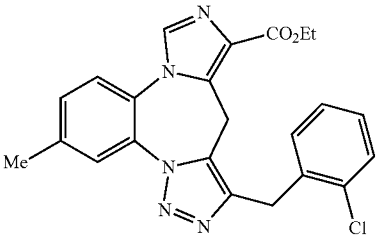 [SMILES: CCOC(=O)c1ncn2c1Cc1c(Cc3ccccc3Cl)nnn1-c1cc(C)ccc1-2] |
| 55 | 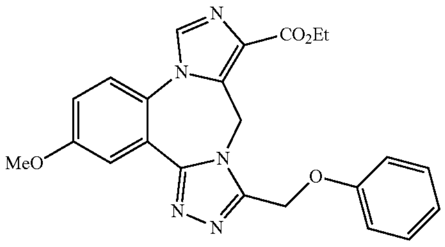 [SMILES: CCOC(=O)c1ncn2c1Cn1c(COc3ccccc3)nnc1-c1cc(OC)ccc1-2] |
-continued
| Compound | Structure |
|---|---|
| 56 | 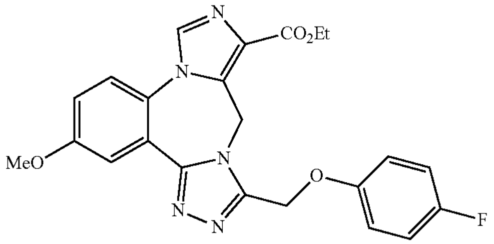 [SMILES: CCOC(=O)c1ncn2c1Cn1c(COc3ccc(F)cc3)nnc1-c1cc(OC)ccc1-2] |
| 101 | 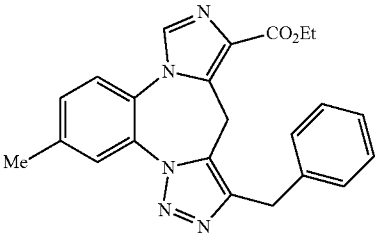 [SMILES: CCOC(=O)c1ncn2c1Cc1c(Cc3ccccc3)nnn1-c1cc(C)ccc1-2] |
| 102 | 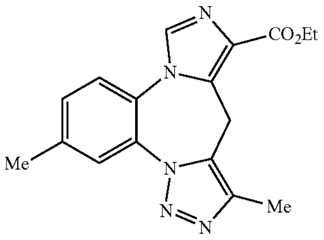 [SMILES: CCOC(=O)c1ncn2c1Cc1c(C)nnn1-c1cc(C)ccc1-2] |
| 103 | 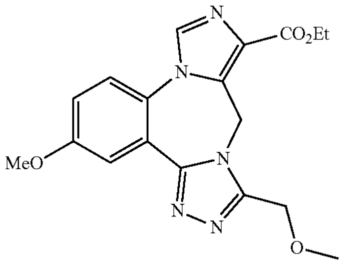 [SMILES: CCOC(=O)c1ncn2c1Cn1c(COC)nnc1-c1cc(OC)ccc1-2] |
| 104 | 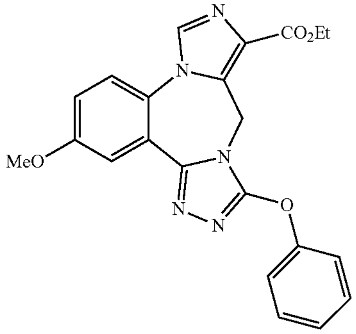 [SMILES: CCOC(=O)c1ncn2c1Cn1c(Oc3ccccc3)nnc1-c1cc(OC)ccc1-2] |

-continued
| Compound | Structure |
|---|---|
| 105 | 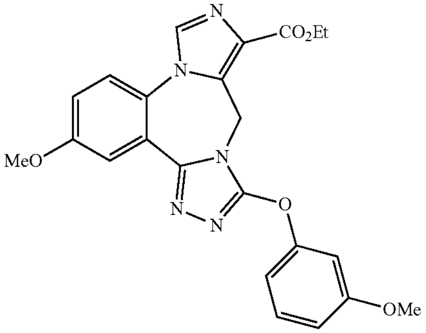 [SMILES: CCOC(=O)c1ncn2c1Cn1c(Oc3cccc(OC)c3)nnc1-c1cc(OC)ccc1-2] |
| 106 | 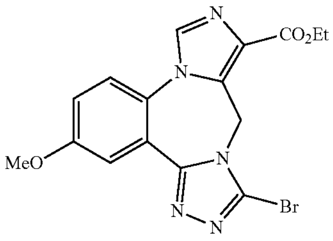 [SMILES: CCOC(=O)c1ncn2c1Cn1c(Br)nnc1-c1cc(OC)ccc1-2] |
| 107 | 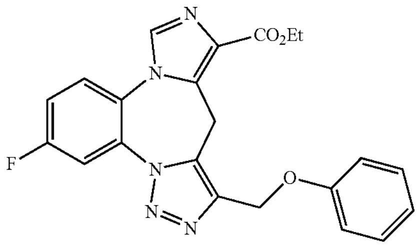 [SMILES: CCOC(=O)c1ncn2c1Cc1c(COc3ccccc3)nnn1-c1cc(F)ccc1-2] |
| 108 | 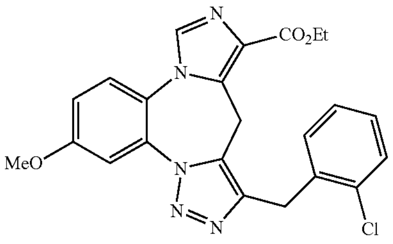 [SMILES: CCOC(=O)c1ncn2c1Cc1c(Cc3ccccc3Cl)nnn1-c1cc(OC)ccc1-2] |
| 109 | 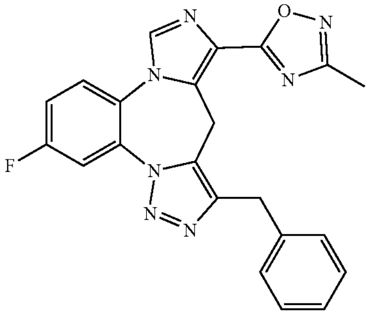 [SMILES: Cc1noc(-c2ncn3c2Cc2c(Cc4ccccc4)nnn2-c2cc(F)ccc2-3)n1] |
-continued
| Compound | Structure |
|---|---|
| 110 | 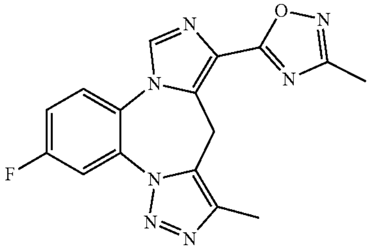 [SMILES: Cc1noc(-c2ncn3c2Cc2c(C)nnn2-c2cc(F)ccc2-3)n1] |
| 111 | 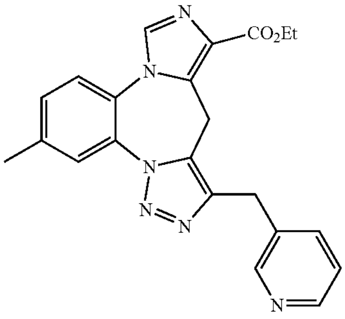 [SMILES: CCOC(=O)c1ncn2c1Cc1c(Cc3cccnc3)nnn1-c1cc(C)ccc1-2] |
| 112 | 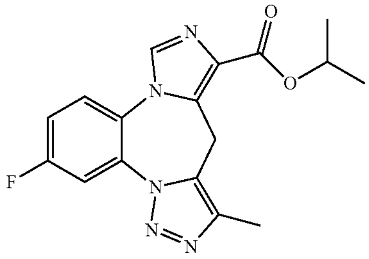 [SMILES: Cc1nnn2c1Cc1c(C(=O)OC(C)C)ncn1-c1ccc(F)cc1-2] |
| 113 | 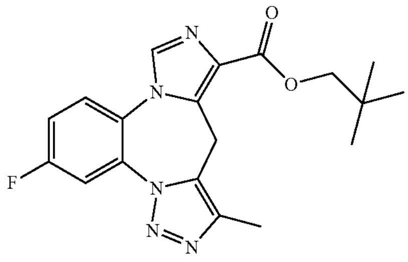 [SMILES: Cc1nnn2c1Cc1c(C(=O)OCC(C)(C)C)ncn1-c1ccc(F)cc1-2] |
| 114 | 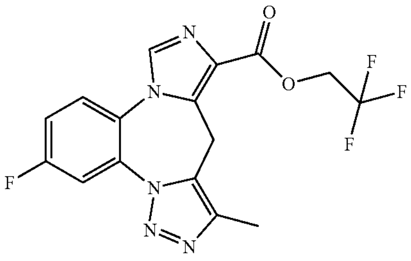 [SMILES: Cc1nnn2c1Cc1c(C(=O)OCC(F)(F)F)ncn1-c1ccc(F)cc1-2] |

-continued
| Compound | Structure |
|---|---|
| 115 | 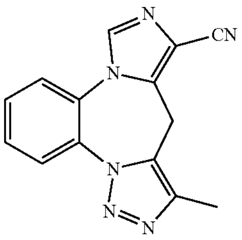 [SMILES: Cc1nnn2c1Cc1c(C#N)ncn1-c1ccccc1-2] |
| 116 | 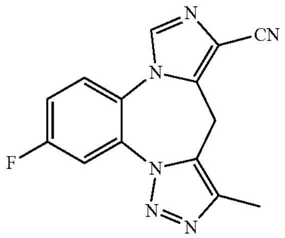 [SMILES: Cc1nnn2c1Cc1c(C#N)ncn1-c1ccc(F)cc1-2] |
| 117 | 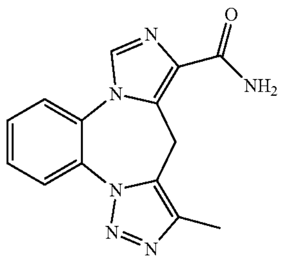 [SMILES: Cc1nnn2c1Cc1c(C(N)=O)ncn1-c1ccccc1-2] |
| 118 | 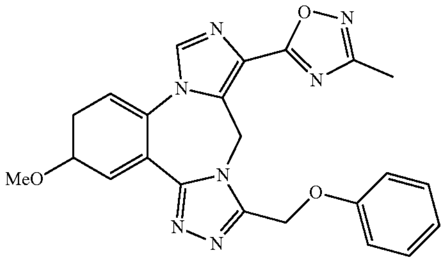 [SMILES: COC1C=C2C(=CC1)n1cnc(-c3nc(C)no3)c1Cn1c(COc3ccccc3)nnc12] |
| 119 | 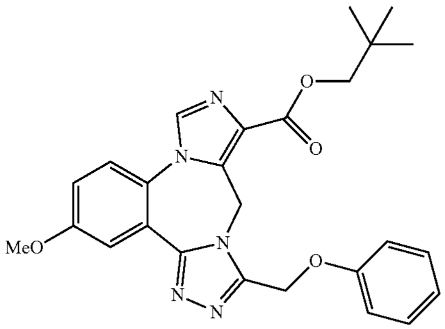 [SMILES: COc1ccc2c(c1)-c1nnc(COc3ccccc3)n1Cc1c(C(=O)OCC(C)(C)C)ncn1-2] |
| 120 | 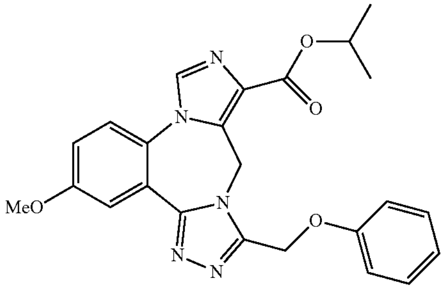 [SMILES: COc1ccc2c(c1)-c1nnc(COc3ccccc3)n1Cc1c(C(=O)OC(C)C)ncn1-2] |
| 121 | 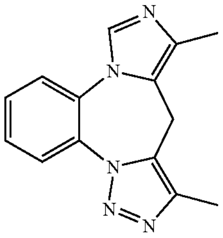 [SMILES: Cc1ncn2c1Cc1c(C)nnn1-c1ccccc1-2] |
| 122 | 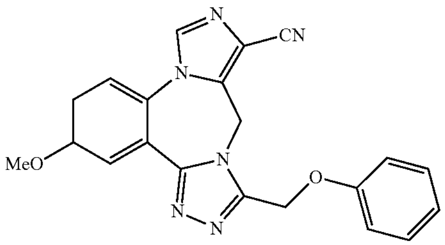 [SMILES: COC1C=C2C(=CC1)n1cnc(C#N)c1Cn1c(COc3ccccc3)nnc12] |
| 123 | 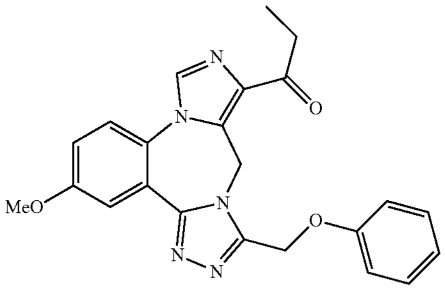 [SMILES: CCC(=O)c1ncn2c1Cn1c(COc3ccccc3)nnc1-c1cc(OC)ccc1-2] |
| 124 | 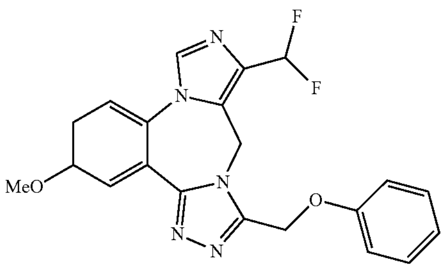 [SMILES: COC1C=C2C(=CC1)n1cnc(C(F)F)c1Cn1c(COc3ccccc3)nnc12] |

-continued
| Compound | Structure |
|---|---|
| 125 | 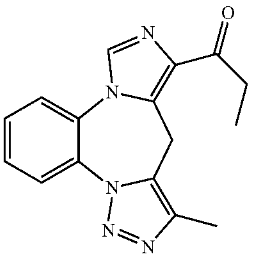 [SMILES: CCC(=O)c1ncn2c1Cc1c(C)nnn1-c1ccccc1-2] |
| 126 | 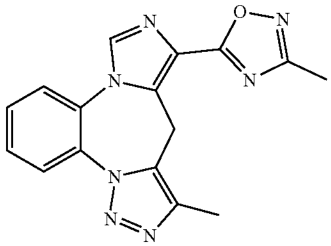 [SMILES: Cc1noc(-c2ncn3c2Cc2c(C)nnn2-c2ccccc2-3)n1] |
| 127 | 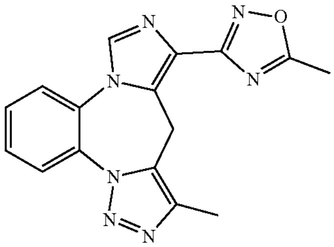 [SMILES: Cc1nc(-c2ncn3c2Cc2c(C)nnn2-c2ccccc2-3)no1] |
| 128 | 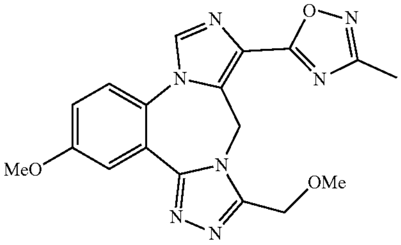 [SMILES: COCc1nnc2n1Cc1c(-c3nc(C)no3)ncn1-c1ccc(OC)cc1-2] |
| 129 | 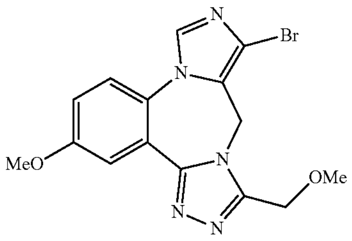 [SMILES: COCc1nnc2n1Cc1c(Br)ncn1-c1ccc(OC)cc1-2] |
| 130 | 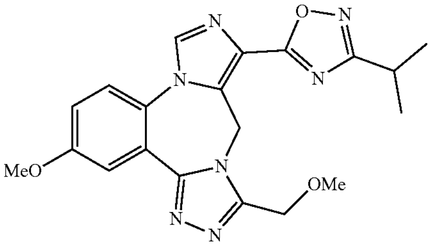 [SMILES: COCc1nnc2n1Cc1c(-c3nc(C(C)C)no3)ncn1-c1ccc(OC)cc1-2] |
-continued
| Compound | Structure |
|---|---|
| 131 | 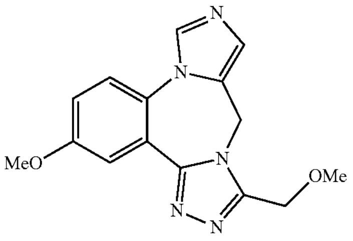 [SMILES: COCc1nnc2n1Cc1cncn1-c1ccc(OC)cc1-2] |
| 132 | 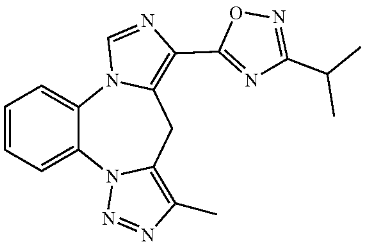 [SMILES: Cc1nnn2c1Cc1c(-c3nc(C(C)C)no3)ncn1-c1ccccc1-2] |
| 133 | 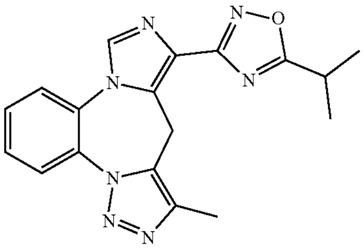 [SMILES: Cc1nnn2c1Cc1c(-c3noc(C(C)C)n3)ncn1-c1ccccc1-2] |
| 134 | 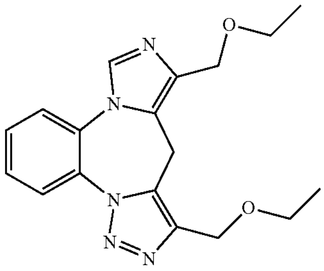 [SMILES: CCOCc1ncn2c1Cc1c(COCC)nnn1-c1ccccc1-2] |
| 135 | 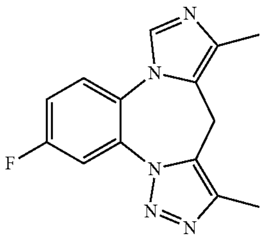 [SMILES: Cc1ncn2c1Cc1c(C)nnn1-c1cc(F)ccc1-2] |
| 136 | 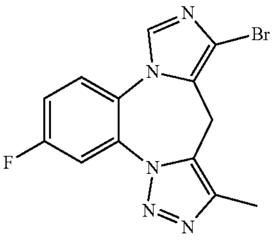 [SMILES: Cc1nnn2c1Cc1c(Br)ncn1-c1ccc(F)cc1-2] |

-continued
| Compound | Structure |
|---|---|
| 137 | 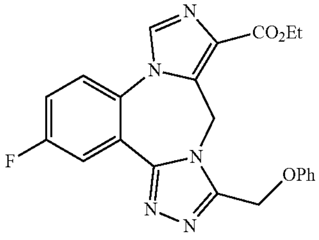 [SMILES: CCOC(=O)c1ncn2c1Cn1c(COc3ccccc3)nnc1-c1cc(F)ccc1-2] |
| 138 | 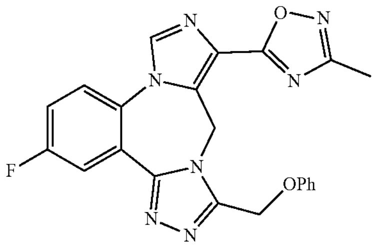 [SMILES: Cc1noc(-c2ncn3c2Cn2c(COc4ccccc4)nnc2-c2cc(F)ccc2-3)n1] |
| 139 | 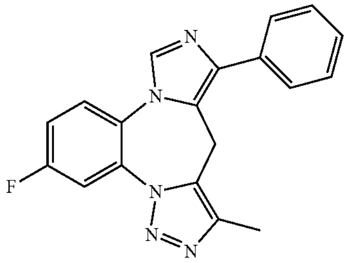 [SMILES: Cc1nnn2c1Cc1c(-c3ccccc3)ncn1-c1ccc(F)cc1-2] |
| 140 | 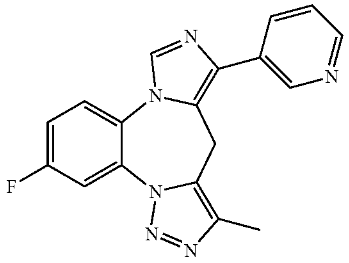 [SMILES: Cc1nnn2c1Cc1c(-c3cccnc3)ncn1-c1ccc(F)cc1-2] |
| 141 | 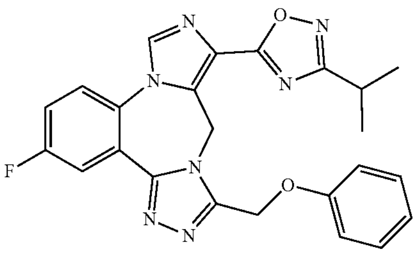 [SMILES: CC(C)c1noc(-c2ncn3c2Cn2c(COc4ccccc4)nnc2-c2cc(F)ccc2-3)n1] |
-continued
| Compound | Structure |
|---|---|
| 142 | 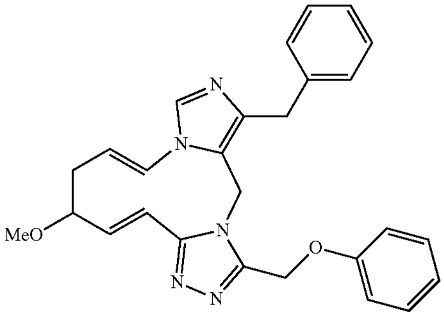 [SMILES: COC1/C=C/c2nnc(COc3ccccc3)n2Cc2c(Cc3ccccc3)ncn2/C=C/C1] |
| 143 | 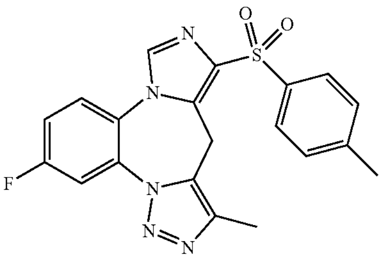 [SMILES: Cc1ccc(S(=O)(=O)c2ncn3c2Cc2c(C)nnn2-c2cc(F)ccc2-3)cc1] |
| 144 | 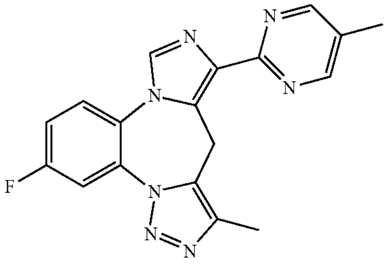 [SMILES: Cc1cnc(-c2ncn3c2Cc2c(C)nnn2-c2cc(F)ccc2-3)nc1] |
| 145 | 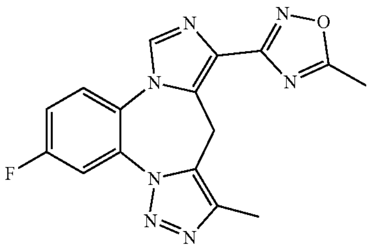 [SMILES: Cc1nc(-c2ncn3c2Cc2c(C)nnn2-c2cc(F)ccc2-3)no1] |
| 146 | 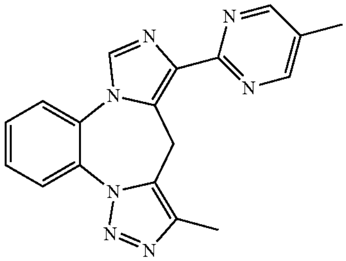 [SMILES: Cc1cnc(-c2ncn3c2Cc2c(C)nnn2-c2ccccc2-3)nc1] |

-continued
| Compound | Structure |
|---|---|
| 147 | 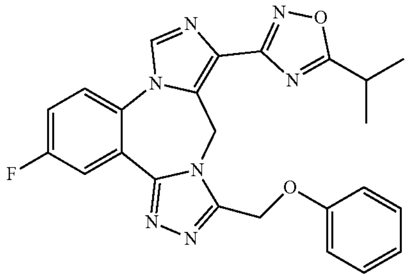 [SMILES: CC(C)c1nc(-c2ncn3c2Cn2c(COc4ccccc4)nnc2-c2cc(F)ccc2-3)no1] |
| 148 | 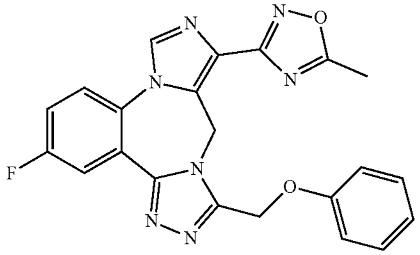 [SMILES: Cc1nc(-c2ncn3c2Cn2c(COc4ccccc4)nnc2-c2cc(F)ccc2-3)no1] |
| 149 | 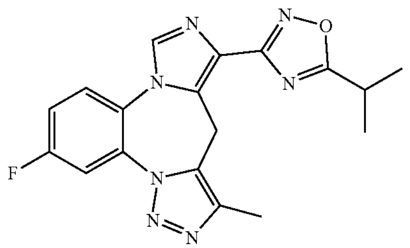 [SMILES: Cc1nnn2c1Cc1c(-c3noc(C(C)C)n3)ncn1-c1ccc(F)cc1-2] |
| 150 | 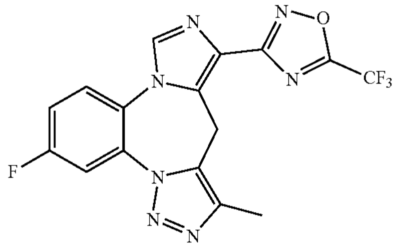 [SMILES: Cc1nnn2c1Cc1c(-c3noc(C(F)(F)F)n3)ncn1-c1ccc(F)cc1-2] |
| 151 | 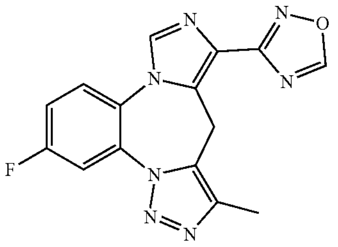 [SMILES: Cc1nnn2c1Cc1c(-c3ncon3)ncn1-c1ccc(F)cc1-2] |
| 152 | 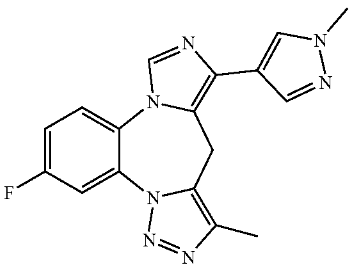 [SMILES: Cc1nnn2c1Cc1c(-c3cnn(C)c3)ncn1-c1ccc(F)cc1-2] |
-continued
| Compound | Structure |
|---|---|
| 153 | 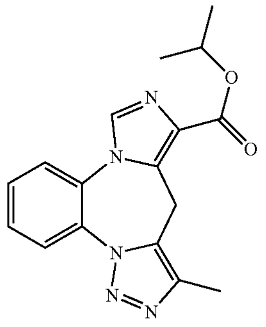 [SMILES: Cc1nnn2c1Cc1c(C(=O)OC(C)C)ncn1-c1ccccc1-2] |
| 154 | 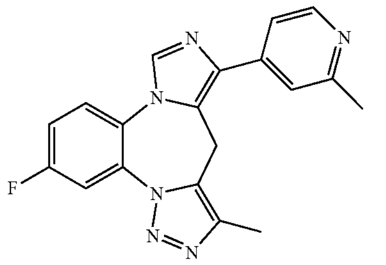 [SMILES: Cc1cc(-c2ncn3c2Cc2c(C)nnn2-c2cc(F)ccc2-3)ccn1] |
| 155 | 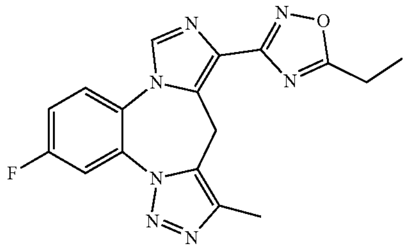 [SMILES: CCc1nc(-c2ncn3c2Cc2c(C)nnn2-c2cc(F)ccc2-3)no1] |
| 156 | 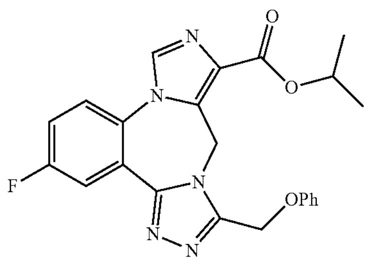 [SMILES: CC(C)OC(=O)c1ncn2c1Cn1c(COc3ccccc3)nnc1-c1cc(F)ccc1-2] |
| 157 | 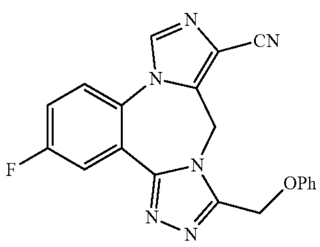 [SMILES: N#Cc1ncn2c1Cn1c(COc3ccccc3)nnc1-c1cc(F)ccc1-2] |

-continued
| Compound | Structure |
|---|---|
| 158 | 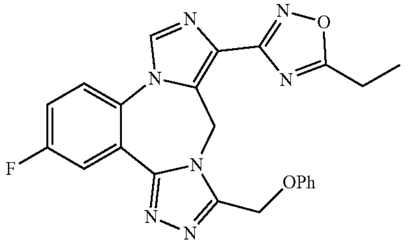 [SMILES: CCc1nc(-c2ncn3c2Cn2c(COc4ccccc4)nnc2-c2cc(F)ccc2-3)no1] |
| 159 | 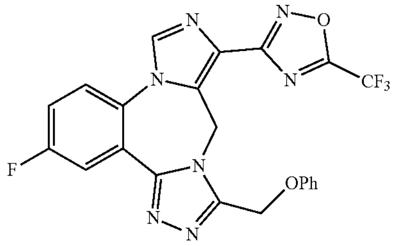 [SMILES: Fc1ccc2c(c1)-c1nnc(COc3ccccc3)n1Cc1c(-c3noc(C(F)(F)F)n3)ncn1-2] |
| 160 | 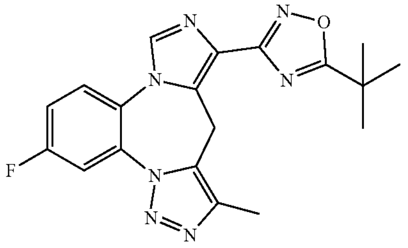 [SMILES: Cc1nnn2c1Cc1c(-c3noc(C(C)(C)C)n3)ncn1-c1ccc(F)cc1-2] |
| 161 | 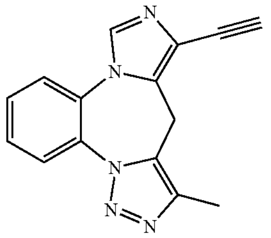 [SMILES: C#Cc1ncn2c1Cc1c(C)nnn1-c1ccccc1-2] |
| 162 | 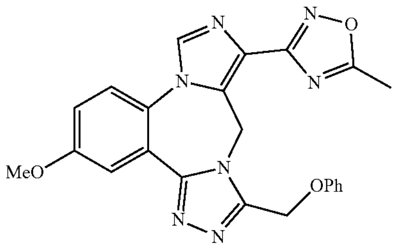 [SMILES: COc1ccc2c(c1)-c1nnc(COc3ccccc3)n1Cc1c(-c3noc(C)n3)ncn1-2] |
| 163 | 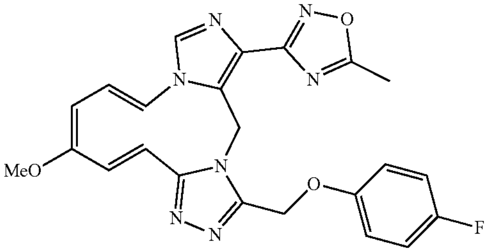 [SMILES: COC1=C/C=C/n2cnc(-c3noc(C)n3)c2Cn2c(nnc2COc2ccc(F)cc2)\C=C\1] |
-continued
| Compound | Structure |
|---|---|
| 164 | 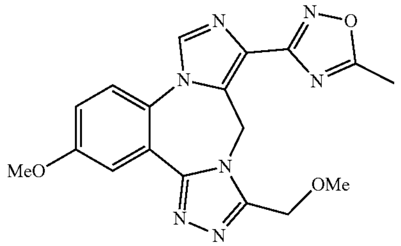 [SMILES: COCc1nnc2n1Cc1c(-c3noc(C)n3)ncn1-c1ccc(OC)cc1-2] |
| 165 | 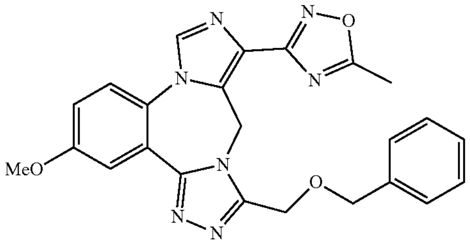 [SMILES: COc1ccc2c(c1)-c1nnc(COCc3ccccc3)n1Cc1c(-c3noc(C)n3)ncn1-2] |
| 166 | 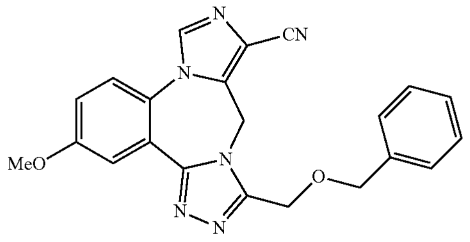 [SMILES: COc1ccc2c(c1)-c1nnc(COCc3ccccc3)n1Cc1c(C#N)ncn1-2] |
| 167 | 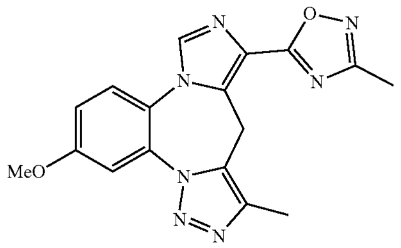 [SMILES: COc1ccc2c(c1)-n1nnc(C)c1Cc1c(-c3nc(C)no3)ncn1-2] |
| 168 | 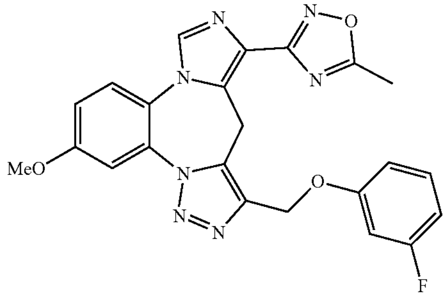 [SMILES: COc1ccc2c(c1)-n1nnc(COc3cccc(F)c3)c1Cc1c(-c3noc(C)n3)ncn1-2] |
| 169 | 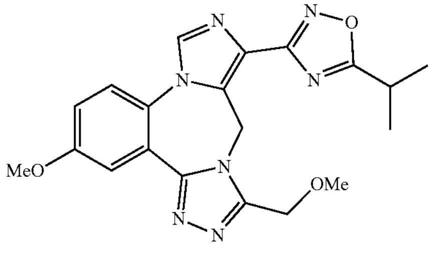 [SMILES: COCc1nnc2n1Cc1c(-c3noc(C(C)C)n3)ncn1-c1ccc(OC)cc1-2] |

-continued
| Compound | Structure |
| --- | --- |
| 170 | 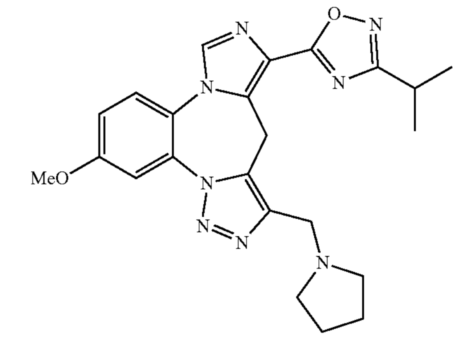 [SMILES: COc1ccc2c(c1)-n1nnc(CN3CCCC3)c1Cc1c(-c3nc(C(C)C)no3)ncn1-2] |
| 171 | 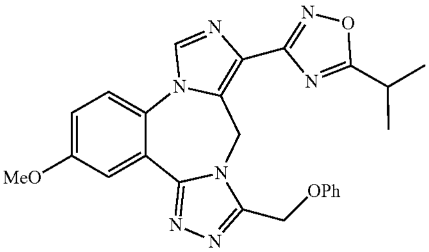 [SMILES: COc1ccc2c(c1)-c1nnc(COc3ccccc3)n1Cc1c(-c3noc(C(C)C)n3)ncn1-2] |
| 172 | 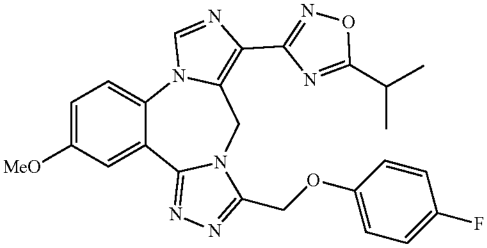 [SMILES: COc1ccc2c(c1)-c1nnc(COc3ccc(F)cc3)n1Cc1c(-c3noc(C(C)C)n3)ncn1-2] |
| 173 | 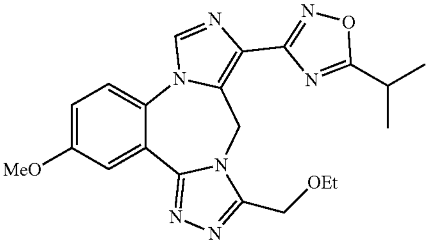 [SMILES: CCOCc1nnc2n1Cc1c(-c3noc(C(C)C)n3)ncn1-c1ccc(OC)cc1-2] |
| 174 | 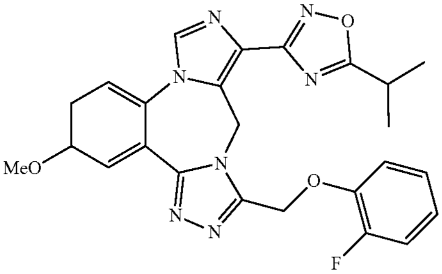 [SMILES: COC1C=C2C(=CC1)n1cnc(-c3noc(C(C)C)n3)c1Cn1c(COc3ccccc3F)nnc12] |
-continued
| Compound | Structure |
| --- | --- |
| 175 | 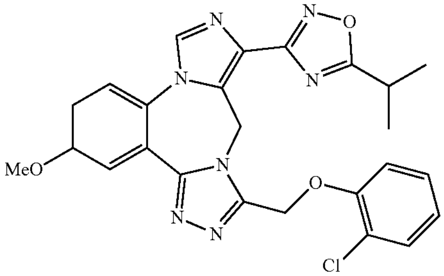 [SMILES: COC1C=C2C(=CC1)n1cnc(-c3noc(C(C)C)n3)c1Cn1c(COc3ccccc3Cl)nnc12] |
| 176 | 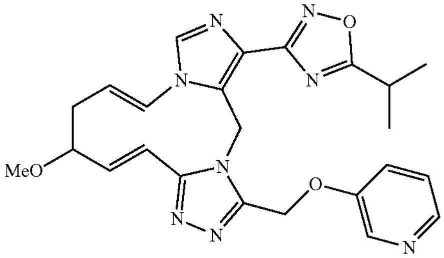 [SMILES: COC1/C=C/c2nnc(COc3cccnc3)n2Cc2c(-c3noc(C(C)C)n3)ncn2/C=C/C1] |
| 177 | 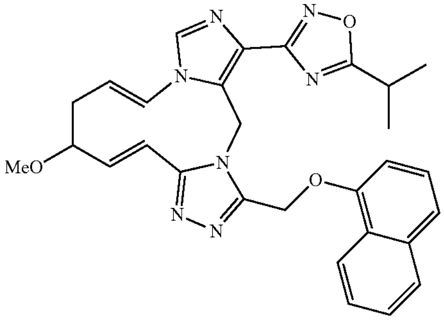 [SMILES: COC1/C=C/c2nnc(COc3cccc4ccccc34)n2Cc2c(-c3noc(C(C)C)n3)ncn2/C=C/C1] |
| 178 | 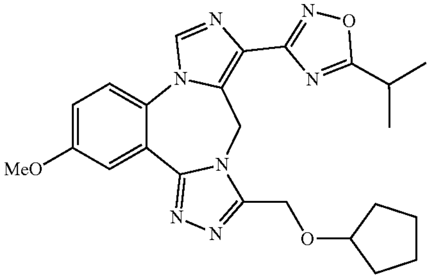 [SMILES: COc1ccc2c(c1)-c1nnc(COC3CCCC3)n1Cc1c(-c3noc(C(C)C)n3)ncn1-2] |
| 179 | 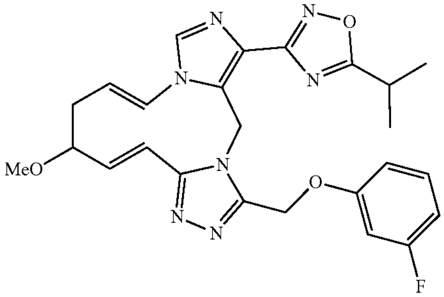 [SMILES: COC1/C=C/c2nnc(COc3cccc(F)c3)n2Cc2c(-c3noc(C(C)C)n3)ncn2/C=C/C1] |

-continued
| Compound | Structure |
| --- | --- |
| 180 | 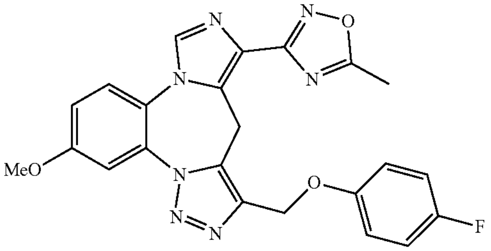 [SMILES: COc1ccc2c(c1)-n1nnc(COc3ccc(F)cc3)c1Cc1c(-c3noc(C)n3)ncn1-2] |
| 181 | 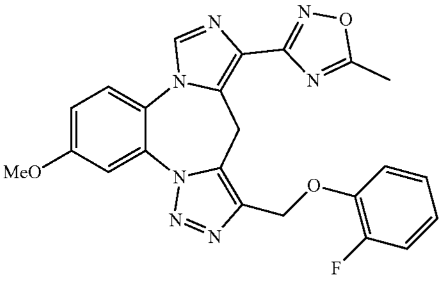 [SMILES: COc1ccc2c(c1)-n1nnc(COc3ccccc3F)c1Cc1c(-c3noc(C)n3)ncn1-2] |
| 182 | 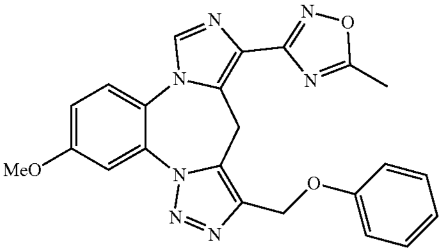 [SMILES: COc1ccc2c(c1)-n1nnc(COc3ccccc3)c1Cc1c(-c3noc(C)n3)ncn1-2] |
| 183 | 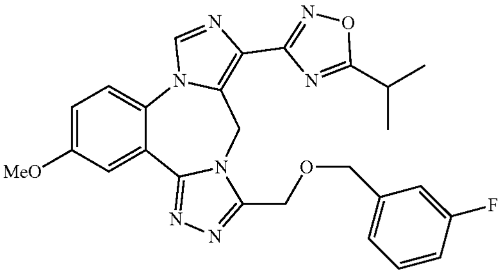 [SMILES: COc1ccc2c(c1)-c1nnc(COCc3cccc(F)c3)n1Cc1c(-c3noc(C(C)C)n3)ncn1-2] |
| 184 | 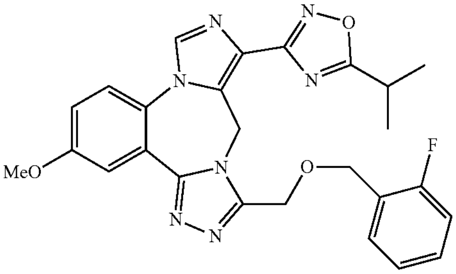 [SMILES: COc1ccc2c(c1)-c1nnc(COCc3ccccc3F)n1Cc1c(-c3noc(C(C)C)n3)ncn1-2] |
-continued
| Compound | Structure |
| --- | --- |
| 185 | 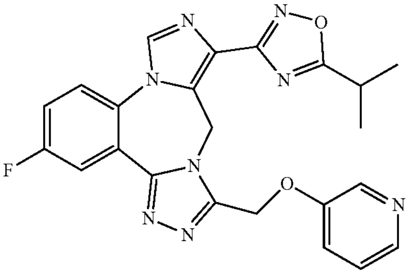 [SMILES: CC(C)c1nc(-c2ncn3c2Cn2c(COc4cccnc4)nnc2-c2cc(F)ccc2-3)no1] |
| 186 | 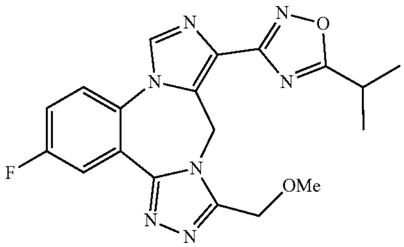 [SMILES: COCc1nnc2n1Cc1c(-c3noc(C(C)C)n3)ncn1-c1ccc(F)cc1-2] |
| 187 | 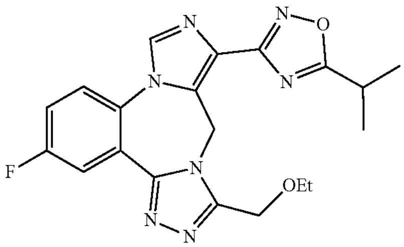 [SMILES: CCOCc1nnc2n1Cc1c(-c3noc(C(C)C)n3)ncn1-c1ccc(F)cc1-2] |
| 188 | 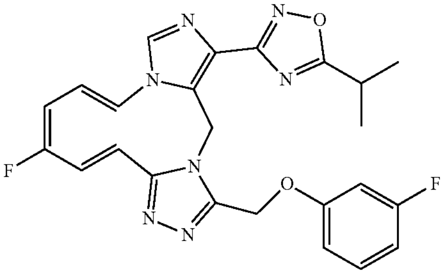 [SMILES: CC(C)c1nc(-c2ncn3c2Cn2c(nnc2COc2cccc(F)c2)/C=C/C(F)=C\C=C\3)no1] |
| 189 | 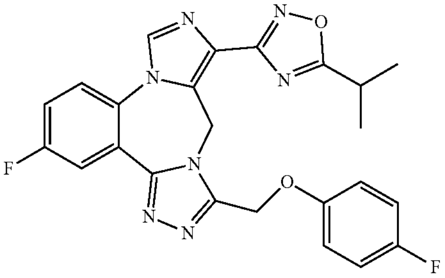 [SMILES: CC(C)c1nc(-c2ncn3c2Cn2c(COc4ccc(F)cc4)nnc2-c2cc(F)ccc2-3)no1] |

-continued
| Compound | Structure |
| --- | --- |
| 190 | 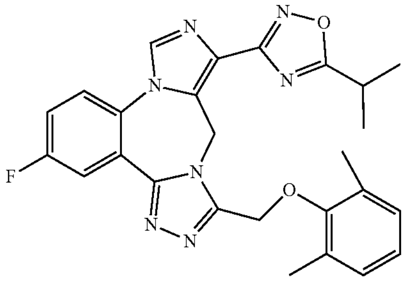 [SMILES: Cc1cccc(C)c1OCc1nnc2n1Cc1c(-c3noc(C(C)C)n3)ncn1-c1ccc(F)cc1-2] |
| 191 | 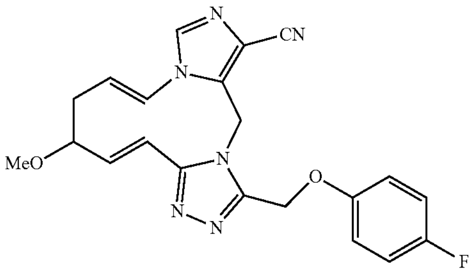 [SMILES: COC1/C=C/c2nnc(COc3ccc(F)cc3)n2Cc2c(C#N)ncn2/C=C/C1] |
| 192 | 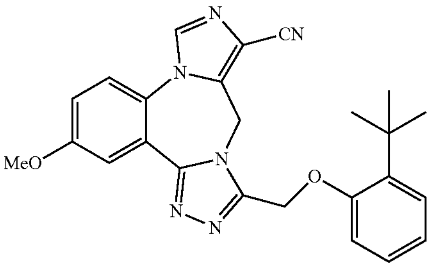 [SMILES: COc1ccc2c(c1)-c1nnc(COc3ccccc3C(C)(C)C)n1Cc1c(C#N)ncn1-2] |
| 193 | 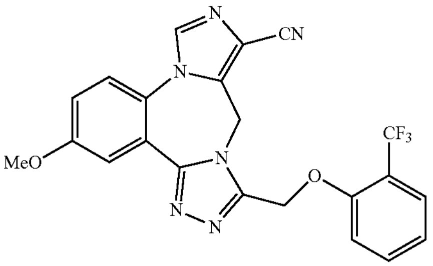 [SMILES: COc1ccc2c(c1)-c1nnc(COc3ccccc3C(F)(F)F)n1Cc1c(C#N)ncn1-2] |
| 194 | 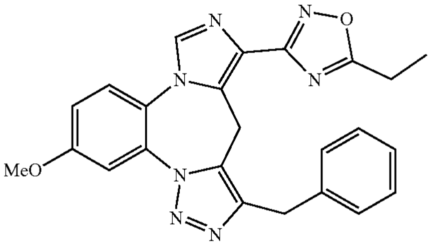 [SMILES: CCc1nc(-c2ncn3c2Cc2c(Cc4ccccc4)nnn2-c2cc(OC)ccc2-3)no1] |
-continued
| Compound | Structure |
| --- | --- |
| 195 | 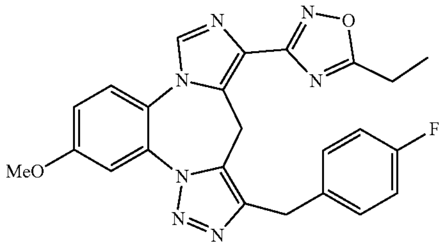 [SMILES: CCc1nc(-c2ncn3c2Cc2c(Cc4ccc(F)cc4)nnn2-c2cc(OC)ccc2-3)no1] |
| 196 | 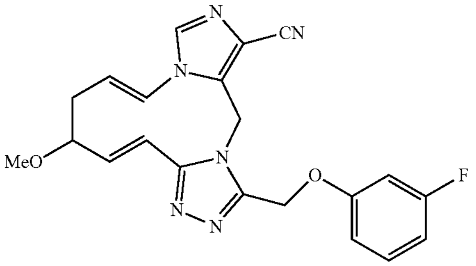 [SMILES: COC1/C=C/c2nnc(COc3cccc(F)c3)n2Cc2c(C#N)ncn2/C=C/C1] |
| 197 | 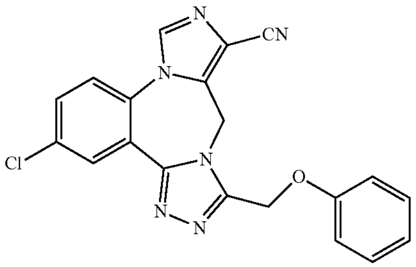 [SMILES: N#Cc1ncn2c1Cn1c(COc3ccccc3)nnc1-c1cc(Cl)ccc1-2] |
| 198 | 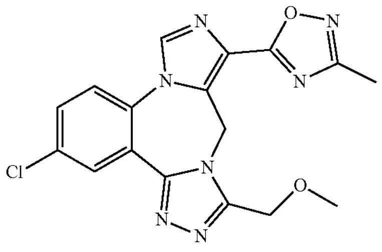 [SMILES: COCc1nnc2n1Cc1c(-c3nc(C)no3)ncn1-c1ccc(Cl)cc1-2] |
| 199 | 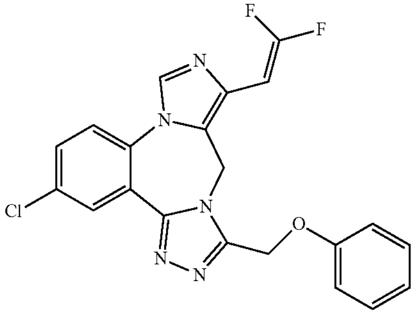 [SMILES: FC(F)=Cc1ncn2c1Cn1c(COc3ccccc3)nnc1-c1cc(Cl)ccc1-2] |

-continued
| Compound | Structure |
|---|---|
| 200 | 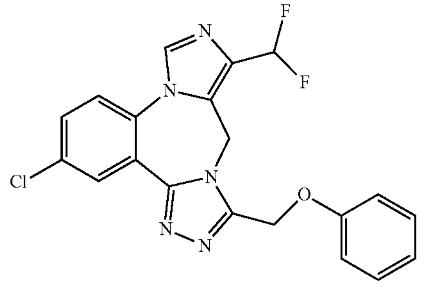 [SMILES: FC(F)c1ncn2c1Cn1c(COc3ccccc3)nnc1-c1cc(Cl)ccc1-2] |
| 201 | 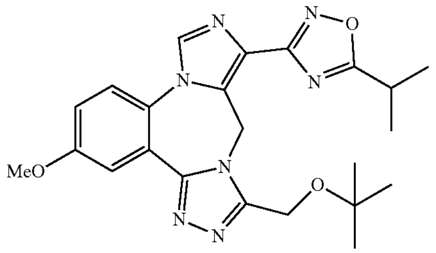 [SMILES: COc1ccc2c(c1)-c1nnc(COC(C)(C)C)n1Cc1c(-c3noc(C(C)C)n3)ncn1-2] |
| 202 | 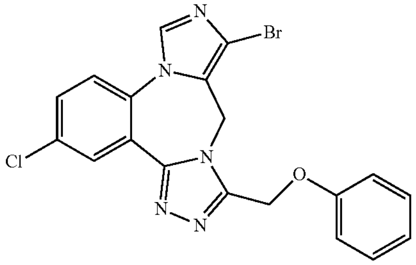 [SMILES: Clc1ccc2c(c1)-c1nnc(COc3ccccc3)n1Cc1c(Br)ncn1-2] |
| 203 | 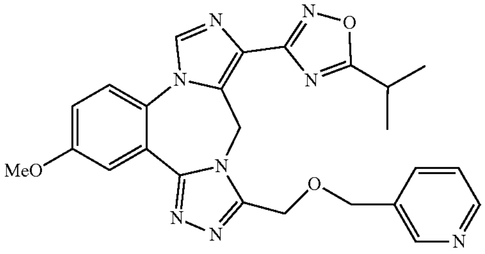 [SMILES: COc1ccc2c(c1)-c1nnc(COCc3cccnc3)n1Cc1c(-c3noc(C(C)C)n3)ncn1-2] |
| 204 | 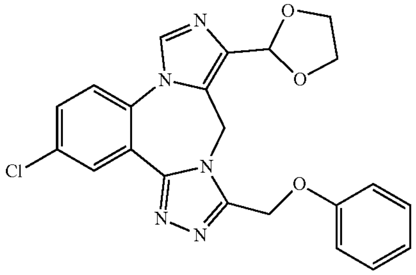 [SMILES: Clc1ccc2c(c1)-c1nnc(COc3ccccc3)n1Cc1c(C3OCCO3)ncn1-2] |
-continued
| Compound | Structure |
|---|---|
| 205 | 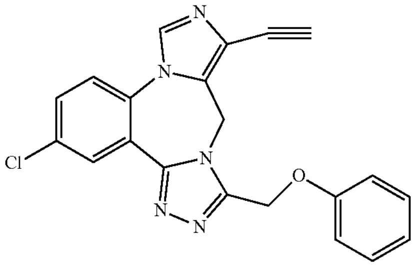 [SMILES: C#Cc1ncn2c1Cn1c(COc3ccccc3)nnc1-c1cc(Cl)ccc1-2] |
| 206 | 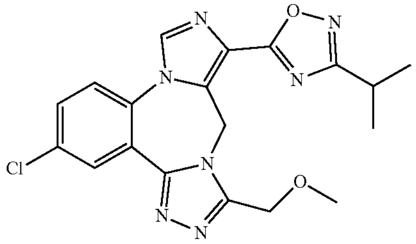 [SMILES: COCc1nnc2n1Cc1c(-c3nc(C(C)C)no3)ncn1-c1ccc(Cl)cc1-2] |
| 207 | 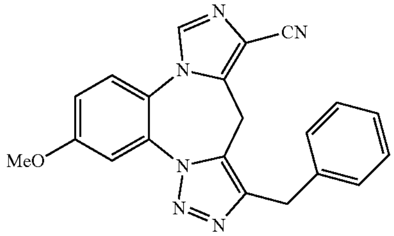 [SMILES: COc1ccc2c(c1)-n1nnc(Cc3ccccc3)c1Cc1c(C#N)ncn1-2] |
| 208 | 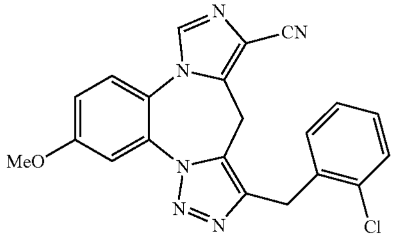 [SMILES: COc1ccc2c(c1)-n1nnc(Cc3ccccc3Cl)c1Cc1c(C#N)ncn1-2] |
| 209 | 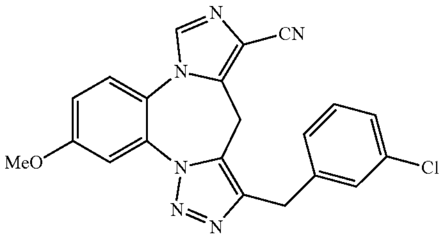 [SMILES: COc1ccc2c(c1)-n1nnc(Cc3cccc(Cl)c3)c1Cc1c(C#N)ncn1-2] |
| 210 | 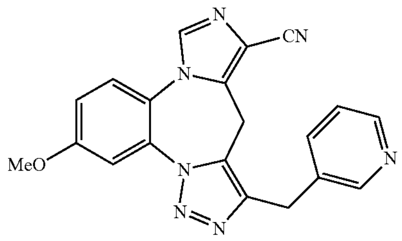 [SMILES: COc1ccc2c(c1)-n1nnc(Cc3cccnc3)c1Cc1c(C#N)ncn1-2] |

-continued
| Compound | Structure |
| --- | --- |
| 211 | 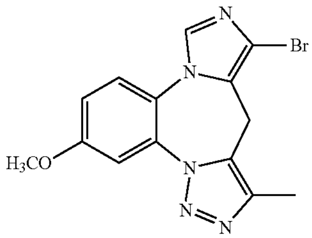 [SMILES: COc1ccc2c(c1)-n1nnc(C)c1Cc1c(Br)ncn1-2] |
| 212 | 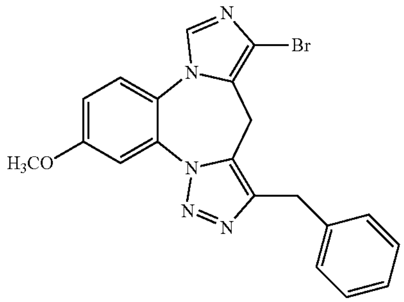 [SMILES: COc1ccc2c(c1)-n1nnc(Cc3ccccc3)c1Cc1c(Br)ncn1-2] |
| 213 | 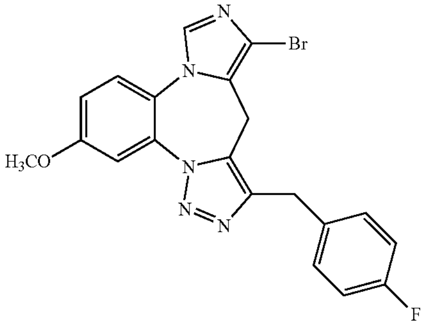 [SMILES: COc1ccc2c(c1)-n1nnc(Cc3ccc(F)cc3)c1Cc1c(Br)ncn1-2] |
| 214 | 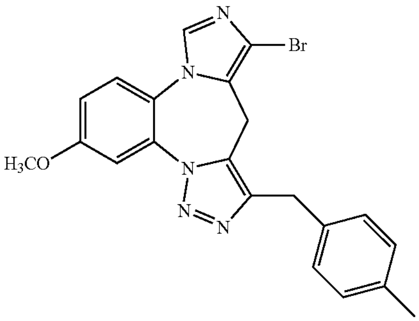 [SMILES: COc1ccc2c(c1)-n1nnc(Cc3ccc(C)cc3)c1Cc1c(Br)ncn1-2] |
| 215 | 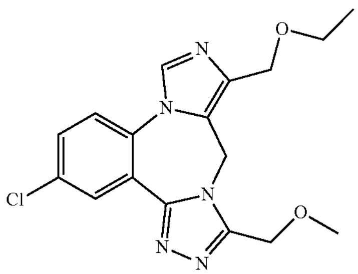 [SMILES: CCOCc1ncn2c1Cn1c(COC)nnc1-c1cc(Cl)ccc1-2] |
-continued
| Compound | Structure |
| --- | --- |
| 216 | 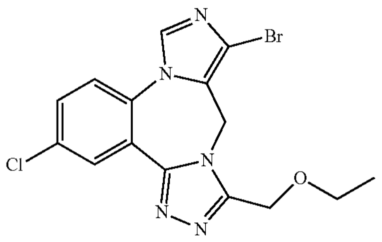 [SMILES: CCOCc1nnc2n1Cc1c(Br)ncn1-c1ccc(Cl)cc1-2] |
| 217 | 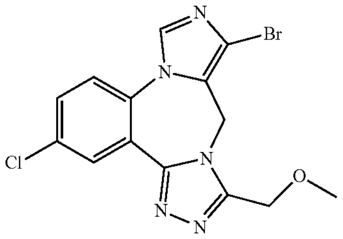 [SMILES: COCc1nnc2n1Cc1c(Br)ncn1-c1ccc(Cl)cc1-2] |
| 218 | 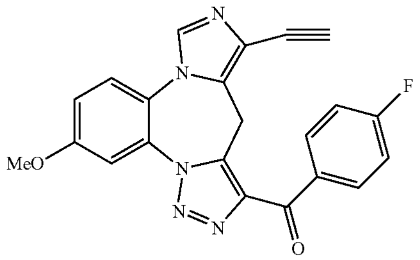 [SMILES: C#Cc1ncn2c1Cc1c(C(=O)c3ccc(F)cc3)nnn1-c1cc(OC)ccc1-2] |
| 219 | 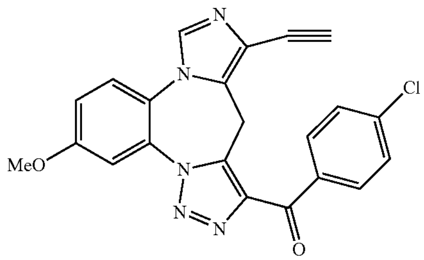 [SMILES: C#Cc1ncn2c1Cc1c(C(=O)c3ccc(Cl)cc3)nnn1-c1cc(OC)ccc1-2] |
| 220 | 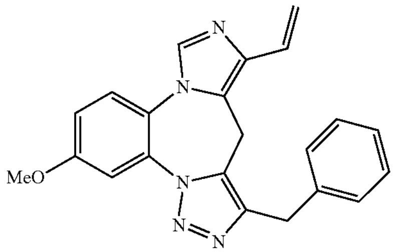 [SMILES: C=Cc1ncn2c1Cc1c(Cc3ccccc3)nnn1-c1cc(OC)ccc1-2] |
| 221 | 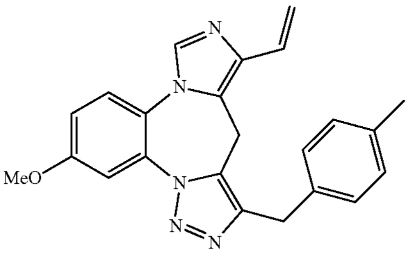 [SMILES: C=Cc1ncn2c1Cc1c(Cc3ccc(C)cc3)nnn1-c1cc(OC)ccc1-2] |

-continued
| Compound | Structure |
|---|---|
| 222 | 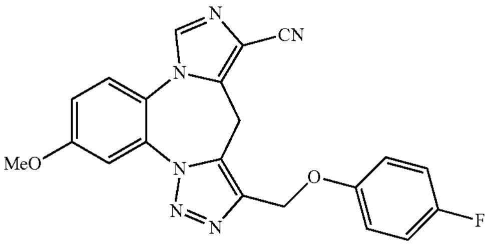 [SMILES: COc1ccc2c(c1)-n1nnc(COc3ccc(F)cc3)c1Cc1c(C#N)ncn1-2] |
| 223 | 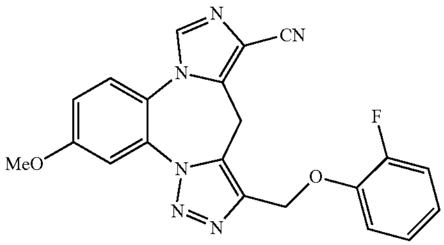 [SMILES: COc1ccc2c(c1)-n1nnc(COc3ccccc3F)c1Cc1c(C#N)ncn1-2] |
| 224 | 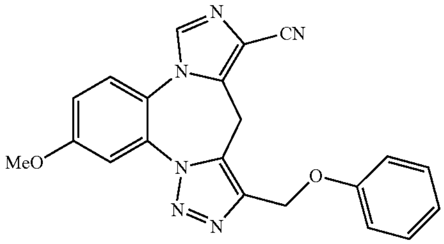 [SMILES: COc1ccc2c(c1)-n1nnc(COc3ccccc3)c1Cc1c(C#N)ncn1-2] |
| 225 | 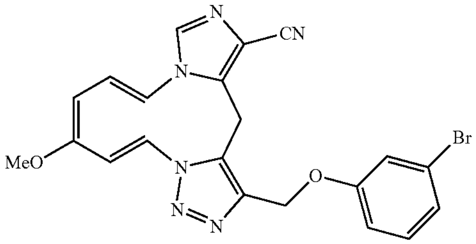 [SMILES: COC1=C/C=C/n2cnc(C#N)c2Cc2c(COc3cccc(Br)c3)nnn2\C=C\1] |
| 226 | 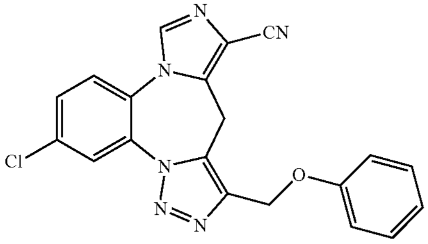 [SMILES: N#Cc1ncn2c1Cc1c(COc3ccccc3)nnn1-c1cc(Cl)ccc1-2] |
| 227 | 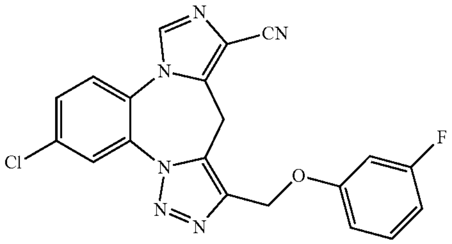 [SMILES: N#Cc1ncn2c1Cc1c(COc3cccc(F)c3)nnn1-c1cc(Cl)ccc1-2] |
-continued
| Compound | Structure |
|---|---|
| 228 | 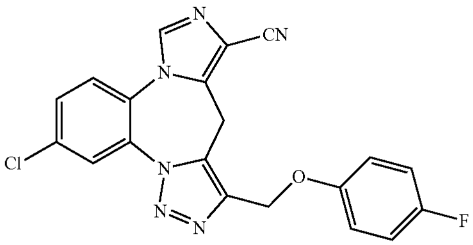 [SMILES: N#Cc1ncn2c1Cc1c(COc3ccc(F)cc3)nnn1-c1cc(Cl)ccc1-2] |
| 229 | 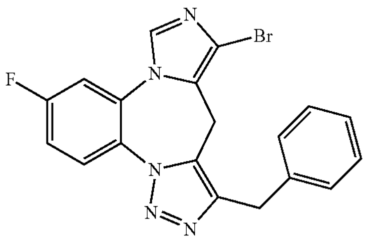 [SMILES: Fc1ccc2c(c1)-n1cnc(Br)c1Cc1c(Cc3ccccc3)nnn1-2] |
| 230 | 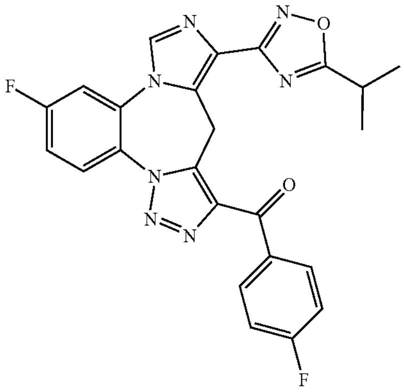 [SMILES: CC(C)c1nc(-c2ncn3c2Cc2c(C(=O)c4ccc(F)cc4)nnn2-c2ccc(F)cc2-3)no1] |
| 231 | 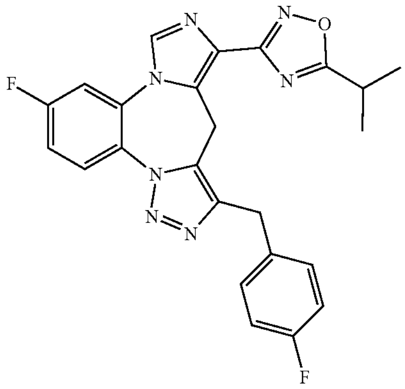 [SMILES: CC(C)c1nc(-c2ncn3c2Cc2c(Cc4ccc(F)cc4)nnn2-c2ccc(F)cc2-3)no1] |
| 232 | 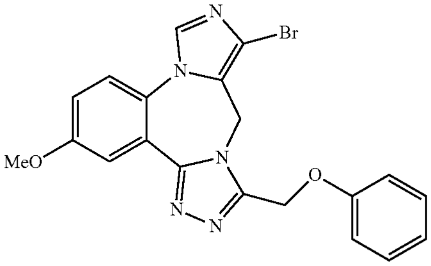 [SMILES: COc1ccc2c(c1)-c1nnc(COc3ccccc3)n1Cc1c(Br)ncn1-2] |

-continued
| Compound | Structure |
|---|---|
| 233 | 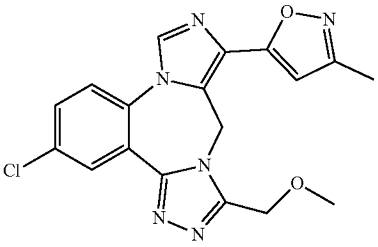 [SMILES: COCc1nnc2n1Cc1c(-c3cc(C)no3)ncn1-c1ccc(Cl)cc1-2] |
| 234 | 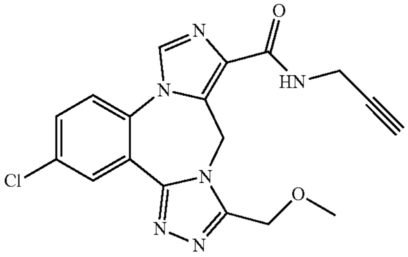 [SMILES: C#CCNC(=O)c1ncn2c1Cn1c(COC)nnc1-c1cc(Cl)ccc1-2] |
| 235 | 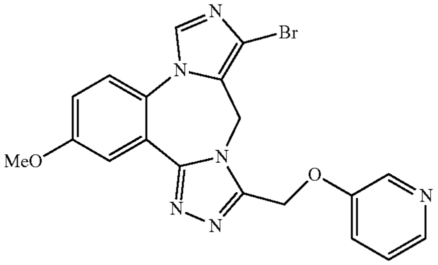 [SMILES: COc1ccc2c(c1)-c1nnc(COc3cccnc3)n1Cc1c(Br)ncn1-2] |
| 236 | 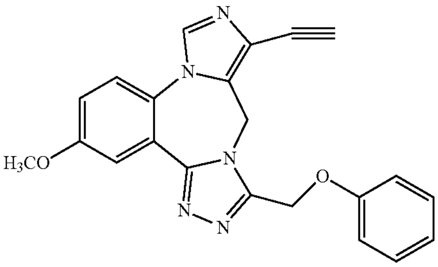 [SMILES: C#Cc1ncn2c1Cn1c(COc3ccccc3)nnc1-c1cc(OC)ccc1-2] |
| 237 | 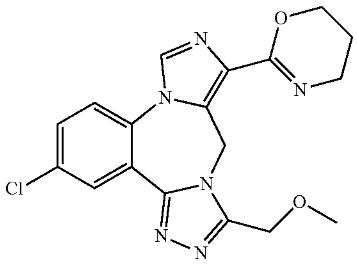 [SMILES: COCc1nnc2n1Cc1c(C3=NCCCO3)ncn1-c1ccc(Cl)cc1-2] |
| 238 | 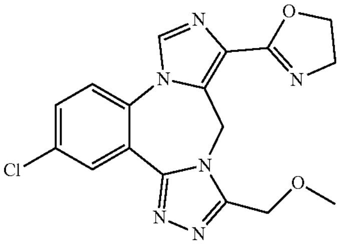 [SMILES: COCc1nnc2n1Cc1c(C3=NCCO3)ncn1-c1ccc(Cl)cc1-2] |
-continued
| Compound | Structure |
|---|---|
| 239 | 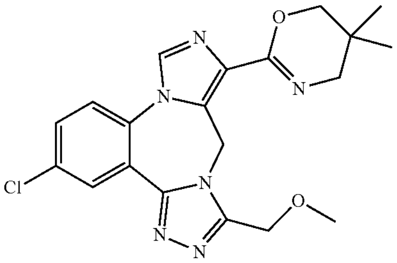 [SMILES: COCc1nnc2n1Cc1c(C3=NCC(C)(C)CO3)ncn1-c1ccc(Cl)cc1-2] |
| 240 | 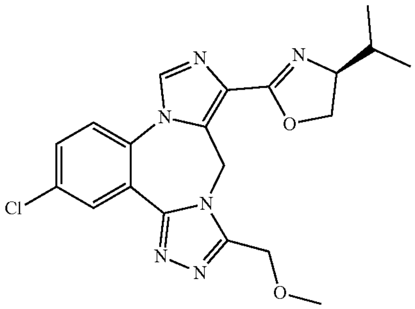 [SMILES: COCc1nnc2n1Cc1c(C3=N[C@@H](C(C)C)CO3)ncn1-c1ccc(Cl)cc1-2] |
| 241 | 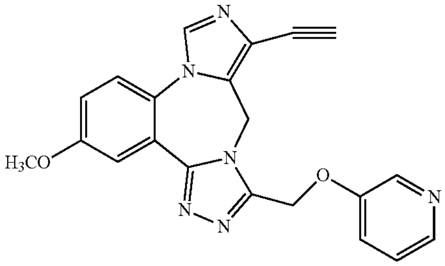 [SMILES: C#Cc1ncn2c1Cn1c(COc3cccnc3)nnc1-c1cc(OC)ccc1-2] |
| 242 | 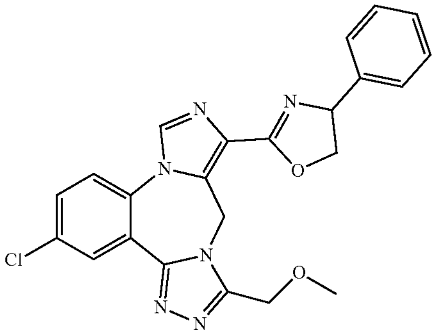 [SMILES: COCc1nnc2n1Cc1c(C3=NC(c4ccccc4)CO3)ncn1-c1ccc(Cl)cc1-2] |
| 243 | 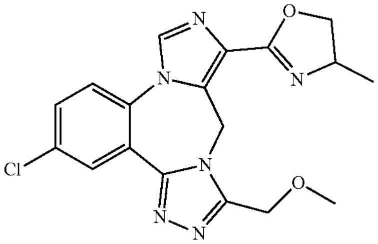 [SMILES: COCc1nnc2n1Cc1c(C3=NC(C)CO3)ncn1-c1ccc(Cl)cc1-2] |

-continued
| Compound | Structure |
|---|---|
| 244 | 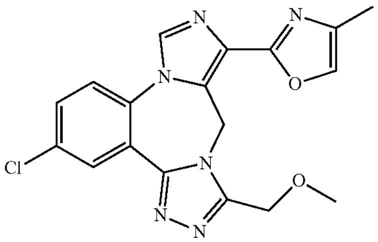 [SMILES: COCc1nnc2n1Cc1c(-c3nc(C)co3)ncn1-c1ccc(Cl)cc1-2] |
| 245 | 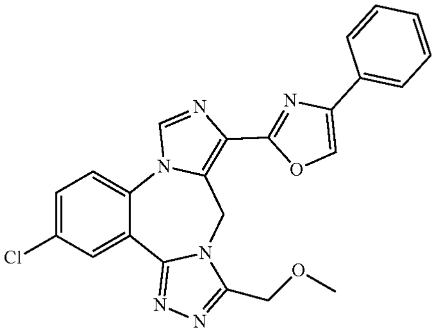 [SMILES: COCc1nnc2n1Cc1c(-c3nc(-c4ccccc4)co3)ncn1-c1ccc(Cl)cc1-2] |
| 246 | 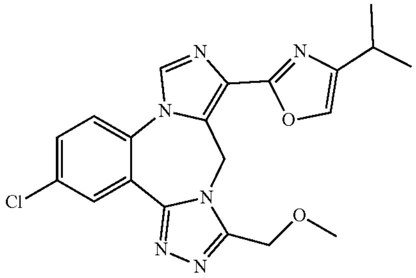 [SMILES: COCc1nnc2n1Cc1c(-c3nc(C(C)C)co3)ncn1-c1ccc(Cl)cc1-2] |
| 247 | 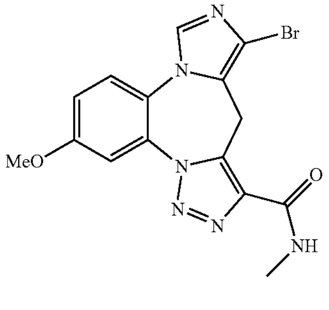 [SMILES: CNC(=O)c1nnn2c1Cc1c(Br)ncn1-c1ccc(OC)cc1-2] |
| 248 | 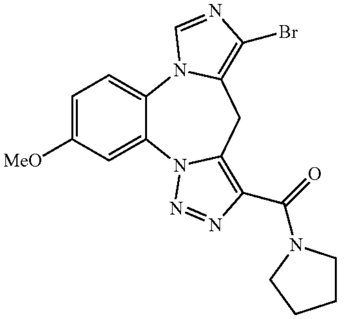 [SMILES: COc1ccc2c(c1)-n1nnc(C(=O)N3CCCC3)c1Cc1c(Br)ncn1-2] |
-continued
| Compound | Structure |
|---|---|
| 249 | 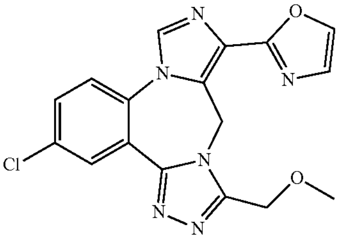 [SMILES: COCc1nnc2n1Cc1c(-c3ncco3)ncn1-c1ccc(Cl)cc1-2] |
| 250 | 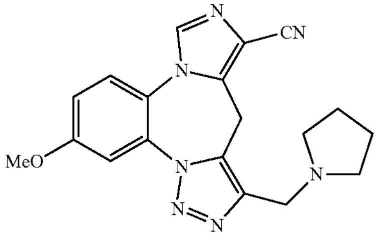 [SMILES: COc1ccc2c(c1)-n1nnc(CN3CCCC3)c1Cc1c(C#N)ncn1-2] |
| 251 | 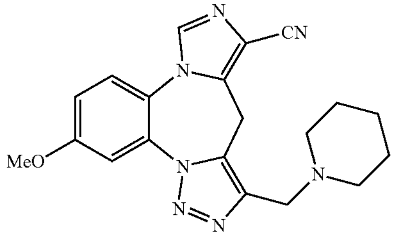 [SMILES: COc1ccc2c(c1)-n1nnc(CN3CCCCC3)c1Cc1c(C#N)ncn1-2] |
| 252 | 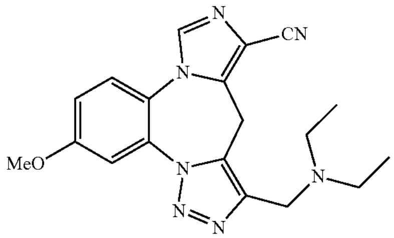 [SMILES: CCN(CC)Cc1nnn2c1Cc1c(C#N)ncn1-c1ccc(OC)cc1-2] |
| 253 | 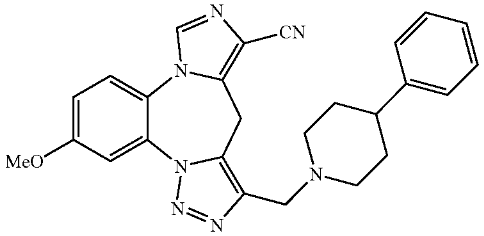 [SMILES: COc1ccc2c(c1)-n1nnc(CN3CCC(c4ccccc4)CC3)c1Cc1c(C#N)ncn1-2] |
| 254 | 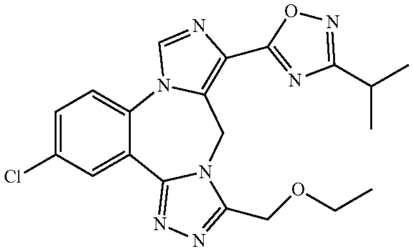 [SMILES: CCOCc1nnc2n1Cc1c(-c3nc(C(C)C)no3)ncn1-c1ccc(Cl)cc1-2] |

-continued
| Compound | Structure |
|---|---|
| 255 | 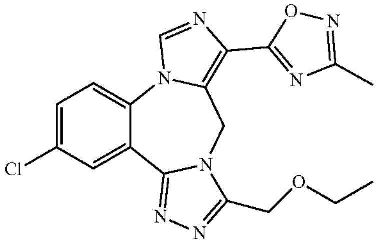 [SMILES: CCOCc1nnc2n1Cc1c(-c3nc(C)no3)ncn1-c1ccc(Cl)cc1-2] |
| 256 | 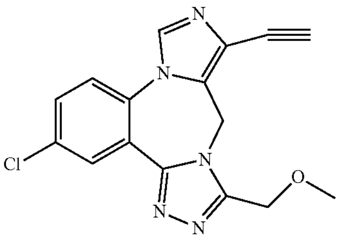 [SMILES: C#Cc1ncn2c1Cn1c(COC)nnc1-c1cc(Cl)ccc1-2] |
| 257 | 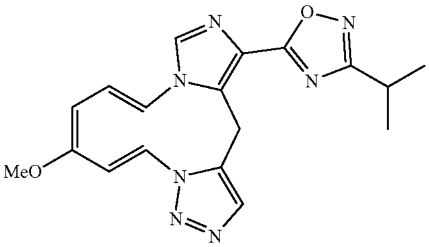 [SMILES: COC1=C/C=C/n2cnc(-c3nc(C(C)C)no3)c2Cc2cnnn2\C=C\1] |
| 258 | 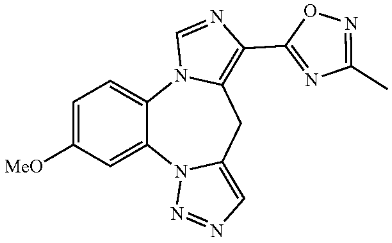 [SMILES: COc1ccc2c(c1)-n1nncc1Cc1c(-c3nc(C)no3)ncn1-2] |
| 259 | 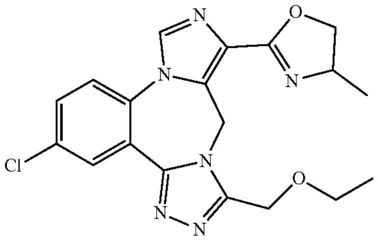 [SMILES: CCOCc1nnc2n1Cc1c(C3=NC(C)CO3)ncn1-c1ccc(Cl)cc1-2] |
| 260 | 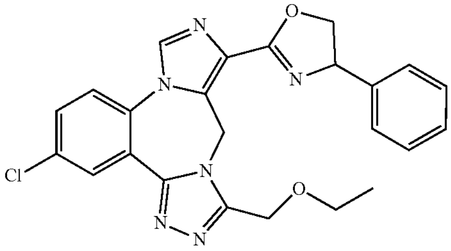 [SMILES: CCOCc1nnc2n1Cc1c(C3=NC(c4ccccc4)CO3)ncn1-c1ccc(Cl)cc1-2] |
-continued
| Compound | Structure |
|---|---|
| 261 | 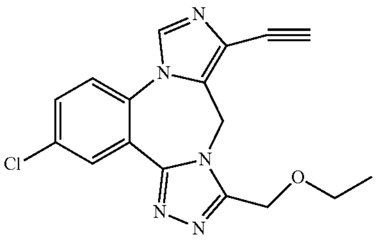 [SMILES: C#Cc1ncn2c1Cn1c(COCC)nnc1-c1cc(Cl)ccc1-2] |
| 262 | 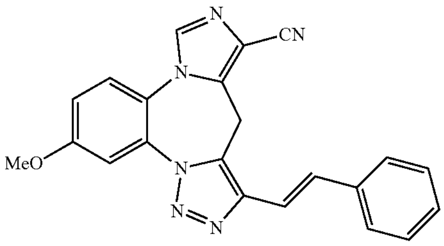 [SMILES: COc1ccc2c(c1)-n1nnc(/C=C/c3ccccc3)c1Cc1c(C#N)ncn1-2] |
| 263 | 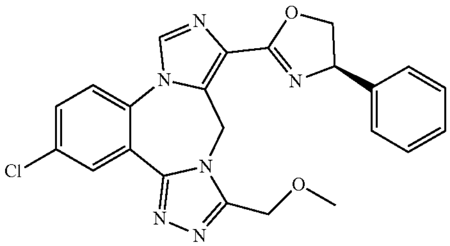 [SMILES: COCc1nnc2n1Cc1c(C3=N[C@H](c4ccccc4)CO3)ncn1-c1ccc(Cl)cc1-2] |
| 264 | 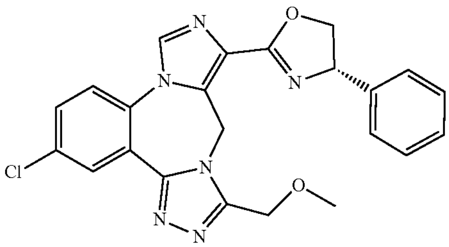 [SMILES: COCc1nnc2n1Cc1c(C3=N[C@@H](c4ccccc4)CO3)ncn1-c1ccc(Cl)cc1-2] |
| 265 | 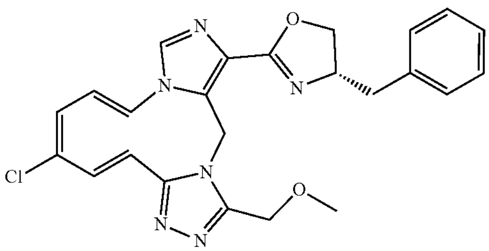 [SMILES: COCc1nnc2n1Cc1c(C3=N[C@@H](Cc4ccccc4)CO3)ncn1/C=C/C=C(Cl)\C=C\2] |
| 266 | 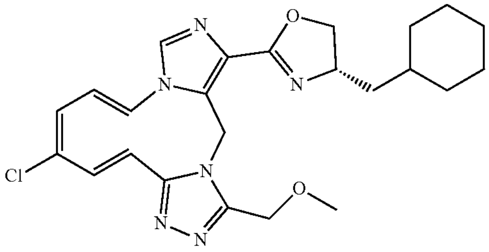 [SMILES: COCc1nnc2n1Cc1c(C3=N[C@@H](CC4CCCCC4)CO3)ncn1/C=C/C=C(Cl)\C=C\2] |

-continued
| Compound | Structure |
|---|---|
| 267 | 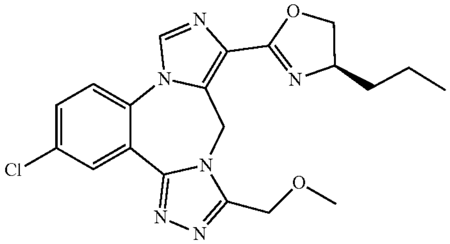 [SMILES: CCC[C@@H]1COC(c2ncn3c2Cn2c(COC)nnc2-c2cc(Cl)ccc2-3)=N1] |
| 268 | 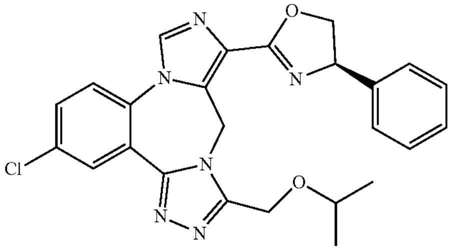 [SMILES: CC(C)OCc1nnc2n1Cc1c(C3=N[C@H](c4ccccc4)CO3)ncn1-c1ccc(Cl)cc1-2] |
| 270 | 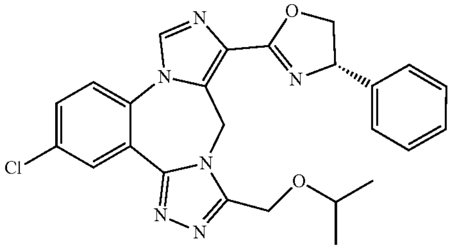 [SMILES: CC(C)OCc1nnc2n1Cc1c(C3=N[C@@H](c4ccccc4)CO3)ncn1-c1ccc(Cl)cc1-2] |
| 271 | 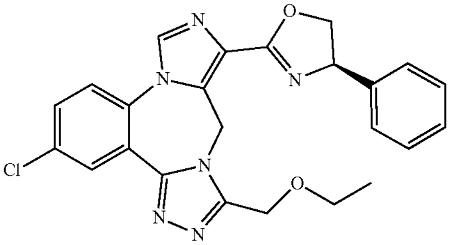 [SMILES: CCOCc1nnc2n1Cc1c(C3=N[C@H](c4ccccc4)CO3)ncn1-c1ccc(Cl)cc1-2] |
| 272 | 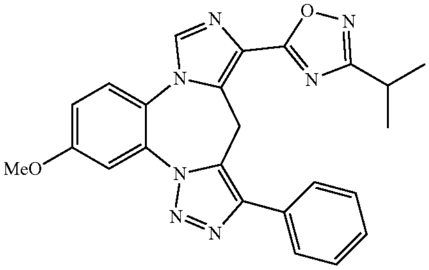 [SMILES: COc1ccc2c(c1)-n1nnc(-c3ccccc3)c1Cc1c(-c3nc(C(C)C)no3)ncn1-2] |
| 273 | 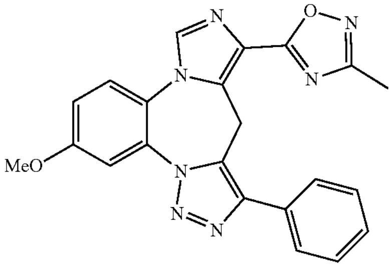 [SMILES: COc1ccc2c(c1)-n1nnc(-c3ccccc3)c1Cc1c(-c3nc(C)no3)ncn1-2] |
-continued
| Compound | Structure |
|---|---|
| 274 | 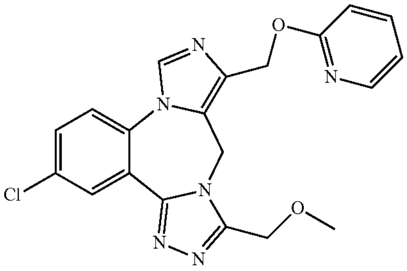 [SMILES: COCc1nnc2n1Cc1c(COc3ccccn3)ncn1-c1ccc(Cl)cc1-2] |
| 275 | 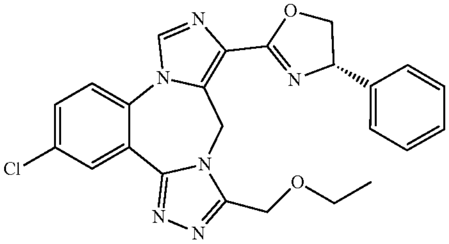 [SMILES: CCOCc1nnc2n1Cc1c(C3=N[C@@H](c4ccccc4)CO3)ncn1-c1ccc(Cl)cc1-2] |
| 276 | 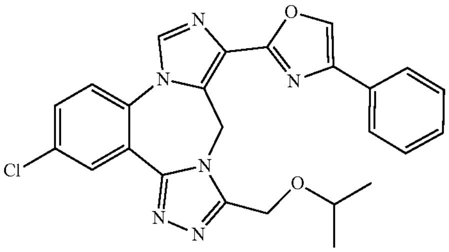 [SMILES: CC(C)OCc1nnc2n1Cc1c(-c3nc(-c4ccccc4)co3)ncn1-c1ccc(Cl)cc1-2] |
| 277 | 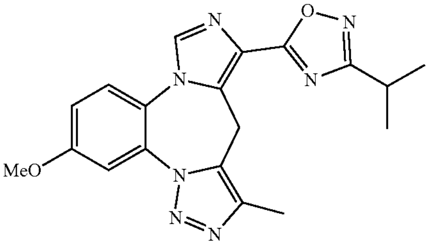 [SMILES: COc1ccc2c(c1)-n1nnc(C)c1Cc1c(-c3nc(C(C)C)no3)ncn1-2] |
| 278 | 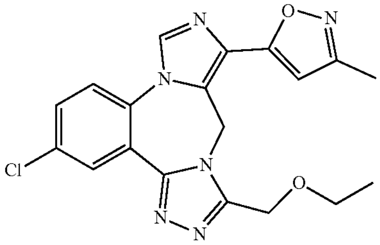 [SMILES: CCOCc1nnc2n1Cc1c(-c3cc(C)no3)ncn1-c1ccc(Cl)cc1-2] |

-continued
| Compound | Structure |
| --- | --- |
| 279 | 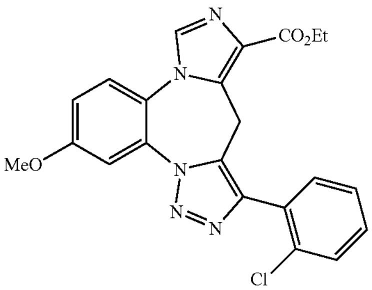 [SMILES: CCOC(=O)c1ncn2c1Cc1c(-c3ccccc3Cl)nnn1-c1cc(OC)ccc1-2] |
| 280 | 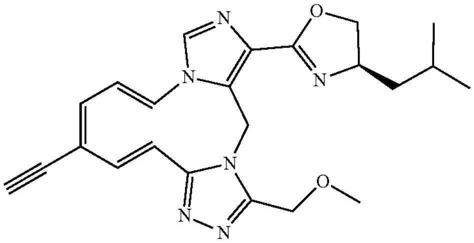 [SMILES: C#CC1=C/C=C/n2cnc(C3=N[C@H](CC(C)C)CO3)c2Cn2c(nnc2COC)\C=C\1] |
| 281 | 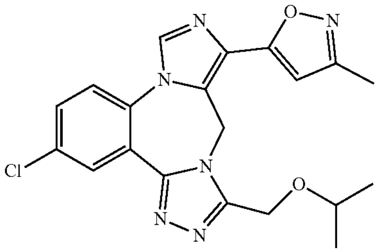 [SMILES: Cc1cc(-c2ncn3c2Cn2c(COC(C)C)nnc2-c2cc(Cl)ccc2-3)on1] |
| 282 | 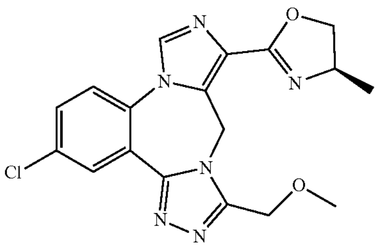 [SMILES: COCc1nnc2n1Cc1c(C3=N[C@H](C)CO3)ncn1-c1ccc(Cl)cc1-2] |
| 283 | 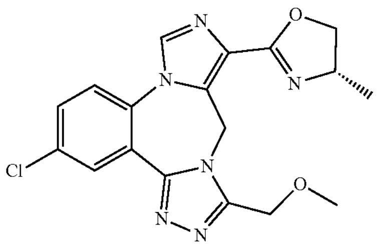 [SMILES: COCc1nnc2n1Cc1c(C3=N[C@@H](C)CO3)ncn1-c1ccc(Cl)cc1-2] |
| 284 | 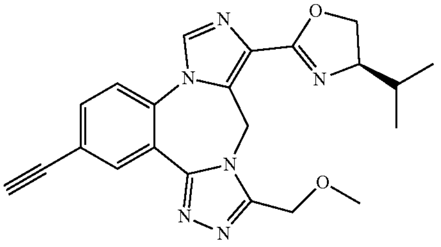 [SMILES: C#Cc1ccc2c(c1)-c1nnc(COC)n1Cc1c(C3=N[C@H](C(C)C)CO3)ncn1-2] |
-continued
| Compound | Structure |
| --- | --- |
| 285 | 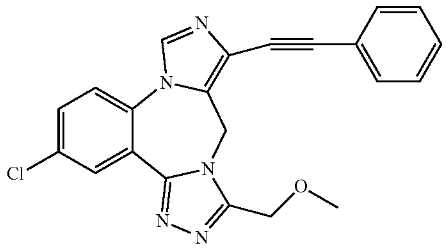 [SMILES: COCc1nnc2n1Cc1c(C#Cc3ccccc3)ncn1-c1ccc(Cl)cc1-2] |
| 286 | 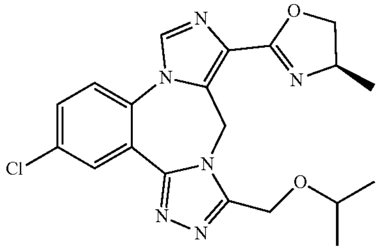 [SMILES: CC(C)OCc1nnc2n1Cc1c(C3=N[C@H](C)CO3)ncn1-c1ccc(Cl)cc1-2] |
| 287 | 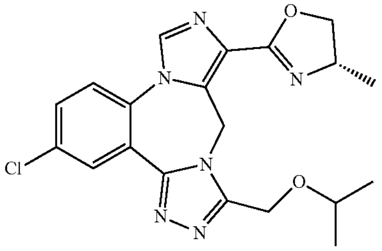 [SMILES: CC(C)OCc1nnc2n1Cc1c(C3=N[C@@H](C)CO3)ncn1-c1ccc(Cl)cc1-2] |
| 288 | 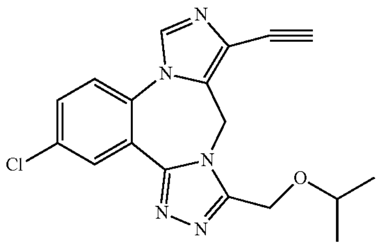 [SMILES: C#Cc1ncn2c1Cn1c(COC(C)C)nnc1-c1cc(Cl)ccc1-2] |
| 289 | 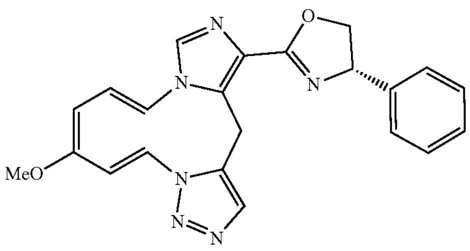 [SMILES: COC1=C/C=C/n2cnc(C3=N[C@@H](c4ccccc4)CO3)c2Cc2cnnn2\C=C\1] |
| 290 | 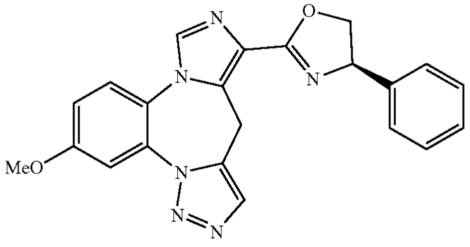 [SMILES: COc1ccc2c(c1)-n1nncc1Cc1c(C3=N[C@H](c4ccccc4)CO3)ncn1-2] |

-continued
| Compound | Structure |
| --- | --- |
| 291 | 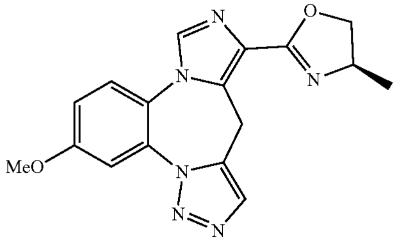 [SMILES: COc1ccc2c(c1)-n1nncc1Cc1c(C3=N[C@H](C)CO3)ncn1-2] |
| 292 | 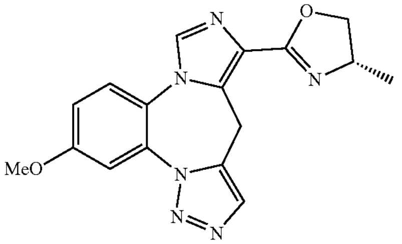 [SMILES: COc1ccc2c(c1)-n1nncc1Cc1c(C3=N[C@@H](C)CO3)ncn1-2] |
| 293 | 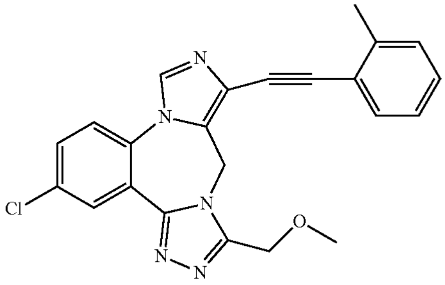 [SMILES: COCc1nnc2n1Cc1c(C#Cc3ccccc3C)ncn1-c1ccc(Cl)cc1-2] |
| 294 | 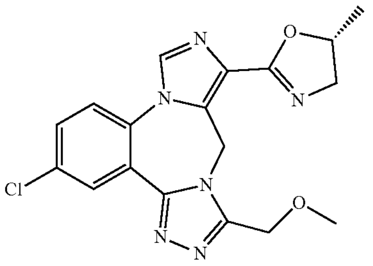 [SMILES: COCc1nnc2n1Cc1c(C3=NC[C@@H](C)O3)ncn1-c1ccc(Cl)cc1-2] |
| 295 | 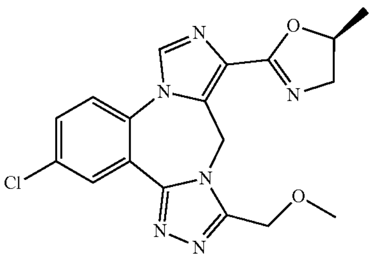 [SMILES: COCc1nnc2n1Cc1c(C3=NC[C@H](C)O3)ncn1-c1ccc(Cl)cc1-2] |
| 296 | 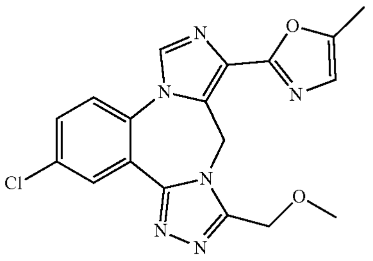 [SMILES: COCc1nnc2n1Cc1c(-c3ncc(C)o3)ncn1-c1ccc(Cl)cc1-2] |
-continued
| Compound | Structure |
| --- | --- |
| 297 | 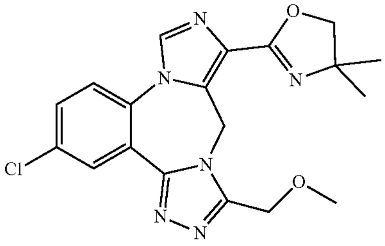 [SMILES: COCc1nnc2n1Cc1c(C3=NC(C)(C)CO3)ncn1-c1ccc(Cl)cc1-2] |
| 298 | 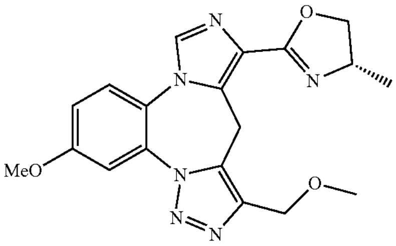 [SMILES: COCc1nnn2c1Cc1c(C3=N[C@@H](C)CO3)ncn1-c1ccc(OC)cc1-2] |
| 299 | 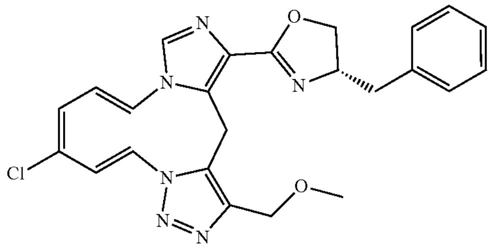 [SMILES: COCc1nnn2c1Cc1c(C3=N[C@@H](Cc4ccccc4)CO3)ncn1/C=C/C=C(Cl)\C=C\2] |
| 300 | 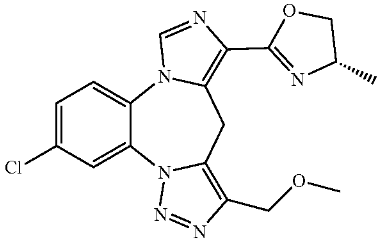 [SMILES: COCc1nnn2c1Cc1c(C3=N[C@@H](C)CO3)ncn1-c1ccc(Cl)cc1-2] |
| 301 | 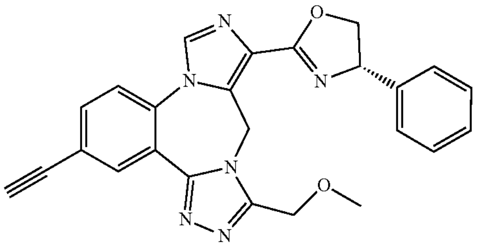 [SMILES: C#Cc1ccc2c(c1)-c1nnc(COC)n1Cc1c(C3=N[C@@H](c4ccccc4)CO3)ncn1-2] |
| 302 | 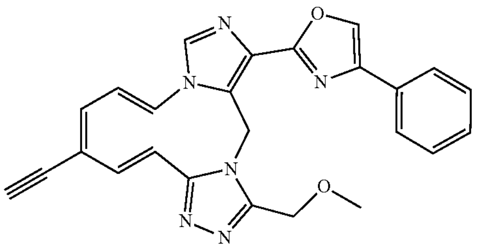 [SMILES: C#CC1=C/C=C/n2cnc(-c3nc(-c4ccccc4)co3)c2Cn2c(nnc2COC)\C=C\1] |

-continued
| Compound | Structure |
|---|---|
| 303 | 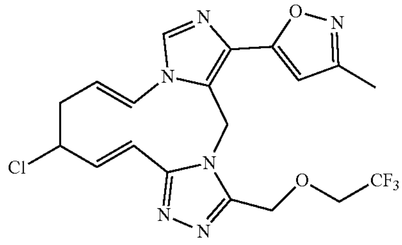 [SMILES: Cc1cc(-c2ncn3c2Cn2c(nnc2COCC(F)(F)F)/C=C/C(Cl)C/C=C/3)on1] |
| 304 | 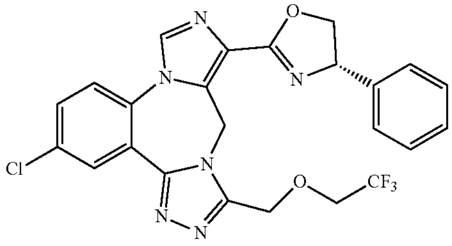 [SMILES: FC(F)(F)COCc1nnc2n1Cc1c(C3=N[C@@H](c4ccccc4)CO3)ncn1-c1ccc(Cl)cc1-2] |
| 305 | 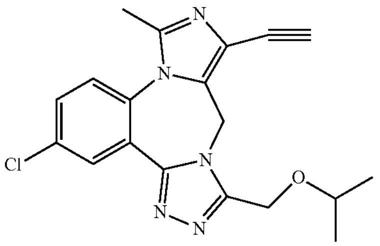 [SMILES: C#Cc1nc(C)n2c1Cn1c(COC(C)C)nnc1-c1cc(Cl)ccc1-2] |
| 306 | 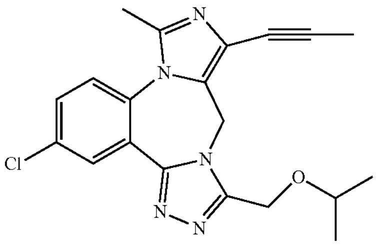 [SMILES: CC#Cc1nc(C)n2c1Cn1c(COC(C)C)nnc1-c1cc(Cl)ccc1-2] |
| 307 | 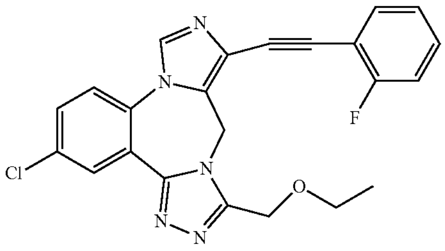 [SMILES: CCOCc1nnc2n1Cc1c(C#Cc3ccccc3F)ncn1-c1ccc(Cl)cc1-2] |
| 308 | 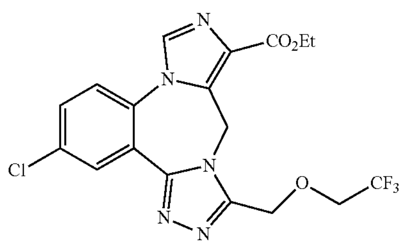 [SMILES: CCOC(=O)c1ncn2c1Cn1c(COCC(F)(F)F)nnc1-c1cc(Cl)ccc1-2] |
-continued
| Compound | Structure |
|---|---|
| 309 | 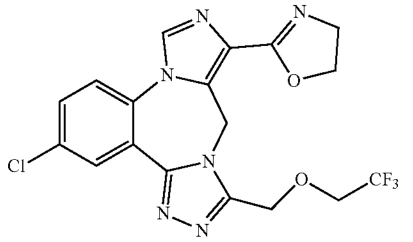 [SMILES: FC(F)(F)COCc1nnc2n1Cc1c(C3=NCCO3)ncn1-c1ccc(Cl)cc1-2] |
| 310 | 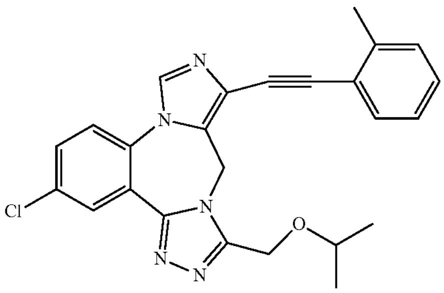 [SMILES: Cc1ccccc1C#Cc1ncn2c1Cn1c(COC(C)C)nnc1-c1cc(Cl)ccc1-2] |
| 311 | 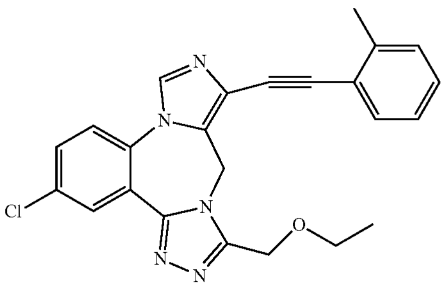 [SMILES: CCOCc1nnc2n1Cc1c(C#Cc3ccccc3C)ncn1-c1ccc(Cl)cc1-2] |
| 312 | 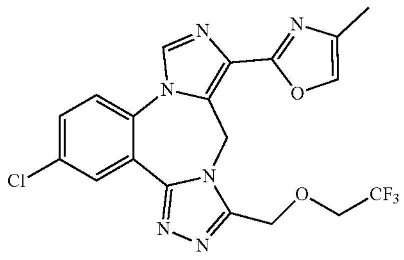 [SMILES: Cc1coc(-c2ncn3c2Cn2c(COCC(F)(F)F)nnc2-c2cc(Cl)ccc2-3)n1] |
| 313 | 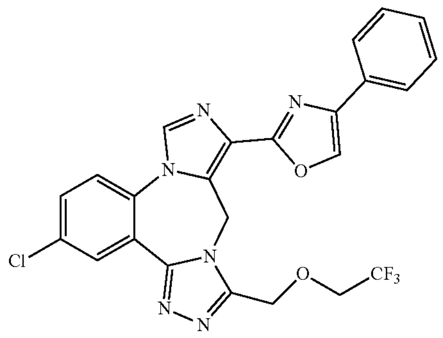 [SMILES: FC(F)(F)COCc1nnc2n1Cc1c(-c3nc(-c4ccccc4)co3)ncn1-c1ccc(Cl)cc1-2] |

-continued
| Compound | Structure |
|---|---|
| 314 | 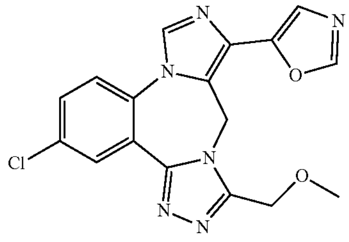 [SMILES: COCc1nnc2n1Cc1c(-c3cnco3)ncn1-c1ccc(Cl)cc1-2] |
| 315 | 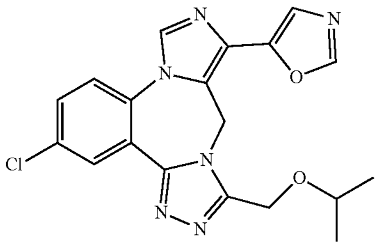 [SMILES: CC(C)OCc1nnc2n1Cc1c(-c3cnco3)ncn1-c1ccc(Cl)cc1-2] |
| 316 | 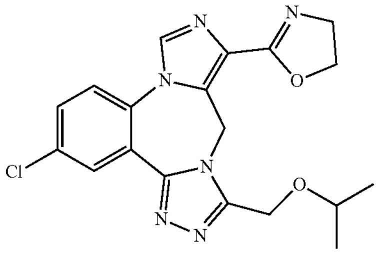 [SMILES: CC(C)OCc1nnc2n1Cc1c(C3=NCCO3)ncn1-c1ccc(Cl)cc1-2] |
| 317 | 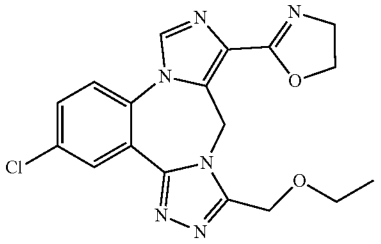 [SMILES: CCOCc1nnc2n1Cc1c(C3=NCCO3)ncn1-c1ccc(Cl)cc1-2] |
| 318 | 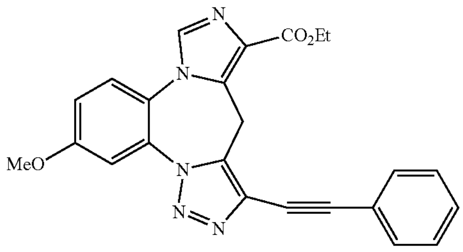 [SMILES: CCOC(=O)c1ncn2c1Cc1c(C#Cc3ccccc3)nnn1-c1cc(OC)ccc1-2] |
| 319 | 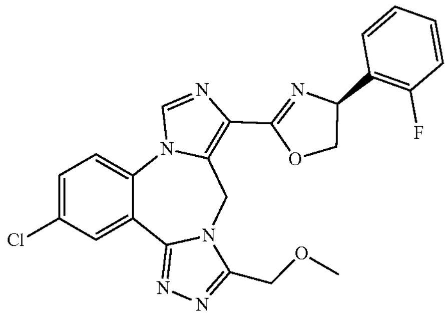 [SMILES: COCc1nnc2n1Cc1c(C3=N[C@@H](c4ccccc4F)CO3)ncn1-c1ccc(Cl)cc1-2] |
-continued
| Compound | Structure |
|---|---|
| 320 | 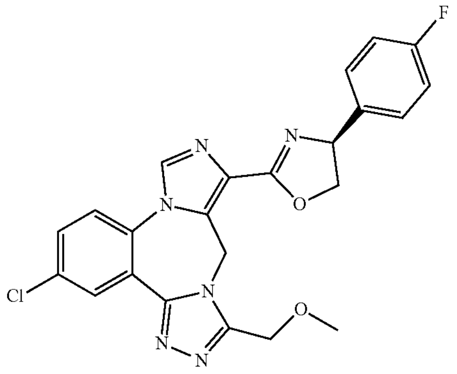 [SMILES: COCc1nnc2n1Cc1c(C3=N[C@@H](c4ccc(F)cc4)CO3)ncn1-c1ccc(Cl)cc1-2] |
| 321 | 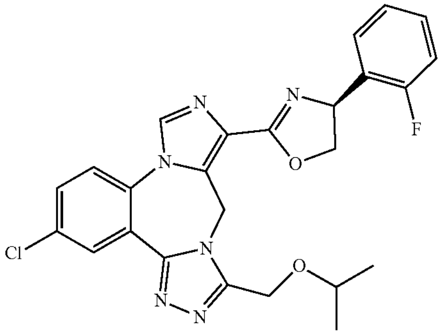 [SMILES: CC(C)OCc1nnc2n1Cc1c(C3=N[C@@H](c4ccccc4F)CO3)ncn1-c1ccc(Cl)cc1-2] |
| 322 | 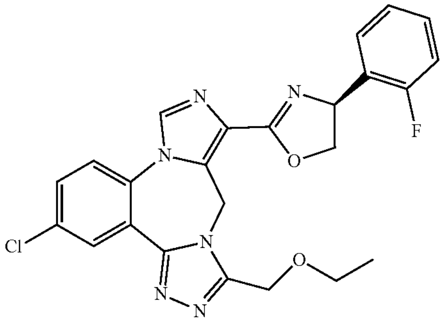 [SMILES: CCOCc1nnc2n1Cc1c(C3=N[C@@H](c4ccccc4F)CO3)ncn1-c1ccc(Cl)cc1-2] |
| 323 | 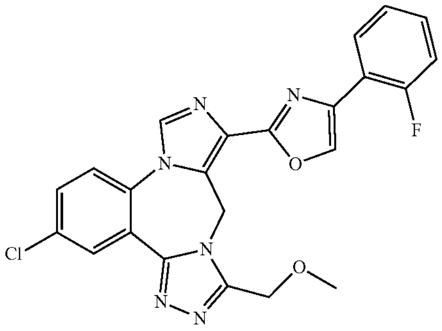 [SMILES: COCc1nnc2n1Cc1c(-c3nc(-c4ccccc4F)co3)ncn1-c1ccc(Cl)cc1-2] |

-continued
| Compound | Structure |
|---|---|
| 324 | 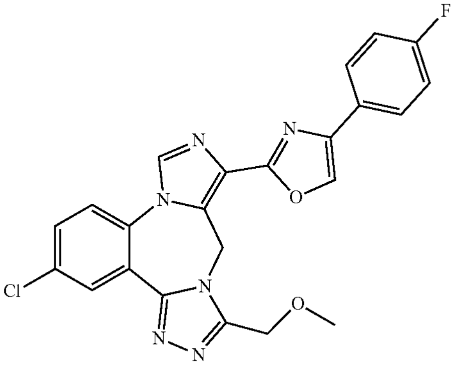 [SMILES: COCc1nnc2n1Cc1c(-c3nc(-c4ccc(F)cc4)co3)ncn1-c1ccc(Cl)cc1-2] |
| 325 | 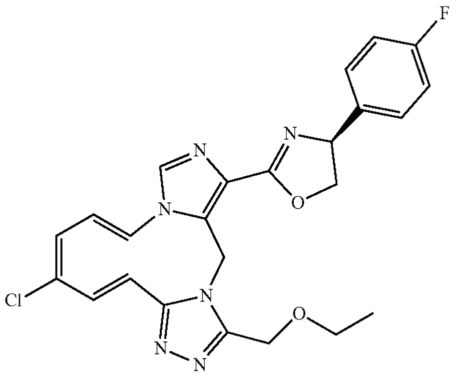 [SMILES: CCOCc1nnc2n1Cc1c(C3=N[C@@H](c4ccc(F)cc4)CO3)ncn1/C=C/C=C(Cl)\C=C\2] |
| 326 | 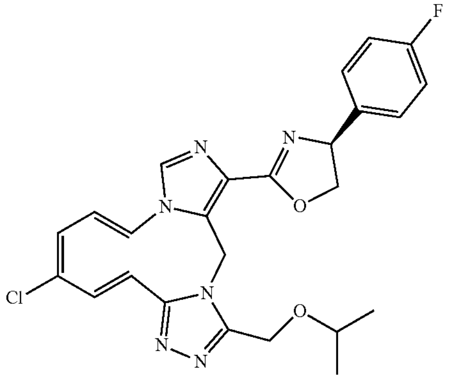 [SMILES: CC(C)OCc1nnc2n1Cc1c(C3=N[C@@H](c4ccc(F)cc4)CO3)ncn1/C=C/C=C(Cl)\C=C\2] |
| 327 | 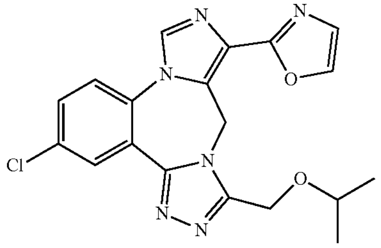 [SMILES: CC(C)OCc1nnc2n1Cc1c(-c3ncco3)ncn1-c1ccc(Cl)cc1-2] |
-continued
| Compound | Structure |
|---|---|
| 328 | 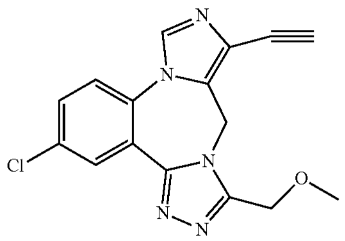 [SMILES: C#Cc1ncn2c1Cn1c(COC)nnc1-c1cc(Cl)ccc1-2] |
| 329 | 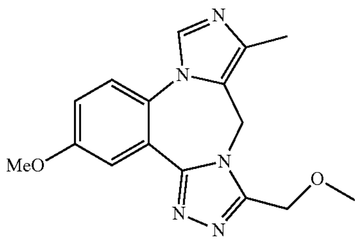 [SMILES: COCc1nnc2n1Cc1c(C)ncn1-c1ccc(OC)cc1-2] |
| 330 | 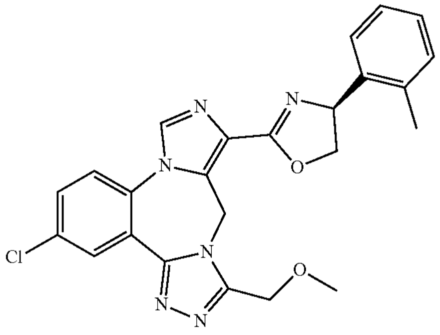 [SMILES: COCc1nnc2n1Cc1c(C3=N[C@@H](c4ccccc4C)CO3)ncn1-c1ccc(Cl)cc1-2] |
| 331 | 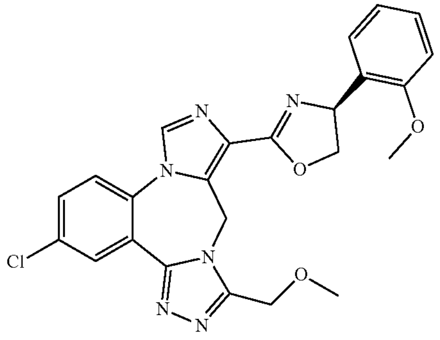 [SMILES: COCc1nnc2n1Cc1c(C3=N[C@@H](c4ccccc4OC)CO3)ncn1-c1ccc(Cl)cc1-2] |
| 332 | 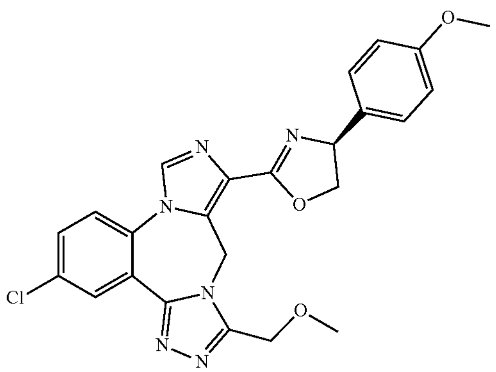 [SMILES: COCc1nnc2n1Cc1c(C3=N[C@@H](c4ccc(OC)cc4)CO3)ncn1-c1ccc(Cl)cc1-2] |

| Compound | Structure |
| --- | --- |
| 333 | 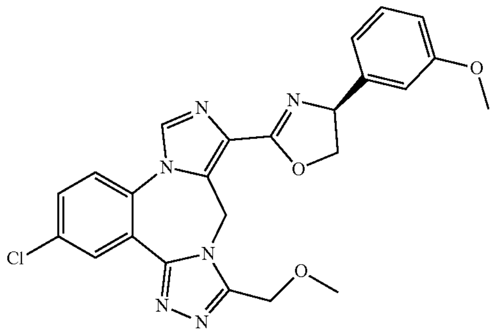 [SMILES: COCc1nnc2n1Cc1c(C3=N[C@@H](c4cccc(OC)c4)CO3)ncn1-c1ccc(Cl)cc1-2] |
| 334 | 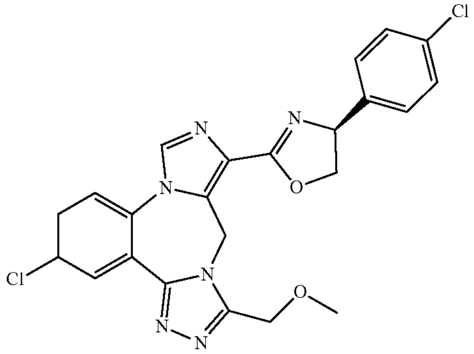 [SMILES: COCc1nnc2n1Cc1c(C3=N[C@@H](c4ccc(Cl)cc4)CO3)ncn1C1=CCC(Cl)C=C12] |
| 335 | 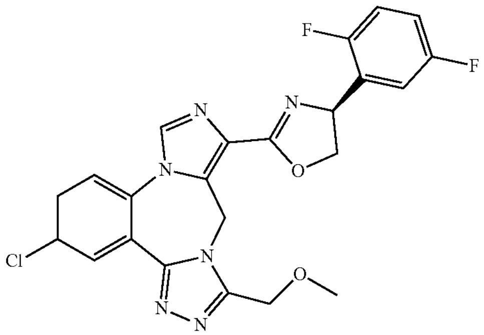 [SMILES: COCc1nnc2n1Cc1c(C3=N[C@@H](c4cc(F)ccc4F)CO3)ncn1C1=CCC(Cl)C=C12] |
| 336 | 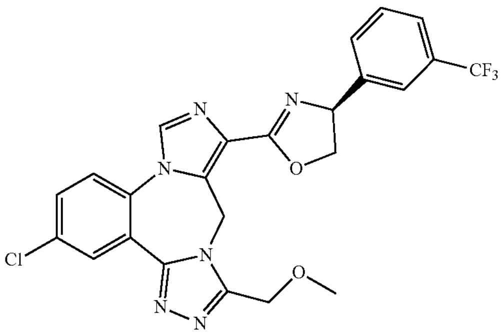 [SMILES: COCc1nnc2n1Cc1c(C3=N[C@@H](c4cccc(C(F)(F)F)c4)CO3)ncn1-c1ccc(Cl)cc1-2] |
| Compound | Structure |
| --- | --- |
| 337 | 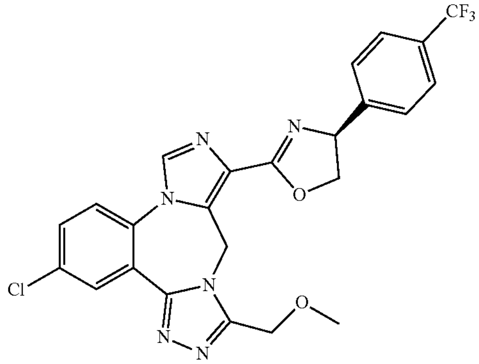 [SMILES: COCc1nnc2n1Cc1c(C3=N[C@@H](c4ccc(C(F)(F)F)cc4)CO3)ncn1-c1ccc(Cl)cc1-2] |
| 338 | 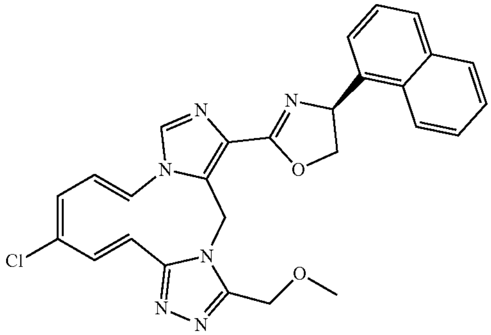 [SMILES: COCc1nnc2n1Cc1c(C3=N[C@@H](c4cccc5ccccc45)CO3)ncn1/C=C/C=C(Cl)\C=C\2] |
| 339 | 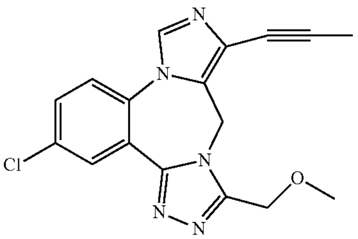 [SMILES: CC#Cc1ncn2c1Cn1c(COC)nnc1-c1cc(Cl)ccc1-2] |
| 340 | 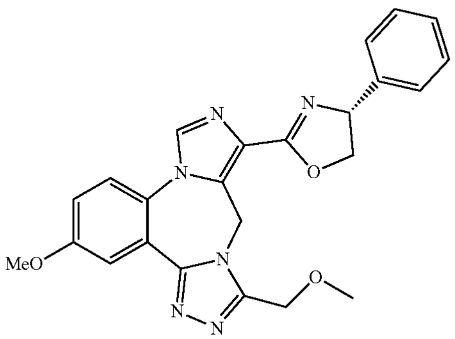 [SMILES: COCc1nnc2n1Cc1c(C3=N[C@H](c4ccccc4)CO3)ncn1-c1ccc(OC)cc1-2] |
| 341 | 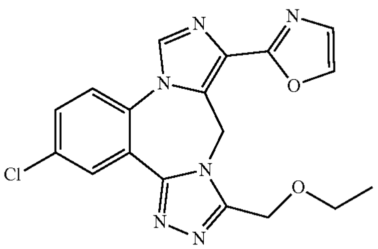 [SMILES: CCOCc1nnc2n1Cc1c(-c3ncco3)ncn1-c1ccc(Cl)cc1-2] |

-continued
| Compound | Structure |
|---|---|
| 342 | 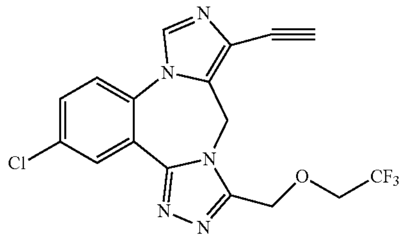 [SMILES: C#Cc1ncn2c1Cn1c(COCC(F)(F)F)nnc1-c1cc(Cl)ccc1-2] |
| 343 | 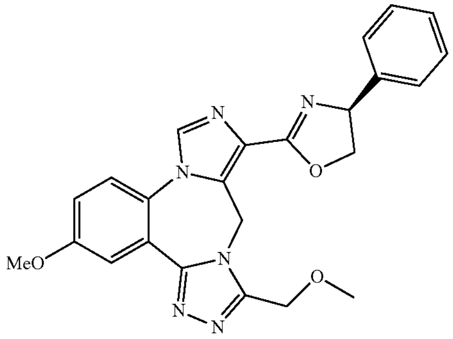 [SMILES: COCc1nnc2n1Cc1c(C3=N[C@@H](c4ccccc4)CO3)ncn1-c1ccc(OC)cc1-2] |
| 344 | 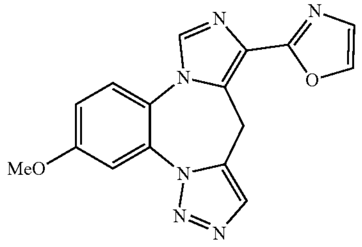 [SMILES: COc1ccc2c(c1)-n1nncc1Cc1c(-c3ncco3)ncn1-2] |
| 345 | 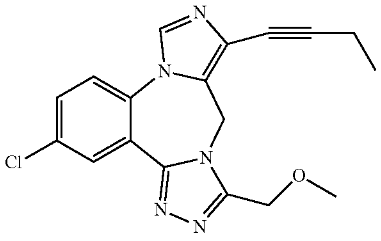 [SMILES: CCC#Cc1ncn2c1Cn1c(COC)nnc1-c1cc(Cl)ccc1-2] |
| 346 | 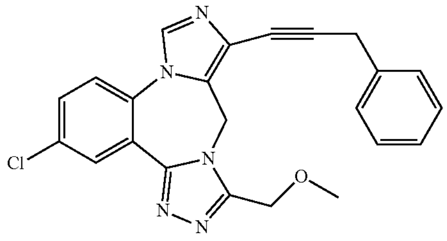 [SMILES: COCc1nnc2n1Cc1c(C#CCc3ccccc3)ncn1-c1ccc(Cl)cc1-2] |
| 347 | 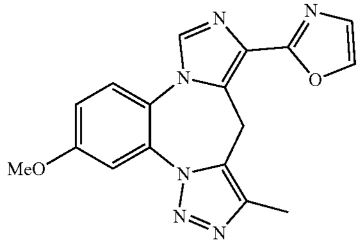 [SMILES: COc1ccc2c(c1)-n1nnc(C)c1Cc1c(-c3ncco3)ncn1-2] |
-continued
| Compound | Structure |
|---|---|
| 348 | 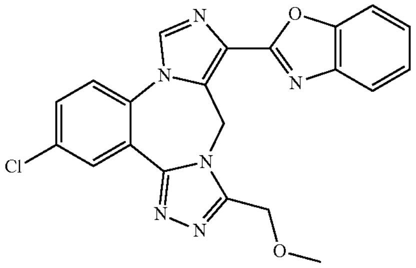 [SMILES: COCc1nnc2n1Cc1c(-c3nc4ccccc4o3)ncn1-c1ccc(Cl)cc1-2] |
| 349 | 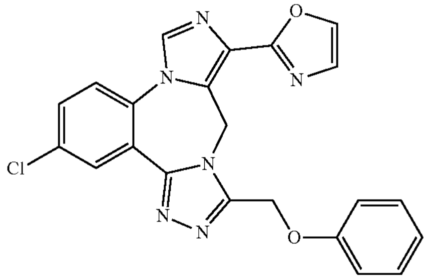 [SMILES: Clc1ccc2c(c1)-c1nnc(COc3ccccc3)n1Cc1c(-c3ncco3)ncn1-2] |
| 350 | 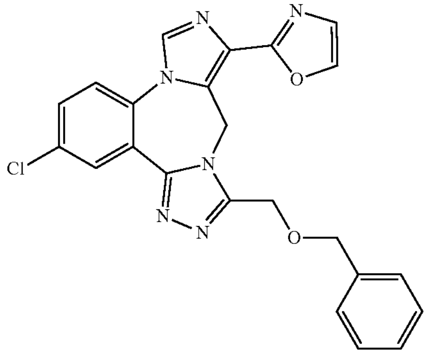 [SMILES: Clc1ccc2c(c1)-c1nnc(COCc3ccccc3)n1Cc1c(-c3ncco3)ncn1-2] |
| 351 | 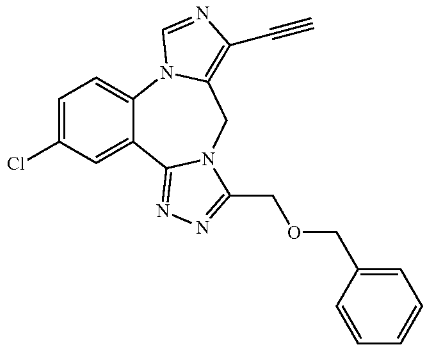 [SMILES: C#Cc1ncn2c1Cn1c(COCc3ccccc3)nnc1-c1cc(Cl)ccc1-2] |

-continued
| Compound | Structure |
| --- | --- |
| 352 | 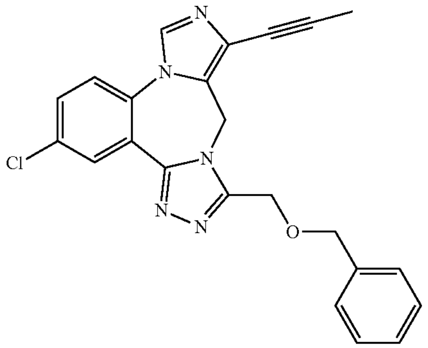 [SMILES: CC#Cc1ncn2c1Cn1c(COCc3ccccc3)nnc1-c1cc(Cl)ccc1-2] |
| 353 | 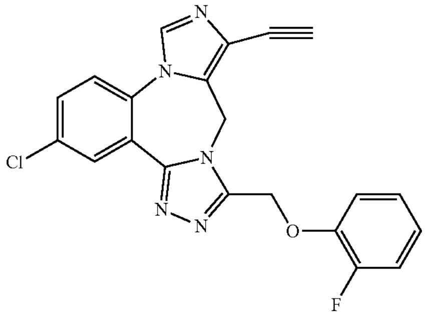 [SMILES: C#Cc1ncn2c1Cn1c(COc3ccccc3F)nnc1-c1cc(Cl)ccc1-2] |
| 354 | 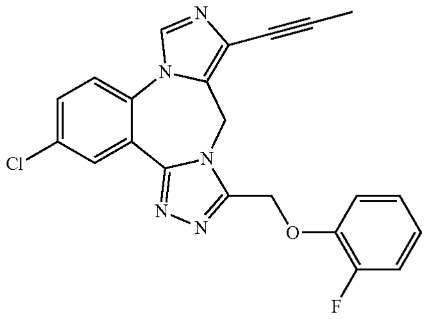 [SMILES: CC#Cc1ncn2c1Cn1c(COc3ccccc3F)nnc1-c1cc(Cl)ccc1-2] |
| 355 | 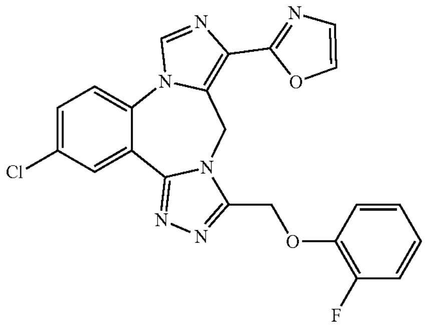 [SMILES: Fc1ccccc1OCc1nnc2n1Cc1c(-c3ncco3)ncn1-c1ccc(Cl)cc1-2] |
| 356 | 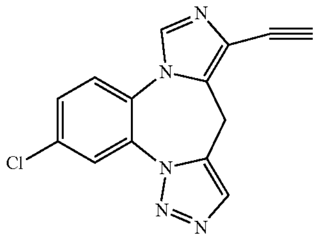 [SMILES: C#Cc1ncn2c1Cc1cnnn1-c1cc(Cl)ccc1-2] |
-continued
| Compound | Structure |
| --- | --- |
| 357 | 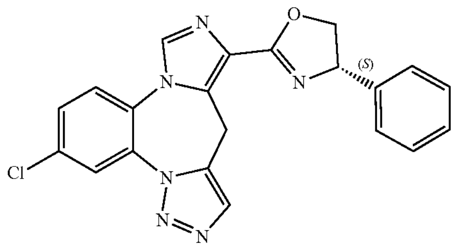 |
| 358 | 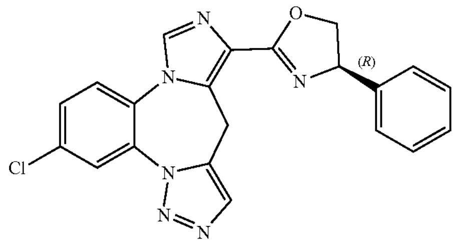 |
| 359 | 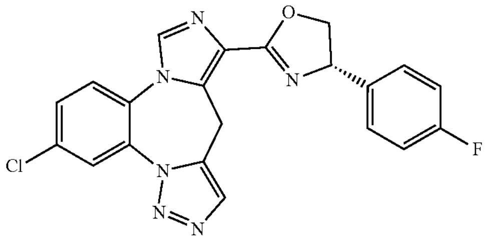 [SMILES: Fc1ccc([C@H]2COC(c3ncn4c3Cc3cnnn3-c3cc(Cl)ccc3-4)=N2)cc1] |
| 360 | 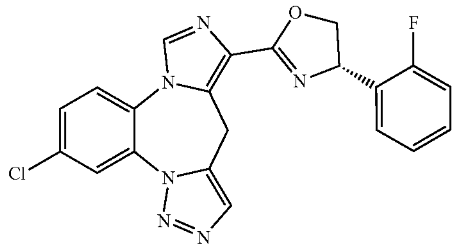 [SMILES: Fc1ccccc1[C@H]1COC(c2ncn3c2Cc2cnnn2-c2cc(Cl)ccc2-3)=N1] |
| 361 | 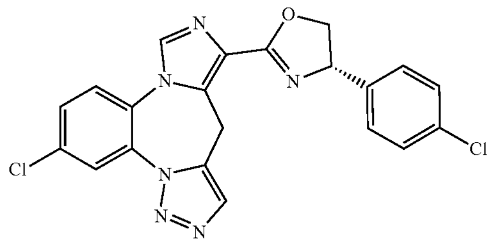 [SMILES: Clc1ccc([C@H]2COC(c3ncn4c3Cc3cnnn3-c3cc(Cl)ccc3-4)=N2)cc1] |
| 362 | 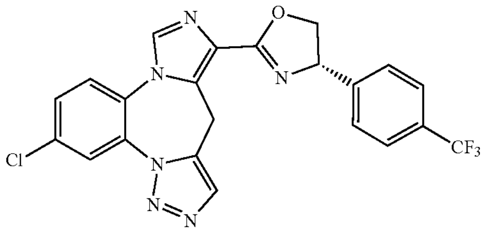 [SMILES: FC(F)(F)c1ccc([C@H]2COC(c3ncn4c3Cc3cnnn3-c3cc(Cl)ccc3-4)=N2)cc1] |

-continued
| Compound | Structure |
|---|---|
| 363 | 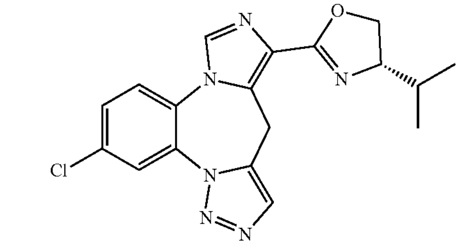 [SMILES: CC(C)[C@H]1COC(c2ncn3c2Cc2cnnn2-c2cc(Cl)ccc2-3)=N1] |
| 364 | 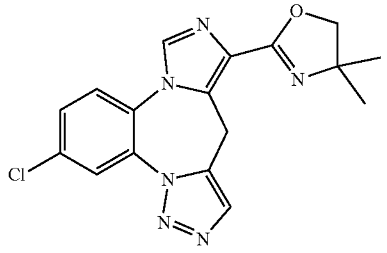 [SMILES: CC1(C)COC(c2ncn3c2Cc2cnnn2-c2cc(Cl)ccc2-3)=N1] |
| 365 | 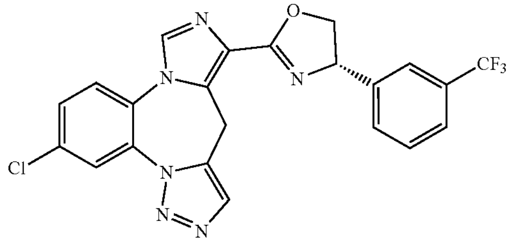 [SMILES: FC(F)(F)c1cccc([C@H]2COC(c3ncn4c3Cc3cnnn3-c3cc(Cl)ccc3-4)=N2)c1] |
| 366 | 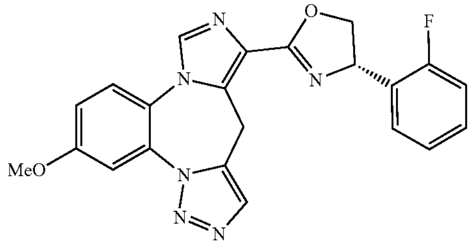 [SMILES: COc1ccc2c(c1)-n1nncc1Cc1c(C3=N[C@@H](c4ccccc4F)CO3)ncn1-2] |
| 367 | 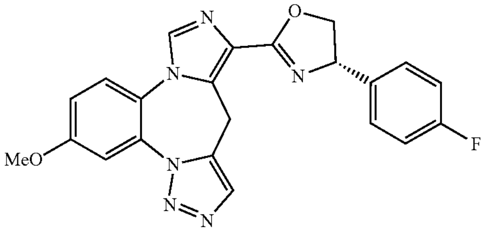 [SMILES: COc1ccc2c(c1)-n1nncc1Cc1c(C3=N[C@@H](c4ccc(F)cc4)CO3)ncn1-2] |
| 368 | 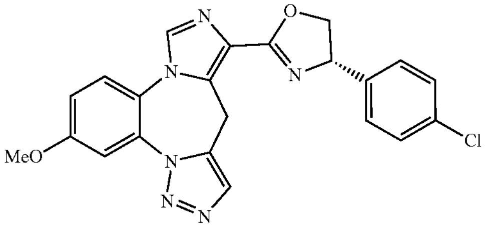 [SMILES: COc1ccc2c(c1)-n1nncc1Cc1c(C3=N[C@@H](c4ccc(Cl)cc4)CO3)ncn1-2] |
| 369 | 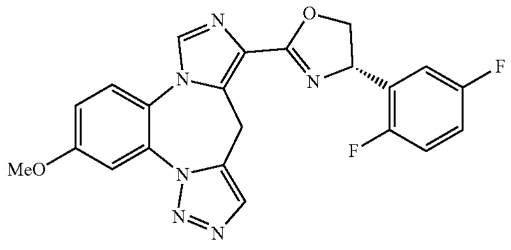 [SMILES: COc1ccc2c(c1)-n1nncc1Cc1c(C3=N[C@@H](c4cc(F)ccc4F)CO3)ncn1-2] |
| 370 | 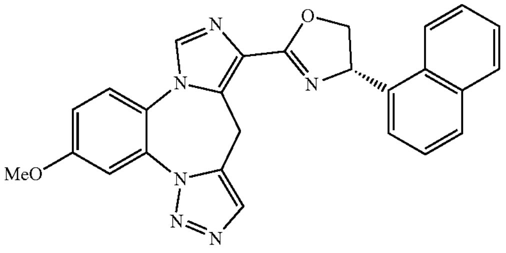 [SMILES: COc1ccc2c(c1)-n1nncc1Cc1c(C3=N[C@@H](c4cccc5ccccc45)CO3)ncn1-2] |
| 371 | 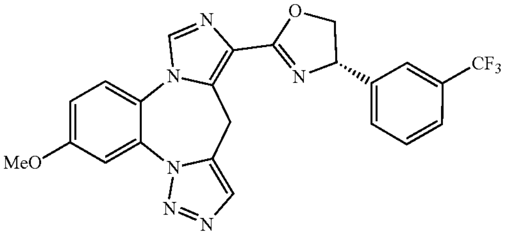 [SMILES: COc1ccc2c(c1)-n1nncc1Cc1c(C3=N[C@@H](c4cccc(C(F)(F)F)c4)CO3)ncn1-2] |
| 372 | 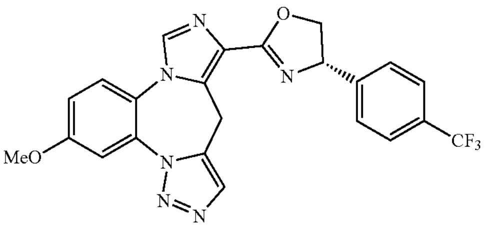 [SMILES: COc1ccc2c(c1)-n1nncc1Cc1c(C3=N[C@@H](c4ccc(C(F)(F)F)cc4)CO3)ncn1-2] |
| 373 | 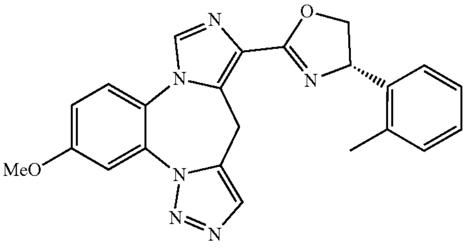 [SMILES: COc1ccc2c(c1)-n1nncc1Cc1c(C3=N[C@@H](c4ccccc4C)CO3)ncn1-2] |
| 374 | 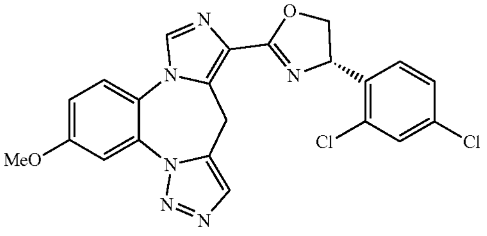 [SMILES: COc1ccc2c(c1)-n1nncc1Cc1c(C3=N[C@@H](c4ccc(Cl)cc4Cl)CO3)ncn1-2] |

-continued
| Compound | Structure |
|---|---|
| 375 | 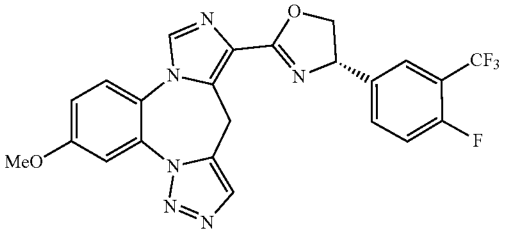 [SMILES: COc1ccc2c(c1)-n1nncc1Cc1c(C3=N[C@@H](c4ccc(F)c(C(F)(F)F)c4)CO3)ncn1-2] |
| 376 | 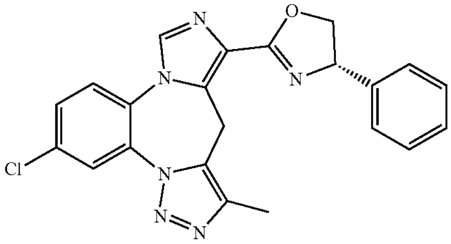 [SMILES: Cc1nnn2c1Cc1c(C3=N[C@@H](c4ccccc4)CO3)ncn1-c1ccc(Cl)cc1-2] |
| 377 | 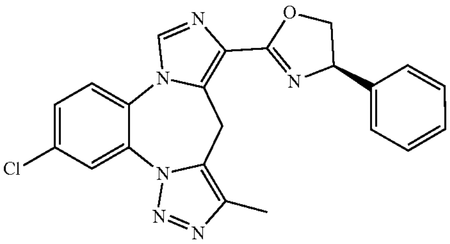 [SMILES: Cc1nnn2c1Cc1c(C3=N[C@H](c4ccccc4)CO3)ncn1-c1ccc(Cl)cc1-2] |
| 378 | 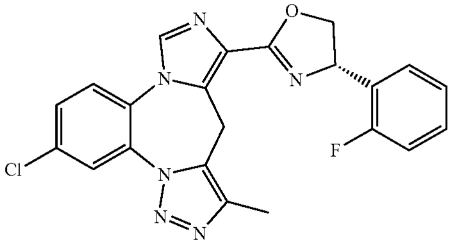 [SMILES: Cc1nnn2c1Cc1c(C3=N[C@@H](c4ccccc4F)CO3)ncn1-c1ccc(Cl)cc1-2] |
| 379 | 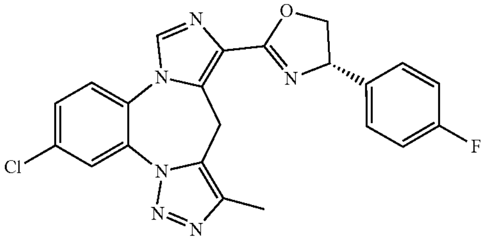 [SMILES: Cc1nnn2c1Cc1c(C3=N[C@@H](c4ccc(F)cc4)CO3)ncn1-c1ccc(Cl)cc1-2] |
| 380 | 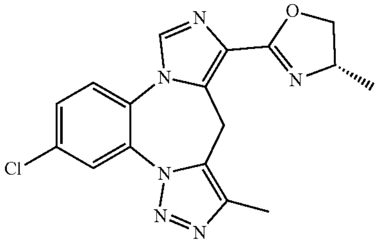 [SMILES: Cc1nnn2c1Cc1c(C3=N[C@@H](C)CO3)ncn1-c1ccc(Cl)cc1-2] |
-continued
| Compound | Structure |
|---|---|
| 381 | 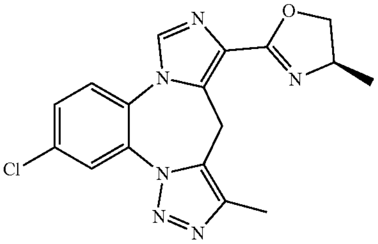 [SMILES: Cc1nnn2c1Cc1c(C3=N[C@H](C)CO3)ncn1-c1ccc(Cl)cc1-2] |
| 382 | 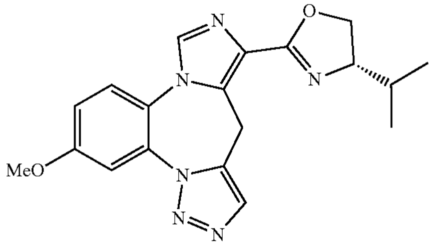 [SMILES: COc1ccc2c(c1)-n1nncc1Cc1c(C3=N[C@@H](C(C)C)CO3)ncn1-2] |
| 383 | 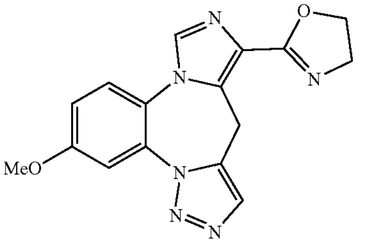 [SMILES: COc1ccc2c(c1)-n1nncc1Cc1c(C3=NCCO3)ncn1-2] |
| 384 | 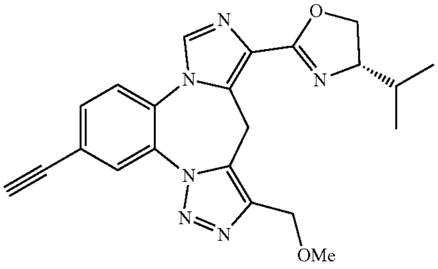 [SMILES: C#Cc1ccc2c(c1)-n1nnc(COC)c1Cc1c(C3=N[C@@H](C(C)C)CO3)ncn1-2] |
| 385 | 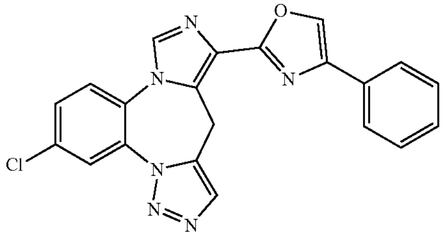 [SMILES: Clc1ccc2c(c1)-n1nncc1Cc1c(-c3nc(-c4ccccc4)co3)ncn1-2] |
| 386 | 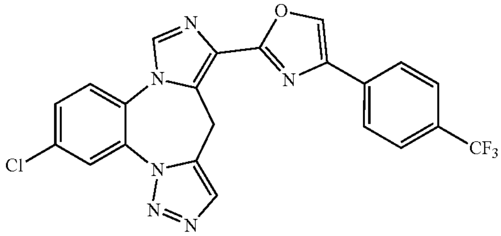 [SMILES: FC(F)(F)c1ccc(-c2coc(-c3ncn4c3Cc3cnnn3-c3cc(Cl)ccc3-4)n2)cc1] |

-continued
| Compound | Structure |
|---|---|
| 387 | 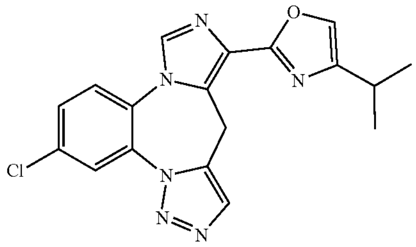 [SMILES: CC(C)c1coc(-c2ncn3c2Cc2cnnn2-c2cc(Cl)ccc2-3)n1] |
| 388 | 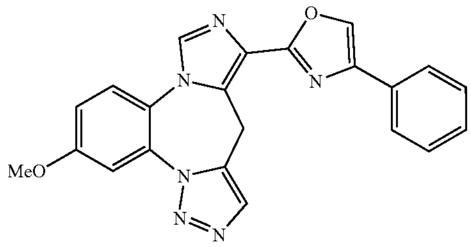 [SMILES: COc1ccc2c(c1)-n1nncc1Cc1c(-c3nc(-c4ccccc4)co3)ncn1-2] |
| 389 | 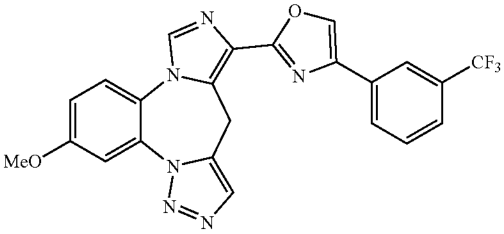 [SMILES: COc1ccc2c(c1)-n1nncc1Cc1c(-c3nc(-c4cccc(C(F)(F)F)c4)co3)ncn1-2] |
| 390 | 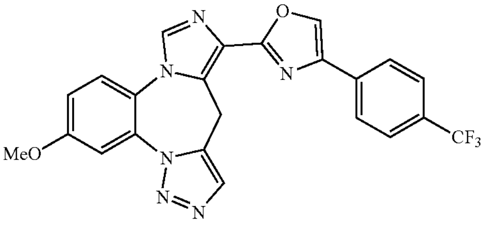 [SMILES: COc1ccc2c(c1)-n1nncc1Cc1c(-c3nc(-c4ccc(C(F)(F)F)cc4)co3)ncn1-2] |
| 391 | 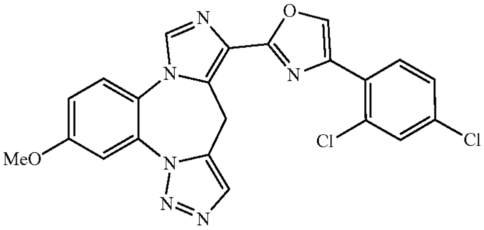 [SMILES: COc1ccc2c(c1)-n1nncc1Cc1c(-c3nc(-c4ccc(Cl)cc4Cl)co3)ncn1-2] |
| 392 | 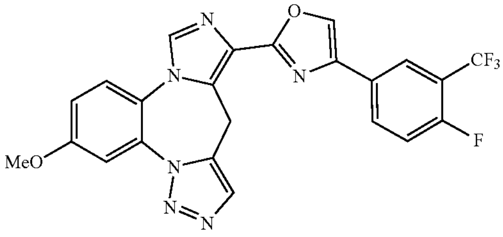 [SMILES: COc1ccc2c(c1)-n1nncc1Cc1c(-c3nc(-c4ccc(F)c(C(F)(F)F)c4)co3)ncn1-2] |
-continued
| Compound | Structure |
|---|---|
| 393 | 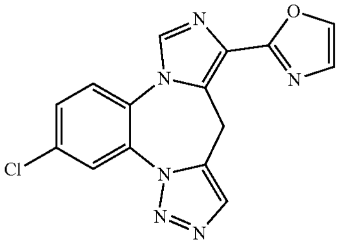 [SMILES: Clc1ccc2c(c1)-n1nncc1Cc1c(-c3ncco3)ncn1-2] |
| 394 | 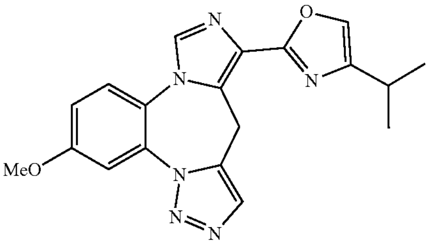 [SMILES: COc1ccc2c(c1)-n1nncc1Cc1c(-c3nc(C(C)C)co3)ncn1-2] |
| 395 | 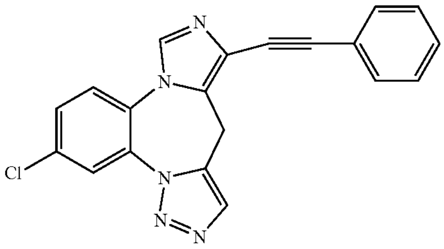 |
| 396 | 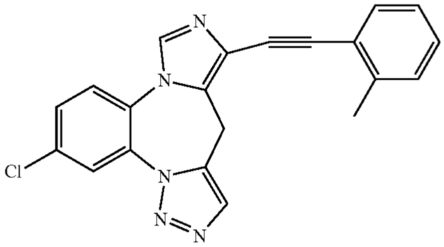 [SMILES: Cc1ccccc1C#Cc1ncn2c1Cc1cnnn1-c1cc(Cl)ccc1-2] |
| 397 | 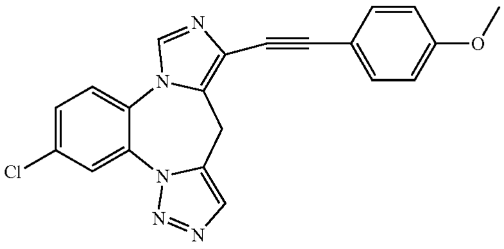 [SMILES: COc1ccc(C#Cc2ncn3c2Cc2cnnn2-c2cc(Cl)ccc2-3)cc1] |
| 398 | 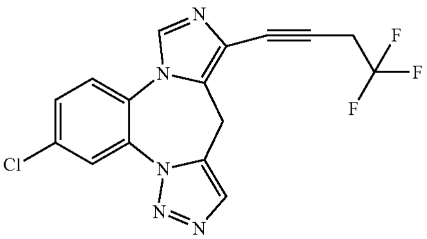 [SMILES: FC(F)(F)CC#Cc1ncn2c1Cc1cnnn1-c1cc(Cl)ccc1-2] |

-continued
| Compound | Structure |
|---|---|
| 399 | 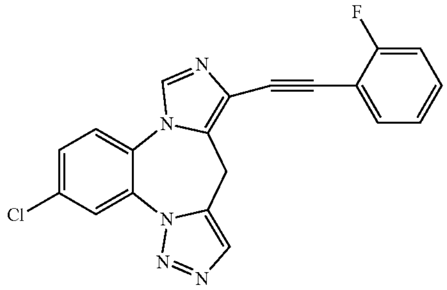 [SMILES: Fc1ccccc1C#Cc1ncn2c1Cc1cnnn1-c1cc(Cl)ccc1-2] |
| 400 | 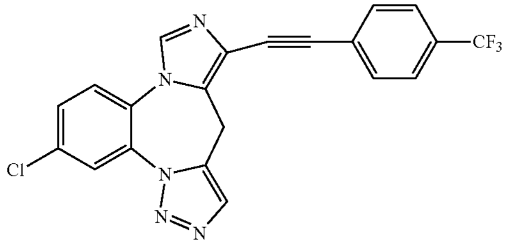 [SMILES: FC(F)(F)c1ccc(C#Cc2ncn3c2Cc2cnnn2-c2cc(Cl)ccc2-3)cc1] |
| 401 | 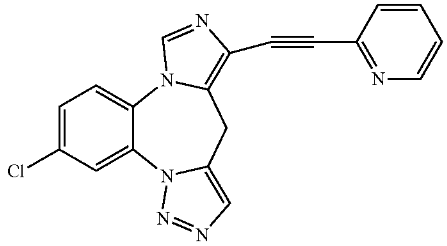 [SMILES: Clc1ccc2c(c1)-n1nncc1Cc1c(C#Cc3ccccn3)ncn1-2] |
| 402 | 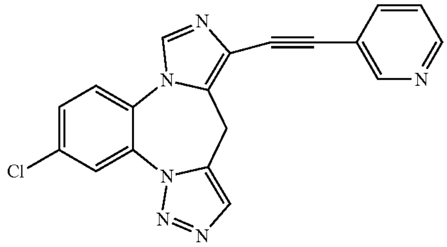 [SMILES: Clc1ccc2c(c1)-n1nncc1Cc1c(C#Cc3cccnc3)ncn1-2] |
| 403 | 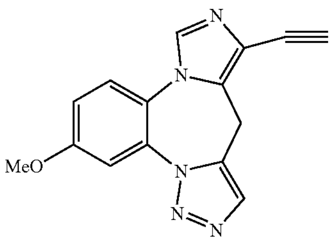 [SMILES: C#Cc1ncn2c1Cc1cnnn1-c1cc(OC)ccc1-2] |
| 404 | 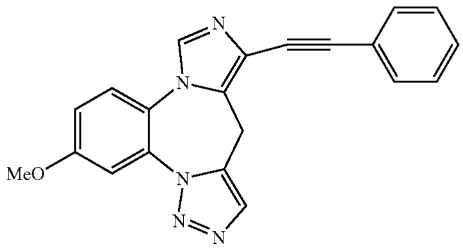 |
-continued
| Compound | Structure |
|---|---|
| 405 | 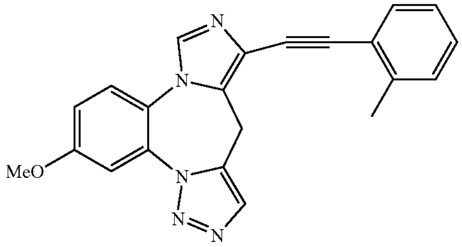 [SMILES: COc1ccc2c(c1)-n1nncc1Cc1c(C#Cc3ccccc3C)ncn1-2] |
| 406 | 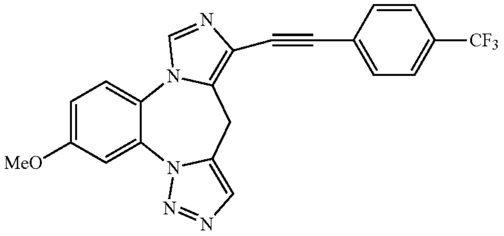 [SMILES: COc1ccc2c(c1)-n1nncc1Cc1c(C#Cc3ccc(C(F)(F)F)cc3)ncn1-2] |
| 407 | 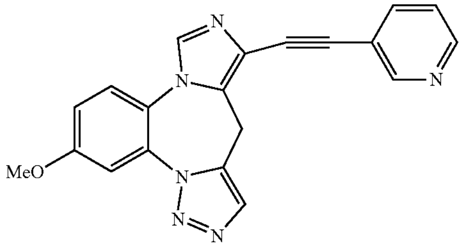 [SMILES: COc1ccc2c(c1)-n1nncc1Cc1c(C#Cc3cccnc3)ncn1-2] |
| 408 | 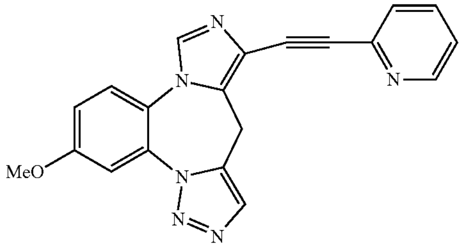 [SMILES: COc1ccc2c(c1)-n1nncc1Cc1c(C#Cc3ccccn3)ncn1-2] |
| 409 | 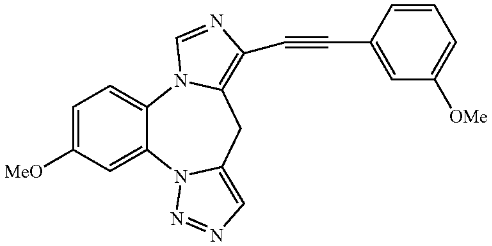 [SMILES: COc1cccc(C#Cc2ncn3c2Cc2cnnn2-c2cc(OC)ccc2-3)c1] |
| 410 | 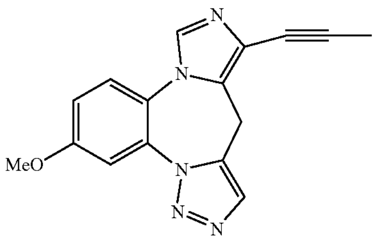 [SMILES: CC#Cc1ncn2c1Cc1cnnn1-c1cc(OC)ccc1-2] |

-continued
| Compound | Structure |
|---|---|
| 411 | 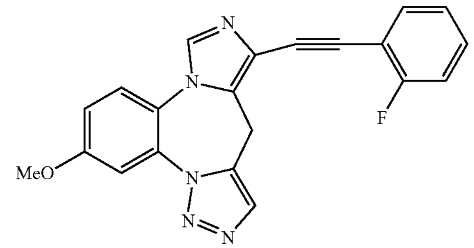 [SMILES: COc1ccc2c(c1)-n1nncc1Cc1c(C#Cc3ccccc3F)ncn1-2] |
| 412 | 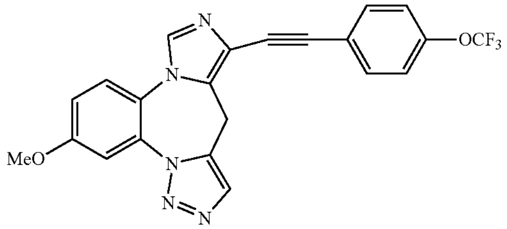 [SMILES: COc1ccc2c(c1)-n1nncc1Cc1c(C#Cc3ccc(OC(F)(F)F)cc3)ncn1-2] |
| 413 | 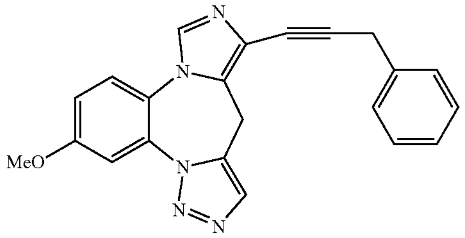 [SMILES: COc1ccc2c(c1)-n1nncc1Cc1c(C#CCc3ccccc3)ncn1-2] |
| 414 | 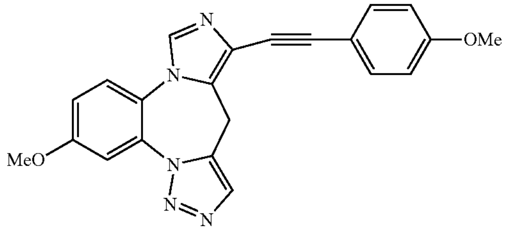 [SMILES: COc1ccc(C#Cc2ncn3c2Cc2cnnn2-c2cc(OC)ccc2-3)cc1] |
| 415 | 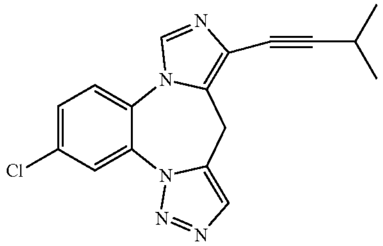 [SMILES: CC(C)C#Cc1ncn2c1Cc1cnnn1-c1cc(Cl)ccc1-2] |
| 416 | 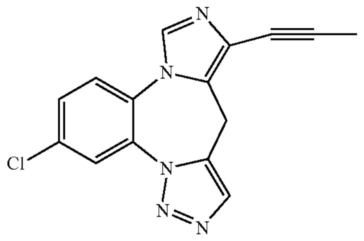 [SMILES: CC#Cc1ncn2c1Cc1cnnn1-c1cc(Cl)ccc1-2] |
-continued
| Compound | Structure |
|---|---|
| 417 | 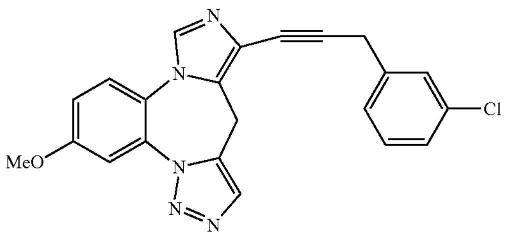 [SMILES: COc1ccc2c(c1)-n1nncc1Cc1c(C#CCc3cccc(Cl)c3)ncn1-2] |
| 418 | 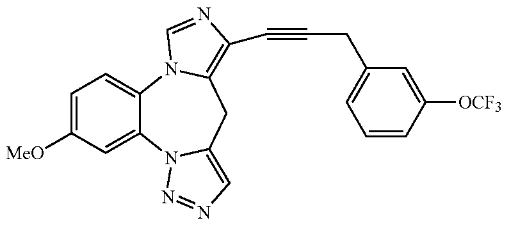 [SMILES: COc1ccc2c(c1)-n1nncc1Cc1c(C#CCc3cccc(OC(F)(F)F)c3)ncn1-2] |
| 419 | 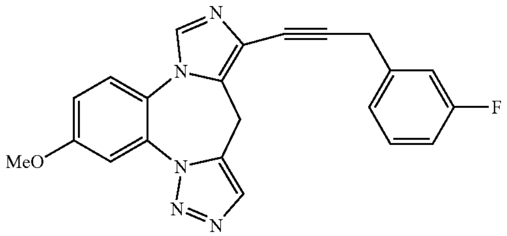 [SMILES: COc1ccc2c(c1)-n1nncc1Cc1c(C#CCc3cccc(F)c3)ncn1-2] |
| 420 | 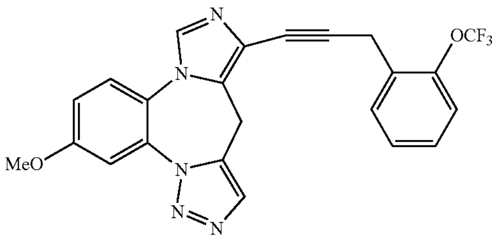 [SMILES: COc1ccc2c(c1)-n1nncc1Cc1c(C#CCc3ccccc3OC(F)(F)F)ncn1-2] |
| 421 | 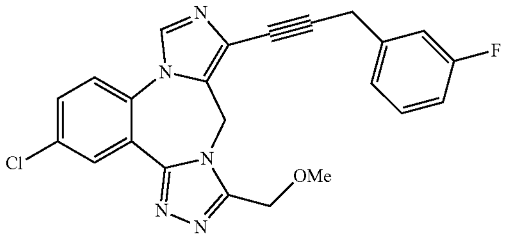 [SMILES: COCc1nnc2n1Cc1c(CCCc3cccc(F)c3)ncn1-c1ccc(Cl)cc1-2] |
| 422 | 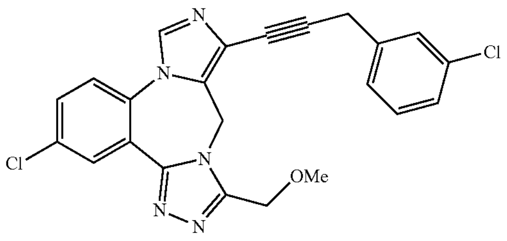 [SMILES: COCc1nnc2n1Cc1c(CCCc3cccc(Cl)c3)ncn1-c1ccc(Cl)cc1-2] |

-continued
| Compound | Structure |
|---|---|
| 423 | 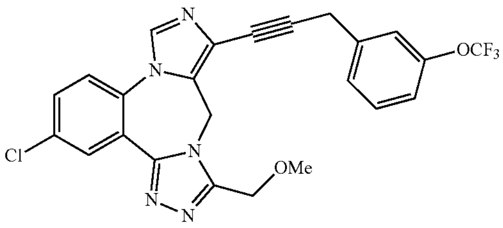 [SMILES: COCc1nnc2n1Cc1c(CCCc3cccc(OC(F)(F)F)c3)ncn1-c1ccc(Cl)cc1-2] |
| 424 | 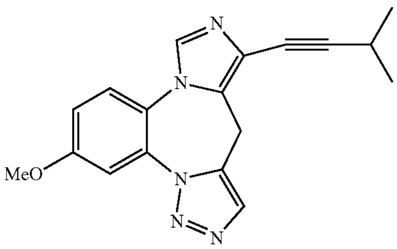 [SMILES: COc1ccc2c(c1)-n1nncc1Cc1c(C#CC(C)C)ncn1-2] |
| 425 | 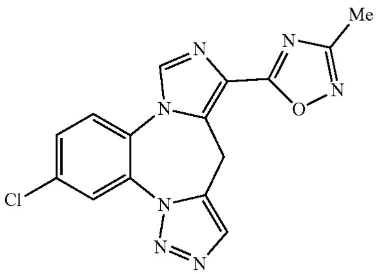 [SMILES: Cc1noc(-c2ncn3c2Cc2cnnn2-c2cc(Cl)ccc2-3)n1] |
| 426 | 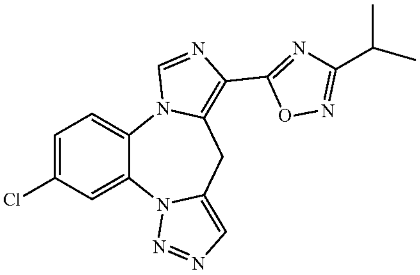 [SMILES: CC(C)c1noc(-c2ncn3c2Cc2cnnn2-c2cc(Cl)ccc2-3)n1] |
| 427 | 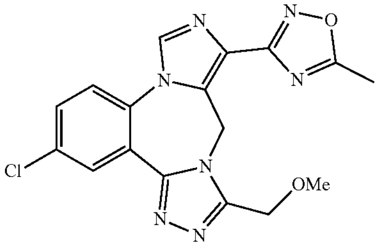 [SMILES: COCc1nnc2n1Cc1c(-c3noc(C)n3)ncn1-c1ccc(Cl)cc1-2] |
| 428 | 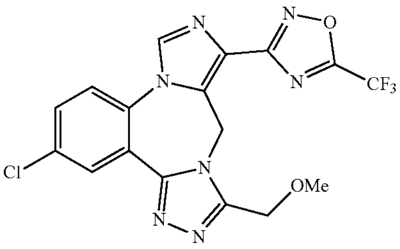 [SMILES: COCc1nnc2n1Cc1c(-c3noc(C(F)(F)F)n3)ncn1-c1ccc(Cl)cc1-2] |
-continued
| Compound | Structure |
|---|---|
| 429 | 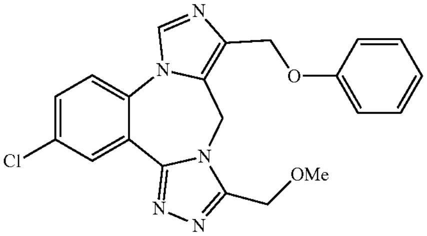 [SMILES: COCc1nnc2n1Cc1c(COc3ccccc3)ncn1-c1ccc(Cl)cc1-2] |
| 430 | 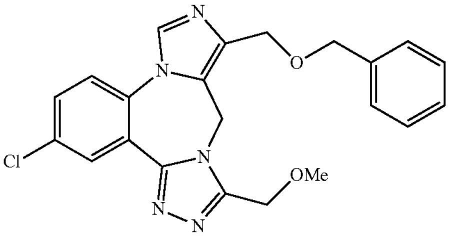 [SMILES: COCc1nnc2n1Cc1c(COCc3ccccc3)ncn1-c1ccc(Cl)cc1-2] |
| 431 | 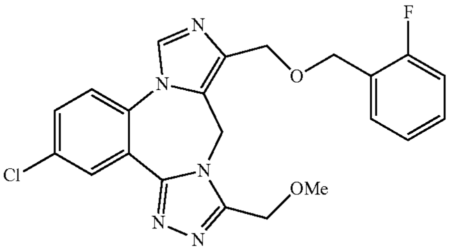 [SMILES: COCc1nnc2n1Cc1c(COCc3ccccc3F)ncn1-c1ccc(Cl)cc1-2] |
| 432 | 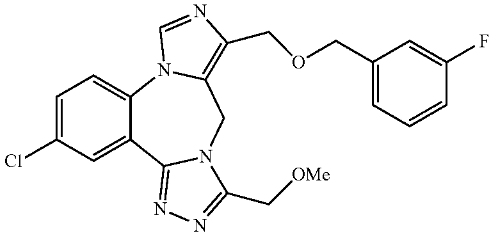 [SMILES: COCc1nnc2n1Cc1c(COCc3cccc(F)c3)ncn1-c1ccc(Cl)cc1-2] |
| 433 | 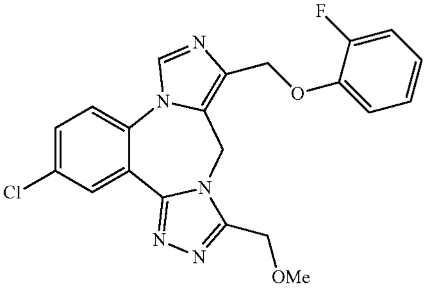 [SMILES: COCc1nnc2n1Cc1c(COc3ccccc3F)ncn1-c1ccc(Cl)cc1-2] |

-continued
| Compound | Structure |
|---|---|
| 434 | 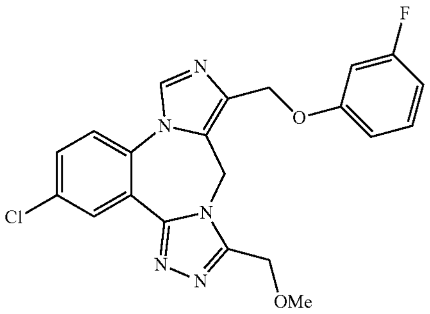 [SMILES: COCc1nnc2n1Cc1c(COc3cccc(F)c3)ncn1-c1ccc(Cl)cc1-2] |
| 435 | 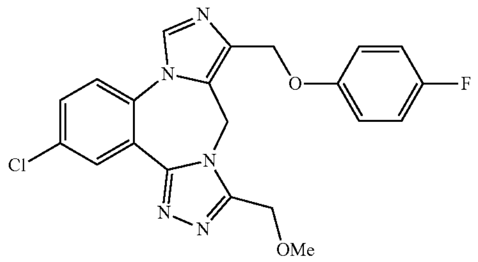 [SMILES: COCc1nnc2n1Cc1c(COc3ccc(F)cc3)ncn1-c1ccc(Cl)cc1-2] |
| 436 | 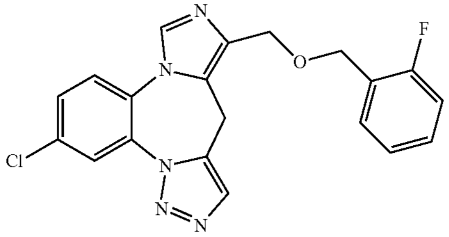 [SMILES: Fc1ccccc1COCc1ncn2c1Cc1cnnn1-c1cc(Cl)ccc1-2] |
| 437 | 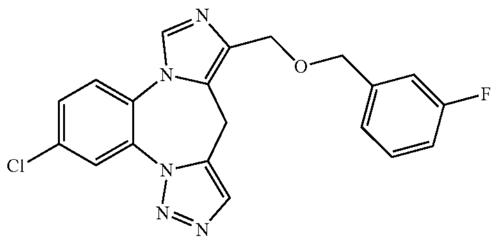 [SMILES: Fc1cccc(COCc2ncn3c2Cc2cnnn2-c2cc(Cl)ccc2-3)c1] |
| 438 | 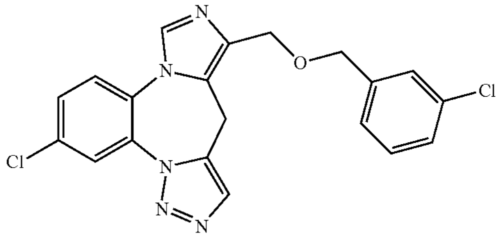 [SMILES: Clc1cccc(COCc2ncn3c2Cc2cnnn2-c2cc(Cl)ccc2-3)c1] |
| 439 | 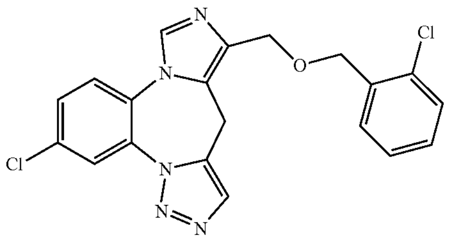 [SMILES: Clc1ccc2c(c1)-n1nncc1Cc1c(COCc3ccccc3Cl)ncn1-2] |
-continued
| Compound | Structure |
|---|---|
| 440 | 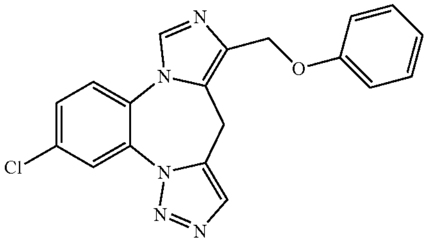 [SMILES: Clc1ccc2c(c1)-n1nncc1Cc1c(COc3ccccc3)ncn1-2] |
| 441 | 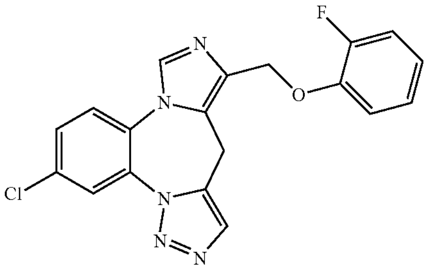 [SMILES: Fc1ccccc1OCc1ncn2c1Cc1cnnn1-c1cc(Cl)ccc1-2] |
| 442 | 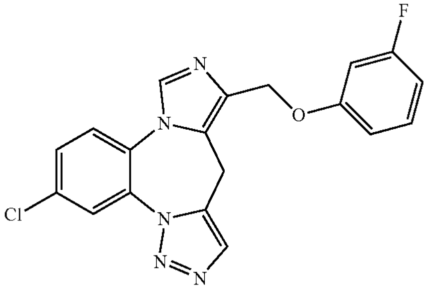 [SMILES: Fc1cccc(OCc2ncn3c2Cc2cnnn2-c2cc(Cl)ccc2-3)c1] |
| 443 | 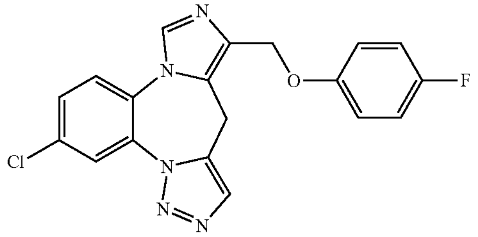 [SMILES: Fc1ccc(OCc2ncn3c2Cc2cnnn2-c2cc(Cl)ccc2-3)cc1] |
| 444 | 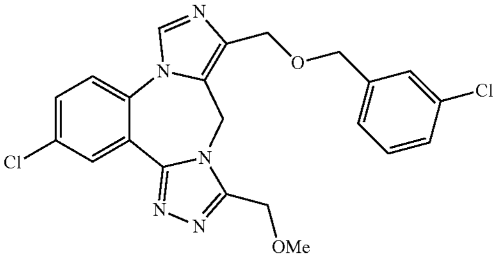 [SMILES: COCc1nnc2n1Cc1c(COCc3cccc(Cl)c3)ncn1-c1ccc(Cl)cc1-2] |

-continued
| Compound | Structure |
|---|---|
| 445 | 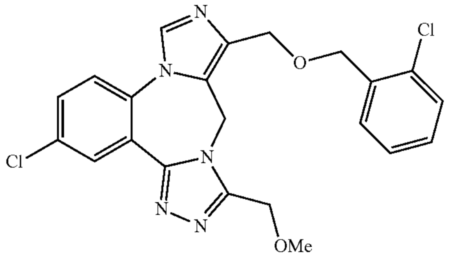 [SMILES: COCc1nnc2n1Cc1c(COCc3ccccc3Cl)ncn1-c1ccc(Cl)cc1-2] |
| 446 | 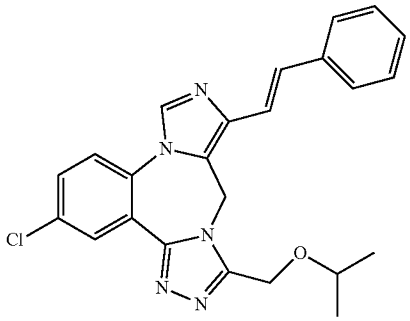 [SMILES: CC(C)OCc1nnc2n1Cc1c(/C=C/c3ccccc3)ncn1-c1ccc(Cl)cc1-2] |
| 447 | 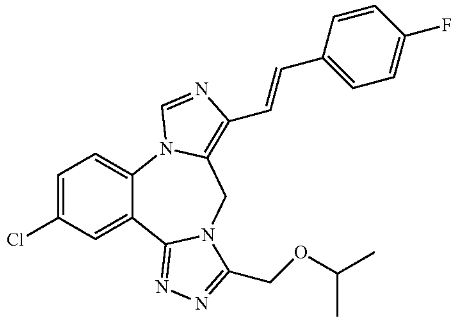 [SMILES: CC(C)OCc1nnc2n1Cc1c(/C=C/c3ccc(F)cc3)ncn1-c1ccc(Cl)cc1-2] |
| 448 | 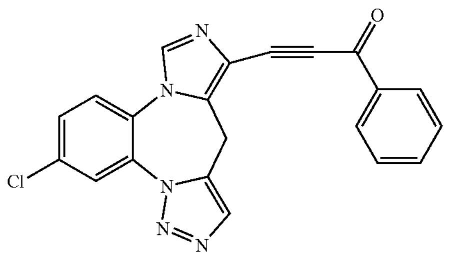 [SMILES: O=C(C#Cc1ncn2c1Cc1cnnn1-c1cc(Cl)ccc1-2)c1ccccc1] |
| 449 | 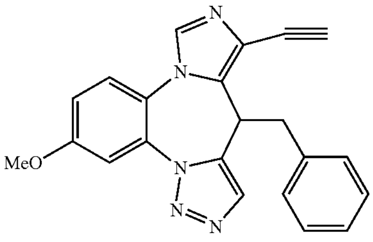 [SMILES: C#Cc1ncn2c1C(Cc1ccccc1)c1cnnn1-c1cc(OC)ccc1-2] |
-continued
| Compound | Structure |
|---|---|
| 450 | 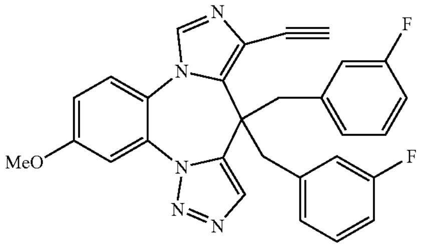 [SMILES: C#Cc1ncn2c1C(Cc1cccc(F)c1)(Cc1cccc(F)c1)c1cnnn1-c1cc(OC)ccc1-2] |
| 451 | 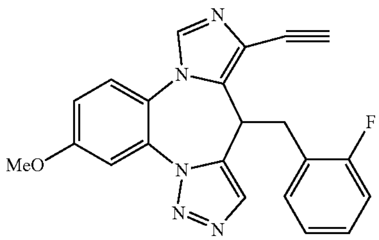 [SMILES: C#Cc1ncn2c1C(Cc1ccccc1F)c1cnnn1-c1cc(OC)ccc1-2] |
| 452 | 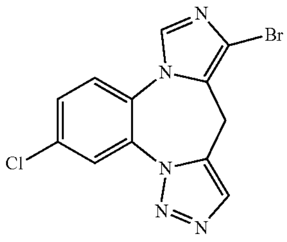 [SMILES: Clc1ccc2c(c1)-n1nncc1Cc1c(Br)ncn1-2] |
| 453 | 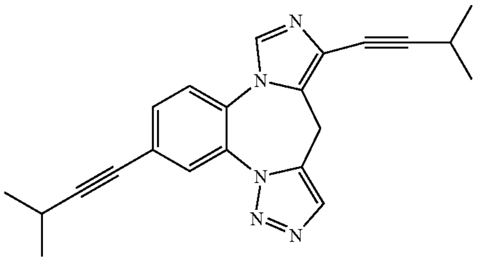 [SMILES: CC(C)C#Cc1ccc2c(c1)-n1nncc1Cc1c(C#CC(C)C)ncn1-2] |
| 454 | 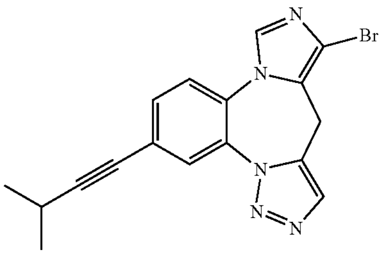 [SMILES: CC(C)C#Cc1ccc2c(c1)-n1nncc1Cc1c(Br)ncn1-2] |
| 455 | 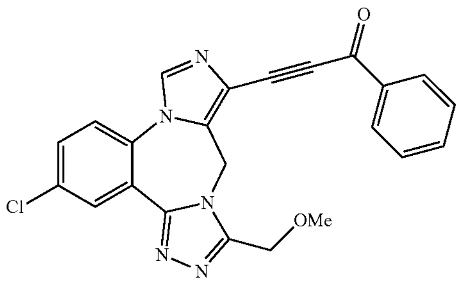 [SMILES: COCc1nnc2n1Cc1c(C#CC(=O)c3ccccc3)ncn1-c1ccc(Cl)cc1-2] |

-continued
| Compound | Structure |
|---|---|
| 456 | 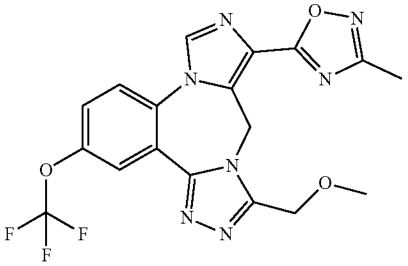 [SMILES: COCc1nnc2n1Cc1c(-c3nc(C)no3)ncn1-c1ccc(OC(F)(F)F)cc1-2] |
| 457 | 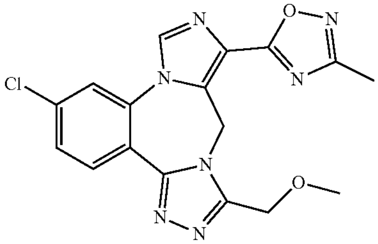 [SMILES: COCc1nnc2n1Cc1c(-c3nc(C)no3)ncn1-c1cc(Cl)ccc1-2] |
| 458 | 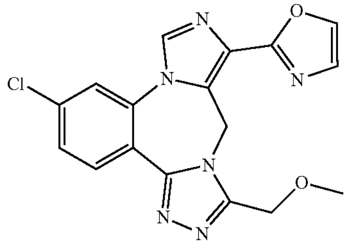 [SMILES: COCc1nnc2n1Cc1c(-c3ncco3)ncn1-c1cc(Cl)ccc1-2] |
| 459 | 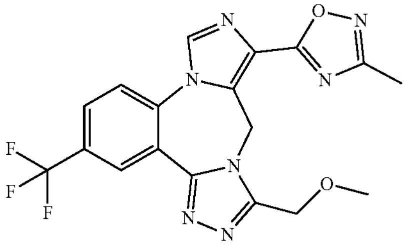 [SMILES: COCc1nnc2n1Cc1c(-c3nc(C)no3)ncn1-c1ccc(C(F)(F)F)cc1-2] |
| 460 | 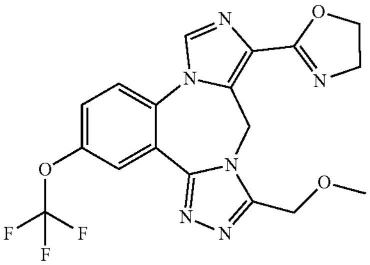 [SMILES: COCc1nnc2n1Cc1c(C3=NCCO3)ncn1-c1ccc(OC(F)(F)F)cc1-2] |
| 461 | 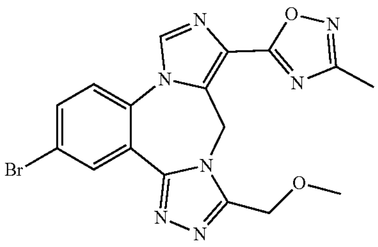 [SMILES: COCc1nnc2n1Cc1c(-c3nc(C)no3)ncn1-c1ccc(Br)cc1-2] |
-continued
| Compound | Structure |
|---|---|
| 462 | 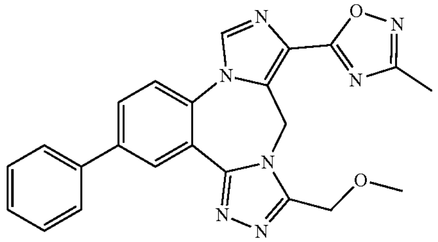 [SMILES: COCc1nnc2n1Cc1c(-c3nc(C)no3)ncn1-c1ccc(-c3ccccc3)cc1-2] |
| 463 | 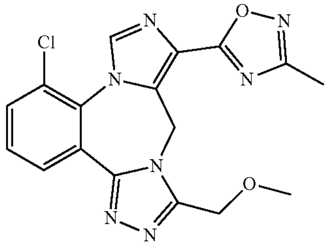 [SMILES: COCc1nnc2n1Cc1c(-c3nc(C)no3)ncn1-c1c(Cl)cccc1-2] |
| 464 | 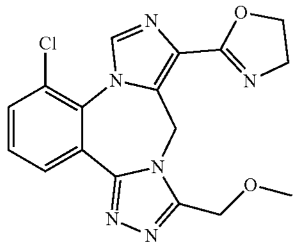 [SMILES: COCc1nnc2n1Cc1c(C3=NCCO3)ncn1-c1c(Cl)cccc1-2] |
| 465 | 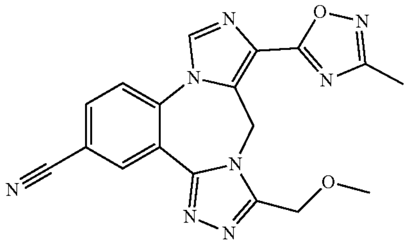 [SMILES: COCc1nnc2n1Cc1c(-c3nc(C)no3)ncn1-c1ccc(C#N)cc1-2] |
| 466 | 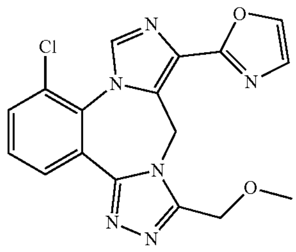 [SMILES: COCc1nnc2n1Cc1c(-c3ncco3)ncn1-c1c(Cl)cccc1-2] |
| 467 | 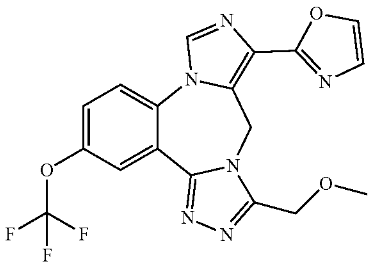 [SMILES: COCc1nnc2n1Cc1c(-c3ncco3)ncn1-c1ccc(OC(F)(F)F)cc1-2] |

-continued

| Compound | Structure |
|---|---|
| 468 | 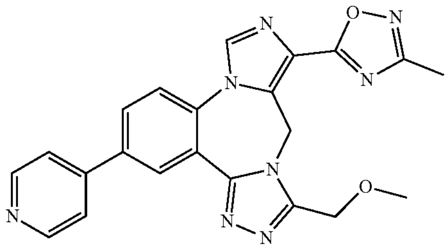 [SMILES: COCc1nnc2n1Cc1c(-c3nc(C)no3)ncn1-c1ccc(-c3ccncc3)cc1-2] |
| 469 | 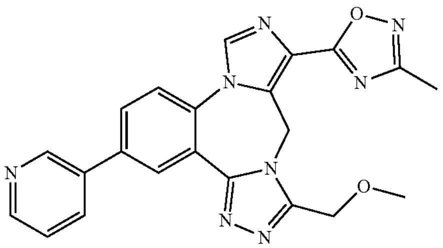 [SMILES: COCc1nnc2n1Cc1c(-c3nc(C)no3)ncn1-c1ccc(-c3cccnc3)cc1-2] |
| 470 | 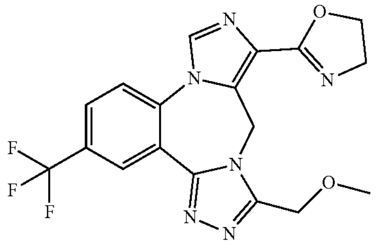 [SMILES: COCc1nnc2n1Cc1c(C3=NCCO3)ncn1-c1ccc(C(F)(F)F)cc1-2] |
| 471 | 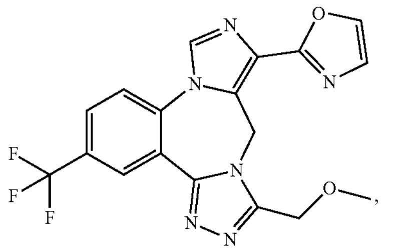 [SMILES: COCc1nnc2n1Cc1c(-c3ncco3)ncn1-c1ccc(C(F)(F)F)cc1-2] |

and their pharmaceutically suitable salt, hydrate, solvate, polymorph, isomer or combination thereof.

The invention also includes various combinations of $R^1$, $R^2$ and $R^3$ as described above. These combinations can in turn be combined with any or all of the values of the other variables described herein. For example, $R_1$ can be —OR or halogen; $R^2$ can be (C1-C4)-alkyl-, —$OR^8$, —$(CH_2)_nOR^8$, or —$(CH_2)_nO(CH_2)_nR^8$; and optionally $R^3$ is —C(O)OR, or —$C(O)N(R)_2$. In another example, $R^1$ is —OR or halogen; $R^2$ is (C1-C4)-alkyl-, —$OR^8$, —$(CH_2)_nOR^8$, or —$(CH_2)_nO(CH_2)_nR^8$; and $R^3$ is a 5- or 6-membered heteroaryl, such as

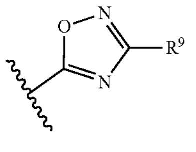

or

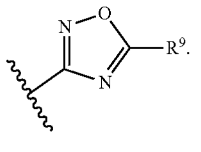

For each of above examples, compounds can have the specific values of the groups described herein.

Any embodiment described herein is also intended to represent unlabeled forms as well as isotopically labeled forms of the compounds, unless otherwise indicated. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes various isotopically labeled compounds as defined herein, for example those into which radioactive isotopes, such as $^3H$, $^{13}C$, and $^{14}C$, are present. Such isotopically labeled compounds are useful in metabolic studies (preferably with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly preferred for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Any of the individual embodiments recited herein may define formula I, II, III, IV, V, VI, VII, VIII, or IX individually or be combined to produce a preferred embodiment of this invention.

General Synthetic Methodology

The compounds of this invention may be prepared in general by methods known to those skilled in the art. Schemes 1-10 below provide general synthetic routes for the preparation of compounds of formulae I-IV. Other equivalent schemes, which will be readily apparent to the ordinary skilled organic chemist, may alternatively be used to synthesize various portions of the molecules as illustrated by the general schemes below.

Scheme 1.
General synthesis of a compound of formula I wherein X, Y, Z, V and W form a 1,2,3-triazole ring, or a compound of formula II.

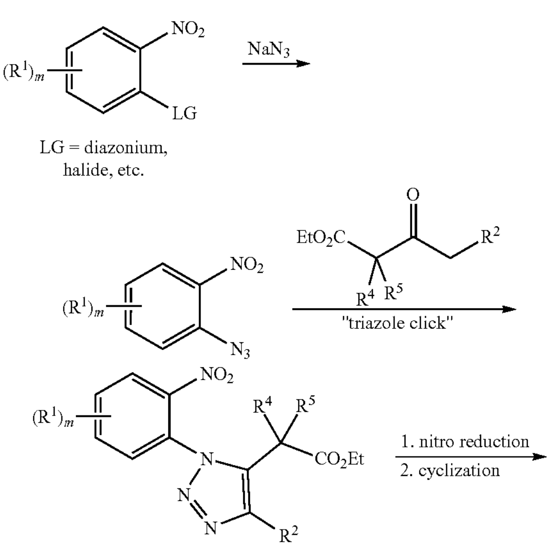

-continued
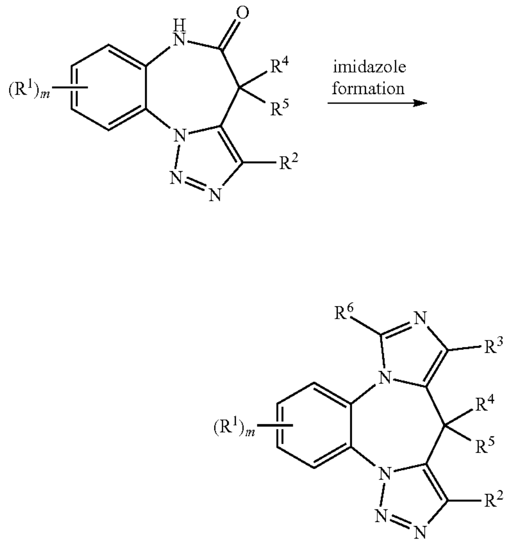
Scheme 2.
General synthesis of a compound of formula I or III, wherein X, Y, Z, V and W form a pyrazole ring.
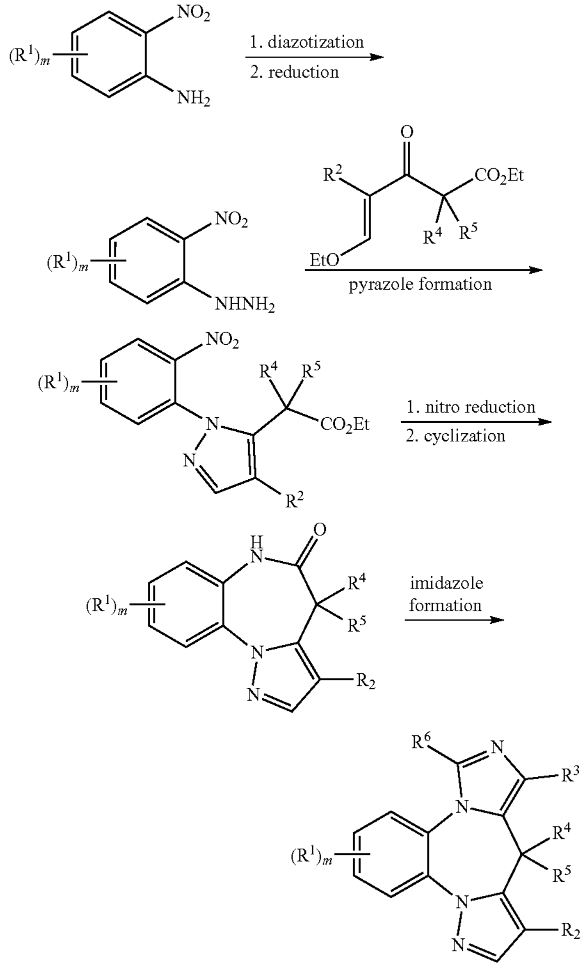
Scheme 3.
General synthesis of a compound of formula I, wherein X, Y, Z, V and W form a phenoxy-substituted 1,2,3-triazole ring, or a comound of formula II.
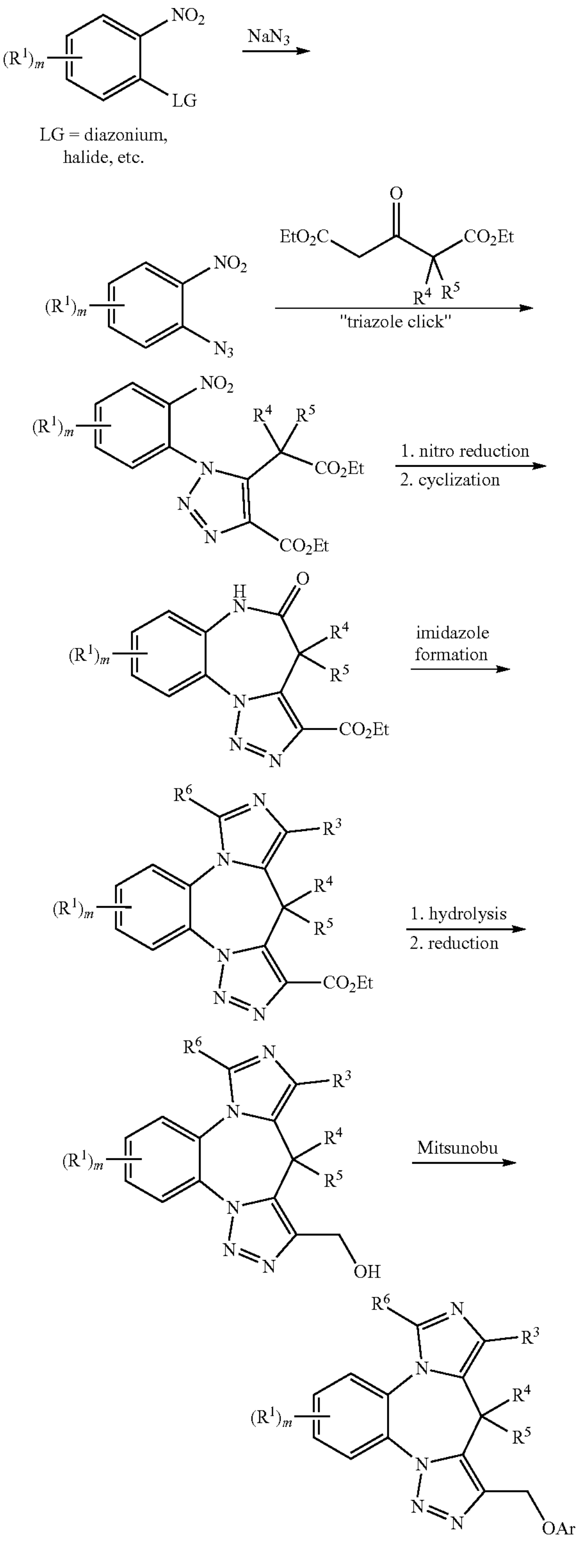

Scheme 4.

General synthesis of compounds of formula I or II to allow for divergent functionalization on the triazole-ring formed by X, Y, Z, V and W.

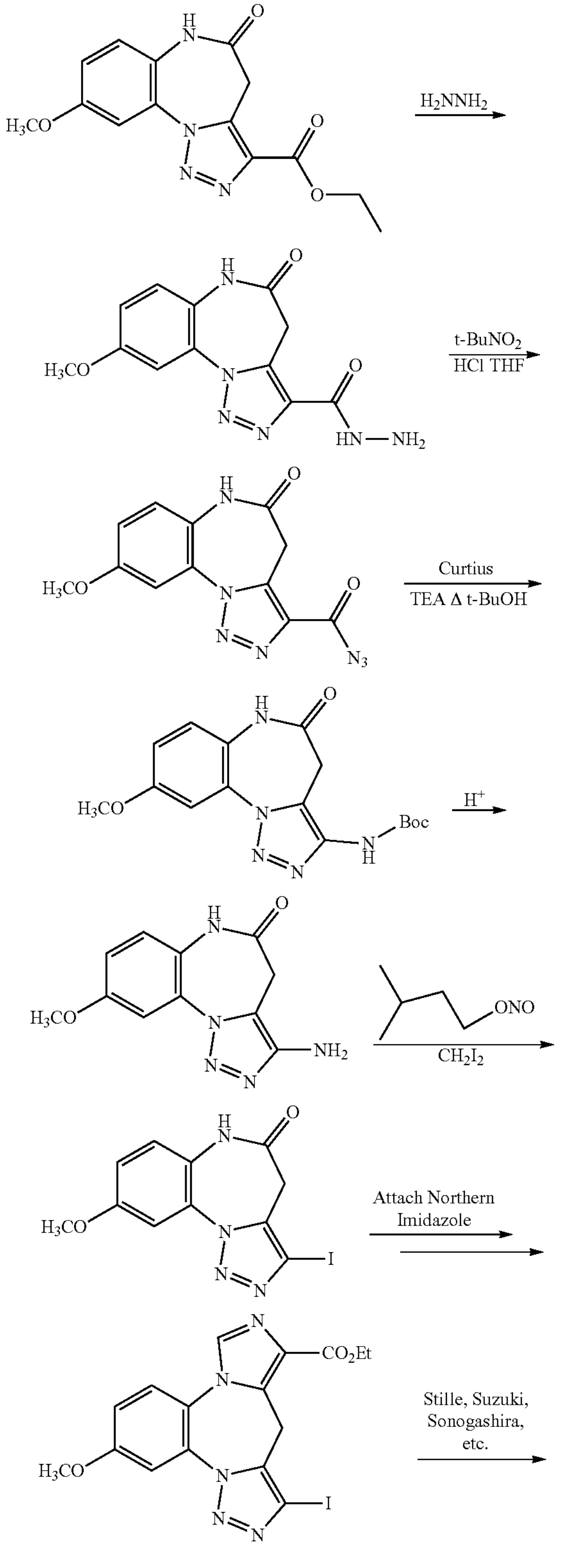

-continued

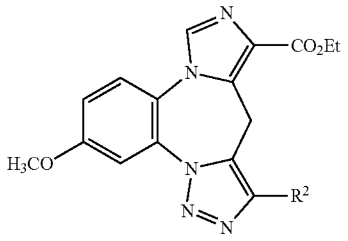

Scheme 5.

General synthesis of a compound of formula I wherein X,Y, Z, V and W form an aminomethyl-substituted 1,2,3-triazole ring, or a compound of formula II.

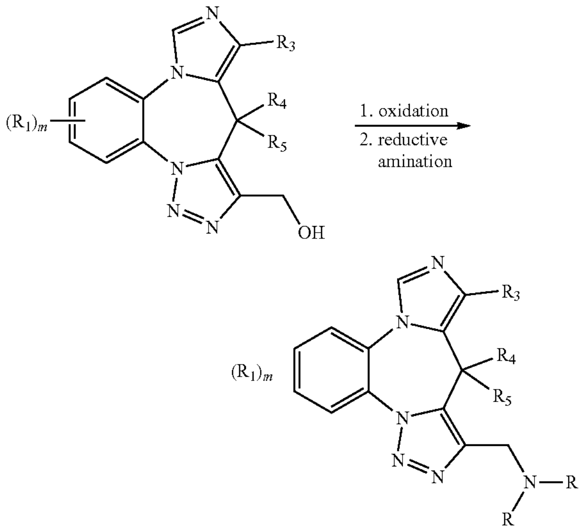

Scheme 6.

General synthesis of a compound of formula I wherein X, Y, Z, V and W form an aralkyl-substituted or heteroaralkyl substituted 1,2,3-triazole ring, or a compound of formula II.

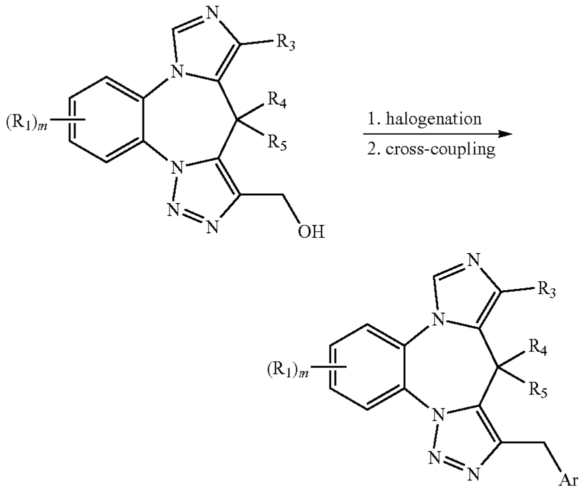

Scheme 7.
General synthesis of a compound of formula I or IV, wherein X, Y, Z, V, and W form a substituted 1,2,4-triazole ring.
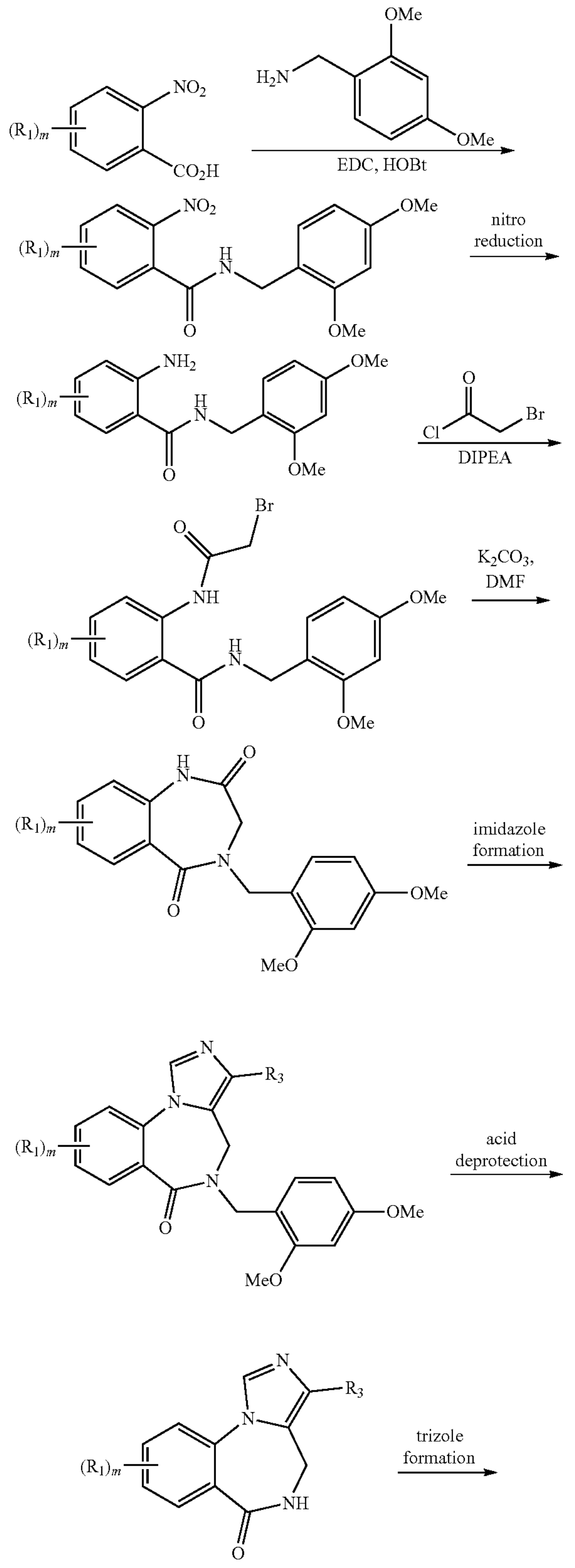
-continued
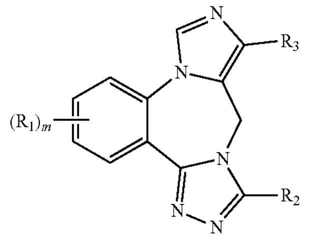
$R^2$ is
—$OR_8$,
—$SR_8$,
—$(CH_2)_nOR_8$,
—$(CH_2)_nO(CH_2)_nR_8$,
—$(CH_2)_pR_8$, or
—$(CH_2)_pN(R'')R_{10}$
Scheme 8.
General synthesis of a compound of formula I, wherein X, Y, Z, V and W form a methyl-substituted 1,2,3-triazole ring, or a comound of formula II.
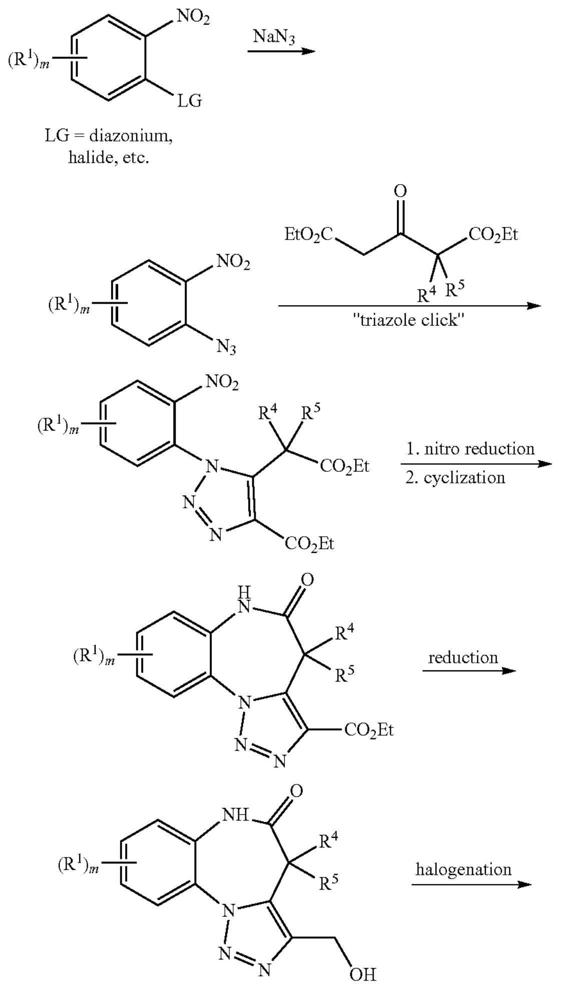

-continued

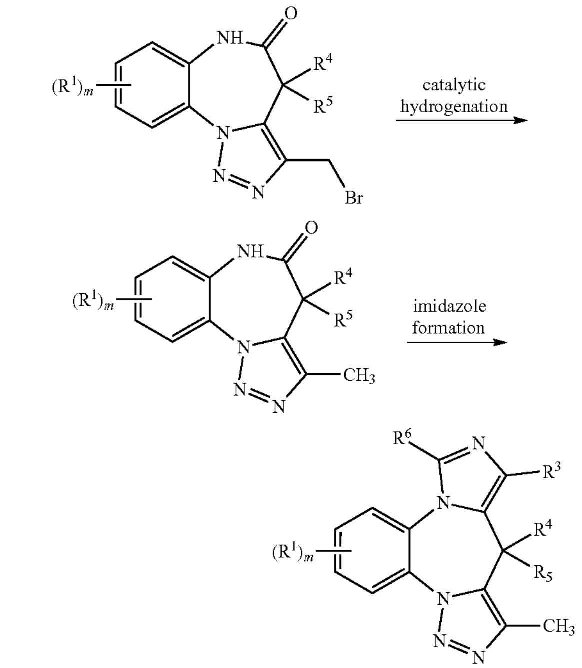

Scheme 9.

General synthesis of a compound of formula I, wherein X, Y, Z, V and W form benzyl-substituted 1,2,3-triazole ring, or a comound of formula II.

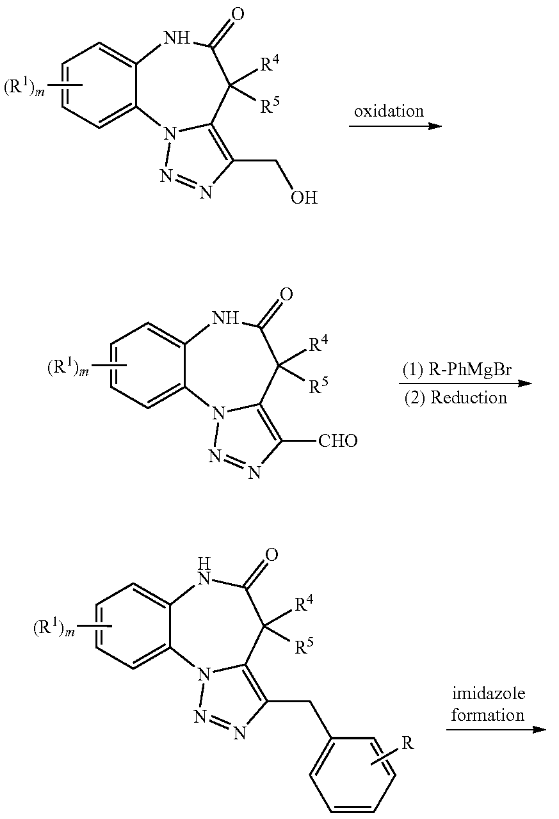

-continued

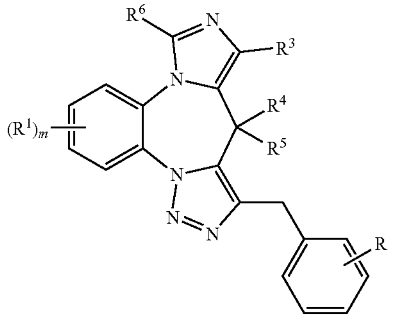

Scheme 10.

General synthesis of a compound of forumla I, II, or IV wherein X, Y, Z, V and W form a substituted triazole ring, such as a 1,2,3-triazole ring or a 1,2,4-triazole ring, and the upper imidazole is substituted with a 1,2,4-oxadizaole ring as illustrated in 10(a) and 10(b).

10(a)

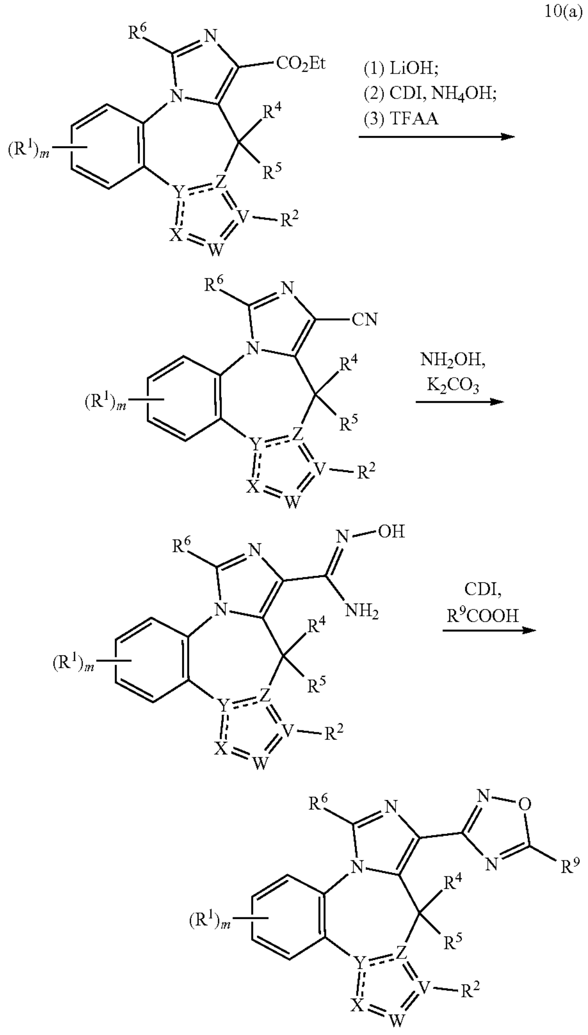

-continued
10(b)
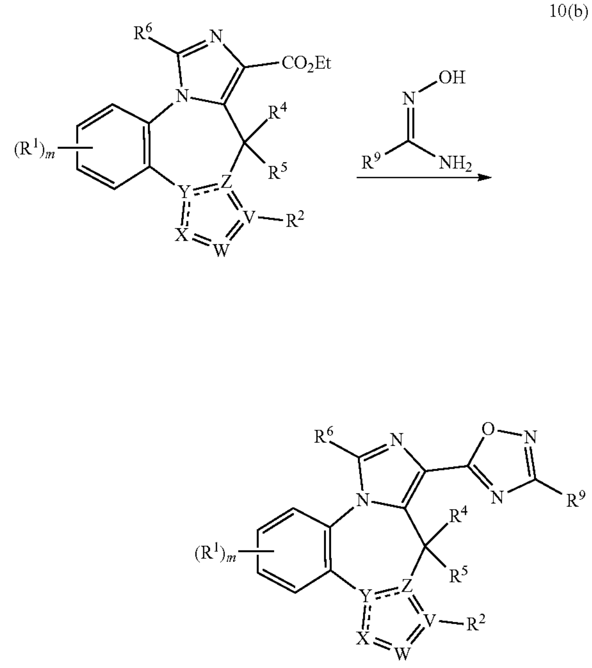
Scheme 10a.
General synthesis of a compound where $R^3$ is an optionally substituted dihydrooxazole or oxazinyl ring is illustrated in scheme 10a.
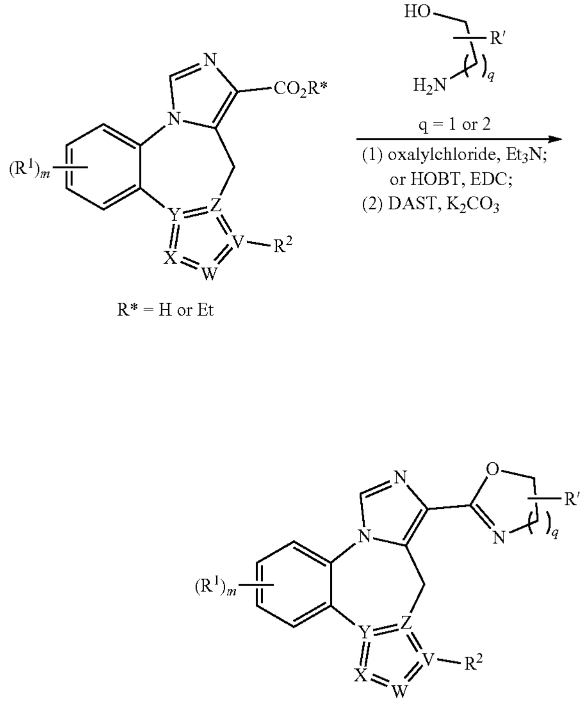
R* = H or Et
Scheme 10b(a) and 10b(b).
General synthesis of a compound where $R^3$ is an optionally substituted oxazole or isoxazole is illustrated in schemes 10b(a) and 10b(b).
(a)
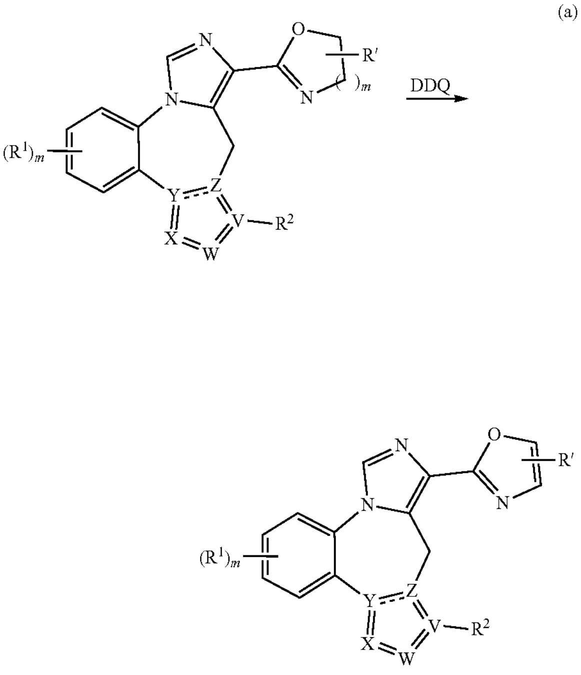
(b)
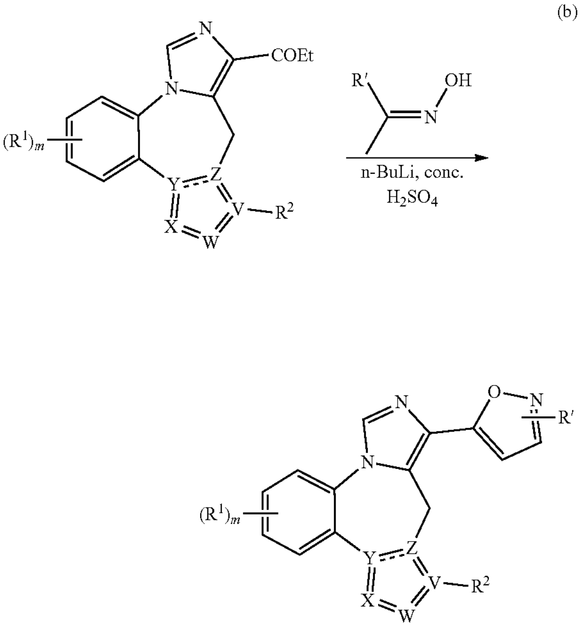

Scheme 10c.
General synthesis of a compound where $R^3$ is an optionally substituted alkynyl group is illustrated in scheme 10c.

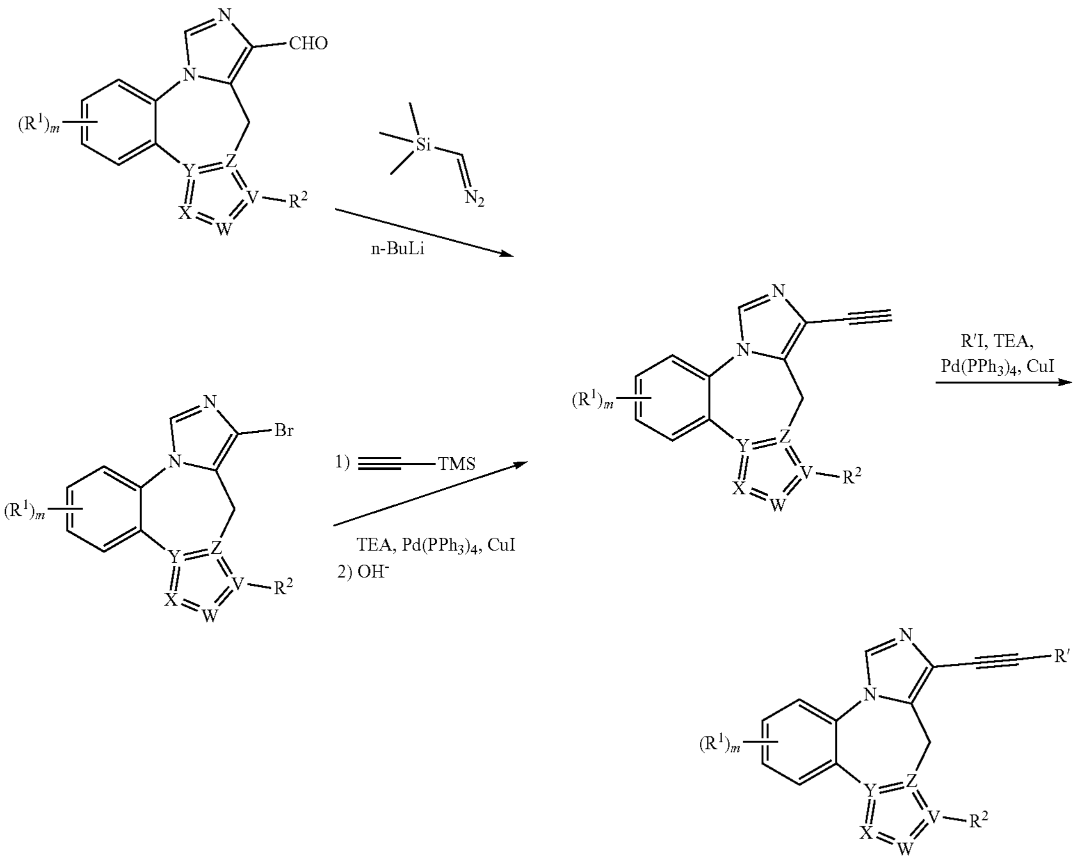

As would be recognized by skilled practitioners, compounds of formulae I-IV with variables other than those depicted above may be prepared by varying chemical reagents or the synthetic routes.

Pharmaceutical Compositions and Modes of Administration

The present invention provides a pharmaceutical composition comprising a pharmaceutically acceptable carrier and a compound of formulae I-IV, or pharmaceutically acceptable salts, hydrates, solvates, polymorphs, isomers, or combinations thereof.

The basic nitrogen-containing groups present in the compounds of the invention may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

It will be appreciated that compounds and agents used in the compositions of this invention preferably should readily penetrate the blood-brain barrier when peripherally administered. Compounds which cannot penetrate the blood-brain barrier, however, can still be effectively administered directly into the central nervous system, e.g., by an intraventricular or other neuro-compatible route.

In some embodiments of this invention, the α5-containing $GABA_A$ R positive allosteric modulator is formulated with a pharmaceutically acceptable carrier. Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. In other embodiments, no carrier is used. For example, the α5-containing $GABA_A$ R agonist (e.g., a α5-containing $GABA_A$ receptor positive allosteric modulator) can be administered alone or as a component of a pharmaceutical formulation (therapeutic composition). The α5-containing $GABA_A$ R agonist (e.g., a α5-containing $GABA_A$ receptor positive allosteric modulator) may be formulated for administration in any convenient way for use in human medicine.

In some embodiments, the therapeutic methods of the invention include administering the composition of a compound or agent topically, systemically, or locally. For example, therapeutic compositions of compounds or agents of the invention may be formulated for administration by, for example, injection (e.g., intravenously, subcutaneously, or intramuscularly), inhalation or insufflation (either through the mouth or the nose) or oral, buccal, sublingual, transdermal, nasal, or parenteral administration. The compositions of compounds or agents described herein may be formulated as part of an implant or device, or formulated for slow or extended release. When administered parenterally, the therapeutic composition of compounds or agents for use in this invention is preferably in a pyrogen-free, physiologically acceptable form. Techniques and formulations generally may be found in Remington's Pharmaceutical Sciences, Meade Publishing Co., Easton, PA.

In certain embodiments, pharmaceutical compositions suitable for parenteral administration may comprise the α5-containing $GABA_A$ R positive allosteric modulator in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

A composition comprising a α5-containing $GABA_A$ R positive allosteric modulator may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

In certain embodiments of the invention, compositions comprising a α5-containing $GABA_A$ R positive allosteric modulator can be administered orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and the like, each containing a predetermined amount of the α5-containing $GABA_A$ R positive allosteric modulator as an active ingredient.

In solid dosage forms for oral administration (capsules, tablets, pills, dragees, powders, granules, and the like), one or more compositions comprising the α5-containing $GABA_A$ R positive allosteric modulator may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the α5-containing $GABA_A$ R positive allosteric modulator, the liquid dosage forms may contain inert diluents commonly used in the art, such as water or other solvents, solubilizing agents and emulsifiers, such as ethyl alcohol (ethanol), isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

As described herein, the compounds, agents, and compositions thereof may be administered for slow, controlled or extended release. The term "extended release" is widely recognized in the art of pharmaceutical sciences and is used herein to refer to a controlled release of an active compound or agent from a dosage form to an environment over (throughout or during) an extended period of time, e.g. greater than or equal to one hour. An extended release dosage form will release drug at substantially constant rate over an extended period of time or a substantially constant amount of drug will be released incrementally over an extended period of time. The term "extended release" used herein includes the terms "controlled release," "prolonged release," "sustained release," "delayed release," or "slow release" as these terms are used in the pharmaceutical sciences. In some embodiments, the extended release dosage is administered in the form of a patch or a pump.

A person of ordinary skill in the art, such as a physician, is readily able to determine the required amount of α5-containing $GABA_A$ R positive allosteric modulator (s) to treat the subject using the compositions and methods of the invention. It is understood that the dosage regimen will be determined for an individual, taking into consideration, for example, various factors that modify the action of α5-containing $GABA_A$ R positive allosteric modulator, the severity or stage of the disease, route of administration, and characteristics unique to the individual, such as age, weight, size, and extent of cognitive impairment.

It is well-known in the art that normalization to body surface area is an appropriate method for extrapolating doses between species. To calculate the human equivalent dose (HED) from a dosage used in the treatment of age-dependent cognitive impairment in rats, the formula HED (mg/kg)=rat dose (mg/kg)×0.16 may be employed (see Estimating the Safe Starting Dose in Clinical Trials for Therapeutics in Adult Healthy Volunteers, December 2002, Center for Biologics Evaluation and Research). For example, using that formula, a dosage of 10 mg/kg in rats is equivalent to 1.6 mg/kg in humans. This conversion is based on a more general formula HED=animal dose in mg/kg×(animal weight in kg/human weight in kg)$^{0.33}$.

In certain embodiments of the invention, the dose of the α5-containing $GABA_A$ R positive allosteric modulator is between 0.0001 and 100 mg/kg/day (which, given a typical human subject of 70 kg, is between 0.007 and 7000 mg/day).

In certain embodiments of the invention, the interval of administration is once every 12 or 24 hours. Administration at less frequent intervals, such as once every 6 hours, may also be used.

If administered by an implant, a device or a slow or extended release formulation, the α5-containing $GABA_A$ R positive allosteric modulator can be administered one time, or one or more times periodically throughout the lifetime of the patient as necessary. Other administration intervals intermediate to or shorter than these dosage intervals for clinical applications may also be used and may be determined by one skilled in the art following the methods of this invention.

Desired time of administration can be determined by routine experimentation by one skilled in the art. For example, the α5-containing $GABA_A$ R positive allosteric modulator may be administered for a period of 1-4 weeks, 1-3 months, 3-6 months, 6-12 months, 1-2 years, or more, up to the lifetime of the patient.

In addition to α5-containing $GABA_A$ R positive allosteric modulator, the compositions of this invention can also include other therapeutically useful agents. These other therapeutically useful agents may be administered in a single formulation, simultaneously or sequentially with the α5-containing $GABA_A$ R positive allosteric modulator according to the methods of the invention.

It will be understood by one of ordinary skill in the art that the compositions described herein may be adapted and modified as is appropriate for the application being addressed and that the compositions described herein may be employed in other suitable applications. For example, the compositions of this application may further comprise a second therapeutic agent. Such other additions and modifications will not depart from the scope hereof.

Pharmaceutical Compositions with Antipsychotics

The compounds or the compositions of this application may be used in combination with an antipsychotic in treating cognitive impairment associated with schizophrenia or bipolar disorder in a subject having or at risk of said schizophrenia or bipolar disorder (e.g., mania). The antipsychotic or a pharmaceutically acceptable salt, hydrate, solvate or polymorph thereof that is useful in the methods and compositions of this invention include both typical and atypical antipsychotics. In some embodiments, the compounds or the compositions of the present invention may be used to treat one or more positive and/or negative symptoms, as well as cognitive impairment, associated with schizophrenia. In some embodiments, the compounds or the compositions of the present invention may be used to treat one or more symptoms, as well as cognitive impairment, associated with bipolar disorder (in particular, mania). In some embodiments of this invention, the compounds or the compositions of this invention prevent or slow the progression of cognitive impairment of schizophrenia or bipolar disorder (in particular, mania) in said subject.

In some embodiments, the antipsychotics suitable for use in the present invention are selected from atypical antipsychotics. Such atypical antipsychotics include, but are not limited to, those disclosed in, for example, U.S. Pat. Nos. 4,734,416; 5,006,528; 4,145,434; 5,763,476; 3,539,573; 5,229,382; 5,532,372; 4,879,288; 4,804,663; 4,710,500; 4,831,031; and 5,312,925, and EP Patents EP402644 and EP368388, and the pharmaceutically acceptable salts, hydrates, solvates, and polymorphs thereof.

In some embodiments, atypical antipsychotics suitable for use in the present invention include, but are not limited to, aripiprazole, asenapine, clozapine, iloperidone, olanzapine, lurasidone, paliperidone, quetiapine, risperidone and ziprasidone, and the pharmaceutically acceptable salts, hydrates, solvates, and polymorphs thereof. In some embodiments, the antipsychotic suitable for use herein is selected from aripiprazole (Bristol-Myers Squibb), olanzapine (Lilly) and ziprasidone (Pfizer), and the pharmaceutically acceptable salts, hydrates, solvates, and polymorphs thereof.

In some embodiments, the antipsychotics suitable for use in the present invention are typical antipsychotics, including, but not limited to, acepromazine, benperidol, bromazepam, bromperidol, chlorpromazine, chlorprothixene, clotiapine, cyamemazine, diazepam, dixyrazine, droperidol, flupentixol, fluphenazine, fluspirilene, haloperidol, heptaminol, isopropamide iodide, levomepromazine, levosulpiride, loxapine, melperone, mesoridazine, molindone, oxypertine, oxyprothepine, penfluridol, perazine, periciazine, perphenazine, pimozide, pipamperone, pipotiazine, prochlorperazine, promazine, promethazine, prothipendyl, pyridoxine, sulpiride, sultopride, tetrabenazine, thioproperazine, thioridazine, tiapride, tiotixene, trifluoperazine, triflupromazine, trihexyphenidyl, and zuclopenthixol, and the pharmaceutically acceptable salts, hydrates, solvates, and polymorphs thereof.

In some embodiments of the present invention, the antipsychotic or a pharmaceutically acceptable salt, hydrate, solvate or polymorph thereof may be selected from compounds that are dopaminergic agents (such as dopamine D1 receptor antagonists or agonists, dopamine $D_2$ receptor antagonists or partial agonists, dopamine D3 receptor antagonists or partial agonists, dopamine D4 receptor antagonists), glutamatergic agents, N-methyl-D-aspartate (NMDA) receptor positive allosteric modulators, glycine reuptake inhibitors, glutamate reuptake inhibitor, metabotropic glutamate receptors (mGluRs) agonists or positive allosteric modulators (PAMs) (e.g., mGluR2/3 agonists or PAMs), glutamate receptor glur5 positive allosteric modulators (PAMs), M1 muscarinic acetylcholine receptor (mAChR) positive allosteric modulators (PAMs), histamine 113 receptor antagonists, α-amino-3-hydroxy-5-methyl-isoxazole-4-propionic acid (AMPA)/kainate receptor antagonists, ampakines (CX-516), glutathione prodrugs, noradrenergic agents (such as alpha-2 adrenergic receptor agonists or antagonists and catechol-O-methyl transferase (COMT) inhibitors), serotonin receptor modulators (such as $5\text{-HT}_{2A}$ receptor antagonists, $5\text{-HT}_{1A}$ receptor partial agonists, $5\text{-HT}_{2C}$ agonists, and 5-HT6 antagonists, serotonin 2C agonists), cholinergic agents (such as alpha-7 nicotinic receptor agonists or PAMs, alpha4-beta2 nicotinic receptor agonists, allosteric modulators of nicotinic receptors and acetylcholinesterase inhibitors, muscarinic receptor agonists and antagonists), cannabinoid CBI antagonists, neurokinin 3 antagonists, neurotensin agonists, monoamine oxidase (MAO) B inhibitors, PDE10 inhibitors, neuronal nitric oxide synthase (nNOS) inhibitors, neurosteroids, and neurotrophic factors.

In some embodiments, an α5-containing $GABA_A$ receptor positive allosteric modulator as described herein and an antipsychotic as described herein, or their pharmaceutically acceptable salts, hydrates, solvates or polymorphs, are administered simultaneously, or sequentially, or in a single formulation, or in separate formulations packaged together. In other embodiments, the α5-containing $GABA_A$ receptor positive allosteric modulator and the antipsychotic, or their pharmaceutically acceptable salts, hydrates, solvates or polymorphs, are administered via different routes. As used herein, "combination" includes administration by any of these formulations or routes of administration.

Pharmaceutical Compositions with Memantine

The compounds or the compositions of this application may be used in combination with memantine or a derivative or an analog thereof in treating cognitive impairment associated with central nervous system (CNS) disorders in a subject in need or at risk thereof, including, without limitation, subjects having or at risk for age-related cognitive impairment, Mild Cognitive Impairment (MCI), amnestic MCI, Age-Associated Memory Impairment (AAMI), Age Related Cognitive Decline (ARCD), dementia, Alzheimer's Disease (AD), prodromal AD, post traumatic stress disorder (PTSD), schizophrenia or bipolar disorder, amyotrophic lateral sclerosis (ALS) and cancer-therapy-related cognitive impairment.

Memantine, chemically also known as 3,5-dimethyladamantan-1-amine or 3,5-dimethyltricyclo[$3.3.1.1^{3,7}$]decan-1-amine, is an uncompetitive N-methyl-D-aspartate (NMDA) receptor antagonist with moderate affinity. The proprietary names for memantine include: Axura® and Akatinol® (Merz), Namenda® (Forest Laboratories), Ebixa® and Abixa® (Lundbeck), and Memox® (Unipharm). Memantine is currently available in the U.S. and in over 42 countries worldwide. It is approved for the treatment of moderate to severe Alzheimer's disease (AD) in the United States at a dose of up to 28 mg/day. Memantine and some of its derivatives and analogs that are useful in the present invention are disclosed in U.S. Pat. Nos. 3,391,142; 4,122,193; 4,273,774; and 5,061,703, all of which are hereby incorporated by reference. Other memantine derivatives or analogs that are useful in the present invention include, but are not limited to, those compounds disclosed in U.S. Patent Application Publication US20040087658, US20050113458, US20060205822, US20090081259, US20090124659, and US20100227852; EP Patent Application Publication EP2260839A2; EP Patent EP1682109B1; and PCT Application Publication WO2005079779, all of which are incorporated herein by reference. Memantine, as used in the present invention, includes memantine and its derivatives and analogs, as well as hydrates, polymorphs, prodrugs, salts, and solvates thereof. Memantine, as used herein, also includes a composition comprising memantine or a derivative or an analog or a pharmaceutically acceptable salt, hydrate, solvate, polymorph, or prodrug thereof, wherein the composition optionally further comprises at least one additional therapeutic agent (such as a therapeutic agent useful for treating a CNS disorder or cognitive impairments associated thereof). In some embodiments, the memantine composition suitable for use in the present invention comprises memantine and a second therapeutic agent that is donepezil (under the trade name Aricept).

In other embodiments of the invention, the α5-containing $GABA_A$ receptor positive allosteric modulator and memantine (or the memantine derivative/analog), or their pharmaceutically acceptable salts, hydrates, solvates, polymorphs, or prodrugs are administered simultaneously, or sequentially, or in a single formulation or in separate formulations packaged together. In other embodiments, the α5-containing $GABA_A$ receptor positive allosteric modulator and memantine (or the memantine derivative/analog), or their pharmaceutically acceptable salts, hydrates, solvates, polymorphs, or prodrugs are administered via different routes. As used herein, "combination" includes administration by any of these formulations or routes of administration.

Pharmaceutical Compositions with Acetylcholine Esterase Inhibitors (AChE-Is)

The compounds or the compositions of this application may be used in combination with an acetylcholine esterase inhibitor in treating cognitive impairment associated with central nervous system (CNS) disorders in a subject in need or at risk thereof, including, without limitation, subjects having or at risk for age-related cognitive impairment, Mild Cognitive Impairment (MCI), amnestic MCI, Age-Associated Memory Impairment (AAMI), Age Related Cognitive Decline (ARCD), dementia, Alzheimer's Disease (AD), prodromal AD, post traumatic stress disorder (PTSD), schizophrenia or bipolar disorder, amyotrophic lateral sclerosis (ALS) and cancer-therapy-related cognitive impairment.

AChE-Is known to a person of ordinary skill in the art may belong to the subcategories of (i) reversible noncompetitive inhibitors or reversible competitive inhibitors, (ii) irreversible, and/or (iii) quasi-irreversible inhibitors.

In certain embodiment, AChE-Is useful in the present invention include those described in PCT applications WO2014039920 and WO2002032412; EP patents Nos. 468187; 481429-A; and U.S. Pat. Nos. 4,816,456; 4,895,841; 5,041,455; 5,106,856; 5,602,176; 6,677,330; 7,340,299; 7,635,709; 8,058,268; 8,741,808; and 8,853,219, all of which are incorporated herein by reference.

In certain embodiment, typical AChE-Is that may be used in accordance with this invention include, but are not limited to, ungeremine, ladostigil, demecarium, echothiophate (Phospholine), edrophonium (Tensilon), tacrine (Cognex), Pralidoxime (2-PAM), pyridostigmine (Mestinon), physostigmine (serine, Antilirium), abmenonium (Mytelase), galantamine (Reminyl, Razadyne), rivastigmine (Exelon, SZD-ENA-713), Huperzine A, Icopezil, neostigmine (Prostigmin, Vagostigmin), Aricept (Donepezil, E2020), Lactucopicrin, monoamine acridines and their derivatives, piperidine and piperazine derivatives, N-benzyl-piperidine derivatives, piperidinyl-alkanoyl heterocyclic compounds, 4-(1-benzyl:piperidyl)-substituted fused quinoline derivatives and cyclic amide derivatives. Other typical AChE-Is include carbamates and organophosphonate compounds such as Metrifonate (Trichlorfon). Benzazepinols such as galantamine are also useful AChE-Is. In some embodiment, AChE-Is suitable for use in combination with the compounds and compositions of this application include: Donepezil (aricept), Galantamine (razadyne), or Rivastigmine (exelon).

In other embodiments of the invention, the α5-containing $GABA_A$ receptor positive allosteric modulator and the AChE-1, or their pharmaceutically acceptable salts, hydrates, solvates, polymorphs, or prodrugs are administered simultaneously, or sequentially, or in a single formulation or in separate formulations packaged together. In other embodiments, the α5-containing $GABA_A$ receptor positive allosteric modulator and the AChE-I, or their pharmaceutically acceptable salts, hydrates, solvates, polymorphs, or prodrugs are administered via different routes. As used herein, "combination" includes administration by any of these formulations or routes of administration.

In some embodiments, the compounds and compositions described herein are for use as a medicament. In some embodiments, the compounds and compositions of the present invention are for use in treating cognitive impairment associated with a CNS disorder in a subject in need of treatment or at risk of said cognitive impairment. In some embodiments, the CNS disorder with cognitive impairment includes, without limitation, age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction.

In some embodiments, this application provides the use of a compound or composition described herein in the preparation of a medicament for the treatment of cognitive impairment associated with a CNS disorder in a subject in need of treatment or at risk of said cognitive impairment. In some embodiments, the CNS disorder with cognitive impairment includes, without limitation, age-related cognitive impairment, Mild Cognitive Impairment (MCI), amnestic MCI (aMCI), Age-Associated Memory Impairment (AAMI), Age Related Cognitive Decline (ARCD), dementia, Alzheimer's Disease (AD), prodromal AD, post traumatic stress disorder (PTSD), schizophrenia, bipolar disorder, amyotrophic lateral sclerosis (ALS), cancer-therapy-related cognitive impairment, mental retardation, Parkinson's disease (PD), autism spectrum disorders, fragile X disorder, Rett syndrome, compulsive behavior, and substance addiction.

Methods of Assessing Cognitive Impairment

Animal models serve as an important resource for developing and evaluating treatments for cognitive impairment associated with CNS disorders. Features that characterize cognitive impairment in animal models typically extend to cognitive impairment in humans. Efficacy in such animal models is, thus, expected to be predictive of efficacy in humans. The extent of cognitive impairment in an animal model for a CNS disorder, and the efficacy of a method of treatment for said CNS disorder may be tested and confirmed with the use of a variety of cognitive tests.

A Radial Arm Maze (RAM) behavioral task is one example of a cognitive test, specifically testing spacial memory (Chappell et al. *Neuropharmacology* 37: 481-487, 1998). The RAM apparatus consists of, e.g., eight equidistantly spaced arms. A maze arm projects from each facet of a center platform. A food well is located at the distal end of each arm. Food is used as a reward. Blocks can be positioned to prevent entry to any arm. Numerous extra maze cues surrounding the apparatus may also be provided. After habituation and training phases, spatial memory of the subjects may be tested in the RAM under control or test compound-treated conditions. As a part of the test, subjects are pretreated before trials with a vehicle control or one of a range of dosages of the test compound. At the beginning of each trial, a subset of the arms of the eight-arm maze is blocked. Subjects are allowed to obtain food on the unblocked arms to which access is permitted during this initial "information phase" of the trial. Subjects are then removed from the maze for a delay period, e.g., a 60 second delay, a 15 minute delay, a one-hour delay, a two-hour delay, a six hour delay, a 24 hour delay, or longer) between the information phase and the subsequent "retention test," during which the barriers on the maze are removed, thus allowing access to all eight arms. After the delay period, subjects are placed back onto the center platform (with the barriers to the previously blocked arms removed) and allowed to obtain the remaining food rewards during this retention test phase of the trial. The identity and configuration of the blocked arms vary across trials. The number of "errors" the subjects make during the retention test phase is tracked. An error occurs in the trial if the subjects entered an arm from which food had already been retrieved in the pre-delay component of the trial, or if it re-visits an arm in the post-delay session that had already been visited. A fewer number of errors would indicate better spatial memory. The number of errors made by the test subject, under various test compound treatment regimes, can then be compared for efficacy of the test compound in treating cognitive impairment associated with CNS disorders.

Another cognitive test that may be used to assess the effects of a test compound on the cognitive impairment of a CNS disorder model animal is the Morris water maze. A water maze is a pool surrounded with a novel set of patterns relative to the maze. The training protocol for the water maze may be based on a modified water maze task that has been shown to be hippocampal-dependent (de Hoz et al., *Eur. J. Neurosci.,* 22:745-54, 2005; Steele and Morris, *Hippocampus* 9:118-36, 1999). The subject is trained to locate a submerged escape platform hidden underneath the surface of the pool. During the training trial, a subject is released in the maze (pool) from random starting positions around the perimeter of the pool. The starting position varies from trial to trial. If the subject does not locate the escape platform within a set time, the experimenter guides and places the subject on the platform to "teach" the location of the platform. After a delay period following the last training trial, a retention test in the absence of the escape platform is given to assess spatial memory. The subject's level of preference for the location of the (now absent) escape platform, as measured by, e.g., the time spent in that location or the number of crossings of that location made by the mouse, indicates better spatial memory, i.e., treatment of cognitive impairment. The preference for the location of the escape platform under different treatment conditions, can then be compared for efficacy of the test compound in treating cognitive impairment associated with CNS disorders.

There are various tests known in the art for assessing cognitive function in humans, for example and without limitation, the clinical global impression of change scale (CIBIC-plus scale); the Mini Mental State Exam (MMSE); the Neuropsychiatric Inventory (NPI); the Clinical Dementia Rating Scale (CDR); the Cambridge Neuropsychological Test Automated Battery (CANTAB); the Sandoz Clinical Assessment-Geriatric (SCAG), the Buschke Selective Reminding Test (Buschke and Fuld, 1974); the Verbal Paired Associates subtest; the Logical Memory subtest; the Visual Reproduction subtest of the Wechsler Memory Scale-Revised (WMS-R) (Wechsler, 1997); the Benton Visual Retention Test, or MATRICS consensus neuropsychological test battery which includes tests of working memory, speed of processing, attention, verbal learning, visual learning, reasoning and problem solving and social cognition. See Folstein et al., *J Psychiatric Res* 12: 189-98, (1975); Robbins et al., Dementia 5: 266-81, (1994); Rey, L'examen clinique en psychologie, (1964); Kluger et al., *J Geriatr Psychiatry*

*Neurol* 12:168-79, (1999); Marquis et al., 2002 and Masur et al., 1994. Also see Buchanan, R. W., Keefe, R. S. E., Umbricht, D., Green, M. F., Laughren, T., and Marder, S. R. (2011) The FDA-NIMH-MATRICS guidelines for clinical trial design of cognitive-enhancing drugs: what do we know 5 years later? Schizophr. Bull. 37, 1209-1217. Another example of a cognitive test in humans is the explicit 3-alternative forced choice task. In this test, subjects are presented with color photographs of common objects consisting of a mix of three types of image pairs: similar pairs, identical pairs and unrelated foils. The second of the pair of similar objects is referred to as the "lure". These image pairs are fully randomized and presented individually as a series of images. Subjects are instructed to make a judgment as to whether the objects seen are new, old or similar. A "similar" response to the presentation of a lure stimulus indicates successful memory retrieval by the subject. By contrast, calling the lure stimulus "old" or "new" indicates that correct memory retrieval did not occur.

In addition to assessing cognitive performance, the progression of age-related cognitive impairment and dementia, as well as the conversion of age-related cognitive impairment into dementia, may be monitored by assessing surrogate changes in the brain of the subject. Surrogate changes include, without limitation, changes in regional brain volumes, perforant path degradation, and changes seen in brain function through resting state fMRI (R-fMRI) and fluorodeoxyglucose positron emission tomography (FDG-PET). Examples of regional brain volumes useful in monitoring the progression of age-related cognitive impairment and dementia include reduction of hippocampal volume and reduction in volume or thickness of entorhinal cortex. These volumes may be measured in a subject by, for example, MRI. Aisen et al., Alzheimer's & Dementia 6:239-246 (2010). Perforant path degradation has been shown to be linked to age, as well as reduced cognitive function. For example, older adults with more perforant path degradation tend to perform worse in hippocampus-dependent memory tests. Perforant path degradation may be monitored in subjects through ultrahigh-resolution diffusion tensor imaging (DTI). Yassa et al., PNAS 107:12687-12691 (2010). Resting-state fMRI (R-fMRI) involves imaging the brain during rest, and recording large-amplitude spontaneous low-frequency (<0.1 Hz) fluctuations in the fMRI signal that are temporally correlated across functionally related areas. Seed-based functional connectivity, independent component analyses, and/or frequency-domain analyses of the signals are used to reveal functional connectivity between brain areas, particularly those areas whose connectivity increase or decrease with age, as well as the extent of cognitive impairment and/or dementia. FDG-PET uses the uptake of FDG as a measure of regional metabolic activity in the brain. Decline of FDG uptake in regions such as the posterior cingulated cortex, temporoparietal cortex, and prefrontal association cortex has been shown to relate to the extent of cognitive decline and dementia. Aisen et al., Alzheimer's & Dementia 6:239-246 (2010), Herholz et al., NeuroImage 17:302-316 (2002).

Age-Related Cognitive Impairment

The invention provides methods and compositions for treating age-related cognitive impairment or the risk thereof using a α5-containing $GABA_A$ receptor positive allosteric modulator (i.e., a compound of the invention), such as one selected from the compounds or pharmaceutically acceptable salts, hydrates, solvates, polymorphs, isomers, or combinations thereof as described herein. In certain embodiments, treatment comprises preventing or slowing the progression, of age-related cognitive impairment. In certain embodiments, treatment comprises alleviation, amelioration or slowing the progression, of one or more symptoms associated with age-related cognitive impairment. In certain embodiments, treatment of age-related cognitive impairment comprises slowing the conversion of age-related cognitive impairment (including, but not limited to MCI, ARCD and AAMI) into dementia (e.g., AD). The methods and compositions may be used for human patients in clinical applications in the treating age-related cognitive impairment in conditions such as MCI, ARCD and AAMI or for the risk thereof. The dose of the composition and dosage interval for the method is, as described herein, one that is safe and efficacious in those applications. In some embodiments of the invention, there is provided a method of preserving or improving cognitive function in a subject with age-related cognitive impairment, the method comprising the step of administering to said subject a therapeutically effective amount of a compound of the invention or a pharmaceutically acceptable salt, hydrate, solvate, polymorph, isomer, or combination thereof.

In some embodiments, a subject to be treated by the methods and compositions of this invention exhibits age-related cognitive impairment or is at risk of such impairment. In some embodiments, the age-related cognitive impairment includes, without limitation, Age-Associated Memory Impairment (AAMI), Mild Cognitive Impairment (MCI) and Age-related Cognitive Decline (ARCD).

Animal models serve as an important resource for developing and evaluating treatments for such age-related cognitive impairments. Features that characterize age-related cognitive impairment in animal models typically extend to age-related cognitive impairment in humans. Efficacy in such animal models is, thus, expected to be predictive of efficacy in humans.

Various animal models of age-related cognitive impairment are known in the art. For example, extensive behavioral characterization has identified a naturally occurring form of cognitive impairment in an outbred strain of aged Long-Evans rats (Charles River Laboratories; Gallagher et al., *Behav. Neurosci.* 107:618-626, (1993)). In a behavioral assessment with the Morris Water Maze (MWM), rats learn and remember the location of an escape platform guided by a configuration of spatial cues surrounding the maze. The cognitive basis of performance is tested in probe trials using measures of the animal's spatial bias in searching for the location of the escape platform. Aged rats in the study population have no difficulty swimming to a visible platform, but an age-dependent impairment is detected when the platform is camouflaged, requiring the use of spatial information. Performance for individual aged rats in the outbred Long-Evans strain varies greatly. For example, a proportion of those rats perform on a par with young adults. However, approximately 40-50% fall outside the range of young performance. This variability among aged rats reflects reliable individual differences. Thus, within the aged population some animals are cognitively impaired and designated aged-impaired (AI) and other animals are not impaired and are designated aged-unimpaired (AU). See, e.g., Colombo et al., *Proc. Natl. Acad. Sci.* 94: 14195-14199, (1997); Gallagher and Burwell, *Neurobiol. Aging* 10: 691-708, (1989); Gallagher et al. *Behav. Neurosci.* 107:618-626, (1993); Rapp and Gallagher, *Proc. Natl. Acad. Sci.* 93: 9926-9930, (1996); Nicolle et al., *Neuroscience* 74: 741-756, (1996); Nicolle et al., *J. Neurosci.* 19: 9604-9610, (1999); International Patent Publication WO2007/019312 and International Patent Publication WO 2004/048551. Such an animal model of age-related cognitive impairment may be used to assay the effectiveness of the methods and compositions this invention in treating age-related cognitive impairment.

The efficacy of the methods and compositions of this invention in treating age-related cognitive impairment may be assessed using a variety of cognitive tests, including the Morris water maze and the radial arm maze, as discussed herein.

Dementia

The invention also provides methods and compositions for treating dementia using a α5-containing $GABA_A$ receptor positive allosteric modulator, such as one selected from the compounds or pharmaceutically acceptable salts, hydrates, solvates, polymorphs, isomers, or combinations thereof as described herein. In certain embodiments, treatment comprises preventing or slowing the progression, of dementia. In certain embodiments, treatment comprises alleviation, amelioration, or slowing the progression of one or more symptoms associated with dementia. In certain embodiments, the symptom to be treated is cognitive impairment. In some embodiments of the invention, there is provided a method of preserving or improving cognitive function in a subject with dementia, the method comprising the step of administering to said subject a therapeutically effective amount of a compound of the invention or a pharmaceutically acceptable salt, hydrate, solvate, polymorph, isomer, or combination thereof. In certain embodiments, the dementia is Alzheimer's disease (AD), vascular dementia, dementia with Lewy bodies, or frontotemporal dementia. The methods and compositions may be used for human patients in clinical applications in treating dementia. The dose of the composition and dosage interval for the method is, as described herein, one that is safe and efficacious in those applications.

Animal models serve as an important resource for developing and evaluating treatments for dementia. Features that characterize dementia in animal models typically extend to dementia in humans. Thus, efficacy in such animal models is expected to be predictive of efficacy in humans. Various animal models of dementia are known in the art, such as the PDAPP, Tg2576, APP23, TgCRND8, J20, hPS2 Tg, and APP+PS1 transgenic mice. Sankaranarayanan, *Curr. Top. Medicinal Chem.* 6: 609-627, 2006; Kobayashi et al. *Genes Brain Behav.* 4: 173-196. 2005; Ashe and Zahns, Neuron. 66: 631-45, 2010. Such animal models of dementia may be used to assay the effectiveness of the methods and compositions of this invention of the invention in treating dementia.

The efficacy of the methods and compositions of this invention in treating dementia, or cognitive impairment associated with dementia, may be assessed in animals models of dementia, as well as human subjects with dementia, using a variety of cognitive tests known in the art, as discussed herein.

Post Traumatic Stress Disorder

The invention also provides methods and compositions for treating post traumatic stress disorder (PTSD) using a α5-containing $GABA_A$ receptor positive allosteric modulator, such as one selected from the compounds or pharmaceutically acceptable salts, hydrates, solvates, polymorphs, isomers, or combinations thereof as described herein. In certain embodiments, treatment comprises preventing or slowing the progression, of PTSD. In certain embodiments, treatment comprises alleviation, amelioration, or slowing the progression of one or more symptoms associated with PTSD. In certain embodiments, the symptom to be treated is cognitive impairment. In some embodiments of the invention, there is provided a method of preserving or improving cognitive function in a subject with PTSD, the method comprising the step of administering to said subject a therapeutically effective amount of a compound of the invention or a pharmaceutically acceptable salt, hydrate, solvate, polymorph, isomer, or combination thereof. The methods and compositions may be used for human patients in clinical applications in treating PTSD. The dose of the composition and dosage interval for the method is, as described herein, one that is safe and efficacious in those applications.

Patients with PTSD (and, to a lesser degree trauma-exposed patients without PTSD) have smaller hippocampal volumes (Woon et al., *Prog. Neuro-Psychopharm. & Biological Psych.* 34, 1181-1188; Wang et al., *Arch. Gen. Psychiatry* 67:296-303, 2010). PTSD is also associated with impaired cognitive performance. Older individuals with PTSD have greater declines in cognitive performance relative to control patients (Yehuda et al., *Bio. Psych.* 60: 714-721, 2006) and have a greater likelihood of developing dementia (Yaffe et al., *Arch. Gen. Psych.* 678: 608-613, 2010).

Animal models serve as an important resource for developing and evaluating treatments for PTSD. Features that characterize PTSD in animal models typically extend to PTSD in humans. Thus, efficacy in such animal models is expected to be predictive of efficacy in humans. Various animal models of PTSD are known in the art.

One rat model of PTSD is Time-dependent sensitization (TDS). TDS involves exposure of the animal to a severely stressful event followed by a situational reminder of the prior stress. The following is an example of TDS. Rats are placed in a restrainer, then placed in a swim tank and made to swim for a period of time, e.g., 20 min. Following this, each rat is then immediately exposed to a gaseous anesthetic until loss of consciousness, and finally dried. The animals are left undisturbed for a number of days, e.g., one week. The rats are then exposed to a "restress" session consisting of an initial stressor, e.g., a swimming session in the swim tank (Liberzon et al., *Psychoneuroendocrinology* 22: 443-453, 1997; Harvery et al., *Psychopharmacology* 175:494-502, 2004). TDS results in an enhancement of the acoustic startle response (ASR) in the rat, which is comparable to the exaggerated acoustic startle that is a prominent symptom of PTSD (Khan and Liberzon, Psychopharmacology 172: 225-229, 2004). Such animal models of PTSD may be used to assay the effectiveness of the methods and compositions of this invention of the invention in treating PTSD.

The efficacy of the methods and compositions of this invention in treating PTSD, or cognitive impairment associated with PTSD, may also be assessed in animals models of PTSD, as well as human subjects with PTSD, using a variety of cognitive tests known in the art, as discussed herein.

Schizophrenia and Bipolar Disorder

The invention additionally provides methods and compositions for treating schizophrenia or bipolar disorder (in particular, mania) using a α5-containing $GABA_A$ receptor positive allosteric modulator, such as one selected from the compounds or pharmaceutically acceptable salts, hydrates, solvates, polymorphs, isomers, or combinations thereof as described herein. In certain embodiments, treatment comprises preventing or slowing the progression of schizophrenia or bipolar disorder (in particular, mania). Schizophrenia is characterized by a wide spectrum of psychopathology, including positive symptoms such as aberrant or distorted mental representations (e.g., hallucinations, delusions), or dopamine dysregulation-associated symptoms (e.g., hyperdopaminergic responses, hyperdopaminergic behavioral responses, dopaminergic hyperactivity, or hyperlocomotor activity, or psychosis), negative symptoms characterized by diminution of motivation and adaptive goal-directed action (e.g., anhedonia, affective flattening, avolition), and cognitive impairment. In certain embodiments, treatment comprises alleviation, amelioration or slowing the progression of one or more positive and/or negative symptoms, as well as cognitive impairment, associated with schizophrenia. Further, there are a number of other psychiatric diseases such as schizotypical and schizoaffective disorder, other acute- and chronic psychoses and bipolar disorder (in particular, mania), which have an overlapping symptomatology with schizophrenia. In some embodiments, treatment comprises alleviation, amelioration or slowing the progression of one or more symptoms, as well as cognitive impairment, associated with bipolar disorder (in particular, mania). In some embodiments of the invention, there is provided a method of preserving or improving cognitive function in a subject with schizophrenia or bipolar disorder, the method comprising the step of administering to said subject a therapeutically effective amount of a compound of the invention or a pharmaceutically acceptable salt, hydrate, solvate, polymorph, isomer, or combination thereof. The methods and compositions may be used for human patients in clinical applications in treating schizophrenia or bipolar disorder (in particular, mania). The dose of the composition and dosage interval for the method is, as described herein, one that is safe and efficacious in those applications.

Cognitive impairments are associated with schizophrenia. They precede the onset of psychosis and are present in non-affected relatives. The cognitive impairments associated with schizophrenia constitute a good predictor for functional outcome and are a core feature of the disorder. Cognitive features in schizophrenia reflect dysfunction in frontal cortical and hippocampal circuits. Patients with schizophrenia also present hippocampal pathologies such as reductions in hippocampal volume, reductions in neuronal size and dysfunctional hyperactivity. An imbalance in excitation and inhibition in these brain regions has also been documented in schizophrenic patients suggesting that drugs targeting inhibitory mechanisms could be therapeutic. See, e.g., Guidotti et al., *Psychopharmacology* 180: 191-205, 2005; Zierhut, *Psych. Res. Neuroimag.* 183:187-194, 2010; Wood et al., *NeuroImage* 52:62-63, 2010; Vinkers et al., *Expert Opin. Investig. Drugs* 19:1217-1233, 2009; Young et al., *Pharmacol. Ther.* 122:150-202, 2009.

Animal models serve as an important resource for developing and evaluating treatments for schizophrenia. Features that characterize schizophrenia in animal models typically extend to schizophrenia in humans. Thus, efficacy in such animal models is expected to be predictive of efficacy in humans. Various animal models of schizophrenia are known in the art.

One animal model of schizophrenia is protracted treatment with methionine. Methionine-treated mice exhibit deficient expression of GAD67 in frontal cortex and hippocampus, similar to those reported in the brain of postmortem schizophrenia patients. They also exhibit prepulse inhibition of startle and social interaction deficits (Tremonlizzo et al., *PNAS,* 99: 17095-17100, 2002). Another animal model of schizophrenia is methylaoxymethanol acetate (MAM)-treatment in rats. Pregnant female rats are administered MAM (20 mg/kg, intraperitoneal) on gestational day 17. MAM-treatment recapitulate a pathodevelopmental process to schizophrenia-like phenotypes in the offspring, including anatomical changes, behavioral deficits and altered neuronal information processing. More specifically, MAM-treated rats display a decreased density of parvalbumin-positive GABAergic interneurons in portions of the prefrontal cortex and hippocampus. In behavioral tests, MAM-treated rats display reduced latent inhibition. Latent inhibition is a behavioral phenomenon where there is reduced learning about a stimulus to which there has been prior exposure with any consequence. This tendency to disregard previously benign stimuli, and reduce the formation of association with such stimuli is believed to prevent sensory overload. Low latent inhibition is indicative of psychosis. Latent inhibition may be tested in rats in the following manner. Rats are divided into two groups. One group is pre-exposed to a tone over multiple trials. The other group has no tone presentation. Both groups are then exposed to an auditory fear conditioning procedure, in which the same tone is presented concurrently with a noxious stimulus, e.g. an electric shock to the foot. Subsequently, both groups are presented with the tone, and the rats' change in locomotor activity during tone presentation is monitored. After the fear conditioning the rats respond to the tone presentation by strongly reducing locomotor activity. However, the group that has been exposed to the tone before the conditioning period displays robust latent inhibition: the suppression of locomotor activity in response to tone presentation is reduced. MAM-treated rats, by contrast show impaired latent inhibition. That is, exposure to the tone previous to the fear conditioning procedure has no significant effect in suppressing the fear conditioning. (see Lodge et al., J. Neurosci., 29:2344-2354, 2009) Such animal models of schizophrenia may be used to assay the effectiveness of the methods and compositions of the invention in treating schizophrenia or bipolar disorder (in particular, mania).

MAM-treated rats display a significantly enhanced locomotor response (or aberrant locomotor activity) to low dose D-amphetamine administration. The MAM-treated rats also display a significantly greater number of spontaneously firing ventral tegmental dopamine (DA) neurons. These results are believed to be a consequence of excessive hippocampal activity because in MAM-treated rats, the ventral hippocampus (vHipp) inactivation (e.g., by intra-vHipp administration of a sodium channel blocker, tetrodotoxin (TTX), to MAM rats) completely reversed the elevated DA neuron population activity and also normalized the augmented amphetamine-induced locomotor behavior. The correlation of hippocampal dysfunction and the hyper-responsivity of the DA system is believed to underlie the augmented response to amphetamine in MAM-treated animals and psychosis in schizophrenia patients. See Lodge D. J. et al. *Neurobiology of Disease* (2007), 27(42), 11424-11430. The use of MAM-treated rats in the above study may be suitable for use to assay the effectiveness of the methods and compositions of the present invention in treating schizophrenia or bipolar disorder (in particular, mania). For example, the methods and compositions of this invention maybe evaluated, using MAM-treated animals, for their effects on the central hippocampus (vHipp) regulation, on the elevated DA neuron population activity and on the hyperactive locomotor response to amphetamine in the MAM-treated animals.

In MAM-treated rats, hippocampal (HPC) dysfunction leads to dopamine system hyperactivity. A benzodiazepine-positive allosteric modulator (PAM), selective for the α5 subunit of the $GABA_A$ receptor, SH-053-2'F—R—$CH_3$, is tested for its effects on the output of the hippocampal (HPC). The effect of SH-053-2'F—R—$CH_3$ on the hyperactive locomotor response to amphetamine in MAM-treated animals is also examined. The α5GABAAR PAM reduces the number of spontaneously active DA neurons in the ventral tegmental area (VTA) of MAM rats to levels observed in saline-treated rats (control group), both when administered systemically and when directly infused into the ventral HPC. Moreover, HPC neurons in both saline-treated and MAM-treated animals show diminished cortical-evoked responses following the α5GABAAR PAM treatment. In addition, the increased locomotor response to amphetamine observed in MAM-treated rats is reduced following the α5$GABA_A$R PAM treatment. See Gill K. M et al. *Neuropsychopharmacology* (2011), 1-9. The use of MAM-treated rats in the above study may be suitable for use in the present invention to assay the effectiveness of the methods and compositions of the invention in treating schizophrenia or bipolar disorder (in particular, mania). For example, the methods and compositions of this invention maybe evaluated, using MAM-treated animals, for their effects on the output of the hippocampal (HPC) and on the hyperactive locomotor response to amphetamine in the MAM-treated animals.

Administration of MAM to pregnant rats on embryonic day 15 (E15) severely impairs spatial memory or the ability to learn the spatial location of four items on an eight-arm radial maze in the offspring. In addition, embryonic day 17 (E17) MAM-treated rats are able to reach the level of performance of control rats at the initial stages of training, but are unable to process and retrieve spatial information when a 30-min delay is interposed, indicating a significant impairment in working memory. See Gourevitch R. et al. (2004). *Behav. Pharmacol,* 15, 287-292. Such animal models of schizophrenia may be used to assay the effectiveness of the methods and compositions of the invention in treating schizophrenia or bipolar disorder (in particular, mania).

Apomorphine-induced climbing (AIC) and stereotype (AIS) in mice is another animal model useful in this invention. Agents are administered to mice at a desired dose level (e.g., via intraperitoneal administration). Subsequently, e.g., thirty minutes later, experimental mice are challenges with apomorphine (e.g., with 1 mg/kg sc). Five minutes after the apomorphine injection, the sniffing-licking-gnawing syndrome (stereotyped behavior) and climbing behavior induced by apomorphine are scored and recorded for each animal. Readings can be repeated every 5 min during a 30-min test session. Scores for each animal are totaled over the 30-min test session for each syndrome (stereotyped behavior and climbing). If an effect reached at least of 50% inhibition, and $ID_{50}$ value (95% confidence interval) is calculated using a nonlinear least squares calculation with inverse prediction. Mean climbing and stereotype scores can be expressed as a percent of control values observed in vehicle treated (e.g., saline-treated) mice that receive apomorphine. See Grauer S. M. et al. *Psychopharmacology* (2009) 204, 37-48. This mouse model may be used to assay the effectiveness of the methods and compositions of the invention in treating schizophrenia or bipolar disorder (in particular, mania).

In another well-established preclinical model of schizophrenia, rats exposed chronically to ketamine, an uncompetitive N-methyl-D-aspartate (NMDA) receptor antagonist, produces positive and negative psychotic symptoms and cognitive impairment. Long-Evans male rats are injected intraperitoneally with ketamine (30 mg/kg, twice a day) for two weeks during adolescence (2 month-old). Rats are behaviorally tested when they reach adulthood (approximately 4-5 month-old) for the behavioral symptoms to ketamine exposure and for the efficacy of treatment to alleviate those symptoms. See, e.g., Enomoto et al. Progress in Neuro-Psychopharmacology & Biological Psychiatry 33 (2009) 668-675.

The efficacy of the methods and compositions of this invention in treating schizophrenia or cognitive impairment associated therewith may also be assessed in animal models of schizophrenia or bipolar disorder (in particular, mania), as well as human subjects with schizophrenia, using a variety of cognitive tests known in the art, as discussed herein.

Amyotrophic Lateral Sclerosis (ALS)

The invention additionally provides methods and compositions for treating ALS using a α5-containing $GABA_A$ receptor positive allosteric modulator, such as one selected from the compounds or pharmaceutically acceptable salts, hydrates, solvates, polymorphs, isomers, or combinations thereof as described herein. In certain embodiments, treatment comprises preventing or slowing the progression, of ALS. In certain embodiments, treatment comprises alleviation, amelioration or slowing the progression, of one or more symptoms associated with ALS. In certain embodiments, the symptom to be treated is cognitive impairment. In some embodiments of the invention, there is provided a method of preserving or improving cognitive function in a subject with ALS, the method comprising the step of administering to said subject a therapeutically effective amount of a compound of the invention or a pharmaceutically acceptable salt, hydrate, solvate, polymorph, isomer, or combination thereof. The methods and compositions may be used for human patients in clinical applications in treating ALS. The dose of the composition and dosage interval for the method is, as described herein, one that is safe and efficacious in those applications.

In addition to the degeneration of motor neurons, ALS is characterized by neuronal degeneration in the entorhinal cortex and hippocampus, memory deficits, and neuronal hyperexcitability in different brain areas such as the cortex.

The efficacy of the methods and compositions of this invention in treating ALS, or cognitive impairment associated with ALS, may also be assessed in animal models of ALS, as well as human subjects with ALS, using a variety of cognitive tests known in the art, as discussed herein.

Cancer Therapy-Related Cognitive Impairment

The invention additionally provides methods and compositions for treating cancer therapy-related cognitive impairment using a α5-containing $GABA_A$ receptor positive allosteric modulator, such as one selected from the compounds or pharmaceutically acceptable salts, hydrates, solvates, polymorphs, isomers, or combinations thereof as described herein. In certain embodiments, treatment comprises preventing or slowing the progression, of cancer therapy-related cognitive impairment. In certain embodiments, treatment comprises alleviation, amelioration or slowing the progression, of one or more symptoms associated with cancer therapy-related cognitive impairment. In some embodiments of the invention, there is provided a method of preserving or improving cognitive function in a subject with cancer therapy-related cognitive impairment, the method comprising the step of administering to said subject a therapeutically effective amount of a compound of the invention or a pharmaceutically acceptable salt, hydrate, solvate, polymorph, isomer, or combination thereof. The methods and compositions may be used for human patients in clinical applications in treating cancer therapy-related cognitive impairment. The dose of the composition and dosage interval for the method is, as described herein, one that is safe and efficacious in those applications.

Therapies that are used in cancer treatment, including chemotherapy, radiation, or combinations thereof, can cause cognitive impairment in patients, in such functions as memory, learning and attention. Cytotoxicity and other adverse side-effects on the brain of cancer therapies are the basis for this form of cognitive impairment, which can persist for decades. (Dietrich et al, Oncologist 13:1285-95, 2008; Soussain et al, Lancet 374:1639-51, 2009).

Cognitive impairment following cancer therapies reflects dysfunction in frontal cortical and hippocampal circuits that are essential for normal cognition. In animal models, exposure to either chemotherapy or radiation adversely affects performance on tests of cognition specifically dependent on these brain systems, especially the hippocampus (Kim et al., J. Radiat. Res. 49:517-526, 2008; Yang et al., Neurobiol. Learning and Mem. 93:487-494, 2010). Thus, drugs targeting these cortical and hippocampal systems could be neuroprotective in patients receiving cancer therapies and efficacious in treating symptoms of cognitive impairment that may last beyond the interventions used as cancer therapies.

Animal models serve as an important resource for developing and evaluating treatments for cancer therapy-related cognitive impairment. Features that characterize cancer therapy-related cognitive impairment in animal models typically extend to cancer therapy-related cognitive impairment in humans. Thus, efficacy in such animal models is expected to be predictive of efficacy in humans. Various animal models of cancer therapy-related cognitive impairment are known in the art.

Examples of animal models of cancer therapy-related cognitive impairment include treating animals with antineoplastic agents such as cyclophosphamide (CYP) or with radiation, e.g., $^{60}$Co gamma-rays. (Kim et al., *J. Radiat. Res.* 49:517-526, 2008; Yang et al., Neurobiol. *Learning and Mem.* 93:487-494, 2010). The cognitive function of animal models of cancer therapy-related cognitive impairment may then be tested with cognitive tests to assay the effectiveness of the methods and compositions of the invention in treating cancer therapy-related cognitive impairment. The efficacy of the methods and compositions of this invention in treating cancer therapy-related cognitive impairment, as well as human subjects with cancer therapy-related cognitive impairment, using a variety of cognitive tests known in the art, as discussed herein.

Parkinson's Disease (PD)

Parkinson's disease (PD) is a neurological disorder characterized by a decrease of voluntary movements. The afflicted patient has reduction of motor activity and slower voluntary movements compared to the normal individual. The patient has characteristic "mask" face, a tendency to hurry while walking, bent over posture and generalized weakness of the muscles. There is a typical "lead-pipe" rigidity of passive movements. Another important feature of the disease is the tremor of the extremities occurring at rest and decreasing during movements.

Parkinson's disease, the etiology of which is unknown, belongs to a group of the most common movement disorders named parkinsonism, which affects approximately one person per one thousand. These other disorders grouped under the name of parkinsonism may result from viral infection, syphilis, arteriosclerosis and trauma and exposure to toxic chemicals and narcotics. Nonetheless, it is believed that the inappropriate loss of synaptic stability may lead to the disruption of neuronal circuits and to brain diseases. Whether as the result of genetics, drug use, the aging process, viral infections, or other various causes, dysfunction in neuronal communication is considered the underlying cause for many neurologic diseases, such as PD (Myrrhe van Spronsen and Casper C. Hoogenraad, *Curr. Neurol. Neurosci. Rep.* 2010, 10, 207-214).

Regardless of the cause of the disease, the main pathologic feature is degeneration of dopaminergic cells in basal ganglia, especially in substantia nigra. Due to premature death of the dopamine containing neurons in substantia nigra, the largest structure of the basal ganglia, the striatum, will have reduced input from substantia nigra resulting in decreased dopamine release. The understanding of the underlying pathology led to the introduction of the first successful treatment which can alleviate Parkinson's disease. Virtually all approaches to the therapy of the disease are based on dopamine replacement. Drugs currently used in the treatment can be converted into dopamine after crossing the blood brain barrier, or they can boost the synthesis of dopamine and reduce its breakdown. Unfortunately, the main pathologic event, degeneration of the cells in substantia nigra, is not helped. The disease continues to progress and frequently after a certain length of time, dopamine replacement treatment will lose its effectiveness.

The invention provides methods and compositions for treating PD using a α5-containing $GABA_A$ receptor positive allosteric modulator, such as one selected from the compounds or pharmaceutically acceptable salts, hydrates, solvates, polymorphs, isomers, or combinations thereof as described herein. In certain embodiments, treatment comprises preventing or slowing the progression of PD. In certain embodiments, treatment comprises alleviation, amelioration, or slowing the progression of one or more symptoms associated with PD. In certain embodiments, the symptom to be treated is cognitive impairment. For example, methods and compositions of the disclosure can be used to improve the motor/cognitive impairments symptomatic of Parkinson's disease. Moreover, methods and compositions of the disclosure may be useful for treating the memory impairment symptomatic of Parkinson's disease. In some embodiments of the invention, there is provided a method of preserving or improving cognitive function in a subject with PD, the method comprising the step of administering to said subject a therapeutically effective amount of a compound of the invention or a pharmaceutically acceptable salt, hydrate, solvate, polymorph, isomer, or combination thereof.

There are a number of animal models for PD. Exemplary animal models for PD include the reserpine model, the methamphetamine model, the 6-hydroxydopamine (6-OHDA) model, the 1-methyl-4-phenyl-1,2,3,6-tetrahydropyridine (MPTP) model, the paraquat (PQ)-Maneb model, the rotenone model, the 3-nitrotyrosine model and genetic models using transgenic mice. Transgenic models include mice that over express α-synuclein, express human mutant forms of α-synuclein, or mice that express LRKK2 mutations. See review of these models by Ranjita B. et al. (Ranjita B. et al. *BioEssays* 2002, 24, 308-318). Additional information regarding these animal models is readily available from Jackson Laboratories (see also http://research.jax.org/grs/parkinsons.html), as well as in numerous publications disclosing the use of these validated models.

The efficacy of the methods and compositions of this invention in treating PD, or cognitive impairment associated with PD, may be assessed in any of the above animal models of PD, as well as human subjects with PD, using a variety of cognitive tests known in the art, as discussed herein.

Autism

Autism is a neurodevelopmental disorder characterized by dysfunction in three core behavioral dimensions: repetitive behaviors, social deficits, and cognitive deficits. The repetitive behavior domain involves compulsive behaviors, unusual attachments to objects, rigid adherence to routines or rituals, and repetitive motor mannerisms such as stereotypies and self-stimulatory behaviors. The social deficit dimension involves deficits in reciprocal social interactions, lack of eye contact, diminished ability to carry on conversation, and impaired daily interaction skills. The cognitive deficits can include language abnormalities. Autism is a disabling neurological disorder that affects thousands of Americans and encompasses a number of subtypes, with various putative causes and few documented ameliorative treatments. The disorders of the autistic spectrum may be present at birth, or may have later onset, for example, at ages two or three. There are no clear cut biological markers for autism. Diagnosis of the disorder is made by considering the degree to which the child matches the behavioral syndrome, which is characterized by poor communicative abilities, peculiarities in social and cognitive capacities, and maladaptive behavioral patterns. The dysfunction in neuronal communication is considered one of the underlying causes for autism (Myrrhe van Spronsen and Casper C. Hoogenraad, *Curr. Neurol. Neurosci. Rep.* 2010, 10, 207-214). Recent studies have shown that there is a $GABA_A$ α5 deficit in autism spectrum disorder (ASD) and support further investigations of the GABA system in this disorder (Mendez M A, et al. Neuropharmacology. 2013, 68:195-201).

The invention also provides methods and compositions for treating autism using a α5-containing $GABA_A$ receptor positive allosteric modulator, such as one selected from the compounds or pharmaceutically acceptable salts, hydrates, solvates, polymorphs, isomers, or combinations thereof as described herein. In certain embodiments, treatment comprises preventing or slowing the progression of autism. In certain embodiments, treatment comprises alleviation, amelioration, or slowing the progression of one or more symptoms associated with autism. In certain embodiments, the symptom to be treated is cognitive impairment or cognitive deficit. For example, methods and compositions of the disclosure can be used to improve the motor/cognitive deficits symptomatic of autism. In some embodiments of the invention, there is provided a method of preserving or improving cognitive function in a subject with autism, the method comprising the step of administering to said subject a therapeutically effective amount of a compound of the invention or a pharmaceutically acceptable salt, hydrate, solvate, polymorph, isomer, or combination thereof.

The valproic acid (VPA) rat model of autism using in vitro electrophysiological techniques, established by Rodier et al. (Rodier, P. M. et al. *Reprod. Toxicol.* 1997, 11, 417-422) is one of the most exhaustively established insult-based animal models of autism and is based on the observation that pregnant women treated with VPA in the 1960s, during a circumscribed time window of embryogenesis, had a much higher risk of giving birth to an autistic child than the normal population. Offspring of VPA-exposed pregnant rats show several anatomical and behavioral symptoms typical of autism, such as diminished number of cerebellar Purkinje neurons, impaired social interaction, repetitive behaviors as well as other symptoms of autism, including enhanced fear memory processing. See, Rinaldi T. et al. *Frontiers in Neural Circuits,* 2008, 2, 1-7. Another mouse model, BTBR T+tf/J (BTBR) mice, an established model with robust behavioral phenotypes relevant to the three diagnostic behavioral symptoms of autism—unusual social interactions, impaired communication, and repetitive behaviors—was used to probe the efficacy of a selective negative allosteric modulator of the mGluR5 receptor, GRN-529. See, e.g., Silverman J. L. et al. Sci Transl. Med. 2012, 4, 131. The efficacy of the methods and compositions of this invention in treating autism, or cognitive deficits associated with autism, may be assessed in the VPA-treated rat model of autism or the BTBR T+tf/J (BTBR) mouse model, as well as human subjects with autism, using a variety of cognitive tests known in the art, as discussed herein.

Mental Retardation

Mental retardation is a generalized disorder characterized by significantly impaired cognitive function and deficits in adaptive behaviors. Mental retardation is often defined as an Intelligence Quotient (IQ) score of less than 70. Inborn causes are among many underlying causes for mental retardation. The dysfunction in neuronal communication is also considered one of the underlying causes for mental retardation (Myrrhe van Spronsen and Casper C. Hoogenraad, *Curr. Neurol. Neurosci. Rep.* 2010, 10, 207-214).

In some instances, mental retardation includes, but are not limited to, Down syndrome, velocariofacial syndrome, fetal alcohol syndrome, Fragile X syndrome, Klinefelter's syndrome, neurofibromatosis, congenital hypothyroidism, Williams syndrome, phenylketonuria (PKU), Smith-Lemli-Opitz syndrome, Prader-Willi syndrome, Phelan-McDermid syndrome, Mowat-Wilson syndrome, ciliopathy, Lowe syndrome and siderium type X-linked mental retardation. Down syndrome is a disorder that includes a combination of birth defects, including some degree of mental retardation, characteristic facial features and, often, heart defects, increased infections, problems with vision and hearing, and other health problems. Fragile X syndrome is a prevalent form of inherited mental retardation, occurring with a frequency of 1 in 4,000 males and 1 in 8,000 females. The syndrome is also characterized by developmental delay, hyperactivity, attention deficit disorder, and autistic-like behavior. There is no effective treatment for fragile X syndrome.

The present invention contemplates the treatment of mild mental retardation, moderate mental retardation, severe mental retardation, profound mental retardation, and mental retardation severity unspecified. Such mental retardation may be, but is not required to be, associated with chromosomal changes, (for example Down Syndrome due to trisomy 21), heredity, pregnancy and perinatal problems, and other severe mental disorders. This invention provides methods and compositions for treating mental retardation using a α5-containing $GABA_A$ receptor positive allosteric modulator, such as one selected from the compounds or pharmaceutically acceptable salts, hydrates, solvates, polymorphs, isomers, or combinations thereof as described herein. In certain embodiments, treatment comprises preventing or slowing the progression of mental retardation. In certain embodiments, treatment comprises alleviation, amelioration, or slowing the progression of one or more symptoms associated with mental retardation. In certain embodiments, the symptom to be treated is cognitive deficit/impairment. For example, methods and compositions of the disclosure can be used to improve the motor/cognitive impairments symptomatic of mental retardation. In some embodiments of the invention, there is provided a method of preserving or improving cognitive function in a subject with mental retardation, the method comprising the step of administering to said subject a therapeutically effective amount of a compound of the invention or a pharmaceutically acceptable salt, hydrate, solvate, polymorph, isomer, or combination thereof.

Several animal models have been developed for mental retardation. For example, a knockout mouse model has been developed for Fragile X syndrome. Fragile X syndrome is a common form of mental retardation caused by the absence of the FMR1 protein, FMRP. Two homologs of FMRP have been identified, FXR1P and FXR2P. FXR2P shows high expression in brain and testis, like FMRP. Both Fxr2 and Fmr1 knockout mice, and Fmr1/Fxr2 double knockout mice are believed to be useful models for mental retardation such as Fragile X syndrome. See, Bontekoe C. J. M. et al. *Hum. Mol Genet.* 2002, 11 (5): 487-498. The efficacy of the methods and compositions of this invention in treating mental retardation, or cognitive deficit/impairment associated with mental retardation, may be assessed in the these mouse models and other animal models developed for mental retardation, as well as human subjects with mental retardation, using a variety of cognitive tests known in the art, as discussed herein.

Compulsive Behavior (Obsessive-Compulsive Disorder)

Obsessive compulsive disorder ("OCD") is a mental condition that is most commonly characterized by intrusive, repetitive unwanted thoughts (obsessions) resulting in compulsive behaviors and mental acts that an individual feels driven to perform (compulsion). Current epidemiological data indicates that OCD is the fourth most common mental disorder in the United States. Some studies suggest the prevalence of OCD is between one and three percent, although the prevalence of clinically recognized OCD is much lower, suggesting that many individuals with the disorder may not be diagnosed. Patients with OCD are often diagnosed by a psychologist, psychiatrist, or psychoanalyst according to the Diagnostic and Statistical Manual of Mental Disorders, 4th edition text revision (DSM-IV-TR) (2000) diagnostic criteria that include characteristics of obsessions and compulsions. Characteristics of obsession include: (1) recurrent and persistent thoughts, impulses, or images that are experienced as intrusive and that cause marked anxiety or distress; (2) the thoughts, impulses, or images are not simply excessive worries about real-life problems; and (3) the person attempts to ignore or suppress such thoughts, impulses, or images, or to neutralize them with some other thought or action. The person recognizes that the obsessional thoughts, impulses, or images are a product of his or her own mind, and are not based in reality. Characteristics of compulsion include: (1) repetitive behaviors or mental acts that the person feels driven to perform in response to an obsession, or according to rules that must be applied rigidly; (2) the behaviors or mental acts are aimed at preventing or reducing distress or preventing some dreaded event or situation; however, these behaviors or mental acts are not actually connected to the issue, or they are excessive.

Individuals with OCD typically perform tasks (or compulsion) to seek relief from obsession-related anxiety. Repetitive behaviors such as handwashing, counting, checking, or cleaning are often performed with the hope of preventing obsessive thoughts or making them go away. Performing these "rituals," however, only provides temporary relief. People with OCD may also be diagnosed with a spectrum of other mental disorders, such as generalized anxiety disorder, anorexia nervosa, panic attack, or schizophrenia.

The dysfunction in neuronal communication is considered one of the underlying causes for obsession disorder (Myrrhe van Spronsen and Casper C. Hoogenraad, *Curr. Neurol. Neurosci. Rep.* 2010, 10, 207-214). Studies suggest that OCD may be related to abnormal levels of a neurotransmitter called serotonin. The first-line treatment of OCD consists of behavioral therapy, cognitive therapy, and medications. Medications for treatment include serotonin reuptake inhibitors (SRIs) such as paroxetine (Seroxat™, Paxil®, Xetanor™, ParoMerck™, Rexetin™), sertraline (Zoloft®, Stimuloton™), fluoxetine (Prozac®, Bioxetin™), escitalopram (Lexapro®), and fluvoxamine (Luvox®) as well as the tricyclic antidepressants, in particular clomipramine (Anafranil®). Benzodiazepines are also used in treatment. As much as 40 to 60% of the patients, however, fail to adequately respond to the SRI therapy and an even greater proportion of patients fail to experience complete remission of their symptoms.

The invention provides methods and compositions for treating OCD using a $\alpha5$-containing $GABA_A$ receptor agonist (e.g., a $\alpha5$-containing $GABA_A$ receptor positive allosteric modulator), such as one selected from the compounds or pharmaceutically acceptable salts, hydrates, solvates, polymorphs, isomers, or combinations thereof as described herein. In certain embodiments, treatment comprises preventing or slowing the progression of OCD. In certain embodiments, treatment comprises alleviation, amelioration, or slowing the progression of one or more symptoms associated with OCD. In certain embodiments, the symptom to be treated is cognitive impairment or cognitive deficit. For example, methods and compositions of the disclosure can be used to treat the cognitive deficits in OCD, and/or to improve cognitive function in patients with OCD. In some embodiments of the invention, there is provided a method of preserving or improving cognitive function in a subject with OCD, the method comprising the step of administering to said subject a therapeutically effective amount of a compound of the invention or a pharmaceutically acceptable salt, hydrate, solvate, polymorph, isomer, or combination thereof.

A quinpirole-sensitized rat model has been developed for OCD. The compulsive checking behavior of the quinpirole-sensitized rats is subject to interruption, which is an attribute characteristic of OCD compulsions. In addition, a schedule-induced polydipsia (SIP) rodent model of obsessive-compulsive disorder was used to evaluate the effects of the novel 5-HT2C receptor agonist WAY-163909. See, e.g., Rosenzweig-Lipson S. et al. Psychopharmacology (Berl) 2007, 192, 159-70. The efficacy of the methods and compositions of this invention in treating OCD, or cognitive impairment or cognitive deficits associated with OCD, may be assessed in the above animal models and other animal models developed for OCD, as well as human subjects with OCD, using a variety of cognitive tests known in the art, as discussed herein.

Substance Addiction

Substance addiction (e.g., drug substance addiction, alcohol substance addiction) is a mental disorder. The substance addiction is not triggered instantaneously upon exposure to substance of abuse. Rather, it involves multiple, complex neural adaptations that develop with different time courses ranging from hours to days to months (Kauer J. A. *Nat. Rev. Neurosci.* 2007, 8, 844-858). The path to substance addiction generally begins with the voluntary use of one or more controlled substances, such as narcotics, barbiturates, methamphetamines, alcohol, nicotine, and any of a variety of other such controlled substances. Over time, with extended use of the controlled substance(s), the voluntary ability to abstain from the controlled substance(s) is compromised due to the effects of prolonged use on brain function, and thus on behavior. As such, substance addiction generally is characterized by compulsive substance craving, seeking and use that persist even in the face of negative consequences. The cravings may represent changes in the underlying neurobiology of the patient which likely must be addressed in a meaningful way if recovery is to be obtained. Substance addiction is also characterized in many cases by withdrawal symptoms, which for some substances are life threatening (e.g., alcohol, barbiturates) and in others can result in substantial morbidity (which may include nausea, vomiting, fever, dizziness, and profuse sweating), distress, and decreased ability to obtain recovery. For example, alcoholism, also known as alcohol dependence, is one such substance addiction. Alcoholism is primarily characterized by four symptoms, which include cravings, loss of control, physical dependence and tolerance. These symptoms also may characterize substance addictions to other controlled substances. The craving for alcohol, as well as other controlled substances, often is as strong as the need for food or water. Thus, an alcoholic may continue to drink despite serious family, health and/or legal ramifications.

Recent work exploring the effects of abusing alcohol, central stimulants, and opiates on the central nervous system (CNS) have demonstrated a variety of adverse effects related to mental health, including substance-induced impairments in cognition. See, Nyberg F. *Cognitive Impairments in Drug Addicts*, Chapter 9. In several laboratories and clinics substantial damages of brain function are seen to result from these drugs. Among the harmful effects of the abusing drugs on brain are those contributing to accelerated obsolescence. An observation that has received special attention during recent years is that chronic drug users display pronounced impairment in brain areas associated with executive and memory function. A remarked neuroadaptation caused by addictive drugs, such as alcohol, central stimulants and opiates involves diminished neurogenesis in the subgranular zone (SGZ) of the hippocampus. Indeed, it has been proposed that decreased adult neurogenesis in the SGZ could modify the hippocampal function in such a way that it contributes to relapse and a maintained addictive behavior. It also raises the possibility that decreased neurogenesis may contribute to cognitive deficits elicited by these abusing drugs.

The invention provides methods and compositions for treating substance addiction using a α5-containing $GABA_A$ receptor positive allosteric modulator, such as one selected from the compounds or pharmaceutically acceptable salts, hydrates, solvates, polymorphs, isomers, or combinations thereof as described herein. In certain embodiments, treatment comprises preventing or slowing the progression of substance addiction. In certain embodiments, treatment comprises alleviation, amelioration, or slowing the progression of one or more symptoms associated with substance addiction. In certain embodiments, the symptom to be treated is cognitive impairment. For example, methods and compositions of the disclosure can be used to treat the cognitive impairment and/or to improve cognitive function in patients with substance addiction. In some embodiments of the invention, there is provided a method of preserving or improving cognitive function in a subject with substance addiction, the method comprising the step of administering to said subject a therapeutically effective amount of a compound of the invention or a pharmaceutically acceptable salt, hydrate, solvate, polymorph, isomer, or combination thereof.

Several animal models have been developed to study substance addiction. For example, a genetically selected Marchigian Sardinian alcohol-preferring (msP) rat models was developed to study the neurobiology of alcoholism. See, Ciccocioppo R. et al. *Substance addiction Biology* 2006, 11, 339-355. The efficacy of the methods and compositions of this invention in treating substance addiction, or cognitive impairment associated with substance addiction, may also be assessed in animal models of substance addiction, as well as human subjects with substance addiction, using a variety of cognitive tests known in the art, as discussed herein.

Brain Cancers

Brain cancer is the growth of abnormal cells in the tissues of the brain usually related to the growth of malignant brain tumors. Brain tumors grow and press on the nearby areas of the brain which can stop that part of the brain from working the way it should. Brain cancer rarely spreads into other tissues outside of the brain. The grade of tumor, based on how abnormal the cancer cells look under a microscope, may be used to tell the difference between slow- and fast-growing tumors. Brain tumors are classified according to the kind of cell from which the tumor seems to originate. Diffuse, fibrillary astrocytomas are the most common type of primary brain tumor in adults.

These tumors are divided histopathologically into three grades of malignancy: World Health Organization (WHO) grade II astrocytoma, WHO grade III anaplastic astrocytoma and WHO grade IV glioblastoma multiforme (GBM), WHO grade II astocytomas are the most indolent of the diffuse astrocytoma spectrum. Astrocytomas display a remarkable tendency to infiltrate the surrounding brain, confounding therapeutic attempts at local control. These invasive abilities are often apparent in low-grade as well as high-grade tumors.

Glioblastoma multiforme is the most malignant stage of astrocytoma, with survival times of less than 2 years for most patients. Histologically, these tumors are characterized by dense cellularity, high proliferation indices, endothelial proliferation and focal necrosis. The highly proliferative nature of these lesions likely results from multiple mitogenic effects. One of the hallmarks of GBM is endothelial proliferation. A host of angiogenic growth factors and their receptors are found in GBMs.

There are biologic subsets of astrocytomas, which may reflect the clinical heterogeneity observed in these tumors. These subsets include brain stem gliomas, which are a form of pediatric diffuse, fibrillary astrocytoma that often follow a malignant course. Brain stem GBMs share genetic features with those adult GBMs that affect younger patients. Pleomorphic xanthoastrocytoma (PXA) is a superficial, low-grade astrocytic tumor that predominantly affects young adults. While these tumors have a bizarre histological appearance, they are typically slow-growing tumors that may be amenable to surgical cure. Some PXAs, however, may recur as GBM. Pilocytic astrocytoma is the most common astrocytic tumor of childhood and differs clinically and histopathologically from the diffuse, fibrillary astrocytoma that affects adults. Pilocytic astrocytomas do not have the same genomic alterations as diffuse, fibrillary astrocytomas. Subependymal giant cell astrocytomas (SEGA) are periventricular, low-grade astrocytic tumors that are usually associated with tuberous sclerosis (TS), and are histologically identical to the so-called "candle-gutterings" that line the ventricles of TS patients. Similar to the other tumorous lesions in TS, these are slowly-growing and may be more akin to hamartomas than true neoplasms. Desmoplastic cerebral astrocytoma of infancy (DCAI) and desmoplastic infantile ganglioglioma (DIGG) are large, superficial, usually cystic, benign astrocytomas that affect children in the first year or two of life.

Oligodendrogliomas and oligoastrocytomas (mixed gliomas) are diffuse, usually cerebral tumors that are clinically and biologically most closely related to the diffuse, fibrillary astrocytomas. The tumors, however, are far less common than astrocytomas and have generally better prognoses than the diffuse astrocytomas. Oligodendrogliomas and oligoastrocytomas may progress, either to WHO grade III anaplastic oligodendroglioma or anaplastic oligoastrocytoma, or to WHO grade IV GBM. Thus, the genetic changes that lead to oligodendroglial tumors constitute yet another pathway to GBM.

Ependymomas are a clinically diverse group of gliomas that vary from aggressive intraventricular tumors of children to benign spinal cord tumors in adults. Transitions of ependymoma to GBM are rare. Choroid plexus tumors are also a varied group of tumors that preferentially occur in the ventricular system, ranging from aggressive supratentorial intraventricular tumors of children to benign cerebellopontine angle tumors of adults. Choroid plexus tumors have been reported occasionally in patients with Li-Fraumeni syndrome and von Hippel-Lindau (VHL) disease.

Medulloblastomas are highly malignant, primitive tumors that arise in the posterior fossa, primarily in children. Medulloblastoma is the most common childhood malignant brain tumor. The most lethal medulloblastoma subtype exhibits a high expression of the $GABA_A$ receptor α5 subunit gene and MYC amplification. See, e.g., J Biomed Nanotechnol. 2016 June; 12(6):1297-302.

Meningiomas are common intracranial tumors that arise in the meninges and compress the underlying brain. Meningiomas are usually benign, but some "atypical" meningiomas may recur locally, and some meningiomas are frankly malignant and may invade the brain or metastasize. Atypical and malignant meningiomas are not as common as benign meningiomas. Schwannomas are benign tumors that arise on peripheral nerves. Schwannomas may arise on cranial nerves, particularly the vestibular portion of the eighth cranial nerve (vestibular schwannomas, acoustic neuromas) where they present as cerebellopontine angle masses. Hemangioblastomas are tumors of uncertain origin that are composed of endothelial cells, pericytes and so-called stromal cells. These benign tumors most frequently occur in the cerebellum and spinal cord of young adults. Multiple hemangioblastomas are characteristic of von Hippel-Lindau disease (VIL). Hemangiopericytomas (HPCs) are dural tumors which may display locally aggressive behavior and may metastasize. The histogenesis of dural-based hemangiopericytoma (HPC) has long been debated, with some authors classifying it as a distinct entity and others classifying it as a subtype of meningioma.

The invention provides methods and compositions for treating brain cancers (for example, brain tumors as described herein) using a α5-containing $GABA_A$ receptor positive allosteric modulator, such as one selected from the compounds or pharmaceutically acceptable salts, hydrates, solvates, polymorphs, isomers, or combinations thereof as described herein. In certain embodiments, treatment comprises preventing or slowing the progression of brain cancers. In certain embodiments, treatment comprises alleviation, amelioration, or slowing the progression of one or more symptoms associated with brain cancers. In certain embodiments, the symptom to be treated is cognitive impairment. For example, methods and compositions of the disclosure can be used to treat the cognitive impairment and/or to improve cognitive function in patients with brain cancers. In some embodiments of the invention, there is provided a method of preserving or improving cognitive function in a subject with brain cancers, the method comprising the step of administering to said subject a therapeutically effective amount of a compound of the invention or a pharmaceutically acceptable salt, hydrate, solvate, polymorph, isomer, or combination thereof. In some embodiments, the brain tumor is medulloblastoma.

Research Domain Criteria (RDoC)

The invention further provides methods and compositions for treating impairment in neurological disorders and neuropsychiatric conditions using a α5-containing $GABA_A$ R positive allosteric modulator or a pharmaceutically acceptable salt, hydrate, solvate, polymorph, isomer, or combination thereof as described herein. In certain embodiments, treatment comprises alleviation, amelioration or slowing the progression, of one or more symptoms associated with such impairment. In another aspect of the invention, there is provided methods and compositions for preserving or improving cognitive function in a subject in need thereof using a compound of the invention or a pharmaceutically acceptable salt, hydrate, solvate, polymorph, isomer, or combination thereof.

Research Domain Criteria (RDoC) are expected to augment clinical criteria, such as DSM and ICD, for diagnosis of disease and disorders affecting the nervous system (see, e.g., *Am. J. Psychiatry* 167:7 (2010)). The RDoC is intended to provide classification based on discoveries in genomics and neuroscience as well as clinical observation. The high expression of α5-containing $GABA_A$ receptors in specific neural circuits in the nervous system could be therapeutic targets for neural circuit dysfunction identified under RDoC.

Assays for $GABA_A$ α5 Subunit Binding and Receptor Positive Allosteric Modulator Activity The affinity of test compounds for a $GABA_A$ receptor comprising the $GABA_A$ α5 subunit may be determined using receptor binding assays that are known in the art. See, e.g., U.S. Pat. Nos. 7,642,267 and 6,743,789, which are incorporated herein by reference.

The activity of the test compounds as a α5-containing $GABA_A$ R positive allosteric modulator may be tested by electrophysiological methods known in the art. See, e.g., U.S. Pat. No. 7,642,267 and Guidotti et al, Psychopharmacology 180: 191-205, 2005. Positive allosteric modulator activity may be tested, for examples, by assaying GABA-induced chloride ion conductance of $GABA_A$ receptors comprising the $GABA_A$α5 subunit. Cells expressing such receptors may be exposed to an effective amount of a compound of the invention. Such cells may be contacted in vivo with compounds of the invention through contact with a body fluid containing the compound, for example through contact with cerebrospinal fluid. In vitro tests may be done by contacting cells with a compound of the invention in the presence of GABA. Increased GABA-induced chloride conductance in cells expressing $GABA_A$ receptors comprising the $GABA_A$ α5 subunit in the presence of the test compound would indicate positive allosteric modulator activity of said compound. Such changes in conductance may be detected by, e.g., using a voltage-clamp assay performed on *Xenopus* oocytes injected with $GABA_A$ receptor subunit mRNA (including $GABA_A$ α5 subunit RNA), HEK 293 cells transfected with plasmids encoding $GABA_A$ receptor subunits, or in vivo, ex vivo, or cultured neurons.

It will be understood by one of ordinary skill in the art that the methods described herein may be adapted and modified as is appropriate for the application being addressed and that the methods described herein may be employed in other suitable applications, and that such other additions and modifications will not depart from the scope hereof.

This invention will be better understood from the Examples which follow. However, one skilled in the art will readily appreciate that the specific methods and results discussed are merely illustrative of the invention as described more fully in the embodiments which follow thereafter.
Example 1: Synthesis of Compound 1
1
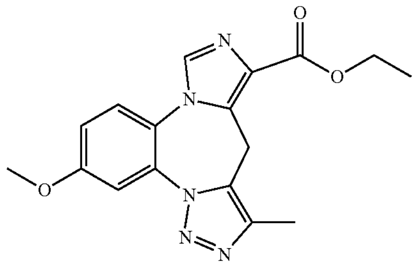
Scheme 11.
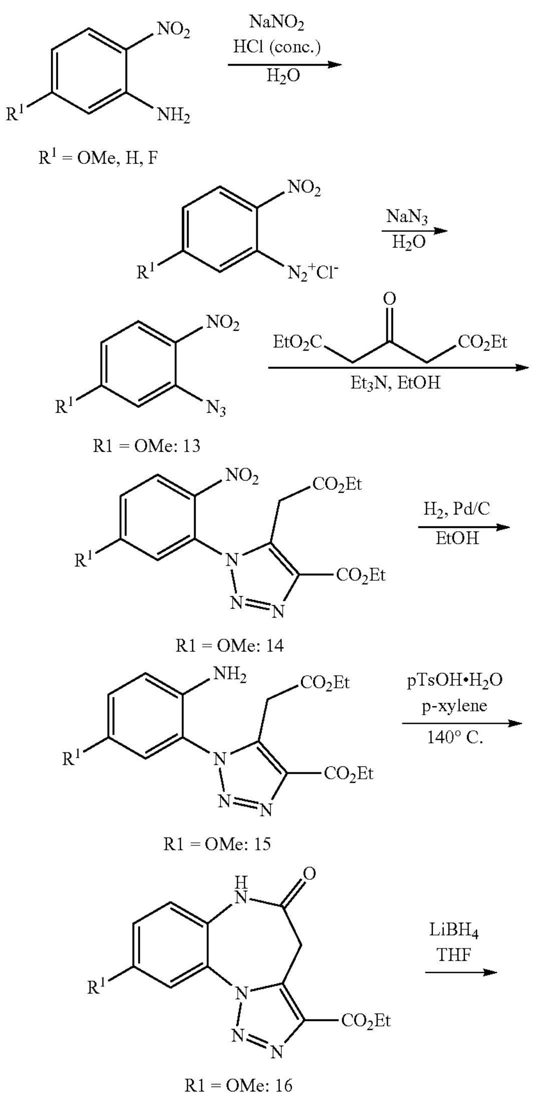
$R^1$ = OMe, H, F
R1 = OMe: 13
R1 = OMe: 14
R1 = OMe: 15
R1 = OMe: 16
-continued
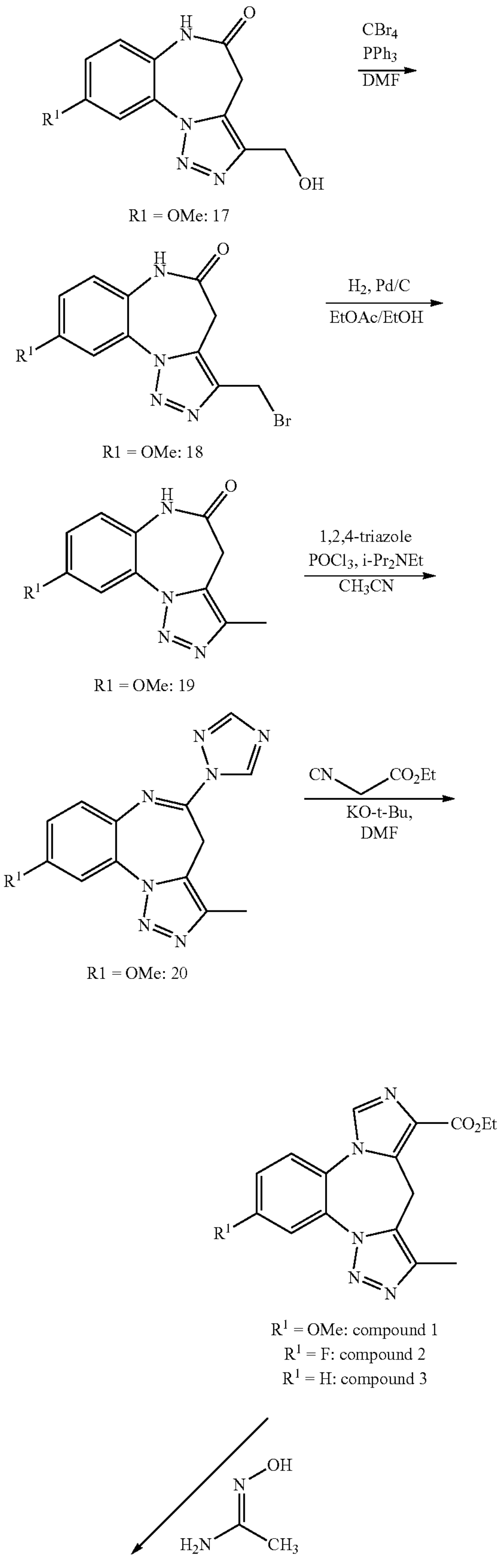
R1 = OMe: 17
R1 = OMe: 18
R1 = OMe: 19
R1 = OMe: 20
$R^1$ = OMe: compound 1
$R^1$ = F: compound 2
$R^1$ = H: compound 3

-continued

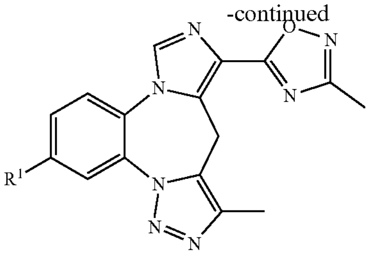

$R^1$ = F: compound 110
$R^1$ = $OCH_3$: compound 167

To a stirred mixture of 5-methoxy-2-nitroaniline (5 g, 29.7 mmol) in HCl (conc. 39 mL) at 0° C. was added drop wise a solution of $NaNO_2$ (2.05 g, 29.7 mmol) in $H_2O$ (19 mL). The internal temperature was kept below 10° C. After addition, the mixture was stirred at room temperature for 1 h. The diazonium salt was collected by filtration, and was used in the next step. To the diazonium salt in a crystallization dish under fast stirring at room temperature was added drop wise a solution of $NaN_3$ (1.93 g, 29.6 mmol) in $H_2O$ (7 mL). After gas evolution stopped (3 h), it was filtered. The collected solid was re-crystallized from MeOH to give 4.342 g (yield 75% for 2 steps) of the product 13 as a yellow solid. To a mixture of the phenylazide 13 (1.94 g, 10 mmol) and diethyl 1,3-acetone-dicarboxylate (2.20 mL, 12 mmol) in EtOH (40 mL) at room temperature was added $Et_3N$ (1.67 mL, 12 mmol). After the mixture was stirred at room temperature for 60 h, the initial suspension turned into a clear yellow solution. The solution was concentrated under vacuum and the residue was purified by chromatography (RediSep 24 g silica-gel column, 10% to 40% EtOAc in hexanes) to give 2.905 g of triazole 14 as a yellow solid. MS: [M+1]=379.

The above triazole 14 (2.95 g, 7.66 mmol) in EtOH (50 mL) with Pd/C (10 wt %, 407 mg, 0.38 mmol) was stirred under $H_2$ (balloon) for 24 h. It was filtered through Celite. The filtrate was concentrated and the residue was purified by chromatography (RediSep 24 g silica-gel column, 10% to 50% EtOAc in hexanes) to give 2.453 g of aniline 15 as a white solid. (70% yield for two steps.) MS: [M+1]- 349.

Compound 15 (2.45 g, 7.03 mmol) and catalytic amount of p-TsOH·$H_2O$ (24 mg) in p-xylene (30 mL) were heated in a 140° C. oil bath overnight. The mixture was cooled and filtered. The solid was washed with cold EtOAc. After drying, it gave 1.88 g (88% yield) of the lactam 16. MS: [M+1]=303.

To a suspension of the lactam ester 16 (837 mg, 2.77 mmol) in THF (20 mL) at room temperature was add $LiBH_4$ (2 M in THF, 1.39 mL, 2.78 mmol). After the mixture was stirred at room temperature for 60 h, more $LiBH_4$ (2 M in THF, 0.28 mL, 0.56 mmol) was added and it was stirred at room temperature for 24 additional h. A mixture of EtOAc/EtOH (10 mL/10 mL) was added to the reaction and it was concentrated in vacuo. The residue was taken up in EtOAc/$CH_2Cl_2$/MeOH and loose silica gel was added. After volatile solvents were evaporated, the solid was loaded onto a RediSep 24 g silica-gel column. Chromatography (solvent A: EtOAc, solvent B: 10:1 v/v $CH_2Cl_2$/MeOH; gradient eluent: A to B) gave 540 mg (75% yield) of the alcohol 17 as white solid. MS: [M+1]=261.

To a solution of the alcohol 17 (105.4 mg, 0.40 mmol) and $CBr_4$ (336 mg, 1.01 mmol) in DMF (3 mL) was slowly added a solution of $PPh_3$ (255 mg, 0.97 mmol) in DMF (1 mL) over 20 min. After addition, TLC showed the reaction went completion. Water was added to quench the reaction and the mixture was extracted with EtOAc thrice. The combined extracts were washed sequentially with $H_2O$, brine and dried over $Na_2SO_4$. Filtration and concentration gave the crude product. Chromatography (RediSep 12 g silica-gel column, $CH_2Cl_2$ to 30% EtOAc in $CH_2Cl_2$) gave 439.2 mg of a mixture of the bromide 18 ([M+1]=324) and $Ph_3PO$. The above mixture (439 mg) in EtOAc/EtOH (8 mL/8 mL) with Pd/C (10 wt %, 200 mg, 0.19 mmol) was stirred under $H_2$ (balloon) for 2 h, then was filtered through Celite. The filtrate was concentrated and residue was purified by chromatography (RediSep 12 g silica-gel column, solvent A: 1:1 v/v $CH_2Cl_2$/hexanes, solvent B: EtOAc; gradient eluent: A to B) to give 99 mg (~80% yield for 2 steps) of product 19 as a white solid. MS: [M+1]=245.

In a separate flask, 1,2,3-triazole (55.3 mg, 0.80 mmol) in $CH_3CN$ (1 mL) at 0° C. was treated with i-$Pr_2NEt$ (146 μL, 0.84 mmol), followed by $POCl_3$ (23 μL, 0.25 mmol). The solution was stirred at 0° C. for 2 h. The lactam 19 was added in one lot and the resulting suspension was heated in an 80° C. oil bath for 20 h. Water was added to quench the reaction. It was extracted with EtOAc thrice. The combined extracts were washed with brine and dried over $Na_2SO_4$. Filtration and concentration gave 48.8 mg of the crude product 20, which was used directly in the next step. A solution of KO-t-Bu (37.2 mg, 0.33 mmol) in DMF (0.5 mL) was cooled to −50° C. Ethyl isocyanoacetate (40 μL, 0.36 mmol) was added drop wise. The mixture was stirred at −50° C. for 1 h. The above crude product 20 in DMF (1 mL) was added drop wise. The mixture was allowed to warm to 10° C. and stirred at 10° C. for 1 h. Saturated $NH_4Cl$ aqueous solution was added and it was extracted with EtOAc thrice. The combined extracts were washed sequentially with water, brine and dried over $Na_2SO_4$. Filtration and concentration gave the crude product.

Chromatography (RediSep 12 g silica-gel column, solvent A: 1:1 v/v $CH_2Cl_2$/hexanes, solvent B: EtOAc; gradient eluent: 20% to 80% B in A) to give 15 mg (21% yield for 2 steps) of Compound 1 (Example 1) as an off-white solid. MS: [M+1]=340. $^1$H-NMR (500 MHz, CDCl3) δ: 7.74 (s, 1H), 7.63 (d, 1H, J=3 Hz), 7.51 (d, 1H, J=8.5 Hz), 7.14 (dd, 1H, J=3.0, 8.5 Hz), 4.44 (q, 2H, J=7.0 Hz), 3.95 (s, 3H), 2.44 (s, 3H), 1.45 (t, 3H, J=7.0 Hz).

Example 2: Synthesis of Compound 2

2

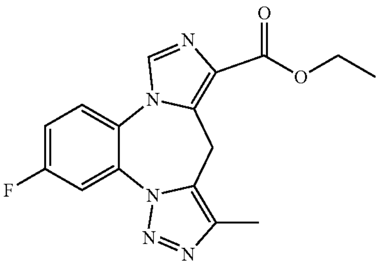

Compound of Example 2 was synthesized in an analogous synthetic route as that described for Example 1, using 5-fluoro-2-nitro-aniline as the starting material to give Compound 2 as a light brown solid: MS: [M+1]=328. $^1$H-NMR (500 MHz, CDCl3) δ: 7.90 (br dd, 1H, J=2.5, 8.5 Hz), 7.77

(s, 1H), 7.62 (br dd, 1H, J=5.0, 9.0 Hz), 7.35 (m, 1H), 4.45 (q, 2H, J=7.0 Hz), 2.45 (s, 3H), 1.45 (t, 3H, J=7.0 Hz).

Example 3: Synthesis of Compound 3

3

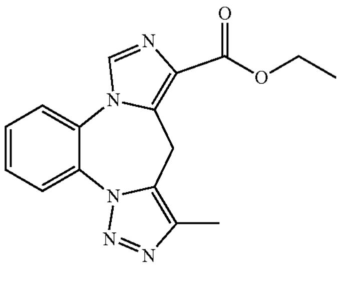

Compound of Example 3 was synthesized in an analogous synthetic route as that described for Example 1, using 2-nitro-aniline as the starting material to give Compound 3 as a light yellow solid: MS: [M+1]=310; $^1$H-NMR (500 MHz, CDC13) δ: 8.161 (br d, 1H, J=8.5 Hz), 7.81 (s, 1H), 7.66 (m, 3H), 4.45 (q, 2H, J=7.0 Hz), 2.45 (s, 3H), 1.46 (t, 3H, J=7.0 Hz).

Example 4: Synthesis of Compound 110

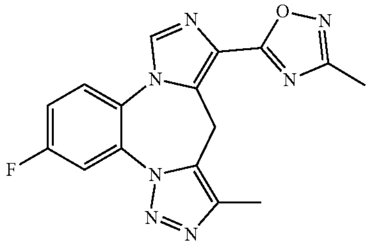 [SMILES: Cc1noc(-c2ncn3c2Cc2c(C)nnn2-c2cc(F)ccc2-3)n1]

Acetamide oxime was azeotroped three times in toluene before use. To a suspension of acetamide oxime (30 mg, 0.4 mmol) in THF (1 mL) was added NaH 60% in oil dispersion (16 mg, 0.4 mmol). The suspension was stirred at room temperature for 15 min. The ester compound 2 (65 mg, 0.2 mmol) was added. The vial containing the ester was rinsed with THF (1 mL) which was added to the reaction mixture. The resulting brown suspension was stirred at room temperature for 30 mins. then heated at 70° C. for 2 h 30 min. The suspension was quenched with MeOH. The solvent was evaporated and the crude oil was purified by chromatography (RediSep 4 g silica-gel column, eluted with 70% EtOAc in Hexanes) to give 28 mg (41% yield) of product. MS: [M+1]=338. H$^1$NMR ($CDCl_3$) δ 7.92 (1H, dd, J=2.5, 8.5 Hz), 7.90 (1H, s), 7.67 (1H, dd, J=4.5, 9.5 Hz), 7.38 (1H, m), 2.51 (3H, s), 2.46 (3H, s).

Example 5: Synthesis of Compound 167

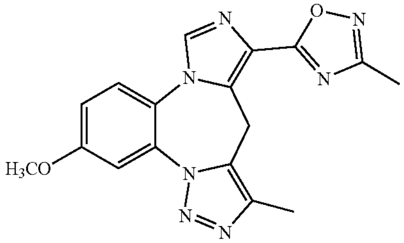 [SMILES: COc1ccc2c(c1)-n1nnc(C)c1Cc1c(-c3nc(C)no3)ncn1-2]

The compound was prepared analogously from Compound 1 to give Compound 167: MS: [M+1]=350. H$^1$NMR ($CDCl_3$) δ 7.87 (1H, s), 7.65 (1H, d, J=3 Hz), 7.55 (1H, d, J=9 Hz), 7.17 (1H, dd, J=2.5, 9 Hz), 3.96 (3H, s), 2.5 (3H, s), 2.45 (3H, s).

Scheme 12.

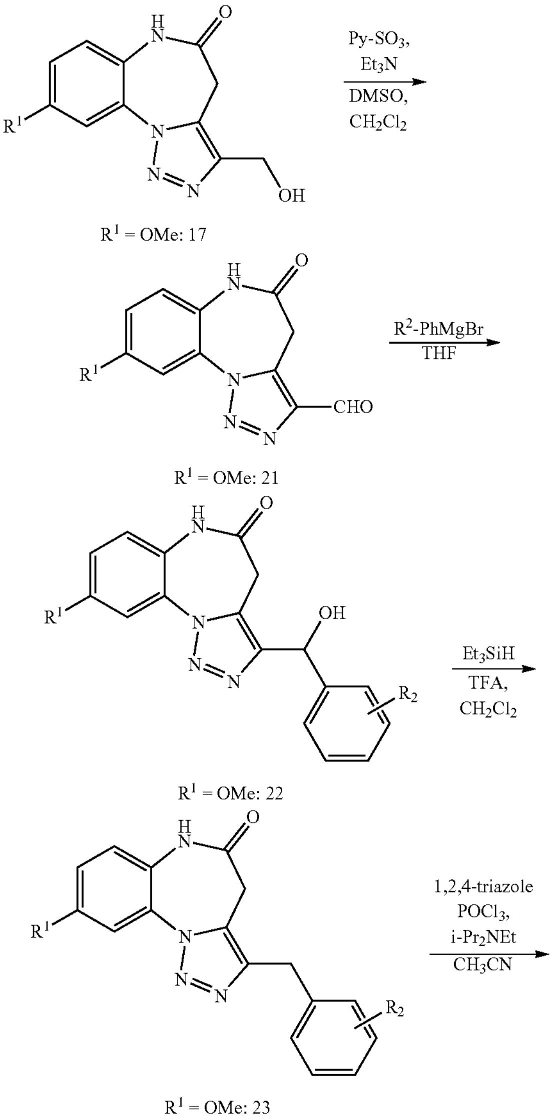

-continued

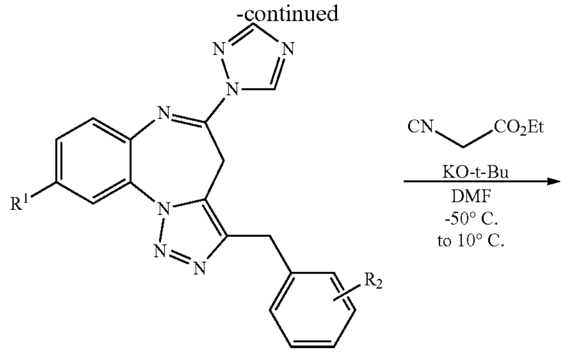

$R^1$ = OMe: 24

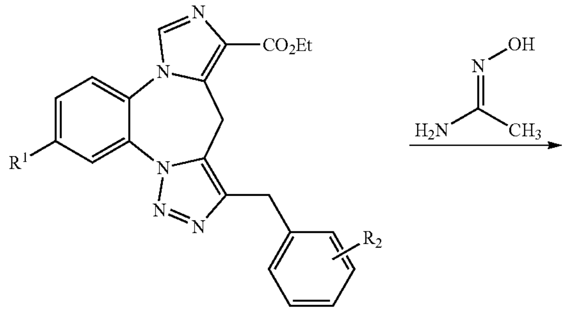

$R^1$ = OMe, $R^2$ = H: compound 4
$R^1$ = H, $R^2$ = H: compound 5
$R^1$ = F, $R^2$ = H: compound 6
$R^1$ = F, $R^2$ = 4-$CH_3$: compound 44
$R^1$ = F, $R^2$ = 4-Cl: compound 45
$R^1$ = F, $R^2$ = 4-F: compound 46
$R^1$ = H, $R^2$ = 4-Cl: compound 47

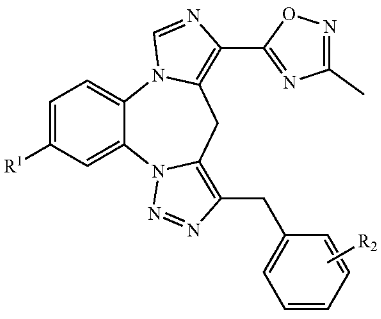

$R^1$ = F, $R^2$ = H: compound 109

Example 6: Synthesis of Compound 4

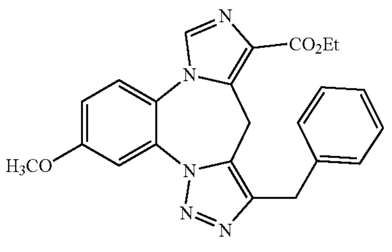

4

To a solution of compound 17 prepared as in Example 1 (260 mg) in DMSO (4 mL) and $CH_2Cl_2$ (6 mL) was added $Et_3N$ (0.7 mL, 5 mmol), followed by Py·$SO_3$ (398 mg, 2.5 mmol). It was stirred at room temperature for 1 h. The reaction mixture was poured into water and extracted with EtOAc thrice. The combined extracts were washed sequentially with $H_2O$, brine and dried over $Na_2SO_4$. Filtration and concentration gave 198.5 mg of the crude aldehyde 21, which was used without further purification. To a suspension of aldehyde 21 (198.5 mg, 0.77 mmol) in THF (10 mL) at 0° C. was added drop wise PhMgBr (1 M in THF, 1.54 mL, 1.54 mmol). It was stirred at 0° C. for 30 min. Saturated $NH_4Cl$ aqueous solution was added and it was extracted with EtOAc thrice.

The combined extracts were washed with brine and dried over $Na_2SO_4$. Filtration and concentration gave 252.9 mg of the benzyl alcohol 22 as a brown foamy solid. This was used in the next step without further purification. To a solution of the above crude alcohol 22 in $CH_2Cl_2$ (8 mL) with $Et_3SiH$ (0.60 mL, 3.76 mmol) was added TFA (0.64 mL, 8.27 mmol). The reaction solution was stirred at room temperature for 4 h. After concentration, the residue was purified by chromatography (RediSep 12 g silica-gel column, 20% to 80% EtOAc in hexanes) to give 34.1 mg (yield 12% for four steps) of the reduced product 23 as white foamy solid. MS: [M+1]- 321.

In a separate flask, a solution of 1,2,4-triazole (27 mg, 0.39 mmol) in $CH_3CN$ (0.5 mL) at 0° C. was treated with i-$Pr_2NEt$ (72 μL, 0.41 mmol), followed by $POCl_3$ (11 μL, 0.12 mmol). The mixture was stirred at 0° C. for 2 h. The lactam material 23 (32.2 mg, 0.1 mmol, solid) was added in one lot to the reaction mixture and it was heated in an 80° C. oil bath for 20 h. The mixture was cooled to room temperature and creamy solid precipitate was observed. Water (0.5 mL) was added and it was stirred at room temperature for 5 min. The solid precipitate was collected by filtration, and washed with 0.5 mL of water, followed by drying under high vacuum to give 15.8 mg (yield 42%) of the adduct 24 as a off-white fluffy solid. MS: [M+1]- 372.

A solution of KO-t-Bu (9.5 mg, 85 μmol) in DMF (0.5 mL) was cooled to −50° C. Ethyl isocyanoacetate (10.4 μL, 95 μmol) was added drop wise. The resulting mixture was stirred at −50° C. for 1 h. The triazole amidine 24 (15.8 mg, 42 μmol, solid) was added in one lot. The stirred mixture was allowed to warm up to 10° C. in 1 h and kept at 10° C. for 1 h. Saturated $NH_4Cl$ aqueous solution was added and it was extracted with EtOAc thrice. The combined extracts were washed sequentially with $H_2O$, brine and dried over $Na_2SO_4$. Filtration and concentration gave the crude product. Chromatography (RediSep 4 g silica-gel column. Solvent A: 1:1 v/v $CH_2Cl_2$/hexanes, solvent B: EtOAc; gradient eluent: A to 50% B in A) gave 16.8 mg (yield 95%) of the compound of Example 6 as a white solid. MS: [M+1]=416. $^1$H-NMR (500 MHz, CDCl3) δ: 7.74 (s, 1H), 7.63 (d, 1H, J=3.0 Hz), 7.50 (d, 1H, J=9.0 Hz), 7.30 (br d, 2H, J=7.0 Hz), 7.29 (br d, 2H, 7.5 Hz), 7.20 (m, 1H), 7.13 (dd, 1H, J=2.5, 9.0 Hz), 4.41 (q, 2H, J=7.5 Hz), 4.17 (s, 2H), 3.95 (s, 3H), 1.43 (t, 3H, 7.5 Hz).

Example 7: Synthesis of Compound 5

5

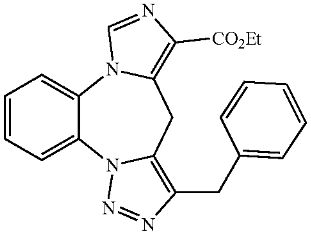

Compound of Example 7 was synthesized in an analogous synthetic route as that described for Example 6, using 2-nitro-aniline as the starting material to give Compound 5 as a brown solid: MS: [M+1]=386. $^1$H-NMR (500 MHz, CDCl3) δ: 8.16 (br d, 1H, J=7.0 Hz), 7.81 (s, 1H), 7.60-7.68 (m, 3H), 7.34 (br d, 2H, J=8.0 Hz), 7.29 (br d, 2H, J=7.0 Hz), 7.20 (m, 1H), 4.42 (q, 2H, J=7.0 Hz), 4.18 (s, 2H), 1.44 (t, 3H, J=7.0 Hz).

Example 8: Synthesis of Compound 6

6

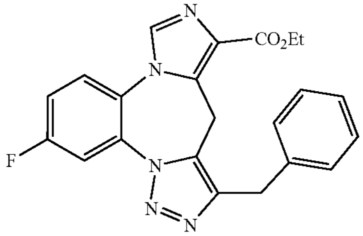

Compound of Example 8 was synthesized in an analogous synthetic route as that described for Example 6, using 5-fluoro-2-nitro-aniline as the starting material to give compound 8 as a brown solid: MS: [M+1]- 404. $^1$H-NMR (500 MHz, CDCl3) δ: 7.90 (dd, 1H, J=3.5, 8.5 Hz), 7.77 (s, 1H), 7.61 (dd, 1H, J=5.0, 10.5 Hz), 7.28-7.37 (m, 5H), 7.21 (m, 1H), 4.43 (q, 2H, J=7.0 Hz), 4.17 (s, 2H), 1.44 (t, 3H, J=7.0 Hz).

Example 9: Synthesis of Compound 44

44

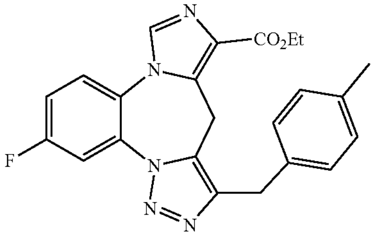

Compound of Example 9 was synthesized in an analogous synthetic route as that described for Example 6, using 5-fluoro-2-nitro-aniline as the starting material to give the compound of Example 9 as a brownish solid: MS: [M+1] =418. $^1$H-NMR (500 MHz, CDCl3) δ: 7.89 (br d, 1H, J=9.5 Hz), 7.76 (s, 1H), 7.60 (dd, 1H, J=5.5, 10.0 Hz), 7.35 (br t, 1H, J=6.0 Hz), 7.22 (br d, 2H, J=8.5 Hz), 7.09 (br d, 2H, J=7.5 Hz), 4.43 (q, 2H, J=7.5 Hz), 4.12 (s, 2H), 2.30 (s, 3H), 1.44 (t, 3H, J=7.5 Hz).

Example 10: Synthesis of Compound 45

45

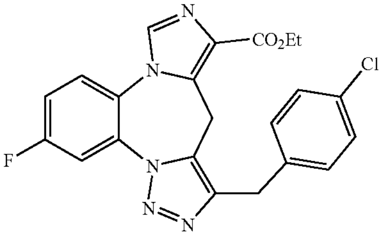

Compound of Example 10 was synthesized in an analogous synthetic route as that described for Example 6, using 5-fluoro-2-nitro-aniline as the starting material to give the compound of Example 10 as a brownish solid: MS: [M+1] =438. $^1$H-NMR (500 MHz, CDCl3) δ: 7.90 (dd, 1H, J=3.0, 8.0 Hz), 7.77 (s, 1H), 7.61 (dd, 1H, J=5.0, 9.0 Hz), 7.36 (m, 1H), 7.25 (br s, 4H), 4.42 (q, 2H, J=7.0 Hz), 4.14 (s, 2H), 1.44 (t, 3H, J=7.0 Hz).

Example 11: Synthesis of Compound 46

46

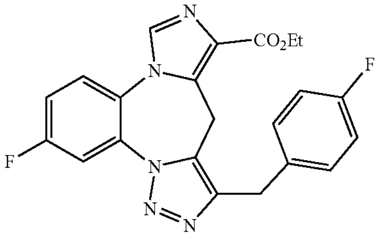

Compound of Example 11 was synthesized in an analogous synthetic route as that described for Example 6, using 5-fluoro-2-nitro-aniline as the starting material to give the compound of Example 11 as a yellowish solid: MS: [M+1] =422. $^1$H-NMR (500 MHz, CDCl3) δ: 7.90 (dd, 1H, J=3.0, 8.5 Hz), 7.77 (s, 1H), 7.61 (dd, 1H, J=5.0, 9.0 Hz), 7.36 (m, 1H), 7.28 (m, 2H), 6.96 (m, 2H), 4.42 (q, 2H, J=7.5 Hz), 4.14 (s, 2H), 1.44 (t, 3H, J=7.0 Hz).

Example 12: Synthesis of Compound 47

47

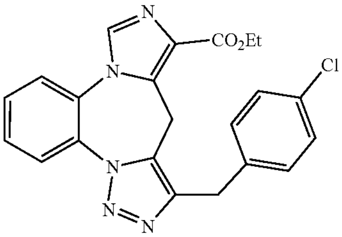

Compound of Example 12 was synthesized in an analogous synthetic route as that described for Example 6, using 2-nitro-aniline as the starting material to give the compound of Example 12 as a yellowish solid: MS: [M+1]=420. $^1$H-NMR (500 MHz, CDCl3) δ: 8.16 (br d, 1H, J=7.0 Hz), 7.80 (s, 1H), 7.64 (m, 3H), 7.25 (m, 4H), 4.41 (q, 2H, J=7.0 Hz), 4.14 (s, 2H), 1.44 (t, 3H, J=8.0 Hz).

Example 13: Synthesis of Compound 109

109

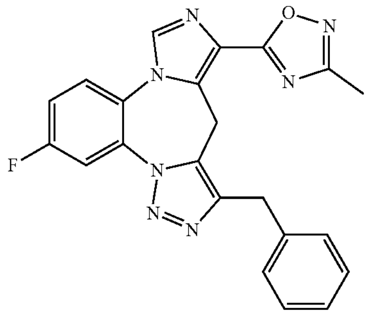

Acetamide oxime (50 mg, 0.67 mmol) was azeotroped with toluene 3 times. THF (5 mL) was added, then NaH 60% in oil dispersion (25 mg, 0.62 mmol). The suspension was stirred at room temperature for 30 min. 2 mL of this suspension was added to ester compound 6 (40 mg, 0.099 mmol) and the resulting solution was heated at 70° C. for 3 h. The solution was quenched with water. The solution was extracted with EtOAc (3×). The combined organic phases were washed with brine, dried over $MgSO_4$. Filtration and concentration gave the crude product. Chromatography (RediSep 12 g silica-gel column. Eluted with 50% EtOAc in Hexanes) gave 6 mg (yield 20%) of the product Compound 109 as yellow solid. MS: [M+1]=414). $H^1$NMR ($CDCl_3$) δ 7.93 (1H, dd, J=3, 8.5 Hz), 7.89 (1H, s), 7.65 (1H, dd, J=5.5, 9 Hz), 7.38 (1H, m), 7.23 (5H, m), 4.2 (2H, s), 2.50 (3H, s).

Example 14: Synthesis of Compound 7

7

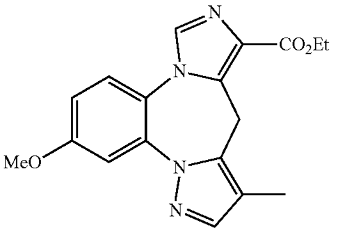

To a stirred mixture of 5-methoxy-2-nitroaniline (5 g, 29.7 mmol) in HCl (conc. 12.9 mL) at 0° C. was added drop wise a solution of $NaNO_2$ (2.05 g, 29.7 mmol) in $H_2O$ (8 mL). The internal temperature was kept below 5° C. After addition, the mixture was allowed to warm up to room temperature in 1 h. The mixture was cooled to 0° C. and a solution of $SnCl_2 \cdot 2H_2O$ (20.13 g, 89.2 mmol) in HCl (conc. 13 mL) was added slowly dropwise. After addition, it was stirred at room temperature for 2 h. The resulting yellow solid was collected by filtration and washed with cold (0° C.) 6 N HCl. After drying in vacuum oven, it gave 3.245 g (yield 50%) of brown solid as aryl hydrazine 25. MS: [M+$H_2O$+Na]=224. In a separate flask, a mixture of diethyl 1,3-acetonedicarboxylate (2.426 g, 12 mmol) and diethoxymethyl acetate (1.946 g, 12 mmol) was heated under microwave radiation at 100° C. for 1 h. The reaction mixture was concentrated in vacuo, and residual volatile component was co-distilled off with toluene (5 ml) in vacuo to give condensation product 26, which was used directly in the next step.

Scheme 13.

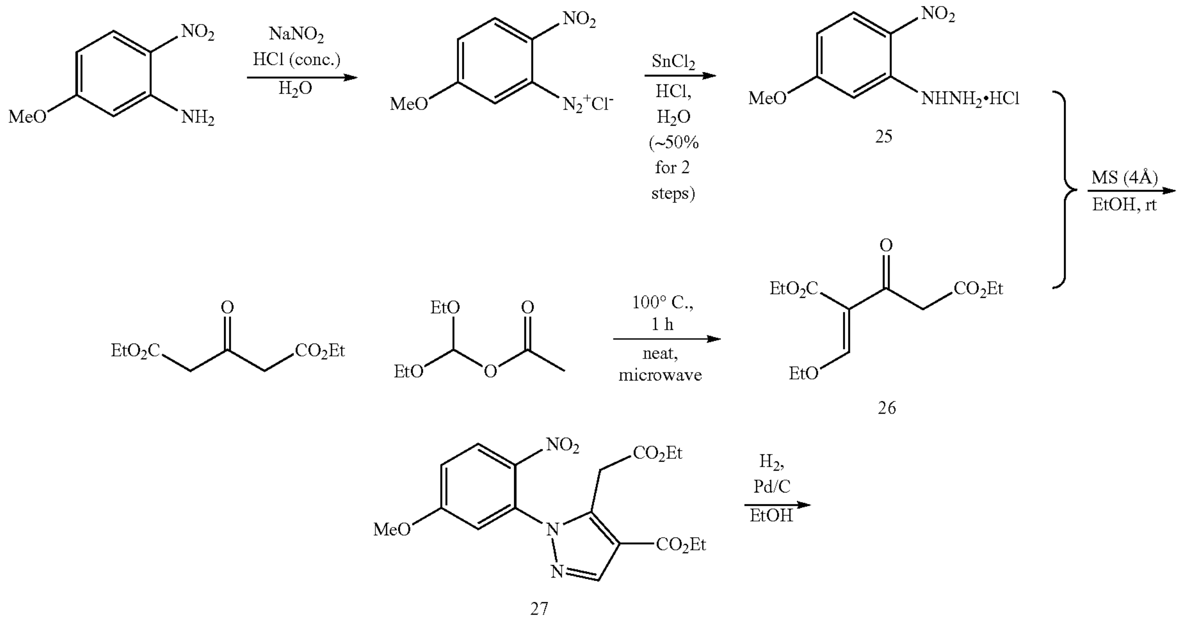

27

-continued

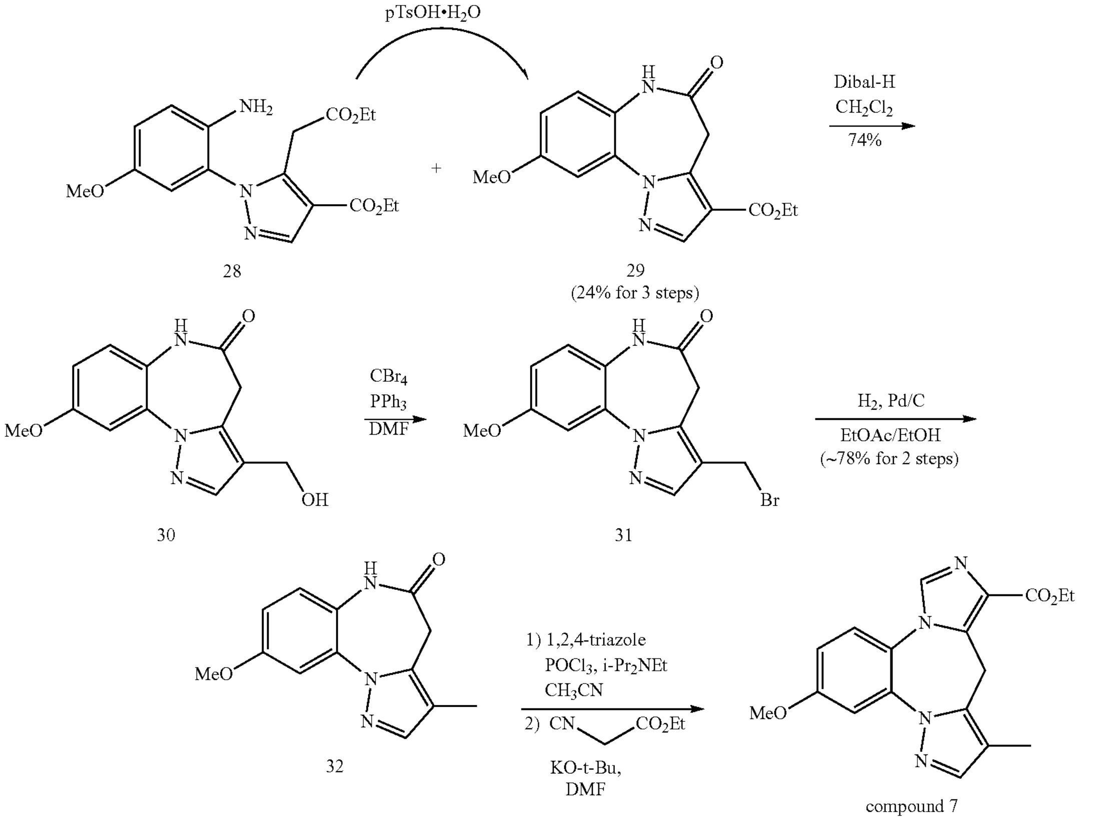

28

29
(24% for 3 steps)

30

31

32 compound 7

Product 26 from above was dissolved in EtOH (30 mL). Molecular sieves (4 Å. 2 g) and hydrazine hydrochloride 25 (2.19 g, 10 mmol) were added. The suspension was stirred at room temperature for 24 h. It was filtered through Celite and the solid was washed with EtOAc (10 mL×3). The filtrate was concentrated. The residue was purified by chromatography (RediSep 40 g silica-gel column, 10% to 40% EtOAc in hexanes) to give 2.091 g of pyrrole 27 which was used without further purification in the next step. MS: [M+1]=378.

The above nitro group on 27 (2.09 g, 5.5 mmol) was reduced in EtOH (40 mL) with Pd/C (10 wt %, 295 mg, 0.28 mmol) under $H_2$ (balloon) for 18 h. The mixture was filtered through Celite. The filtrate was concentrated and the residue was purified by chromatography (RediSep 24 g silica-gel column, hexanes to 50% EtOAc in hexanes) to give 1.127 g of the un-cyclized product 28 as a yellow sticky oil ([M+1]=348), plus 154 mg of cyclized product 29 as a gray solid (MS: [M+1]=302). The un-cyclized aniline 28 (1.127 g, 3.2 mmol) in p-xylene (20 mL) was treated with catalytic amount of p-TsOH·$H_2O$ (15 mg) in a 140° C. oil bath for 20 h. The reaction mixture was cooled, concentrated, and the residue was triturated with cold (0° C.) EtOAc. Filtration gave 559 mg of the lactam product 29 as a yellow solid. The total weight of the lactam product 29 combined is 713 mg (24% for 3 steps). MS: [M+1]=302.

To a suspension of the ester 29 (566 mg, 1.88 mmol) in $CH_2C2$ (35 mL) at −78° C. was added Dibal-H (1 M in hexane, 6.60 mL, 6.60 mmol). The suspension was stirred for 10 min at −78° C. The cold bath was removed and it was stirred for 20 min while the temperature rose to room temperature. At this point, TLC showed ~80% reaction completion. It was cooled to −78° C. and more Dibal-II (1 M in hexane, 1.0 mL, 1.0 mmol) was added. After stirring at −78° C. for 30 min, LCMS showed the reaction proceeded to completion. The reaction was quenched by addition of Rochelle's salt aqueous solution (20%) followed by EtOAc. It was vigorously stirred at room temperature until it became a clear two-layer mixture. The layers were separated and the aqueous layer was extracted with EtOAc thrice. The combined organic phase was washed with brine and dried over $Na_2SO_4$. Filtration and concentration gave 480 mg of the crude alcohol 30 as a slightly yellow solid. MS: [M+1]=260.

To a solution of alcohol 30 (200 mg, 0.77 mmol) and $CBr_4$ (640 mg, 1.93 mmol) in DMF (8 mL) was added a solution of $PPh_3$ (486 mg, 1.85 mmol) in DMF (2 mL) slowly in 30 min. After addition, it was stirred at room temperature for 30 min. Water was added to quench the reaction and the mixture was extracted with EtOAc thrice. The combined extracts were washed sequentially with $H_2O$, brine and dried over $Na_2SO_4$. Filtration and concentration gave the crude product. Chromatography (RediSep 12 g silica-gel column, solvent A: 1:1 v/v $CH_2Cl_2$/hexanes, solvent B: EtOAc; gradient eluent: 10% to 40% B in A) gave 221 mg of a mixture of the bromide 31 and $Ph_3PO$.

The above mixture in EtOAc/EtOH (8 mL/8 mL) with Pd/C (10 wt %, 200 mg, 0.19 mmol) was stirred under $H_2$ (balloon) for 1 h. It was filtered through Celite. The filtrate was concentrated and residue was purified by chromatography (RediSep 12 g silica-gel column, solvent A: 1:1 v/v $CH_2Cl_2$/hexanes, solvent B: EtOAc; gradient eluent: 10% to 40% B in A) to give 146 mg of a mixture of the reduction product 32 ([M+1]=244) and $Ph_3PO$.

In a separate flask, 1,2,4-triazole (81 mg, 1.17 mmol) in $CH_3CN$ (1 mL) at 0° C. was treated with i-$Pr_2NEt$ (214 μL, 1.23 mmol), followed by $POCl_3$ (34 μL, 0.36 mmol). The solution was stirred at 0° C. for 2 h. The lactam 32 (~60% purity by LCMS) was added in one lot and the resulting suspension was heated in an 80° C. oil bath for 18 h. Water was added to quench the reaction. It was extracted with EtOAc thrice. The combined extracts were washed sequentially with $H_2O$, brine and dried over $Na_2SO_4$. Filtration and concentration gave 126.6 mg of the crude product 33 as a yellow glue, which was used directly in the next reaction. MS: [M+1]=295. A solution of KO-t-Bu (97 mg, 0.86 mmol) in DMF (1 mL) was cooled to −50° C. Ethyl isocyanoacetate (104 μL, 0.95 mmol) was added drop wise. The mixture was stirred at −50° C. for 1 h. The above crude product 33 in DMF (1.5 mL) was added drop wise. The mixture was allowed to warm to 10° C. and stirred at 10° C. for 1 h. Saturated $NH_4Cl$ aqueous solution was added and it was extracted with EtOAc thrice. The combined extracts were washed sequentially with water, brine and dried over $Na_2SO_4$. Filtration and concentration gave the crude product. Chromatography (RediSep 12 g silica-gel column, solvent A: 1:1 v/v $CH_2Cl_2$/hexanes, solvent B: EtOAc; gradient eluent: 10% to 40% B in A) to give 22 mg of a white solid, which was further purified by preparative TLC (developed with 1:1 A/B) to give 12.8 mg of the final product Compound 7 (Example 14) as a white solid. MS: [M+1]=339. $^1$H-NMR (500 MHz, CDCl3) δ: 7.70 (s, 1H), 7.56 (s, 1H), 7.50 (d, 1H, J=3.0 Hz), 7.43 (d, 1H, J=8.5 Hz), 7.00 (dd, 1H, J=2.5, 9.5 Hz), 5.29 (br s, 1H), 4.44 (q, 2H, J=7.0 Hz), 3.92 (s, 3H), 3.55 (br s, 1H), 2.17 (s, 3H), 1.45 (t, 3H, J=7.0 Hz).

Example 15: Synthesis of Compound 8

8

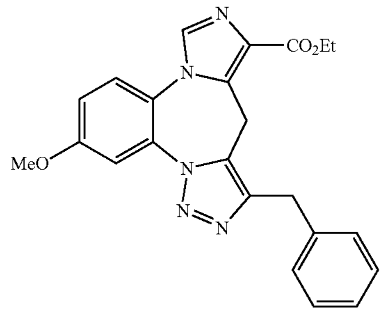

Scheme 14.

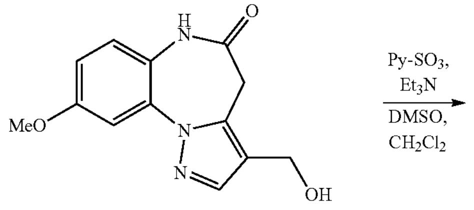

30

-continued

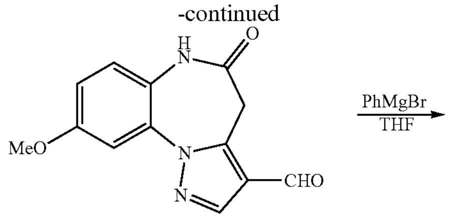

34

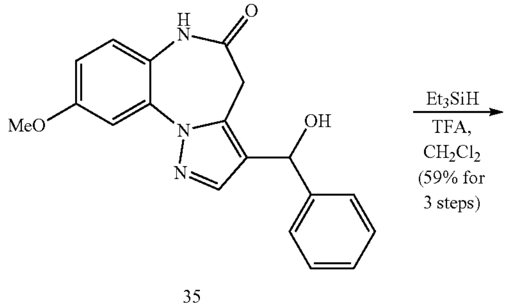

35

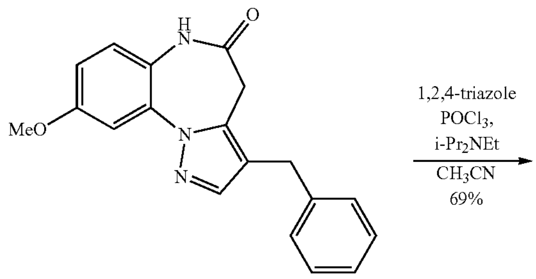

36

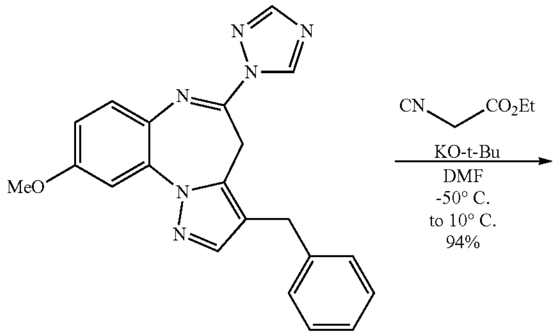

37

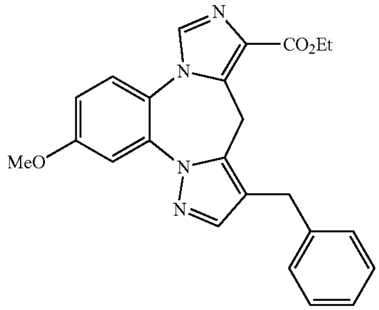

compound 8

To a solution of the alcohol 30 (261 mg, 1.0 mmol) which was prepared in Example 14 in DMSO (4 mL) and $CH_2Cl_2$ (6 mL) was added $Et_3N$ (0.7 mL, 5 mmol), followed by $Py{\cdot}SO_3$ (398 mg, 2.5 mmol). It was stirred at room temperature for 1 h. The reaction mixture was poured into water and extracted with EtOAc thrice. The combined extracts were washed sequentially with $H_2O$, brine and dried over $Na_2SO_4$. Filtration and concentration gave 226 mg of the crude aldehyde 34 as a yellow solid. It was used in the next step without purification. MS: [M+1]=258.

To a suspension of the crude aldehyde 34 (202 mg, 0.79 mmol) in THF (10 mL) at 0° C. was added drop wise PhMgBr (1 M in THF, 1.58 mL, 1.58 mmol). It was stirred at 0° C. for 30 min. Saturated $NH_4Cl$ aqueous solution was added and it was extracted with EtOAc thrice. The combined extracts were washed with brine and dried over $Na_2SO_4$. Filtration and concentration gave 275 mg of the crude product 35 as a yellow foamy solid, which was used in the next step without purification.

To a solution of the above crude alcohol 35 in $CH_2C12$ (10 mL) with $Et_3SiH$ (0.66 mL, 4.10 mmol) was added TFA (0.70 mL, 9.02 mmol). The reaction solution was stirred at room temperature for 1 h. After concentration, the residue was purified by chromatography (RediSep 24 g silica-gel column, 10% to 50% EtOAc in hexanes) to give 187.8 mg (yield 59% for three steps) of the product 36 as a gray solid. MS: [M+1]=320.

In a separate flask, a solution of 1,2,4-triazole (127 mg, 1.83 mmol) in $CH_3CN$ (1.6 mL) at 0° C. was treated with $i\text{-}Pr_2NEt$ (336 μL, 1.93 mmol), followed by $POCl_3$ (53 μL, 0.56 mmol). The mixture was stirred at 0° C. for 2 h. Lactam 36 (150 mg, 0.47 mmol, solid) was added in one lot to the reaction mixture and it was heated in an 80° C. oil bath for 18 h. The mixture was cooled to room temperature and solid precipitate was observed. Water (2.1 mL) was added and it was stirred at room temperature for 10 min. Filtration, washing the solid with 2 mL of water, followed by drying under high vacuum gave 118.8 mg (yield 69%) of the triazole amidine 37 as an off-white fluffy solid. MS: [M+1]=371. A solution of KO-t-Bu (72 mg, 0.64 mmol) in DMF (2 mL) was cooled to −50° C. Ethyl isocyanoacetate (77 μL, 0.71 mol) was added drop wise. The resulting mixture was stirred at −50° C. for 1 h. The triazole amidine 37 (118.8 mg, 42 μmol, solid) was added in lot. The stirred mixture was allowed to warm up to 10° C. in 1 h and kept at 10° C. for 1 h. Saturated $NH_4Cl$ aqueous solution was added and it was extracted with EtOAc thrice. The combined extracts were washed sequentially with $H_2O$, brine and dried over $Na_2SO_4$. Filtration, concentration, then chromatography (RediSep 12 g silica-gel column. solvent A: 1:1 v/v $CH_2Cl_2$/hexanes, solvent B: EtOAc; gradient eluent: A to 40% B in A) gave 125.1 mg (yield 94%) of Compound 8 as a white solid. MS: [M+1]- 415. $^1$H-NMR (500 MHz; $CDCl_3$) δ: 7.72 (s, 1H), 7.54 (s, 1H), 7.51 (br s, 1H), 7.44 (br d, 1H, J=9.5 Hz), 7.29 (br d, 2H, J=7.5 Hz), 7.20 (m, 3H), 7.01 (br d, 1H, J=7.5 Hz), 5.30 (br s, 1H), 4.38 (q, 2H, J=7.0 Hz), 3.92 (br s, 5H), 3.54 (br s, 1H), 1.41 (t, 3H, J=7.0 Hz).

Example 16: Synthesis of Compound 9

9

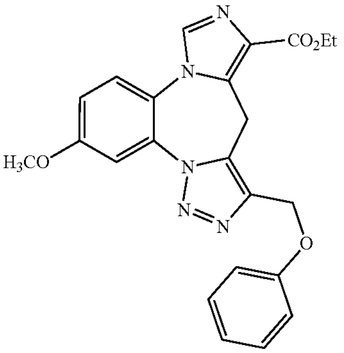

Scheme 15.

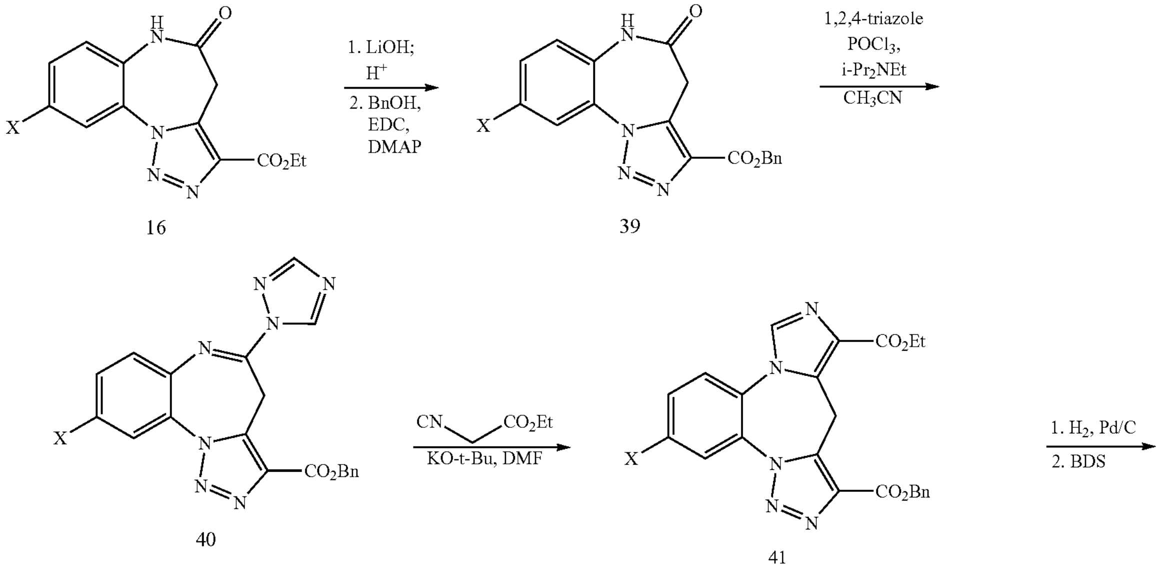

-continued

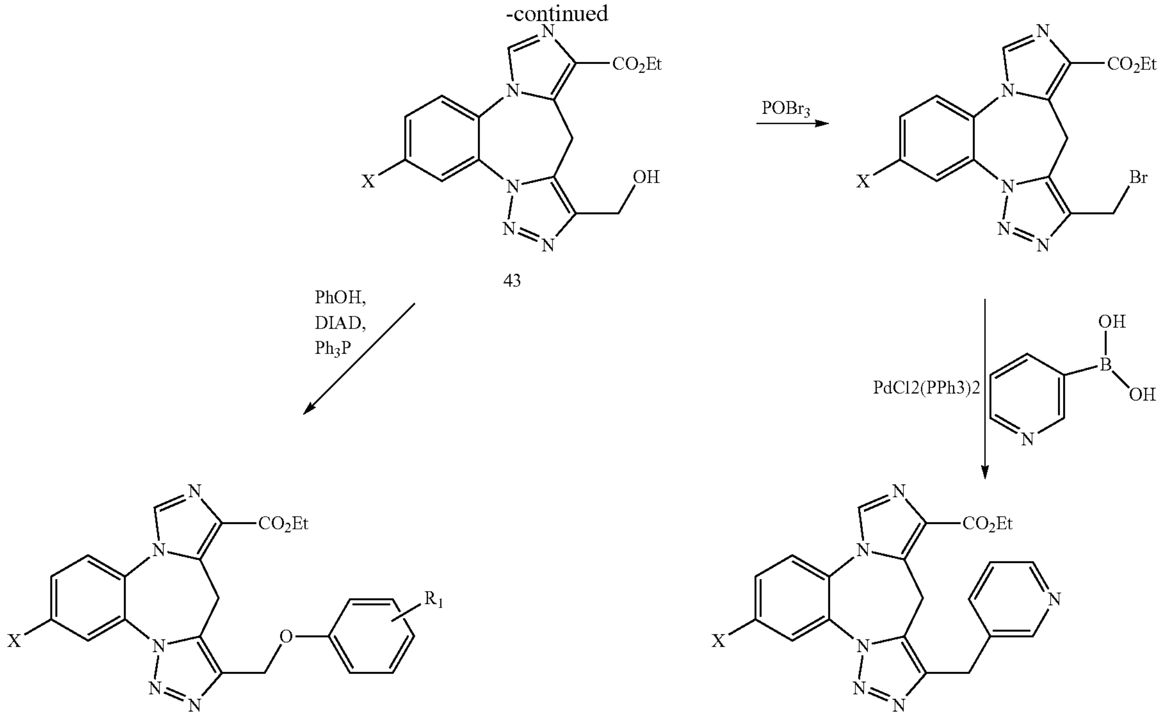

43

$R_1$ = H, X = $OCH_3$: compound 9
$R_1$ = 4-F, X = $OCH_3$: compound 10
$R_1$ = 3-$OCH_3$, X = $OCH_3$: compound 11
$R_1$ = 2,4-di-$CH_3$, X = $OCH_3$: compound 12
$R_1$ = H, X = F: compound 107

$R_1$ = $CH_3$, X = F: compound 111

LiOH (1.09 g, 45.5 mmol) was added to a stirring solution of ester 16 (prepared in Example 1) (2.75 g, 9.10 mmol) in THF (24 mL) and water (20 mL) at room temperature. MeOH (4 mL) was added, and stirring continued for 2 h at room temperature at which point LCMS indicated complete consumption of the ester. Upon concentration in vacuo, the reaction mixture was acidified to pH 3-4 by adding 2N HCl (20 mL). After 20 min stirring, the reaction mixture was cooled to 0° C., a solid precipitate was collected by filtration, washed with 3-4 ml water, and dried to give 1.59 g (64%) of the corresponding acid 38 as a grayish solid. MS: [M+1] =275. To acid 38 (1.59 g, 5.8 mmol) suspended and stirred in DCM (30 ml) was added EDC (5.6 g, 29.2 mmol), benzyl alcohol (2.5 g, 23.2 mmol) and DMAP (3.54 g, 29.2 mmol). After 3 days of stirring at room temperature, the reaction was concentrated in vacuo. Water (80 mL) was added to the slurry, followed by diethyl ether (40 mL), and the mixture was stirred vigorously for 40 min, at which point the slurry turned into a precipitate, and was collected by suction filtration. The solid was washed with water and small amount of diethyl ether, and dried to give 1.65 g (78%) benzyl ester 39 as a white solid. MS: [M+1]=365.

Compound 1,2,4-triazole (1.22 g, 17.7 mmol) in $CH_3CN$ (15 mL) at 0° C. was treated with i-$Pr_2NEt$ (3.24 mL, 18.6 mmol), followed by $POCl_3$ (0.507 mL, 5.44 mmol). The solution was stirred at 0° C. for 2 h. Benzyl ester 39 (1.65 g, 4.53 mmol) was added in lot and the resulting suspension was heated in an 80° C. oil bath for 18 h. LCMS showed 5-10% starting lactam remained. In a separate flask, 1,2,4-triazole (307 mg, total 4.9 eq) in $CH_3CN$ (3.8 mL) was treated with i-$Pr_2NEt$ (0.82 mL, total 5.1 eq) and $POCl_3$ (0.127 ml; total 1.5 eq) at 0° C. for 2 h. The resulting clear solution was transferred into the above reaction mixture. After 2 h heating at 80° C., the reaction was cooled to room temperature, water was added slowly to quench the reaction (10 min). Upon cooling in an ice bath, the solids formed were collected by filtration, washed with water (5 ml), and dried to give 1.61 g (86%) product 40 as a lightly yellow solid. MS: [M+1]- 416.

A solution of KO-t-Bu (0.739 g, 6.59 mmol) in DMF (11 mL) was cooled to −50° C. Ethyl isocyanoacetate (0.810 mL, 7.00 mmol) was added drop wise. The mixture was stirred at −50° C. for 1 h. The above triazole intermediate 40 (1.61 g, 3.87 mmol) was added. The mixture was stirred at −50° C. for 30 min, and slowly warmed to room temperature over 4-5 h. Saturated $NH_4Cl$ aqueous solution (10 mL) was added, followed by EtOAc (10 mL). The mixture was sonicated to breakup solid chunks, then stirred thoroughly for 30 min. The precipitate was collected by filtration, washed with water, $Et_2O$, and dried to give crude product as a white solid. Filtrate was partitioned between water and EtOAc; aqueous layer was separated and extracted with EtOAc twice; the combined EtOAc layer was washed with brine and dried over $MgSO_4$. Filtration and solvent removal gave a solid residue which was combined with the solid obtained above for chromatographic purification, using RediSep 24 g silica-gel column and gradient elution with 0.5 to 5% MeOH in DCM, to give 1.78 g (100%) imidazole 41 as a white solid. MS: [M+1]=460. The benzyl ester 41 (1.78 g, 3.87 mmol) was subjected to hydrogenolysis (hydrogen balloon) in the presence of catalytic amount of 10% Pd on charcoal in a solvent mixture of THF (40 mL), MeOH (20 mL) and EtOAc (20 mL) for 20 h. LCMS showed complete disappearance of the starting material. The solid catalyst was removed by filtration over Celite, and rinsed repeatedly with ample amount of 30% MeOH in DCM until almost all products were recovered (TLC monitor). Filtrate containing the product was concentrated in vacuo to give 1.22 g (85%) of acid product 42 was obtained as a yellowish solid. MS: [M+1]=370.

To the acid 42 (1.22 g, 3.30 mmol) suspended and stirred in THF (25 mL) at 0° C. was added borane dimethylsulfide complex (2M THF; 19 mL, 38 mmol) dropwise. Ice bath was removed and the reaction mixture was stirred at room temperature for 16 h. Upon cooling in an ice bath, the reaction was carefully quenched with MeOH (20 mL), and then stirred at room temperature overnight. Solvents were removed in vacuo. MeOH was added and removed in vacuo two more times. ISCO purification (RediSep 24 g column) using a gradient of 1 to 8% MeOH in DCM gave 0.625 g (53%) of alcohol product 43 as a white solid. MS: [M+1]=356.

Diisopropyl azodicarboxylate (48.3 mg, 0.233 mmol) was added drop-wise into a stirring solution of alcohol 43 (37.5 mg, 0.106 mmol), phenol (14.9 mg, 0.158 mmol), and $Ph_3P$ (55.6 mg, 0.212 mmol) in anhydrous THF (0.8 mL) at 0° C. Ice bath was removed and stirring continued at room temperature for 16 h. LCMS showed complete disappearance of the starting alcohol. The reaction mixture was partitioned between sat. $NaHCO_3$ and EtOAc. The organic layer was separated and washed with water, brine, and dried over $MgSO_4$. The desired product was isolated from the reaction mixture by two consecutive preparative TLC (4% MeOH in DCM, and hexanes/EtOAc/MeOH=47.5/47.5/5, v/v/v) to give 5.3 mg (12%) of product which is Compound 9 as a white solid. MS: [M+1]=432. $^1$H-NMR (500 MHz, CDCl3) δ: 7.77 (s, 1H), 7.63 (d, 1H, J=3.5 Hz), 7.53 (d, 1H, J=9.0 Hz), 7.31 (m, 2H), 7.17 (dd, 1H, J=3.0, 8.5 Hz), 7.08 (d, 2H, J=7.0 Hz), 6.99 (t, 1H, J=6.5 Hz), 5.30 (s, 2H), 4.40 (q, 2H, J=7.0 Hz), 3.96 (s. 3H), 1.38 (t, 3H, J=7.0 Hz).

Example 17: Synthesis of Compound 10

10

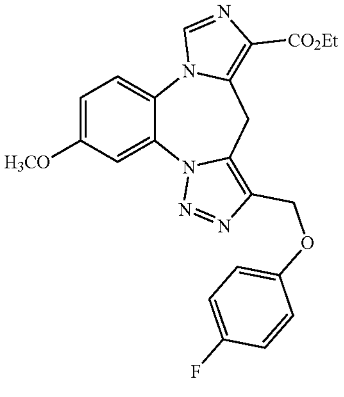

Compound of Example 17 was synthesized in an analogous synthetic route as that described for Example 16, using 4-fluoro-phenol in the ultimate step to give Compound 10 (4.9 mg) as a white solid: MS: [M+1]=450. $^1$H-NMR (500 MHz, CDCl3) δ: 7.76 (s, 1H), 7.64 (d, 1H, J=3.5 Hz), 7.53 (d, 1H, J=8.0 Hz), 7.17 (dd, 1H, J=2.5, 8.0 Hz), 7.01 (m, 4H), 5.26 (s, 2H), 4.40 (q, 2H, J=7.0 Hz), 3.96 (s, 3H), 1.40 (t, 3H, J=7.0 Hz).

Example 18: Synthesis of Compound 11

11

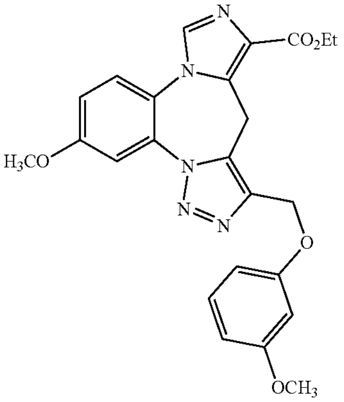

Compound of Example 18 was synthesized in an analogous synthetic route as that described for Example 16, using 3-methoxy-phenol in the ultimate step to give Compound 11 (6.1 mg) as a white solid: MS: [M+1]=462. $^1$H-NMR (500 MHz, CDCl3) δ: 7.76 (s, 1H), 7.63 (d, 1H, J=2.5 Hz), 7.53 (d, 1H, J=9.0 Hz), 7.15-7.22 (m, 2H), 6.67 (m, 2H), 6.55 (br dd, 1H, J=2.5, 8.0 Hz), 5.28 (s, 2H), 4.39 (q, 2H, J=7.0 Hz), 3.96 (s, 3H), 3.81 (s, 3H), 1.39 (t, 3H, J=7.0 Hz).

Example 19: Synthesis of Compound 12

12

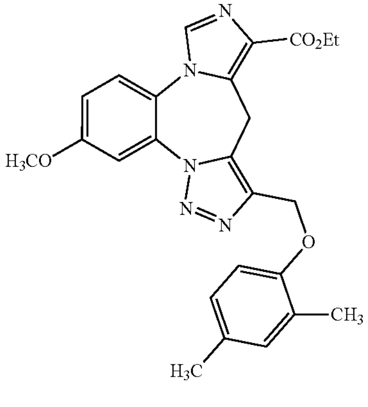

Compound of Example 19 was synthesized in an analogous synthetic route as that described for Example 16, using 2,4-dimethylphenol in the ultimate step to give Compound 12 (3.1 mg) as a white solid: MS: [M+1]=460. $^1$H-NMR (500 MHz, CDCl3) δ: 7.76 (s, 1H), 7.65 (d, 1H, J=3.0 Hz), 7.53 (d, 1H, J=9.0 Hz), 7.17 (dd, 1H, J=2.5, 8.5 Hz), 6.98 (m, 3H), 5.26 (s, 2H), 4.37 (q, 2H, J=7.0 Hz), 3.96 (s, 3H), 2.26 (s, 3H), 2.20 (s, 3H), 1.36 (t, 3H, J=7.01 Hz).

Example 20: Synthesis of Compound 107

107

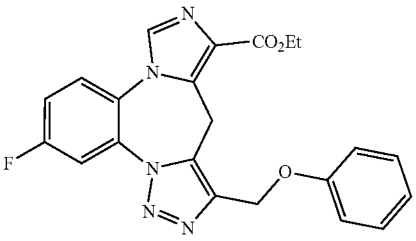

To a solution of alcohol 43 where X=F (prepared in an identical manner to example where X=$OCH_3$) (60 mg, 0.17 mmol) in THF (0.8 mL) was added phenol (30 mg, 0.32 mmol), triphenylphosphine (84 mg, 0.32 mmol). The reaction mixture was stirred at room temperature for 15 min. It was then cooled with an ice bath and DIAD (64 μL, 0.32 mmol) in THF (0.2 mL) was added slowly. The ice bath was removed and the reaction mixture was stirred at room temperature for 18 h. LCMS indicated still the presence of some starting material. Phenol (10 mg), triphenylphosphine (28 mg) and DIAD (21 μL) were added to the reaction mixture and stirred for another hour. The solvent was evaporated and the crude material was purified by Chromatography (RediSep 12 g silica-gel column. Eluting solvent: EtOAc) and prep TLC (eluting solvent: 5% MeOH/47.5% EtOAc/47.5% Hexanes) to give 11.4 mg (yield 16%) of the product Compound 107. [M+1]- 421). $H^1NMR$ ($CDCl_3$) δ 7.92 (1H, dd, J=3.5, 8.5 Hz), 7.80 (1H, s), 7.63 (1H, dd, J=5, 10 Hz), 7.38 (1H, m), 7.31 (2H, t, J=8.5 Hz), 7.07 (2H, d, J=8.5 Hz), 7.00 (1H, t, J=8.5 Hz), 5.3 (2H, s), 4.39 (2H, q, J=7 Hz), 1.38 (3H, t, J=7 Hz).

Example 21: Synthesis of Compound 111

111

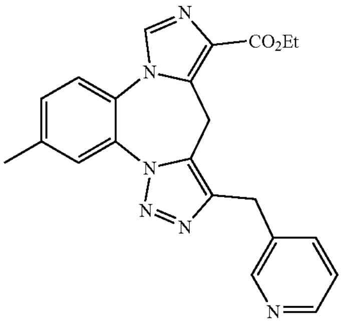

To a suspension of alcohol 43 (X=Me) (160 mg, 0.47 mmol) in acetonitrile (9 mL) was added $POBr_3$ (405 mg, 1.41 mmol). The reaction mixture was heated at 80 C for 5 h. The reaction mixture was cooled down with an ice bath and sat. aq. $NaHCO_3$ solution was added. The resulting solution was extracted with DCM (3×). The combined organic phases were washed with brine and dried over $MgSO_4$. The solvent was concentrated to afford the desired product, 166 mg, 88% yield, [M+1]=403).

To a suspension of the above alkyl bromide derivative (30 mg; 0.075 mmol) in deoxygenated DME (2.7 mL) was added 3-pyridine boronic acid (14 mg, 0.11 mmol) and a 2M $Na_2CO_3$ solution (0.22 mL, 0.44 mmol). The suspension was stirred at room temperature for 5 min, then $PdCl_2(PPh_3)_2$ (10 mg, 0.015 mmol) was added. The suspension was heated in a MW at 85 C for 1 hour. The reaction mixture was cooled and diluted with water and extracted with EtOAc (twice). The combined extracts were washed with brine and dried over $MgSO_4$. Filtration and concentration gave the crude product which was purified by 2 prep TLC (eluting system: 3% MeOH in DCM) to give 5.3 mg (yield 18%) of the product Compound 111. MS: [M+1]=401. $H^1NMR$ ($CDCl_3$) δ 8.66 (1H, bs), 8.48 (1H, bs), 7.96 (1H, s), 7.79 (1H, s), 7.66 (1H, d, J=8 Hz), 7.50 (1H, d, J=8 Hz), 7.43 (1H, d, J=7 Hz), 7.23 (1H, m), 4.42 (2H, q, J=7 Hz), 4.18 (2H, s), 2.54 (3H, s), 1.44 (3H, t, J=7 Hz).

Example 22: Synthesis of Compound 48

48

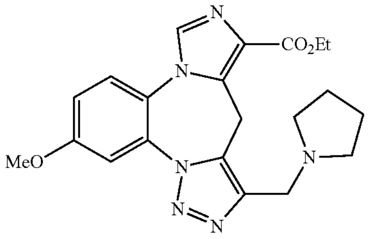

Scheme 16.

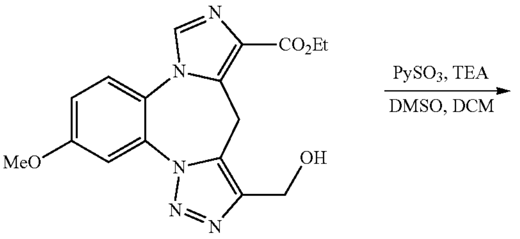

43

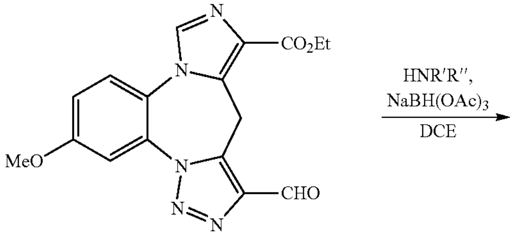

57

-continued

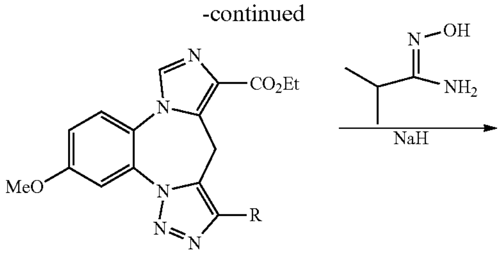

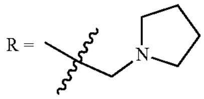

compound 48

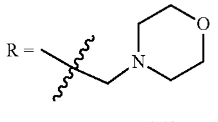

compound 49

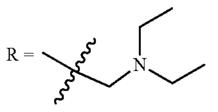

compound 50

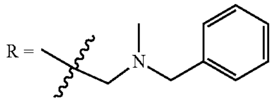

compound 51

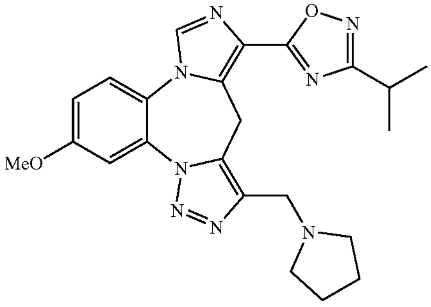

compound 170

To alcohol 43 (186 mg, 0.523 mmol) stirring in DMSO (1 mL) and dichloromethane (2.5 mL) at room temperature was added triethylamine (0.394 mL, 2.82 mmol) and pyridine sulfur trioxide complex (225 mg, 1.41 mmol). After 3 h stirring, the reaction was quenched with water (5 mL), and extracted with ethyl acetate three times. The combined organic solution was washed with water, brine, and dried over $MgSO_4$. The aldehyde product 57 was isolated by ISCO flash column chromatography (RediSep 4 g column) using a gradient elution of 0.5 to 8% MeOH in DCM. 84.4 mg (46%) was obtained as a yellowish foamy solid. MS: [M+1]=354.

To a stirring solution of aldehyde 57 (15.5 mg, 0.0439 mmol) in 1,2-dichloroethane (0.3 mL) at room temperature was added pyrrolidine (5.5 uL, 0.0658 mmol). After 2 min stirring, the solution turned clear, and $NaBH(OAc)_3$ (14.4 mg) was added. The reaction mixture was stirred for 4 h, and was quenched with saturated $NaHCO_3$, and extracted with ethyl acetate three times. The combined organic layer was washed with water, brine, and dried over $Na_2SO_4$. Prep TLC with 10% MeOH in DCM gave 13.1 mg (73%) of the desired Compound 48 as a clear filmy solid. MS: [M+1]- 409. $^1$H-NMR (500 MHz, CDCl3) δ: 7.74 (s, 1H), 7.62 (d, 1H, J=3.0 Hz), 7.51 (d, 1H, J=9.0 Hz), 7.14 (dd, 1H, J=3.5, 9.0 Hz), 4.42 (q, 2H, J=6.5 Hz), 3.94 (s, 3H), 3.87 (br s, 2H), 2.65 (br s, 4H), 1.79 (br s, 4H), 1.44 (t, 3H, J=7.0 Hz).

Example 23: Synthesis of Compound 49

49

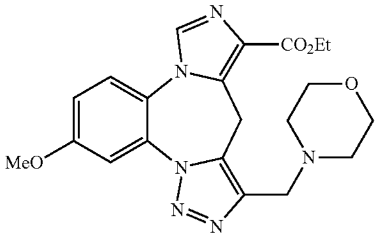

Compound of Example 23 was synthesized in an analogous synthetic route as that described for Example 22, using morpholine in the ultimate step to give the compound of Example 23 as a clear filmy solid: MS: [M+1]=425. $^1$H-NMR (500 MHz, CDCl3) δ: 7.75 (s, 1H), 7.63 (d, 1H, J=3.0 Hz), 7.52 (d, 1H, J=9.5 Hz), 7.15 (dd, 1H, J=3.0, 9.0 Hz), 4.42 (q, 2H, J=7.5 Hz), 3.95 (s, 3H), 3.76 (br s, 2H), 3.71 (br s, 4H), 2.57 (br s, 4H), 1.44 (t, 3H, J=8.0 Hz).

Example 24: Synthesis of Compound 50

50

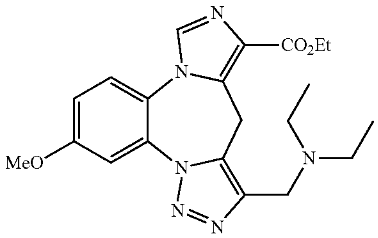

Compound of Example 24 was synthesized in an analogous synthetic route as that described for Example 22, using diethylamine in the ultimate step to give the compound of Example 24 as a clear filmy solid: MS: [M+1]=411. $^1$H-NMR (500 MHz, CDCl3) δ: 7.74 (s, 1H), 7.64 (br d, 1H, J=3.0 Hz), 7.51 (d, 1H, J=9.0 Hz), 7.15 (dd, 1H, J=2.5, 9.0 Hz), 4.43 (q, 2H, J=6.5 Hz), 3.96 (s, 3H), 3.86 (br s, 2H), 2.64 (br s, 4H), 1.44 (t, 3H, J=8.5 Hz), 1.15 (br s, 6H).

Example 25: Synthesis of Compound 51

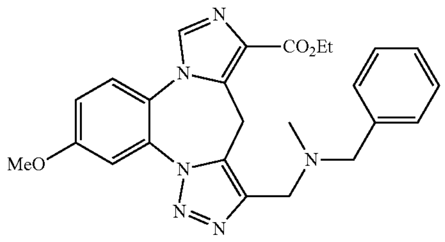

51

Compound of Example 25 was synthesized in an analogous synthetic route as that described for Example 22, using methyl benzyl amine in the ultimate step to give the compound of Example 25 as a clear filmy solid: MS: [M+1] =459. $^1$H-NMR (500 MHz, CDCl3) δ: 7.75 (s, 1H), 7.63 (d, 1H, J=3.0 Hz), 7.51 (d, 1H, J=8.5 Hz), 7.36 (br d, 2H, J=8.0 Hz), 7.30 (m, 2H), 7.23 (m, 1H), 7.15 (dd, 1H, J=3.0, 9.0 Hz), 4.38 (q, 2H, J=7.5 Hz), 3.95 (s, 3H), 3.85 (br s, 2H), 3.63 (br s, 2H), 2.25 (s, 3H), 1.41 (t, 3H, J=7.0 Hz).

Example 26: Synthesis of Compound 170

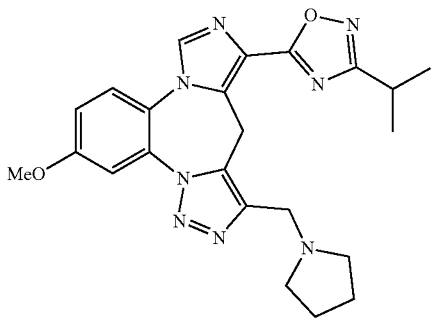

170

Isobutyramidoxime (41.8 mg, 0.41 mmol) and ester 48 (27.9 mg, 0.0683 mmol) in a round bottom flask was azeotroped in toluene on a Rotavap several times, suspended in anhydrous THF (0.6 mL), and then cooled to 0° C. NaH (60% oil suspension; 10.9 mg, 0.273 mmol) was added. Ice bath was removed and the reaction mixture was stirred at RT for 20 min before being heated at 70° C. for 6 hrs, and cooled. Water (4 mL) was added, and the mixture was extracted with EtOAc three times. The combined organic solution was washed with brine and dried over MgSO4. Prep. TLC with 10% MeOH in EtOAc gave 10.4 mg (34%) of the desired product Compound 170 as a clear filmy solid. MS: [M+1]=447.

Example 27: Synthesis of Compound 52

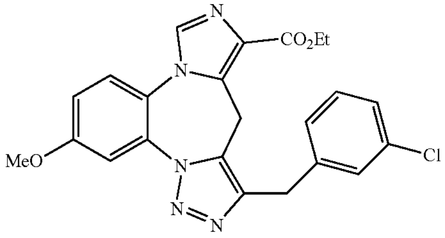

52

Scheme 17.

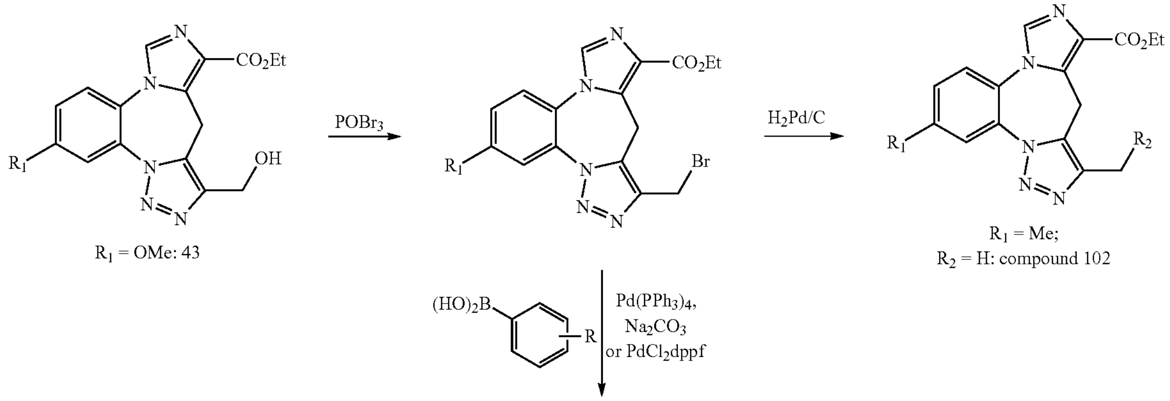

-continued

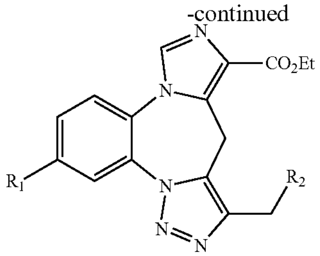

$R_1$ = OMe; $R_2$ = m-Cl-Ph: compound 52
$R_1$ = OMe; $R_2$ = m-CN-Ph: compound 53
$R_1$ = Me; $R_2$ = o-Cl-Ph: compound 54
$R_1$ = Me; $R_2$ = Ph: compound 101
$R_1$ = OMe; o-Cl-Ph: compound 108

The starting alcohol 43 (160 mg, 0.45 mmol) was treated with phosphorous oxide tribromide (400 mg, 1.4 mmol) in acetonitrile (10 ml) at 80° C. for 5 h. The reaction was then cooled down to 0° C., quenched with sat. NaHCO3, and extracted with dichloromethane twice. Combined dichloromethane solution was washed with brine and dried over $MgSO_4$. Filtration and solvent removal in vacuo gave 173.3 mg (92%) of the bromide as a yellowish foamy solid. MS: [M+1]=418.

To a suspension of bromide (55 mg, 0.131 mmol) in dimethoxyethane (2 ml; degassed) was added 2M $Na_2CO_3$ (0.39 ml, 0.78 mmol) and 3-chlorophenyl boronic acid (42.2 mg, 0.27 mmol). The reaction mixture was stirred at room temperature for 2 min, then $Pd(PPh_3)_4$ (75 mg, 0.065 mmol) was added, and the suspension was heated in a 85° C. oil bath for 90 min. Upon cooling, the reaction mixture was diluted with EtOAc and washed with brine. The aqueous layer was separated and extracted with EtOAc three times. All organic layers were pooled and dried over $Na_2SO_4$, then filtered and solvent was removed in vacuo. The product was isolated by successive prep TLC purifications, using 20% hexanes in EtOAc followed by 5% MeOH in DCM. 9.6 mg product (Compound 52) was obtained as a brownish solid. MS: [M+1]=450. $^1$H-NMR (500 MHz, CDCl3) δ: 7.75 (s, 1H), 7.64 (d, 1H, J=3.0 Hz), 7.51 (d, 1H, J=9.5 Hz), 7.31 (br s, 1H), 7.23 (br s, 1H), 7.17 (m, 3H), 4.43 (q, 2H, J=7.0 Hz), 4.15 (s, 2H), 3.96 (s, 3H), 1.44 (t, 3H, J=8.0 Hz).

Example 28: Synthesis of Compound 53

53

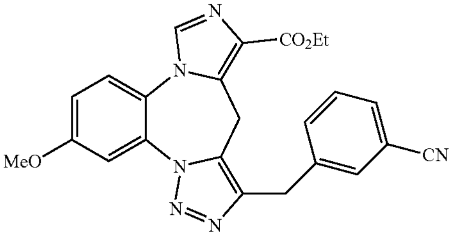

Compound of Example 28 was synthesized in an analogous synthetic route as that described for Example 27, using 3-cyanophenyl boronic acid in the ultimate step to give the compound of Example 28 as a brownish solid: MS: [M+1]–441. $^1$H-NMR (500 MHz, CDCl3) δ: 7.75 (s, 1H), 7.66 (br s, 1H), 7.64 (d, 1H, J=3.0 Hz), 7.61 (br d, 1H, J=7.5 Hz), 7.39 (t, 1H, J=7.5 Hz), 7.16 (dd, 1H, J=3.5, 9.5 Hz), 4.45 (q, 2H, J=7.0H), 4.20 (s, 2H), 3.96 (s, 3H), 1.45 (t, 3H, J=7.0 Hz).

Example 29: Synthesis of Compound 54

54

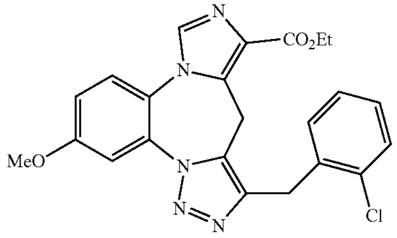

Compound of Example 29 was synthesized in an analogous synthetic route as that described for Example 27, starting with the alcohol where $R_1$=methyl, and using 2-chlorophenyl boronic acid in the ultimate step to give the compound of Example 29 as a brownish solid: MS: [M+1]–434.

Example 30: Synthesis of Compound 101

101

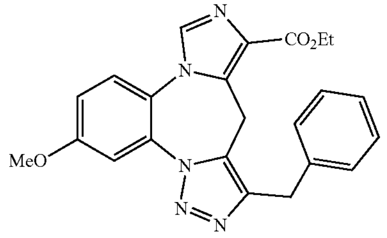

Compound of Example 30 was synthesized in an analogous synthetic route as that described for Example 27, starting with the alcohol where $R_1$-methyl, and using phenyl boronic acid in the ultimate step to give the compound of Example 30 as a brownish solid product which was purified by chromatography (RediSep 4 g silica-gel column. Eluting solvent: EtOAc) then a prep TLC (eluting system: 40% DCM/40% Hexanes/17% EtOAc/3% MeOH) to give 5.9 mg (yield 31%) of the product Compound 101. MS: [M+1] =402. H[1]NMR ($CDCl_3$) δ 7.96 (1H, s), 7.77 (1H, s), 7.55 (1H, m), 7.47 (1H, m), 7.32 (5H, m), 4.41 (2H, q, J=7 Hz), 4.17 (2H, s), 2.53 (3H, s), 1.43 (3H, t, J=7 Hz).

Example 31: Synthesis of Compound 102

102

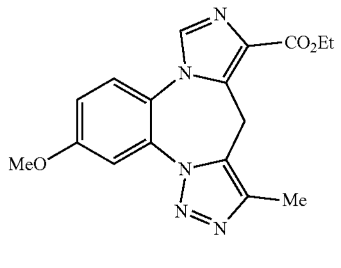

To a suspension of the bromide in EtOAc (2 mL) and MeOH (2 mL) was added activated 10% Pd/C (5 mg). The suspension was stirred under a hydrogen atmosphere for 48 h. The solution was filtered over celite. The filtrate was concentrated and purified by chromatography (RediSep 4 g silica-gel column. Eluting solvent: EtOAc) to give 15.9 mg (33%) of the desired product Compound 102. MS: [M+1]=324. H[1]NMR ($CDCl_3$) δ 7.96 (1H, s), 7.78 (1H, s), 7.49 (1H, d, J=9 Hz), 7.42 (1H, d, J=8 Hz), 4.43 (2H, q, J=7.5 Hz), 2.53 (3H, s), 2.44 (3H, s), 1.45 (3H, t, J=7.5 Hz).

Example 32: Synthesis of Compound 108

108

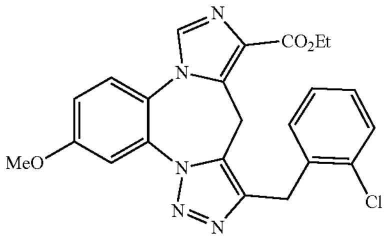

To a suspension of the bromide derivative where $R_1$=OMe, (18 mg; 0.043 mmol) in deoxygenated DME (2 mL) was added 2-chlorophenyl boronic acid (10 mg, 0.065 mmol) and a 2M $Na_2CO_3$ solution (0.13 mL, 0.26 mmol). The suspension was stirred at room temperature for 15 min, then $PdCl_2$dppf (7 mg, 0.009 mmol) was added. The suspension was heated in an oil bath at 85 C for 1 hour. The reaction mixture was diluted with water and extracted with EtOAc (twice). The combined extracts were washed with brine and dried over $Na_2SO_4$. Filtration and concentration gave the crude product which was purified by PrepTLC (eluting system: 5% MeOH/47.5% Hex/47.5% EtOAc) to give 3.5 mg (yield 18%) of the product Compound 108. MS: [M+1]- 451. H[1]NMR ($CDCl_3$) δ 7.77 (1H, s), 7.63 (1H, d, J=3 Hz), 7.52 (1H, d, J=11.5 Hz), 7.36 (1H, m), 7.31 (1H, m), 7.18 (2H, m), 7.14 (1H, dd, J=3, 9 Hz), 4.38 (2H, q, J=7 Hz), 4.27 (2H, s), 3.94 (3H, s), 1.41 (3H, t, J=7 Hz).

Scheme 18a.

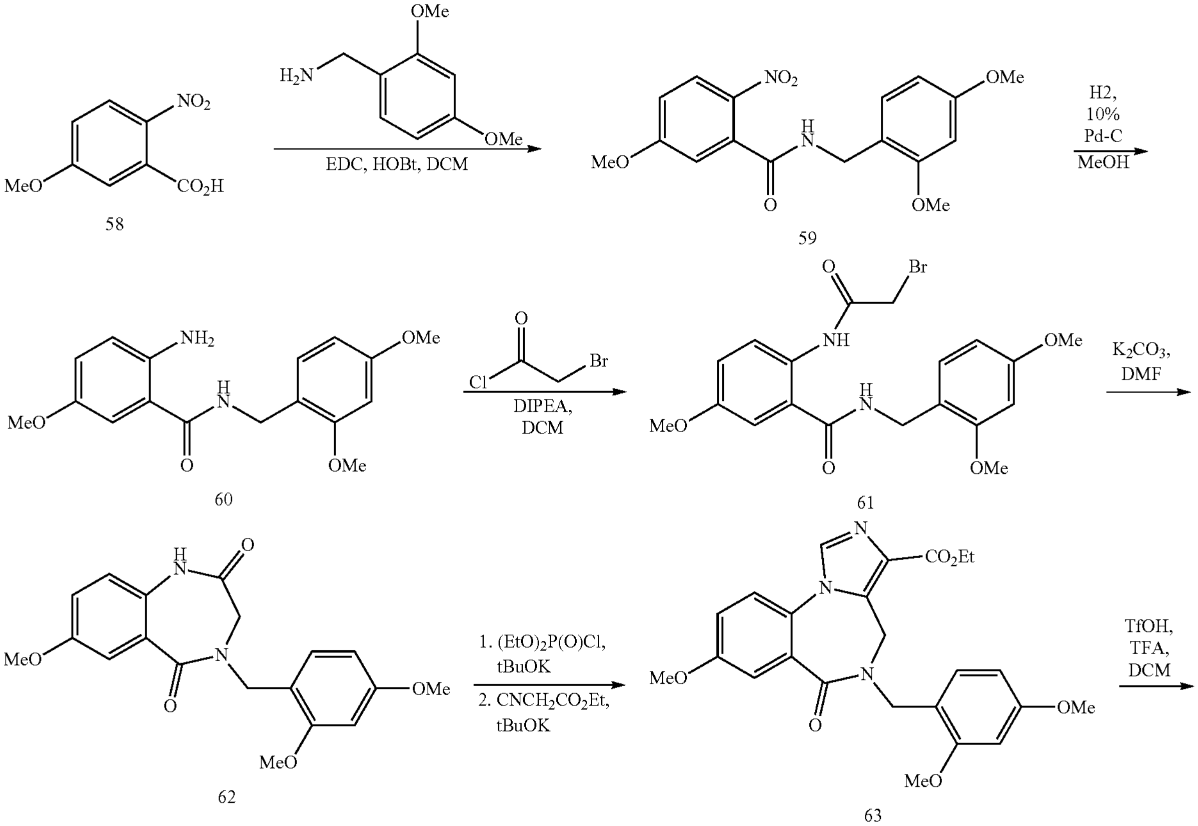

58
59
60
61
62
63

-continued
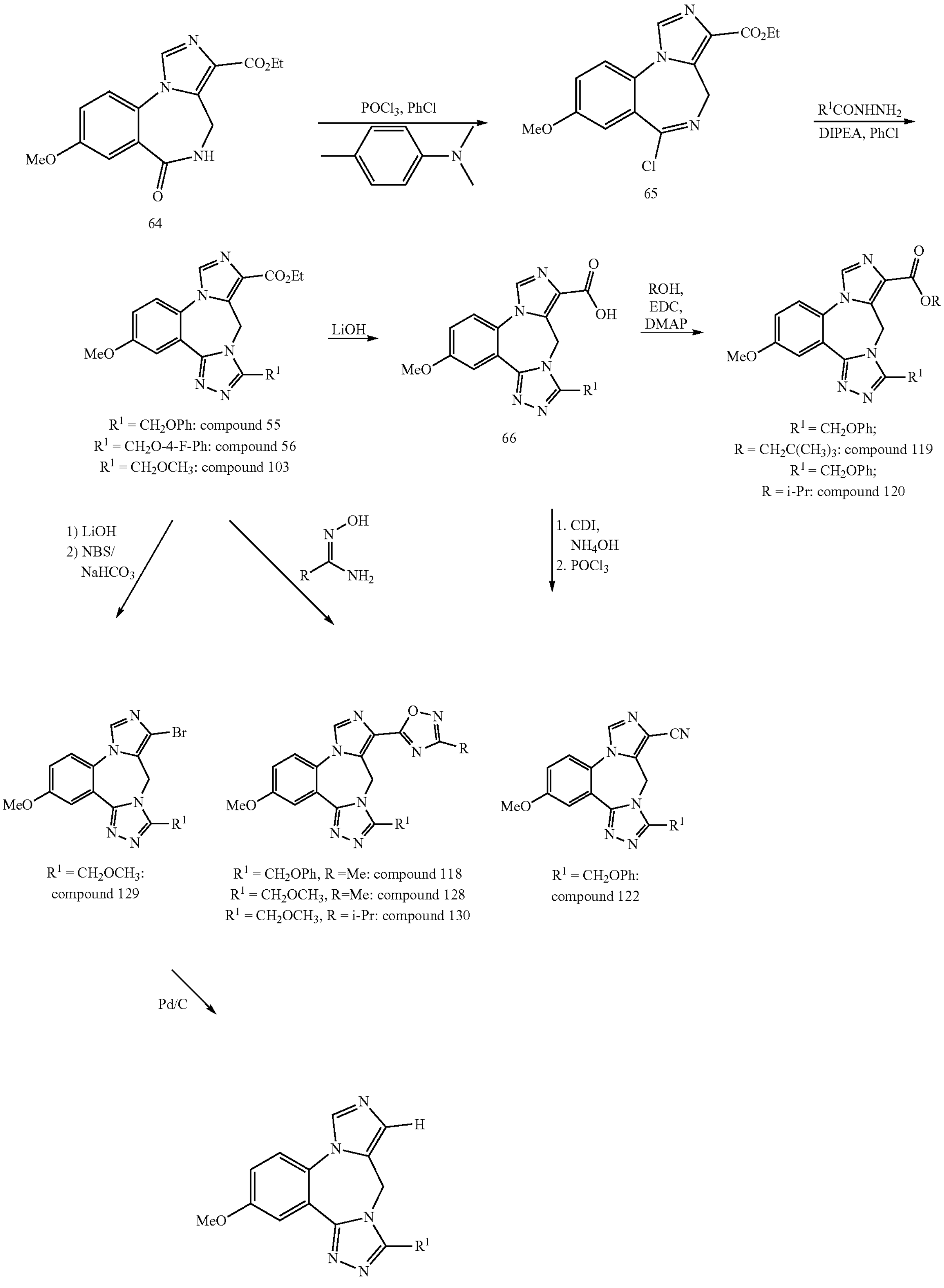
64
65
$R^1 = CH_2OPh$: compound 55
$R^1 = CH_2O$-4-F-Ph: compound 56
$R^1 = CH_2OCH_3$: compound 103
66
$R^1 = CH_2OPh$;
$R = CH_2C(CH_3)_3$: compound 119
$R^1 = CH_2OPh$;
R = i-Pr: compound 120
$R^1 = CH_2OCH_3$:
compound 129
$R^1 = CH_2OPh$, R =Me: compound 118
$R^1 = CH_2OCH_3$, R=Me: compound 128
$R^1 = CH_2OCH_3$, R = i-Pr: compound 130
$R^1 = CH_2OPh$:
compound 122
$R^1 = CH_2OCH_3$: compound 131

Scheme 18b.

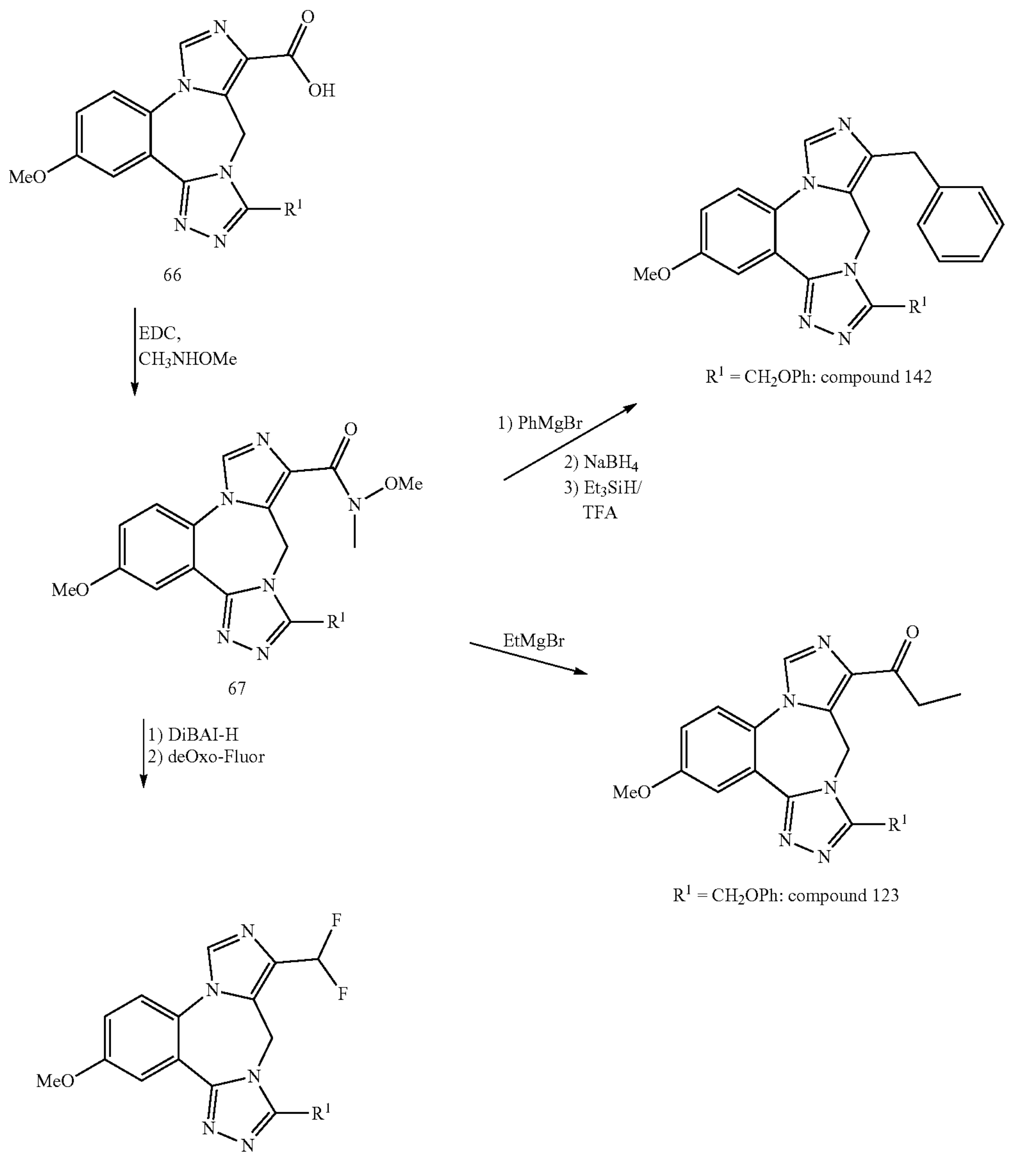

66

67

$R^1$ = $CH_2OPh$: compound 142

$R^1$ = $CH_2OPh$: compound 123

$R^1$ = $CH_2OPh$: compound 124

Example 33: Synthesis of Compound 55

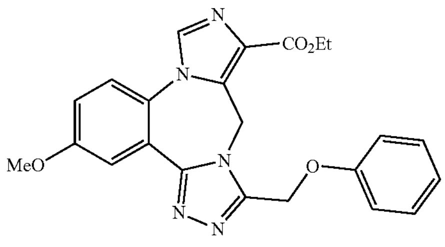

To a solution of compound 58 (6.6 g, 33.5 mmol) in dichloromethane (100 mL) were added DIPEA (8.65 g, 67 mmol), HOBt (5.4 g, 36.85 mmol) and EDCI (9.6 g, 50.3 mmol). After about 15 min stirring, to the homogeneous reaction mixture was added a solution of 2,4-dimethoxybenzyl amine (5.6 g, 33.5 mmol) in dichloromethane (50 mL) dropwise under nitrogen atmosphere. The resulting mixture was stirred under nitrogen atmosphere at room temperature for 16 h. The reaction mixture was washed successively with 1N NaOH (100 mL), water (100 mL) and brine (100 mL). The organic phase was then dried over $Na_2SO_4$ and evaporated to give a crude solid product 59 that crystallized from ethyl ether. Filtration and open air suction drying afforded an off-white solid pure product 9.8 g (96%), (MS: [M+1]=347).

To a solution of compound 59 (9.8 g, 28.3 mmol) in MeOH/EtOAc (1:1, 100 mL) was added 10% wet Pd—C (1.8 g, 10% mmol). After three consecutive vacuuming and flushing with nitrogen, the heterogeneous reaction mixture was subjected to a balloon hydrogenation at atmosphere pressure up until the absorption of hydrogen ceases, about 4 h. The reaction mixture was filtered through a celite pad and evaporated to afford the pure desired product 60 as a brown oil 8.63 g (96%), (MS: [M+1=317]). This product was used directly in the next step.

To a solution of compound 60 (8.63 g, 27.3 mmol) in dichloromethane (100 ml) was added triethylamine (5.5 g, 54.6 mmol). The mixture was cooled with ice bath and treated with bromo acetyl chloride (5.2 g, 32.76 mmol) under nitrogen atmosphere. The ice bath was removed and the mixture left stirring for 18 h. The reaction mixture was washed successively with saturated $NaHCO_3$ (100 mL), water (100 mL) and brine (100 mL). The organic phase was then dried over $Na_2SO_4$ and evaporated to give a crude solid product 61. The crude product was crystallized from methanol, filtered and dried to afford a brown solid pure product 10.3 g (87%), [MS: 439].

To a solution of compound 61 (10 g, 22.9 mmol) in DMF (1000 mL) was added $K_2CO_3$ (4.8 g, 45.8 mmol). The mixture was heated at 50° C. for 24 h. LCMS showed a complete conversion to the desired product. The mixture was cooled to room temperature and the inorganic solid was filtered. The solvent was removed under high vacuum. The resulting crude product 62 was crystallized from methanol, filtered and dried to give a pure brown solid product 6.4 g (78%), (MS: [M+1]=357).

To compound 62 (4.46 g, 12.52 mmol) dissolved in 2.5:1 THF/DMF (50 mL) at −20° C. was added t-BuOK (97%, 1.88 g, 16.28 mmol). The mixture was warmed to 25° C., and after stirring for 30 min was cooled again to −20° C. Following dropwise addition of diethyl chlorophosphate (2.35 mL, 16.28 mmol), the mixture was stirred for 3 h while warming from −20 to 25° C. The reaction mixture was re-cooled to 0° C. and to it was added ethyl isocyanoacetate (1.92 mL, 17.53 mmol). Subsequent cooling to −78° C. was followed by addition of t-BuOK (97%, 1.88 g, 16.28 mmol) and stirring at RT for 5 h. Progress was monitored by LC/MS. The reaction was quenched by addition of 1:1 saturated $NaHCO_3/H_2O$ (140 mL), the precipitate was filtered, washed with $H_2O$ and air dried overnight to afford 4.81 g (85%) of imidazole derivative 63 as a yellow solid (MS: [M+1]=452).

To compound 63 (4.81 g, 10.65 mmol) in dichloromethane (35 mL) at 0° C. was added trifluoroacetic acid (35 mL) followed by dropwise trifluoromethanesulfonic acid (1.9 mL, 21.31 mmol). The mixture was warmed to RT, stirred for 2 h, then concentrated to afford a residue which was dissolved in dichloromethane (120 mL). The crude solution was partitioned between chilled saturated $NaHCO_3$ and dichloromethane. The organic extractions were combined, dried ($MgSO_4$), filtered and concentrated to afford 3.2 g (99%) of deprotected product 64 (brown solid) of sufficient purity to take on the next step (MS: [M+1]=302).

To lactam 64 (51.8 mg, 0.172 mmol) and N,N-dimethyl-p-toluidine (93.0 mg, 0.688 mmol) stirring in chlorobenzene (1 ml) under nitrogen was added $POCl_3$ (52.7 mg, 0.344 mmol). The reaction was then heated at 135° C. for 2 h. Upon cooling to room temperature, phenoxy acetic acid hydrazide (228.4 mg, 1.36 mmol) was added in situ to the imino-chloride 65, followed by DIPEA (90 ul). The reaction was stirred at room temperature for 30 min, then heated at 100° C. for 90 min. The reaction mixture was cooled, saturated $NaHCO_3$ (aq.) was added, and extracted with ethyl acetate three times; combined organic layer was washed with brine, and dried over $MgSO_4$. After filtration and concentration, the product as Compound 55 was isolated by ISCO flash column chromatography (RediSep 4 g column, 1 to 10% MeOH in DCM as eluting gradient) as a white solid, Wt: 8.6 mg. MS: [M+1]=432. $^1$H-NMR (500 MHz, CDCl3) δ: 7.81 (s, 1H), 7.71 (d, 1H, J=3.5 Hz), 7.52 (d, 1H, J=9.0 Hz), 7.32 (m, 2H), 7.21 (dd, 1H, J=2.5, 8.5 Hz), 7.11 (d, 2H, J=8.5 Hz), 7.02 (m, 1H), 5.44 (s, 2H), 4.38 (q, 2H, J=7.5 Hz), 3.94 (s, 3H), 1.39 (t, 3H, J=7.0 Hz).

Example 34: Synthesis of Compound 56

56

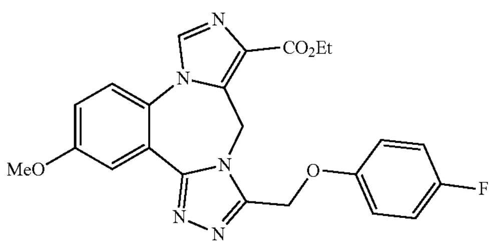

Compound of Example 34 was synthesized in an analogous synthetic route as that described for Example 33, using 4-fluoro-phenoxy acetic acid hydrazide in the ultimate step to give the compound of Example 34 as a yellowish solid: MS: [M+1]=450. $^1$H-NMR (500 MHz, CDCl3) δ: 7.82 (s, 1H), 7.73 (d, 1H, J=3.5 Hz), 7.53 (d, 1H, J=10.0 Hz), 7.22 (dd, 1H, J=3.5, 9.0 Hz), 7.08-6.99 (m, 4H), 5.41 (s, 2H), 4.41 (q, 2H, J=7.0 Hz), 3.95 (s, 3H), 1.42 (t, 3H, J=6.5 Hz).

Example 35: Synthesis of Compound 103

103

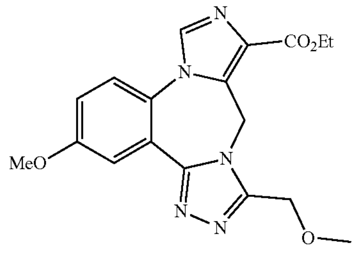

Compound of Example 35 was synthesized in an analogous synthetic route as that described for Example 33, using 2-methoxy acetic acid hydrazide in the ultimate step to give the compound of Example 35 as a yellowish solid: MS: [M+1]=370.

Example 36: Synthesis of Compound 118

118

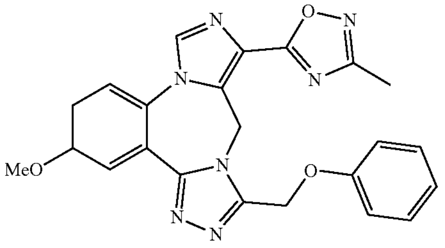

Acetamide oxime (8.4 mg, 0.108 mmol) was azeotroped in toluene three times on a Rotavap, then suspended in THF (1.0 mL). NaH (60% mineral suspension; 3.3 mg, 0.081 mmol) was added, and the mixture was stirred at RT for 10 min. Ester 55 (23.2 mg, 0.054 mmol) was added next. After 40 min stirring at RT, the reaction mixture was heated at 70° C. for 4 h. Upon cooling, cold water (5 mL) was added to the reaction mixture, and ppts were collected by filtration, washed with water, and dried to give 9.7 mg (41%) of the desired product as a yellowish solid. MS: [M+1]=442.

Example 37: Synthesis of Compound 128

128

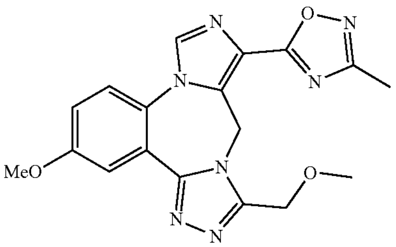

Compound of Example 37 was synthesized in an analogous synthetic route as that described for Example 36 above, using ester Compound 103 in the ultimate step to give the compound of Example 37 as a brownish solid: MS: [M+1] =380.

Example 38: Synthesis of Compound 130

130

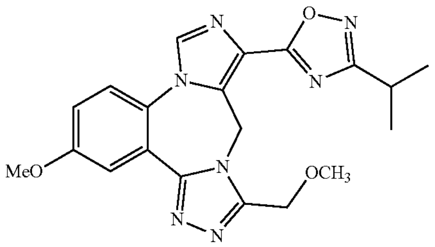

Compound of Example 38 was synthesized in an analogous synthetic route as that described for Example 36, starting with ester Compound 103 and condensing with isobutyramidoxime to give the compound of Example 38 as a yellowish solid: MS: [M+1]- 408.

Example 39: Synthesis of Compound 119

119

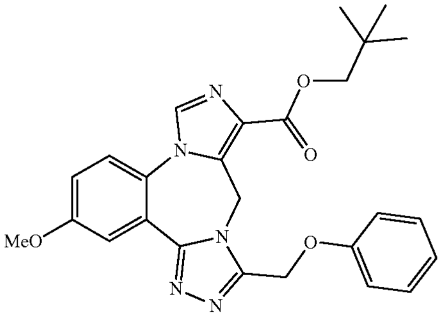

To the carboxylic acid (13.9 mg, 0.0345 mmol; obtained through LiOH hydroxysis of the precursor ester 55) stirring in DCM (0.2 mL) was added Neopentyl alcohol (30.4 mg, 0.345 mmol), DMAP (4.2 mg, 0.0345 mmol), and EDC (20 mg, 0.104 mmol). After five hour stirring, the reaction mixture was diluted with EtOAc, washed with sat. $NH_4Cl$, sat. $NaHCO_3$, brine, and dried over $MgSO_4$. Silica gel chromatographic purification using a gradient of 0 to 8% MeOH in EtOAc gave 11.7 mg (72%) of the desired product Compound 119 as a yellowish solid. MS: [M+1]=474.

Example 40: Synthesis of Compound 120

120

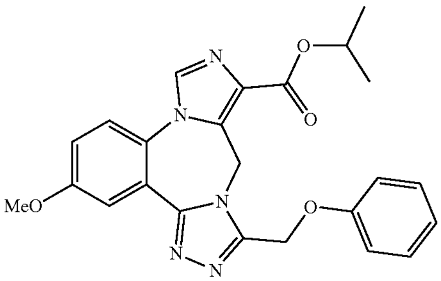

Compound of Example 40 was synthesized in an analogous synthetic route as that described for Example 39 above, using 2-propyl alcohol in the ultimate step to give the compound of Example 40 as a yellowish solid: MS: [M+1]=446.

Example 41: Synthesis of Compound 129

129

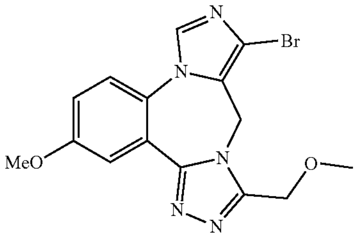

Compound 103 (Scheme 18a) (66.1 mg, 0.179 mmol) was hydrolyzed in a solvent system of THF/water/MeOH (1.8 ml total, 6/5/1 ratio) by treating with LiOH (21.4 mg, 0.895 mmol) at RT for 2 h. Dil. HCl was added to acidify (pH ~3) the reaction mixture. The precipitate was collected by filtration, washed with water, and dried to give 49.0 mg (80%) of the acid as a brownish solid.

The acid thus obtained was stirred in DMF (0.7 mL) at 0° C. $NaHCO_3$ (48.1 mg, 0.572 mmol) was added, followed by N-bromosuccinamide (96.7 mg, 0.543 mmol). After overnight stirring, the reaction was diluted with EtOAc, and washed with sat. $NaHCO_3$. Aq. Layer was separated and extracted with EtOAc. Combined organic layer was washed with brine, dried over $MgSO_4$, filtered, and concentrated. The product bromide was obtained by silica gel column chromatography with a gradient elution of 0 to 13% MeOH in EtOAc as a white solid (Compound 129). Wt: 28.6 mg (53%). MS: [M+1]=377.

Example 42: Synthesis of Compound 131

131

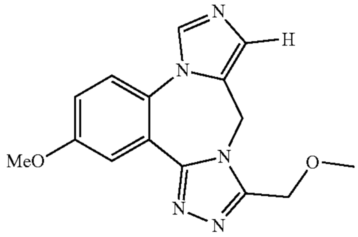

Compound 129 (22.6 mg, 0.060 mmol) was hydrogenated over 10% Pd—C in EtOAc (1 mL) and MeOH (1 mL) for 16 h. Filtration over Celite, and solvent removal gave 14.9 mg (84%) of the des-bromo product Compound 131 as a lightly yellowish solid. MS: [M+1]=298.

Example 43: Synthesis of Compound 122

122

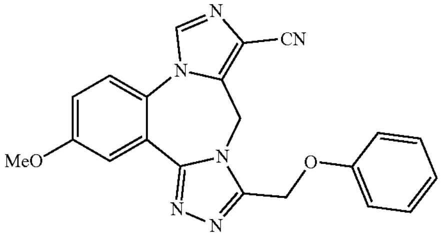

The phenoxy analog (Scheme 18a, $R_1$=OPh) of acid 66 (20.4 mg, 0.0506 mmol) was suspended and stirred in DCM (0.5 mL) at RT. Carbonyl diimidazole (16.4 mg, 0.101 mmol) was added. After 2 h stirring, the resulting suspension was cooled to 0° C., and ammonia (30 uL) was added dropwise. After 20 min stirring, ice bath was removed and the reaction was allowed to proceed at RT for 1 hr. The reaction was concentrated by removing DCM in vacuo. Water (3 mL) was added, and precipitate was collected by filtration, washed with water, and dried to give 16.2 mg of the crude primary amide which was used without further purification.

The primary amide (16.2 mg, 0.0402 mmol) was treated with $POCl_3$ (46.2 mg, 0.302 mmol) in 1,4-dioxane (0.5 mL) at 95° C. overnight. The reaction mixture was then quenched with sat. $NaHCO_3$ (5 mL), cooled to 0° C., and precipitate collected by suction filtration, washed with water, and dried to give 13.6 mg (88%) of the nitrile as a brownish solid, Compound 122. MS: [M+1]=385.

Example 44: Synthesis of Compound 123

123

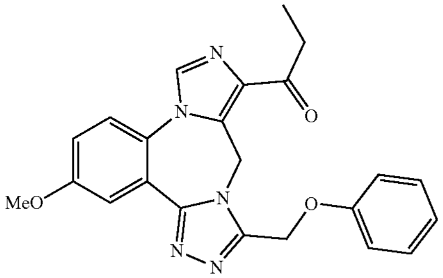

To Acid 66 (15.8 mg, 0.0392 mmol) stirring in THF (0.15 mL) and DCM (0.15 ml) was added N,O-dimethylhydroxylamine HCl (4.6 mg, 0.047 mmol) and N-hydroxylbenzotriazole hydrate (6.0 mg). EDC (11.3 mg, 0.0588 mmol) and triethylamine (11.9 mg, 0.118 mmol) were then added, and the reaction was stirred at RT for 12 hrs, diluted with EtOAc, washed with sat. $NH_4Cl$, brine, and dried over $MgSO_4$. Filtration and solvent removal in vacuo gave 14.4 mg (82%) of the Weinreb amide which was used without further purification.

To the Weinreb amide (14.4 mg, 0.0323 mmol) stirring in THF (0.3 mL) at 0° C. was added ethyl magnesium bromide etherate (3M; 0.323 mL). The reaction was allowed to warm to RT and stirred for 14 hrs., quenched with sat. $NH_4Cl$, extracted with EtOAc three times; combined organic layer washed with brine and dried over $MgSO_4$. Filtration and solvent removal gave the crude ketone product which was purified by prep. TLC using 8% MeOH in EtOAc. Wt: 4.6 mg (34%) of Compound 123. MS: [M+1]=416.

Example 45: Synthesis of Compound 124

124

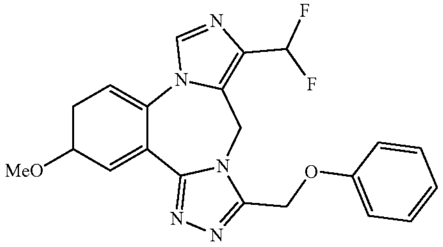

Weinreb amide (18.0 mg, 0.0403 mmol) described above was treated with DIBAL (1M THF; 0.363 mL) at −78° C. for 1 hr, then still at −78° C. quenched with Rochelle salt solution (20%) overnight. The aq. solution was extracted with EtOAc three times; combined organic layer was washed with brine, and dried over $MgSO_4$. Filtration and solvent removal in vacuo gave 13.7 mg of the crude aldehyde which was used without further purification.

The crude aldehyde (13.7 mg) in DCM (0.7 mL) at RT was treated with Deoxo-Fluor (54.8 mg, 0.248 mmol) for 16 hrs. The reaction was quenched with sat. $NaHCO_3$ (5 mL) for 20 min, extracted with EtOAc three times; combined organic layer washed with brine, and dried over $MgSO_4$. Filtration and solvent removal followed by prep. TLC purification using 10% MeOH in EtOAc gave 7.5 mg (52%) of the desired difluoride Compound 124 as a yellowish solid. MS: [M+1]=410.

Example 46: Synthesis of Compound 142

142

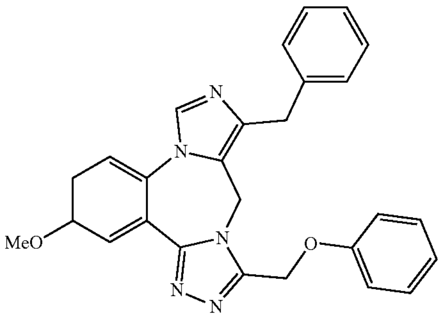

Weinreb amide (8.8 mg, 0.0197 mmol) from above in THF (0.15 mL) at 0° C. was treated with phenylmagnesium bromide (1M THF; 0.54 mL) for 2.5 hrs, quenched with sat. $NH_4Cl$, extracted with EtOAc twice; combined organic layer washed with brine and dried over $MgSO_4$. Filtration and solvent removal gave the crude ketone which was used without further purification. The ketone in THF (0.5 mL) was treated with $NaBH_4$ (6 mg) at RT for 2 hrs., then quenched with sat. $NH_4Cl$, extracted with EtOAc three times; combined organic layer washed with brine, and dried over $MgSO_4$. Filtration and solvent removal gave the crude alcohol which was used without further purification. The thus obtained alcohol in DCM (1.4 mL) was treated with triethylsilane (86.4 mg, 0.75 mmol) and trifluoroacetic acid (171.0 mg, 1.5 mmol) at 40° C. overnight, then concentrated in vacuo, diluted with EtOAc, washed with sat. $NaHCO_3$, brine, and dried over $MgSO_4$. Filtration and solvent removal gave the crude benzyl product which was purified by silica gel column chromatography using 0 to 12% MeOH in EtOAc as eluent; 3.6 mg of Compound 142 was obtained as a yellowish solid. MS: [M+1]=450.

Scheme 19

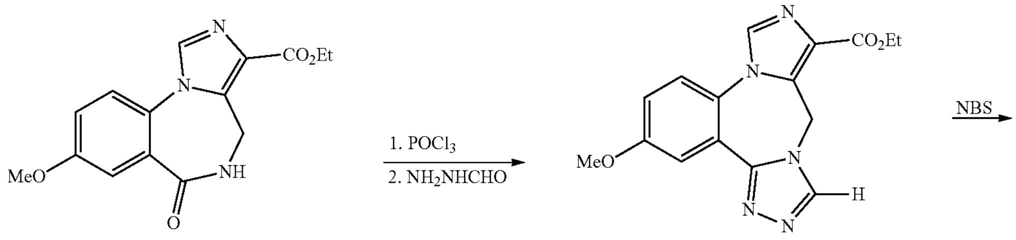

64

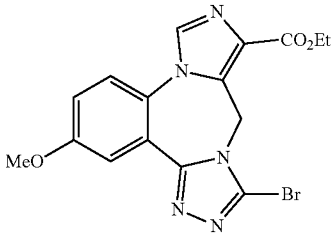

Compound 106

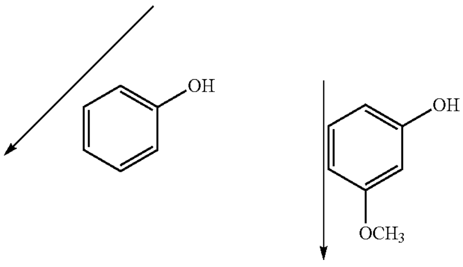

-continued

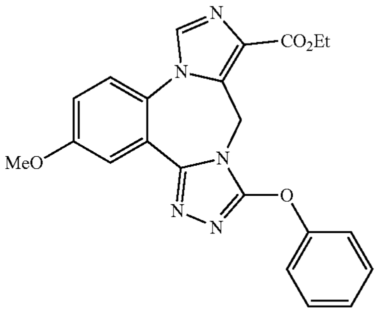

Compound 104

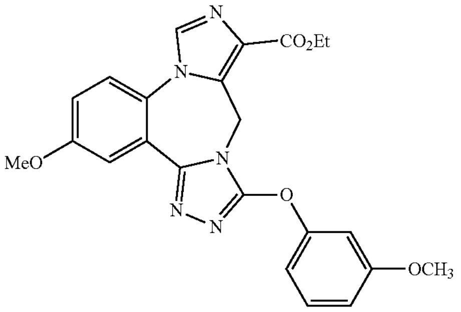

Compound 105

Example 47: Synthesis of Compound 106

106

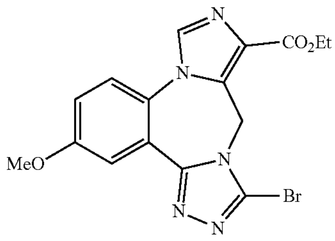

To lactam 64 (185.7 mg, 0.616 mmol) in chlorobenzene (5 mL) was added N,N-dimethyl-p-toluidine (333.3 mg, 2.465 mmol) and phosphorous oxychloride (188.9 mg, 1.232 mmol). The reaction mixture was heated at 135° C. for 2 hrs, cooled to RT, and formylhydrazide (296.0 mg, 4.93 mmol) was added, followed by diisopropyl ethyl amine (238.8 mg, 1.85 mmol). Following 30 min stirring at RT, the reaction was heated at 100° C. for 1 hr., cooled, and sat. $NaHCO_3$ (15 mL) added, extracted with EtOAc twice; combined organic layer washed with brine, and dried over $MgSO_4$. Filtration and solvent removal gave the crude triazole product which was purified by silica gel column chromatography using 0 to 15% MeOH in EtOAc elution, 35.9 mg (18%) was obtained as a brownish solid. MS: [M+1]=326.

The triazole from above in DCM (1 mL) was treated with N-bromosuccinimide (37.6 mg, 0.21 mmol) at 0° C. The reaction was allowed to warm to RT slowly, and proceeded at RT overnight, diluted with EtOAc, washed with sat. $NaHCO_3$, brine, and dried over $MgSO_4$. Filtration and solvent removal gave the crude bromide which was purified by silica gel column chromatography using 0 to 10% MeOH in EtOAc gradient; 22.9 mg (51%) of Compound 106 was obtained as an off-white solid. [MS]: 406.

Example 48: Synthesis of Compound 104

104

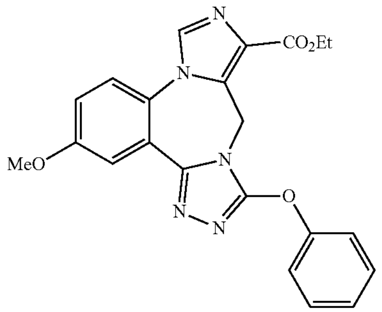

A microwave reaction vessel was charged with phenol (20.3 mg, 0.216 mmol), the bromide substrate from Example 47 (29.1 mg, 0.0719 mmol), $Cs_2CO_3$ (117.0 mg, 0.360 mmol), diethyl 1,3-acetonedicarboxylate (14.5 mg, 0.0719 mmol), and DMF (0.5 ml). The vessel was flushed with nitrogen gas. CuI (6.8 mg, 0.036 mmol) was added, and the mixture was stirred at RT for 5 min before heated @140° C. under MW radiation conditions for 60 min. The reaction mixture was diluted with EtOAc, washed with water; aq. Layer separated and extracted with EtOAc twice: combined organic solution was washed with brine and dried over $MgSO_4$. Filtration and solvent removal gave the crude ether product which was purified by prep. TLC using 5% MeOH in DCM; 6.6 mg of Compound 104 was obtained as a yellowish solid. MS: [M+1]=418.

Example 49: Synthesis of Compound 105

105

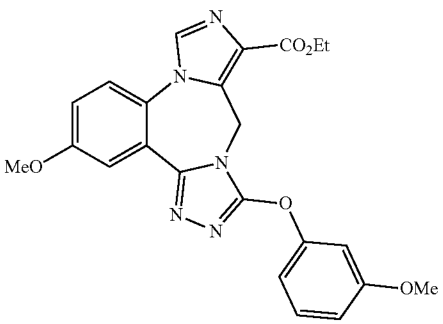

Compound of Example 49 was synthesized in an analogous synthetic route as that described for Example 48 above, using 3-methoxy phenol in the place of phenol, to give the compound of Example 49 as a yellowish foamy solid: MS: [M+1]=448.

To a solution of Compound 2 (160 mg, 0.49 mmol) in THF (6 mL), water (5 mL) and MeOH (1 mL) was added LiOH (59 mg, 2.45 mmol). The solution was stirred at room temperature for 3 h. The solution was concentrated and the crude material was acidified with 1N HCl until pH 3-4. No Scheme 20

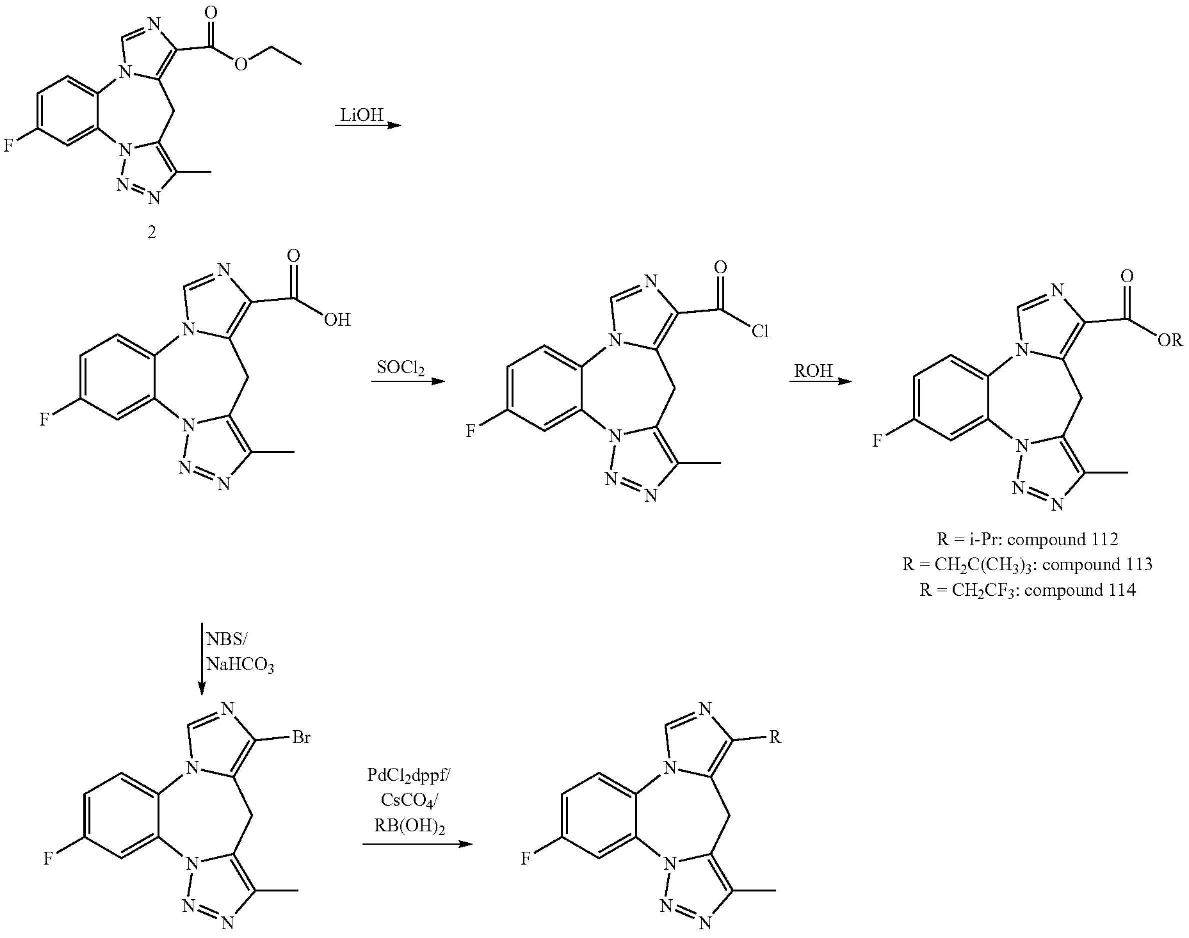

2

R = i-Pr: compound 112
R = $CH_2C(CH_3)_3$: compound 113
R = $CH_2CF_3$: compound 114 compound 136

R = Ph: Compound 139
R = 3-Pyridyl: Compound 140
R = 1-Me-4-Pyrazolyl: Compound 152
R = 2-Me-4-Pyridyl: Compound 154

Example 50: Synthesis of Compound 112

112

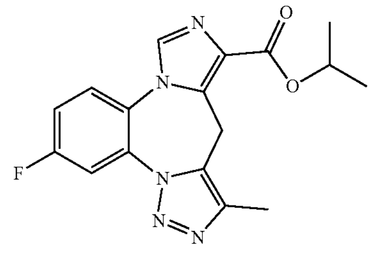

solid was observed. EtOAc was added and the organic phase was extracted (3×). The combined extracts were washed with brine and dried over $MgSO_4$. Filtration and concentration gave 112 mg (77% yield) of the desired carboxylic acid product as an orange solid MS: [M+1]=300.

To a suspension of acid (30 mg, 0.1 mmol) in dichloroethane (0.2 mL) was added thionyl chloride (0.4 mL; 5 mmol) and DMF (20 μL). The resulting solution was heated at 70 C for 1 hour. Another 0.2 mL of thionyl chloride was added and the solution was heated for another 30 min. The solvent was removed. The crude material was dried under vacuo.

The crude acid chloride (0.1 mmol) was suspended in isopropanol and stirred at room temperature for 18 h. The solvent was evaporated and the crude material was purified by chromatography. (RediSep 4 g silica-gel column, eluted with 10% MeOH in DCM) to give 8.6 mg (25% yield) of product Compound 112 [M+1]=342).

$H^1NMR$ ($CDCl_3$) δ 7.90 (1H, d, J=9 Hz), 7.79 (1H, bs), 7.63 (1H, bs), 7.36 (1H, bs), 3.48 (1H, m), 2.45 (3H, s), 1.43 (6H, d, J=6.5 Hz).

Example 51: Synthesis of Compound 113

113

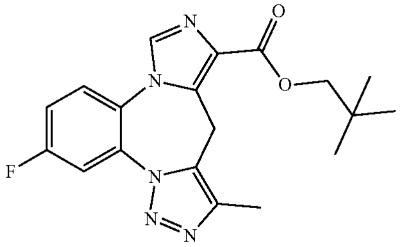

The crude acid chloride prepared above (0.066 mmol) was suspended in dichloroethane (1 mL) and 2,2-dimethyl-1-propanol (300 mg, 3.4 mmol) was added. The solution was stirred at room temperature for 18 h. No product was formed. To the solution above, was added DMAP (5 mg, 0.004 mmol) and DCC (15 mg, 0.073 mmol). The solution was stirred at room temperature for 2 h. The reaction mixture was directly applied on a prep TLC (eluting system: 75 EtOAc in Hexanes) to give 7.2 mg (30% yield) of product Compound 113. MS: [M+1]=370. $H^1NMR$ ($CDCl_3$) δ 7.91 (1H, dd, J=3, 9 Hz), 7.79 (1H, s), 7.61 (1H, dd, J=4.5, 9 Hz), 7.35 (1H, m), 4.11 (2H, s), 2.44 (3H, s), 1.07 (9H, s).

Example 52: Synthesis of Compound 114

114

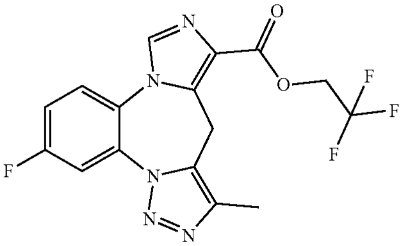

The crude acid chloride prepared above (0.066 mmol) was suspended in dichloroethane (1 mL) and 2,2,2-trifluoroethanol (0.1 mL, 1.4 mmol) followed by triethylamine (0.6 mL, 4.3 mmol) was added. The solution was stirred at room temperature for 2 h 30 min. The solvent was evaporated and the crude material was purified by chromatography. (RediSep 4 g silica-gel column, eluted with EtOAc) then purified with a prep TLC (eluting system: 70% EtOAc in Hexanes) to give 8.1 mg (32% yield) of product Compound 114 [M+1]=382).

$H^1NMR$ ($CDCl_3$) δ 7.91 (1H, dd, J=3.5, 9.5 Hz), 7.83 (1H, s), 7.63 (1H, dd, J=4.5, 9.5 Hz), 7.35 (1H, m), 4.77 (2H, m), 2.43 (3H, s).

Example 53: Synthesis of Compound 136

136

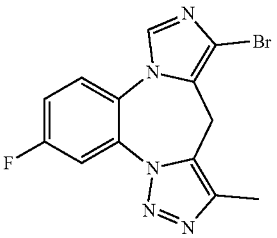

To a solution of acid prepared in Example 50 (100 mg, 0.33 mmol) in DMF (1.5 mL) cooled with an ice bath was added $NaHCO_3$ (111 mg, 1.32 mmol) followed by NBS (117 mg, 0.66 mmol). The solution was stirred at room temperature for 14 h. The reaction mixture was diluted with water and extracted with EtOAc (5×). The combined extracts were washed with brine (2×) and dried over $MgSO_4$. Filtration and concentration gave a crude product. Chromatography (RediSep 4 g silica-gel column, eluted with EtOAc) to give 93 mg (85% yield) of product Compound 136 [M+1]=334). $H^1NMR$ ($CDCl_3$) δ 7.87 (1H, dd, J=2.5, 8.5 Hz), 7.72 (1H, s), 7.56 (1H, dd, J=6, 10 Hz), 7.33 (1H, m), 2.44 (3H, s).

Example 54 Synthesis of Compound 139

139

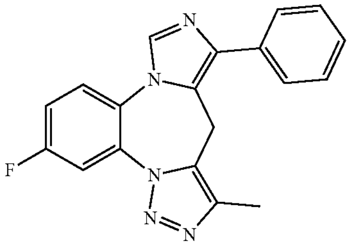

General coupling procedure: To a solution of Compound 136 (20 mg, 0.061 mmol) in degassed DME (0.9 mL) and water (0.1 mL) was added phenyl boronic acid (11 mg, 0.092 mmol), cesium carbonate (80 mg, 0.24 mmol) and Pd $Cl_2$dppf (5 mg, 0.066 mmol). The suspension was heated at 80° C. for one hour. The reaction mixture was diluted with water, extracted with EtOAc (3×). The combined extracts were washed with brine (2×) and dried over $MgSO_4$. Filtration and concentration gave a crude product which was purified by prep TLC (eluting system: 3% MeOH in EtOAc).

Compound 139 was prepared using phenyl boronic acid. 10.8 mg (54% yield) of product was obtained. MS: [M+1]=332. $H^1NMR$ ($CDCl_3$) δ 7.87 (1H, dd, J=3.5, 9.5 Hz), 7.85 (1H, s), 7.63 (3H, m), 7.50 (2H, t, J=6.5 Hz), 7.35 (2H, m), 2.41 (3H, s).

Example 55: Synthesis of Compound 140

140

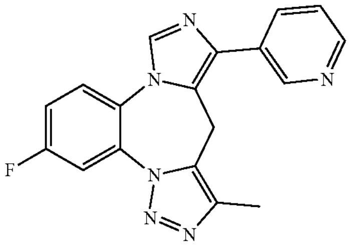

Compound 140 was prepared similarly using 3-pyridine boronic acid. 8.9 mg (27% yield) of product was obtained. MS: [M+1]=333. H[1]NMR ($CDCl_3$) δ 8.86 (1H, s), 8.63 (1H, d, J=5 Hz), 8.01 (1H, m), 7.90 (2H, m), 7.64 (1H, dd, J=5.5, 9 Hz), 7.44 (1H, m), 7.36 (1H, m), 2.39 (3H, s).

Example 56: Synthesis of Compound 152

152

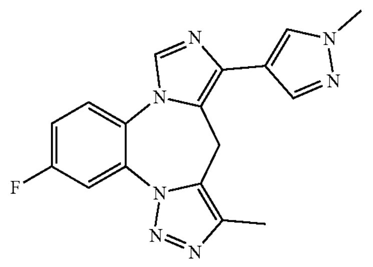

Compound 152 was prepared using 1-methylpyrazole-4-boronic acid, HCl. 12.5 mg (63% yield) of product was obtained. MS: [M+1]=336. H[1]NMR ($CDCl_3$+$MeOD_4$) δ 9.04 (1H, bs), 7.99 (1H, bs), 7.75 (2H, m), 7.41 (2H, m), 3.95 (3H, s), 2.32 (3H, s).

Example 57: Synthesis of Compound 154

154

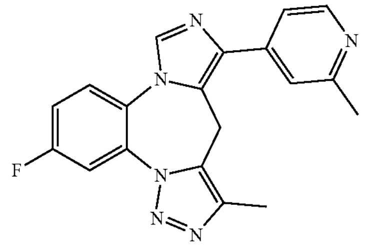

Compound 154 was prepared using 2-methylpyridine-4-boronic acid pinacol ester. 7.1 mg (34% yield) of product was obtained. MS: [M+1]=347. H[1]NMR ($CDCl_3$) δ 8.6 (1H, d, J=6 Hz), 7.89 (1H, dd, J=3.5, 8.5 Hz), 7.87 (1H, s), 7.64 (1H, dd, J=5.5, 9 Hz), 7.48 (1H, s), 7.36 (2H, m), 2.64 (3H, s), 2.41 (3H, s).

Scheme 21

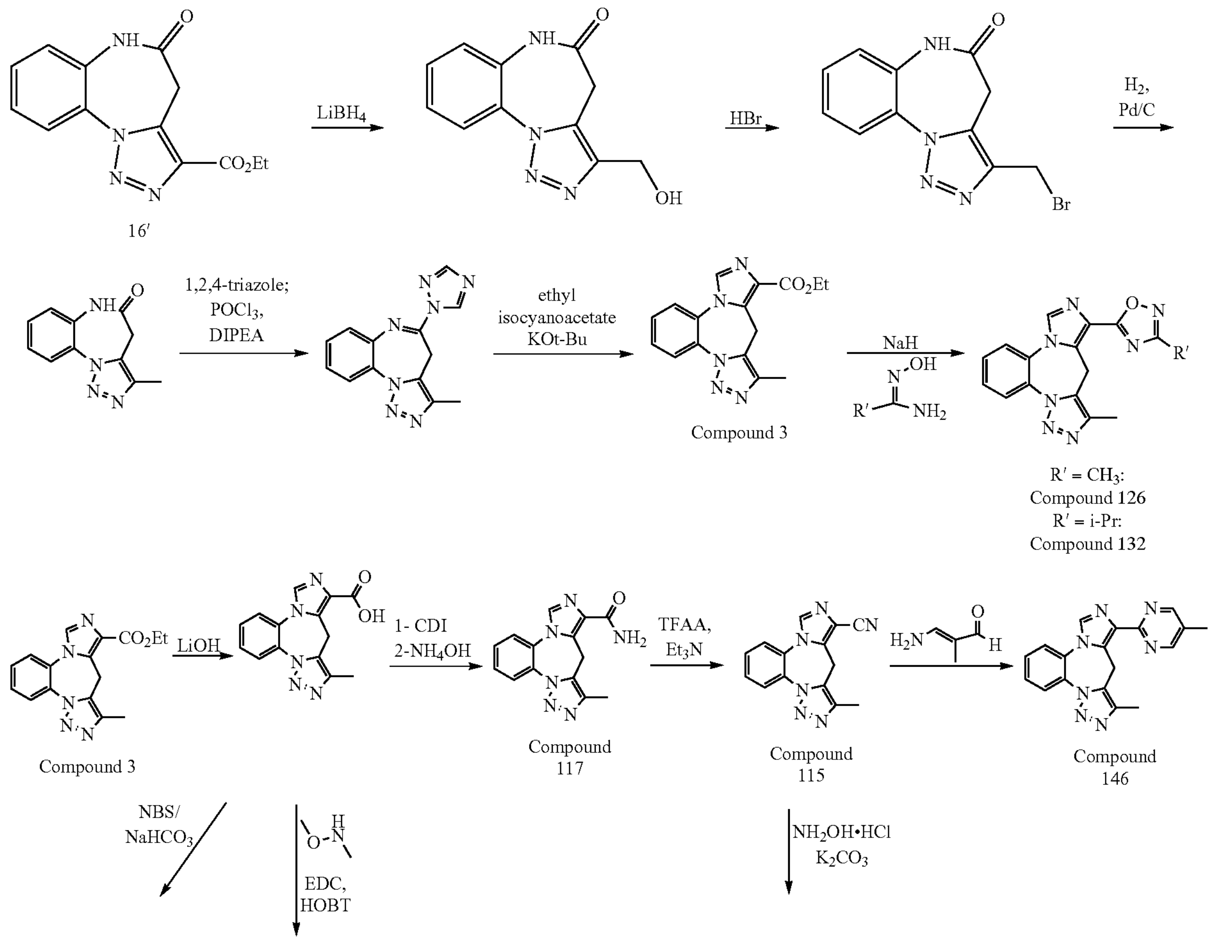

-continued

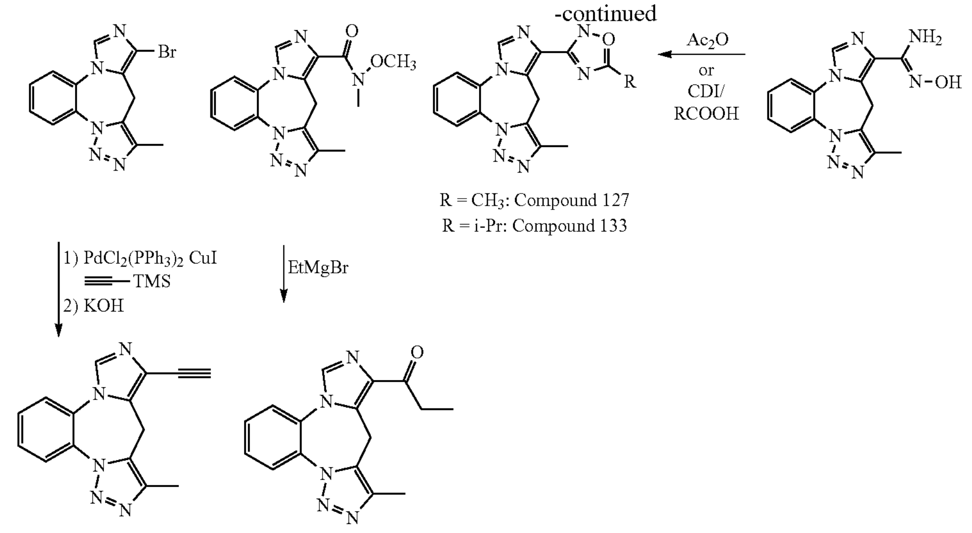

R = $CH_3$: Compound 127
R = i-Pr: Compound 133

Compound 161

Compound 125

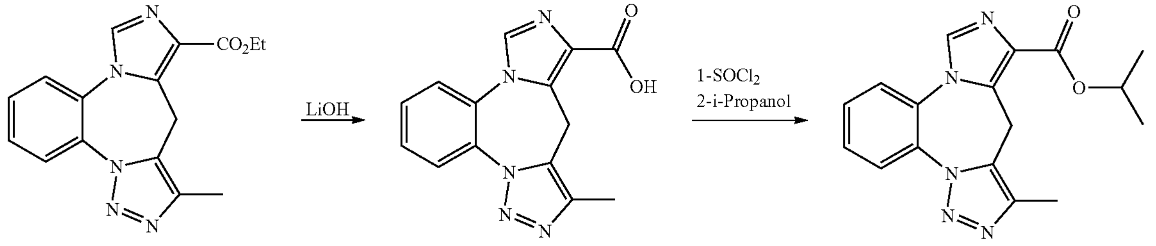

Compound 3

Compound 153

Example 58: Synthesis of Compound 117

117

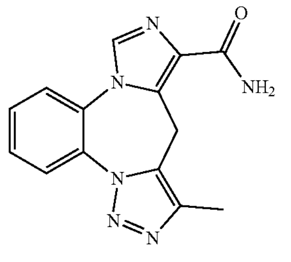

In a 100 mL round-bottom flask, the lactam ester 16'(2 g, 7.35 mmol; which was prepared in analogous fashion as 16 described in Scheme 11) was dissolved in 60 mL of anhydrous THF. The solution was stirred at room temperature under a nitrogen atmosphere. $LiBH_4$ (2 M in THF, 4 mL, 8 mmol) was added slowly. The reaction mixture was stirred under a nitrogen atmosphere for 18 h. More $LiBH_4$ (2 M in THF, 2 mL, 4 mmol) was added slowly. The reaction mixture was stirred for another 24 h. A mixture of EtOAc/EtOH (20 mL/20 mL) was added to the reaction mixture and it was concentrated. The residue was taken up in MeOH and silica gel was added. After volatile solvents were evaporated, the solid was loaded onto a RediSep 40 g silica-gel column. The desired product was eluted with 5:1 v/v $CH_2Cl_2$/MeOH. The alcohol was obtained as a white solid (1.14 g, 67% yield). MS: [M+1]=231.

The alcohol (1.14 g, 4.96 mmol) was suspended in 16 mL of HBr 33% in AcOH and heated at 80° C. for 18 h. The solution was cooled down with an ice bath and diluted with EtOAc. A white solid could be observed. Slowly, a sat. aq. $NaHCO_3$ solution was added. Large amount of EtOAc and MeOH were used to solubilize the solid. The organic phase was extracted (3×) and the combined organic phases were washed with brine, dried over $MgSO_4$. Filtration and concentration gave a crude product which was used in the next step without further purification. MS: [M+1]- 293.

To a solution of alkyl bromide derivative (4.96 mmol) in EtOAc (50 mL), MeOH (200 mL) and THF (50 mL) was added wet 10% Pd/C (250 mg) and the resulting suspension was stirred under a hydrogen atmosphere for 7 days. The suspension was filtered through Celite and the resulting solution was concentrated and co-evaporated with toluene. The crude product was used in the next step without further purification.

To a solution of 1,2,4-triazole (2.7 g, 39.7 mmol) in anhydrous $CH_3CN$ (20 mL) at 0° C. was added i-$Pr_2NEt$ (7.6 mL, 43.6 mmol). Once all the triazole was dissolved, $POCl_3$ (1.11 mL, 11.9 mmol) was added. The mixture was stirred at 0° C. for 2 h. The solution was transferred into the flask containing the lactam (4.96 mmol). The resulting solution was heated in an oil bath at 80° C. for 16 h. The viscous mixture was cooled with an ice bath and the solvent evaporated. Diluted with EtOAc and water was added. It was extracted with EtOAc five times. The combined extracts were washed with brine and dried over $MgSO_4$. Filtration and concentration gave a crude product, which was used directly in the next reaction. MS: [M+1]=266.

A solution of KOtBu (1.11 g, 9.92 mmol) in DMF (10 mL) was cooled to −50° C. under a nitrogen atmosphere. Ethyl isocyanoacetate (1.2 mL, 10.9 mmol) was added slowly. The mixture was stirred between −60° C. to −40° C. for 1 h. The above crude 1,2,4-triazolo intermediate from step 4 (4.96 mmol) in DMF (5 mL) was added slowly. The mixture was allowed to warm to room temperature over 16 h. Saturated $NH_4Cl$ aqueous solution was added and it was extracted with EtOAc three times. The combined extracts were washed with brine (3×) and dried over $MgSO_4$. Filtration and concentration gave a crude product. Chromatography (RediSep 24 g silica-gel column, eluted with 70% EtOAc in Hexanes) to give 296 mg (20% yield for 4 steps) of product. MS: [M+1]=310.

To a solution of ester derivative (260 mg, 0.84 mmol) in THF (6 mL), water (5 mL) and MeOH (1 mL) was added LiOH (117 mg, 4.85 mmol). The solution was stirred at room temperature for 3 h. The solution was concentrated and the crude material was acidified with 1N HCl until pH 3-4. The solid was collected by multiple filtrations to give 178 mg (75% yield) of the desired product. MS: [M+1]=282.

To a suspension of acid (80 mg, 0.28 mmol) in THF (2 mL) was added CDI (50 mg, 0.31 mmol). The suspension was heated at 65 C for 3 h. LCMS indicated that the reaction was incomplete. More CDI (10 mg) was added and the solution heated for another hour. The solution was cooled down to room temperature and a $NH_4OH$ solution (1 mL) was added. The solution was stirred for one hour. The solid was collected by filtration to give 33 mg (42%) of the Compound 117 as the desired product as a white solid. MS: [M+1]=281. $H^1NMR$ ($MeOD_4$) δ 8.1 (1H, s), 7.9 (1H, s), 7.73 (3H, m), 7.07 (2H, s), 2.40 (3H, s).

Example 59: Synthesis of Compound 115

115

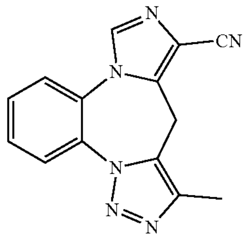

To a suspension of Compound 117 (8 mg, 0.029 mmol) and triethylamine (8 μL; 0.058 mmol) in THF (1 mL) was added trifluoroacetic anhydride (8 μL; 0.058 mmol). The reaction mixture was stirred at room temperature for 16 h. LCMS indicated only 30% conversion. More trifluoroacetic anhydride (30 μL) and triethylamine (30 μL) were added. The solution became clear and stirred for another hour. The reaction was quenched with MeOH. The solvent was evaporated and the crude material was purified by prep TLC (eluting system: 70% EtOAc in Hexanes) to give 6.6 mg (83%) of the Compound 115. MS: [M+1]- 263. $H^1NMR$ ($CDCl_3$) δ 8.17 (1H, d, J=7 Hz), 7.88 (1H, s), 7.67 (3H, in), 2.46 (3H, s).

Example 60: Synthesis of Compound 127

127

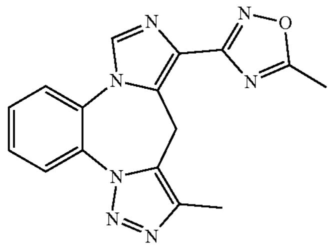

To a suspension of Compound 115 (16 mg, 0.06 mmol) in EtOH (0.8 mL) and water (0.2 mL) was added hydroxylamine hydrochloride (6 mg, 0.09 mmol) and potassium carbonate (12 mg, 0.09 mmol). The suspension was heated at 80° C. for 16 h. The solution was diluted with EtOAc and washed with water. Aq. Layer was separated and extracted with EtOAc (3×). The combined organic phases were washed with brine, dried over $MgSO_4$. Filtration and concentration gave 12.2 mg (67% yield) of the desired product. MS: [M+1]=296.

A suspension of oxime (10 mg, 0.034 mmol) in acetic anhydride (0.5 mL) was heated at 110 C for 1 hour. Then, the solution was heated at 130 C for 1 hour. Finally, the temperature was increased to 140° C. and heated for another 2 h. The reaction mixture was cooled down and EtOH (1 mL) was added to the reaction mixture which was heated for 16 h at 80° C. The solvent was evaporated and the crude material was purified by prep TLC (eluting system: EtOAc) to give 6.1 mg (56% yield) of the desired product Compound 127. MS: [M+1]=320). $H^1NMR$ ($CDCl_3$) δ 8.16 (1H, m), 7.92 (1H, s), 7.65 (3H, m), 2.68 (3H, s), 2.46 (3H, s).

Example 61: Synthesis of Compound 133

133

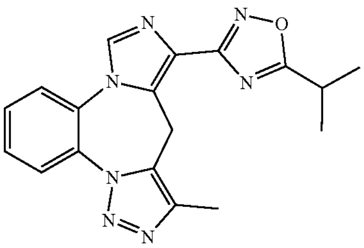

To a solution of isobutyric acid (19 μL, 0.2 mmol) in THF (0.5 mL) was added CDI (10 mg, 0.062 mmol). The solution was stirred at room temperature for 2 h. The solution was then transferred into a vial containing the oxime derivative described above (12 mg, 0.041 mmol) and heated at 70° C. for 2 h. LCMS indicated that the reaction was incomplete. Another batch of reagent (isobutyric acid and CDI) was prepared and added to the reaction mixture which was heated at 70° C. for another hour. LCMS indicated that all starting material was consumed. The solvent was evaporated and the crude material was suspended in isobutyric acid (1 mL) and heated at 130° C. for one hour. The solvent was evaporated and the crude material was purified by Prep TLC (eluting system: 70% EtOAc in Hexanes) to give 6.7 mg (71%) of the desired product Compound 133. MS: [M+1]=348.

$H^1NMR$ ($CDCl_3$) δ 8.16 (1H, m), 7.92 (1H, s), 7.65 (3H, m), 3.32 (1H, m), 2.46 (3H, s), 1.5 (6H, d, J=7 Hz).

Example 62: Synthesis of Compound 126

126

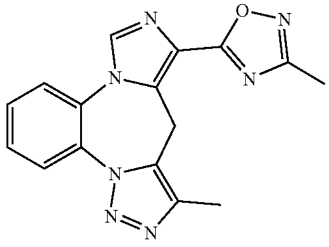

Acetamide oxime was azeotroped three times in toluene before use. To a suspension of acetamide oxime (24 mg, 0.32 mmol) in THF (1 mL) was added NaH 60% in oil dispersion (13 mg, 0.32 mmol). The suspension was stirred at room temperature for 15 min. Compound 3 (50 mg, 0.16 mmol) was added. The vial containing the ester was rinsed with DMF (1 mL) which was added to the reaction mixture. The resulting brown suspension was stirred at room temperature for 30 min then heated at 70° C. for 2 h. The suspension was quenched with water and the solution was kept in the fridge overnight. The solid was collected by multiple filtrations to give 16 mg (31% yield) of product Compound 126. MS: [M+1]=320. $H^1NMR$ ($CDCl_3$) δ 8.18 (1H, m), 7.94 (1H, s), 7.67 (3H, m), 2.51 (3H, s), 2.46 (3H, s).

Example 63: Synthesis of Compound 125

125

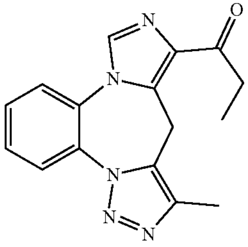

To a suspension of the carboxylic acid derived from Compound 3 (30 mg, 0.11 mmol), N,O-dimethylhydroxylamine hydrochloride (13 mg, 0.13 mmol), 1-hydroxybenzotriazole hydrate (17 mg, 0.11 mmol) and triethylamine (46 μL, 0.33 mmol) in THF (0.3 mL) and DCM (0.3 mL) was added 1-(3-dimethylaminopropyl)-3-ethylcarbodiimide hydrochloride (32 mg, 0.17 mmol). The solution was stirred at room temperature for 16 h. The reaction mixture was quenched with a saturated ammonium chloride solution and extracted with EtOAc (3×). The combined extracts were washed with brine and dried over $MgSO_4$. Filtration and concentration gave 31.2 mg (88% yield) of an orange solid which was used in the next step without further purification. MS: [M+1]=325.

To a solution of above Weinreb amide derivative (31.2 mg, 0.093 mmol) in THF (0.5 mL) cooled at −78° C. was added a solution of 3 M ethyl magnesium bromide (0.31 mL, 0.93 mmol). The reaction mixture was stirred below −10° C. over a period of 60 min. Then, it was quenched with a saturated ammonium chloride solution and extracted with EtOAc (2×). The combined extracts were washed with brine and dried over $MgSO_4$. Filtration and concentration gave a crude product. Chromatography (RediSep 4 g silica-gel column, eluted with 80% EtOAc in Hexanes) to give 11.1 mg (410% yield) of product Compound 125. MS: [M+1]=294. $H^1NMR$ ($CDCl_3$) δ 8.15 (1H, m), 7.76 (1H, s), 7.65 (3H, m), 3.08 (2H, q, J=7 Hz), 2.44 (3H, s), 1.22 (3H, t, J=7 Hz).

Example 64: Synthesis of Compound 132

132

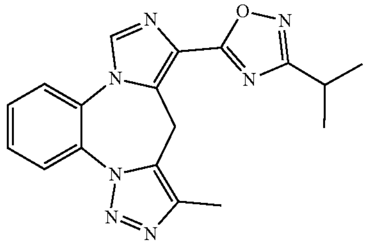

To a solution of isobutyronitrile (2.6 mL; 29 mmol) in EtOH (30 mL) and water (10 mL) was added hydroxylamine hydrochloride (2.01 g, 29 mmol) and potassium carbonate (4 g, 29 mmol). The resulting suspension was heated at 80° C. for 16 h. The solvent was removed under vacuo. The residue was co-evaporated with toluene. The crude material was washed with EtOH and filtered to remove the sodium chloride. The filtrate was evaporated, co-evaporated with toluene several times and dried under vacuo to give 2 g (69%) of N-hydroxybutyramidine.

To a suspension of N-hydroxybutyramidine (47 mg, 0.46 mmol) in THF (1 mL) was added NaH 60% in oil dispersion (18 mg, 0.46 mmol). The suspension was stirred at room temperature for 30 min. Compound 3 (47 mg, 0.15 mmol) in THF (1 mL) was added. The resulting suspension was stirred at room temperature for 30 min then heated at 70° C. for 2 h. After one hour, only 50% conversion was observed. No change was observed after another hour. More reagent (N-hydroxybutyramidine and NaH) as described above was prepared and added to the reaction mixture which was heated for another 40 min. At this point, LCMS showed that the reaction was complete. The suspension was quenched with water. Some MeOH was added to help a complete dissolution, and the solution was extracted with EtOAc (3×). The combined extracts were washed with brine (3×) and dried over $MgSO_4$. Filtration and concentration gave a crude product. Chromatography (RediSep 4 g silica-gel column, eluted with EtOAc) to give 20 mg (38% yield) of product Compound 132. MS: [M+1]=348. $H^1NMR$ ($CDCl_3$) δ 8.18 (1H, d, J=8 Hz), 7.93 (1H, s), 7.69 (3H, m), 3.22 (1H, m), 2.46 (3H, s), 1.43 (6H, d, J=9.5 Hz)

Example 65: Synthesis of Compound 161

161

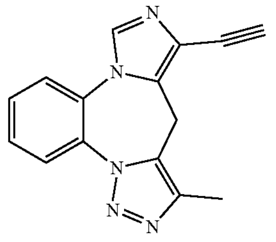

To a solution of acid derived from Compound 3 (90 mg, 0.32 mmol) in DMF (2 mL) cooled with an ice bath was added $NaHCO_3$ (108 mg, 1.28 mmol) followed by NBS (114 mg, 0.64 mmol). The solution was stirred at room temperature for 18 h. The reaction mixture was diluted with water and extracted with EtOAc (3×). The combined extracts were washed with brine (2×) and dried over $MgSO_4$. Filtration and concentration gave a crude product. Chromatography (RediSep 4 g silica-gel column, eluted with EtOAc) to give 54 mg (53% yield) of product. MS: [M+1]=316.

To a solution of bromide derivative (30 mg, 0.1 mmol) in dioxane (1 mL) and triethylamine (1 mL) was added TMS-acetylene (71 μL, 0.5 mmol), Cut (2 mg, 0.01 mmol) and $PdCl_2(PPh_3)_2$ (7 mg, 0.01 mmol). The solution was heated at 110° C. for 6 h. More Pd catalyst (7 mg) and TMS-acetylene (0.2 mL) were added and the reaction mixture heated for an additional 12 h. At this time, LCMS showed about 80% conversion. More Pd catalyst (7 mg) and TMS-acetylene (0.2 mL) were added and the reaction mixture heated for an additional 12 h. LCMS showed complete conversion. The reaction mixture was then diluted with water and extracted with EtOAc (3×). The combined extracts were washed with brine (2×) and dried over $MgSO_4$. Filtration and concentration gave a crude product. Chromatography (RediSep 4 g silica-gel column, eluted with 70% EtOAc in Hexanes) to give 23 mg (69% yield) of product. MS: [M+1]=334.

To a solution of alkyne derivative (23 mg, 0.069 mmol) in MeOH (0.6 mL) and $H_2O$ (0.2 mL) was added KOH (4 mg, 0.076 mmol) at 0 C. The solution was let warm to room temperature over 16 h. The reaction mixture was diluted with a saturated aqueous ammonium chloride solution and extracted with EtOAc (2×). The combined extracts were washed with brine (2×) and dried over $MgSO_4$. Filtration and concentration gave a crude product which was purified by prep TLC (eluting system: 80% EtOAc in Hexanes) to give 8.1 mg (45% yield) of product Compound 161. MS: [M+1]- 262. $H^1NMR$ ($CDCl_3$) δ 8.13 (1H, m), 7.76 (1H, s), 7.62 (3H, m), 4.09 (2H, bs), 3.28 (1H, s), 2.44 (3H, s).

Example 66: Synthesis of Compound 146

146

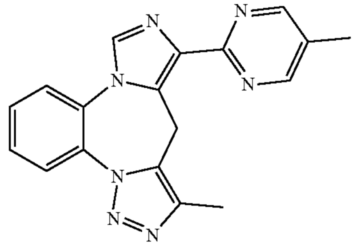

To a solution of 3-amino-2-methylacrolein (65 mg, 0.76 mmol) in anhydrous THF (2 mL) was added NaH 60% in oil dispersion (30 mg, 0.76 mmol). The suspension was stirred at room temperature for 15 min. Compound 115 (50 mg, 0.19 mmol) was added and the reaction mixture was heated at 65° C. for 3 h. The reaction mixture was cooled down with an ice bath and water was added. The reaction mixture was stored in the fridge overnight. The solid was collected by filtration to give 27.5 mg (44% yield) of a white solid Compound 146. MS: [M+1]- 330. $H^1NMR$ ($CDCl_3$) δ 8.66 (2H, s), 8.15 (1H, m), 7.89 (1H, s), 7.65 (3H, m), 2.44 (3H, s), 2.36 (3H, s).

Example 67: Synthesis of Compound 153

153

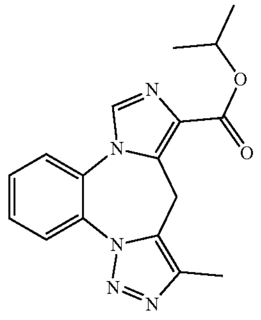

To a suspension of acid derived from Compound 3 (30 mg, 0.11 mmol) in dichloroethane (0.2 mL) was added thionyl chloride (1 mL; 13.8 mmol) and DMF (20 μL). The resulting solution was heated at 70° C. for 1 hour. The solvent was removed. The crude material was dried under vacuo. The crude material was suspended in isopropanol (2 mL) and stirred at room temperature for 16 h. The solvent was evaporated, co-evaporated with methanol and the crude material was purified by prep TLC (eluting system: EtOAc) to give 7.2 mg (21% yield) of the product Compound 153. MS: [M+1]=324. $H^1NMR$ ($CDCl_3$) δ 8.15 (1H, d, J=8 Hz), 7.81 (1H, s), 7.64 (3H, m), 5.32 (1H, q, J=7 Hz), 2.45 (3H, s), 1.43 (6H, d, J=7 Hz).

Scheme 22
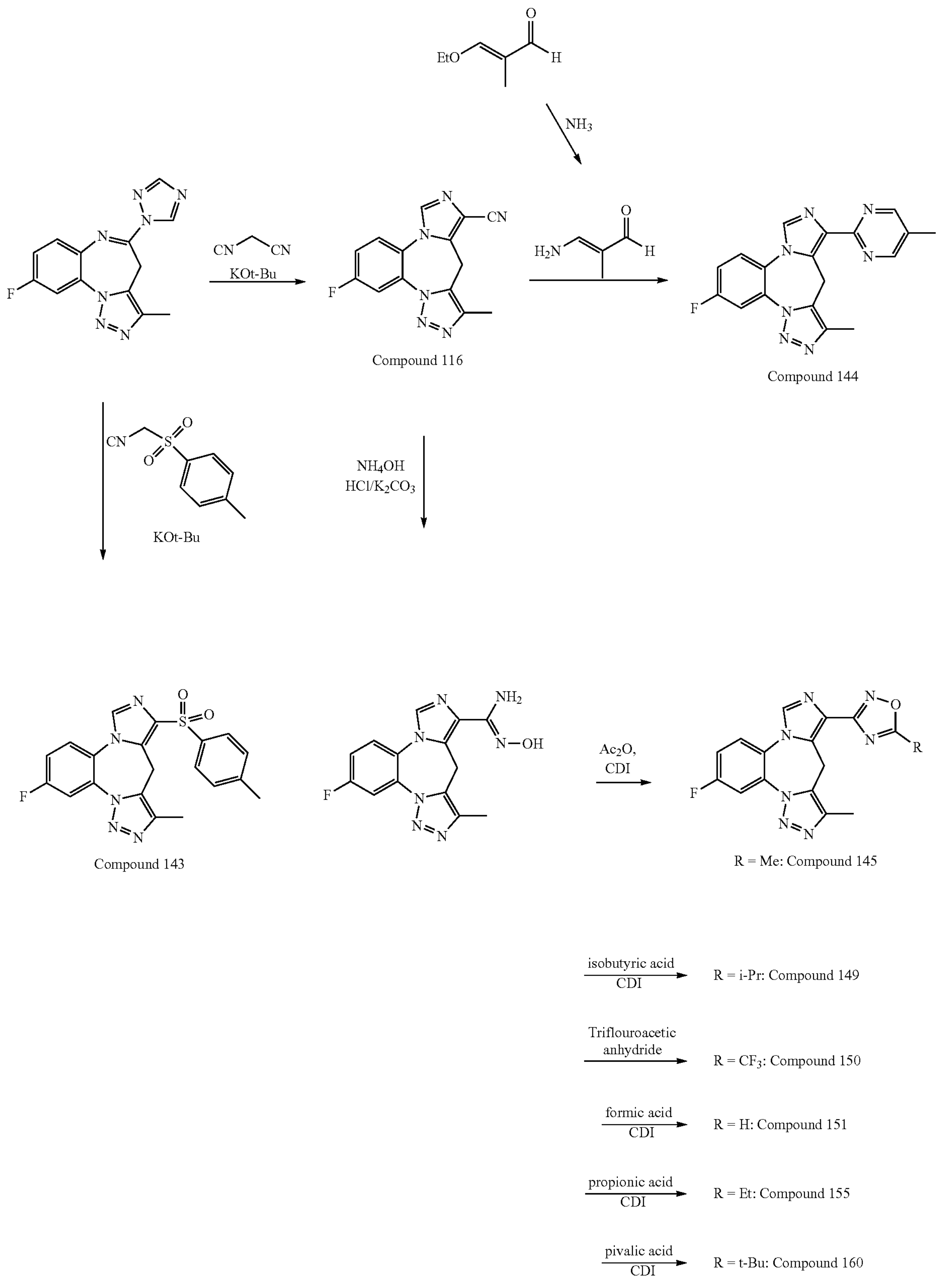
Compound 116
Compound 144
Compound 143
R = Me: Compound 145
R = i-Pr: Compound 149
R = $CF_3$: Compound 150
R = H: Compound 151
R = Et: Compound 155
R = t-Bu: Compound 160

Example 68: Synthesis of Compound 116

116

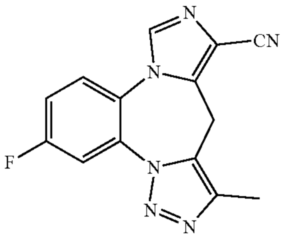

An alternate route to the nitrile-substituted imidazole derivatives was also implemented. As an example, Compound 116 was prepared from imino-derivative as shown in Scheme 22. A solution of isocyanoacetonitrile (206 mg, 3.12 mmol) in DMF (7 mL) was cooled to −50° C. under a nitrogen atmosphere. KOtBu (320 mg, 2.85 mmol) was added. The mixture was stirred at −50° C. for 1 h. The imino derivative (prepared in identical fashion to the imino derivative shown above in Scheme 21) (350 mg, 1.24 mmol) was added slowly at −50° C. The mixture was allowed to warm to room temperature over 16 h. Saturated $NH_4Cl$ aqueous solution was added and it was extracted with EtOAc three times. The combined extracts were washed with brine (3×) and dried over $MgSO_4$. Filtration and concentration gave a crude product. Chromatography (RediSep 12 g silica-gel column, eluted with 70% EtOAc in Hexanes) to give 230 mg (70% yield) of the product Compound 116. MS: [M+1]=281. $H^1NMR$ ($CDCl_3$) δ 7.92 (1H, dd, J=3, 8.5 Hz), 7.81 (1H, s), 7.61 (1H, dd, J=4.5, 9 Hz), 7.38 (1H, m), 2.47 (3H, s).

Example 69: Synthesis of Compound 145

145

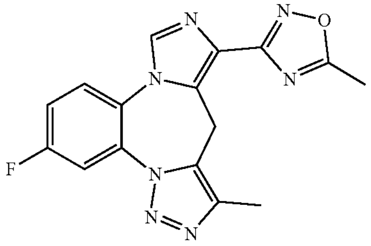

To a suspension of cyanide derivative Compound 116 (50 mg, 0.18 mmol) in EtOH (1.6 mL) and water (0.4 mL) was added hydroxylamine hydrochloride (17 mg, 0.24 mmol) and potassium carbonate (28 mg, 0.2 mmol). The suspension was heated at 80° C. for 30 min then cooled down to room temperature. A solid precipitate was collected by filtration to give 37.8 mg (68% yield) of the desired amino oxime product, [M+1]=314.

A suspension of amide oxime (10 mg, 0.032 mmol) in acetic anhydride (0.5 mL) was heated at 140 C for 4 h. The reaction mixture was cooled down and EtOH (1 mL) was added to the reaction mixture which was heated for 16 h at 80° C. The solvent was evaporated and the crude material was purified by prep TLC (eluting system: EtOAc) to give 6.6 mg (61% yield) of the desired product Compound 145. MS: [M+1]=338. $H^1NMR$ ($CDCl_3$) δ 7.91 (1H, dd, J=3.5, 8.5 Hz), 7.89 (1H, s), 7.65 (1H, dd, J=5.5, 10 Hz), 7.35 (1H, m), 2.69 (3H, s), 2.45 (3H, s).

Example 70: Synthesis of Compound 149

149

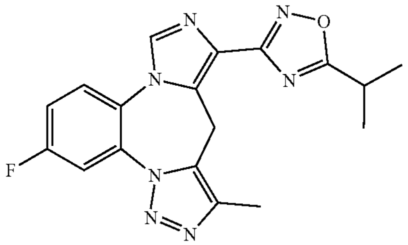

To a solution of isobutyric acid (30 μL, 0.32 mmol) in THF (0.5 mL) was added CDI (16 mg, 0.096 mmol). The solution was stirred at room temperature for 2 h. The above amide oxime derivative (10 mg, 0.032 mmol) was added and the reaction mixture was heated at 70 C for 45 min. The solvent was evaporated and the crude material was suspended in isobutyric acid (1 mL) and heated at 130° C. for 3 h. The solvent was evaporated and the crude material was purified by Prep TLC (eluting system: 80% EtOAc in Hexanes) to give 10.6 mg (91%) of the desired product Compound 149. MS: [M+1]- 366. $H^1NMR$ ($CDCl_3$) δ 7.90 (1H, dd, J=3.5, 9 Hz), 7.89 (1H, s), 7.66 (1H, dd, J=4.5, 8.5 Hz), 7.36 (1H, m), 3.32 (1H, q, J=6.5 Hz), 2.46 (3H, s), 1.49 (6H, d, J=8 Hz).

Example 71: Synthesis of Compound 150

150

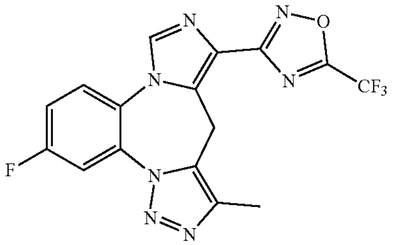

A suspension of the above amide oxime (10 mg, 0.032 mmol) in trifluoroacetic anhydride (0.5 mL) was heated under reflux for 10 min. The solvent was evaporated and the crude material was purified by Prep TLC (eluting system: 80% EtOAc in Hexanes) to give 11.8 mg (94%) of the desired product Compound 150. MS: [M+1]=392. $H^1NMR$ ($CDCl_3$) δ 7.92 (2H, m), 7.69 (1H, dd, J=5.5, 9.5 Hz), 7.39 (1H, m), 2.45 (3H, s).

Example 72: Synthesis of Compound 151

151

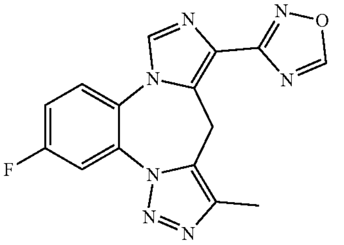

To a solution of formic acid (12 μL, 0.32 mmol) in THF (0.5 mL) was added CDI (16 mg, 0.096 mmol). The solution was stirred at room temperature for 2 h. The above amide oxime derivative (10 mg, 0.032 mmol) was added and the reaction mixture was heated at 70° C. for 45 min. The solvent was evaporated and the crude material was suspended in formic acid (1 mL) and heated at 60° C. for 3 h. The solvent was evaporated and the crude material was purified by Prep TLC (eluting system: 80% EtOAc in Hexanes) to give 2.1 mg (20%) of the desired product Compound 151. MS: [M+1]=324. $H^1NMR$ ($CDCl_3$) δ 8.83 (1H, s), 7.92 (1H, dd, J=3.5, 8 Hz), 7.91 (1H, s), 7.65 (1H, dd, J=4.5, 9 Hz), 7.37 (1H, m), 2.45 (3H, s).

Example 73: Synthesis of Compound 155

155

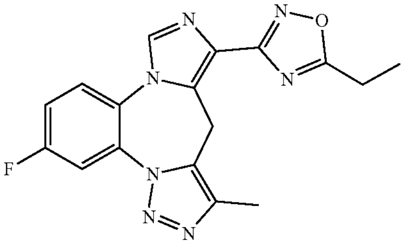

To a solution of propionic acid (22 μL, 0.29 mmol) in THF (0.5 mL) was added CDI (14 mg, 0.087 mmol). The solution was stirred at room temperature for 1 hour. The above amide oxime derivative (10 mg, 0.032 mmol) in THF (0.5 mL) was added and the reaction mixture was heated at 70° C. for 90 min. The solvent was evaporated and the crude material was suspended in propionic acid (1 mL) and heated at 130° C. for 1 h. The solvent was evaporated and the crude material was purified by Prep TLC (eluting system: 80% EtOAc in Hexanes) to give 9.4 mg (94%) of the desired product Compound 155. MS: [M+1]- 352. $H^1NMR$ ($CDCl_3$) δ 7.91 (1H, dd, J=2, 8.5 Hz), 7.88 (1H, s), 7.65 (1H, dd, J=6, 9.5 Hz), 7.36 (1H, m), 3.01 (2H, q, J=8.5 Hz), 2.46 (3H, s), 1.48 (3H, t, J=8.5 Hz).

Example 74: Synthesis of Compound 160

160

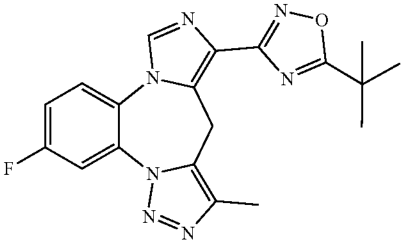

To a solution of pivalic acid (30 mg, 0.29 mmol) in THF (0.5 mL) was added CDI (14 mg, 0.087 mmol). The solution was stirred at room temperature for 1 hour. The above amide oxime derivative (10 mg, 0.032 mmol) in THF (0.5 mL) was added and the reaction mixture was heated at 70° C. for 90 min. The solvent was evaporated and the crude material was suspended in acetic acid (1 mL) and heated under reflux for 3 h. The solvent was evaporated and the crude material was purified by Prep TLC (eluting system: 80% EtOAc in Hexanes) to give 7.4 mg (67%) of the desired product Compound 160. MS: [M+1]=380. $H^1NMR$ ($CDCl_3$) δ 7.90 (1H, dd, J=2.7, 9 Hz), 7.88 (1H, s), 7.65 (1H, dd, J=4.5, 9 Hz), 7.35 (1H, m), 2.47 (3H, s), 1.53 (9H, s).

Example 75: Synthesis of Compound 143

143

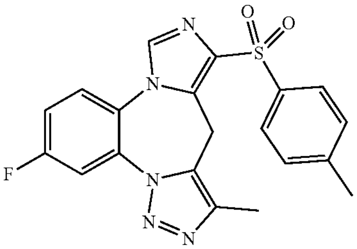

A solution of KOtBu (40 mg, 0.36 mmol) in DMF (3 mL) was cooled to −50° C. under a nitrogen atmosphere. p-Toluenselfonylmethyl isocyanide (76 mg, 0.39 mmol) was added. The mixture was stirred at −50° C. for 1 h. The imino-derivative from Scheme 22 (50 mg, 0.18 mmol) was added and the mixture was allowed to warm to room temperature over 16 h. Saturated $NH_4Cl$ aqueous solution was added and it was extracted with EtOAc five times. The combined extracts were washed with brine (3×) and dried over $MgSO_4$. Filtration and concentration gave the crude product. Chromatography (RediSep 4 g silica-gel column, eluted with 70% EtOAc in Hexanes) followed by a prep TLC (eluting system: 30% EtOAc in DCM) to give 22.2 mg (30% yield) of a white solid Compound 143. MS: [M+1]-410.

$H^1NMR$ ($CDCl_3$) δ 7.91 (2H, d, J=8 Hz), 7.87 (1H, dd, J=2.5, 8.5 Hz), 7.74 (1H, s), 7.65 (1H, dd, J=5.5, 9 Hz), 7.34 (3H, m), 2.50 (3H, s), 2.42 (3H, s).

Example 76: Synthesis of Compound 144

144

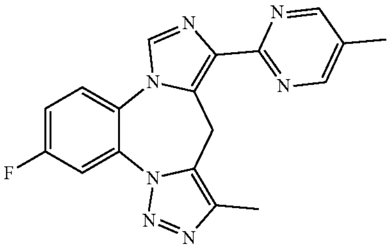

To 3-ethoxymethacrolein (100 mg, 0.88 mmol) was added 7 N ammonia in methanol (1.3 mL, 8.8 mmol). The solution was stirred at room temperature for 16 h. The solvent was evaporated and the crude yellow solid corresponding to 3-amino-2-methylacrolein was used in the next step without further purification.

To a solution of 3-amino-2-methylacrolein (7 mg, 0.087 mmol) in anhydrous THF (1 mL) was added NaH 60% in oil dispersion (6 mg, 0.16 mmol). The suspension was stirred at room temperature for 15 min. The cyanide derivative (22 mg, 0.079 mmol) in THF (1 mL) was added and the reaction mixture was heated at 65° C. for 1 hour. As described above, a new batch of reagents was prepared with 3-amino-2-methylacrolein (20 mg) and NaH (20 mg) in THF (1 mL), and added to the reaction mixture which was heated at 65° C. for another hour. LCMS indicated completion of the reaction. The reaction mixture was quenched with methanol. The solvent was evaporated. The crude material was suspended in water and a solid was collected by filtration to give 5.2 mg (19% yield) of a light red solid Compound 144. MS: [M+1]=348. $H^1NMR$ ($CDCl_3$) δ 8.67 (2H, s), 7.90 (1H, d, J=9.5 Hz), 7.85 (1H, s), 7.65 (1H, dd, J=4.5, 9 Hz), 7.34 (1H, m), 2.44 (3H, s), 2.36 (3H, s).

Scheme 23

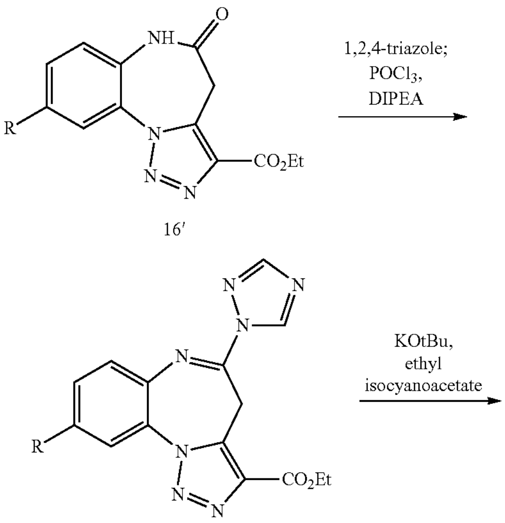

-continued

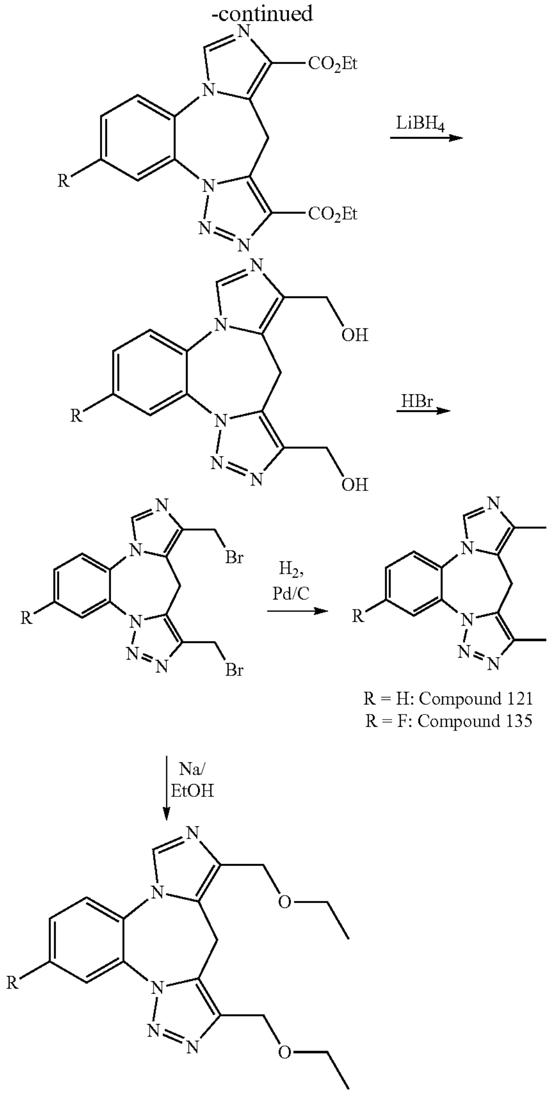

R = H: Compound 121
R = F: Compound 135

R = H: Compound 134

Example 77: Synthesis of Compound 121

121

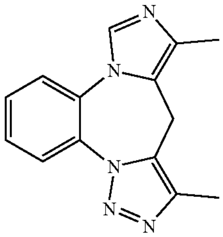

To a solution of 1,2,4-triazole, (2.03 g, 29.4 mmol) in anhydrous $CH_3CN$ (20 mL) at 0° C. was added i-$Pr_2NEt$ (5.6 mL, 32.4 mmol). Once all the triazole was dissolved, $POCl_3$ (0.82 mL, 8.8 mmol) and compound 16' (1 g, 3.68 mmol) were added. The mixture was stirred at 0° C. for 2 h. The resulting solution was heated in an oil bath at 80° C. for 16 h. The mixture was cooled with an ice bath, diluted with EtOAc, and water was added. It was extracted with EtOAc three times. The combined extracts were washed with brine and dried over $MgSO_4$. Filtration and concentration gave 1.05 g (88% yield) of an orange solid which was used directly in the next step. MS: [M+1]=324.

A solution of KOtBu (696 mg, 6.2 mmol) in DMF (15 mL) was cooled to −50° C. under a nitrogen atmosphere. Ethyl isocyanoacetate (0.75 mL, 6.8 mmol) was added slowly. The mixture was stirred at −50° C. for 1 h. The above crude product from step 1 (1 g, 3.1 mmol) was added and the mixture was allowed to warm to room temperature over 18 h. Saturated $NH_4Cl$ aqueous solution was added and it was extracted with EtOAc eight times. The combined extracts were washed with brine (3×) and dried over $MgSO_4$. Filtration and concentration gave the crude product. Chromatography (RediSep 24 g silica-gel column, eluted with 70% EtOAc in Hexanes) to give 950 mg (83% yield) of product. MS: [M+1]=368.

To a solution of diester (200 mg, 0.54 mmol) in anhydrous THF (4 mL) stirred at room temperature under a nitrogen atmosphere was added LiBH4 (2 M in THF, 0.66 mL, 1.3 mmol). The reaction mixture was stirred under a nitrogen atmosphere for 24 h. A mixture of EtOAc/EtOH (3 mL/3 mL) was added to the reaction mixture and it was concentrated. The residue was taken up in MeOH and silica gel was added. After volatile solvents were evaporated, the solid was loaded onto a RediSep 4 g silica-gel column. The desired product was eluted with 10:1 v/v CH2Cl2/MeOH. The diol was obtained as a solid (60 mg, 39% yield). MS: [M+1]=284.

The diol (60 mg, 0.21 mmol) was suspended in 5 mL of HBr 33% in AcOH and heated at 80° C. for 18 h. The solution was cooled down with an ice bath and diluted with EtOAc. Slowly, a saturated aqueous $NaHCO_3$ solution was added. The solution was extracted with EtOAc (3×), and the combined organic phases were washed with brine, dried over $MgSO_4$. Filtration and concentration gave a crude product which was used in the next step without further purification. MS: [M+1]=408.

To a solution of dialkyl bromide derivative (0.21 mmol) in EtOAc (10 mL) and MeOH (10 mL) was added wet 10% Pd/C (catalytic amount) and the resulting suspension was stirred under a hydrogen atmosphere for 60 h. The suspension was filtered through Celite and the resulting solution was concentrated. The crude product was purified by multiple prep TLC (eluting system: 3% MeOH in EtOAc) to give 6.2 mg (12% yield over 2 steps) of the desired product Compound 121. MS: [M+1]=252. $H^1NMR$ ($CDCl_3$) δ 8.09 (1H, m), 7.74 (1H, s), 7.56 (3H, m), 7.90 (2H, m), 2.42 (3H, s), 2.29 (3H, s).

Example 78: Synthesis of Compound 135

135

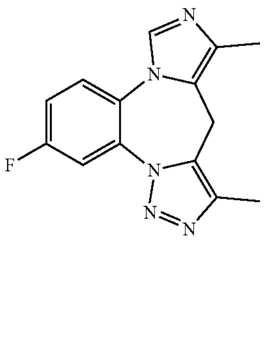

Compound 135 was synthesized in an analogous manner to Compound 121 as follows: To a solution of 1,2,4-triazole (952 mg, 13.8 mmol) in anhydrous $CH_3CN$ (20 mL) at 0° C. was added i-$Pr_2NEt$ (2.6 mL, 15.2 mmol). Once all the triazole was dissolved, $POCl_3$ (0.45 mL, 4.8 mmol) and the lactam ester (1 g, 3.45 mmol) was added. The mixture was stirred at 0° C. for 2 h. The resulting solution was heated in an oil bath at 80° C. for 16 h. The mixture was cooled with an ice bath, diluted with EtOAc, and water was added. It was extracted with EtOAc three times. The combined extracts were washed with brine and dried over $MgSO_4$. Filtration and concentration gave 1.03 g (87% yield) of an orange solid which was used directly in the next step. MS: [M+1]=342. A solution of KOtBu (658 mg, 5.9 mmol) in DMF (15 mL) was cooled to −50° C. under a nitrogen atmosphere. Ethyl isocyanoacetate (0.71 mL, 6.5 mmol) was added slowly. The mixture was stirred at −50° C. for 1 h. The above crude product from step 1 (1 g, 2.9 mmol) was added and the mixture was allowed to warm to room temperature over 18 h. Saturated $NH_4Cl$ aqueous solution was added and it was extracted with EtOAc eight times. The combined extracts were washed with brine (3×) and dried over $MgSO_4$. Filtration and concentration gave the crude product. Chromatography (RediSep 24 g silica-gel column, eluted with 70% EtOAc in Hexanes) to give 1.02 g (90% yield) of product. MS: [M+1]=386.

To a solution of diester (600 mg, 1.56 mmol) in anhydrous THF (8 mL) stirred at room temperature under a nitrogen atmosphere was added $LiBH_4$ (2 M in THF, 3.1 mL, 6.24 mmol). The reaction mixture was stirred under a nitrogen atmosphere for 24 h. A mixture of EtOAc/EtOH (10 mL/10 mL) was added to the reaction mixture and it was concentrated. The residue was taken up in MeOH and silica gel was added. After volatile solvents were evaporated, the solid was loaded onto a RediSep 12 g silica-gel column. The desired product was eluted with 10:1 v/v $CH_2Cl_2$/MeOH. The diol was obtained as a solid (187 mg, 40% yield). MS: [M+1] =302.

The diol (80 mg, 0.27 mmol) was suspended in 7 mL of HBr 33% in AcOH and heated at 80° C. for 48 h. The solution was cooled down with an ice bath and diluted with EtOAc. Slowly, a saturated aqueous $NaHCO_3$ solution was added. The solution was extracted (3×) and the combined organic phases were washed with brine, dried over $MgSO_4$. Filtration, concentration and co-evaporation with toluene gave 100 mg (88% yield) of a beige solid which was used in the next step without further purification. MS: [M+1]=426.

To a solution of dialkyl bromide derivative (70 mg, 0.16 mmol) in EtOAc (10 mL) and MeOH (10 mL) was added 10% Pd/C (catalytic amount) and the resulting suspension was stirred under a hydrogen atmosphere for 48 h. The suspension was filtered through Celite and the resulting solution was concentrated. The crude product was purified by multiple prep TLC (eluting system 1: 75% EtOAc in Hexanes; eluting system 2: 5% MeOH in EtOAc; eluting system 3: EtOAc) to give 4.1 mg (10% yield) of the desired product Compound 135. MS: [M+1]- 270. $H^1NMR$ ($CDCl_3$) δ 7.84 (1H, dd, J=2.5, 9 Hz), 7.70 (1H, s), 7.54 (1H, dd, J=5, 8 Hz), 7.30 (1H, m), 2.42 (3H, s), 2.28 (3H, s).

Example 79: Synthesis of Compound 134

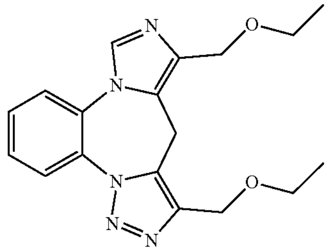

134

To a suspension of dialkyl bromide derivative described in Scheme 23, R=H, (30 mg, 0.074 mmol) in EtOH (1 mL), and heated at 80° C. was added a freshly prepared NaOEt 2M solution (75 μL, 0.15 mmol). The solution was heated for 10 min. The solvent was evaporated. The crude material was suspended in EtOAc and filtered. The filtrate was concentrated and purified by prep TLC (eluting system: EtOAc) to give 3.1 mg (12% yield) of the desired product Compound 134. MS: [M+1]=340.

Scheme 24

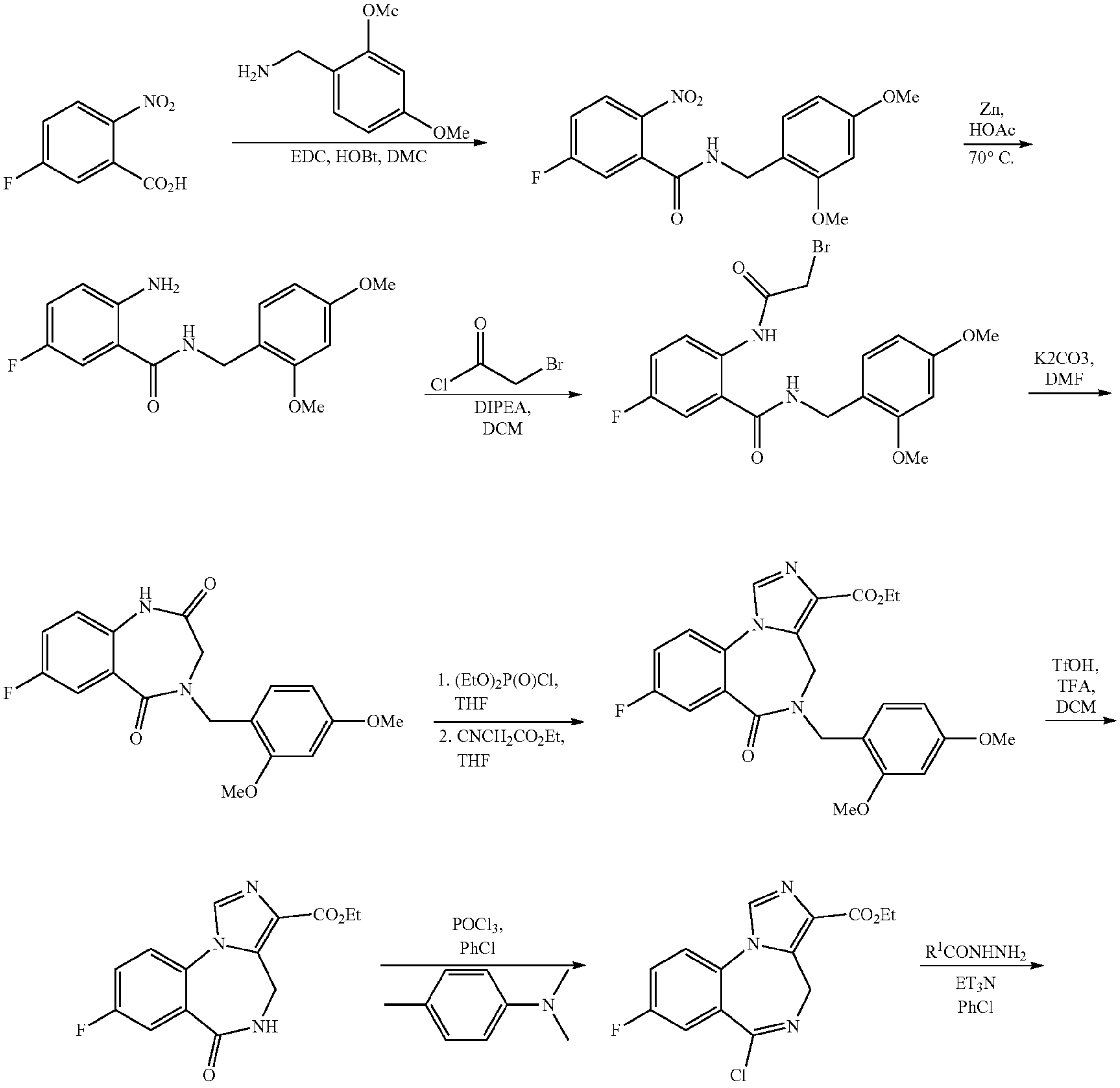

-continued

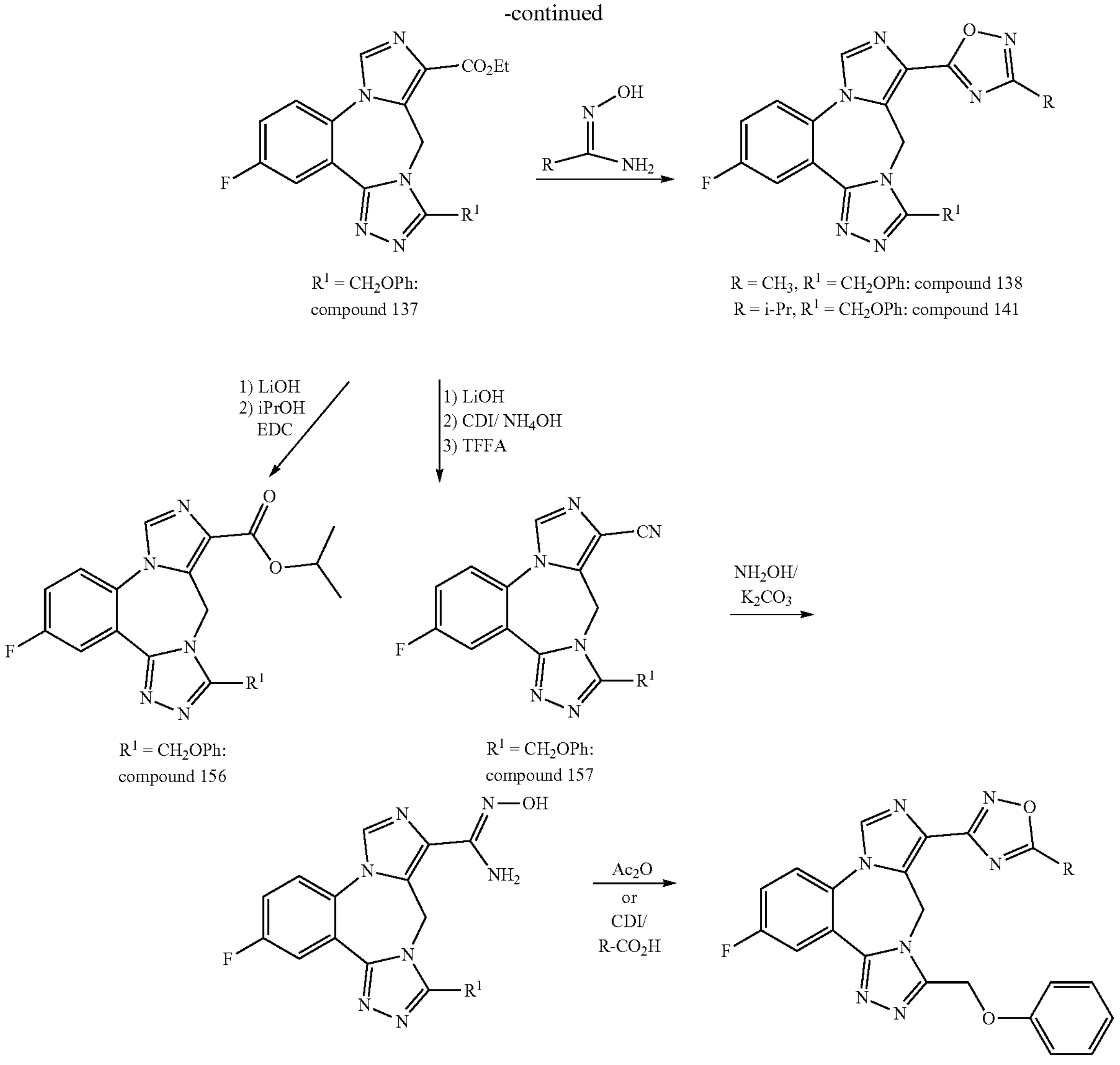

$R^1 = CH_2OPh$: compound 137

R = $CH_3$, $R^1 = CH_2OPh$: compound 138
R = i-Pr, $R^1 = CH_2OPh$: compound 141

$R^1 = CH_2OPh$: compound 156

$R^1 = CH_2OPh$: compound 157

R = i-Pr: compound 147
R = Me: compound 148
R = Et: compound 158
R = $CF_3$: compound 159

Example 80: Synthesis of Compound 137

137

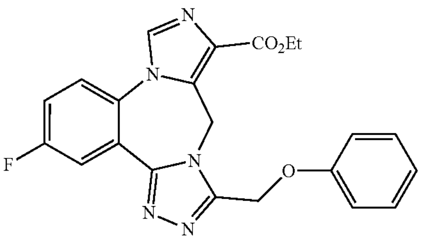

To a solution of 5-fluoro-2-nitrobenzoic acid (6.6 g, 35.66 mmol) in dichloromethane (100 mL) were added DIPEA (9.22 g, 71.3 mmol), HOBt (6.0 g, 39.2 mmol) and EDCI (10.2 g, 53.5 mmol). After about 15 min stirring, to the reaction mixture was added a solution of 2,4-dimethoxy-benzyl amine (5.96 g, 35.66 mmol) in dichloromethane (50 mL) dropwise under nitrogen atmosphere. The resulting mixture was stirred under nitrogen atmosphere at room temperature for 16 h. The reaction mixture was washed successively with 1N HCL (100 mL), sat. $NaHCO_3$ (100 mL) and brine (100 mL). The organic phase was then dried over $MgSO_4$. Filtration and solvent removal in vacuo afforded a yellowish solid, wt: 9.3 g (78%). MS: [M+1] =335.

To the nitro benzene analog (9.3 g, 27.8 mmol) suspended and stirred in a solvent mixture of HOAc/THF/MeOH/$H_2O$ (25/100/50/25 mL) at RT was added Zn powder. The mixture was heated to 70° C. for 20 hr., cooled, and filtered. Solid was rinsed with THF, and the combined filtrate was concentrated in vacuo. To the resulting slurry was added sat. $NaHCO_3$ slowly and carefully to avoid excessive forming formation until pH reach 7 to 8. The mixture was extracted with EtOAc (3×); combined organic layer washed with brine, and dried over $MgSO_4$. Filtration and solvent removal gave the crude amine product as a dark brown gummy paste, wt: 8.7 g.

To a solution of the aniline from above (8.7 g) in dichloromethane (150 ml) was added triethylamine (3.37 g, 33.4 mmol). The mixture was cooled with ice bath and treated with bromo acetyl chloride (4.81 g, 30.6 mmol) under nitrogen atmosphere. The ice bath was removed and the mixture left stirring for 72 hr. The reaction mixture was concentrated in vacuo, the resulting slurry treated with $Et_2O$ (100 mL) and water (100 mL). Product precipitate was collected by filtration, and dried to give 5.6 g product as a brown solid. $Et_2O$ layer was separated from aq. Layer and diluted with DCM (50 mL), washed with brine, and dried over $MgSO_4$. Filtration and solvent removal gave 5.3 g additional product as a foamy brown solid. Total wt: 11 g (100%).

To a solution of the bromide (11 g) in DMF (550 mL) was added $K_2CO_3$ (7.1 g, 51.7 mmol). The mixture was heated at 50° C. for 48 hrs. The mixture was cooled to room temperature and the inorganic solid was filtered off. Filtrate was concentrated in vacuo, treated with water/MeOH (60/10 mL), extracted with DCM (3×); combined organic layer was washed with brine and dried over $MgSO_4$. Filtration and solvent removal followed by silica gel column chromatography using 5 to 50% EtOAc in DCM gave 3.2 g (36%) of the 7-member lactam as a brownish solid. MS: [M+1]=345.

To the lactam (1.32 g, 3.83 mmol) dissolved and stirred in THF (20 mL) and DMF (3 mL) at −20° C. was added t-BuOK (0.645 g, 5.75 mmol). After 30 min stirring at −20° C., diethyl chlorophosphate (1.19 mL, 6.89 mmol) was added dropwise, and the mixture was stirred for 3 h while warming from −20 to 20° C. The reaction mixture was cooled to −78° C. and to it was added ethyl isocyanoacetate (0.791 mL, 6.89 mmol), followed by addition of t-BuOK (0.645 g, 5.75 mmol) and stirring continued overnight while temperature reached to RT. The reaction was quenched with saturated $NH_4Cl$, extracted with EtOAc (2×); combined organic solution was washed with brine and dried over $MgSO_4$. Filtration and solvent removal gave a crude product which was purified by silica gel column chromatography using 15 to 100% EtOAc in DCM, wt: 0.861 g (47%), as a brown solid. MS: [M+1]=440.

To the imidazole ester from above (861 mg) in dichloromethane (5 mL) at 0° C. was added trifluoroacetic acid (5 mL) followed by trifluoromethanesulfonic acid (0.345 mL). The mixture was warmed to RT, stirred for 3 h, then concentrated to afford a residue which was dissolved in dichloromethane (50 mL). To which was added sat. $NaHCO_3$ (50 mL), followed by 20 min stirring. pH of the top aq. Layer was tested basic, and was separated, extracted with DCM (3×); combined DCM solution washed with brine and dried over $MgSO_4$. Filtration and solvent removal gave 0.58 g (100%) of the lactam as a yellowish solid. MS: [M+1]=290.

To lactam (209.1 mg, 0.723 mmol) and N,N-dimethyl-p-toluidine (234.7 mg, 1.74 mmol) stirring in chlorobenzene (2.5 mL) under nitrogen was added $POCl_3$ (133.0 mg, 0.867 mmol). The reaction was then heated at 135° C. for 2 h. Upon cooling to room temperature, phenoxy acetic acid hydrazide (189.0 mg, 1.08 mmol) was added, followed by DIPEA (0.455 mL). The reaction was stirred at room temperature for 30 min, then heated at 100° C. for 60 min. The reaction mixture was cooled, saturated $NH_4Cl$ (aq.) was added, and extracted with ethyl acetate three times; combined organic layer was washed with brine, and dried over $MgSO_4$. After filtration and concentration, the product was isolated by ISCO flash column chromatography using 0 to 10% MeOH in EtOAc, wt: 116.7 mg (36%) of Compound 137 as a yellowish filmy solid. MS: [M+1]=420.

Example 81: Synthesis of Compound 156

156

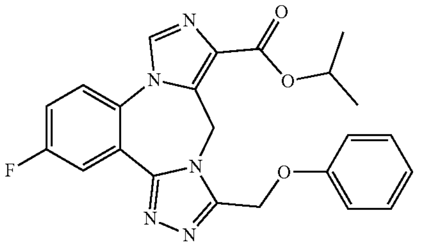

Ethyl ester Compound 137 (244.2 mg, 0.582 mmol) in a solvent system of THF/water/MeOH (6.0 mL total, 6/5/1 ratio) was treated with LiOH (69.7 mg, 2.91 mmol) at RT for 4 hrs, concentrated in vacuo, acidified to pH~3, and precipitate collected by filtration. After water washing and drying, 179.3 mg (79%) of the acid was obtained as a yellowish solid. MS: [M+1]- 392.

To the acid (10.8 mg, 0.0276 mmol) stirring in DCM (0.1 ml) at RT was added EDCI (21.3 mg, 0.11 mmol), DMAP (6.7 mg, 0.0552 mmol) and isopropyl alcohol (13.2 mg, 0.221 mmol). After 12 hrs, the reaction was diluted with EtOAc, washed with sat. $NaHCO_3$; aq. Layer separated and extracted with EtOAc, combined organic layer washed with brine, and dried over $MgSO_4$. Filtration and prep. TLC purification of the concentrate using 10% MeOH in EtOAc gave 8.7 mg (73%) of the isopropyl ester Compound 156 as a yellowish foamy solid. MS: [M+1]=434.

Example 82: Synthesis of Compound 138

138

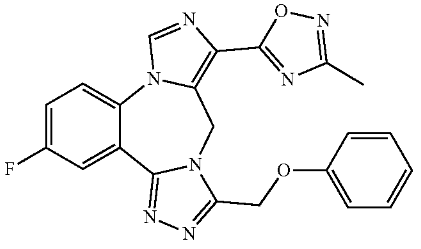

Acetamide oxime (10.7 mg, 0.144 mmol) was azeotroped four times in toluene, and added to the ethyl ester Compound 137 (9.5 mg, 0.0226 mmol). THF (0.3 mL) was added, followed by NaH 60% oil suspension (4.5 mg, 0.112 mmol). The reaction mixture was stirred at RT for 30 min, then heated at 70° C. for 2 h, cooled to RT, and solvent removed in vacuo, water (1.5 ml) added to quench the reaction, stirred for 20 min, and cooled to 4° C. Precipitate was collected by filtration, washed with water, and dried to give 5.2 mg (59%) of the oxadiazole product Compound 138 as a light yellow solid. MS: [M+1]=430.

Example 83: Synthesis of Compound 141

141

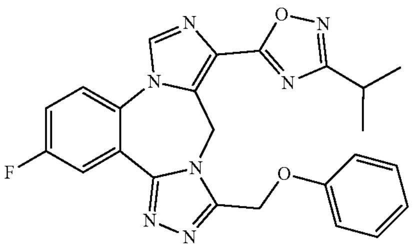

Compound of Example 83 was synthesized in an analogous synthetic route as that described for Example 82, using isobutyramidoxime in place of acetamide oxime to give the compound of Example 83 as a yellowish solid: MS: [M+1]=458.

Example 84: Synthesis of Compound 157

157

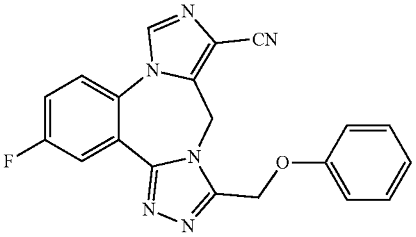

To the acid prepared above in Example 81 (60.2 mg, 0.154 mmol) stirring in DCM (0.7 mL) at RT was added carbonyl diimidazole (49.9 mg, 0.308 mmol). The mixture was stirred for 40 min, then cooled to 0° C., and ammonia (0.112 ml) added, warmed to RT while stirring continued overnight. The reaction was concentrated, water (8 mL) added, and stirred well for 30 min. Resulting precipitate was collected by filtration, washed with water, and dried to give 51.1 mg (85%) of the primary amide as a brownish solid. MS: [M+1]=391.

The amide (51.1 mg) from above was treated with $POCl_3$ (200.8 mg, 1.31 mmol) in 1,4-dioxane (0.9 mL) at 90° C. for 14 hrs. Upon cooling to RT, the reaction was carefully quenched with sat. $NaHCO_3$ (5 mL), stirred for 20 min. Precipitate was collected by filtration, washed with water, and dried to give 40.9 mg (85%) of nitrile product Compound 157 as a brownish solid. MS: [M+1]=373.

Example 85: Synthesis of Compound 147

147

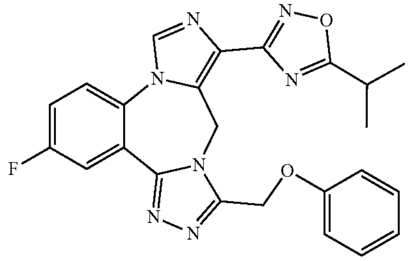

To the nitrile (45.8 mg, 0.123 mmol) in a round bottom flask was added hydroxylamine hydrochloride (14.5 mg, 0.209 mmol), $K_2CO_3$ (22.3 mg, 0.161 mmol), ethanol (0.6 mL), and water (0.15 mL). The reaction mixture was heated at 80° C. for 30 min, cooled down, and concentrated in vacuo. The resulting slurry was treated with water (1.5 mL), sonicated to help mixing, and stirred at RT for 1 h before being cooled to 4° C. The resulting precipitate was collected by filtration, washed with cold water (1 mL), and dried to give 40.8 mg (82%) of the adduct as an off-white solid. MS: [M+1]=406.

Isobutyric acid (31.4 mg, 0.582 mmol) was treated with carbonyl diimidazole (28.4 mg, 0.175 mmol) in THF (0.5 mL) for 2 hrs. The N-hydroxycarboxamide adduct (11.8 mg, 0.0291 mmol) was added, and the reaction was stirred at RT for 30 min. More isobutyric acid (0.5 mL) was added and the reaction mixture was heated at 110° C. for 16 h, cooled, sat. $NaHCO_3$ (8 mL) added, and extracted with EtOAc (3×); combined organic layer washed with brine, and dried over $MgSO_4$. Prep. TLC (5% MeOH in EtOAc) of the concentrated filtrate gave 11.2 mg (84%) of the oxadiazole Compound 147 as a white solid. MS: [M+1]=458.

Example 86: Synthesis of Compound 148

148

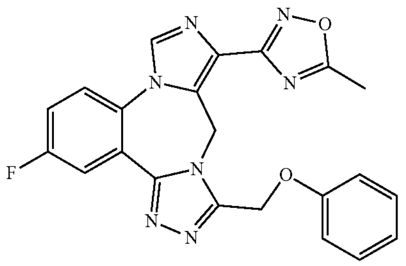

Compound of Example 86 was synthesized in an analogous synthetic route as that described for Example 85, using acetic acid in place of isobutyric acid to give the compound of Example 86 as a white solid: MS: [M+1]- 430.

Example 87: Synthesis of Compound 158

158

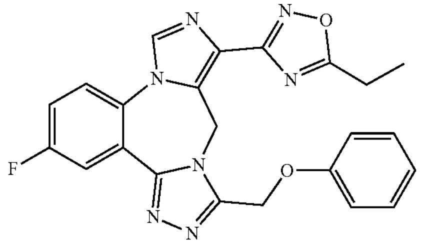

Compound of Example 87 was synthesized in an analogous synthetic route as that described for Example 85, using propionic acid in place of isobutyric acid to give the compound of Example 87 as a white solid: MS: [M+1]=444.

Example 88: Synthesis of Compound 159

159

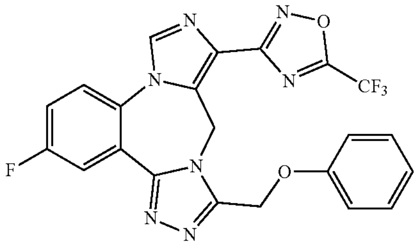

Trifluoroacetic anhydride (196.9 mg, 0.938 mmol) was added to the N-hydroxycarboxamide adduct (19.0 mg, 0.0469 mmol) suspended and stirred in THF (0.2 mL) at RT. After 30 min stirring, the reaction was heated to 70° C. for 1 h, cooled to RT, and diluted with EtOAc (10 mL), to which was added sat. $NaHCO_3$ and stirred for 30 min. Aq. Layer was separated and extracted with EtOAc (1×); combined organic layer was washed with brine, and dried over $MgSO_4$. Filtration and solvent removal gave a paste to which was added nBuOH (5 ml) and HOAc (0.5 mL). This was heated at 115° C. for 16 h, cooled and concentrated in vacuo, diluted with EtOAc, washed with sat. $NaHCO_3$, brine, and dried over $MgSO_4$. Prep. TLC (5% MeOH in EtOAc) of the concentrated filtrate gave 11.5 mg (51%) of the desired trifluoromethyl oxadiazole analog Compound 159 as a yellowish solid. MS: [M+1]=484.

Scheme 25

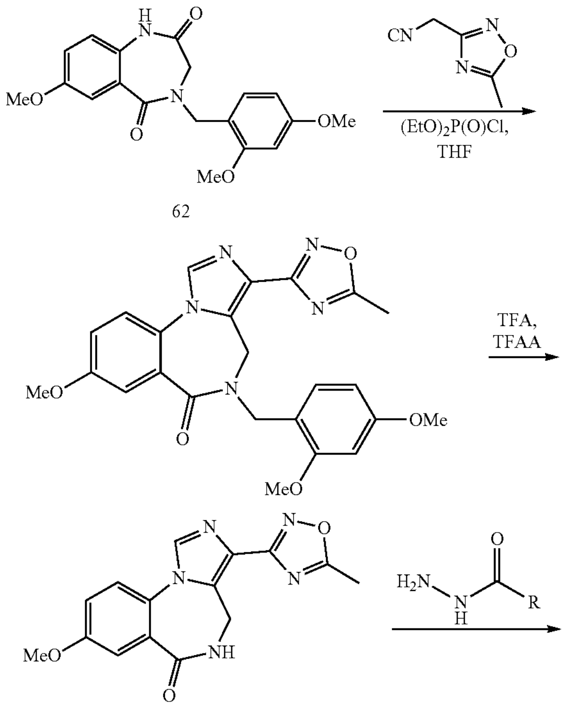

-continued

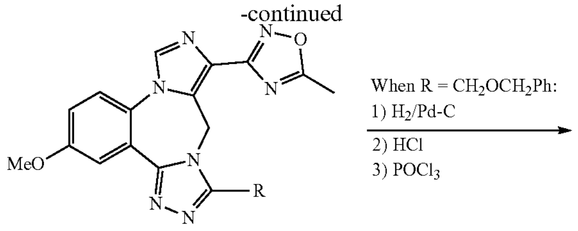

R = $CH_2OPh$: compound 162
R = $CH_2O$-4-F-Ph: compound 163
R = $CH_2OCH_3$: compound 164
R = $CH_2OCH_2Ph$: compound 165

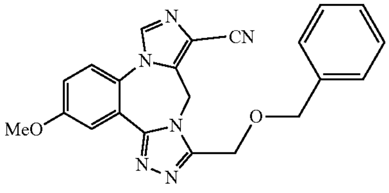

compound 166

Example 89: Synthesis of Compound 162

162

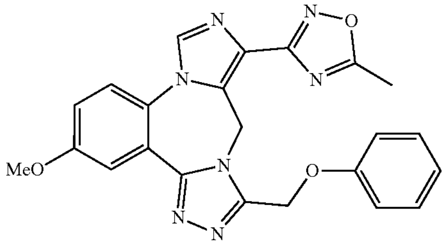

To lactam 62 (503.4 mg, 1.42 mmol) stirring in THF (2.9 ml) and DMF (0.8 mL) at −20° C. was added tBuOK (240.2 mg). After 30 min stirring, diethyl chlorophosphate (377.7 mg, 2.12 mmol) was added dropwise, and the reaction mixture was slowly warmed to 8° C. in 3 h before being cooled down to −20° C. 2.26 mL (2.26 mmol) of oxadiazole isocyanate (ref. *JMC,* 1996, 39, 170; prepared as 1M THF solution) was added. The reaction mixture was further cooled to −78° C., tBuOK (238.4 mg) was added, and the reaction was slowly warmed to RT overnight. Sat. $NH_4Cl$ (5 mL) was added and the mixture was extracted with EtOAc (2×), washed with brine, and dried over $MgSO_4$. Upon filtration and concentration, the product was isolated by silica gel column chromatography using a gradient elution of 0 to 10% MeOH in EtOAc to give 246.0 mg imidazole product as a yellowish solid. MS: [M+1]=462.

The imidazole (246.0 mg, 0.533 mmol) obtained above was stirred in DCM (3 ml). Trifluoroacetic acid (3 mL) was added, followed by trifluoromethyl sulfonic acid (160.0 mg, 1.07 mmol). After 3 h stirring, the reaction was diluted with DCM (20 mL), washed with sat. $NaHCO_3$; aq. Layer was separated and extracted with DCM (2×); combined DCM solution was washed with brine, and dried over $MgSO_4$. Filtration and solvent removal in vacuo gave 208.7 mg of the crude lactam product as a yellowish flaky solid. [M+1]=312.

Phosphorous oxychloride (29.9 mg, 0.195 mmol) was added to a solution of the above obtained lactam (22.5 mg, 0.0723 mmol) and N,N-dimethyl-p-toluidine (51.8 mg, 0.383 mmol) stirring in chlorobenzene (0.45 mL) under nitrogen atmosphere. The reaction mixture was heated at 135° C. for 3 h, then cooled to RT. Diisopropylethylamine (75.7 mg, 0.586 mmol) and phenoxyacetic hydrazide (50.1 mg, 0.302 mmol) was added, and the reaction mixture was heated at 100° C. for 14 h, cooled to RT, and partitioned between sat. $NH_4Cl$ and EtOAc. Aq. Layer was separated and extracted with EtOAc; combined EtOAc solution was washed with brine, and dried over $MgSO_4$. Upon filtration and concentration, the product Compound 162 was isolated by silica gel column chromatography using a gradient elution of 0 to 10% MeOH in EtOAc as a yellowish solid. Wt: 11.8 mg (37%). MS: [M+1]=442.

Example 90: Synthesis of Compound 163

163

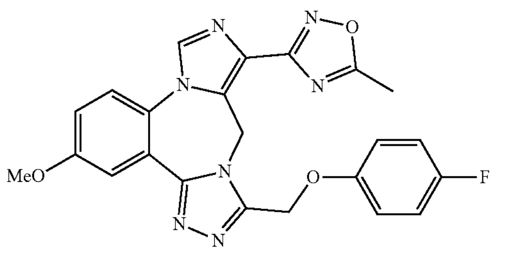

Compound of Example 90 was synthesized in an analogous synthetic route as that described for Example 89, using 4-fluorophenoxyacetic hydrazide in place of phenoxyacetic hydrazide to give the compound of Example 90 as a yellowish solid: MS: [M+1]=460.

Example 91: Synthesis of Compound 164

164

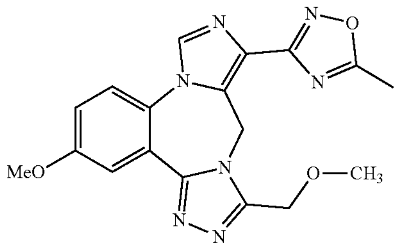

Compound of Example 91 was synthesized in an analogous synthetic route as that described for Example 89, using methoxyacetic hydrazide in place of phenoxyacetic hydrazide to give the compound of Example 91 as a yellowish solid: MS: [M+1]=380.

Example 92: Synthesis of Compound 165

165

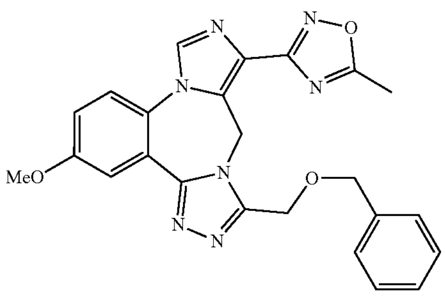

Preparation of benzyloxy acetic hydrazide: carbonyl diimidazole (1.52 g, 9.39 mmol) was added to benzyloxy acetic acid (1.2 g, 7.22 mmol) stirring in THF (60 mL) at 0° C. Ice bath was removed and the stirring continued for 1 hr. The resulting cloudy solution was added to hydrazine (0.927 g, 28.9 mmol) stirring in THF (40 mL) at RT. After 16 hrs, the reaction mixture was concentrated to a slurry, to which was added water (120 mL), extracted with DCM (3×); combined DCM solution washed with brine, and dried over $MgSO_4$. Filtration and solvent removal gave 0.908 g (70%) of the hydrazide as a clear viscous oil. This was azeotroped in toluene a few times before use. Compound of Example 92 was synthesized in an analogous synthetic route as that described for Example 89, using benzyloxy acetic hydrazide in place of phenoxyacetic hydrazide to give the compound of Example 92 as a yellowish solid: MS: [M+1]- 456.

Example 93: Synthesis of Compound 166

166

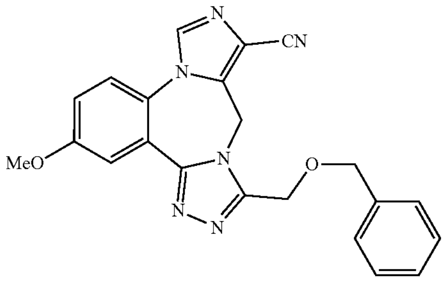

Compound 165 from above (58.5 mg, 0.128 mmol) was treated with 10% Pd—C (catalytic) in EtOAc (4 mL) and MeOH (4 mL) under hydrogen atmosphere for 2 h. Catalyst was removed by filtration over Celite. To the filtrate was added conc. HCl (0.89 mL), and the mixture was stirred at RT for 16 h. Excess $Na_2CO_3$ (aq.) was added, and the solution was extracted with EtOAc (2×); combined organic solution was washed with brine, and dried over $MgSO_4$. Prep. TLC of the concentrated filtrate using 15% MeOH in EtOAc gave 14.9 mg of the primary amide ([M+1]=417) as a yellowish solid. This primary amide was treated with phosphorous oxychloride (54.9 mg, 0.358 mmol) in 1,4-dioxane (1 mL) at 90° C. for 14 h. Upon cooling, the reaction mixture was diluted with EtOAc, washed with sat. $NaHCO_3$; aq. layer separated and extracted with EtOAc (1×), combined organic solution was washed with brine, and dried over $MgSO_4$. Prep. TLC of the concentrated filtrate using 5% MeOH in EtOAc gave 5.2 mg of the desired nitrile product Compound 166 as white needles. [M+1]=399.

Scheme 26
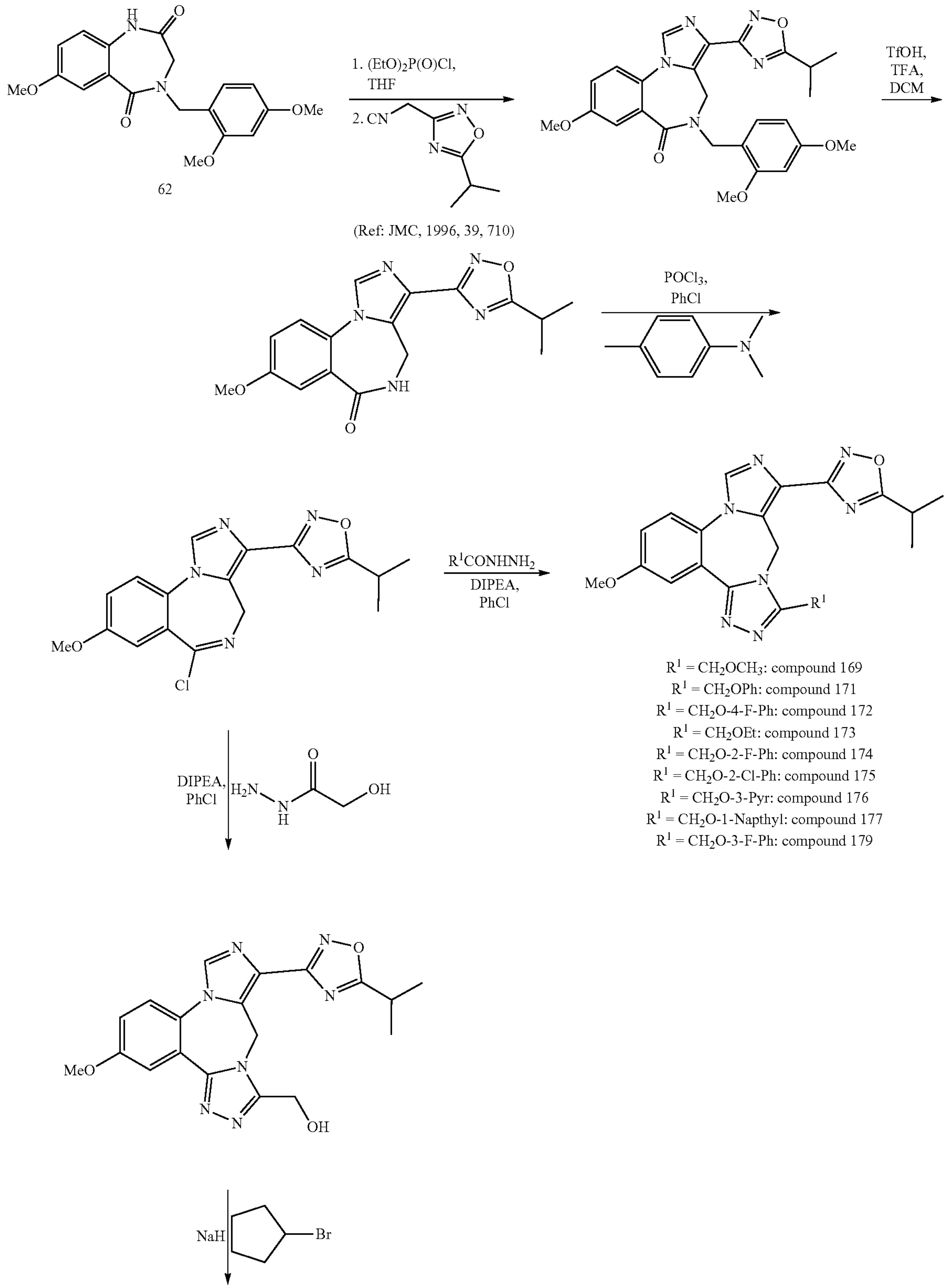

-continued

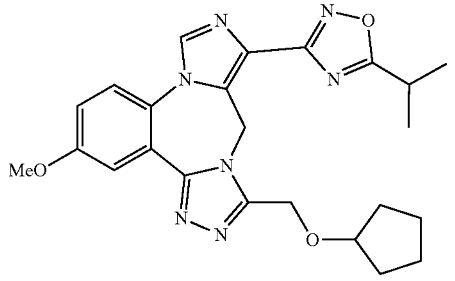

compound 178 (2135)

Example 94: Synthesis of Compound 169

169

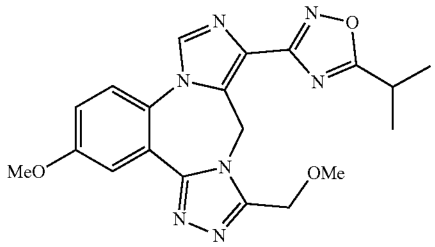

To lactam 62 (2.23 g, 6.24 mmol) stirring in THF (10 mL) and DMF (3 ml) at −20° C. was added tBuOK (1.05 g, 9.36 mmol). After 30 min stirring, diethyl chlorophosphate (1.66 g, 9.36 mmol) was added dropwise, and the reaction mixture was slowly warmed to 8-10° C. in 3 h before being cooled down to −20° C. 10.0 ml (10.0 mmol) of oxadiazole isocyanate (ref. *JMC,* 1996, 39, 170; prepared as 1M THF solution) was added. The reaction mixture was further cooled to −78° C., tBuOK (1.05 g, 9.36 mmol) was added, and the reaction was slowly warmed to RT overnight. Sat. $NH_4Cl$ (20 mL) was added and the mixture was extracted with EtOAc (3×), washed with brine, and dried over $MgSO_4$. Upon filtration and concentration, the product was isolated by silica gel column chromatography using a gradient elution of 10 to 100% EtOAc in DCM to give 1.07 g (35%) imidazole product as a yellowish foamy solid. MS: [M+1]−490.

The imidazole (1.07 g, 2.18 mmol) obtained above was stirred in DCM (11 mL). Trifluoroacetic acid (11 mL) was added, followed by trifluoromethyl sulfonic acid (0.656 g, 4.37 mmol). After 4 h stirring, the reaction was concentrated in vacuo, diluted with DCM (50 mL), washed with sat. $NaHCO_3$; aq. layer was separated and extracted with DCM (2×); combined DCM solution was washed with brine, and dried over $MgSO_4$. Filtration and solvent removal in vacuo gave 0.872 g of the crude lactam product as a brownish solid. [M+1]=340.

Phosphorous oxychloride (51.0 mg, 0.333 mmol) was added to a solution of the above obtained lactam (45.0 mg, 0.133 mmol) and N,N-dimethyl-p-toluidine (89.6 mg, 0.663 mmol) stirring in chlorobenzene (0.60 mL) under nitrogen atmosphere. The reaction mixture was heated at 135° C. for 3 h, then cooled to RT. Diisopropylethylamine (137.5 mg, 1.06 mmol) and methoxyacetic hydrazide (83.1 mg, 0.798 mmol) was added, and the reaction mixture was heated at 100° C. for 4 h, cooled to RT, diluted with EtOAc, washed with sat. $NaHCO_3$, brine, and dried over $MgSO_4$. Upon filtration and concentration, the product Compound 169 was isolated by silica gel column chromatography using a gradient elution of 0 to 13% MeOH in EtOAc as a brownish solid. Wt: 14.3 mg (26%). MS: [M+1]=408.

Example 95: Synthesis of Compound 171

171

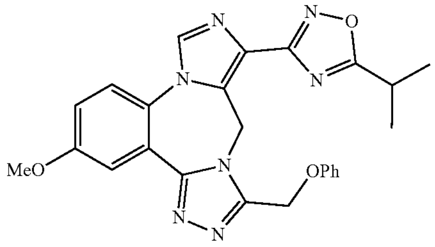

Compound of Example 95 was synthesized in an analogous synthetic route as that described for Example 94, using phenoxyacetic hydrazide in place of methoxyacetic hydrazide to give the compound of Example 95 as a yellowish solid: MS: [M+1]=470.

Example 96: Synthesis of Compound 172

172

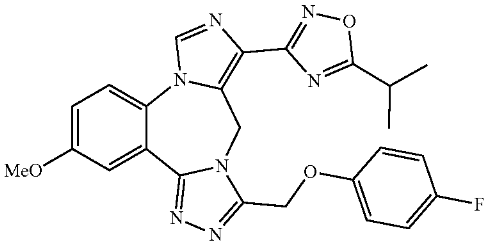

Compound of Example 96 was synthesized in an analogous synthetic route as that described for Example 94, using 4-fluoro-phenoxyacetic hydrazide in place of methoxyacetic hydrazide to give the compound of Example 96 as a yellowish solid: MS: [M+1]=488.

Example 97: Synthesis of Compound 173

173

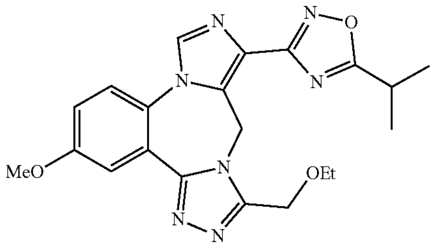

Compound of Example 97 was synthesized in an analogous synthetic route as that described for Example 94, using ethoxyacetic hydrazide in place of methoxyacetic hydrazide to give the compound of Example 97 as a yellowish solid: MS: [M+1]- 422.

Example 98: Synthesis of Compound 174

174

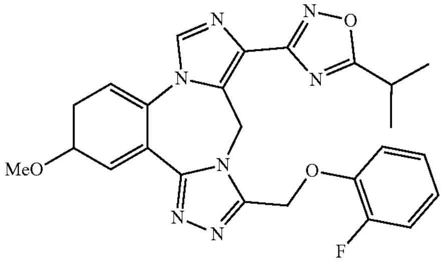

Compound of Example 98 was synthesized in an analogous synthetic route as that described for Example 94, using 2-fluoro-phenoxyacetic hydrazide in place of methoxyacetic hydrazide to give the compound of Example 98 as a yellowish solid: MS: [M+1]=488.

Example 99: Synthesis of Compound 175

175

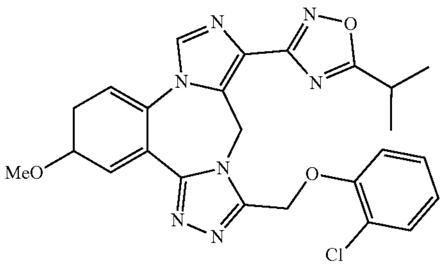

Compound of Example 99 was synthesized in an analogous synthetic route as that described for Example 94, using 2-chloro-phenoxyacetic hydrazide in place of methoxyacetic hydrazide to give the compound of Example 99 as a yellowish solid: MS: [M+1]=504.

Example 100: Synthesis of Compound 176

176

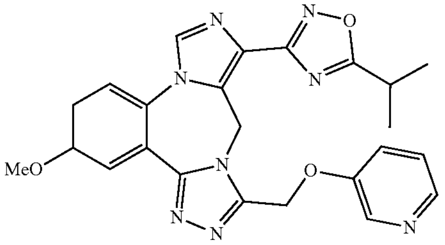

Preparation of 3-pyridyloxy acetic hydrazide: a solution of ethyl 3-pyridyloxy acetate (0.50 g, 2.76 mmol) and hydrazine (0.31 g, 9.66 mmol) in isopropyl alcohol (35 mL) was heated at 85° C. for 30 hr., cooled, and concentrated in vacuo. The resulting white solid was dissolved in small amount of sat. NaCl solution, and extracted with EtOAc repeatedly. The combined organic solution was dried over $MgSO_4$. Filtration and solvent removal gave 177 mg of the desired acetic hydrazide as a white solid. Residual water moisture was removed by azeotroping in toluene.

Compound of Example 100 was synthesized in an analogous synthetic route as that described for Example 94, using 3-pyridyloxy acetic hydrazide in place of methoxyacetic hydrazide to give the compound of Example 100 as a yellowish solid: MS: [M+1]=471.

Example 101: Synthesis of Compound 177

177

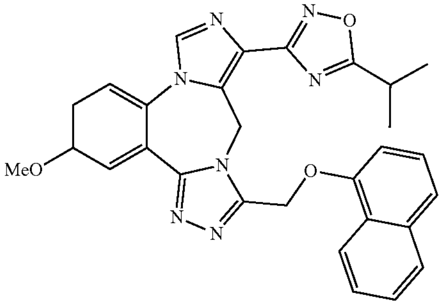

Compound of Example 101 was synthesized in an analogous synthetic route as that described for Example 94, using 1-naphthoxy acetic hydrazide in place of methoxyacetic hydrazide to give the compound of Example 101 as an off white solid: MS: [M+1]=520.

Example 102: Synthesis of Compound 179

179

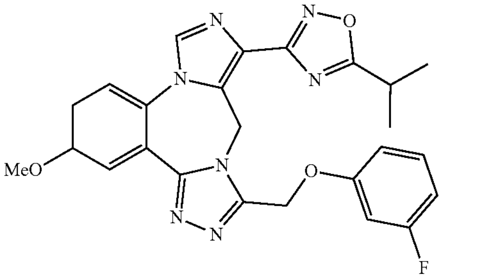

Compound of Example 102 was synthesized in an analogous synthetic route as that described for Example 94, using 3-fluorophenoxy acetic hydrazide in place of methoxyacetic hydrazide to give the compound of Example 102 as a yellowish solid: MS: [M+1]=488.

Example 103: Synthesis of Compound 178

178

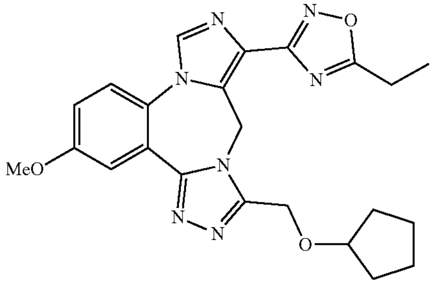

Phosphorous oxychloride (64.8 mg, 0.422 mmol) was added to a solution of the oxadiazolyl imidazole lactam (57.5 mg, 0.169 mmol) and N,N-dimethyl-p-toluidine (114.6 mg, 0.847 mmol) stirring in chlorobenzene (0.70 ml) under nitrogen atmosphere. The reaction mixture was heated at 135° C. for 3 h, then cooled to RT. Diisopropylethylamine (174.7 mg, 1.35 mmol), t-BuOH (0.3 ml), and 2-hydroxy acetic hydrazide (91.3 mg, 1.01 mmol) was added. The reaction mixture was stirred at RT for 20 min, then warmed at 50° C. for one hour followed by 80° C. heating for one hour before finally heated at 100° C. overnight. Upon cooling to RT, the reaction was diluted with EtOAc, washed with brine, and dried over $MgSO_4$. Silica gel column chromatography of the concentrated filtrate using a gradient elution of 0 to 20% MeOH in EtOAc gave the desired hydroxymethyl triazole product as a yellowish solid. Wt: 18.1 mg (27%). MS: [M+1]=394.

To a solution of hydroxymethyl triazole from above (18.1 mg, 0.046 mmol), cyclopentyl bromide (274.0 mg, 1.84 mmol), and HMPA (16.5 mg, 0.092 mmol) stirring in THF (0.5 ml) was added NaH (60% suspension: 18.4 mg, 0.46 mmol). After 10 min, the reaction was heated at 100° C. for 6 hrs, cooled, quenched with sat. $NaHCO_3$, and extracted with EtOAc (2×), washed with brine, and dried over $MgSO_4$. Prep. TLC of the concentrated filtrate using 8% MeOH in EtOAc gave 5.5 mg (26%) of the desired ether Compound 178 as a yellowish solid. [M+1]– 462.

Scheme 27

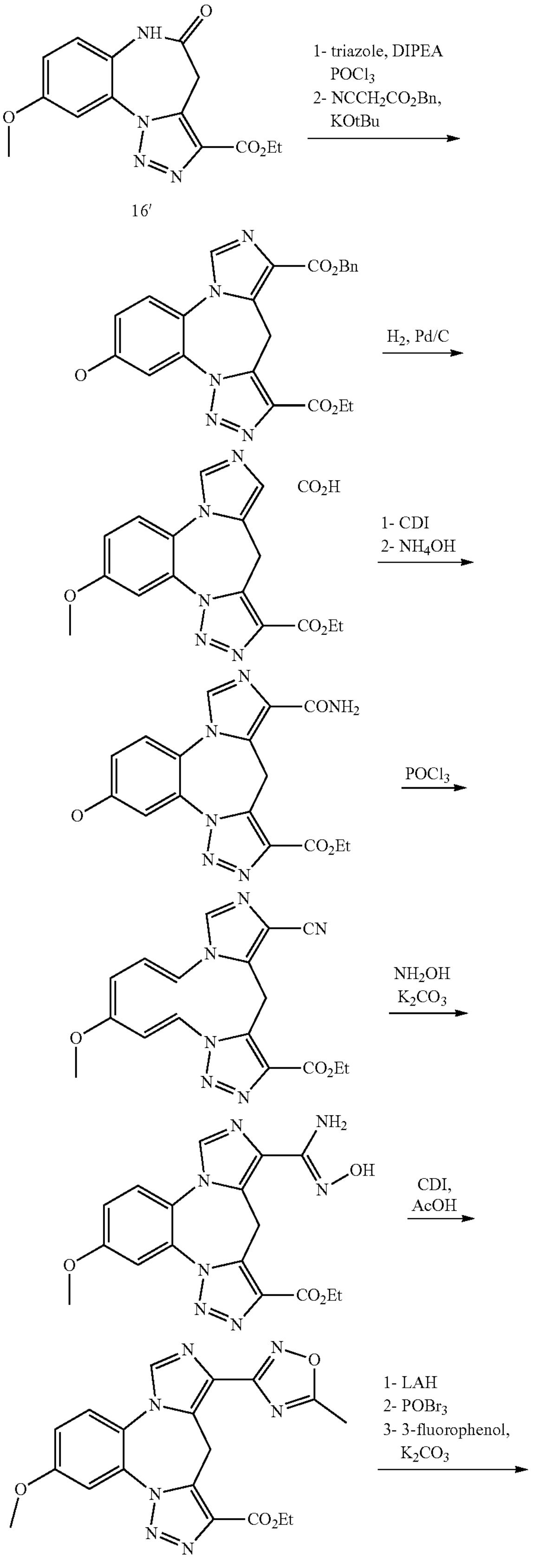

16'

-continued

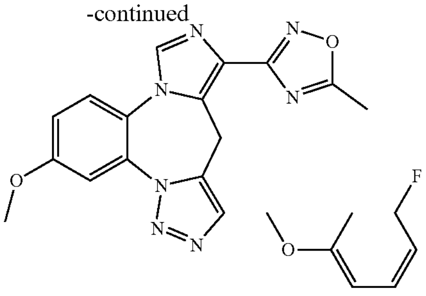

Compound 168

Example 104: Synthesis of Compound 168

168

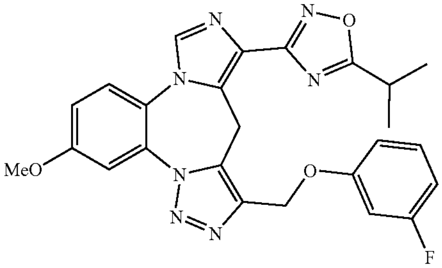

To a suspension of benzyl glycinate hydrochloride (5 g, 24.8 mmol) in DCM (100 mL) was added EDC·HCl (6.2 g, 33.2 mmol) and triethylamine (5.2 mL, 37.2 mmol). The suspension was cooled down to −50° C. then formic acid (1.4 mL, 37.2 mmol) in DCM (5 mL) was added. The reaction mixture was stirred at −50 C for one hour then at 4° C. for 3 h. The solution was diluted with 1N HCl and extracted with DCM (2×). The combined organic phases were washed with brine and dried over $MgSO_4$. Filtration and concentration gave 3.89 g (81% yield) of formylated glycine as an oil (M+1=194)

To a solution of formylated glycine derivative (1 g, 5.2 mmol) in DCM (30 ml) was added triethylamine (3.2 mL, 23 mmol). The solution was cooled down to −50° C. and $POCl_3$ (1.9 mL, 20.8 mmol) was added slowly. The solution was stirred at −50 C for 10 min, then stirred at room temperature for 40 min. The solution turned light red-brown. It was diluted with DCM and a 20% sodium carbonate solution (100 mL) was added. The reaction mixture was stirred vigorously for 15 min. The organic phase was separated twice and dried over $MgSO_4$. Filtration and concentration to give the desired benzyl isocyanoacetate in quantitative yield which was used in the next step without further purification.

To a solution of 1,2,4-triazole (914 mg, 13.2 mmol) in anhydrous $CH_3CN$ (20 mL) at 0° C. was added i-$Pr_2NEt$ (2.5 mL, 14.6 mmol). Once all the triazole was dissolved, $POCl_3$ (0.43 mL, 4.6 mmol) was added. The mixture was stirred at 0° C. for 2 h. The lactam ester 16' (1 g, 3.31 mmol) was added. The resulting solution was heated in an oil bath at 80° C. for 16 h. The mixture was cooled with an ice bath. Diluted with EtOAc then water was added. Aq. layer was separated and extracted with EtOAc four times. The combined organic extracts was washed with brine and dried over $MgSO_4$. Filtration and concentration gave a light yellow solid which was used directly in the next step (M+1=354).

A solution of benzyl isocyanoacetate (892 mg, 5.1 mmol) in DMF (10 mL) was cooled to −50° C. under a nitrogen atmosphere. KOtBu (514 mg, 4.6 mmol) was added. The mixture was stirred at −50° C. for 1 h. The triazole derivative prepared above (900 mg, 2.55 mmol) in DMF (5 mL) was added slowly at −50° C. The mixture was allowed to warm to room temperature over 16 h. Saturated aqueous $NH_4Cl$ solution was added and it was extracted with EtOAc three times. The combined extracts were washed with brine (3×) and dried over $MgSO_4$. Filtration and concentration gave a crude product. Chromatography (RediSep 24 g silica-gel column, eluted with 70% EtOAc in Hexanes) to give 886 mg (76% yield) of product (M+1=460).

To a solution of benzyl ester derivative (770 mg, 1.68 mmol) in EtOAc (10 mL) and MeOH (30 mL) was added wet Pd/C (60 mg) and the resulting suspension was stirred under a hydrogen atmosphere for 48 h. The suspension was filtered through Celite and the resulting solution was concentrated. The crude debenzylated product (530 mg, 86% yield) was used in the next step without further purification (M+1=370).

To a suspension of acid (530 mg, 1.44 mmol) in DCM (10 mL) was added CDI (931 mg, 5.75 mmol). The solution was stirred at room temperature for 2 h. The solution was cooled down with an ice bath and a $NH_4OH$ solution (6 ml) was added. The solution was stirred for 30 min and it was concentrated. The solid was collected by filtration and washed with water to give 422 mg (80%) of the desired product as a brown solid. (M+1=369).

To a suspension of primary amide derivative (422 mg, 1.15 mmol) in dioxane (10 mL) was added $POCl_3$ (160 µL, 1.7 mmol). The suspension was heated at 90° C. for 2 h. The resulting solution was cooled down with an ice bath and quenched with a saturated aqueous $NaHCO_3$ solution. The solid was collected by filtration to give 308 mg (77% yield) of the desired cyanide derivative. (M+1=351).

To a suspension of cyanide derivative (150 mg, 0.44 mmol) in EtOH (4 mL) and water (1 mL) was added hydroxylamine hydrochloride (40 mg, 0.57 mmol) and potassium carbonate (67 mg, 0.48 mmol). The suspension was stirred at room temperature for 16 h. LCMS indicated about 50% conversion. More hydroxylamine hydrochloride (40 mg, 0.57 mmol) and potassium carbonate (67 mg, 0.48 mmol) were added, and stirred for another 24 h. The solution was diluted with EtOAc and washed with water. The combined organic phases were washed with brine, dried over $MgSO_4$. Filtration and concentration gave 145 mg (86% yield) of the desired product. (M+1=384).

To a solution of acetic acid (0.22 mL, 3.8 mmol) in THF (5 mL) was added CDI (123 mg, 0.76 mmol). The solution was stirred at room temperature for 2 h. The solution was then poured into a flask containing the oxime derivative (145 mg, 0.38 mmol) and heated at 70 C for 1 hour. The solvent was evaporated and the crude material was suspended in acetic acid (8 mL) and heated at 130° C. for one hour. The solvent was evaporated and the crude material was triturated with water to give 134 mg (86%) of the desired product (M+1=408).

To a suspension of ester derivative (50 mg, 0.12 mmol) in THF (1 mL) was added lithium aluminum hydride (7 mg, 0.18 mmol). The suspension was stirred at room temperature for 2 h. LCMS indicated about 70% conversion along some other side products and some remaining starting material. More lithium aluminum hydride (4 mg) was added and the reaction mixture was stirred at room temperature for another 30 min. The reaction mixture was quenched with 1N HCl. The solution was extracted with EtOAc (3×). The combined organic phases were washed with brine, dried over $MgSO_4$. Filtration and concentration gave 20 mg (45% yield) of the desired alcohol product. (M+1=366).

To a suspension of alcohol (20 mg, 0.055 mmol) in dioxane (1 mL) was added $POBr_3$ (31 mg, 0.11 mmol). The reaction mixture was heated at 110° C. for 1 hour. The reaction mixture was cooled down with an ice bath and sat. aq. $NaHCO_3$ solution was added. The resulting solution was extracted with EtOAc (3×). The combined organic phases were washed with brine and dried over $MgSO_4$. The solvent was concentrated to give 22 mg (96% yield) of the desired product (M+1=428).

To a vial containing alkyl bromide derivative (22 mg, 0.052 mmol) was added 3-fluorophenol (58 mg, 0.52 mmol) in dioxane (1 mL) and potassium carbonate (72 mg, 0.52 mmol). The reaction mixture was heated at 90° C. for 1 hour. The reaction mixture was diluted with sat. aq. $NaHCO_3$ solution. The resulting solution was extracted with EtOac (3×). The combined organic phases were washed with brine and dried over $MgSO_4$. Filtration and concentration gave a crude product. Purification by prep TLC (eluting system: EtOAc) to give 5 mg (21% yield) of the desired product Compound 168 (M+1=460). $H^1$NMR ($CDCl_3$) δ 7.87 (1H, s), 7.65 (1H, d, J=3.5 Hz), 7.57 (1H, d, J=10 Hz), 7.24 (1H, m), 7.19 (1H, dd, J=3.5, 9 Hz), 6.77 (1H, dd, J=2.5, 9.5 Hz), 6.72 (2H, m), 5.26 (2H, s), 3.97 (3H, s), 2.48 (3H, s).

Synthesis of Compounds 215-313

Scheme 28

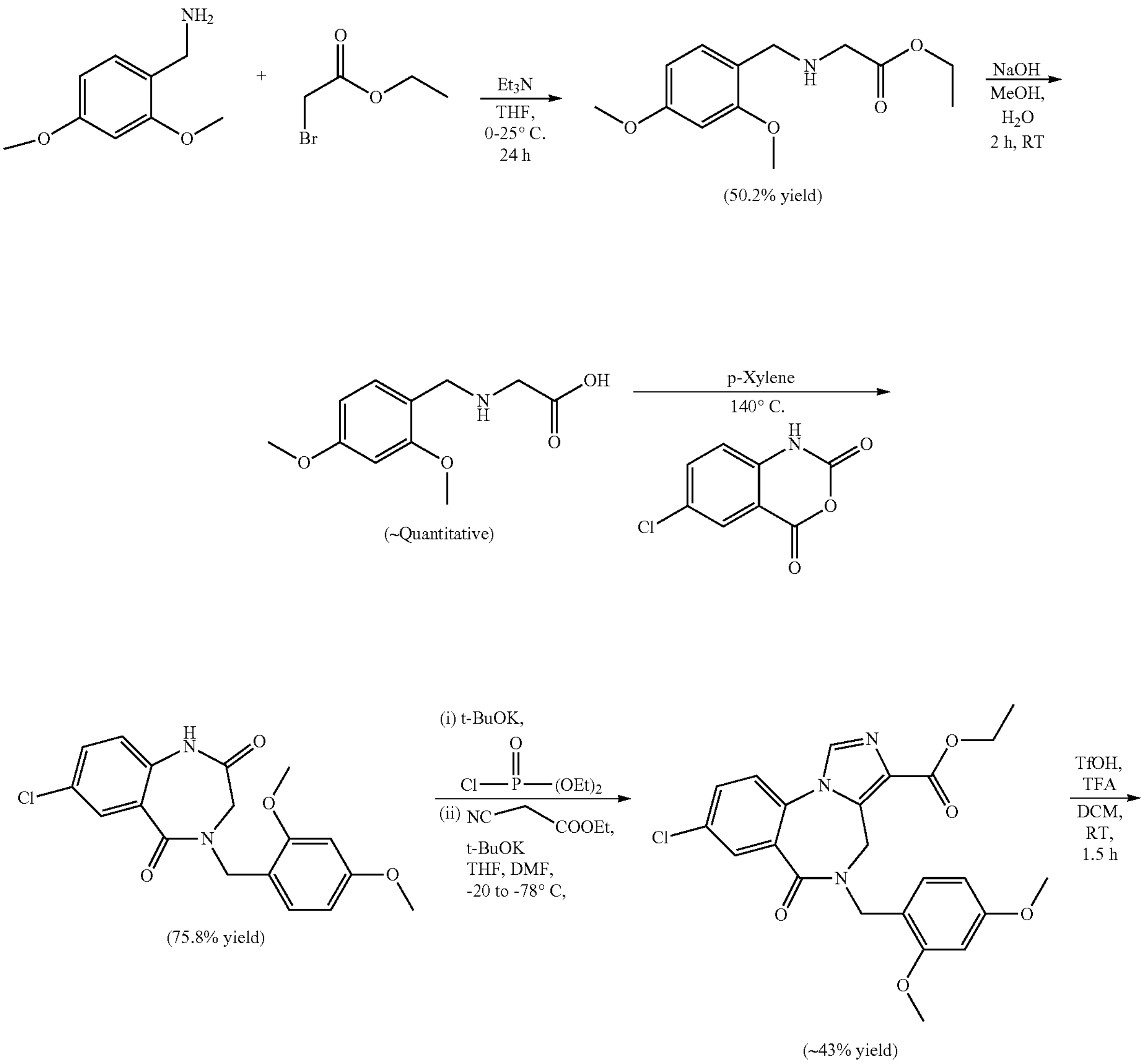

-continued

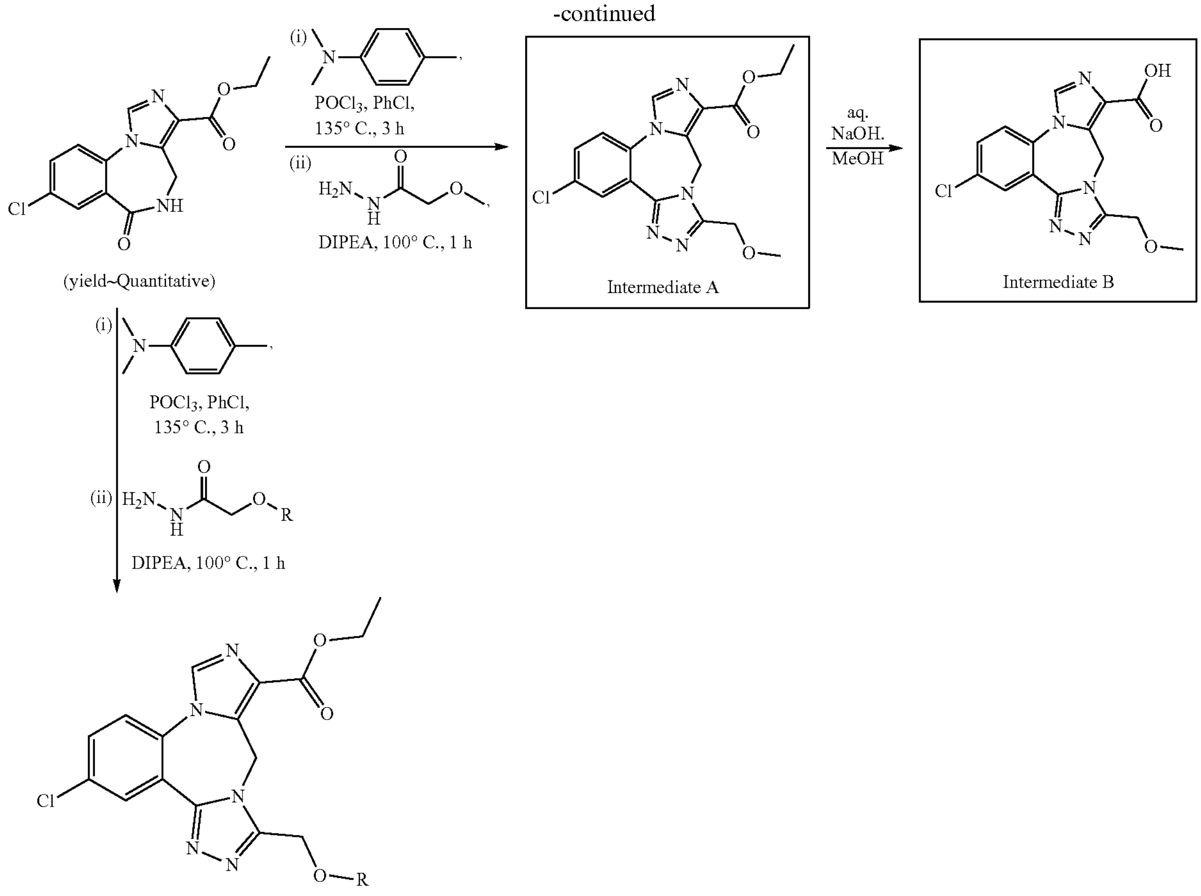

Intermediate C
R = Ph
Intermediate D
R = Bn

Synthesis of Intermediate A (ethyl 15-chloro-9-(methoxymethyl)-2,4,8,10,11-penta-azatetracyclo [11.4.0.0$^{2,6}$ 0.0$^{8,12}$]heptadeca-1(17),3,5,9,11,13,15-heptaene-5-carboxylate)

Ethyl bromoacetate (Scheme 28) (10.0 gm, 59.87 mmol) solution in 20.0 mL of anhydrous THF was added dropwise to a solution of (2,4-dimethoxybenzyl)amine (10.0 gm, 59.81 mmol) and triethyl amine (6.06 gm, 59.87 mmol) in anhydrous THF (20.0 mL) at 0° C. under nitrogen atmosphere. The reaction mixture was warmed to room temperature and stirred overnight. Brine was added ~100 mL, and the reaction mixture was extracted with ethyl acetate (2x~100 mL). Combined extracts were dried over anhydrous $MgSO_4$ and concentrated under reduced pressure. The purification was performed using combiFlash chromatography, Gradient: 20:80 to 50:50 v/v Ethylacetate:Hexane. 7.6 gm (yield 50.2%) of the alkylation product was obtained as a colorless liquid. m/z calculated for $C_{13}H_{19}NO_4[M+H]^+$: 254; Obtained: 254.1.

The ester (7.5 gm, 29.6 mmol) was dissolved in 40.0 mL of methanol. The reaction mixture was cooled and 2N aq. NaOH (88.82 mmol, 44.0 ml) solution was added dropwise. The reaction mixture was warmed to room temperature and stirred for 2 h. The reaction mixture was diluted with ~75.0 mL of water, cooled in ice bath and neutralized down to ~5.0 to 4.5 pH using 2N aq. HCL. The excess water was concentrated under reduced pressure and air streamed to obtain white solid powder. The solid was dissolved in 85:15 v/v, DCM:MeOH (100.0 mL) and filtered, the filtrate was evaporated to obtain 7.1 gm of carboxylic acid as a white powder (Hygroscopic). m/z calculated for $C_{11}H_{15}NO_4[M+Na]^+$: 248; Obtained: 248.1.

The above compound (7.0 gm, 31.08 mmol) and 6.14 gm, 31.08 mmol of 5-chloroisatoic anhydride were mixed in 70.0 mL of p-Xylene and refluxed at 140° C. temperature for 3 h. The reaction mixture filtered and crude product recrystallized from methanol. 8.5 gm of 7-chloro-4-[(2,4-dimethoxyphenyl)methyl]-2,3,4,5-tetrahydro-1H-1,4-benzodiazepine-2,5-dione was obtained as a white powder (75.8% yield). m/z calculated for $C_{18}H_{17}ClN_2O_4[M+H]^+$: 361: Obtained: 361.1.

The above benzodiazepine-2,5-dione (4 gm, 11.1 mmol) was dissolved in THF/DMF (57.2/12.7 mL) and cooled at −20° C. temperature. Finely divided potassium-tert-butoxide powder (1.9 gm, 16.6 mmol) was added and reaction mixture stirred at −20° C. for 20.0 min. 3.1 gm, 17.7 mmol of diethylchlorophosphate was dropwise added to the reaction mixture at −20° C. and allowed to 0-5° C. for 3 h. The reaction mixture was stirred at ambient temperature for 10.0 min. 2.1 gm, 18.4 mmol of ethylisocyanoacetate was added to the reaction mixture at −20° C. and the reaction mixture was further cooled down to −78° C. 1.9 gm, 16.6 mmol of finely divided potassium-tert-butoxide powder was added at −78° C. and the reaction mixture was stirred overnight by slowly warming to ambient temperature. The reaction mixture was quenched with saturated aq. $NH_4Cl$ solution (10 mL), extracted with ethyl acetate (3×20 mL). Combined extracts were dried over anhydrous $MgSO_4$ and concentrated under reduced pressure. The crude product was recrystallized from ethylacetate to obtain 2.2 gm of ethyl 12-chloro-8-[(2,4-dimethoxyphenyl)methyl]-9-oxo-2,4,8-triazatricyclo[8.4.0.0$^{2}$,$^{6}$]tetradeca-1(14), 3,5,10,12-pentaene-5-carboxylate as a white solid. A second crop was obtained from the mother liquor to afford another 3.5 g of product (64% yield).

The dimethoxybenzyl protecting group was removed by dissolving the above compound (2.2 gm, 4.83 mmol) in DCM (25.0 mL), followed by addition of 25.0 mL of trifluoroacetic acid and 1.45 gm, 9.65 mmol of trifluoromethanesulfonic acid. The reaction mixture was stirred at room temperature for 90 min. The reaction mixture was neutralized with aq. $NaHCO_3$ and the ppts were filtered, washed with water and dried to afford 1.9 gm of ethyl 12-chloro-9-oxo-2,4,8-triazatricyclo[8.4.0.0$^{2}$,$^{6}$]tetradeca-1(14),3,5,10,12-pentaene-5-carboxylate as a solid product. m/z calculated for $C_{14}H_{12}ClN_3O_3[M+H]^+$: 306; Obtained: 306.1.

In the first step, the ethyl 12-chloro-9-oxo-2,4,8-triazatricyclo[8.4.0.0$^{2}$,$^{6}$]tetradeca-1(14),3,5,10,12-pentaene-5-carboxylate from above (1.9 gm, 6.21 mmol) was dissolved in 25.0 mL of chlorobenzene, followed by addition of 2.52 gm, 18.64 mmol of 4,N,N-trimethylaniline, 1.42 gm, 9.32 mmol of $POCl_3$ and the reaction mixture was refluxed at 135° C. for 2 h. LCMS shows ~50% starting material remained unreacted. 1.68 gm, 12.42 mmol of additional 4,N,N-trimethylaniline and 0.95 gm, 6.21 mmol of $POCl_3$ were further added to the reaction mixture at room temperature and refluxed at 135° C. for 1 h. LCMS shows ~10% starting material remained unreacted. An additional 0.84 gm, 6.21 mmol of 4,N,N-trimethylaniline (total 6.0 eq.) and 0.48 gm, 3.11 mmol of $POCl_3$ (total 3 eq.) were further added to the reaction mixture at room temperature and refluxed at 135° C. for 1 h.

In the second step, 4.67 gm, 44.75 mmol of methoxyaceticacid hydrazide (total 7.2 eq.), followed by 7.71 gm, 59.66 mmol of N,N-diisopropylethylamine were added to the reaction mixture at room temperature and refluxed at 100° C. for 1 h. The reaction mixture was cooled to room temperature and neutralized with aq. $NaHCO_3$ solution (~25.0 mL). The organic was extracted with ethyl acetate (75 mL×3), followed by DCM (50.0 mL×3) and washed with brine. The EtOAc organic layer was separated by filtering the insoluble ppts (0.805 gm pure product) and combined organic layers were dried over anhydrous $MgSO_4$, concentrated under reduced pressure. The crude product was purified by Combiflash chromatography (Mobile phase: 0-10% MeOH:EtOAc) to yield an additional 0.8 gm of yellow solid. Total yield for the last two steps of Intermediate A (ethyl 15-chloro-9-(methoxymethyl)-2,4,8,10,11-penta azatetracyclo[11.4.0.0$^{2}$,$^{6}$0.0$^{8}$,$^{12}$]heptadeca-1(17),3,5,9,11,13,15-heptaene-5-carboxylate) was 72.58%. m/z calculated for $C_{17}H_{16}ClN_5O_3[M+1]^+$: 374; Obtained: 374.1.

Synthesis of Intermediate B (15-chloro-9-(methoxymethyl)-2,4,8,10,11-penta-azatetracyclo[11.4.0.0$^{2}$,$^{6}$0.0$^{8}$,$^{12}$]heptadeca-1(17),3,5,9,11,13,15-heptaene-5-carboxylic acid)

Intermediate A (0.4 gm, 1.07 mmol) was dissolved in mixture of THF/$H_2O$/MeOH (3.2/4.8/8.0 v/v mL). 0.05 gm, 2.14 mmol of LiOH was added and the reaction mixture was stirred at room temperature for 3 h. The reaction mixture was acidified with aq. 2N HCl solution, ppts were collected and washed with DI water. After drying 0.36 gm of Intermediate B (15-chloro-9-(methoxymethyl)-2,4,8,10,11-penta-azatetracyclo[11.4.0.0$^{2}$,$^{6}$0.0$^{8}$,$^{12}$]heptadeca-1(17),3,5,9,11,13,15-heptaene-5-carboxylic acid) was obtained as a white solid. m/z calculated for $C_{15}H_{12}ClN_5O_3[M+H]^+$: 346; Obtained: 345.9.

Intermediates C (ethyl 15-chloro-9-(phenoxymethyl)-2,4,8,10,11-pentaazatetracyclo[11.4.0.0$^{2}$,$^{6}$0.0$^{8}$,$^{12}$]heptadeca-1(17),3,5,9,11,13,15-heptaene-5-carboxylate) and D (ethyl 15-chloro-9-(benzyloxymethyl)-2,4,8,10,11-pentaazatetracyclo[11.4.0.0$^{2}$,$^{6}$0.0$^{8}$,$^{12}$]heptadeca-1(17),3,5,9,11,13,15-heptaene-5-carboxylate) were synthesized analogously to Intermediate A using, respectively, 2-phenoxyacetohydrazide and 2-(benzyloxy)acetohydrazide in place of 2-methoxyacetohydrazide.

Scheme 29 illustrates some selected examples using Intermediate A to generate new analogs.

Scheme 29
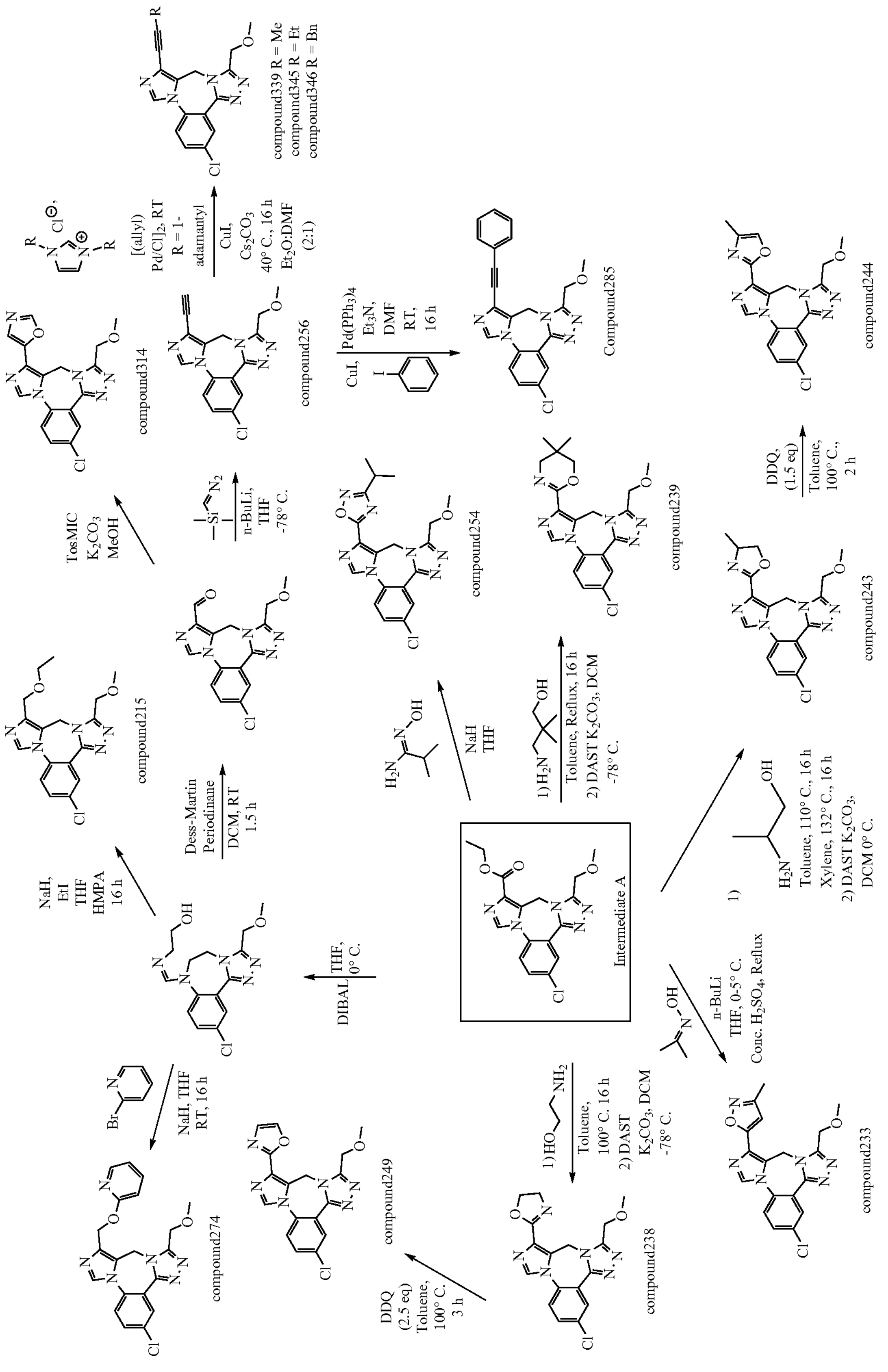

Synthesis of Compound 233 compound 233

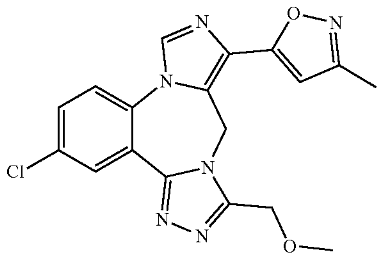

Acetoxime (0.22 gm, 0.31 mmol) was dissolved in anhydrous THF (0.5 mL). 0.38 mL, 0.62 mmol of 1.6 M n-BuLi was added dropwise and reaction mixture stirred at 0-5° C. for 1 h in separate flask. A solution of Intermediate A (0.05 gm, 0.13 mmol) in 1.0 mL of THF was added by cannula at 0-5° C. and the rxn was stirred for 16 h by gradually warming at room temperature. LCMS indicated starting material and intermediate m/z: 374.1 (~45/14%, two peak merged), m/z 401 (~10), m/z 402 (18).

The reaction mixture was quenched with 0.03 mL of Conc. $H_2SO_4$, followed by 0.03 mL of DI water and refluxed for 2 h. LCMS indicated starting material, product and intermediate m/z: 374.1 (~43%), m/z 383 (~40%), m/z 402 (17%).

The reaction mixture was concentrated under reduced pressure and neutralized with aq. $NaHCO_3$ solution, the ppts collected and washed with DI water. After drying gave 22.0 mg of crude ppts. Compound was purified by prep-TLC plate using 1:99 MeOH:$CHCl_3$.

Synthesis of Compound 238 compound 238

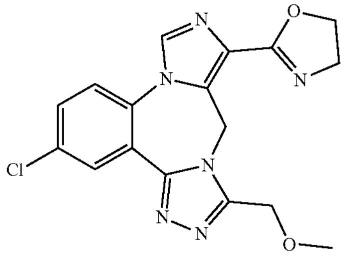

Step: 1 Intermediate A (0.045 gm, 0.12 mmol) was dissolved in anhydrous toluene (3.0 mL). 0.05 mL, 0.25 mmol of aminoethanol (35.0 eq) was added and reaction mixture was refluxed for 16 h. The toluene was evaporated and reaction mixture was dissolved in DCM (25.0 mL). The DCM layer was washed with brine followed by DI water, separated and dried over anhydrous $MgSO_4$. The evaporation of organic layer gave 38.3 mg of the corresponding amide. LCMS indicated product formation m/z: 389

Step: 2 The above amide (0.038 gm, 0.09 mmol) was dissolved in dry DCM (2.0 mL). 0.026 mL, 0.2 mmol of DAST (2.0 eq) was added to the reaction mixture at 0° C. temperature and stirred for 1.5 h at 0° C. 0.065 gm solid $K_2CO_3$ (4.8 eq) was added at 0° C. and reaction mixture was stirred for 30 min. The reaction mixture was diluted with aq. $NaHCO_3$ solution and extracted with DCM (15.0 mL×3). The organic layer was washed with brine, separated and dried over anhydrous $MgSO_4$. The evaporation of solvent gave 36 mg of white solid product. m/z calculated for $C_{17}H_{15}ClN_6O_2[M+H]^+$: 371; Obtained: 371.

Synthesis of Compound 239 compound 239

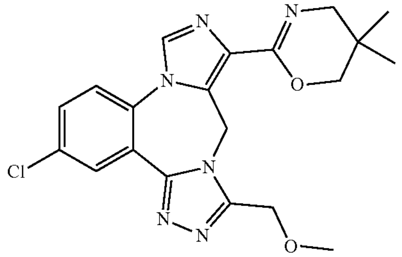

Step: 1 Intermediate A (0.05 gm, 0.13 mmol) was dissolved in anhydrous toluene (3.0 mL). 0.28 gm, 2.67 mmol of aminoethanol (20.0 eq) was added and reaction mixture was refluxed for 16 h. The toluene was evaporated and reaction mixture was dissolved in DCM (25.0 mL). The DCM layer was washed with brine followed by DI water, separated and dried over anhydrous $MgSO_4$. The evaporation of organic layer gave the amide. LCMS indicated product formation m/z: 431

Step: 2 The above amide (0.057 gm, 0.13 mmol) of was dissolved in dry DCM (2.0 mL). 0.035 mL, 0.3 mmol of DAST (2.0 eq) was added to the reaction mixture at 0 C temperature and stirred for 1.5 h at 0 C. LCMS indicated product formation m/z 413. 0.088 gm solid $K_2CO_3$ (4.8 eq) was added at 0° C. and reaction mixture was stirred for 30 min. The reaction mixture was diluted with aq. $NaHCO_3$ solution and extracted with DCM (15.0 mL×3). The organic layer was washed with brine, separated and dried over anhydrous $MgSO_4$. Concentration of the organic layer afforded product which was triturated with 20/80 Hex/EtOAc to give a solid which was collected by filtration and dried: 49.4 mg (89%).

Synthesis of Compound 243 compound 243

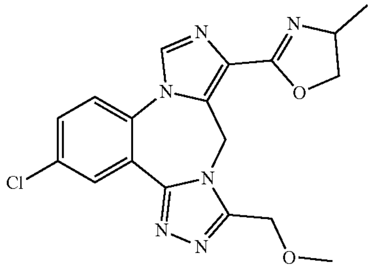

Step: 1 Intermediate A (0.05 gm, 0.13 mmol) was dissolved in anhydrous toluene (3.0 mL). 0.02 mL, 2.67 mmol of the amino alcohol (20.0 eq) was added and reaction mixture was refluxed for 16 h. LCMS indicated starting material left. Xylene was placed (3.0 mL) and 10.0 eq of 3-aminobutan-1-ol added and reaction mixture refluxed for 16 h. Finally total 40.0 eq of amino ethanol was required to convert all starting material into product in refluxing xylene. The rxn mixture cooled to 0° C. and ppts filtered. The filtrate was extracted with DCM (15.0 mL×4). The DCM layer was washed with brine followed by DI water, separated and dried over anhydrous $MgSO_4$. The evaporation of organic layer gave the corresponding amide. LCMS indicated product formation m/z: 403.

Step: 2 The above amide (0.054 gm, 0.13 mmol) was dissolved in dry DCM (2.0 mL). 0.05 mL, 0.33 mmol of DAST was added to the reaction mixture at 0° C. temperature and stirred for 1.5 h at 0° C. LCMS indicted product formation. 0.09 gm solid $K_2CO_3$ was added at 0° C. and reaction mixture was gradually warmed to room temperature. The reaction mixture was diluted with aq. $NaHCO_3$ solution and extracted with DCM (15.0 mL×3). The organic layer was washed with brine, separated and dried over anhydrous $MgSO_4$. The evaporation of solvent gave crude product. Purification was performed by prep TLC, Mobile Phase: 95:05, DCM:MeOH. m/z calculated for $C_{18}H_{17}ClN_6O_2[M+H]^+$: 385; Obtained: 385.

Synthesis of Compound 244 compound 244

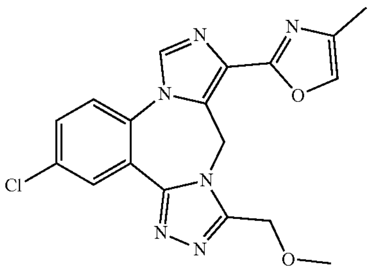

Compound 243 from above (0.011 gm, 0.03 mmol) was dissolved in toluene (2.0 mL). 0.010 gm, 0.04 mmol of DDQ was added and reaction mixture was stirred at 50° C. for 1 h. LCMS indicated starting material m/z 385 and little amount of product m/z 383. The rxn mixture was stirred at 60° C. for 3 h. LCMS indicated starting material m/z 385, product m/z 383. The rxn mixture was stirred at 70° C. for 2 h. LCMS indicated starting material m/z 385, product m/z 383 and side product m/z 421. The reaction mixture was stirred at 40° C. for 16 h. LCMS indicated major amount of product m/z 383 and little amount of side product m/z 421 and starting material. The toluene was evaporated and crude product was purified by prep-TLC plate. Mobile phase DCM:MeOH, 95:05 v/v to obtain 4.4 mg of product. m/z calculated for $C_{18}H_{15}ClN_6O_2[M+1]^+$: 383; Obtained: 383.

Synthesis of Compound 249 compound 249

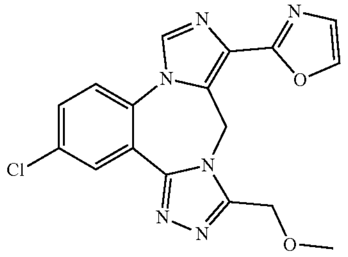

Compound 238 from above (0.016 gm, 0.05 mmol) was dissolved in toluene (2.0 mL). 0.015 gm, 0.07 mmol of DDQ was added and reaction mixture was stirred at 50° C. for 1 h. LCMS indicated starting material m/z 371. The rxn mixture was stirred at 60° C. for 5 h. LCMS indicated starting material m/z 371, product m/z 369 and undesired m/z 407. The rxn mixture was stirred at 30° C. for 16 h. LCMS indicated starting material m/z 371, product m/z 369 and side product m/z 407. The reaction mixture was stirred at 65° C. for 4 h. LCMS indicated product m/z 369, side product m/z 407 and little amount of starting material. The toluene was evaporated and crude product was purified by prep-TLC plate. Mobile phase DCM:MeOH, 95:05 v/v to obtain 2.3 mg of product. m/z calculated for $C_{17}H_{13}ClN_6O_2[M+H]^+$: 369; Obtained: 369.

Synthesis of Compound 256 compound 256

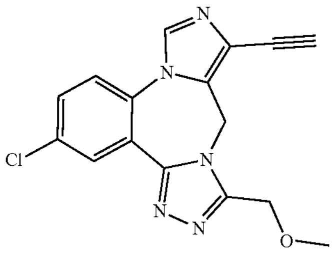

Step 1: Intermediate A (0.1 gm, 0.27 mmol) was dissolved in anhydrous THF (3.0 mL). 0.67 mL, 0.67 mmol of 1.0 M solution of DIBAL in THF was added dropwise and reaction mixture stirred at 0-5° C. for 2 h. LCMS shows alcohol reduction product formation m/z 332. The reaction was quenched with MeOH (1.0 mL), followed by water (0.5 mL). The saturated solution of $NaHCO_3$ was added and ppts were filtered through celite bed. The product was extracted using DCM (25.0 mL×3). The combined DCM layers was washed with brine, separated and dried over anhydrous $Na_2SO_4$. The evaporation of solvent gave 46.1 mg of [15-chloro-9-(methoxymethyl)-2,4,8,10,11-pentaazatetracyclo [11.4.0.$0^{2,6}$0.$0^{8,12}$]heptadeca-1(17),3,5,9,11,13,15-heptaen-5-yl]methanol as a solid product, Yield 51.9%. m/z calculated for $C_{15}H_{14}ClN_5O_2[M+H]^+$: 332; Obtained: 332.

Step 2: The above alcohol (0.05 gm, 0.14 mmol) of was dissolved in anhydrous DCM (3.0 mL). 0.09 gm of Dess-Martin Periodinane was added and reaction mixture was stirred at room temperature for 2 h. LCMS shows product formation m/z 330. The reaction was quenched with 1N NaOH solution (2-mL). The saturated solution of $NaHCO_3$ was added and the product was extracted using DCM (20.0 mL×3). The combined DCM layers was washed with brine, separated and dried over anhydrous $Na_2SO_4$. The evaporation of solvent gave desired aldehyde (15-chloro-9-(methoxymethyl)-2,4,8,10,11-pentaazatetracyclo[11.4.0.0$^2$,$^6$0.0$^8$,$^{12}$]heptadeca-1(17),3,5,9,11,13,15-heptaene-5-carbaldehyde) as a solid product, Yield Quantitative. m/z calculated for $C_{15}H_{12}ClN_5O_2[M+H]^+$: 330; Obtained: 330.

Step 3: 1.6 M n-BuLi solution in hexane (0.68 mL, 1.08 mmol) was added dropwise into 1.4 mL, 0.86 mmol of trimethylsilyldiazomethane solution in hexane dissolved in 3.0 mL of THF at −78° C. temperature. The reaction mixture was stirred at −78° C. temperature for 30.0 min. The aldehyde obtained in Step 2 (0.142 gm, 0.43 mmol) in solution in 3.0 mL of THF was added dropwise into the reaction mixture at −78° C. temperature and gradually warmed to room temperature. LCMS shows product formation m/z 326 and starting material m/z 330. The reaction mixture was quenched with saturated $NH_4Cl$ solution. The product was extracted using DCM (15.0 mL×3). The combined DCM layers was washed with brine, separated and dried over anhydrous $Na_2SO_4$. The purification of crude product was performed by ISCO Combiflash purification system, Mobile Phase: Ethyl acetate/Hexane. 19.0 mg of Compound 256 was obtained and 71.6 mg of starting material was isolated. m/z calculated for $C_{16}H_{12}ClN_5O$ $[M+H]^-$: 326; Obtained: 326.

Synthesis of Compound 285

Compound 285

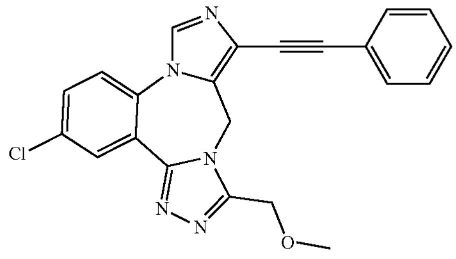

Compound 256 (0.025 gm, 0.08 mmol) was dissolved in degassed DMF (2.0 mL). 0.03 mL, 0.23 mmol of iodobenzene was added to the reaction mixture followed by 0.06 mL, 0.41 mmol of TEA. The reaction mixture was stirred at room temperature. 0.04 gm, 0.04 mmol of $Pd(PPh_3)_4$ and 0.003 gm, 0.015 mmol of CuI mixture was added to the reaction mixture and stirred for 16 h. LCMS shows product formation m/z 402. The reaction mixture was diluted with DI water. The product was extracted using DCM (10.0 mL×3). The combined DCM layers was washed with brine, separated and dried over anhydrous $Na_2SO_4$. The crude reaction mixture was purified through prep-TLC plate. Mobile Phase: EtOAc/MeOH. m/z calculated for $C_{22}H_{16}ClN_5O$ $[M+H]^+$: 402; Obtained: 402.

Synthesis of Compound 314

Compound 314

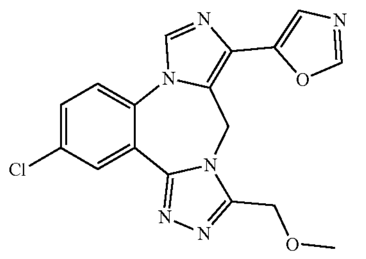

The aldehyde (15-chloro-9-(methoxymethyl)-2,4,8,10,11 penta-azatetracyclo [11.4.0.0$^2$,$^6$0.0$^8$,$^{12}$]heptadeca-1(17),3,5,9,11,13,15-heptaene-5-carbaldehyde) from Synthesis of Compound 256; Step 2 (0.015 g, 0.04 mmol) and 0.011 g (0.055 mmol) of TosMIC was dissolved in MeOH (2.5 mL). 0.013 g (0.09 mmol) of $K_2CO_3$ was added and reaction mixture was stirred at 60° C. for 2 h. LCMS shows product formation m/z 369.1. The MeOH was evaporated and ppts were dissolved in water and acidified with aq. 2N HCl solution. The ppts were filtered and washed with DI water to give 10.4 mg (62%) of Compound 314; m/z calculated for $C_{17}H_{13}ClN_6O_2[M+H]^+$: 369; Obtained: 369.1.

Synthesis of Compound 339

Compound 339

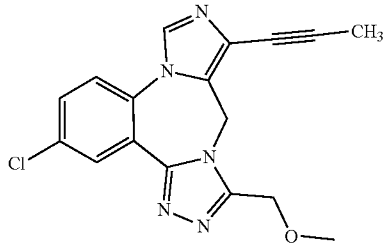

1,3-Bis(1-adamantly)imidazolium chloride (0.07 g, 0.01 mmol), $[(allyl)PdCl]_2$ (0.003 g, 0.009 mmol), CuI (0.004 g, 0.02 mmol) and $Cs_2CO_3$ (0.04 g, 0.13 mmol) were added in vial under nitrogen. A mixture of diethylether and DMF (2:1, 2.0 mL) was added, followed by 0.03 gm (0.09 mmol) of Compound 256 and 0.014 g (0.1 mmol) of MeI. The reaction mixture was stirred at 40.0° C. temperature for 16 h. LCMS shows product formation m/z 340.2. The reaction mixture was quenched with water (20.0 mL) and diluted with ethyl acetate (40.0 mL). The combined layers were filtered. The organic layer was separated and dried over anhydrous $Na_2SO_4$. The evaporation of organic layer gave crude product. The purification of crude product was performed by prep-TLC plate: Mobile Phase: EtOAc:MeOH, 97:03 v/v mL to give 8.5 mg of Compound 339 (27%): m/z calculated for $C_{17}H_{14}ClN_5O[M+H]^+$ 340, Obtained 340.2.

Synthesis of Compound 345

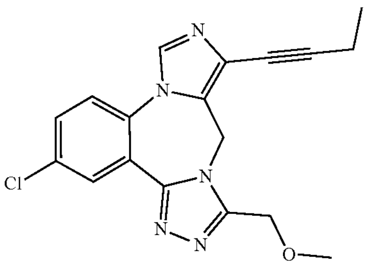

Compound 345

Compound 345 was prepared in an analogous fashion to compound 339 (Scheme 29) using ethyl iodide in place of methyl iodide to afford compound m/z calculated for $C_{18}H_{16}ClN_5O[M+H]^+$ 354, Obtained 354.2.

Synthesis of Compound 346

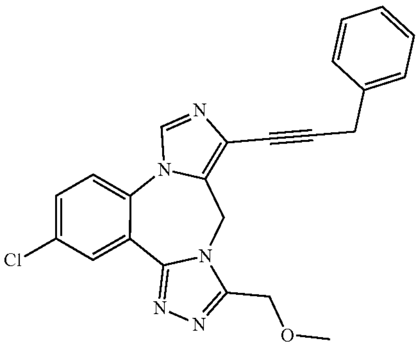

Compound 346

Compound 346 was prepared in an analogous fashion to compound 339 (Scheme 29) using benzyl bromide in place of methyl iodide to afford compound m/z calculated for $C_{23}H_{18}ClN_5O$ $[M+H]^+$ 416, Obtained 416.3

Synthesis of Compound 329

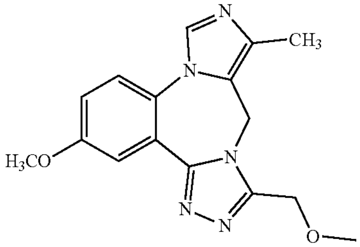

Compound 329

The alcohol [15-chloro-9-(methoxymethyl)-2,4,8,10,11-Pentaazatetracyclo-[11.4.0.0$^{2}$,$^{6}$0.0$^{8}$,$^{12}$]heptadeca-1(17),3,5,9,11,13,15-heptaen-5-yl]methanol Synthesis of Compound 254

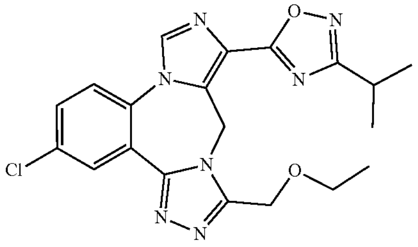

Compound 254

Isobutyronitrile (10.0 gm, 144.70 mmol) was dissolved in EtOH:Water (150:50 mL, v/v), followed by addition of 10.0 gm, 144.70 mmol of hydroxylamine hydrochloride and 20.0 gm, 144.70 mmol of $K_2CO_3$. The reaction mixture was refluxed at 80° C. for 6 h. The solvent was evaporated under reduced pressure and the resulting solid was treated with 150 mL of ethanol, sonicated, filtered and washed with 100 mL of ethanol. The combined filtrate was evaporated under reduced pressure and azeotrope with toluene (25.0 mL×3) to afford 8.1 gm of N'-hydroxy-2-methylpropinidamide as a colorless liquid slurry (54.8% yield). The above amide-oxime (1.37 gm, 13.38 mmol) was azeotroped with toluene (10 mL×5) before use and dissolved in 20.0 mL of anhydrous THF. 0.27 gm, 6.69 mmol of NaH was added in three portion to the reaction mixture at 0° C. and stirred at ambient temperature for 30.0 min. 0.5 gm, 1.34 mmol of Intermediate A was added and reaction mixture was stirred for 45.0 min at ambient temperature and refluxed at 67° C. for 90.0 min. The solvent was evaporated under reduced pressure and resulting yellow paste treated with 25.0 mL of aq. saturated $NaHCO_3$ solution. The ppts were filtered through funnel and washed with water 10.0 mL and hexane 10.0 mL to afford 0.380 gm solid (69.1% yield). m/z calculated for $C_{19}H_{18}ClN_7O_2[M+H]^+$: 412.0; Obtained: 412.1.

Synthesis of Compound 215

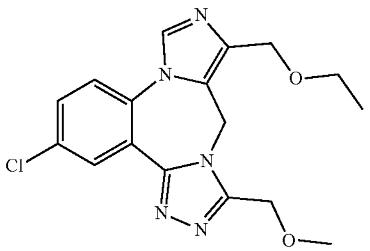

Compound 215

The alcohol [15-chloro-9-(methoxymethyl)-2,4,8,10,11-pentaazatetracyclo [11.4.0.0$^{2}$,$^{6}$0.0$^{8}$,$^{12}$]heptadeca-1(17),3,5,9,11,13,15-heptaen-5-yl]methanol (prepared in Compound 256, Step 1) (34 mg, 0.1025 mmol) was suspended in dry THF (2 mL). HMPA (36.7 mg, 0.205 mmol) was added followed by ethyl iodide (0.33 mL) and NaH (41 mg of 60% suspension in oil). The reaction was stirred at RT for 5 min, then heated to 70° C. overnight. The mixture was cooled and partitioned between EtOAc and brine. The organic phase was dried and concentrated to afford an oil which was purified by column chromatography (0% to 10% MeOH in DCM) to give 3.7 mg of compound 215 as an oil.

Synthesis of Compound 274

Compound 274

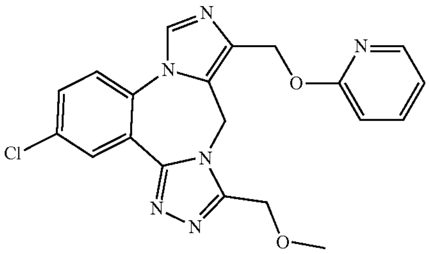

[15-chloro-9-(methoxymethyl)-2,4,8,10,11 pentaazatetracyclo[11.4.0.0$^{2,6}$0.0$^{8,12}$]heptadeca-1(17),3,5,9,11,13,15-heptaen-5-yl]methanol (0.02 gm, 0.06 mmol) was dissolved in anhydrous THF (3.0 mL). 0.003 gm of NaH was added and reaction mixture was stirred at room temperature for 30.0 min. 0.012 mL, 0.12 mmol of 2-bromopyridine was added dropwise and reaction mixture stirred at room temperature for 16 h. The reaction mixture was refluxed for additional 2 h. LCMS shows m/z 409. The reaction was concentrated under reduced pressure and diluted with saturated solution of $NaHCO_3$. The product was extracted using DCM (10.0 mL×4). The combined DCM layers was washed with brine, separated and dried over anhydrous $Na_2SO_4$. Purification was performed by prep TLC, Mobile Phase: 95:05, DCM:MeOH. ~1.0 mg of product obtained. m/z calculated for $C_{20}H_{17}ClN_6O_2[M+H]^+$: 409; Obtained: 409. Scheme 30 illustrates some selected examples using Intermediate B to generate new analogs.

Scheme 30
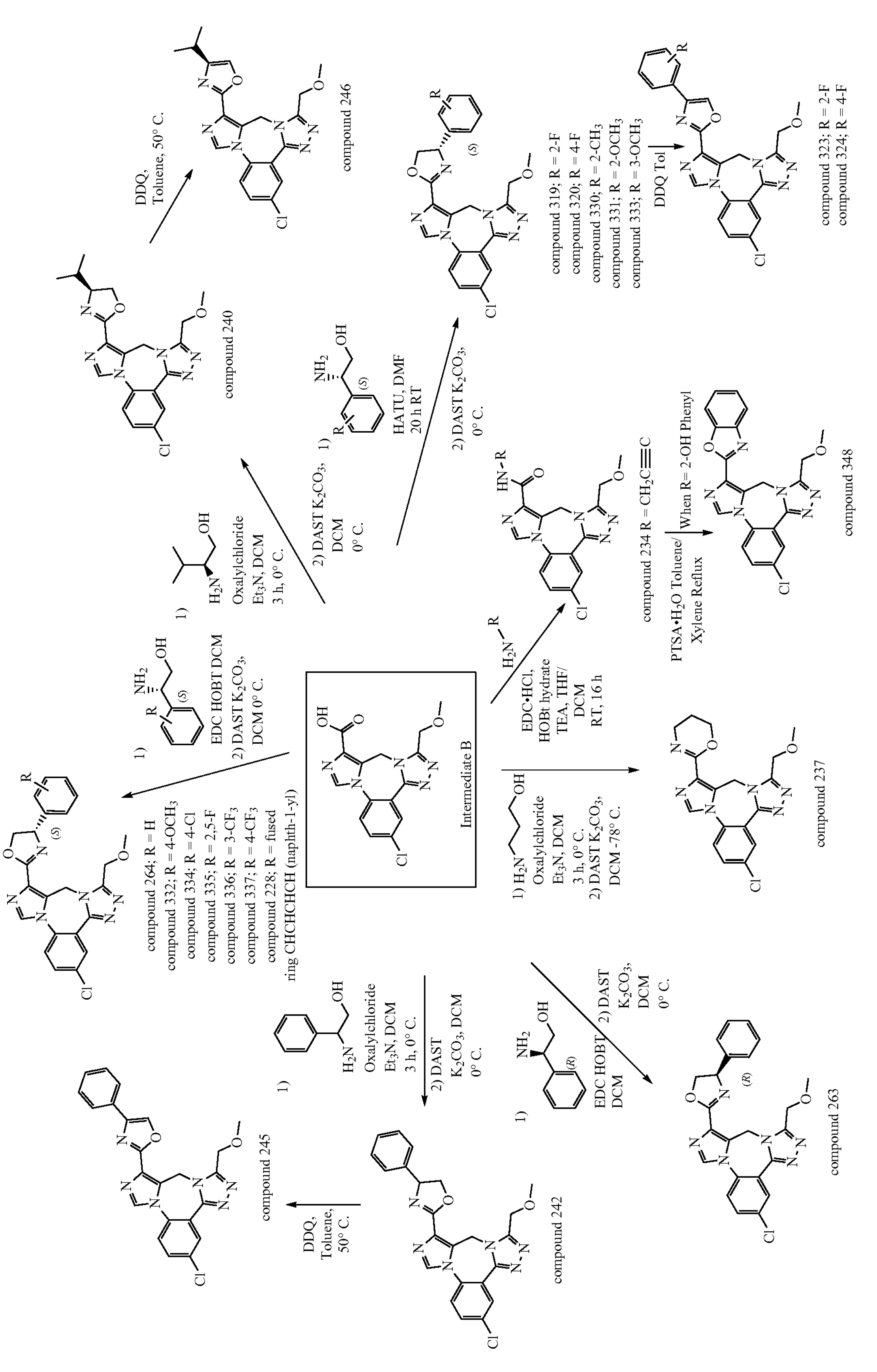
Intermediate B
compound 264; R = H
compound 332; R = 4-OCH3
compound 334; R = 4-Cl
compound 335; R = 2,5-F
compound 336; R = 3-CF3
compound 337; R = 4-CF3
compound 228; R = fused ring CHCHCHCH (naphth-1-yl)
compound 240
compound 246
compound 319; R = 2-F
compound 320; R = 4-F
compound 330; R = 2-CH3
compound 331; R = 2-OCH3
compound 333; R = 3-OCH3
compound 323; R = 2-F
compound 324; R = 4-F
compound 234 R = CH2C≡CH
compound 348
compound 237
compound 263
compound 242
compound 245

Synthesis of Compound 234 compound 234

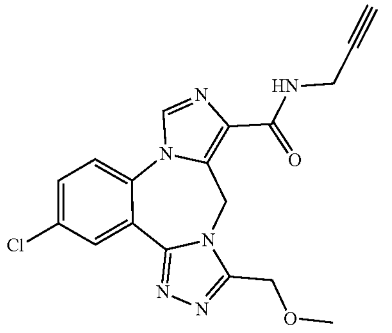

Intermediate B (0.043 gm, 0.12 mmol), 0.3 mmol of EDC·HCl and 0.048 gm, 0.31 mmol of HOBt hydrate were dissolved in THF/DCM (1:1, v/v 1.5 mL), followed by addition of 0.09 mL, 0.62 mmol of trimethylaniline and 0.016 mL, 0.25 mmol of propargylamine. The reaction mixture was stirred at room temperature for 16 h. The reaction mixture was diluted with aq. Ammonium chloride and extracted with ethylacetate. Combined layers were washed with brine, separated and dried over anhydrous $MgSO_4$. Evaporation of organic layer gave crude product ~13.0 mg. The crude product was purified through preparative TLC plate, Mobile Phase: 5:95, MeOH, Ethylacetate. m/z calculated for $C_{18}H_{15}ClN_6O_3[M+H]^-$: 383; Obtained: 383.1

Synthesis of Compound 348

Step 1: In a manner similar to the synthesis of compound 234, Intermediate B was converted to 15-chloro-N-(2-hydroxyphenyl)-9-(methoxymethyl)-2,4,8,10,11-pentaazatetracyclo[11.4.0.0$^2$,$^6$0.0$^8$,$^{12}$]heptadeca-1(17),3,5,9,11,13,15-heptaene-5-carboxamide.

Step 2: The above amide (0.017 g, 0.038 mmol) was dissolved in anhydrous toluene (2.5 mL). The p-toluene sulfonic acid monohydrate (0.043 g, 0.23 mmol) was added and reaction mixture was refluxed for 16 h. LCMS shows ~50:50 ratio of product and starting material. The toluene was replaced by xylene (2.5 mL) and reaction mixture was heated at 130° C. for 6 h. LCMS shows product formation m/z 419.2. The reaction mixture was concentrated and diluted with ethyl acetate (25.0 mL). The organic layer was washed with saturated solution of $NaHCO_3$ followed by brine. The organic layer was separated and dried over anhydrous $Na_2SO_4$. The evaporation of solvent gave crude product. The purification of crude product was performed by prep-TLC plate, Mobile phase: EtOAc:MeOH, 95:05 v/v to afford compound 348.

Synthesis of Compound 240 compound 240

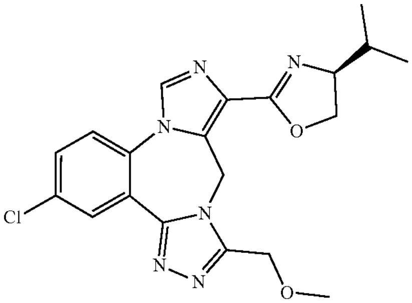

Step 1 Intermediate B (0.05 gm, 0.15 mmol) was dissolved in dry DCM (2.0 mL). 0.05 mL, 0.36 mmol of trimethylamine (2.5 eq), followed by 0.024 mL, 0.29 mmol of oxalylchloride (2.0 eq) were added and reaction mixture stirred for 60 min at room temperature. 0.076 mL, 0.7 mmol of amino-alcohol (5.0 eq) was added to reaction mixture at 0° C. and stirred for 2.5 h. The reaction mixture was diluted with aq. solution of $NaHCO_3$ and extracted with DCM (15.0 mL×3). The combined organic layers were washed with brine, separated and dried over anhydrous $MgSO_4$. The evaporation of organic layer gave 54.1 mg the amide. LCMS indicated product formation m/z: 431

Step 2 (2S)-2-amino-3-methylbutyl 15-chloro-9-(methoxymethyl)-2,4,8,10,11-pentaazatetracyclo[11.4.0.0$^2$, $^6$0.0$^8$,$^{12}$]heptadeca-1(17),3,5,9,11,13,15-heptaene-5-carboxylate (0.027 gm, 0.06 mmol) was dissolved in dry DCM (2.0 mL). 0.016 mL, 0.13 mmol of DAST was added to the reaction mixture at 0° C. temperature and stirred for 3 h at 0-5° C. LCMS indicted product formation. 0.04 gm solid $K_2CO_3$ was added at 0° C. and reaction mixture was gradually warmed to room temperature. The reaction mixture was diluted with aq. $NaHCO_3$ solution and extracted with DCM (15.0 mL×3). The organic layer was washed with brine, separated and dried over anhydrous $MgSO_4$. The evaporation of solvent gave crude product. Purification was performed by prep TLC, Mobile Phase: 95:05, DCM:MeOH. 23.7 mg of solid product was obtained. Mass. m/z calculated for $C_{20}H_{21}ClN_6O_2[M+H]^+$: 413: Obtained: 413.

Synthesis of Compound 246 compound 246

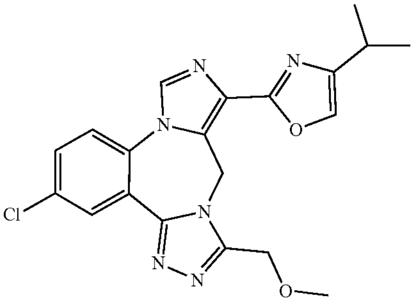

Compound 240 was converted to Compound 246 using DDQ, Toluene at 50 C in an analogous manner to Compound 245 to give 5.5 mg (37%) of Compound 246. LCMS indicated product formation m/z: 411.

Synthesis of Compound 242 compound 242

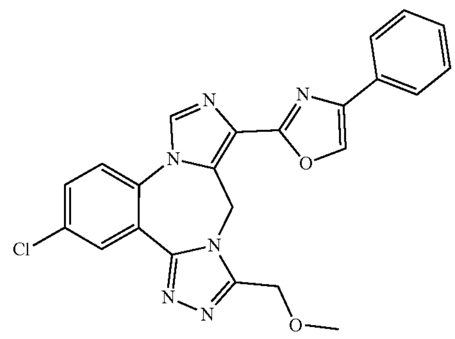

Step 1: Intermediate B (0.025 gm, 0.07 mmol) was dissolved in dry DCM (2.0 mL). 0.03 mL, 0.21 mmol of trimethylamine (3.0 eq), followed by 0.015 mL, 0.18 mmol of oxalylchloride (2.5 eq) were added and reaction mixture stirred for 60 min at room temperature. 0.05 gm, 0.36 mmol of (R,S)-2-amino-2-phenylethan-1-ol (5.0 eq) was added to reaction mixture at 0° C. and stirred for 2.5 h at room temperature. The reaction mixture was diluted with aq. solution of $NaHCO_3$ and extracted with DCM (15.0 mL×3). The combined organic layers were washed with brine, separated and dried over anhydrous $MgSO_4$. The evaporation of organic layer gave the desired amide. LCMS indicated product formation m/z: 465

Step 2: The above amide (0.034 gm, 0.07 mmol) was dissolved in dry DCM (2.0 mL). 0.03 mL, 0.22 mmol of DAST was added to the reaction mixture at 0° C. temperature and stirred at 0° C. for 1.5 h. LCMS indicated product formation. 0.05 gm solid $K_2CO_3$ was added at 0° C. and reaction mixture was gradually warmed to room temperature. The reaction mixture was diluted with aq. $NaHCO_3$ solution and extracted with DCM (15.0 mL×3). The organic layer was washed with brine, separated and dried over anhydrous $MgSO_4$. The evaporation of solvent gave crude product. Purification was performed by prep TLC, Mobile Phase: 95:05, DCM:MeOH. m/z calculated for $C_{23}H_{19}ClN_6O_2[M+H]^+$: 447; Obtained: 447.

Synthesis of Compound 245 compound 245

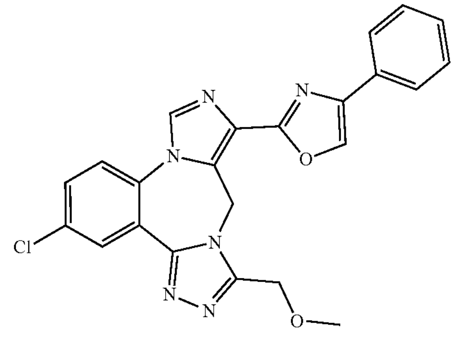

Compound 242 (0.015 gm, 0.03 mmol) was dissolved in toluene (1.5 mL). 0.009 gm, 0.04 mmol of DDQ was added and reaction mixture was stirred at 50° C. for 1.5 h. LCMS indicated starting material m/z 447 and product m/z 445 in 1:3 ratio. 0.005 gm, 0.022 mmol of DDQ was further added and rxn mixture was stirred at 50° C. for 1.5 h. starting material m/z 447 and product m/z 445 in 1:6 ratio. The reaction mixture was stirred at room temperature for 16 h. Purification was performed by prep TLC, Mobile Phase: 95:05, DCM:MeOH. The band with m/z: 445 was isolated and 9.3 mg of solid compound was obtained (Yield 62.4%). m/z calculated for $C_{23}H_{17}ClN_6O_2[M+H]^+$: 445; Obtained: 445.

Synthesis of Compound 237 compound 237

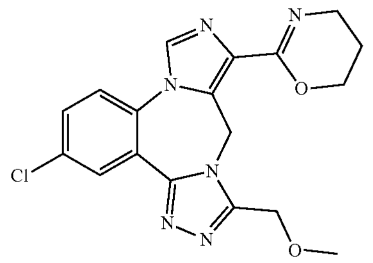

Step 1: Intermediate B (0.025 gm, 0.07 mmol) was dissolved in dry DCM. 0.009 mL, 0.02 mL, 0.14 mmol of trimethylamine, followed by 0.11 mmol of oxalylchloride were added and reaction mixture stirred for 30 min at room temperature. 0.028 mL, 0.36 mmol of 3-amino-1-propanol was added to reaction mixture at 0° C. and stirred for 2.5 h and then concentrated. LCMS indicated product formation m/z: 403, little starting material left.

Step 2: The crude amide from Step 1 (0.018 gm, 0.045 mmol) was dissolved in dry DCM (2.0 mL). 0.012 mL, 0.09 mmol of DAST was added to the reaction mixture at −78° C. temperature and gradually warmed to 0° C. 0.03 gm solid $K_2CO_3$ was added at −78° C. and reaction mixture was gradually warmed to room temperature. The reaction mixture was diluted with aq. $NaHCO_3$ solution and extracted with DCM (15.0 mL×3). The organic layer was washed with brine, separated and dried over anhydrous $MgSO_4$. The evaporation of solvent gave 14.7 mg of compound 237 as a white solid product. m/z calculated for $C_{18}H_{17}ClN_6O_2[M+H]^+$: 385; Obtained: 385.1.

Synthesis of Compound 263

Compound 263

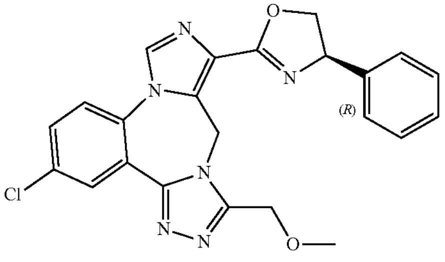

Step 1: Intermediate B (0.03 gm, 0.09 mmol), 0.034 gm, 0.17 mmol of EDC·HCl and 0.027 gm, 0.17 mmol of HOBt·x$H_2O$ were dissolved in anhydrous DCM (2.5 mL). 0.024 gm, 0.17 mmol of R—(−)-2-Phenylglycinol was added and reaction mixture was stirred for 6 h at room temperature. LCMS indicated product formation m/z 464.9. The rxn mixture was diluted with DI water and extracted with DCM (10.0 mL×3). The combined DCM layers were washed with brine, separated and dried over anhydrous $Na_2SO_4$. The evaporation of organic layer gave crude product. A liquid syrup was obtained. m/z calculated for $C_{23}H_{21}ClN_6O_3[M+H]^+$: 465; Obtained: 464.9.

Step 2: The above amide (0.04 gm, 0.086 mmol) of was dissolved in dry DCM (2.0 mL). 0.03 mL, 0.21 mmol of DAST was added and reaction mixture was stirred at 0° C. temperature for 2 h. LCMS indicated product formation m/z 446.9. 0.06 gm solid $K_2CO_3$ was added at 0° C. and reaction mixture was gradually warmed to room temperature. The reaction mixture was diluted with aq. $NaHCO_3$ solution and extracted with DCM (15.0 mL×3). The organic layer was washed with brine, separated and dried over anhydrous $Na_2SO_4$. The evaporation of solvent gave crude product. Purification was performed by prep TLC, Mobile Phase: 95:05, DCM:MeOH. 25.0 mg of solid product was obtained. m/z calculated for $C_{23}H_{19}ClN_6O_2[M+H]^+$: 447; Obtained: 446.9.

Synthesis of Compound 264

Compound 264

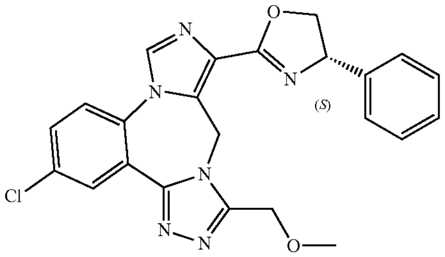

Step 1: Intermediate B (0.03 gm, 0.09 mmol), 0.034 gm, 0.17 mmol of EDC·HCl and 0.027 gm, 0.17 mmol of HOBt·x$H_2O$ were dissolved in anhydrous DCM (2.5 mL). 0.024 gm, 0.17 mmol of S-(+)-2-Phenylglycinol was added and reaction mixture was stirred for 6 h at room temperature. LCMS indicated product formation m/z 464.9. The rxn mixture was diluted with DI water and extracted with DCM (10.0 mL×3). The combined DCM layers were washed with brine, separated and dried over anhydrous $Na_2SO_4$. The evaporation of organic layer gave crude product. A liquid syrup was obtained. m/z calculated for $C_{23}H_{21}ClN_6O_3[M+H]^+$: 465; Obtained: 464.9.

Step: 2: The above amide (0.04 gm, 0.086 mmol) was dissolved in dry DCM (2.0 mL). 0.03 mL, 0.21 mmol of DAST was added and reaction mixture was stirred at 0° C. temperature for 2 h. LCMS indicated product formation m/z 446.9. 0.06 gm solid $K_2CO_3$ was added at 0° C. and reaction mixture was gradually warmed to room temperature. The reaction mixture was diluted with aq. $NaHCO_3$ solution and extracted with DCM (15.0 mL×3). The organic layer was washed with brine, separated and dried over anhydrous $Na_2SO_4$. The evaporation of solvent gave crude product. Purification was performed by prep TLC, Mobile Phase:

95:05, DCM:MeOH. 26.4 mg of solid product was obtained. m/z calculated for $C_{23}H_{19}ClN_6O_2[M+H]^+$: 447; Obtained: 446.9.

Compounds 332, 334, 335, 336, 337, and 338 were prepared using a synthetic procedure that is similar to the one used for the synthesis of Compound 264 as depicted in Scheme 30.

Compounds 180, 181, and 182 were prepared using a synthetic procedure that is similar to the one used for the synthesis of Compound 168 as depicted in Scheme 27.

Compounds 183-193 were prepared using a synthetic procedure that is similar to the one used for the syntheses of Compounds 169-179 as depicted in Scheme 26.

Compounds 194 and 195 were prepared using a synthetic procedure that is similar to the one depicted in Schemes 21 and 22.

Compounds 196-198, and 206 were prepared using a synthetic procedure that is similar to the one depicted in Scheme 18a.

Compound 202 was prepared using a synthetic procedure that is similar to the one used for the synthesis of Compound 129 as depicted in Scheme 18a.

Compounds 199, 200, 204, and 205 were prepared using a synthetic procedure that is similar to the one depicted in Scheme 18b.

Compounds 201 and 203 were prepared using a synthetic procedure that is similar to the one depicted in Scheme 24.

Compounds 207-210 were prepared using a synthetic procedure that is similar to the one depicted in Scheme 17. The nitrile substituents in Compounds 207-210 were generated analogously to those transformations shown in Scheme 22.

Compounds 211-214 were prepared using a synthetic procedure that is similar to the one depicted in Scheme 20.

Compound 255 was prepared from the appropriate starting materials using the synthetic routes described in Schemes 28 and 29; similar to compound 254.

Compound 259 was prepared from the appropriate starting materials using the synthetic routes described in Schemes 28 and 29; similar to compound 243.

Compound 260 was prepared from the appropriate starting materials using the synthetic routes described in Schemes 28 and 30; similar to compound 242.

Compound 261 was prepared from the appropriate starting materials using the synthetic routes described in Schemes 28 and 30; similar to compound 256.

Compound 265 was prepared from the appropriate starting materials using the synthetic routes described in Schemes 28 and 30; similar to compound 264.

Compound 266 was prepared from the appropriate starting materials using the synthetic routes described in Schemes 28 and 30; similar to compound 264.

Compound 267 was prepared from the appropriate starting materials using the synthetic routes described in Schemes 28 and 30; similar to compound 264.

Compound 268 was prepared from the appropriate starting materials using the synthetic routes described in Schemes 28 and 30; similar to compound 263.

Compound 270 was prepared from the appropriate starting materials using the synthetic routes described in Schemes 28 and 30; similar to compound 264.

Compound 271 was prepared from the appropriate starting materials using the synthetic routes described in Schemes 28 and 30; similar to compound 264.

Compound 275 was prepared from the appropriate starting materials using the synthetic routes described in Schemes 28 and 30; similar to compound 264.

Compound 276 was prepared from the appropriate starting materials using the synthetic routes described in Schemes 28 and 30; similar to compound 245.

Compound 278 was prepared from the appropriate starting materials using the synthetic routes described in Schemes 28 and 29; similar to compound 233.

Compound 281 was prepared from the appropriate starting materials using the synthetic routes described in Schemes 28 and 29; similar to compound 233.

Compounds 282, 283, 286, 287 were prepared from the appropriate starting materials using the synthetic routes described in Schemes 28 and 29; similar to compound 243.

Compound 288 was prepared from the appropriate starting materials using the synthetic routes described in Schemes 28 and 29; similar to compound 256.

Compound 293 was prepared from the appropriate starting materials using the synthetic routes described in Schemes 28 and 29; similar to compound 285.

Compounds 294, 295, and 296 were prepared from the appropriate starting materials using the synthetic routes described in Schemes 28 and 29; similar to compounds 243 and 244.

Compound 303 was prepared from the appropriate starting materials using the synthetic routes described in Schemes 28 and 29; similar to compound 233.

Compound 304 was prepared from the appropriate starting materials using the synthetic routes described in Schemes 28 and 29; similar to compound 264.

Compound 297 was prepared from the appropriate starting materials using the synthetic routes described in Schemes 28 and 29; similar to compound 243.

Compound 307 was prepared from the appropriate starting materials using the synthetic routes described in Schemes 28 and 29; similar to compound 285.

Compound 308 was prepared from the appropriate starting materials using the synthetic routes described in Scheme 28; similar to Intermediate A.

Compound 309 was prepared from the appropriate starting materials using the synthetic routes described in Schemes 28 and 29; similar to compound 238.

Compound 310 was prepared from the appropriate starting materials using the synthetic routes described in Schemes 28 and 29; similar to compound 285.

Compound 311 was prepared from the appropriate starting materials using the synthetic routes described in Schemes 28 and 29; similar to compound 285.

Compound 312 was prepared from the appropriate starting materials using the synthetic routes described in Schemes 28 and 29; similar to compound 244.

Compound 313 was prepared from the appropriate starting materials using the synthetic routes described in Schemes 28 and 29; similar to compound 244.

Compound 315 was prepared from the appropriate starting materials using synthetic routes described in Schemes 28 and 29; similar to compound 314.

Compound 316 was prepared from the appropriate starting materials using synthetic routes described in Schemes 28 and 29; similar to compound 238.

Compound 317 was prepared from the appropriate starting materials using synthetic routes described in Schemes 28 and 29; similar to compound 238.

Synthesis of Compound 319

Compound 319

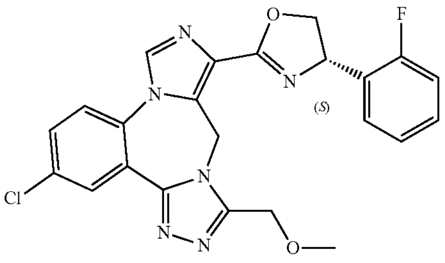

Step 1: Intermediate B (0.04 g, 0.12 mmol) was dissolved in anhydrous DMF (1.0 mL). HATU (0.088 g, 0.23 mmol) and triethyl amine (0.048 mL, 0.35 mmol) were added to the reaction mixture followed by (S)-2-amino-2-(2-fluorophenyl)-ethan-1-ol (0.044 g, 0.23 mmol). The reaction mixture was stirred at room temperature for 16 h. LCMS shows product formation m/z 483.0 and little amount of starting material. 0.044 g, (0.23 mmol) of (S)-2-amino-2-(2-fluorophenyl)-ethan-1-ol was further added at room temperature and rxn mixture was stirred for additional 4 h. LCMS indicated product formation m/z 483.0. The rxn mixture was diluted with DI-water and extracted with DCM (10.0 mL×3). The combined DCM layers were washed with brine, separated and dried over anhydrous $Na_2SO_4$. The evaporation of organic layer gave crude product. m/z calculated for $C_{23}H_{20}ClFN_6O_3[M+H]^+$: 483; Obtained: 483.0

Step 2: The above amide (0.06 g, 0.12 mmol) was dissolved in dry DCM (2.5 mL). 0.03 mL (0.23 mmol) of DAST was added and reaction mixture was stirred at 0° C. temperature for 2 h. LCMS indicated product formation m/z 465.2. Solid $K_2CO_3$ (0.06 g, 0.46 mmol) was added at 0° C. and reaction mixture was gradually warmed to room temperature. The reaction mixture was diluted with aq. $NaHCO_3$ solution and extracted with DCM (10.0 mL×3). The organic layer was washed with brine, separated and dried over anhydrous $Na_2SO_4$. The evaporation of solvent gave crude product. Purification was performed by prep TLC, Mobile Phase: 95:05, DCM:MeOH. Pure product Compound 319 (44.2 mg) was obtained as a solid (Yield 82.2%); m/z calculated for $C_{23}H_{18}ClFN_6O_3[M+H]^+$: 465; Obtained: 465.2.

Compound 320 was prepared from the appropriate starting materials using the synthetic routes described in Schemes 28 and 30; similar to compound 319.

Compound 321 was prepared from the appropriate starting materials using the synthetic routes described in Schemes 28 and 30; similar to compound 319.

Compound 322 was prepared from the appropriate starting materials using the synthetic routes described in Schemes 28 and 30; similar to compound 319.

Compound 325 was prepared from the appropriate starting materials using the synthetic routes described in Schemes 28 and 30; similar to compound 320.

Compound 326 was prepared from the appropriate starting materials using the synthetic routes described in Schemes 28 and 30; similar to compound 320.

Compound 330 was prepared from the appropriate starting materials using the synthetic routes described in Schemes 28 and 30; similar to compound 319.

Compound 331 was prepared from the appropriate starting materials using the synthetic routes described in Schemes 28 and 30; similar to compound 319.

Compound 333 was prepared from the appropriate starting materials using the synthetic routes described in Schemes 28 and 30; similar to compound 319.

Compound 340 was prepared from the appropriate starting materials (chiral center derived from (2R)-2-amino-2-phenylethan-1-ol) using the synthetic routes described in Schemes 28 and 30; similar to compound 319.

Compound 343 was prepared from the appropriate starting materials (chiral center derived from (2S)-2-amino-2-phenylethan-1-ol) using the synthetic routes described in Schemes 28 and 30; similar to compound 319.

Synthesis of Compound 323

Compound 323

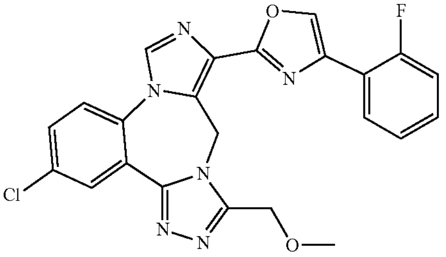

Compound 319 (0.018 g, 0.04 mmol) was dissolved in toluene (2.0 mL). DDQ (0.011 g, 0.05 mmol) was added and reaction mixture was stirred at 50° C. for 3 h. LCMS indicated starting material m/z 465.2 and product m/z 463.2 in ~1:0.9 ratio. The rxn mixture was stirred at 65° C. for 2 h, LCMS shows starting material m/z 465.2 and product m/z 463.2 in 1:1.6 ratio. Additional DDQ (0.003 g, 0.012 mmol) was added and reaction mixture was stirred at 75° C. for 5 h. LCMS indicated reaction completion. The reaction mixture was concentrated in vacuum. The purification was performed by prep TLC, Mobile Phase: 80:20, EtOAc: Hexane. ~5.8 mg of Compound 323 was obtained; m/z calculated for $C_{23}H_{16}ClFN_6O_2[M+H]^+$: 463.2; Obtained: 463.2

Compound 324 was prepared from Compound 320 using the same conditions as shown for the synthesis of Compound 323.

Synthesis of Compounds 305 and 306

Scheme 31

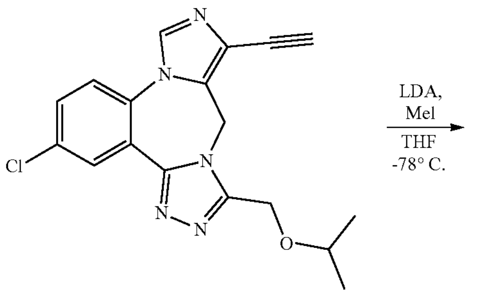

Compound 288

-continued

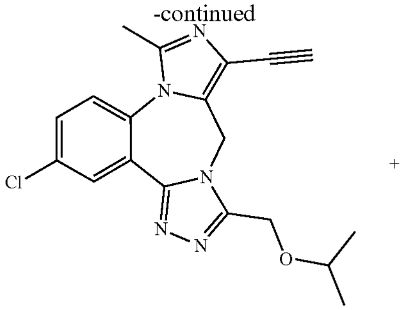

Compound 305

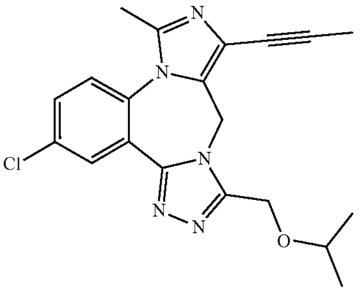

Compound 306

Compound 288 (0.015 gm, 0.042 mmol) was dissolved in anhydrous THF (3.0 mL). 0.003 mL, 0.05 mmol of methyl iodide was added at −78° C. temperature, followed by 0.05 mL, 0.05 mmol of 1.0 M LDA solution. The reaction mixture was stirred at −78° C. and gradually warmed at room temperature. LCMS shows product formation m/z 368 major, unreacted starting material m/z 354 and dimethylated unknown product m/z 382.1. The reaction mixture was quenched with saturated $NH_4CL$ solution and extracted with EtOAC. Organic layer was dried and concentrated. The purification of crude reaction mixture was performed by prep-TLC plate, Mobile Phase: EtOAc:Hexane 75:25 v/v mL to isolate three bands. It was found through MS that $1^{st}$ band confirmed m/z 354 of starting material, $2^{nd}$ band confirmed m/z 368 of mono methyl substituted product Compound 305 and $3^{rd}$ band confirmed m/z 382.1 of dimethyl substituted product Compound 306. $^1H$ NMR ($CDCl_3$) data confirmed the mono methyl substitution on Imidazole ring. Note: $^1H$ NMR data confirmed products formation and pure products isolation.

Compound 216 was prepared similarly as compound 129 in Scheme 18a. MS: [M+1]− 395.

Compound 217 was prepared similarly as compound 129 in Scheme 18a. MS: [M+1]=381.

Scheme 32
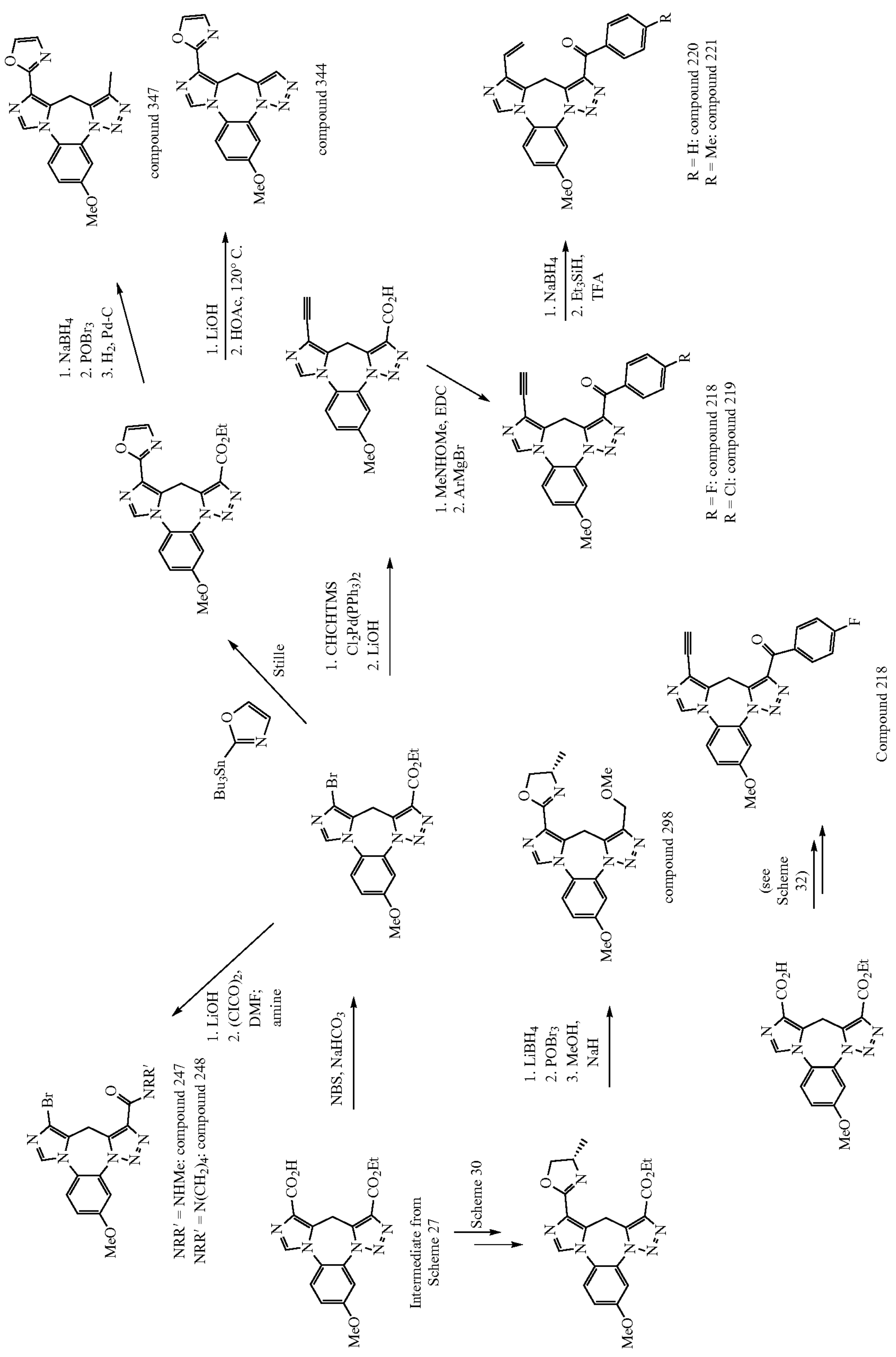

Synthesis of Compound 218

Compound 218

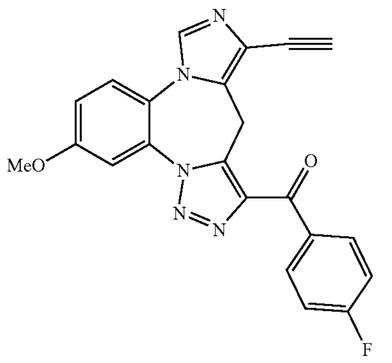

To 5-(ethoxycarbonyl)-16-methoxy-2,3,4,10,12-pentaazatetracyclo $[11.4.0.0^{2,6}.0^{8,12}]$heptadeca-1(17),3,5,8,10,13,15-heptaene-9-carboxylic acid from Scheme 27 (0.609 g, 1.65 mmol) stirring in DMF (10 ml) at 0° C. was added $NaHCO_3$ (0.749 g, 8.9 mmol) and NBS (0.793 g, 4.45 mmol). The reaction was allowed to proceed to ambient temperature overnight. The reaction was then diluted with EtOAc, cooled to 0° C., and sat. sodium thiosulfate was added carefully under stirring. After foaming stopped, organic layer was separated, washed with sat. $NaHCO_3$, brine, and dried over $MgSO_4$. Filtration and solvent removal gave the crude bromide which was purified by flash column chromatography using a gradient elution of 0 to 80% EtOAc in hexanes. 424.2 mg (64%) was obtained as a yellowish solid. MS: [M+1]=405.

To the bromide (286.7 mg, 0.709 mmol) from above in a thick walled rbf was added CuI (121.5 mg, 0.638 mmol), trimethylsilyl acetylene (1.04 g, 10.7 mmol), triethyl amine (0.717 g, 7.09 mmol), dicyclohexyl(2',6'-dimethoxybiphenyl-2-yl) phosphine (0.349 g, 0.851 mmol) and 1,4-dioxane (2.5 ml; degassed). The reaction vessel was flushed with nitrogen gas, and bis(triphenylphosphine) palladium(II) dichloride (298.2 mg, 0.425 mmol) was added. The reaction mixture was stirred at rt for 30 min then heated at 100° C. under sealed tube conditions for 16 hrs, diluted with EtOAc, and washed with sat. $NaHCO_3$, brine, and dried ($MgSO_4$). Silica gel column chromatography of the filtered and concentrated reaction mixture using a gradient of 0 to 100% EtOAc in hexanes gave 157.9 mg (53%) of the desired trimethylsilyl acetylene product as a brownish solid. MS: [M+1]=422.

The trimethylsilyl alkyne obtained above (128.7 mg, 0.305 mmol) was treated with lithium hydroxide (36.6 mg, 1.53 mmol) in a solvent mixture of THF (0.9 ml), water (0.75 ml) and MeOH (0.15 ml) at it for two hrs. The mixture was then acidified to pH 3-4 with dil. Hydrochloric acid, and extracted with EtOAc (3×). The remaining precipitate in the aq. Layer was found to be product and was collected by filtration, and was combined with the product isolated from the organic layer to give 95.6 mg of the acid as a yellowish solid.

To the acid (95.6 mg, 0.298 mmol) in THF (1.3 ml) and dichloromethane (1.3 ml) was added N,O-dimethylhydroxylamine hydrochloride (232.4 mg, 2.38 mmol), EDC hydrochloride (456.7 mg, 2.38 mmol), HOBt hydrate (91.2 mg), and triethyl amine (0.833 ml, 5.93 mmol). After 16 hrs stirring, the reaction was diluted with EtOAc, and washed with sat. $NH_4Cl$. Aq. Layer was separated and extracted with EtOAc (3×), combined organic layer was washed with sat. $NaHCO_3$, brine, and dried ($MgSO_4$). Filtration followed by solvent removal gave 104.8 mg of the amide as a yellowish solid.

To the Weinreb amide from above (20.1 mg, 0.0552 mmol) stirring in anh. THF (0.8 ml) cooled in an ice-salt bath was added 4-fluorophenyl magnesium bromide solution (1M THF; 0.828 ml) slowly. The reaction mixture was stirred to ambient temperature over 4 hrs, then quenched with sat. $NH_4Cl$, extracted with EtOAc (3×), washed with sat. $NaHCO_3$, brine, and dried ($MgSO_4$). Prep. TLC of the filtered concentrated mixture using 5% MeOH in DCM gave 2.0 mg of Compound 218 as an off-white solid. MS: [M+1]=400.

Compound 219 was prepared similarly as compound 218 as depicted in Scheme 32. MS: [M+1]=416.

Synthesis of Compound 220

Compound 220

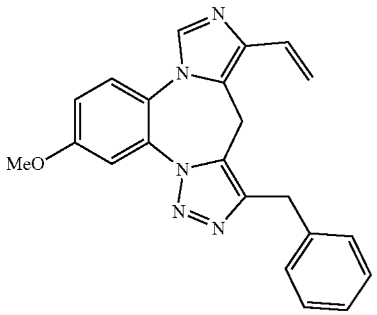

5-benzoyl-9-ethynyl-16-methoxy-2,3,4,10,12-pentaazatetracyclo $[11.4.0.0^{2,6}.0^{8,12}]$heptadeca-1(17),3,5,8,10,13,15-heptaene (90.3 mg, 0.237 mmol; obtained similarly as 218, was stirred in THF (1.5 ml) at rt. $NaBH_4$ (26.8 mg, 0.71 mmol) was added. After 1 hr, the reaction was quenched with $NH_4Cl$ for 5 min, and extracted with EtOAc. Organic layer was separated and washed with brine and dried over $MgSO_4$. Filtration and solvent removal in vacuo gave a clear viscous oil, which was treated with triethylsilane (241.9 mg, 2.08 mmol) and trifluoroacetic acid (0.32 ml) in DCM (1.5 ml) for 3 hrs. The reaction mixture was placed on Rotovap for solvent removal, diluted with EtOAc, and washed with sat. $NaHCO_3$. Aq. Layer was separated and extracted with EtOAc, the combined organic layer was washed with brine, and dried over $MgSO_4$. Prep. TLC of the filtered concentrate using 2% MeOH in DCM/EtOAc (1:1) gave 2.5 mg of Compound 220 as a clear filmy solid. MS: [M+1]=370.

Compound 221 was prepared similarly as compound 220 as depicted in Scheme 32. MS: [M+1]=384.

Synthesis of Compound 344

Compound 344

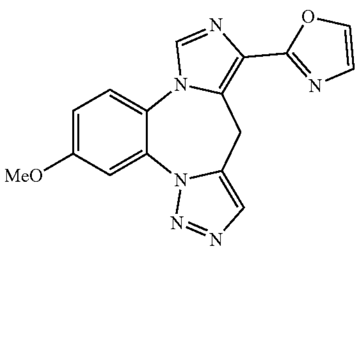

The bromide intermediate in Scheme 32 (26.5 mg, 0.0656 mmol), 2-(tri-n-butylstannyl)-oxazole (58.7 mg, 0.164 mmol) and dichloro 1,1'-bis(diphenylphosphino)ferrocene palladium(II) dichloromethane adduct (7.2 mg) in dioxane (0.5 mL) was heated under nitrogen atm. at 150° C. for 5 h. Upon cooling, the reaction mixture was diluted with ethyl acetate, washed with sat. $NaHCO_3$, brine, and dried over $MgSO_4$. Prep. TLC separation using 5% MeOH in ethyl acetate as eluent gave 6.4 mg (25%) of the oxazole ethyl ester product as a yellowish solid.

The ethyl ester (6.4 mg) from above was treated with lithium hydroxide (6.0 mg) in a solvent mixture of THF/$H_2O$/MeOH (6:5:1; 0.24 mL) for 16 hrs. Acetic acid (3 mL) was added and the reaction was heated at 120° C. for 4 hrs. Upon cooling, the reaction mixture was diluted with EtOAc, washed with sat. $NaHCO_3$. Aq. Layer was separated and extracted with EtOAc (3×). The combined organic solution was washed with brine and dried over $MgSO_4$. Prep. TLC using 8% MeOH in DCM as eluent solvent system gave 1.6 mg (31% over two steps) of the decarboxylated product compound 344 as a yellowish solid. MS: [M+1]=321.

Synthesis of Compound 347

Compound 347

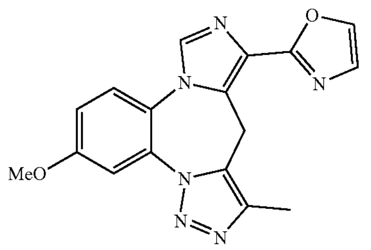

The oxazole Stille coupling product in Scheme 32 (21.2 mg, 0.054 mmol) was treated with sodium borohydride (0.44 mL, 0.5M in 2-methoxy ethyl ether) at 0° C. for three days, then quenched with acetone (2 mL) for 60 min. The reaction mixture was diluted with EtOAc, washed with sat. $NaHCO_3$, brine, and dried over $MgSO_4$. The crude alcohol was obtained after filtration and solvent removal, and was treated with phosphorous oxybromide (55 mg) in acetonitrile (1 mL) at 85° C. for 7 hrs. Upon cooling, the reaction was diluted with EtOAc, washed with sat. $NaHCO_3$, brine, and dried over $MgSO_4$. Filtration and solvent removal under reduced pressure gave the crude bromide product as a greenish solid.

The bromide from above was hydrogenated with catalytic amount of 10% Pd on charcoal in EtOAc/MeOH (5 mL, 1:1 v/v) for 2 hrs. Filtration through Celite, washed with 10% MeOH in DCM, and solvent removal in vacuo following the hydrogenation gave the desired methyl product, which was purified by prep. TLC (8% MeOH in DCM as eluent), giving 3.6 mg (20% over three steps) compound 347 as a yellowish solid. MS: [M+1]=335.

Scheme 33

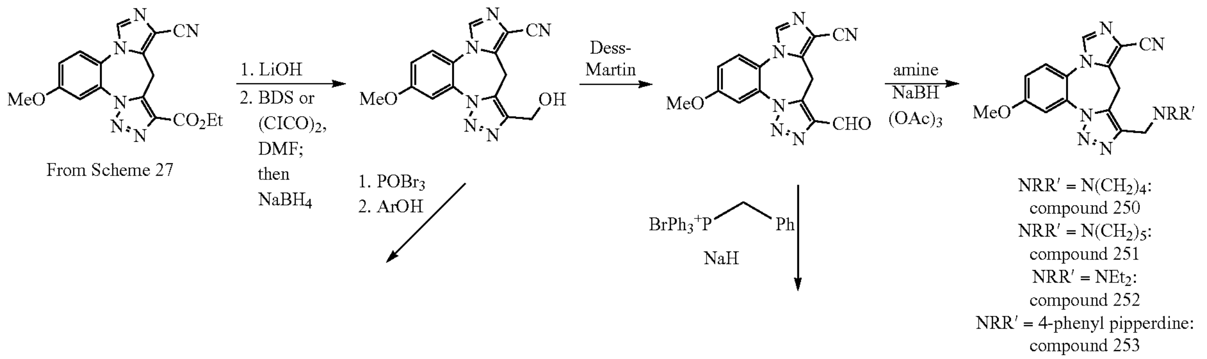

-continued

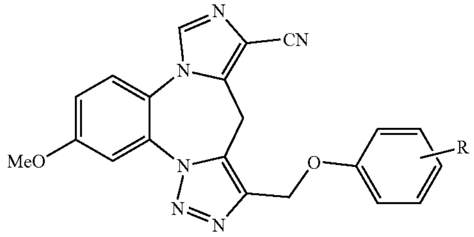

R = 4-F: compound 222
R = 2-F: compound 223
R = H: compound 224
R = 3-Br: compound 225

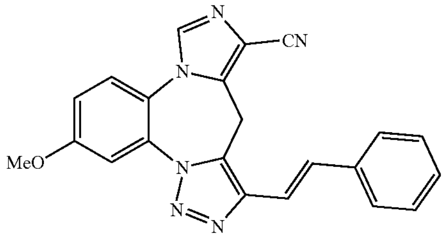

compound 262

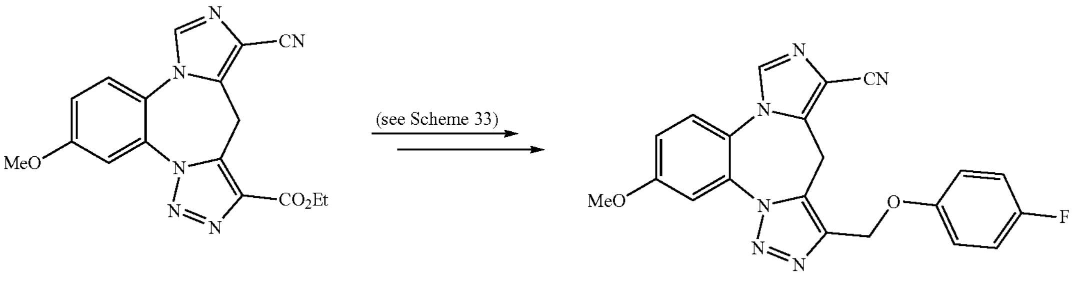

Compound 222

Synthesis of Compound 222

Compound 222

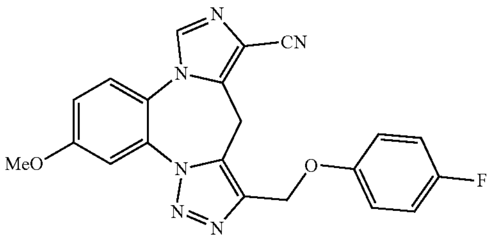

The cyano ester (407.1 mg, 1.16 mmol) was treated with lithium hydroxide (83.5 mg, 3.49 mmol) in a solvent mixture of THF (6 ml), water (5 ml) and MeOH (1 ml) at rt for 16 hrs, then concentrated in vacuo, acidified to pH 3-4 with dil. HCl, and cooled at 0° C. Precipitate was collected by filtration, washed with small amount of water, and dried to give 271.9 mg (73%) acid as a greyish solid. This acid (271.9 mg) was suspended and stirred in THF (2 ml) at 0° C., to which was added borane dimethylsulfide solution (2M TF; 8.4 ml) dropwise. The reaction was allowed to proceed to ambient temperature overnight, cooled in an ice bath, quenched with MeOH (10 ml) for two hrs, and concentrated in vacuo. The resulting solid residue was partitioned between DCM and sat. $NaHCO_3$ and stirred for 20 min. Aq. Layer was separated and extracted with DCM (3×). Combined organic layer was washed with brine and dried over $MgSO_4$. Filtration and solvent removal gave 137.8 mg of the crude alcohol product as a yellowish waxy solid. The alcohol from above (137.8 mg) was treated with phosphorus oxybromide (256.3 mg, 0.894 mmol) in 1,4-dioxane (5 ml) at 100° C. for 3 hrs. Upon cooling in an ice bath, the reaction mixture was treated with sat. $NaHCO_3$ (15 ml) and EtOAc (15 ml) under stirring conditions for about 20 min. The basic aq. Layer was separated and extracted with EtOAc (2×). Combined organic layer was washed with brine and dried over $MgSO_4$. Filtration and solvent removal in vacuo gave the crude primary bromide as a solid paste which was stored in cold and used without further purification when needed.

The crude bromide from above (27.0 mg, 0.0727 mmol) was treated with 4-fluorophenol (65.2 mg, 0.585 mmol) and cesium carbonate (47.4 mg, 0.145 mmol) at rt for 16 hrs. The reaction mixture was diluted with EtOAc, washed with brine, and dried over $MgSO_4$. Prep. TLC of the filtered concentrate using 5% MeOH in DCM/EtOAc (1:1) gave 1.2 mg of Compound 222 as a yellowish solid. MS: [M+1]=403.

Compound 223 was prepared similarly as compound 222 as depicted in Scheme 33. MS: [M+1]=403.

Compound 224 was prepared similarly as compound 222 as depicted in Scheme 33. MS: [M+1]=385.

Compound 225 was prepared similarly as compound 222 as depicted in Scheme 33. MS: [M+1]=464.

Scheme 34

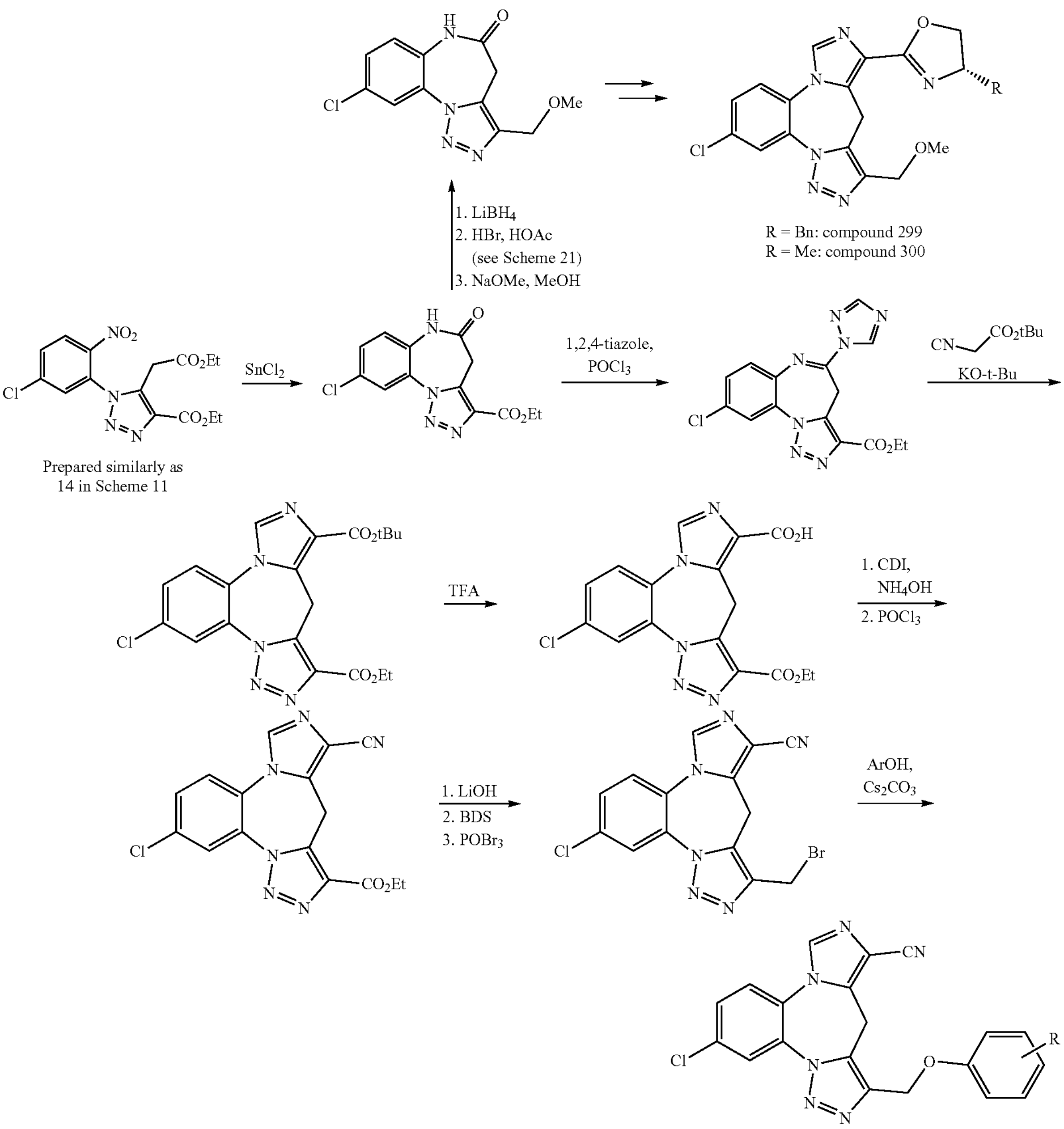

R = Bn: compound 299
R = Me: compound 300

Prepared similarly as
14 in Scheme 11

R = H: compound 226
R = 3-F: compound 227
R = 4-F: compound 228

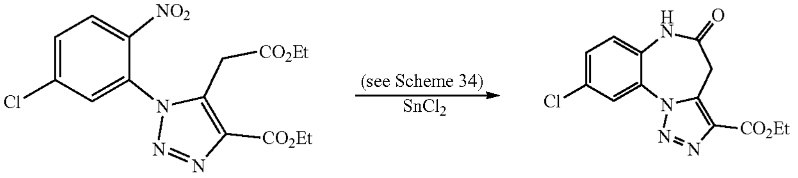

Ethyl 1-(5-chloro-2-nitrophenyl)-5-(2-ethoxy-2-oxoethyl)-1H-1,2,3-triazole-4-carboxylate (21.2 g; obtained similarly as 14 in Scheme 11) was treated with tin (II) chloride hydrate (60 g) in a mixture solvent of EtOAc/EtOH (1:2, 300 ml) at 70° C. for 3 hrs. HCl (40 ml; 37%) was added and heating continued for 3 days. More tin (II) chloride hydrate (25 g) and HCl (15 ml) added and heating continued for 2 days. The reaction was cooled, concentrated under reduced pressure to a brownish oil, diluted with EtOAc (250 ml), and carefully basified to pH 8-9 with sodium carbonate solution. The aq. Layer was separated and extracted with EtOAc repeatedly. Combined organic layer was washed with brine and dried over $MgSO_4$. Filtration and solvent removal followed by recrystallization in MeOH gave 3.3 g (51%) of the cyclized mono-ester as a yellowish solid. MS: [M+1]=307.

Preparation of tert-butyl isocyanoacetate

To a suspension of tert-butyl glycinate hydrochloride (10.0 g, 60 mmol) in DCM (200 ml) was added EDC·HCl (14.9 g, 78 mmol) and triethylamine (12.5 mL, 89.8 mmol). The reaction mixture was cooled down to −50° C., formic acid (3.4 mL, 89.8 mmol) in DCM (10 mL) was added slowly. The reaction mixture was stirred at −50° C. for one hour then at 4° C. for 3 h. Water (150 ml) was added. After 30 min stirring, aq. Layer was separated and extracted with DCM (3×). Combined organic layer was washed with brine and dried over $MgSO_4$. Filtration and solvent removal under reduced pressure gave 10 g (100%) of the formyl amide as a clear viscous oil. $H^1NMR$ ($CDCl_3$) δ 8.23 (1H, s), 6.17 (1H, br s), 3.98 (2H, d, J=5.5 Hz), and 1.48 (9H, s).

To a solution of formyl amide (10.5 g, 66 mmol) in DCM (180 mL) was added triethylamine (36.8 mL, 264 mmol). The solution was cooled in a salt-ice bath, and $POCl_3$ (7.4 mL, 79.2 mmol) was added slowly. The reaction was stirred in the cold bath for one hr. Then sodium carbonate (7.7 g, 72.6 mmol) in water (90 ml) was added to the cold reaction mixture. After 15 min, cold bath was removed and stirring continued at ambient temperature for one hr. Aq. Layer was separated and extracted with DCM (3×). Combined organic layer was washed with brine and dried over $MgSO_4$. Filtration and solvent removal under reduced pressure gave 7.9 g (84%) tert-butyl isocyanoacetate as a dark brown liquid. $H^1NMR$ ($CDCl_3$) δ 4.12 (2H, s), and 1.51 (9H, s).

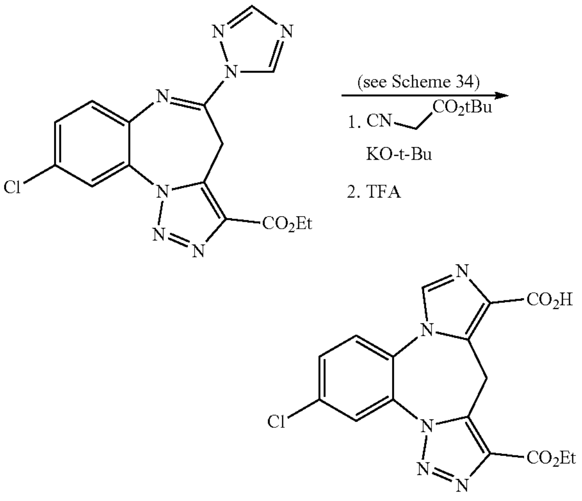

A solution of tert-butyl isocyanoacetate (1.51 g, 10.7 mmol) in DMF (43 ml) was cooled to −50° C. under nitrogen atmosphere. Potassium t-butoxide (1.05 g, 9.4 mmol; finely pressed) was added. After one hr stirring at −50° C., the 1,2,4-triazole intermediate (2.32 g, 6.48 mmol; prepared similarly as compound 20 in Scheme 11) was added to the resulting reddish clear solution, and the reaction was stirred to ambient temperature overnight. Sat. $NaHCO_3$ (15 ml) was added, and the reaction mixture was extracted with diethyl ether (5×), washed with brine, and dried ($MgSO_4$). Silica gel chromatography of the filtered concentrate using a gradient of 0 to 100% EtOAc in hexanes gave 2.5 g (89%) of the imidazole t-butyl ester product as a yellowish solid. MS: [M+1−tBu]=374.

The imidazole t-butyl ester from above (1.1 g, 2.56 mmol) was treated with trifluoroacetic acid (13 ml) in DCM (13 ml) for 3 hr or until all starting t-butyl ester was hydrolyzed. The reaction was then concentrated under reduced pressure. Residual TFA was removed with repeated addition and evaporation of toluene. The acid product was obtained as a dark brown viscous oily material, and was used without further purification. MS: [M+1]=374.

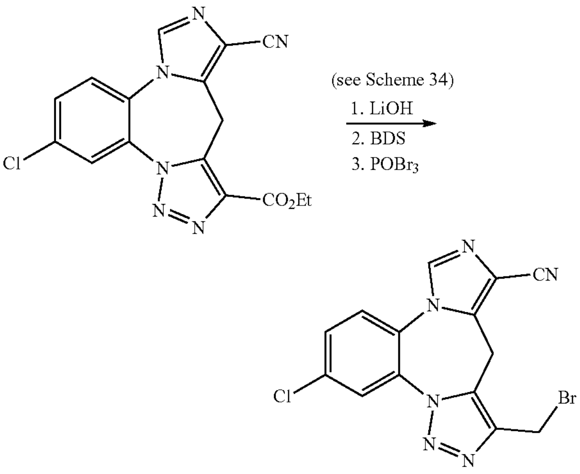

Ethyl 16-chloro-9-cyano-2,3,4,10,12-pentaazatetracyclo[$11.4.0.0^{2,6}.0^{8,12}$]heptadeca-1(17),3,5,8,10,13,15-heptaene-5-carboxylate (477 mg, 1.34 mmol); obtained similarly as ethyl 9-cyano-16-methoxy-2,3,4,10,12-pentaazatetracyclo[$11.4.0.0^{2,6}.0^{8,12}$]heptadeca-1(17),3,5,8,10,13,15-heptaene-5-carboxylate in Scheme 27) was treated with lithium hydroxide (80.5 mg, 3.36 mmol) in a solvent mixture of THF (6 ml), water (5 ml) and MeOH (1 ml) at rt for 16 hrs. The reaction was concentrated under reduced pressure, acidified to pH 3-4 with dil. HCl, and cooled to 0° C. Precipitate was collected by filtration, washed with small amount of water, and further dried to give 396.2 mg crude triazolo carboxylic acid product, MS: [M+1]=327.

To a suspension of the crude acid from above (396.2 mg) in anhydrous THF (7 ml) at 0° C. was added borane dimethylsulfide complex (10.9 ml; 2M THF) dropwise. The reaction was allowed to proceed to ambient temperature overnight, and was cooled to 0° C., then slowly quenched with MeOH. After 30 min stirring, the reaction mixture was concentrated in vacuo. The resulting slurry was treated with MeOH which was subsequently removed in vacuo. This process was repeated several times. The resulting residue was then treated with 5% MeOH in DCM, and washed with sat. $NaHCO_3$. Aq. Layer was extracted with DCM (3×), combined organic layer was washed with brine and dried over $MgSO_4$. Filtration and solvent removal gave a mixture of the crude alcohol product ([M+1]=313) and the corresponding primary amide due to hydrolysis of the cyano group ([M+1]=331). 388.8 mg of this crude mixture was obtained and was used without further purification.

The alcohol mixture (388.8 mg) from above was treated with phosphorus oxybromide (2.02 g) in 1,4-dioxane (10 ml) at 100° C. for 8 hrs. The reaction was cooled to 0° C., and carefully quenched with sat. $NaHCO_3$ (15 ml). After 20 min stirring, the reaction mixture was extracted with EtOAc (3×), washed with brine, and dried over $MgSO_4$. Filtration and solvent removal under reduced pressure gave the crude bromide as a viscous paste, which was used for the next step without further purification.

compound 226

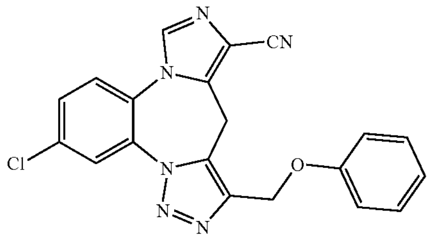

Compound 226 was prepared similarly as Compound 222 in Scheme 33 using the bromide prepared from above. MS: [M+1]=389.

Compound 227 was prepared in a similar fashion as Compound 226, depicted in Scheme 34. MS: [M+1]=407.

Compound 228 was prepared in a similar fashion as Compound 226, depicted in Scheme 34. MS: [M+1]=407.

Synthesis of Compound 229

The benzyl analog 229, shown in Scheme 35, was prepared similarly as the benzyl compound 220 in Scheme 32. MS: [M+1]=411.

Synthesis of Compound 230

The ketone analog 230, shown in Scheme 35, was prepared similarly as ketone 218 in Scheme 32. MS: [M+1]-474.

Synthesis of Compound 231

The benzyl analog 231, shown in Scheme 35, was prepared similarly as the benzyl compound 220 in Scheme 32. MS: [M+1]=460.

Scheme 35

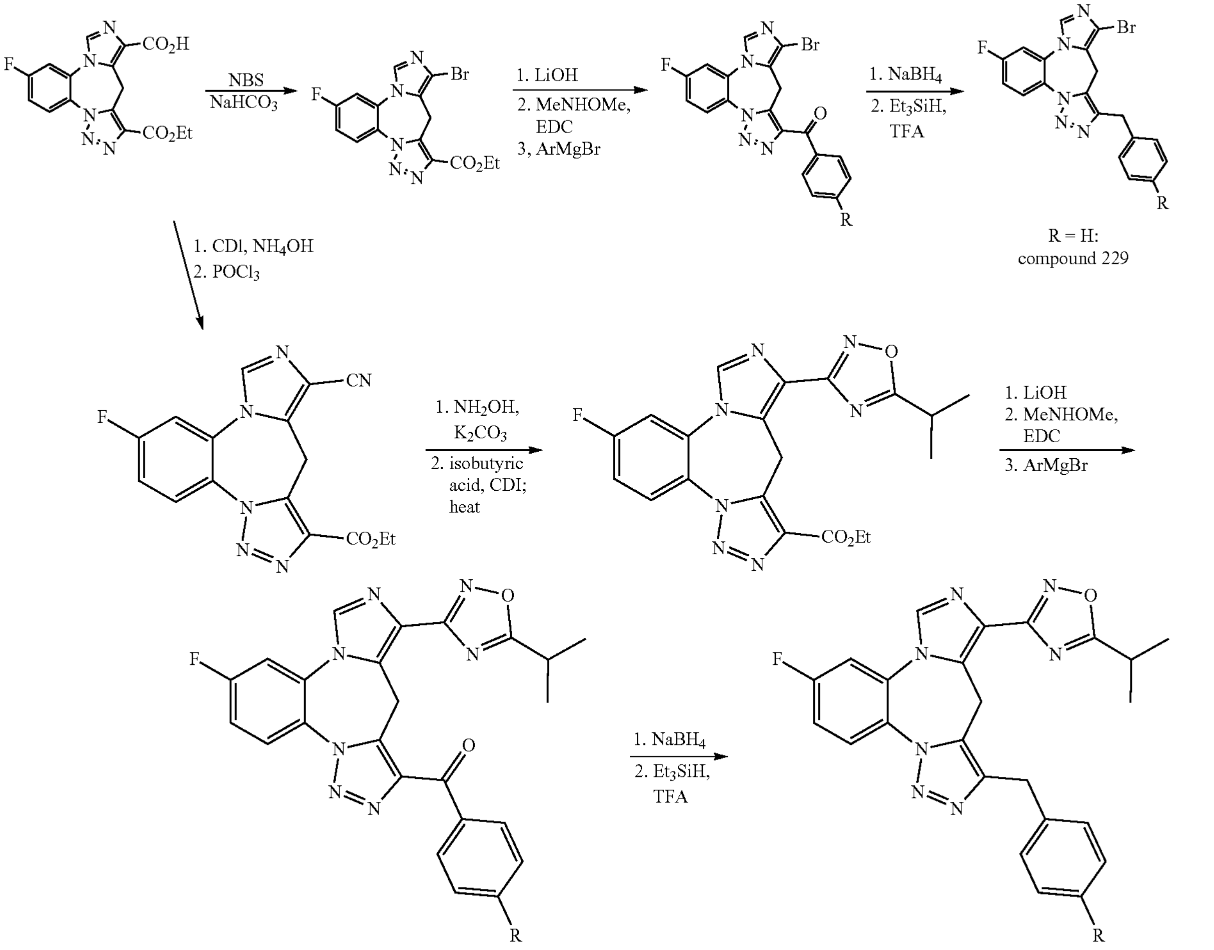

R = F: compound 230

R = F: compound 231

Scheme 36

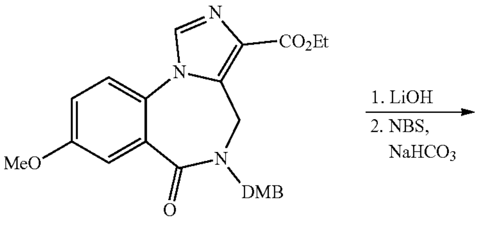

63 (scheme 18a)
DMB: dimethoxy benzyl

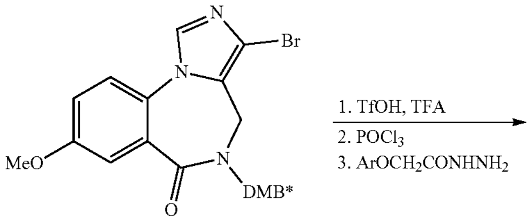

DMB*:
monobrominated
DMB

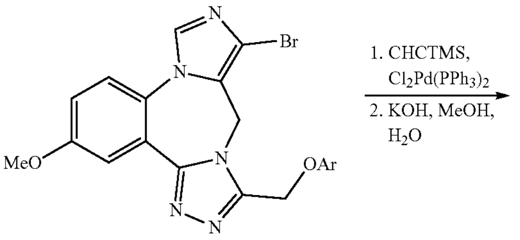

Ar = Ph: compound 232
Ar = 3-pyridyl: compound 235

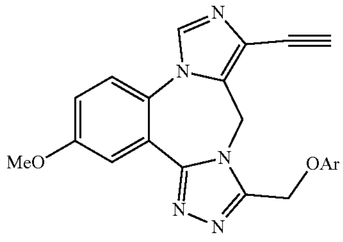

Ar = Ph: compound 236
Ar = 3-pyridyl: compound 241

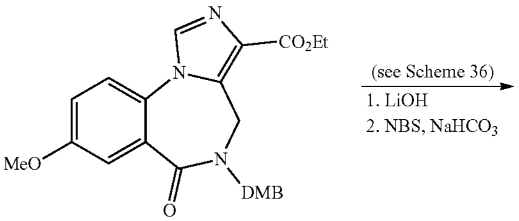

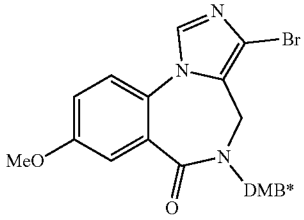

Compound 63 (0.805 g, 1.78 mmol; from Scheme 18a) was treated with lithium hydroxide (0.128 g, 5.34 mmol) in a solvent mixture of THF (6 ml), water (5 ml) and MeOH (1 ml) at rt for 16 hrs. The reaction was then concentrated in vacuo, acidified to pH 3-4 with dil. HCl. Resulting precipitate was collected by filtration, washed with water and dried to give 0.638 g acid as a yellow solid. MS: [M+1]=424.

The acid from above (0.638 g, 1.5 mmol) was treated with NBS (1.61 g, 9 mmol) and $NaHCO_3$ (1.51 g, 18 mmol) at rt for 16 hrs. The reaction mixture was cooled to 0° C., sat. sodium thiosulfate (aq.) was carefully and slowly added. This was extracted with EtOAc (2×), washed with sat. $NaHCO_3$, brine, and dried over $MgSO_4$. Silica gel chromatography of the filtered concentrate with a gradient of 0 to 100% EtOAc in hexanes gave 0.580 g (72%) of the dibromo product as a yellowish solid. MS: [M+1]=538.

Compound 232 was prepared similarly as Compound 55 in Scheme 18a, using the bromide prepared above. MS: [M+1]=439.

Compound 235 was prepared similarly as Compound 55 in Scheme 18a, using the bromide prepared above. MS: [M+1]=440.

Compound 236 The alkyne moiety was prepared similarly as Compound 161 in Scheme 21. MS: [M+1]=384.

Compound 241 The alkyne moiety was prepared similarly as Compound 161 in Scheme 21. MS: [M+1]=385.

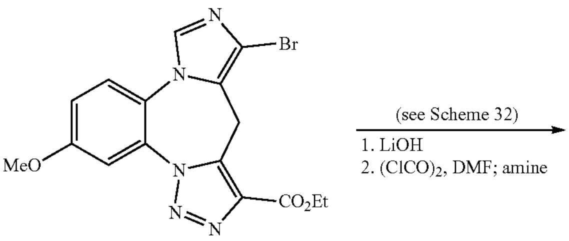

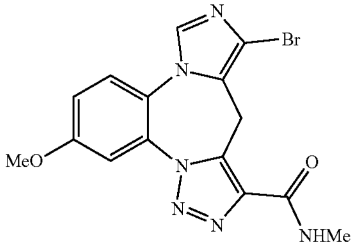

compound 247

Synthesis of Compound 247

The bromide ester (13.9 mg, 0.0344 mmol) was treated with lithium hydroxide (10 mg) in a solvent mixture of THF (0.3 ml), water (0.25 ml) and MeOH (0.05 ml) at rt for 16 hrs. The reaction was then concentrated in vacuo, acidified to pH 3-4 with dil. HCl and cooled to 0° C. Resulting precipitate was collected by filtration, washed with water and dried to give 9.5 mg (74%) acid as a light brown solid. MS: [M+1]=377. To the acid from above (5.1 mg, 0.0136 mmol) stirring in DCM (0.15 ml) was added oxalyl chloride (8.6 mg, 0.0678 mmol), and DMF (5 ul). After 2 hrs stirring, solvent and excess reagent was removed in vacuo. Resulting residue was re-suspended in DCM (0.15 ml), cooled in an ice-salt bath, and ethanolic methyl amine (100 ul; 33%) was added dropwise. After 20 min stirring, the reaction mixture was applied to a prep. TLC plate and product was isolated using 5% MeOH in DCM as eluent. 4.3 mg (81%) Compound 247 was obtained as a white solid. MS: [M+1]- 390.

Compound 248 was prepared similarly as Compound 247, as depicted in Scheme 32. MS: [M+1]=430.

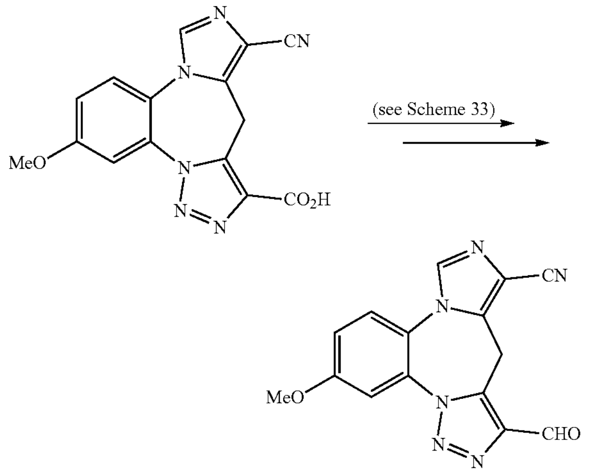

To the acid (108.0 mg, 0.335 mmol) suspended in DCM (2 ml) at 0° C. was added oxalyl chloride (170.1 mg, 1.34 mmol) slowly, followed by DMF (20 ul). After bubbling stopped, ice bath was removed and the reaction was allowed to proceed at rt for 2 hrs. Solvent and excess reagent was removed in vacuo. Resulting light brown solid was cooled to 0° C. $NaBH_4$ solution (2.2 ml; 1.5M in methoxyethoxy ethane) was added. After 30 min, the reaction was quenched with 1N HCl (0.2 ml), and stirring continued until bubbling stopped. EtOAc (10 ml) and sat. $NaHCO_3$ (10 ml) was added and this was stirred overnight. Aq. Layer was separated and extracted with EtOAc (3×); combined organic layer was washed with brine and dried over $MgSO_4$. Filtration and solvent removal gave 97.0 mg (94%) of the alcohol as a yellowish solid. MS: [M+1]=309.

The alcohol from above (97.0 mg, 0.315 mmol) was treated with Dess-Martin Periodinane (266.9 mg, 0.629 mmol) in DCM (2 ml) for 1 hr. The reaction mixture was diluted with DCM, washed with sat. $NaHCO_3$. Aq. Layer was separated and extracted with DCM (3×), combined organic layer washed with brine, and dried over $MgSO_4$. Filtration and solvent removal under reduced pressure gave quantitative yield of the crude aldehyde as a brownish solid, which was used without further purification.

Compound 250 was prepared similarly as compound 48 in Scheme 16 using the aldehyde from above, as depicted in Scheme 33. MS: [M+1]=362

Compound 251 was prepared similarly as compound 250, as depicted in Scheme 33. MS: [M+1]=376.

Compound 252 was prepared similarly as compound 250, as depicted in Scheme 33. MS: [M+1]=364.

Compound 253 was prepared similarly as compound 250, as depicted in Scheme 33. MS: [M+1]=452.

Scheme 37

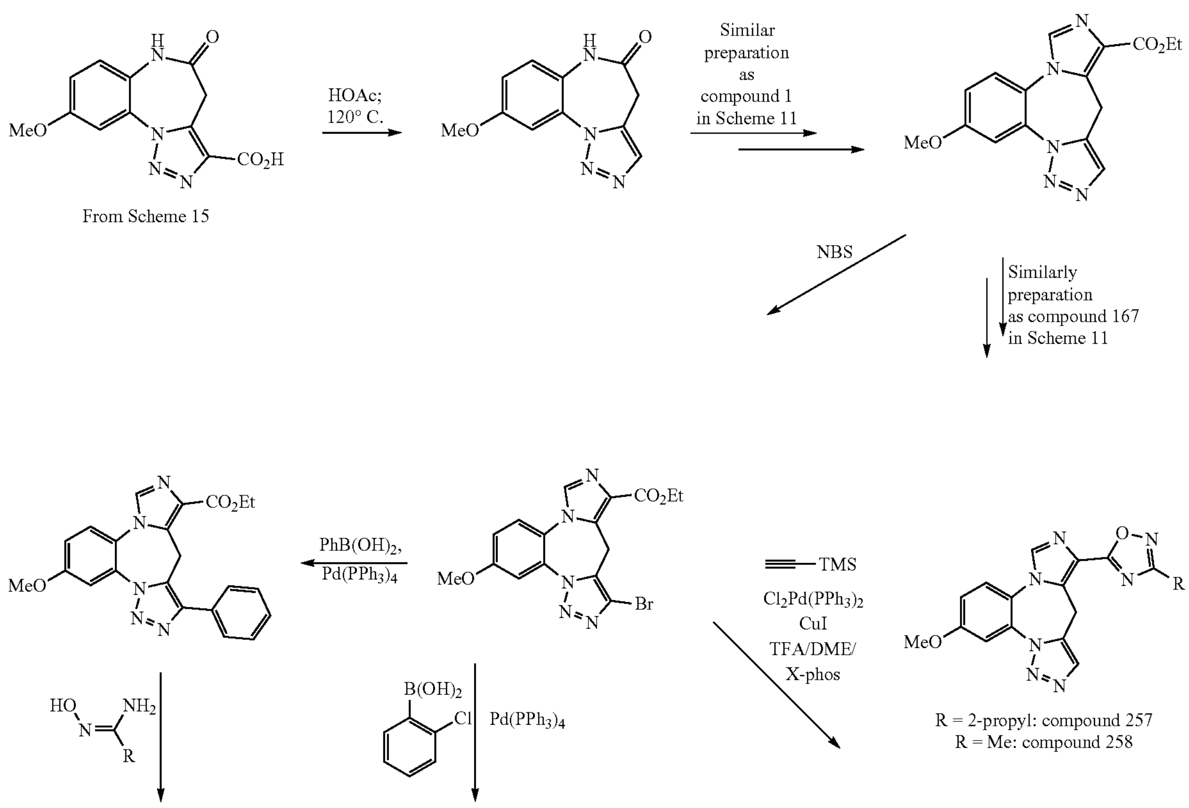

-continued

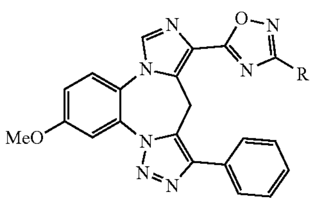

R = 2-propyl: compound 272
R = Me: compound 273

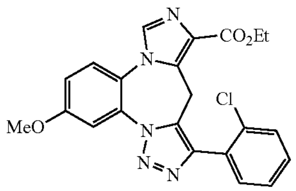

compound 279

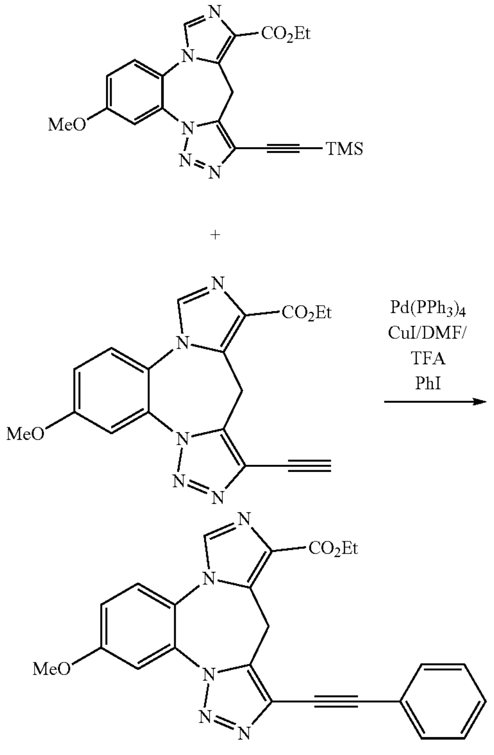

Compound 318

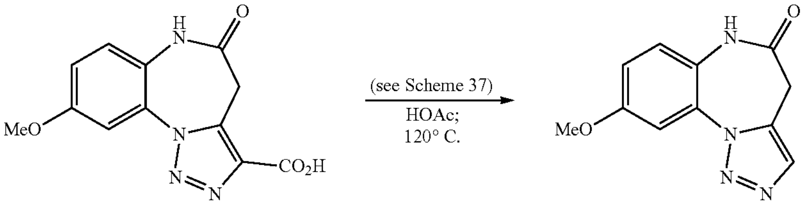

The acid (16 in Scheme 15, X—OMe; 258.1 mg, 0.941 mmol) was treated with acetic acid (2 ml) at 120° C. for 5 hr. Solvent was then removed in vacuo. Solid residue was treated in water (7 ml) with sonication, filtered, washed with water, and dried to give 158.4 mg (73%) decarboxylated product as a brownish solid. MS: [M+1]=231.

compound 257

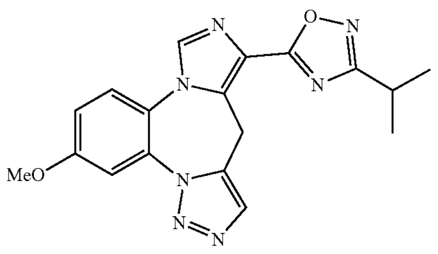

Compound 257 was prepared in a similarly fashion as compound 167 in Scheme 11. MS: [M+1]=364.

Compound 258 was prepared in a similarly fashion as compound 167 in Scheme 11. MS: [M+1]=336.

Synthesis of Compound 262

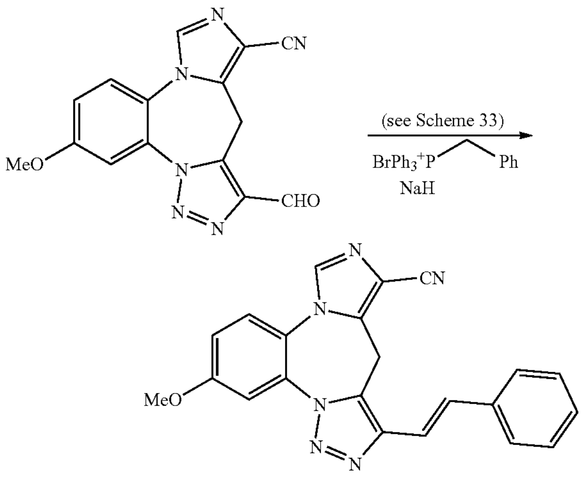

compound 262

Benzyl triphenyl phosphonium bromide (29.0 mg, 0.0669 mmol) was stirred in THF (0.5 ml) cooled in a salt-ice bath.

Sodium hydride (4.12 mg, 0.103 mmol; 60% oil suspension) was added. After 20 min stirring, aldehyde (15.8 mg, 0.0515 mmol) was added. The reaction was allowed to slowly warm to rt over four hrs, then quenched with sat. $NH_4Cl$, extracted with EtOAc (3×), washed with brine, and dried over $MgSO_4$. Compound 262 was isolated by repeated prep. TLCs using 2% MeOH in DCM. 1.1 mg was isolated as a white solid. MS: [M+1]=381.

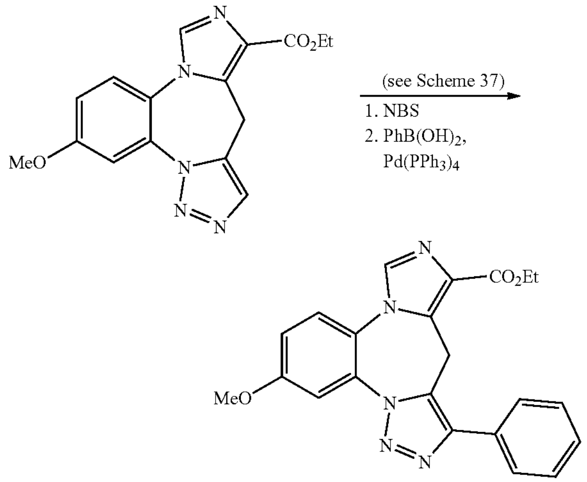

The starting ester (76.4 mg, 0.235 mmol) was treated with N-bromosuccinamide (83.6 mg, 0.470 mmol) in acetonitrile (2.3 ml) at rt for three days. To the reaction mixture was added sat. sodium thiosulfate. After 15 min stirring, aq. Layer was separated and extracted with EtOAc (2×). Combined organic layer was washed with brine and dried over $MgSO_4$. The bromide product was isolated by prep. TLC using hexanes:EtOAc=1:3 as the eluting solvent. 50.2 mg (52%) was obtained as a light brown foamy solid. MS: [M+1]=405.

To the bromide from above (24.1 mg, 0.0596 mmol) under nitrogen atm. was added phenyl boronic acid (10.3 mg, 0.083 mmol), tetrakis(triphenylphosphine)palladium(0) (6.9 mg, 0.006 mmol), dimethoxyethane (0.69 mL; degassed), and aq. $Na_2CO_3$ solution (77 ul; 2M). The reaction was heated at 100° C. for 5 hrs, cooled to rt, diluted with EtOAc, washed with sat. $NaHCO_3$, brine, and dried over $MgSO_4$. Prep. TLC with hexanes:EtOAc=1:3 gave 17.2 mg (72%) Suzuki coupling product as a yellowish amorphous material. MS: [M+1]=402.

Syntheses of Compound 272, 273 and 277

Compound 272 was prepared similarly as compound 167 in Scheme 11, starting from the imidazole ester above. MS: [M+1]=440.

Compound 273 was prepared similarly as compound 167 in Scheme 11, starting from the imidazole ester above. MS: [M+1]=412.

Compound 277 was prepared similarly as compound 167 in Scheme 11. MS: [M+1]=378.

Compound 279 was prepared via Suzuki coupling in a similar fashion as detailed above (see Scheme 37). MS: [M+1]=436.

Synthesis of Compound 318

Step 1. Bromide starting material 5-bromo-16-methoxy-2,3,4,10,12 pentaazatetracyclo-[11.4.0.0$^{2}$,$^{6}$0.0$^{8}$,$^{12}$]heptadeca-1(17),3,5,8,10,13,15-heptaene-9-carboxylate (35.4 mg, 0.088 mmol) prepared in Scheme 37 was treated with CuI (13.3 mg, 0.07 mmol), X-Phos (35.9 mg, 0.088 mmol), in DME (0.55 mL) and TFA (0.122 mL). The flask was purged with $N_2$ and to this mixture was added $Cl_2Pd(PPh_3)_2$ (30.7 mg, 0.0438 mmol). The reaction was heated to 100 C for 20 h, cooled, and partitioned between EtOAc and water. The organic phase was dried and concentrated to afford crude product as well as de-silylated material, ethyl 5-ethynyl-16-methoxy-2,3,4,10,12-pentaazatetracyclo[11.4.0.0$^{2}$,$^{6}$0.0$^{8}$,$^{12}$]heptadeca-1(17),3,5,8,10,13,15-heptaene-9-carboxylate. The two compounds were separated by prep-TLC (Hex/EtOAc 1:2).

Step 2. The ethyl 5-ethynyl-16-methoxy-2,3,4,10,12-pentaazatetracyclo-[11.4.0.0$^{2}$,$^{6}$0.0$^{8}$,$^{12}$]heptadeca-1(17),3,5,8,10,13,15-heptaene-9-carboxylate (6.2 mg, 0.0177 mmol) from Step 1 was dissolved in DMF (0.2 mL). To the solution was added iodobenzene (10.9 mg, 0.0532 mmol), TEA (12.5 uL), CuI (0.7 mg, 0.0035 mmol), and $Pd(PPh_3)_4$ (10.2 mg, 0.009 mmol). The mixture was stirred at RT overnight. The mixture was diluted with water and extracted 3× with EtOAc. The organic phase was washed with brine and dried. Concentration gave 9.7 mg of pure Compound 318.

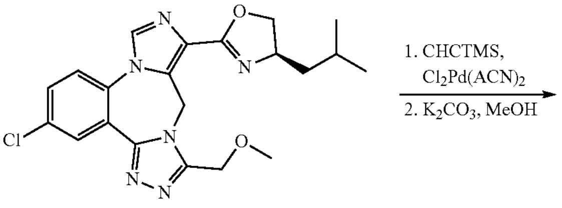

compound 267

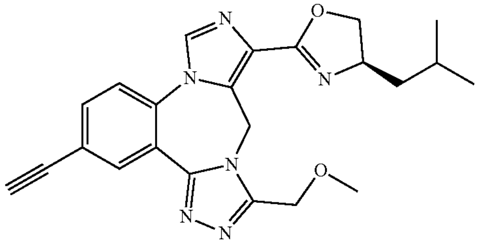

compound 280

Synthesis of Compound 280

To compound 267 (11.7 mg, 0.0274 mmol) under nitrogen atmosphere was added dicyclohexyl[2-(2,4,6-triisopropylphenyl) phenyl]phosphane (7.8 mg, 0.0164 mmol), cesium carbonate (22.3 mg, 0.0685 mmol), and acetonitrile (0.30 ml). The reaction flask was flushed with nitrogen gas, and dichlorobis(acetonitrile)palladium (II) (1.42 mg, 0.0055 mol) was added. After stirring at it for 30 min, trimethylsilyl acetylene (80.7 mg, 0.822 mmol) was added, and the reaction was heated at 90° C. for 5 hrs, cooled to rt, diluted with EtOAc, and washed with sat. $NaHCO_3$. Aq. Layer was separated and extracted with EtOAc (2×), combined organic layer was washed with brine and dried over $MgSO_4$. Prep. TLC of the filtered concentrate using 5% MeOH in DCM/EtOAc (1:1) gave 4.1 mg trimethylsilyl acetylene derivative as a yellowish solid. MS: [M+1]=489.

The trimethylsilyl acetylene (4.1 mg, 0.0084 mmol) from above was treated with potassium carbonate (1.2 mg, 0.0084 mmol) in methanol (0.2 ml) at rt for 3 hrs. Prep. TLC using 7% MeOH in DCM/EtOAc (1:1) as eluting solvent gave 1.6 mg Compound 280 as a yellowish solid. MS: [M+1]=417.

Syntheses of Compound 284, 301 and 302

Compound 284 was prepared similarly as compound 280, starting from compound 240. MS: [M+1]=403.

Compound 301 was prepared similarly as compound 280 starting from compound 264. MS: [M+1]- 437.

Compound 302 was prepared similarly as compound 280 starting from compound 245. MS: [M+1]=435.

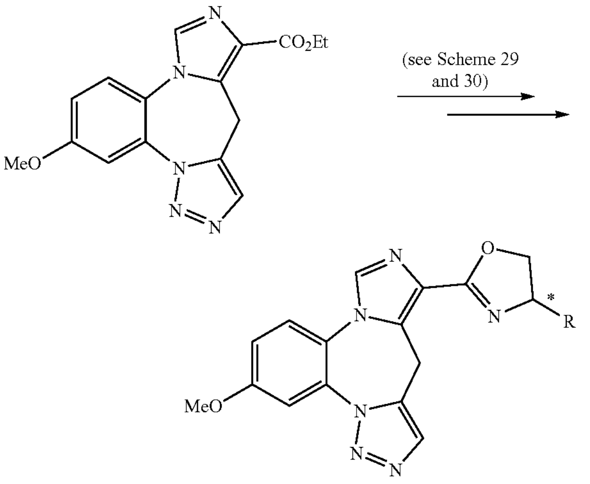

R = (S)-Ph: compound 289
R = (R)-Ph: compound 290
R = (R)-Me: compound 291
R = (S)-Me: compound 292

Syntheses of Compound 289, 290, 291 and 292

Compound 289 was prepared similarly as compound 263 as depicted in Scheme 30. MS: [M+1]=399.

Compound 290 was prepared similarly as compound 263 as depicted in Scheme 30. MS: [M+1]=399.

Compound 291 was prepared similarly as compound 243 as depicted in Scheme 29. MS: [M+1]- 337.

Compound 292 was prepared similarly as compound 243 as depicted in Scheme 29. MS: [M+1]=337.

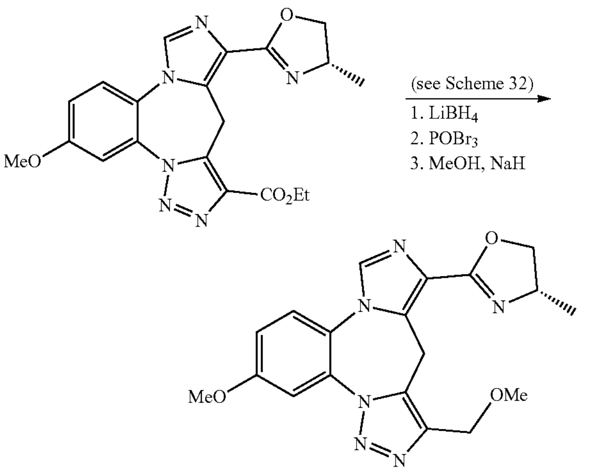

compound 298

Synthesis of Compound 298

The ester (107.9 mg, 0.264 mmol) in THF (2.4 ml) was treated with lithium borohydride solution (0.264 ml; 2M THF) at 0° C. The reaction was allowed to warm to ambient temperature over 4 hrs, then quenched with sat. $NaHCO_3$ slowly, extracted with EtOAc (4×), washed with brine, and dried over $MgSO_4$. Filtration and solvent removal gave 77.3 mg (86%) alcohol as a yellowish solid.

Alcohol from above (16.4 mg, 0.0448 mmol) was treated with phosphorus oxybromide (25.7 mg, 0.0895 mmol) in 1,4-dioxane (0.5 ml) at 95° C. for 3 hrs. The reaction was then cooled to 0° C., quenched with sat. $NaHCO_3$ (5 ml) for 20 min, and extracted with EtOAc (3×), washed with brine, and dried over $MgSO_4$. Filtration and drying gave 16.6 mg yellowish solid which was dissolved in anhydrous MeOH (18 ul) and THF (0.35 ml). This was cooled to 0° C., and NaH (9.2 mg; 60% suspension) was added. After 2 hrs stirring at 0° C., the reaction was quenched with sat. $NaHCO_3$, extracted with EtOAc (3×), washed with brine, and dried over $MgSO_4$. Prep. TLC using 10% MeOH in DCM gave 0.8 mg Compound 298 as a yellowish solid. MS: [M+1]=381.

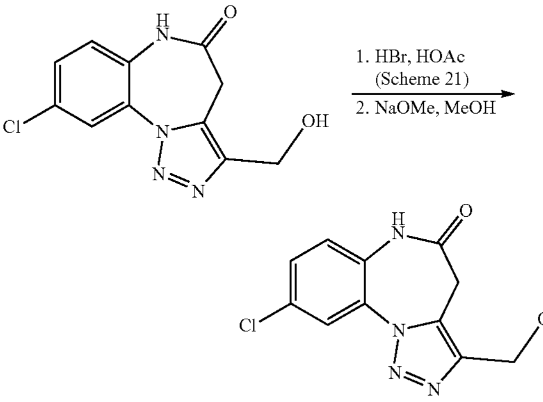

The starting alcohol (616 mg) was converted to the corresponding bromide as described earlier (see Scheme 21). The resulting crude bromide was dissolved in anhydrous methanol (23 ml), and cooled to 0° C. NaH (932 mg; 60% suspension) was added portionwise. After bubbling stopped, the reaction mixture was heated to reflux for 30 min, then cooled to rt, and treated with 2N HCl (11 ml). Resulting precipitate was collected by filtration, and the desired methyl ether was isolated by silica gel chromatography, using a gradient elution of 0 to 10% MeOH in DCM. 217 mg was collected as a yellowish solid. MS: [M+1]- 279.

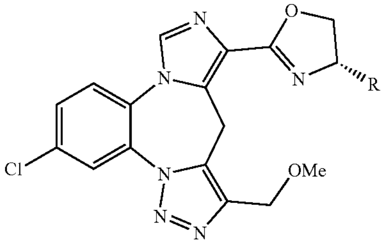

R = Bn: compound 229
R = Me: 300

Syntheses of Compounds 299 and 300

Compound 299 was prepared similarly as Compound 289, using the methyl ether intermediate above. MS: [M+1]=461.

Compound 300 was prepared similarly as Compound 289, using the methyl ether intermediate above. MS: [M+1]=385.

Scheme 38

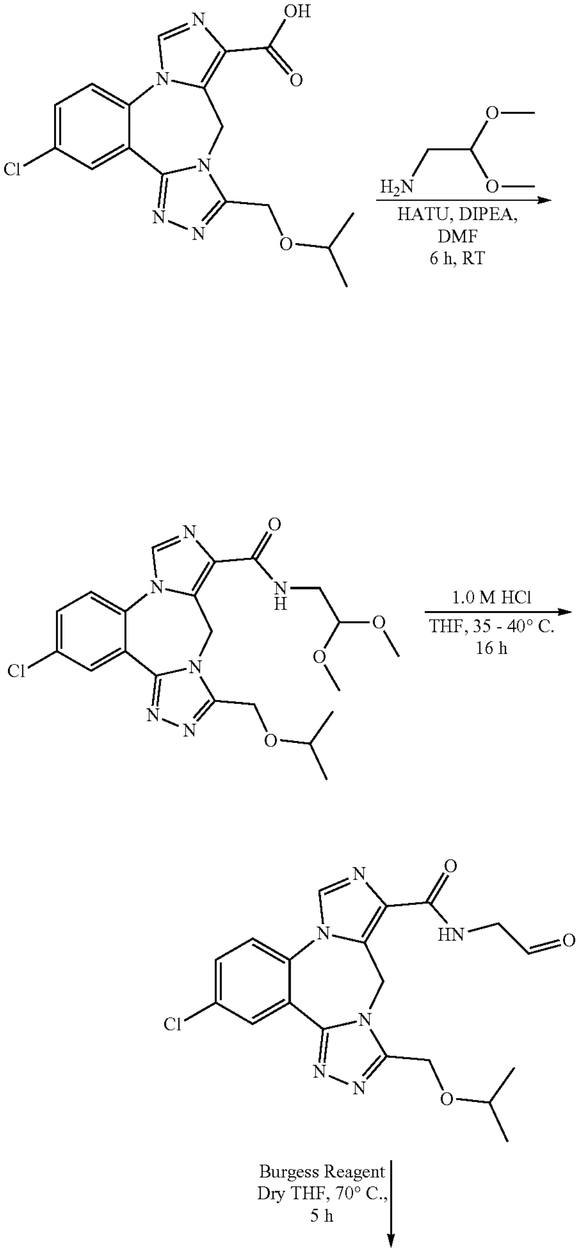

-continued

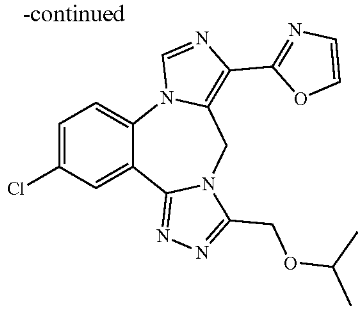

compound 327

Synthesis of Compound 327 compound 327

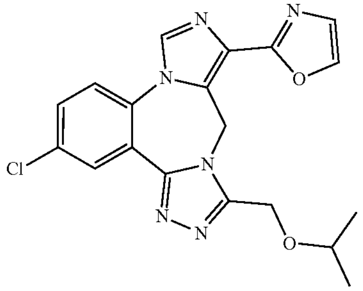

Step 1. The isopropoxy analog (15-chloro-9-[(propan-2-yloxy)methyl]-2,4,8,10,11-pentaazatetracyclo[11.4.0.0$^{2}$,$^{6}$0.0$^{8}$,$^{12}$]heptadeca-1(17),3,5,9,11,13,15-heptaene-5-carboxylic acid) of Intermediate B was prepared in an analogous fashion using the same reaction sequence as shown in Scheme 28. This compound (0.05 g, 0.13 mmol) was dissolved in anhydrous DMF (2.5 mL). HATU (0.061 g, 0.16 mmol) and aminoacetaldehyde dimethylacetal (0.029 mL, 0.27 mmol) were added to the reaction mixture followed by 0.047 mL (0.26 mmol) of diisopropyl ethylamine. The reaction mixture was stirred at room temperature for 4 h. LCMS shows product formation m/z 461.3 and little amount of starting material. An additional 0.030 g, (0.08 mmol) of HATU and 0.029 mL (0.27 mmol) of aminoacetaldehyde dimethylacetal were added to the reaction mixture and rxn mixture was stirred for additional 2 h. LCMS indicated reaction completion. The rxn mixture was diluted with DI-water and extracted with ethylacetate (15.0 mLx3). The combined ethyl acetate layers were washed with brine, separated and dried over anhydrous $Na_2SO_4$. The evaporation of organic layer gave crude product 15-chloro-N-(2,2-dimethoxyethyl)-9-[(propan-2-yloxy)methyl]-2,4,8,10,11-pentaazatetracyclo-[11.4.0.0$^{2}$,$^{6}$0.0$^{8}$,$^{12}$]heptadeca-1(17),3,5,9,11,13,15-heptaene-5-carboxamide (62 mg, 100%); m/z calculated for $C_{21}H_{25}ClN_6O_4[M+H]^+$: 461; Obtained: 461.3.

Step 2. The acetal moiety was removed by stirring the above compound (0.062 g, 0.13 mmol) in THF (2.0 mL) with 1.3 mL, (1.3 mmol) of 1.0 M HCl solution at 35-40° C. temperature for 16 h. LCMS shows deprotected aldehyde m/z 415.3. The reaction mixture was diluted with ethylacetate 30.0 mL and washed with saturated solution of $NaHCO_3$ followed by brine. The organic layer was separated and dried over anhydrous $Na_2SO_4$. The evaporation of solvent gave crude product (15-chloro-N-(2-oxoethyl)-9-[(propan-2-yloxy)methyl]-2,4,8,10,11-pentaazatetracyclo [11.4.0.0$^{2}$,$^{6}$0.0$^{8}$,$^{12}$]heptadeca-1(17),3,5,9,11,13,15-heptaene-5-carboxamide (55 mg, 100%); m/z calculated for $C_{19}H_{19}ClN_6O_3$[M+H]$^+$ 415, Obtained 415.3.

Step 3. The above aldehyde (0.055 g, 0.13 mmol) was dissolved in anhydrous THF (5.0 mL). Burgess Reagent (0.064 g, 0.26 mmol) was added and reaction mixture was heated at 70° C. for 2 h. LCMS shows mixture of starting material m/z 415 and product; m/z 397.2. Additional Burgess Reagent (0.032 g, 0.13 mmol) was further added and reaction mixture was heated at 70° C. for 3 h. LCMS shows product formation m/z 397.2. The reaction mixture was diluted with ethyl acetate (30.0 mL) and washed with saturated solution of $NaHCO_3$ followed by brine. The organic layer was separated and dried over anhydrous $Na_2SO_4$. The evaporation of solvent gave crude product. The purification of crude product was performed by prep-TLC plate: Mobile Phase: EtOAc:MeOH, 96:04 v/v mL. 13.5 mg of solid Compound 327 was obtained (25.4% Yield); m/z calculated for $C_{19}H_{17}ClN_6O_3$[M+H]$^+$ 397, Obtained 397.2.

Compound 341 was prepared similarly as Compound 327, as shown in Scheme 38.

Synthesis of Compound 349 compound 349

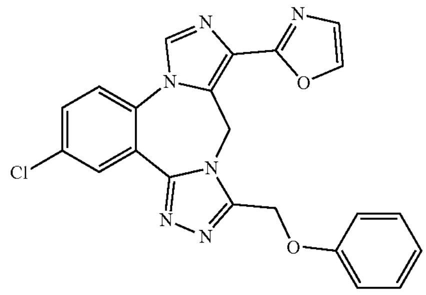

Intermediate C (prepared in Scheme 28) was converted into the corresponding carboxylic acid (15-chloro-9-(phenoxymethyl)-2,4,8,10,11 pentaazatetracyclo[11.4.0.0$^{2}$,$^{6}$0.0$^{8}$,$^{12}$heptadeca-1(17),3,5,9,11,13,15-heptaene-5-carboxylic acid analogously to the transformation of Intermediate A to Intermediate B. The compound was then converted to Compound 349 in a three step sequence analogously to compound 327 shown in Scheme 38 using the appropriate reagents.

Synthesis of Compound 350 compound 350

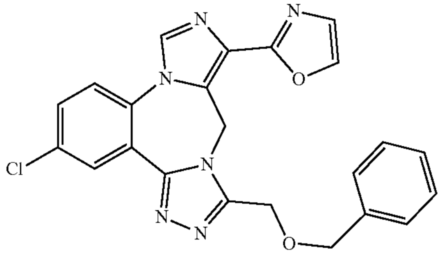

Compound 350 was synthesized in an analogous manner as shown for compound 349 using the appropriate starting materials and the same reactions depicted in Scheme 38.

Synthesis of Compound 355 compound 355

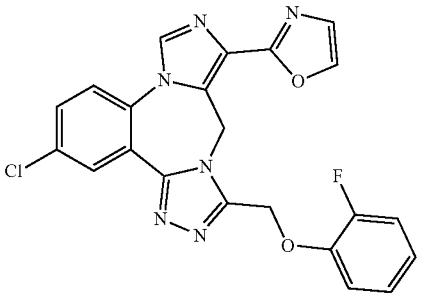

Compound 355 was synthesized in an analogous manner as shown for compound 349 using the appropriate starting materials and the same reactions depicted in Scheme 38.

Scheme 39

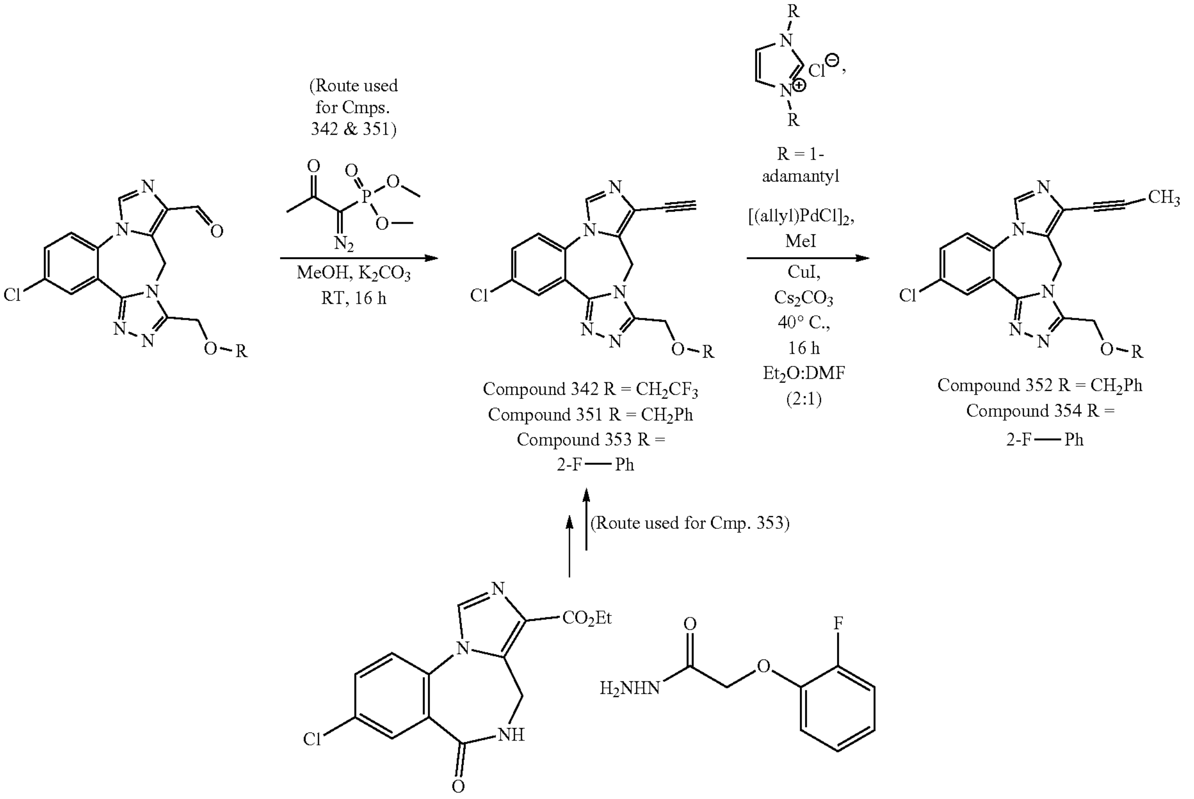

Synthesis of Compound 342

Compound 342

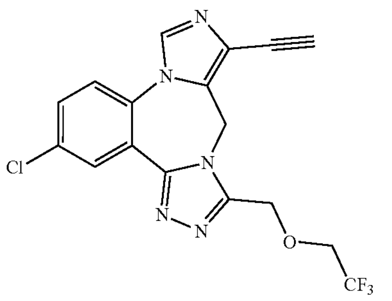

The above aldehyde, R=$CH_2CF_3$, (15-chloro-9-[(2,2,2-trifluoroethoxy)methyl]-2,4,8,10,11-pentaazatetracyclo [11.4.0.0$^{2}$,$^{6}$0.0$^{8}$,$^{12}$]heptadeca-1(17),3,5,9,11,13,15-heptaene-5-carbaldehyde) was prepared analogously to the aldehyde shown in Scheme 29 (15-chloro-9-(methoxymethyl)-2,4,8,10,11 penta-azatetracyclo[11.4.0.0$^{2}$,$^{6}$0.0$^{8}$,$^{12}$] heptadeca-1(17),3,5,9,11,13,15-heptaene-5-carbaldehyde). This compound (0.04 g, 0.1 mmol) was dissolved in 3.0 mL of dry MeOH and $K_2CO_3$ (0.028 g, 0.2 mmol) was added at room temperature. Ohira Bestman reagent (0.02 mL, 0.14 mmol) was dropwise added and reaction mixture was stirred at room temperature for 16 h. LCMS shows product formation m/z 394.2. The reaction mixture was concentrated in vacuo and diluted with 20.0 mL of aq. sodium bicarbonate solution. The ppts were filtered and washed with DI water to obtain 34.0 mg of solid after drying (Yield 85.9%); m/z calculated for $C_{17}H_{11}ClF_3N_5O$ $[M+H]^+$: 394; Obtained: 394.

Synthesis of Compound 351

Compound 351

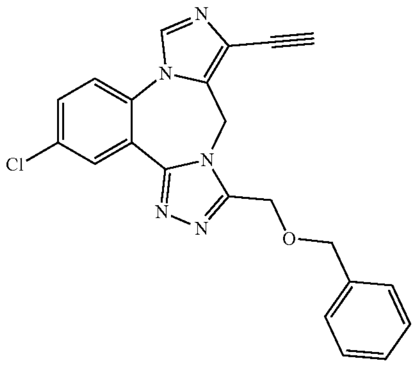

The above aldehyde, R=$CH_2Ph$, 9-[(benzyloxy)methyl]-15-chloro-2,4,8,10,11-pentaazatetracyclo[11.4.0.0$^{2}$,$^{6}$0.0$^{8}$,$^{12}$]heptadeca-1(17),3,5,9,11,13,15-heptaene-5-carbaldehyde was prepared analogously to the aldehyde shown in Scheme 29 (15-chloro-9-(methoxymethyl)-2,4,8,10,11 penta-azatetracyclo[11.4.0.0$^{2}$,$^{6}$0.0$^{8}$,$^{12}$]heptadeca-1(17),3,5,9,11,13,15-heptaene-5-carbaldehyde). It was converted to compound 351 analogously to compound 342 as shown in Scheme 39.

Synthesis of Compound 353

The above acetylene derivative compound 353 (15-chloro-5-ethynyl-9-(2-fluorophenoxymethyl)-2,4,8,10,11-pentaazatetracyclo[11.4.0.0$^{2,6}$0.0$^{8,12}$]heptadeca-1(17),3,5,9,11,13,15-heptaene) was prepared from ethyl 12-chloro-9-oxo-2,4,8-triazatricyclo[11.4.0.0$^{2,6}$]tetradeca-1(10),3,5,11,13-pentaene-5-carboxylate and 2-(2-fluorophenoxy) acetohydrazide with analogous sequences to those described in Scheme 28.

Synthesis of Compound 328

The aldehyde (15-methoxy-9-(methoxymethyl)-2,4,8,10,11-pentaazatetracyclo-[11.4.0.0$^{2,6}$0.0$^{8,12}$]heptadeca-1(17),3,5,9,11,13,15-heptaene-5-carbaldehyde) was prepared analogously as was described in Scheme 29 for 15-chloro-9-(methoxymethyl)-2,4,8,10,11 pentaazatetracyclo [11.4.0.0$^{2,6}$0.0$^{8,12}$]heptadeca-1(17),3,5,9,11,13,15-heptaene-5-carbaldehyde. This compound was converted to Compound 328 analogously as shown in Scheme 39 for Compound 342 to afford 5-ethynyl-15-methoxy-9-(methoxymethyl)-2,4,8,10,11-pentaazatetracyclo[11.4.0.0$^{2}$,$^{6}$0.0$^{8}$,$^{12}$]heptadeca-1(17),3,5,9,11,13,15-heptaene (Compound 328).

Syntheses of Compounds 352 and 354

Compounds 352 and 354 were prepared, respectively, from compounds 351 and 353 in a manner analogously to that reported in Scheme 29 for compound 339.

Scheme 40

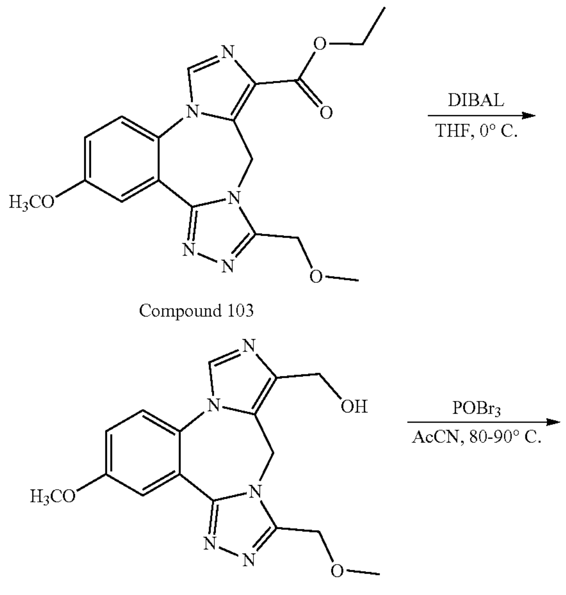

Compound 103

-continued

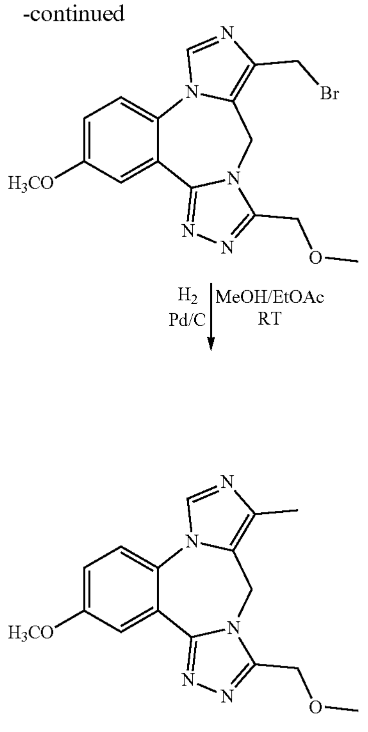

compound 329

Synthesis of Compound 329

Step 1: Compound 103 (described in Scheme 18a) (107 mg, 0.29 mmol) was stirred in THF (1.5 mL) at 0 C and to it was added DIBAL (0.73 mL, 1M sol in hexane, 0.73 mmol). The mixture was stirred for 2 h. Additional 0.5 eq of DIBAL was added to push the reaction to completion. After 30 min, the mixture was quenched with saturated $NaHCO_3$ and extracted with EtOAc (3×). The organic phase was washed with brine and dried ($MgSO_4$). Concentration afforded crude product which was purified by prep TLC (10% MeOH/DCM) to give 57 mg (61%) of [15-methoxy-9-(methoxymethyl)-2,4,8,10,11-pentaazatetracyclo [11.4.0.0$^{2,6}$0.0$^{8,12}$]heptadeca-1(17),3,5,9,11,13,15-heptaen-5-yl]methanol.

Step 2: The above alcohol (18.9 mg, 0.0577 mmol) was stirred in AcCN (1 mL) and to it was added the $POBr_3$ (50 mg, 0.173 mmol). The mixture was stirred at 90 C for 3 h, cooled, diluted with EtOAc, and treated with sat'd $NaHCO_3$. Mixture was extracted with EtOAc. The organic phases were combined, washed with brine, dried, and concentrated to afford crude product which was used directly in the next reaction.

Step 3: The above crude bromide was stirred with 10% Pd/C (catalytic amt.) in 8 mL of 1:1 MeOH/EtOAc under a $H_2$ filled balloon for 48 h. Mixture was filtered through Celite. Concentration afforded crude product which was purified by prep TLC (15% MeOH/DCM) to give 11.3 mg of compound 329 as a white solid.

Synthesis of Compound 356

Compound 356

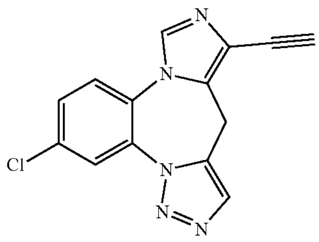

Scheme 41

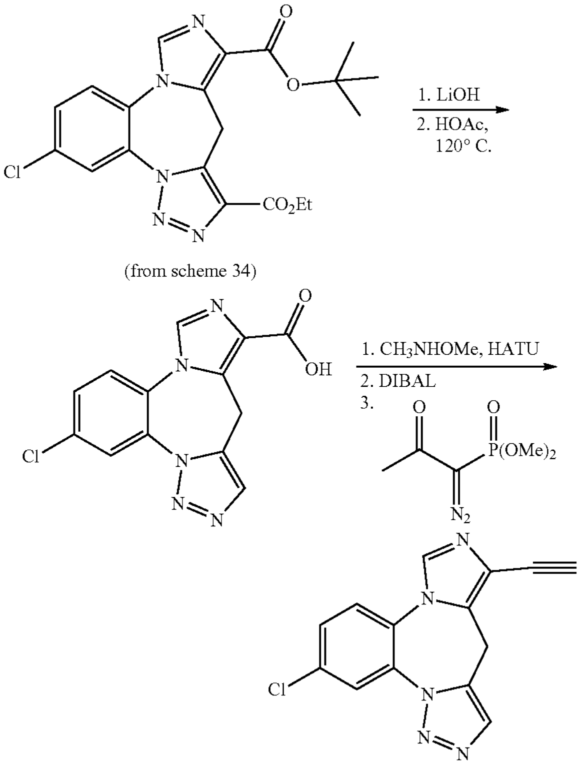

Compound 356

9-tert-butyl 5-ethyl 16-chloro-2,3,4,10,12-pentaazatetracyclo[11.4.0.0$^{2}$,$^{6}$0.0$^{8}$,$^{12}$]heptadeca-1(17),3,5,8,10,13,15-heptaene-5,9-dicarboxylate (prepared in Scheme 34) (100.7 mg, 0.234 mmol) was treated with lithium hydroxide (28.1 mg, 1.17 mmol) in a solvent mixture of THF (0.6 mL), water (0.5 mL), and MeOH (0.1 ml) for 12 hr. The reaction mixture was then concentrated by removing most organic solvents under reduced pressure, re-suspended in acetic acid (3 mL), and heated at 120° C. for 20 hrs. Resulting brownish clear solution was then added dropwise into a 30 mL stirring cold water. The solution was then cooled in an ice bath for over 30 min. The resulting precipitate was collected by filtration, washed with water, and further dried to give 45.4 mg (64% over two steps) of 16-chloro-2,3,4,10,12-pentaazatetracyclo[11.4.0.0$^{2}$,$^{6}$0.0$^{8}$,$^{12}$]heptadeca-1(17),3,5,8,10,13,15-heptaene-9-carboxylic acid as a brownish solid. MS: [M+1]=302.

To the above mono-acid (45.3 mg, 0.150 mmol) in DMF (0.5 mL) was added N,O-dimethyl hydroxylamine hydrochloride (22.0 mg, 0.225 mmol), HATU (62.7 mg, 0.165 mmol), and N,N-diisopropyl ethylamine (58.2 mg, 0.450 mmol). After two hour stirring, the reaction mixture was diluted with EtOAc, washed with 0.5N HCl, sat. $NaHCO_3$, brine, and dried over $MgSO_4$. Filtration followed by solvent removal in vacuo gave 40.8 mg (79%) Weinreb amide as a yellowish solid. MS: [M+1]=345.

To the above amide (40.8 mg, 0.118 mmol) in anhydrous THF (0.5 mL) at −78° C. was added diisobutylalumium hydride solution (0.5 mL; 1M in hexane). After 1 h stirring, the reaction was allowed to slowly warm up to −10° C., and cooled back down to −78° C. A saturated aqueous solution of potassium sodium tartrate (5 mL) was added, and stirred for 60 min. The solution was extracted with EtOAc (4×), washed with brine, dried over $MgSO_4$. Filtration and solvent removal gave 18.7 mg (55%) of 16-chloro-2,3,4,10,12-pentaazatetracyclo[11.4.0.0$^{2}$,$^{6}$0.0$^{8}$,$^{12}$]heptadeca-1(17),3,5,8,10,13,15-heptaene-9-carbaldehyde as a yellowish solid. MS: [M+1]=286.

To the above aldehyde (18.7 mg, 0.0655 mmol) stirring in MeOH (1 mL) at rt was added potassium carbonate (18.1 mg, 0.131 mmol) and dimethyl 1-diazo-2-oxopropyl phosphonate (21.4 mg, 0.111 mmol). After 16 hr stirring, the reaction was diluted with EtOAc, washed with sat. $NaHCO_3$, aq. Layer was separated and extracted with EtOAc twice; the combined organic solution was washed with brine, and dried over $MgSO_4$. Filtration and solvent removal gave a crude mixture from which the desired alkyne compound 356 was isolated by prep. TLC using 5% MeOH in EtOAc/dichloromethane (1:1) as the eluent. 8.7 mg Compound 356 was obtained as a light yellow solid. MS: [M+1]−282.

Compounds 357-375, 382, 383, 385-398, 399-412, 414, 416, and 425-428 were prepared in an analogous manner to those described in Schemes 29, 30, and 34 using the appropriate starting materials. For Compound 398, trifluoroethyl iodide was used in the Sonogashira reaction.

Compounds 376-381 were prepared as shown in Scheme 21 before installing the oxazoline moiety.

Compound 384 was prepared similarly to Compound 280, after installing the oxazoline portion.

Compound 413 was prepared as shown in Scheme 39 using benzyl bromide in the place of methyl iodide.

Compound 415 was prepared similarly to Compound 280, starting with compound 452 and 3-methyl-1-butyne. Two additional compounds were formed in this reaction mixture—compounds 453 (bis-alkyne product) and compound 454 (A-ring Cl atom replaced by alkyne moiety).

Compounds 417-423 were prepared as shown in Scheme 39 using appropriately substituted benzyl bromide in the place of methyl iodide.

Compound 424 was prepared similarly to Compound 280, using bromide as the starting material.

Compound 429 was prepared by the Mitsunobu reaction between phenol and imidazoyl methyl alcohol (see Scheme 15 and ensuing examples for reaction conditions).

Compound 430 was prepared as shown in Scheme 29, by alkylating imidazoyl methyl alcohol with BnBr using NaH in THF as the basic medium.

Compounds 431-432 were prepared as shown in Scheme 29, by alkylating imidazoyl methyl alcohol with the appropriately substituted benzyl bromide using NaH in THF as the basic medium.

Compounds 433-435 were prepared similar to Compound 429 using the appropriately substituted phenol.

Compound 436 was prepared similar to Compound 430 by alkylating appropriate starting alcohol with 2-F benzyl bromide under the same basic condition.

Compound 437 was prepared similar to Compound 430 by alkylating appropriate starting alcohol with 3-F benzyl bromide under the same basic condition.

Compound 438 was prepared similar to Compound 430 by alkylating appropriate starting alcohol with 3-Cl benzyl bromide under the same basic condition.

Compound 439 was prepared similar to Compound 430 by alkylating appropriate starting alcohol with 2-Cl benzyl bromide under the same basic condition.

Compounds 440-443 were prepared similar to Compound 429 by Mitsunobu reaction between phenol and the corresponding primary alcohol.

Compounds 444-445 were prepared similar to Compounds 274 and 215 as shown in Scheme 29, by alkylating imidazoyl methyl alcohol with the appropriately substituted benzyl bromide using NaH in THF as the basic medium.

Compounds 446-447: Starting with similar aldehyde as shown in Scheme 39, these compounds were prepared analogously using olefination condition as shown in Scheme 33.

Compounds 448 was prepared starting with compound 356 and analogous to the condition in Scheme 29, Sonogashira reaction was performed using benzoyl chloride in place of Ph-I, under $PdCl_2(PPh_3)_2$ catalysis.

Compound 449 was prepared starting with compound 403, benzylation was performed using BnBr as the alkylating agent, and NaH in THF as the basic condition, heating as necessary.

Compound 450 was prepared starting with compound 403, benzylation was performed using 3-F-BnBr as the alkylating agent, and NaH in THF as the basic condition, heating as necessary.

Compound 451 was prepared starting with compound 403, benzylation was performed using 2-F-BnBr as the alkylating agent, and NaH in THF as the basic condition, heating as necessary.

Compound 455 was prepared starting with compound 256 and analogous to the condition in Scheme 29, Sonogashira reaction was performed using benzoyl chloride in place of Ph-I, under $PdCl_2(PPh_3)_2$ catalysis.

Compounds 452-454 were synthesized under the same conditions as compound 280, starting with compound 452 and 3-methyl-1-butyne.

Compounds 456-471 were prepared in an analogous manner to those described in Schemes 28, and 29; using the appropriate starting materials. NaH replaced KO$^t$Bu to form the imidazole ring.

Compounds 180-471 were characterized by MS and $^1$H NMR. The MS characterization is summarized below in Table 5.

TABLE 5

MS characterization of Compounds 180-471:

| Cmp No. | Structure | Observed MS (M + 1) |
|---|---|---|
| 180 | 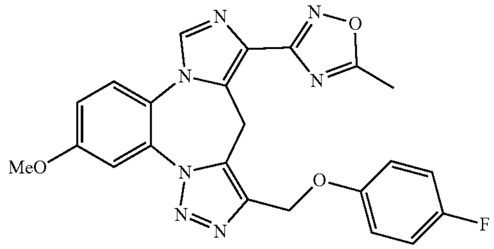 [SMILES: COc1ccc2c(c1)-n1nnc(COc3ccc(F)cc3)c1Cc1c(-c3noc(C)n3)ncn1-2] | 460 |
| 181 | 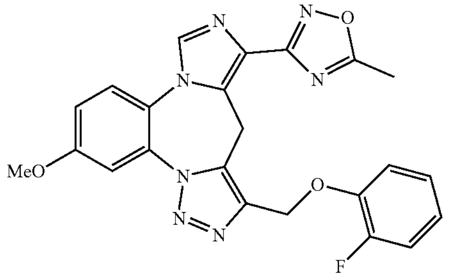 [SMILES: COc1ccc2c(c1)-n1nnc(COc3ccccc3F)c1Cc1c(-c3noc(C)n3)ncn1-2] | 460 |
| 182 | 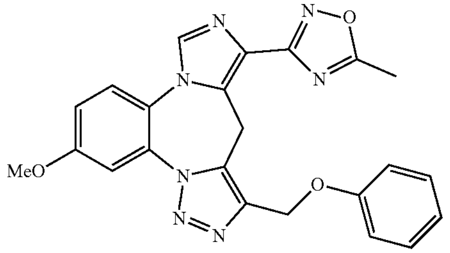 [SMILES: COc1ccc2c(c1)-n1nnc(COc3ccccc3)c1Cc1c(-c3noc(C)n3)ncn1-2] | 442 |

TABLE 5-continued
| MS characterization of Compounds 180-471: | | |
|---|---|---|
| Cmp No. | Structure | Observed MS (M + 1) |
| 183 | 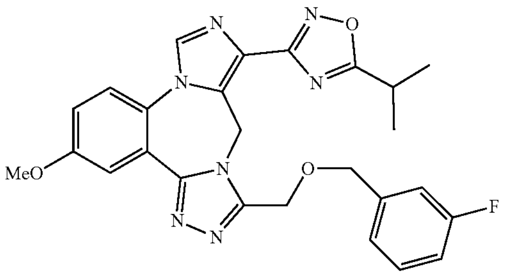 [SMILES: COc1ccc2c(c1)-c1nnc(COCc3cccc(F)c3)n1Cc1c(-c3noc(C(C)C)n3)ncn1-2] | 502 |
| 184 | 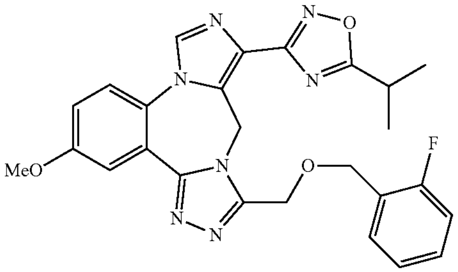 [SMILES: COc1ccc2c(c1)-c1nnc(COCc3ccccc3F)n1Cc1c(-c3noc(C(C)C)n3)ncn1-2] | 502 |
| 185 | 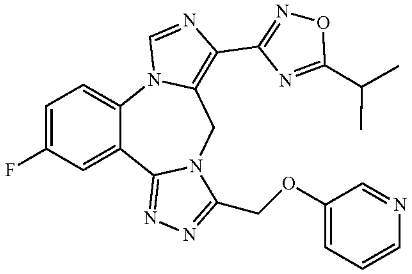 [SMILES: CC(C)c1nc(-c2ncn3c2Cn2c(COc4cccnc4)nnc2-c2cc(F)ccc2-3)no1] | 459 |
| 186 | 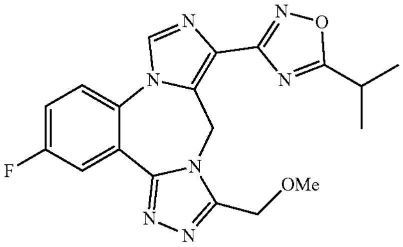 [SMILES: COCc1nnc2n1Cc1c(-c3noc(C(C)C)n3)ncn1-c1ccc(F)cc1-2] | 396 |
| 187 | 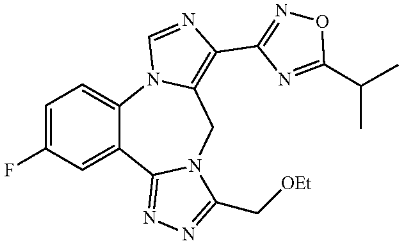 | 410 |

TABLE 5-continued
| MS characterization of Compounds 180-471: | | |
|---|---|---|
| Cmp No. | Structure | Observed MS (M + 1) |
| 188 | 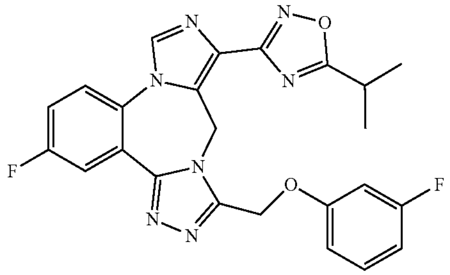 [SMILES: CC(C)c1nc(-c2ncn3c2Cn2c(COc4cccc(F)c4)nnc2-c2cc(F)ccc2-3)no1] | 476 |
| 189 | 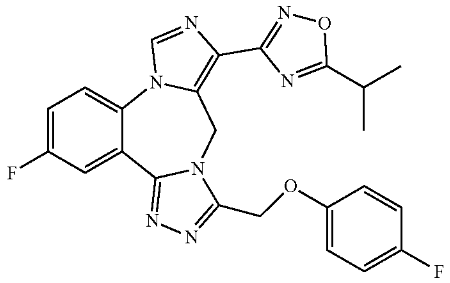 [SMILES: CC(C)c1nc(-c2ncn3c2Cn2c(COc4ccc(F)cc4)nnc2-c2cc(F)ccc2-3)no1] | 476 |
| 190 | 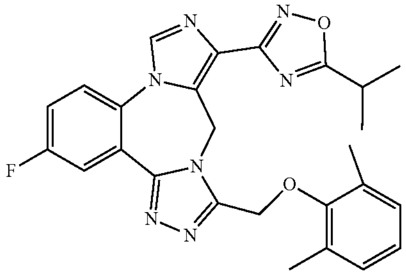 [SMILES: Cc1cccc(C)c1OCc1nnc2n1Cc1c(-c3noc(C(C)C)n3)ncn1-c1ccc(F)cc1-2] | 486 |
| 191 | 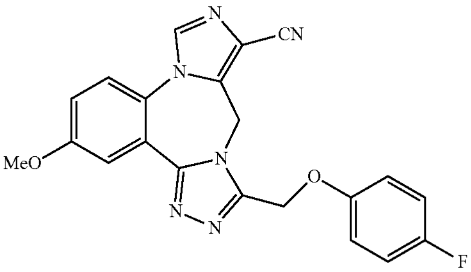 [SMILES: COc1ccc2c(c1)-c1nnc(COc3ccc(F)cc3)n1Cc1c(C#N)ncn1-2] | 403 |
| 192 | 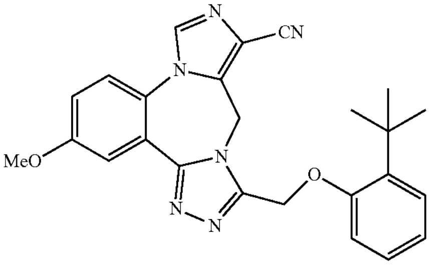 [SMILES: COc1ccc2c(c1)-c1nnc(COc3ccccc3C(C)(C)C)n1Cc1c(C#N)ncn1-2] | 441 |

TABLE 5-continued
| MS characterization of Compounds 180-471: | | |
|---|---|---|
| Cmp No. | Structure | Observed MS (M + 1) |
| 193 | 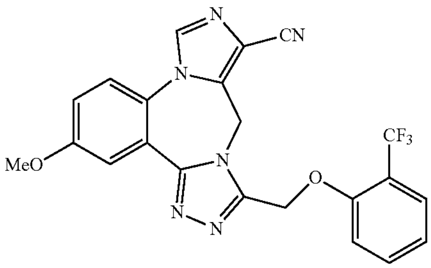 [SMILES: COc1ccc2c(c1)-c1nnc(COc3ccccc3C(F)(F)F)n1Cc1c(C#N)ncn1-2] | 453 |
| 194 | 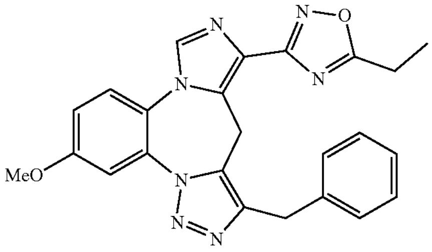 [SMILES: CCc1nc(-c2ncn3c2Cc2c(Cc4ccccc4)nnn2-c2cc(OC)ccc2-3)no1] | 440 |
| 195 | 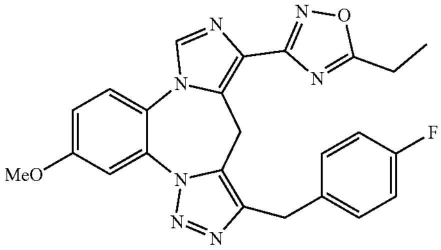 [SMILES: CCc1nc(-c2ncn3c2Cc2c(Cc4ccc(F)cc4)nnn2-c2cc(OC)ccc2-3)no1] | 458 |
| 196 | 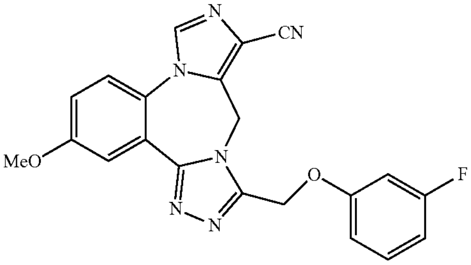 [SMILES: COc1ccc2c(c1)-c1nnc(COc3cccc(F)c3)n1Cc1c(C#N)ncn1-2] | 403 |
| 197 | 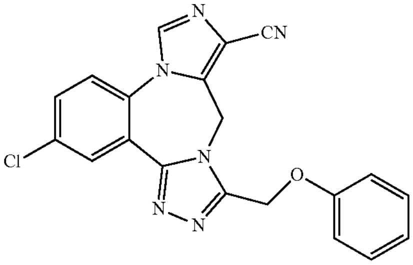 [SMILES: N#Cc1ncn2c1Cn1c(COc3ccccc3)nnc1-c1cc(Cl)ccc1-2] | 389 |

TABLE 5-continued
| MS characterization of Compounds 180-471: | | |
|---|---|---|
| Cmp No. | Structure | Observed MS (M + 1) |
| 198 | 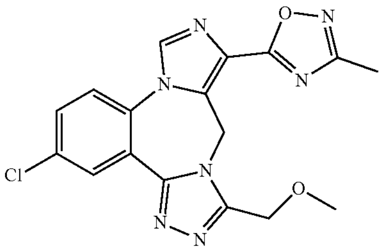 [SMILES: COCc1nnc2n1Cc1c(-c3nc(C)no3)ncn1-c1ccc(Cl)cc1-2] | 384 |
| 199 | 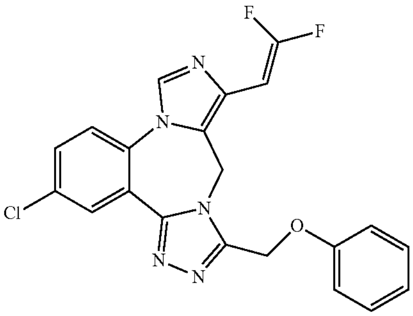 [SMILES: FC(F)=Cc1ncn2c1Cn1c(COc3ccccc3)nnc1-c1cc(Cl)ccc1-2] | 426 |
| 200 | 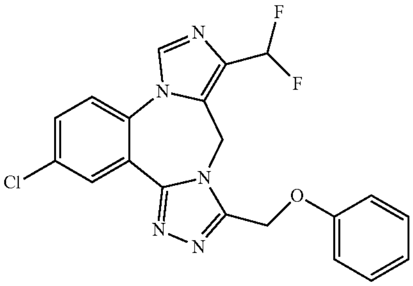 [SMILES: FC(F)c1ncn2c1Cn1c(COc3ccccc3)nnc1-c1cc(Cl)ccc1-2] | 414 |
| 201 | 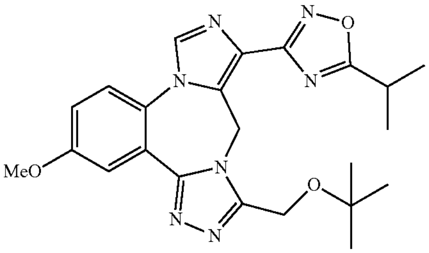 [SMILES: COc1ccc2c(c1)-c1nnc(COC(C)(C)C)n1Cc1c(-c3noc(C(C)C)n3)ncn1-2] | 450 |
| 202 | 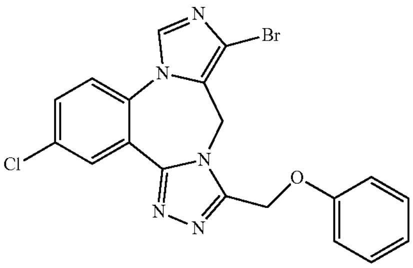 [SMILES: Clc1ccc2c(c1)-c1nnc(COc3ccccc3)n1Cc1c(Br)ncn1-2] | 443 |

TABLE 5-continued
| MS characterization of Compounds 180-471: | | |
|---|---|---|
| Cmp No. | Structure | Observed MS (M + 1) |
| 203 | 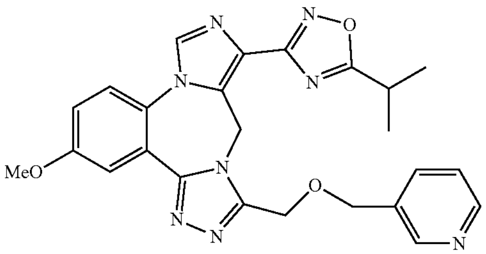 [SMILES: COc1ccc2c(c1)-c1nnc(COCc3cccnc3)n1Cc1c(-c3noc(C(C)C)n3)ncn1-2] | 485 |
| 204 | 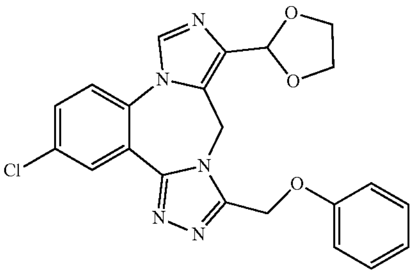 [SMILES: Clc1ccc2c(c1)-c1nnc(COc3ccccc3)n1Cc1c(C3OCCO3)ncn1-2] | 436 |
| 205 | 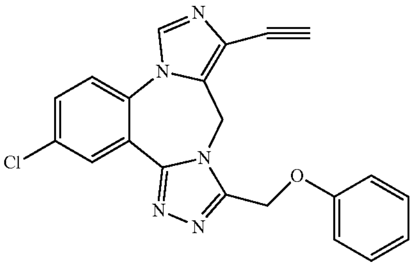 [SMILES: C#Cc1ncn2c1Cn1c(COc3ccccc3)nnc1-c1cc(Cl)ccc1-2] | 388 |
| 206 | 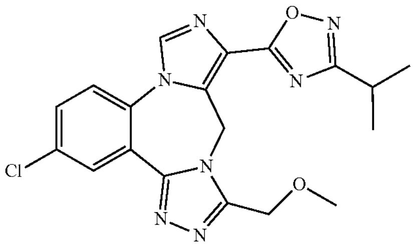 [SMILES: COCc1nnc2n1Cc1c(-c3nc(C(C)C)no3)ncn1-c1ccc(Cl)cc1-2] | 412 |
| 207 | 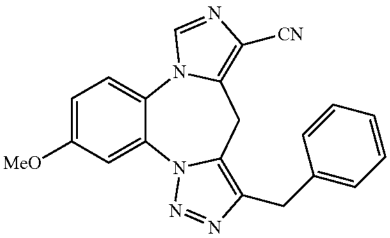 [SMILES: COc1ccc2c(c1)-n1nnc(Cc3ccccc3)c1Cc1c(C#N)ncn1-2] | 369 |

TABLE 5-continued
| MS characterization of Compounds 180-471: | | |
|---|---|---|
| Cmp No. | Structure | Observed MS (M + 1) |
| 208 | 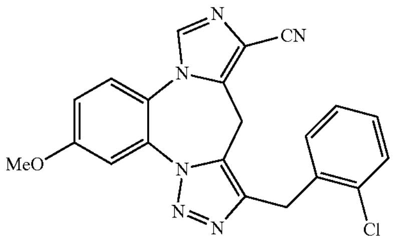 [SMILES: COc1ccc2c(c1)-n1nnc(Cc3ccccc3Cl)c1Cc1c(C#N)ncn1-2] | 403 |
| 209 | 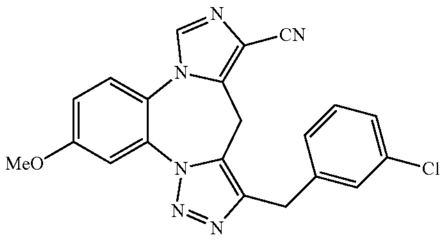 [SMILES: COc1ccc2c(c1)-n1nnc(Cc3cccc(Cl)c3)c1Cc1c(C#N)ncn1-2] | 403 |
| 210 | 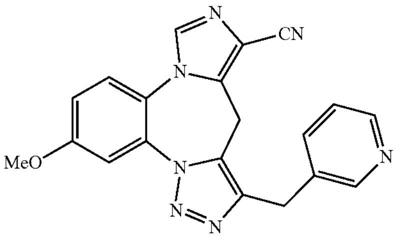 [SMILES: COc1ccc2c(c1)-n1nnc(Cc3cccnc3)c1Cc1c(C#N)ncn1-2] | 370 |
| 211 | 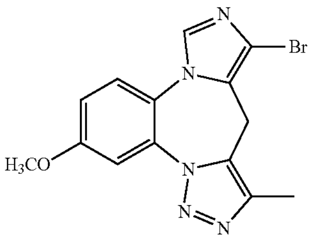 [SMILES: COc1ccc2c(c1)-n1nnc(C)c1Cc1c(Br)ncn1-2] | 347 |
| 212 | 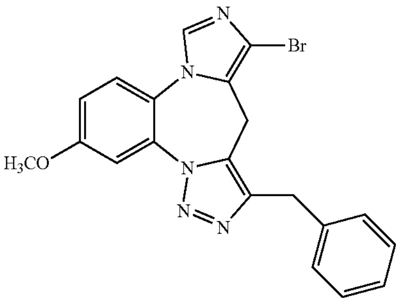 [SMILES: COc1ccc2c(c1)-n1nnc(Cc3ccccc3)c1Cc1c(Br)ncn1-2] | 423 |

TABLE 5-continued
| MS characterization of Compounds 180-471: | | |
|---|---|---|
| Cmp No. | Structure | Observed MS (M + 1) |
| 213 | 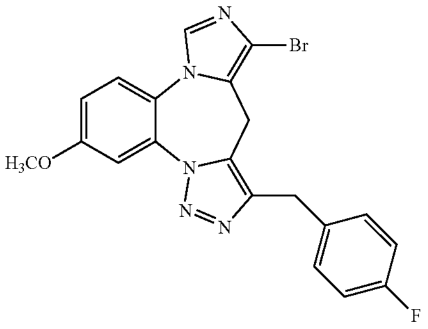 [SMILES: COc1ccc2c(c1)-n1nnc(Cc3ccc(F)cc3)c1Cc1c(Br)ncn1-2] | 441 |
| 214 | 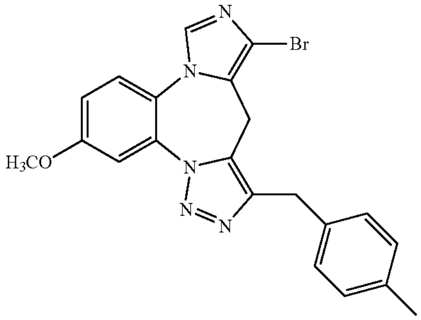 [SMILES: COc1ccc2c(c1)-n1nnc(Cc3ccc(C)cc3)c1Cc1c(Br)ncn1-2] | 437 |
| 215 | 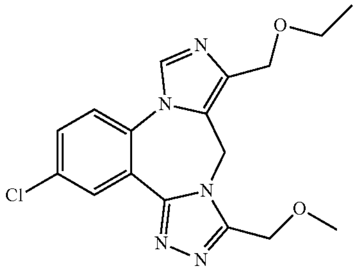 [SMILES: CCOCc1ncn2c1Cn1c(COC)nnc1-c1cc(Cl)ccc1-2] | 360 |
| 216 | 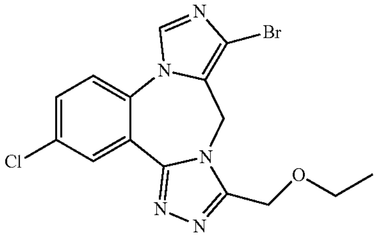 [SMILES: CCOCc1nnc2n1Cc1c(Br)ncn1-c1ccc(Cl)cc1-2] | 395 |
| 217 | 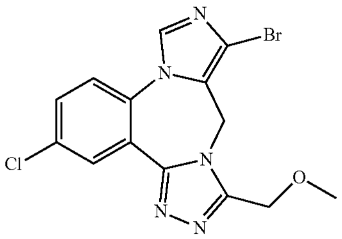 [SMILES: COCc1nnc2n1Cc1c(Br)ncn1-c1ccc(Cl)cc1-2] | 381 |

TABLE 5-continued
| Cmp No. | Structure | Observed MS (M + 1) |
| --- | --- | --- |
| 218 | 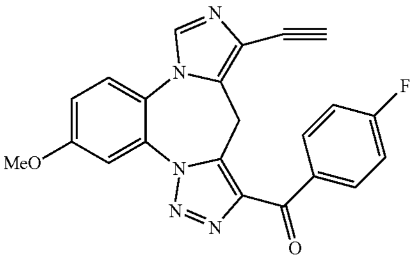 [SMILES: C#Cc1ncn2c1Cc1c(C(=O)c3ccc(F)cc3)nnn1-c1cc(OC)ccc1-2] | 400 |
| 219 | 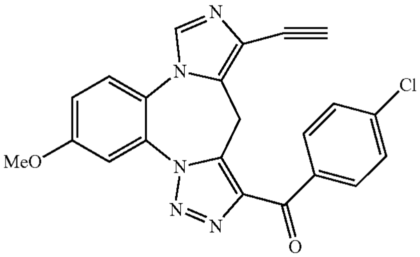 [SMILES: C#Cc1ncn2c1Cc1c(C(=O)c3ccc(Cl)cc3)nnn1-c1cc(OC)ccc1-2] | 416 |
| 220 | 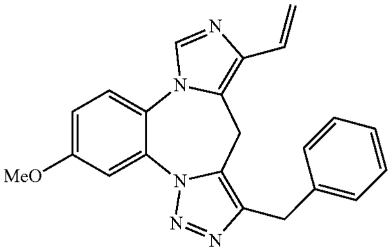 [SMILES: C=Cc1ncn2c1Cc1c(Cc3ccccc3)nnn1-c1cc(OC)ccc1-2] | 370 |
| 221 | 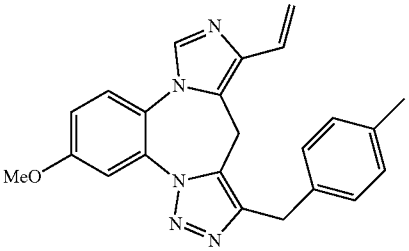 [SMILES: C=Cc1ncn2c1Cc1c(Cc3ccc(C)cc3)nnn1-c1cc(OC)ccc1-2] | 384 |
| 222 | 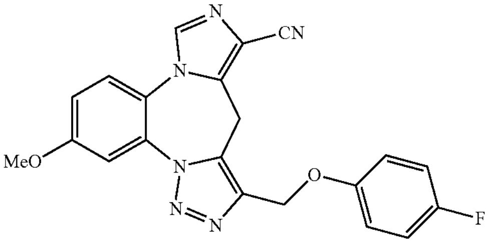 [SMILES: COc1ccc2c(c1)-n1nnc(COc3ccc(F)cc3)c1Cc1c(C#N)ncn1-2] | 403 |
| 223 | 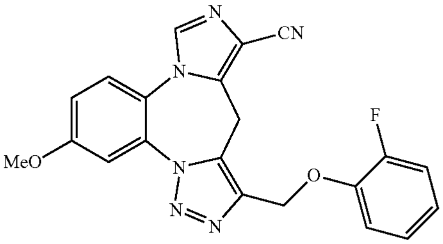 [SMILES: COc1ccc2c(c1)-n1nnc(COc3ccccc3F)c1Cc1c(C#N)ncn1-2] | 403 |
MS characterization of Compounds 180-471:

TABLE 5-continued
MS characterization of Compounds 180-471:
| Cmp No. | Structure | Observed MS (M + 1) |
| --- | --- | --- |
| 224 | 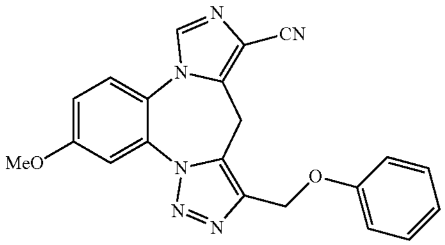 [SMILES: COc1ccc2c(c1)-n1nnc(COc3ccccc3)c1Cc1c(C#N)ncn1-2] | 385 |
| 225 | 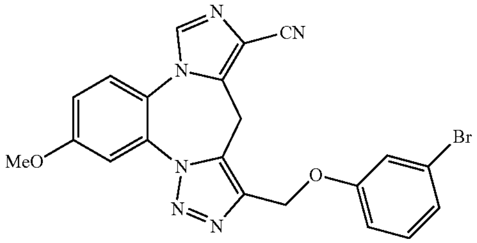 [SMILES: COc1ccc2c(c1)-n1nnc(COc3cccc(Br)c3)c1Cc1c(C#N)ncn1-2] | 464 |
| 226 | 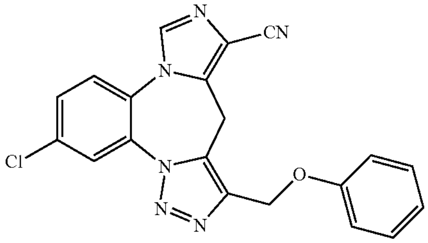 [SMILES: N#Cc1ncn2c1Cc1c(COc3ccccc3)nnn1-c1cc(Cl)ccc1-2] | 389 |
| 227 | 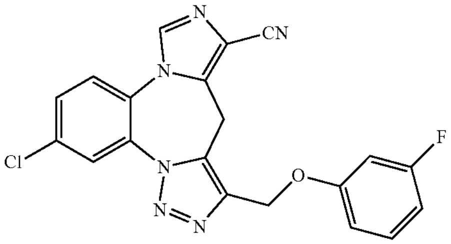 [SMILES: N#Cc1ncn2c1Cc1c(COc3cccc(F)c3)nnn1-c1cc(Cl)ccc1-2] | 407 |
| 228 | 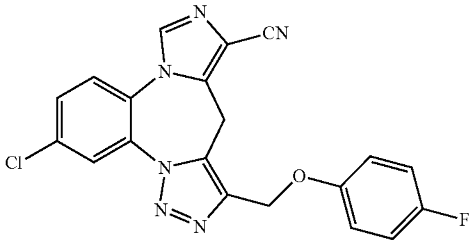 [SMILES: N#Cc1ncn2c1Cc1c(COc3ccc(F)cc3)nnn1-c1cc(Cl)ccc1-2] | 407 |
| 229 | 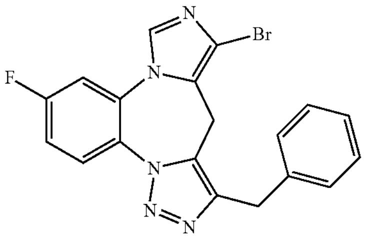 [SMILES: Fc1ccc2c(c1)-n1cnc(Br)c1Cc1c(Cc3ccccc3)nnn1-2] | 411 |

TABLE 5-continued
| MS characterization of Compounds 180-471: | | |
|---|---|---|
| Cmp No. | Structure | Observed MS (M + 1) |
| 230 | 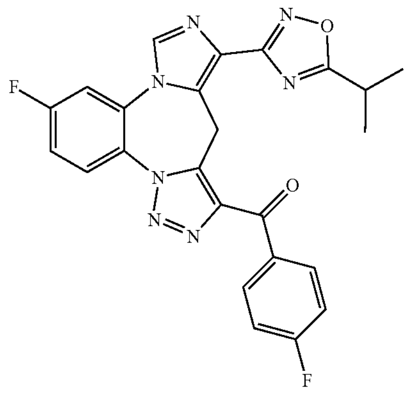 [SMILES: CC(C)c1nc(-c2ncn3c2Cc2c(C(=O)c4ccc(F)cc4)nnn2-c2ccc(F)cc2-3)no1] | 474 |
| 231 | 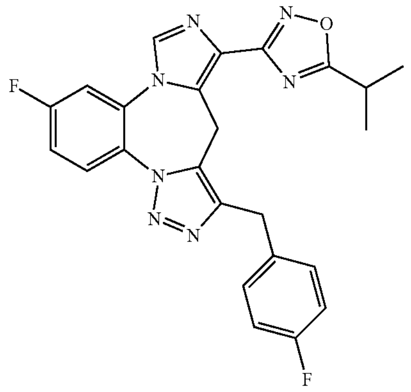 [SMILES: CC(C)c1nc(-c2ncn3c2Cc2c(Cc4ccc(F)cc4)nnn2-c2ccc(F)cc2-3)no1] | 460 |
| 232 | 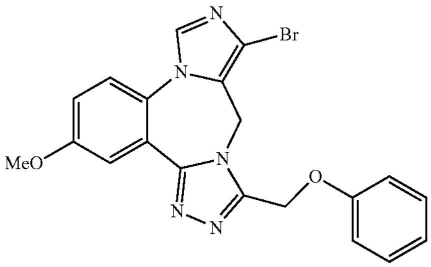 [SMILES: COc1ccc2c(c1)-c1nnc(COc3ccccc3)n1Cc1c(Br)ncn1-2] | 439 |
| 233 | 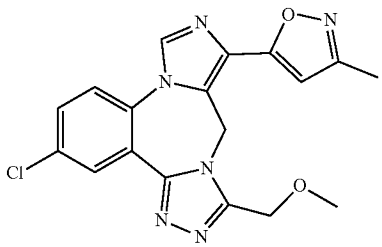 [SMILES: COCc1nnc2n1Cc1c(-c3cc(C)no3)ncn1-c1ccc(Cl)cc1-2] | 383 |

TABLE 5-continued
| MS characterization of Compounds 180-471: | | |
|---|---|---|
| Cmp No. | Structure | Observed MS (M + 1) |
| 234 | 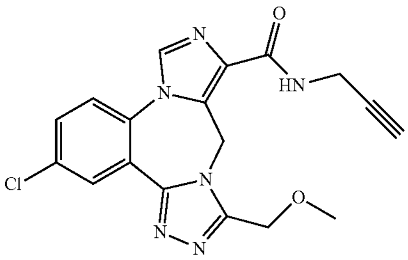 [SMILES: C#CCNC(=O)c1ncn2c1Cn1c(COC)nnc1-c1cc(Cl)ccc1-2] | 383 |
| 235 | 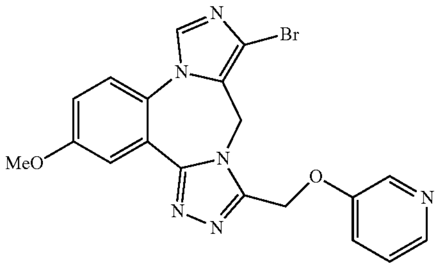 [SMILES: COc1ccc2c(c1)-c1nnc(COc3cccnc3)n1Cc1c(Br)ncn1-2] | 440 |
| 236 | 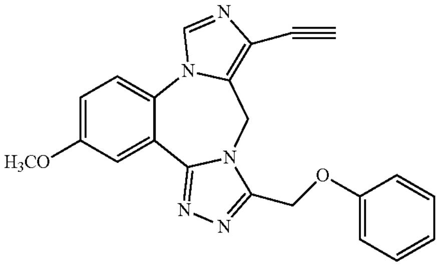 [SMILES: C#Cc1ncn2c1Cn1c(COc3ccccc3)nnc1-c1cc(OC)ccc1-2] | 384 |
| 237 | 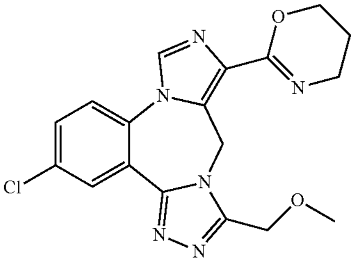 [SMILES: COCc1nnc2n1Cc1c(C3=NCCCO3)ncn1-c1ccc(Cl)cc1-2] | 385 |
| 238 | 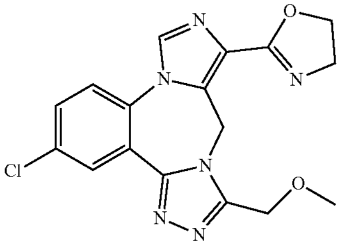 [SMILES: COCc1nnc2n1Cc1c(C3=NCCO3)ncn1-c1ccc(Cl)cc1-2] | 371 |

TABLE 5-continued
| MS characterization of Compounds 180-471: | | |
|---|---|---|
| Cmp No. | Structure | Observed MS (M + 1) |
| 239 | 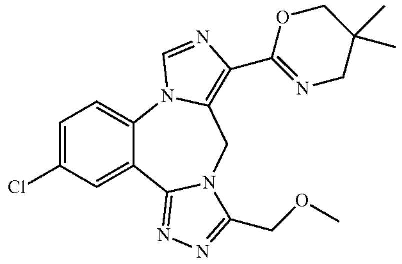 [SMILES: COCc1nnc2n1Cc1c(C3=NCC(C)(C)CO3)ncn1-c1ccc(Cl)cc1-2] | 413 |
| 240 | 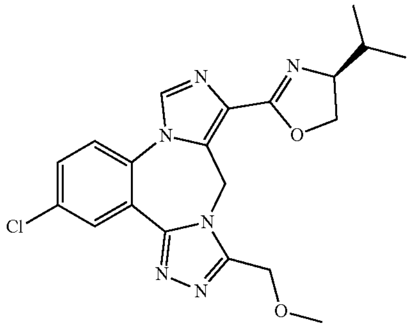 [SMILES: COCc1nnc2n1Cc1c(C3=N[C@@H](C(C)C)CO3)ncn1-c1ccc(Cl)cc1-2] | 413 |
| 241 | 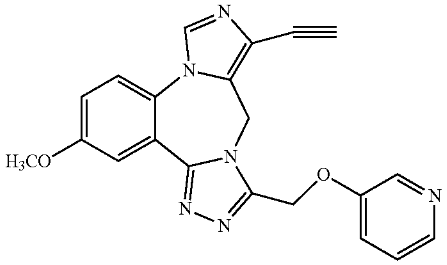 [SMILES: C#Cc1ncn2c1Cn1c(COc3cccnc3)nnc1-c1cc(OC)ccc1-2] | 385 |
| 242 | 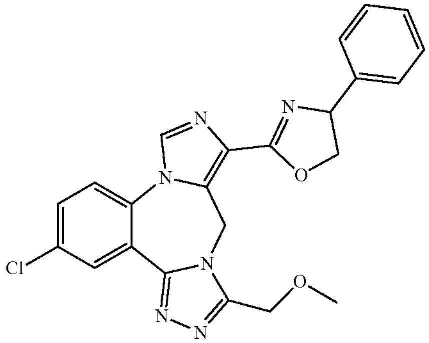 [SMILES: COCc1nnc2n1Cc1c(C3=NC(c4ccccc4)CO3)ncn1-c1ccc(Cl)cc1-2] | 447 |
| 243 | 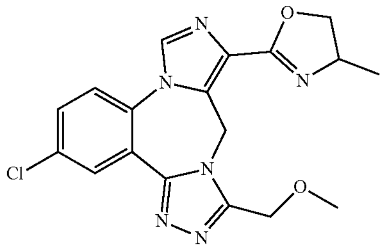 [SMILES: COCc1nnc2n1Cc1c(C3=NC(C)CO3)ncn1-c1ccc(Cl)cc1-2] | 385 |

TABLE 5-continued
| MS characterization of Compounds 180-471: | | |
|---|---|---|
| Cmp No. | Structure | Observed MS (M + 1) |
| 244 | 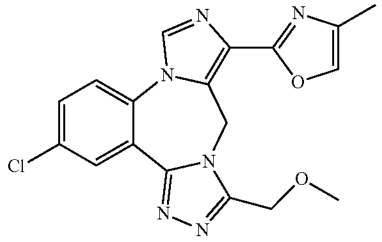 [SMILES: COCc1nnc2n1Cc1c(-c3nc(C)co3)ncn1-c1ccc(Cl)cc1-2] | 383 |
| 245 | 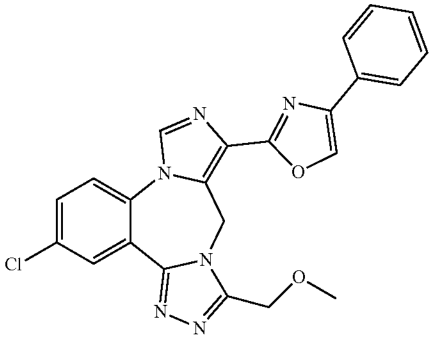 [SMILES: COCc1nnc2n1Cc1c(-c3nc(-c4ccccc4)co3)ncn1-c1ccc(Cl)cc1-2] | 445 |
| 246 | 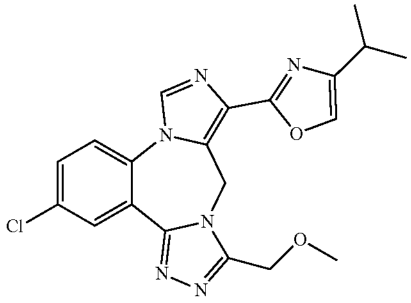 [SMILES: COCc1nnc2n1Cc1c(-c3nc(C(C)C)co3)ncn1-c1ccc(Cl)cc1-2] | 411 |
| 247 | 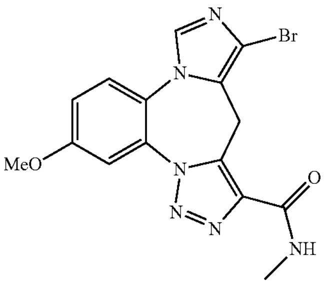 [SMILES: CNC(=O)c1nnn2c1Cc1c(Br)ncn1-c1ccc(OC)cc1-2] | 390 |
| 248 | 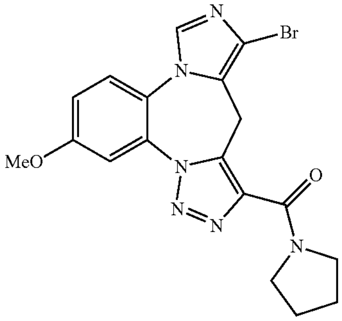 [SMILES: COc1ccc2c(c1)-n1nnc(C(=O)N3CCCC3)c1Cc1c(Br)ncn1-2] | 430 |

TABLE 5-continued
| MS characterization of Compounds 180-471: | | |
|---|---|---|
| Cmp No. | Structure | Observed MS (M + 1) |
| 249 | 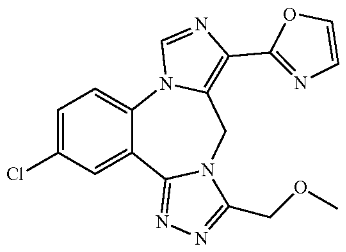 [SMILES: COCc1nnc2n1Cc1c(-c3ncco3)ncn1-c1ccc(Cl)cc1-2] | 369 |
| 250 | 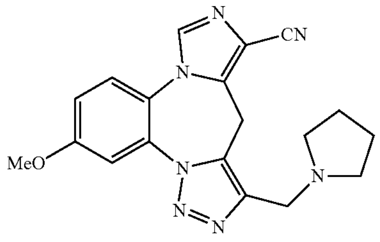 [SMILES: COc1ccc2c(c1)-n1nnc(CN3CCCC3)c1Cc1c(C#N)ncn1-2] | 362 |
| 251 | 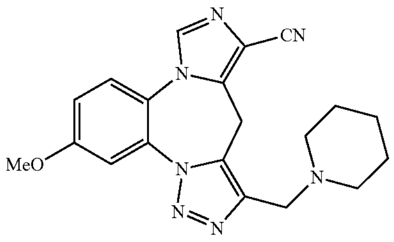 [SMILES: COc1ccc2c(c1)-n1nnc(CN3CCCCC3)c1Cc1c(C#N)ncn1-2] | 376 |
| 252 | 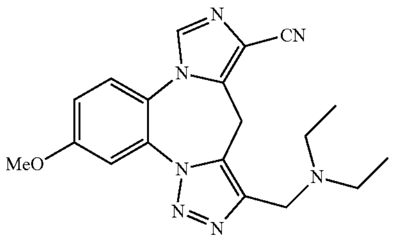 [SMILES: CCN(CC)Cc1nnn2c1Cc1c(C#N)ncn1-c1ccc(OC)cc1-2] | 364 |
| 253 | 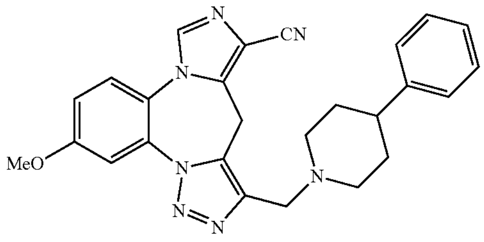 [SMILES: COc1ccc2c(c1)-n1nnc(CN3CCC(c4ccccc4)CC3)c1Cc1c(C#N)ncn1-2] | 452 |
| 254 | 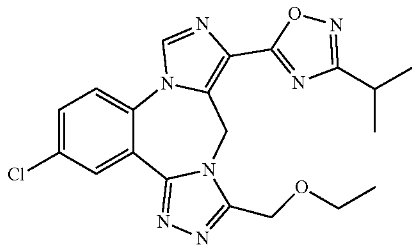 [SMILES: CCOCc1nnc2n1Cc1c(-c3nc(C(C)C)no3)ncn1-c1ccc(Cl)cc1-2] | 426 |

TABLE 5-continued
MS characterization of Compounds 180-471:
| Cmp No. | Structure | Observed MS (M + 1) |
| --- | --- | --- |
| 255 | 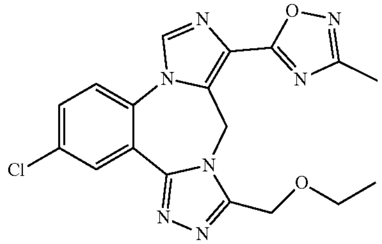 [SMILES: CCOCc1nnc2n1Cc1c(-c3nc(C)no3)ncn1-c1ccc(Cl)cc1-2] | 398 |
| 256 | 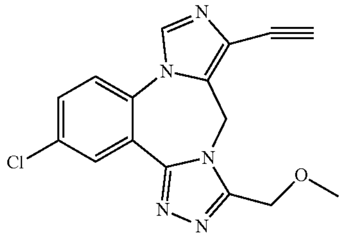 [SMILES: C#Cc1ncn2c1Cn1c(COC)nnc1-c1cc(Cl)ccc1-2] | 326 |
| 257 | 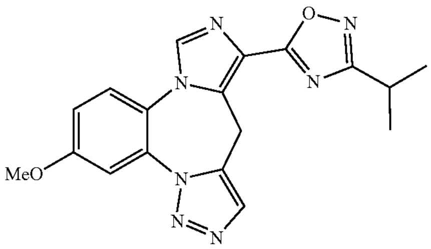 [SMILES: COc1ccc2c(c1)-n1nncc1Cc1c(-c3nc(C(C)C)no3)ncn1-2] | 364 |
| 258 | 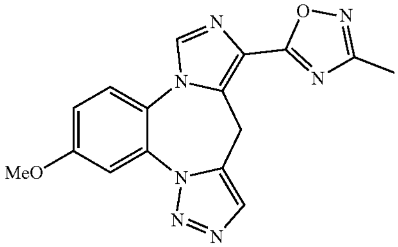 [SMILES: COc1ccc2c(c1)-n1nncc1Cc1c(-c3nc(C)no3)ncn1-2] | 336 |
| 259 | 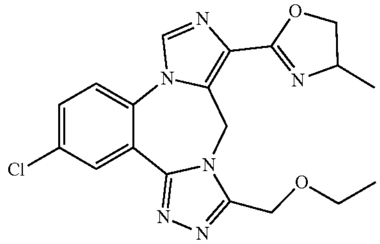 [SMILES: CCOCc1nnc2n1Cc1c(C3=NC(C)CO3)ncn1-c1ccc(Cl)cc1-2] | 399 |
| 260 | 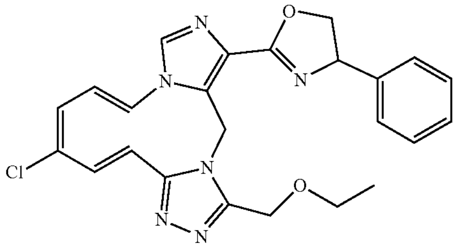 [SMILES: CCOCc1nnc2n1Cc1c(C3=NC(c4ccccc4)CO3)ncn1/C=C/C=C(Cl)\C=C\2] | 461 |

TABLE 5-continued
MS characterization of Compounds 180-471:
| Cmp No. | Structure | Observed MS (M + 1) |
|---|---|---|
| 261 | 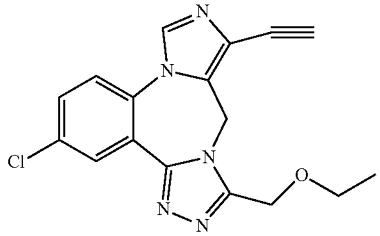 [SMILES: C#Cc1ncn2c1Cn1c(COCC)nnc1-c1cc(Cl)ccc1-2] | 340 |
| 262 | 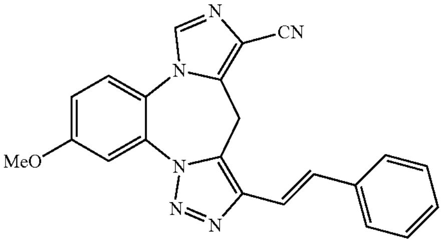 [SMILES: COc1ccc2c(c1)-n1nnc(/C=C/c3ccccc3)c1Cc1c(C#N)ncn1-2] | 381 |
| 263 | 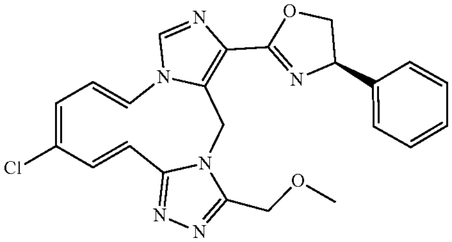 [SMILES: COCc1nnc2n1Cc1c(C3=N[C@H](c4ccccc4)CO3)ncn1/C=C/C=C(Cl)\C=C\2] | 447 |
| 264 | 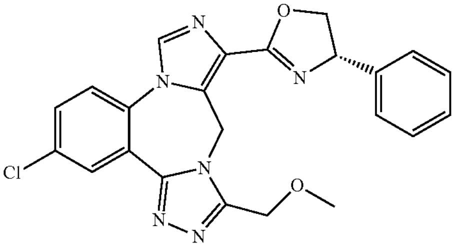 [SMILES: COCc1nnc2n1Cc1c(C3=N[C@@H](c4ccccc4)CO3)ncn1-c1ccc(Cl)cc1-2] | 447 |
| 265 | 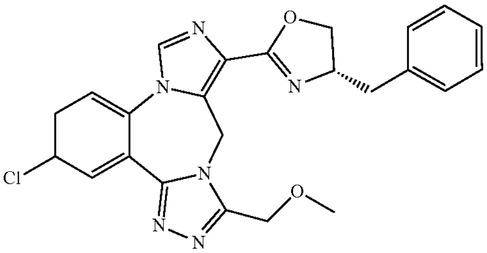 [SMILES: COCc1nnc2n1Cc1c(C3=N[C@@H](Cc4ccccc4)CO3)ncn1C1=CCC(Cl)C=C12] | 461 |
| 266 | 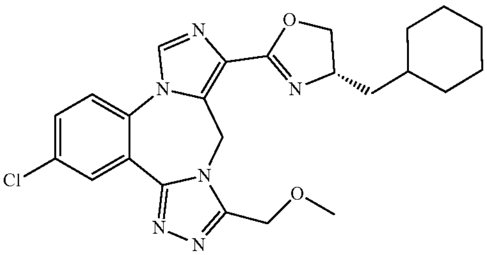 [SMILES: COCc1nnc2n1Cc1c(C3=N[C@@H](CC4CCCCC4)CO3)ncn1-c1ccc(Cl)cc1-2] | 467 |

TABLE 5-continued
MS characterization of Compounds 180-471:
| Cmp No. | Structure | Observed MS (M + 1) |
|---|---|---|
| 267 | 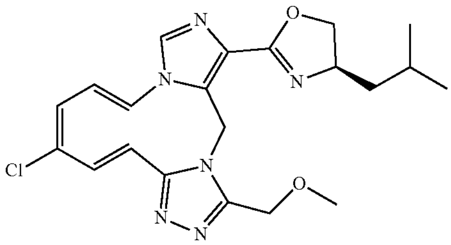 [SMILES: COCc1nnc2n1Cc1c(C3=N[C@H](CC(C)C)CO3)ncn1/C=C/C=C(Cl)\C=C\2] | 427 |
| 268 | 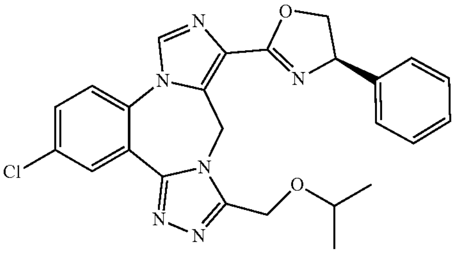 [SMILES: CC(C)OCc1nnc2n1Cc1c(C3=N[C@H](c4ccccc4)CO3)ncn1-c1ccc(Cl)cc1-2] | 475 |
| 270 | 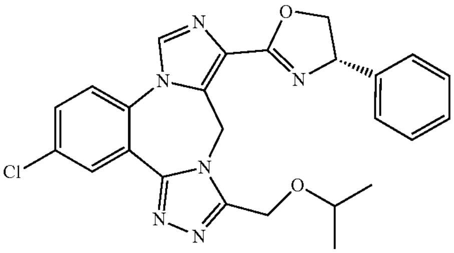 [SMILES: CC(C)OCc1nnc2n1Cc1c(C3=N[C@@H](c4ccccc4)CO3)ncn1-c1ccc(Cl)cc1-2] | 475 |
| 271 | 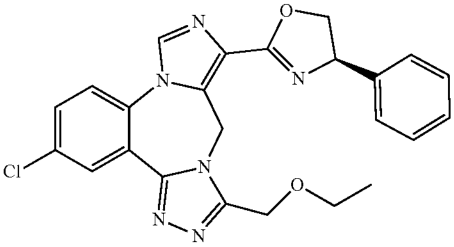 [SMILES: CCOCc1nnc2n1Cc1c(C3=N[C@H](c4ccccc4)CO3)ncn1-c1ccc(Cl)cc1-2] | 461 |
| 272 | 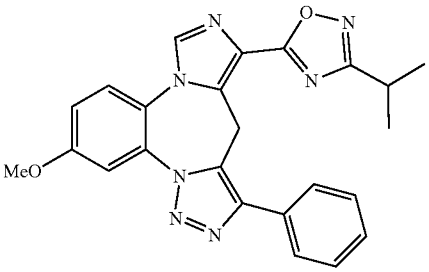 [SMILES: COc1ccc2c(c1)-n1nnc(-c3ccccc3)c1Cc1c(-c3nc(C(C)C)no3)ncn1-2] | 440 |

TABLE 5-continued
| MS characterization of Compounds 180-471: | | |
|---|---|---|
| Cmp No. | Structure | Observed MS (M + 1) |
| 273 | 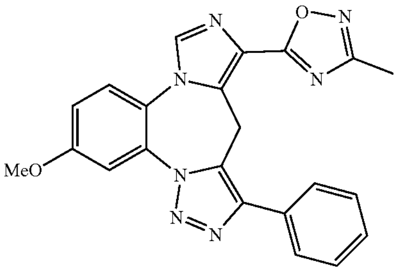 [SMILES: COc1ccc2c(c1)-n1nnc(-c3ccccc3)c1Cc1c(-c3nc(C)no3)ncn1-2] | 412 |
| 274 | 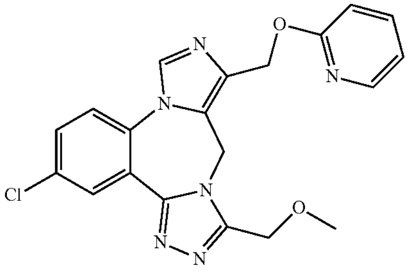 [SMILES: COCc1nnc2n1Cc1c(COc3ccccn3)ncn1-c1ccc(Cl)cc1-2] | 409 |
| 275 | 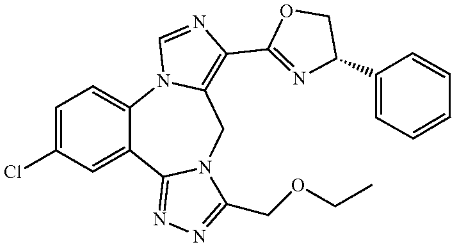 [SMILES: CCOCc1nnc2n1Cc1c(C3=N[C@@H](c4ccccc4)CO3)ncn1-c1ccc(Cl)cc1-2] | 461 |
| 276 | 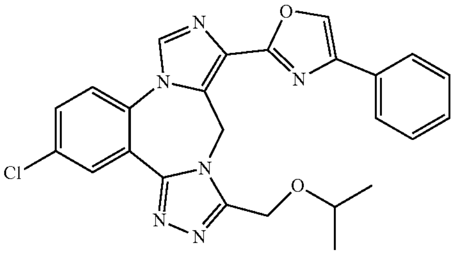 [SMILES: CC(C)OCc1nnc2n1Cc1c(-c3nc(-c4ccccc4)co3)ncn1-c1ccc(Cl)cc1-2] | 473 |
| 277 | 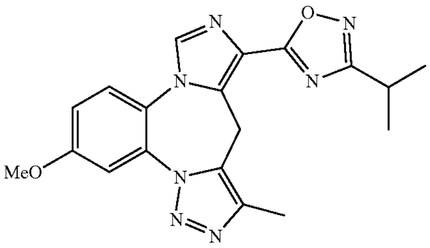 [SMILES: COc1ccc2c(c1)-n1nnc(C)c1Cc1c(-c3nc(C(C)C)no3)ncn1-2] | 378 |

TABLE 5-continued
| MS characterization of Compounds 180-471: | | |
|---|---|---|
| Cmp No. | Structure | Observed MS (M + 1) |
| 278 | 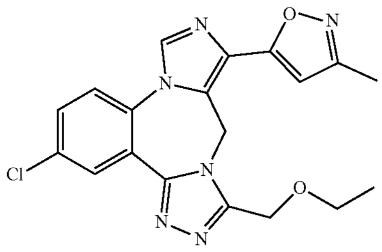 [SMILES: CCOCc1nnc2n1Cc1c(-c3cc(C)no3)ncn1-c1ccc(Cl)cc1-2] | 397 |
| 279 | 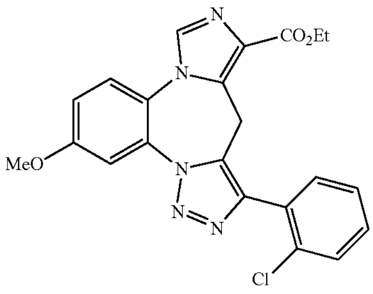 [SMILES: CCOC(=O)c1ncn2c1Cc1c(-c3ccccc3Cl)nnn1-c1cc(OC)ccc1-2] | 436 |
| 280 | 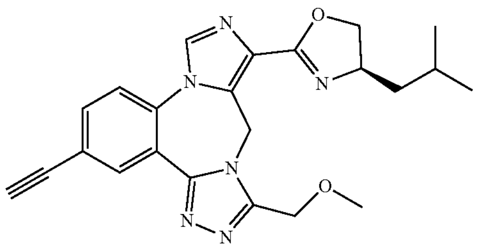 [SMILES: C#Cc1ccc2c(c1)-c1nnc(COC)n1Cc1c(C3=N[C@H](CC(C)C)CO3)ncn1-2] | 417 |
| 281 | 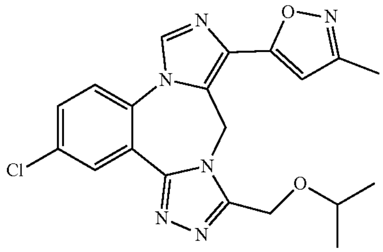 [SMILES: Cc1cc(-c2ncn3c2Cn2c(COC(C)C)nnc2-c2cc(Cl)ccc2-3)on1] | 411 |
| 282 | 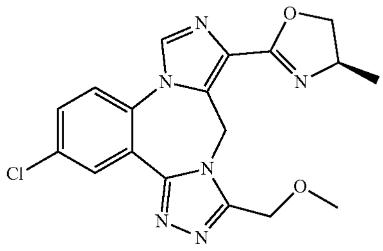 [SMILES: COCc1nnc2n1Cc1c(C3=N[C@H](C)CO3)ncn1-c1ccc(Cl)cc1-2] | 385 |

TABLE 5-continued
| Cmp No. | Structure | Observed MS (M + 1) |
|---|---|---|
| | MS characterization of Compounds 180-471: | |
| 283 | 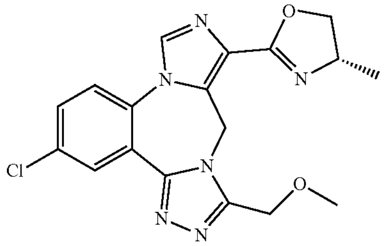 [SMILES: COCc1nnc2n1Cc1c(C3=N[C@@H](C)CO3)ncn1-c1ccc(Cl)cc1-2] | 385 |
| 284 | 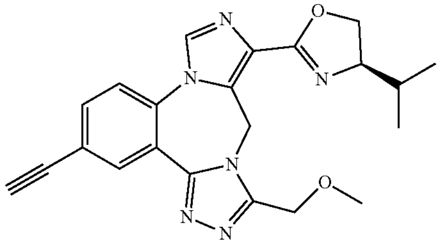 [SMILES: C#Cc1ccc2c(c1)-c1nnc(COC)n1Cc1c(C3=N[C@H](C(C)C)CO3)ncn1-2] | 403 |
| 285 | 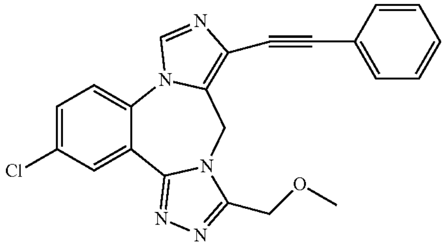 [SMILES: COCc1nnc2n1Cc1c(C#Cc3ccccc3)ncn1-c1ccc(Cl)cc1-2] | 402 |
| 286 | 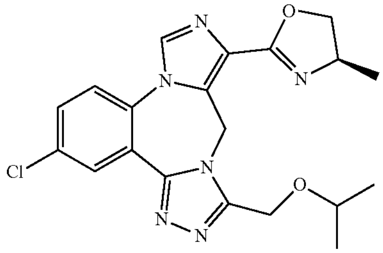 [SMILES: CC(C)OCc1nnc2n1Cc1c(C3=N[C@H](C)CO3)ncn1-c1ccc(Cl)cc1-2] | 413 |
| 287 | 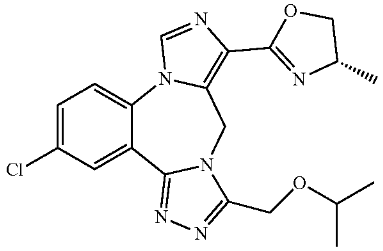 [SMILES: CC(C)OCc1nnc2n1Cc1c(C3=N[C@@H](C)CO3)ncn1-c1ccc(Cl)cc1-2] | 413 |
| 288 | 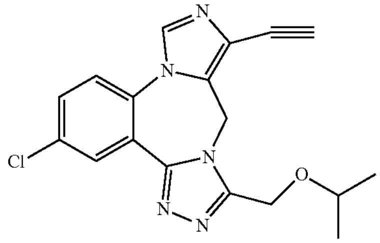 [SMILES: C#Cc1ncn2c1Cn1c(COC(C)C)nnc1-c1cc(Cl)ccc1-2] | 354 |

TABLE 5-continued
| MS characterization of Compounds 180-471: | | |
|---|---|---|
| Cmp No. | Structure | Observed MS (M + 1) |
| 289 | 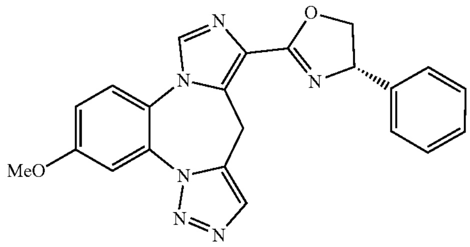 [SMILES: COc1ccc2c(c1)-n1nncc1Cc1c(C3=N[C@@H](c4ccccc4)CO3)ncn1-2] | 399 |
| 290 | 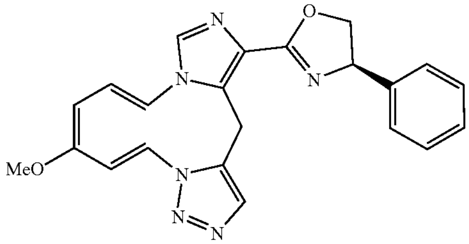 [SMILES: COC1=C/C=C/n2cnc(C3=N[C@H](c4ccccc4)CO3)c2Cc2cnnn2\C=C\1] | 399 |
| 291 | 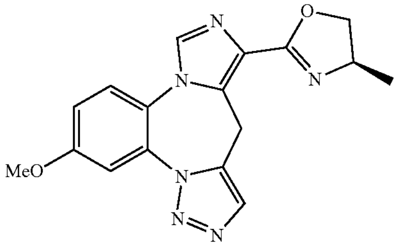 [SMILES: COc1ccc2c(c1)-n1nncc1Cc1c(C3=N[C@H](C)CO3)ncn1-2] | 337 |
| 292 | 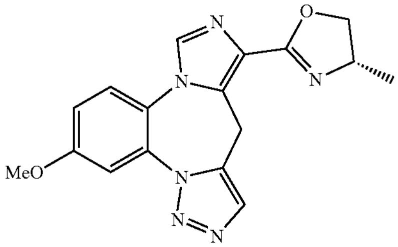 [SMILES: COc1ccc2c(c1)-n1nncc1Cc1c(C3=N[C@@H](C)CO3)ncn1-2] | 337 |
| 293 | 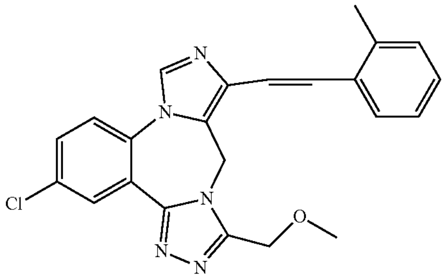 [SMILES: COCc1nnc2n1Cc1c(C=Cc3ccccc3C)ncn1-c1ccc(Cl)cc1-2] | 416 |

TABLE 5-continued
MS characterization of Compounds 180-471:
| Cmp No. | Structure | Observed MS (M + 1) |
|---|---|---|
| 294 | 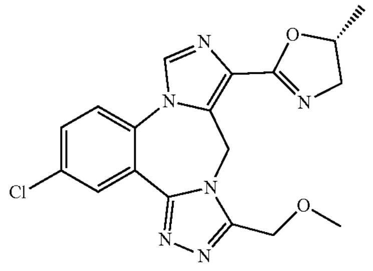 [SMILES: COCc1nnc2n1Cc1c(C3=NC[C@@H](C)O3)ncn1-c1ccc(Cl)cc1-2] | 385 |
| 295 | 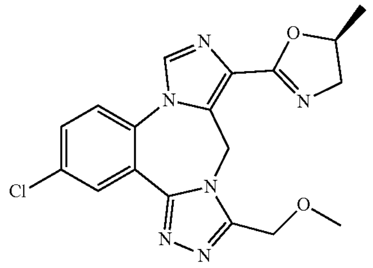 [SMILES: COCc1nnc2n1Cc1c(C3=NC[C@H](C)O3)ncn1-c1ccc(Cl)cc1-2] | 385 |
| 296 | 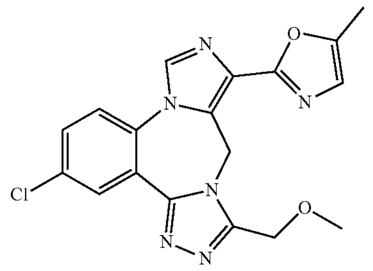 [SMILES: COCc1nnc2n1Cc1c(-c3ncc(C)o3)ncn1-c1ccc(Cl)cc1-2] | 383 |
| 297 | 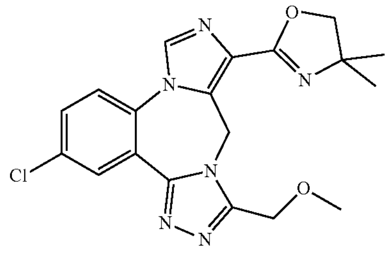 [SMILES: COCc1nnc2n1Cc1c(C3=NC(C)(C)CO3)ncn1-c1ccc(Cl)cc1-2] | 399 |
| 298 | 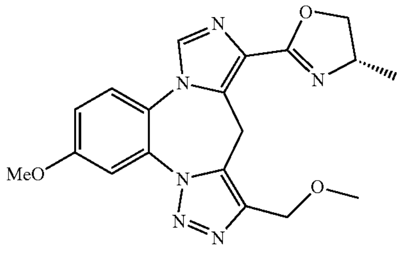 [SMILES: COCc1nnn2c1Cc1c(C3=N[C@@H](C)CO3)ncn1-c1ccc(OC)cc1-2] | 381 |

TABLE 5-continued
MS characterization of Compounds 180-471:
| Cmp No. | Structure | Observed MS (M + 1) |
|---|---|---|
| 299 | 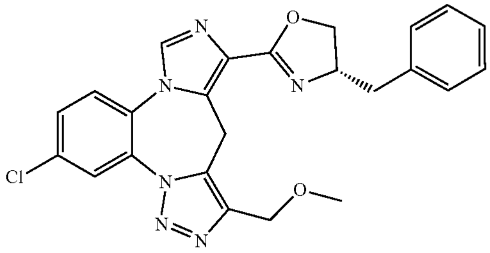 [SMILES: COCc1nnn2c1Cc1c(C3=N[C@@H](Cc4ccccc4)CO3)ncn1-c1ccc(Cl)cc1-2] | 461 |
| 300 | 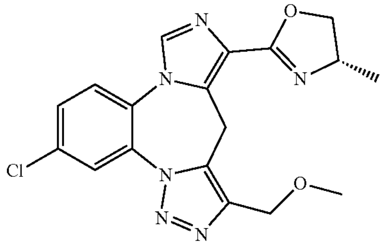 [SMILES: COCc1nnn2c1Cc1c(C3=N[C@@H](C)CO3)ncn1-c1ccc(Cl)cc1-2] | 385 |
| 301 | 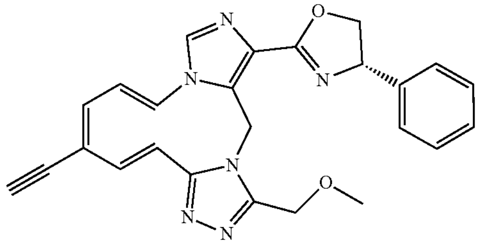 [SMILES: C#CC1=C/C=C/n2cnc(C3=N[C@@H](c4ccccc4)CO3)c2Cn2c(nnc2COC)\C=C\1] | 437 |
| 302 | 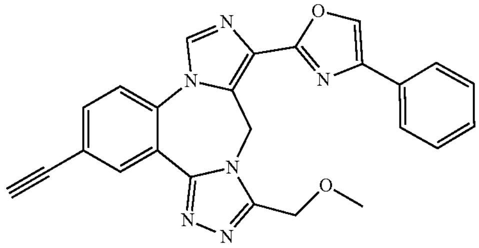 [SMILES: C#Cc1ccc2c(c1)-c1nnc(COC)n1Cc1c(-c3nc(-c4ccccc4)co3)ncn1-2] | 435 |
| 303 | 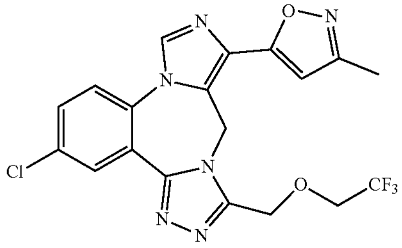 [SMILES: Cc1cc(-c2ncn3c2Cn2c(COCC(F)(F)F)nnc2-c2cc(Cl)ccc2-3)on1] | 451 |
| 304 | 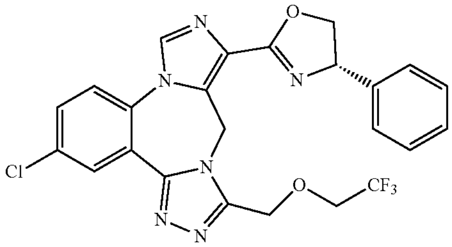 [SMILES: FC(F)(F)COCc1nnc2n1Cc1c(C3=N[C@@H](c4ccccc4)CO3)ncn1-c1ccc(Cl)cc1-2] | 515 |

TABLE 5-continued
MS characterization of Compounds 180-471:
| Cmp No. | Structure | Observed MS (M + 1) |
| --- | --- | --- |
| 305 | 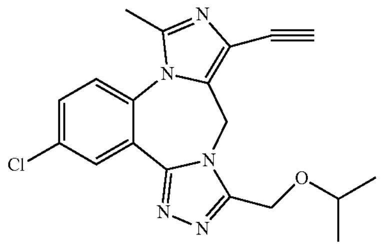 [SMILES: C#Cc1nc(C)n2c1Cn1c(COC(C)C)nnc1-c1cc(Cl)ccc1-2] | 368 |
| 306 | 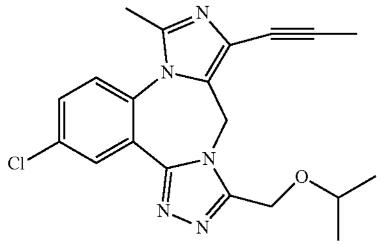 [SMILES: CC#Cc1nc(C)n2c1Cn1c(COC(C)C)nnc1-c1cc(Cl)ccc1-2] | 382 |
| 307 | 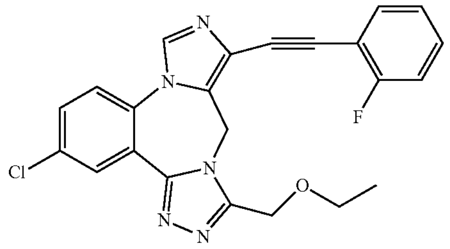 [SMILES: CCOCc1nnc2n1Cc1c(C#Cc3ccccc3F)ncn1-c1ccc(Cl)cc1-2] | 434 |
| 308 | 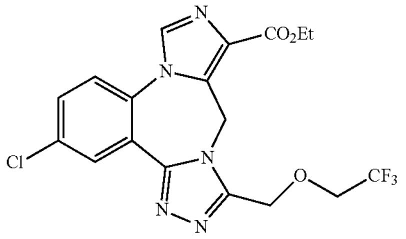 [SMILES: CCOC(=O)c1ncn2c1Cn1c(COCC(F)(F)F)nnc1-c1cc(Cl)ccc1-2] | 442 |
| 309 | 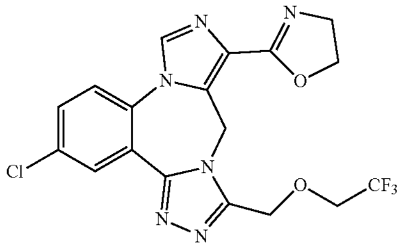 [SMILES: FC(F)(F)COCc1nnc2n1Cc1c(C3=NCCO3)ncn1-c1ccc(Cl)cc1-2] | 439 |
| 310 | 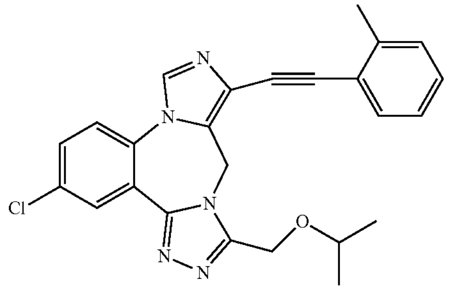 [SMILES: Cc1ccccc1C#Cc1ncn2c1Cn1c(COC(C)C)nnc1-c1cc(Cl)ccc1-2] | 444 |

TABLE 5-continued
| MS characterization of Compounds 180-471: | | |
|---|---|---|
| Cmp No. | Structure | Observed MS (M + 1) |
| 311 | 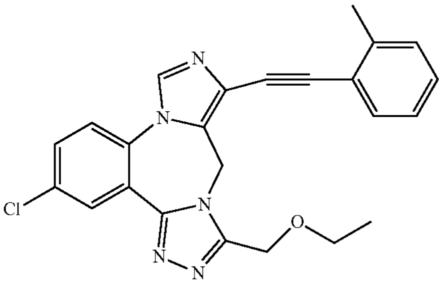 [SMILES: CCOCc1nnc2n1Cc1c(C#Cc3ccccc3C)ncn1-c1ccc(Cl)cc1-2] | 430 |
| 312 | 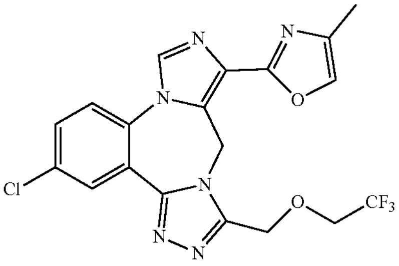 [SMILES: Cc1coc(-c2ncn3c2Cn2c(COCC(F)(F)F)nnc2-c2cc(Cl)ccc2-3)n1] | 451 |
| 313 | 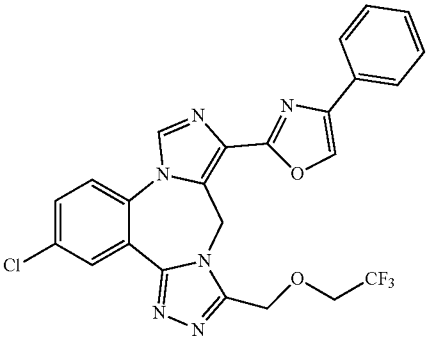 [SMILES: FC(F)(F)COCc1nnc2n1Cc1c(-c3nc(-c4ccccc4)co3)ncn1-c1ccc(Cl)cc1-2] | 513 |
| 314 | 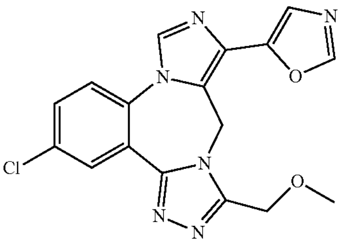 [SMILES: COCc1nnc2n1Cc1c(-c3cnco3)ncn1-c1ccc(Cl)cc1-2] | 369 |
| 315 | 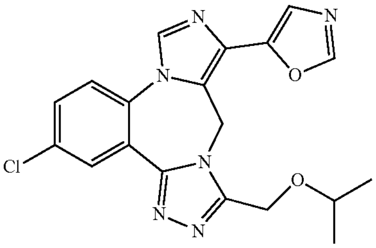 [SMILES: CC(C)OCc1nnc2n1Cc1c(-c3cnco3)ncn1-c1ccc(Cl)cc1-2] | 397 |

TABLE 5-continued
| MS characterization of Compounds 180-471: | | |
|---|---|---|
| Cmp No. | Structure | Observed MS (M + 1) |
| 316 | 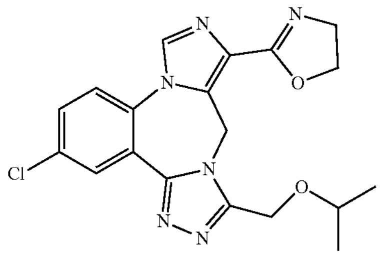 [SMILES: CC(C)OCc1nnc2n1Cc1c(C3=NCCO3)ncn1-c1ccc(Cl)cc1-2] | 399 |
| 317 | 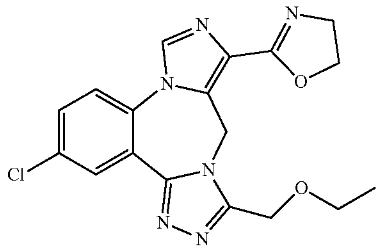 [SMILES: CCOCc1nnc2n1Cc1c(C3=NCCO3)ncn1-c1ccc(Cl)cc1-2] | 385 |
| 318 | 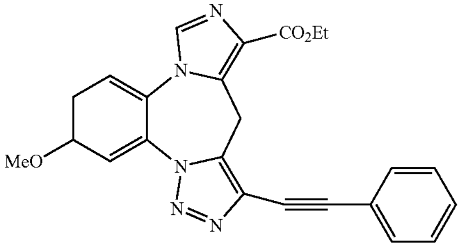 [SMILES: CCOC(=O)c1ncn2c1Cc1c(C#Cc3ccccc3)nnn1C1=CC(OC)CC=C12] | 426 |
| 319 | 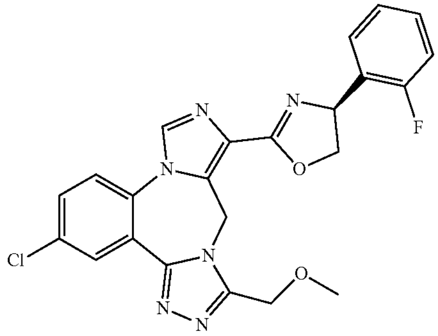 [SMILES: COCc1nnc2n1Cc1c(C3=N[C@@H](c4ccccc4F)CO3)ncn1-c1ccc(Cl)cc1-2] | 465 |
| 320 | 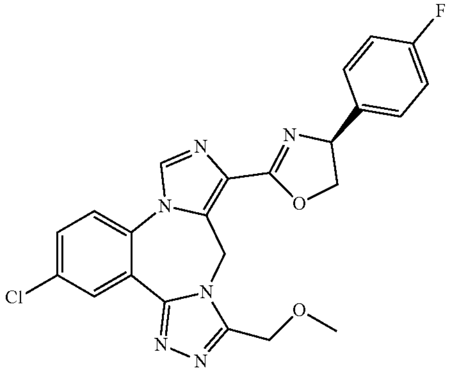 [SMILES: COCc1nnc2n1Cc1c(C3=N[C@@H](c4ccc(F)cc4)CO3)ncn1-c1ccc(Cl)cc1-2] | 465 |

TABLE 5-continued
MS characterization of Compounds 180-471:
| Cmp No. | Structure | Observed MS (M + 1) |
|---|---|---|
| 321 | 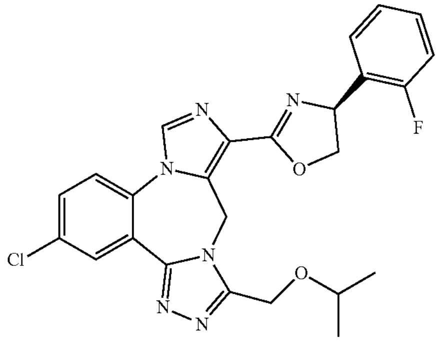 [SMILES: CC(C)OCc1nnc2n1Cc1c(C3=N[C@@H](c4ccccc4F)CO3)ncn1-c1ccc(Cl)cc1-2] | 493 |
| 322 | 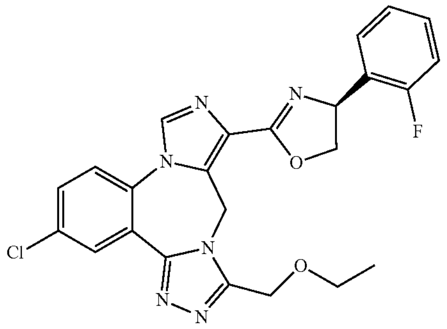 [SMILES: CCOCc1nnc2n1Cc1c(C3=N[C@@H](c4ccccc4F)CO3)ncn1-c1ccc(Cl)cc1-2] | 479 |
| 323 | 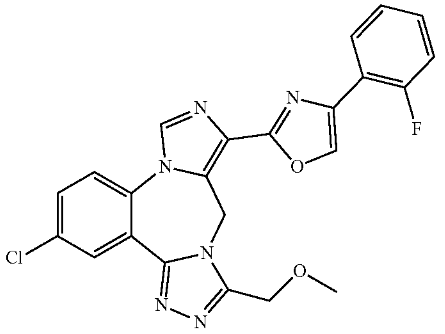 [SMILES: COCc1nnc2n1Cc1c(-c3nc(-c4ccccc4F)co3)ncn1-c1ccc(Cl)cc1-2] | 463 |
| 324 | 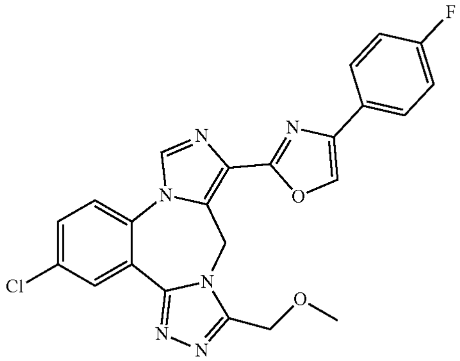 [SMILES: COCc1nnc2n1Cc1c(-c3nc(-c4ccc(F)cc4)co3)ncn1-c1ccc(Cl)cc1-2] | 463 |

TABLE 5-continued
MS characterization of Compounds 180-471:
| Cmp No. | Structure | Observed MS (M + 1) |
|---|---|---|
| 325 | 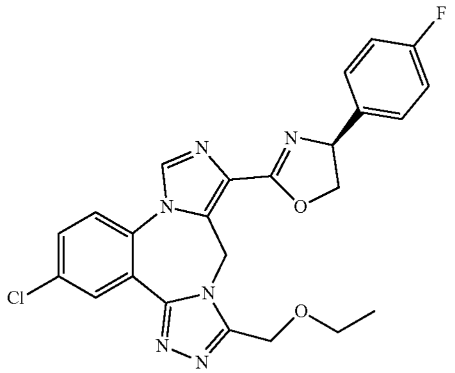 [SMILES: CCOCc1nnc2n1Cc1c(C3=N[C@@H](c4ccc(F)cc4)CO3)ncn1-c1ccc(Cl)cc1-2] | 479 |
| 326 | 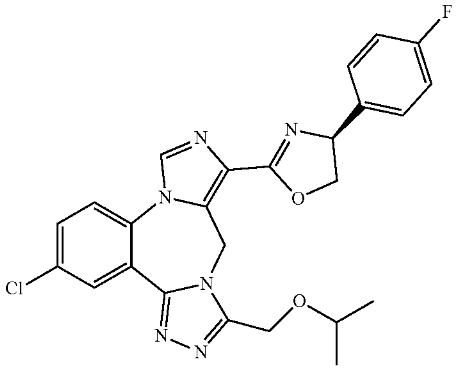 [SMILES: CC(C)OCc1nnc2n1Cc1c(C3=N[C@@H](c4ccc(F)cc4)CO3)ncn1-c1ccc(Cl)cc1-2] | 493 |
| 327 | 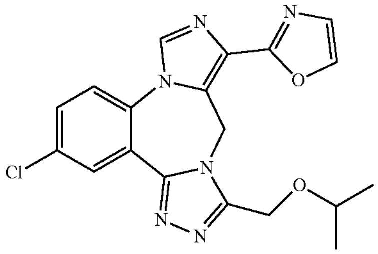 [SMILES: CC(C)OCc1nnc2n1Cc1c(-c3ncco3)ncn1-c1ccc(Cl)cc1-2] | 397 |
| 328 | 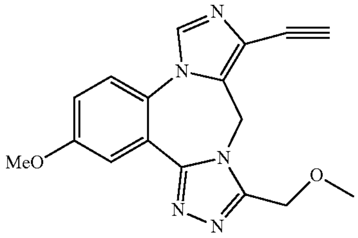 [SMILES: C#Cc1ncn2c1Cn1c(COC)nnc1-c1cc(OC)ccc1-2] | 322 |
| 329 | 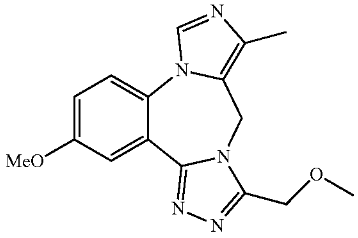 [SMILES: COCc1nnc2n1Cc1c(C)ncn1-c1ccc(OC)cc1-2] | 312 |

TABLE 5-continued
| MS characterization of Compounds 180-471: | | |
|---|---|---|
| Cmp No. | Structure | Observed MS (M + 1) |
| 330 | 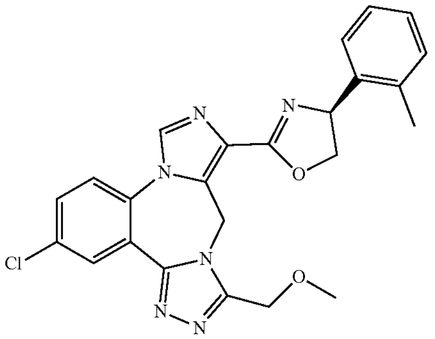 [SMILES: COCc1nnc2n1Cc1c(C3=N[C@@H](c4ccccc4C)CO3)ncn1-c1ccc(Cl)cc1-2] | 461 |
| 331 | 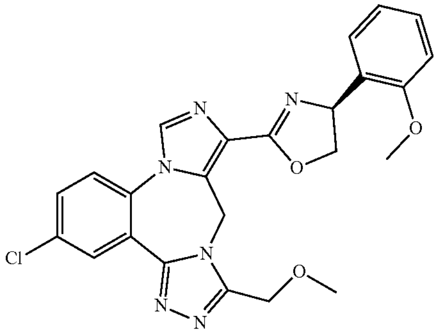 [SMILES: COCc1nnc2n1Cc1c(C3=N[C@@H](c4ccccc4OC)CO3)ncn1-c1ccc(Cl)cc1-2] | 477 |
| 332 | 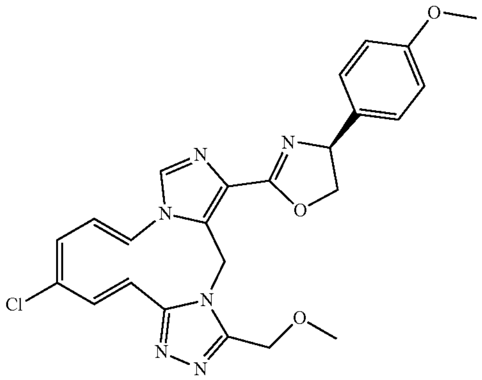 [SMILES: COCc1nnc2n1Cc1c(C3=N[C@@H](c4ccc(OC)cc4)CO3)ncn1/C=C/C=C(Cl)\C=C\2] | 477 |
| 333 | 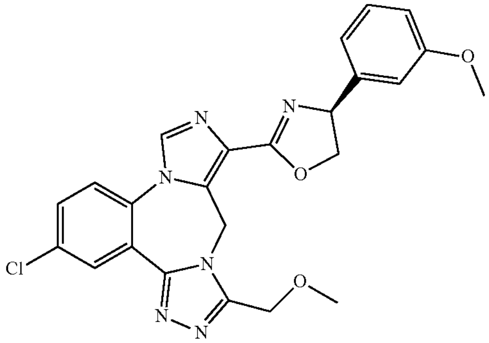 [SMILES: COCc1nnc2n1Cc1c(C3=N[C@@H](c4cccc(OC)c4)CO3)ncn1-c1ccc(Cl)cc1-2] | 477 |

TABLE 5-continued
| MS characterization of Compounds 180-471: | | |
|---|---|---|
| Cmp No. | Structure | Observed MS (M + 1) |
| 334 | 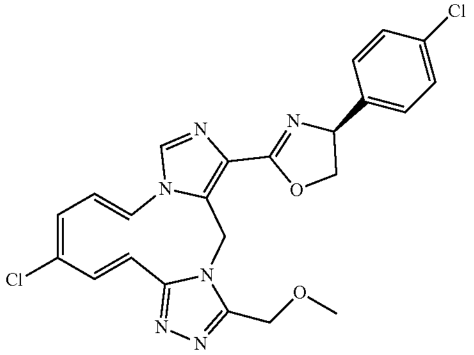 [SMILES: COCc1nnc2n1Cc1c(C3=N[C@@H](c4ccc(Cl)cc4)CO3)ncn1/C=C/C=C(Cl)\C=C\2] | 482 |
| 335 | 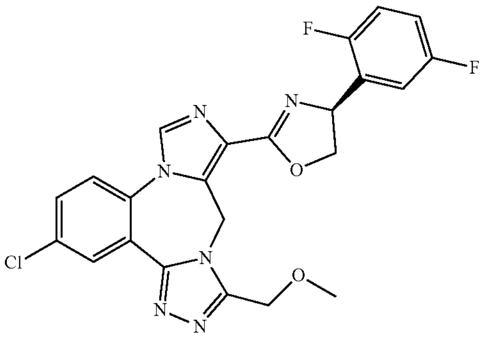 [SMILES: COCc1nnc2n1Cc1c(C3=N[C@@H](c4cc(F)ccc4F)CO3)ncn1-c1ccc(Cl)cc1-2] | 483 |
| 336 | 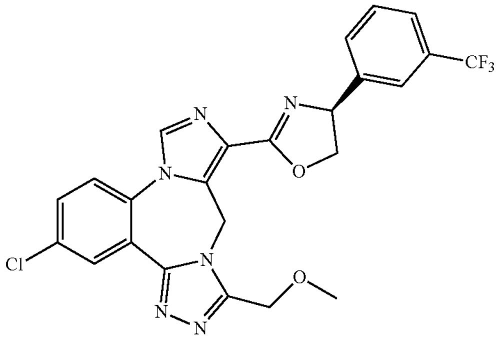 [SMILES: COCc1nnc2n1Cc1c(C3=N[C@@H](c4cccc(C(F)(F)F)c4)CO3)ncn1-c1ccc(Cl)cc1-2] | 515 |
| 337 | 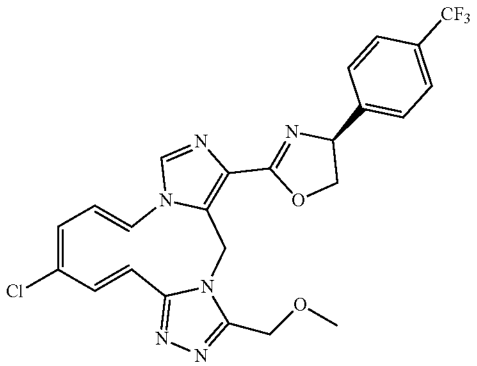 [SMILES: COCc1nnc2n1Cc1c(C3=N[C@@H](c4ccc(C(F)(F)F)cc4)CO3)ncn1/C=C/C=C(Cl)\C=C\2] | 515 |

TABLE 5-continued
| MS characterization of Compounds 180-471: | | |
|---|---|---|
| Cmp No. | Structure | Observed MS (M + 1) |
| 338 | 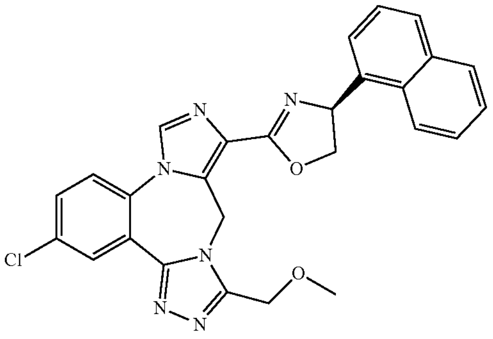 [SMILES: COCc1nnc2n1Cc1c(C3=N[C@@H](c4cccc5ccccc45)CO3)ncn1-c1ccc(Cl)cc1-2] | 497 |
| 339 | 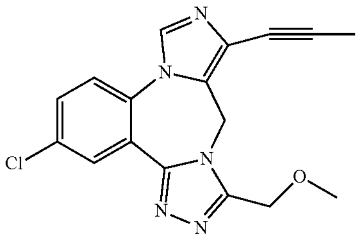 [SMILES: CC#Cc1ncn2c1Cn1c(COC)nnc1-c1cc(Cl)ccc1-2] | 340 |
| 340 | 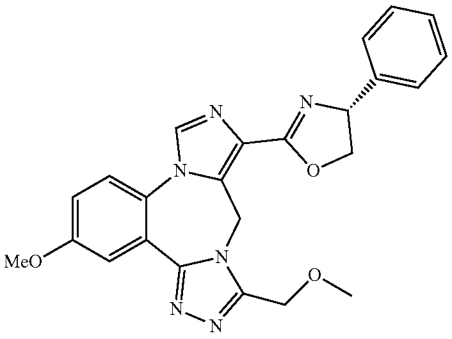 [SMILES: COCc1nnc2n1Cc1c(C3=N[C@H](c4ccccc4)CO3)ncn1-c1ccc(OC)cc1-2] | 443 |
| 341 | 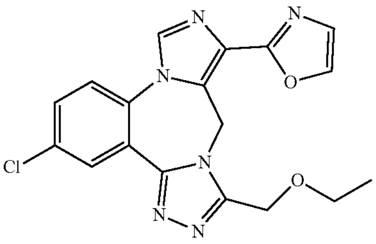 [SMILES: CCOCc1nnc2n1Cc1c(-c3ncco3)ncn1-c1ccc(Cl)cc1-2] | 383 |
| 342 | 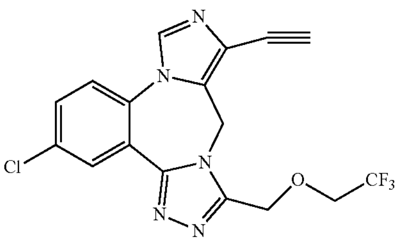 [SMILES: C#Cc1ncn2c1Cn1c(COCC(F)(F)F)nnc1-c1cc(Cl)ccc1-2] | 394 |

TABLE 5-continued
| MS characterization of Compounds 180-471: | | |
|---|---|---|
| Cmp No. | Structure | Observed MS (M + 1) |
| 343 | 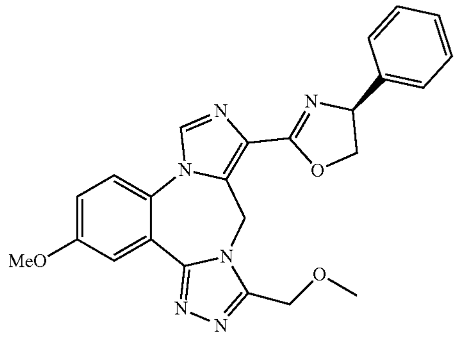 [SMILES: COCc1nnc2n1Cc1c(C3=N[C@@H](c4ccccc4)CO3)ncn1-c1ccc(OC)cc1-2] | 443 |
| 344 | 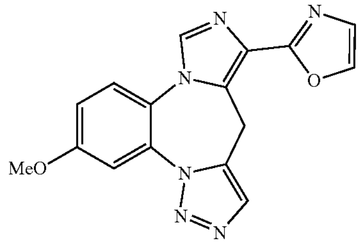 [SMILES: COc1ccc2c(c1)-n1nncc1Cc1c(-c3ncco3)ncn1-2] | 321 |
| 345 | 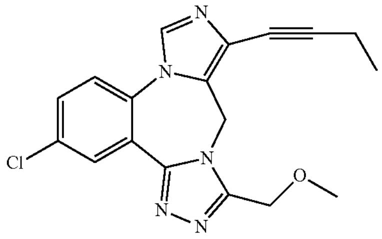 [SMILES: CCC#Cc1ncn2c1Cn1c(COC)nnc1-c1cc(Cl)ccc1-2] | 354 |
| 346 | 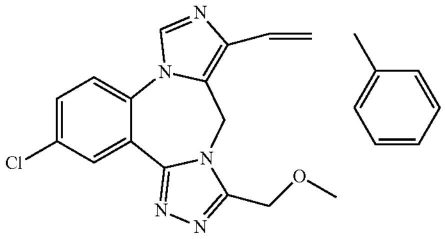 | 416 |
| 347 | 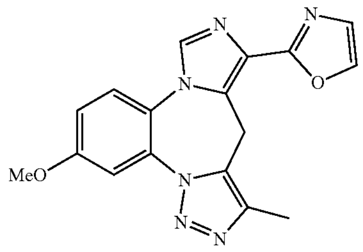 [SMILES: COc1ccc2c(c1)-n1nnc(C)c1Cc1c(-c3ncco3)ncn1-2] | 335 |

TABLE 5-continued
| MS characterization of Compounds 180-471: | | |
|---|---|---|
| Cmp No. | Structure | Observed MS (M + 1) |
| 348 | 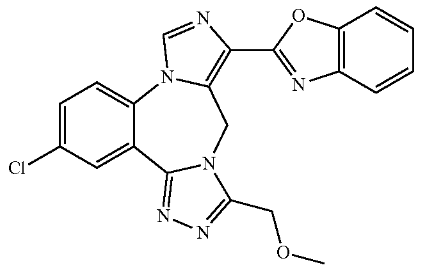 [SMILES: COCc1nnc2n1Cc1c(-c3nc4ccccc4o3)ncn1-c1ccc(Cl)cc1-2] | 419 |
| 349 | 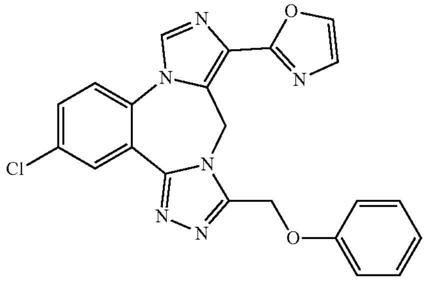 [SMILES: Clc1ccc2c(c1)-c1nnc(COc3ccccc3)n1Cc1c(-c3ncco3)ncn1-2] | 431 |
| 350 | 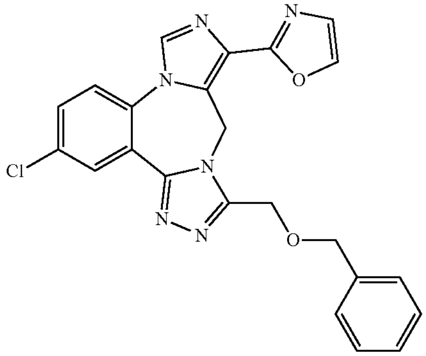 [SMILES: Clc1ccc2c(c1)-c1nnc(COCc3ccccc3)n1Cc1c(-c3ncco3)ncn1-2] | 445 |
| 351 | 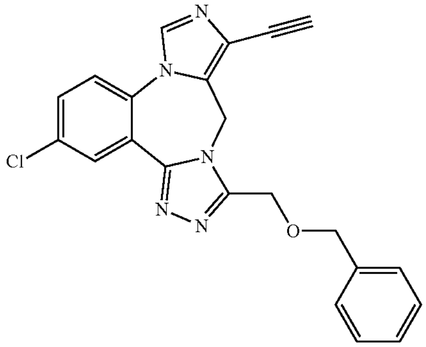 [SMILES: C#Cc1ncn2c1Cn1c(COCc3ccccc3)nnc1-c1cc(Cl)ccc1-2] | 402 |

TABLE 5-continued
| MS characterization of Compounds 180-471: | | |
|---|---|---|
| Cmp No. | Structure | Observed MS (M + 1) |
| 352 | 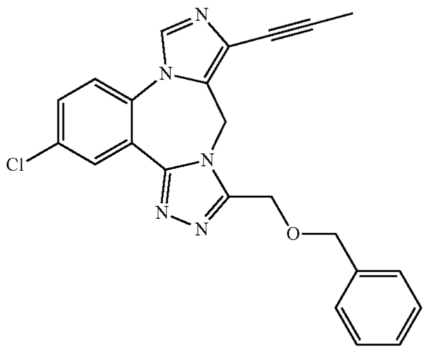 [SMILES: CC#Cc1ncn2c1Cn1c(COCc3ccccc3)nnc1-c1cc(Cl)ccc1-2] | 416 |
| 353 | 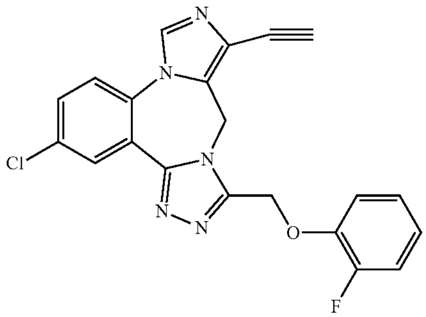 [SMILES: C#Cc1ncn2c1Cn1c(COc3ccccc3F)nnc1-c1cc(Cl)ccc1-2] | 406 |
| 354 | 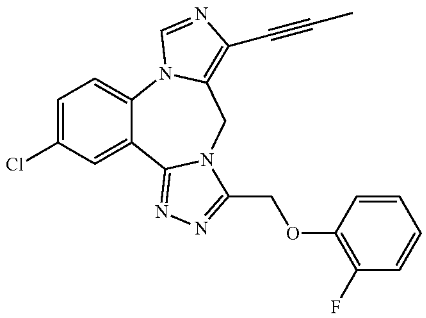 [SMILES: CC#Cc1ncn2c1Cn1c(COc3ccccc3F)nnc1-c1cc(Cl)ccc1-2] | 420 |
| 355 | 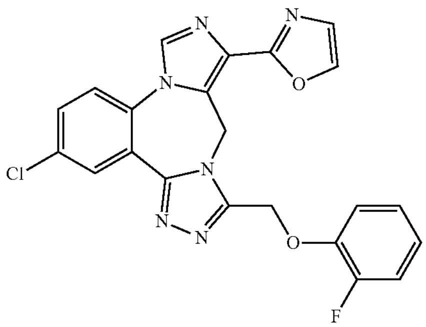 [SMILES: Fc1ccccc1OCc1nnc2n1Cc1c(-c3ncco3)ncn1-c1ccc(Cl)cc1-2] | 449 |

TABLE 5-continued
MS characterization of Compounds 180-471:
| Cmp No. | Structure | Observed MS (M + 1) |
|---|---|---|
| 356 | 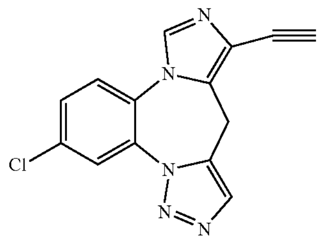 [SMILES: C#Cc1ncn2c1Cc1cnnn1-c1cc(Cl)ccc1-2] | 282 |
| 357 | 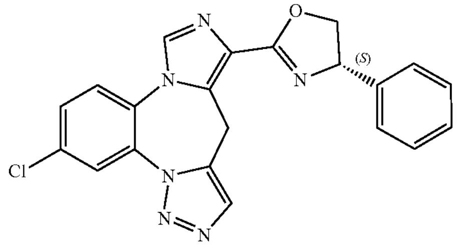 | 403 |
| 358 | 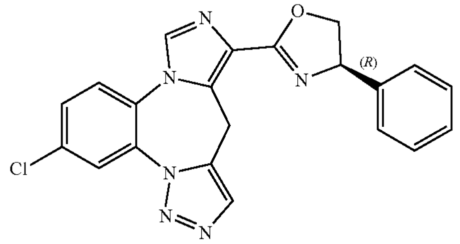 | 403 |
| 359 | 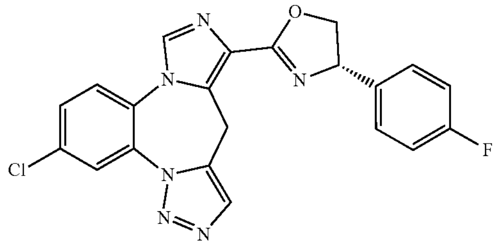 [SMILES: Fc1ccc([C@H]2COC(c3ncn4c3Cc3cnnn3-c3cc(Cl)ccc3-4)=N2)cc1] | 421 |
| 360 | 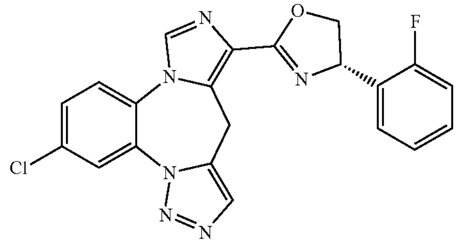 [SMILES: Fc1ccccc1[C@H]1COC(c2ncn3c2Cc2cnnn2-c2cc(Cl)ccc2-3)=N1] | 421 |
| 361 | 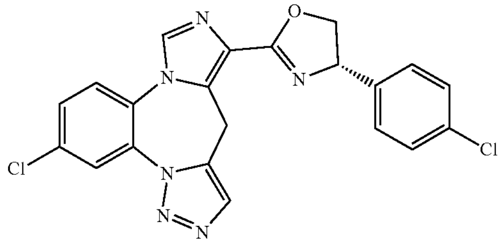 [SMILES: Clc1ccc([C@H]2COC(c3ncn4c3Cc3cnnn3-c3cc(Cl)ccc3-4)=N2)cc1] | 438 |

TABLE 5-continued
MS characterization of Compounds 180-471:
| Cmp No. | Structure | Observed MS (M + 1) |
|---|---|---|
| 362 | 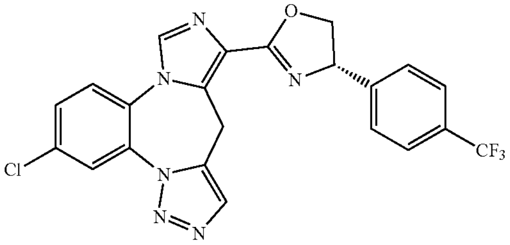 [SMILES: FC(F)(F)c1ccc([C@H]2COC(c3ncn4c3Cc3cnnn3-c3cc(Cl)ccc3-4)=N2)cc1] | 471 |
| 363 | 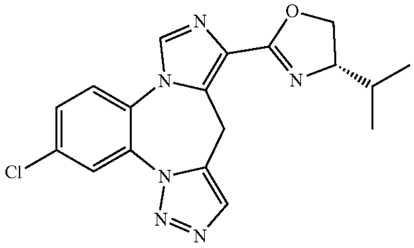 [SMILES: CC(C)[C@H]1COC(c2ncn3c2Cc2cnnn2-c2cc(Cl)ccc2-3)=N1] | 369 |
| 364 | 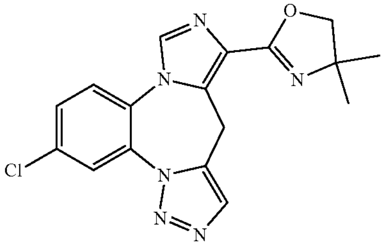 [SMILES: CC1(C)COC(c2ncn3c2Cc2cnnn2-c2cc(Cl)ccc2-3)=N1] | 355 |
| 365 | 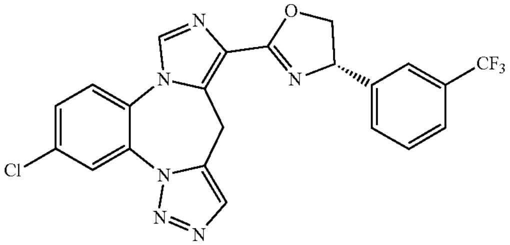 [SMILES: FC(F)(F)c1cccc([C@H]2COC(c3ncn4c3Cc3cnnn3-c3cc(Cl)ccc3-4)=N2)c1] | 471 |
| 366 | 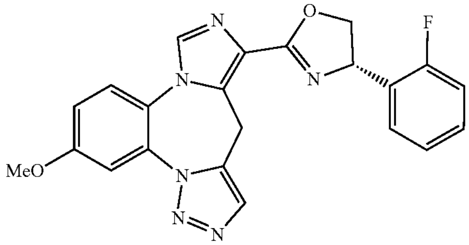 [SMILES: COc1ccc2c(c1)-n1nncc1Cc1c(C3=N[C@@H](c4ccccc4F)CO3)ncn1-2] | 417 |
| 367 | 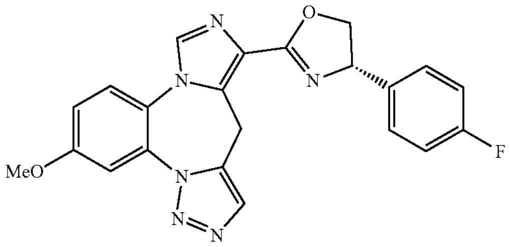 [SMILES: COc1ccc2c(c1)-n1nncc1Cc1c(C3=N[C@@H](c4ccc(F)cc4)CO3)ncn1-2] | 417 |

TABLE 5-continued
| MS characterization of Compounds 180-471: | | |
|---|---|---|
| Cmp No. | Structure | Observed MS (M + 1) |
| 368 | 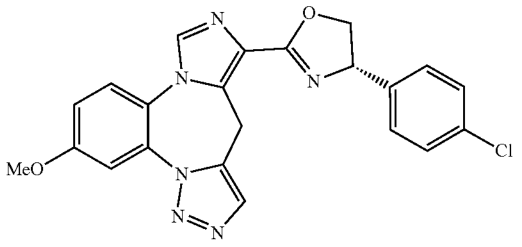 [SMILES: COc1ccc2c(c1)-n1nncc1Cc1c(C3=N[C@@H](c4ccc(Cl)cc4)CO3)ncn1-2] | 433 |
| 369 | 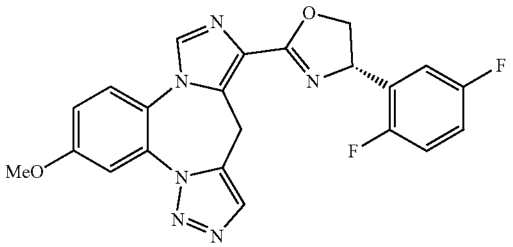 [SMILES: COc1ccc2c(c1)-n1nncc1Cc1c(C3=N[C@@H](c4cc(F)ccc4F)CO3)ncn1-2] | 435 |
| 370 | 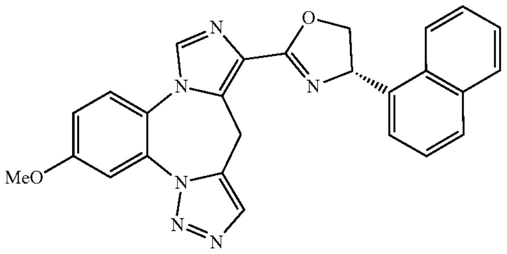 [SMILES: COc1ccc2c(c1)-n1nncc1Cc1c(C3=N[C@@H](c4cccc5ccccc45)CO3)ncn1-2] | 449 |
| 371 | 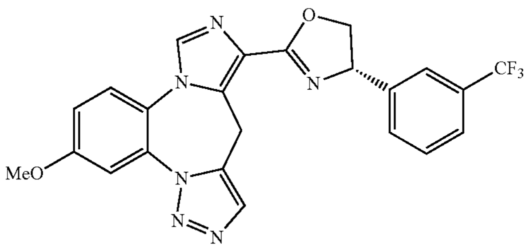 [SMILES: COc1ccc2c(c1)-n1nncc1Cc1c(C3=N[C@@H](c4cccc(C(F)(F)F)c4)CO3)ncn1-2] | 467 |
| 372 | 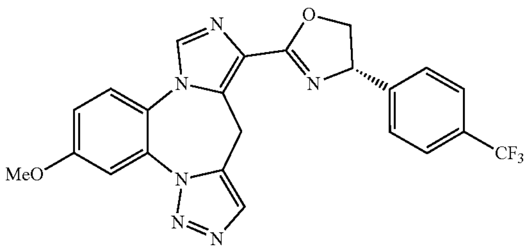 [SMILES: COc1ccc2c(c1)-n1nncc1Cc1c(C3=N[C@@H](c4ccc(C(F)(F)F)cc4)CO3)ncn1-2] | 467 |
| 373 | 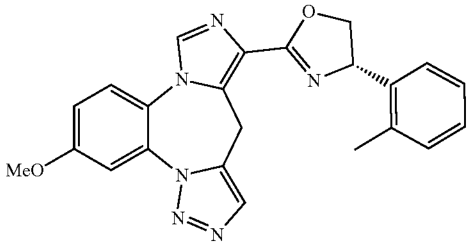 [SMILES: COc1ccc2c(c1)-n1nncc1Cc1c(C3=N[C@@H](c4ccccc4C)CO3)ncn1-2] | 413 |

TABLE 5-continued
| MS characterization of Compounds 180-471: | | |
|---|---|---|
| Cmp No. | Structure | Observed MS (M + 1) |
| 374 | 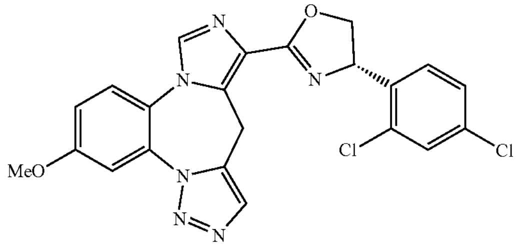 [SMILES: COc1ccc2c(c1)-n1nncc1Cc1c(C3=N[C@@H](c4ccc(Cl)cc4Cl)CO3)ncn1-2] | 468 |
| 375 | 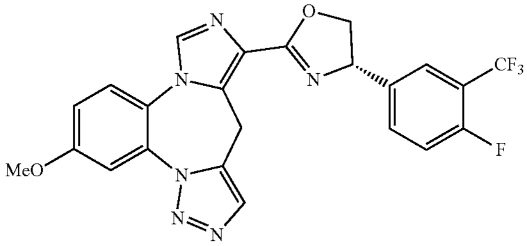 [SMILES: COc1ccc2c(c1)-n1nncc1Cc1c(C3=N[C@@H](c4ccc(F)c(C(F)(F)F)c4)CO3)ncn1-2] | 485 |
| 376 | 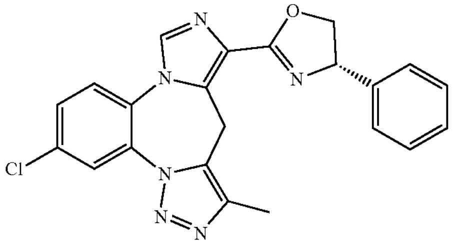 [SMILES: Cc1nnn2c1Cc1c(C3=N[C@@H](c4ccccc4)CO3)ncn1-c1ccc(Cl)cc1-2] | 417 |
| 377 | 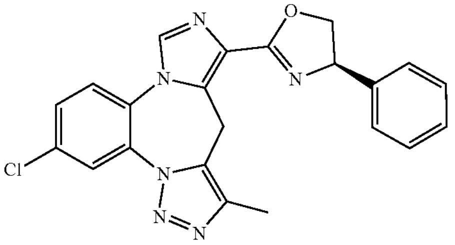 [SMILES: Cc1nnn2c1Cc1c(C3=N[C@H](c4ccccc4)CO3)ncn1-c1ccc(Cl)cc1-2] | 417 |
| 378 | 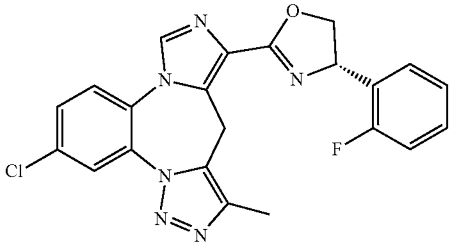 [SMILES: Cc1nnn2c1Cc1c(C3=N[C@@H](c4ccccc4F)CO3)ncn1-c1ccc(Cl)cc1-2] | 435 |
| 379 | 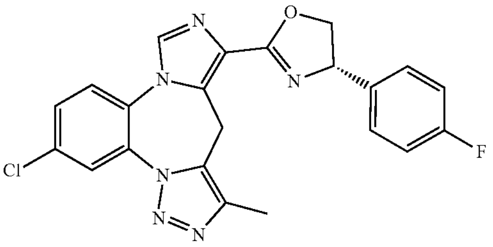 [SMILES: Cc1nnn2c1Cc1c(C3=N[C@@H](c4ccc(F)cc4)CO3)ncn1-c1ccc(Cl)cc1-2] | 435 |

TABLE 5-continued
| MS characterization of Compounds 180-471: | | |
|---|---|---|
| Cmp No. | Structure | Observed MS (M + 1) |
| 380 | 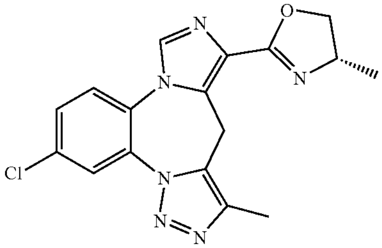 [SMILES: Cc1nnn2c1Cc1c(C3=N[C@@H](C)CO3)ncn1-c1ccc(Cl)cc1-2] | 355 |
| 381 | 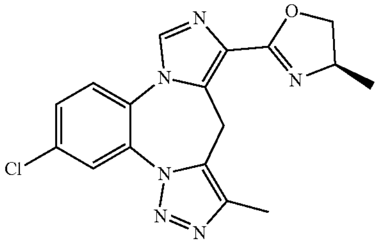 [SMILES: Cc1nnn2c1Cc1c(C3=N[C@H](C)CO3)ncn1-c1ccc(Cl)cc1-2] | 355 |
| 382 | 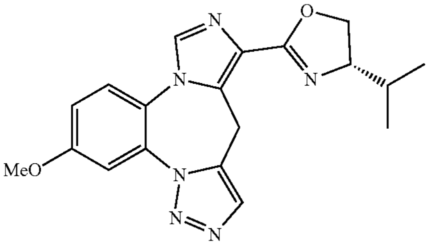 [SMILES: COc1ccc2c(c1)-n1nncc1Cc1c(C3=N[C@@H](C(C)C)CO3)ncn1-2] | 365 |
| 383 | 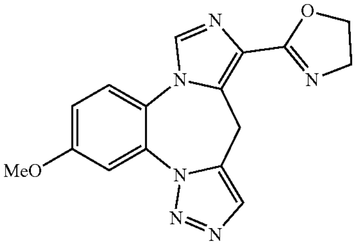 [SMILES: COc1ccc2c(c1)-n1nncc1Cc1c(C3=NCCO3)ncn1-2] | 323 |
| 384 | 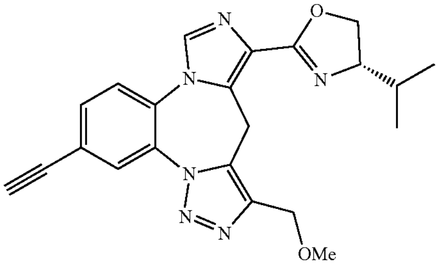 [SMILES: C#Cc1ccc2c(c1)-n1nnc(COC)c1Cc1c(C3=N[C@@H](C(C)C)CO3)ncn1-2] | 403 |
| 385 | 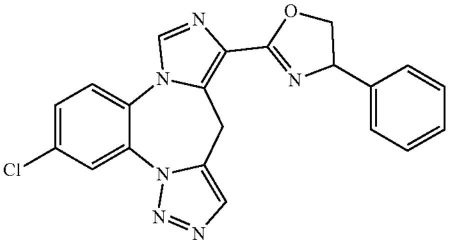 [SMILES: Clc1ccc2c(c1)-n1nncc1Cc1c(C3=NC(c4ccccc4)CO3)ncn1-2] | 401 |

TABLE 5-continued
MS characterization of Compounds 180-471:
| Cmp No. | Structure | Observed MS (M + 1) |
|---|---|---|
| 386 | 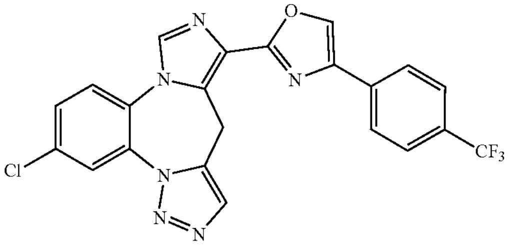 [SMILES: FC(F)(F)c1ccc(-c2coc(-c3ncn4c3Cc3cnnn3-c3cc(Cl)ccc3-4)n2)cc1] | 469 |
| 387 | 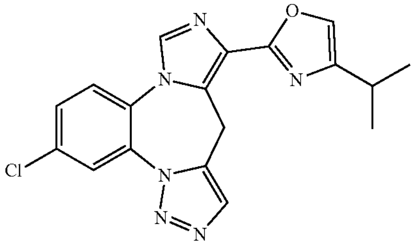 [SMILES: CC(C)c1coc(-c2ncn3c2Cc2cnnn2-c2cc(Cl)ccc2-3)n1] | 467 |
| 388 | 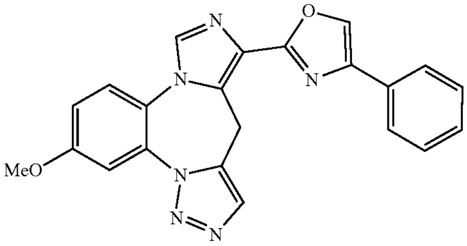 [SMILES: COc1ccc2c(c1)-n1nncc1Cc1c(-c3nc(-c4ccccc4)co3)ncn1-2] | 397 |
| 389 | 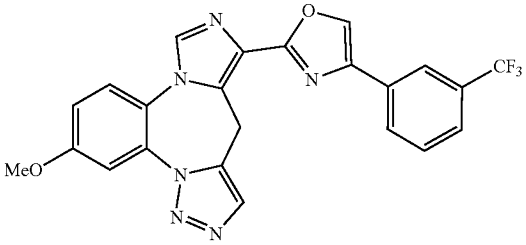 [SMILES: COc1ccc2c(c1)-n1nncc1Cc1c(-c3nc(-c4cccc(C(F)(F)F)c4)co3)ncn1-2] | 465 |
| 390 | 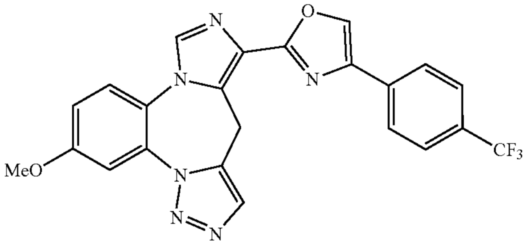 [SMILES: COc1ccc2c(c1)-n1nncc1Cc1c(-c3nc(-c4ccc(C(F)(F)F)cc4)co3)ncn1-2] | 465 |
| 391 | 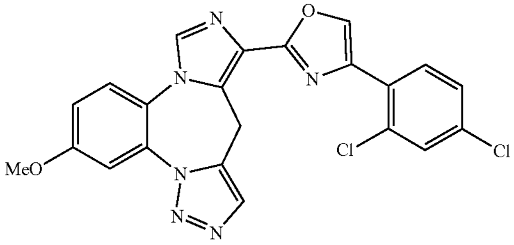 [SMILES: COc1ccc2c(c1)-n1nncc1Cc1c(-c3nc(-c4ccc(Cl)cc4Cl)co3)ncn1-2] | 466 |

TABLE 5-continued
| MS characterization of Compounds 180-471: | | |
|---|---|---|
| Cmp No. | Structure | Observed MS (M + 1) |
| 392 | 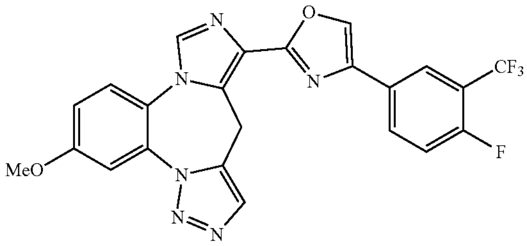 [SMILES: COc1ccc2c(c1)-n1nncc1Cc1c(-c3nc(-c4ccc(F)c(C(F)(F)F)c4)co3)ncn1-2] | 483 |
| 393 | 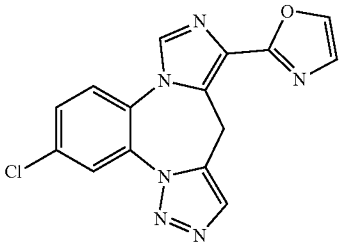 [SMILES: Clc1ccc2c(c1)-n1nncc1Cc1c(-c3ncco3)ncn1-2] | 325 |
| 394 | 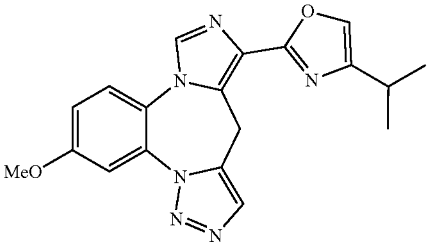 [SMILES: COc1ccc2c(c1)-n1nncc1Cc1c(-c3nc(C(C)C)co3)ncn1-2] | 363 |
| 395 | 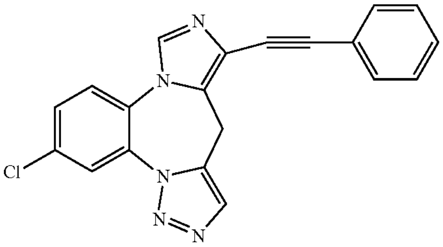 | 358 |
| 396 | 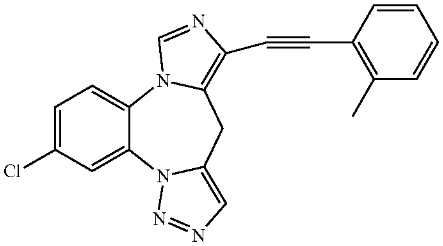 [SMILES: Cc1ccccc1C#Cc1ncn2c1Cc1cnnn1-c1cc(Cl)ccc1-2] | 372 |
| 397 | 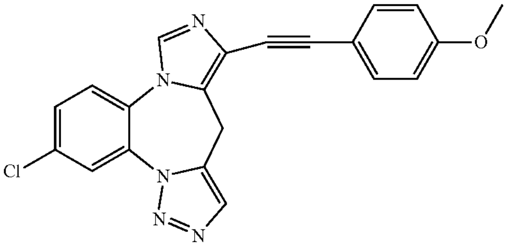 [SMILES: COc1ccc(C#Cc2ncn3c2Cc2cnnn2-c2cc(Cl)ccc2-3)cc1] | 388 |

TABLE 5-continued
| MS characterization of Compounds 180-471: | | |
|---|---|---|
| Cmp No. | Structure | Observed MS (M + 1) |
| 398 | 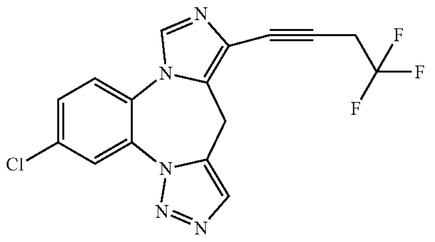 [SMILES: FC(F)(F)CC#Cc1ncn2c1Cc1cnnn1-c1cc(Cl)ccc1-2] | 364 |
| 399 | 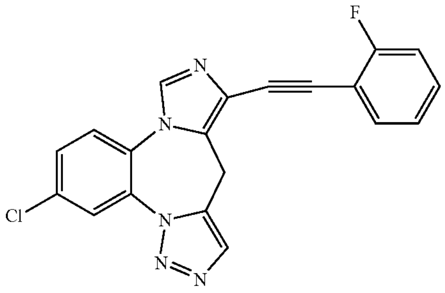 [SMILES: Fc1ccccc1C#Cc1ncn2c1Cc1cnnn1-c1cc(Cl)ccc1-2] | 376 |
| 400 | 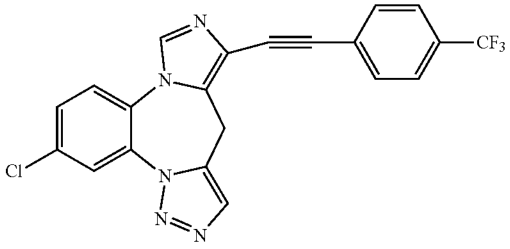 [SMILES: FC(F)(F)c1ccc(C#Cc2ncn3c2Cc2cnnn2-c2cc(Cl)ccc2-3)cc1] | 426 |
| 401 | 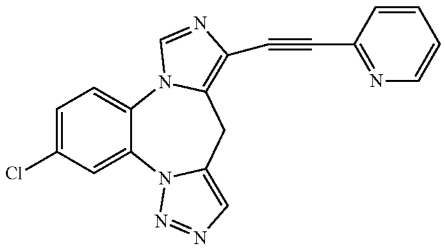 [SMILES: Clc1ccc2c(c1)-n1nncc1Cc1c(C#Cc3ccccn3)ncn1-2] | 359 |
| 402 | 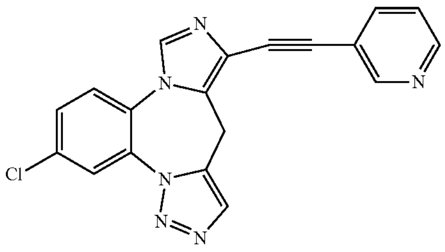 [SMILES: Clc1ccc2c(c1)-n1nncc1Cc1c(C#Cc3cccnc3)ncn1-2] | 359 |

TABLE 5-continued
MS characterization of Compounds 180-471:
| Cmp No. | Structure | Observed MS (M + 1) |
|---|---|---|
| 403 | 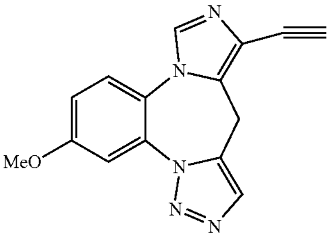 [SMILES: C#Cc1ncn2c1Cc1cnnn1-c1cc(OC)ccc1-2] | 278 |
| 404 | 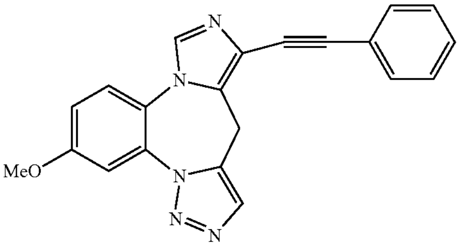 | 354 |
| 405 | 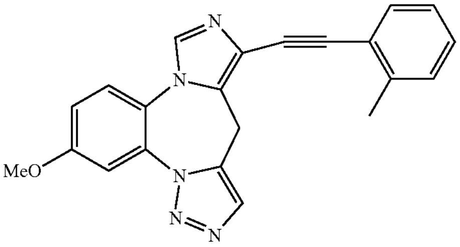 | 368 |
| 406 | 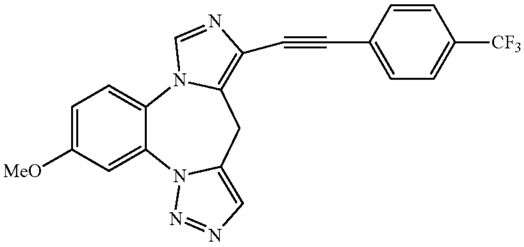 [SMILES: COc1ccc2c(c1)-n1nncc1Cc1c(C#Cc3ccc(C(F)(F)F)cc3)ncn1-2] | 422 |
| 407 | 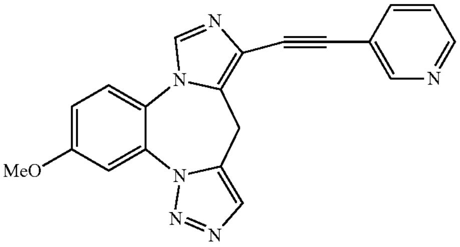 [SMILES: COc1ccc2c(c1)-n1nncc1Cc1c(C#Cc3cccnc3)ncn1-2] | 355 |
| 408 | 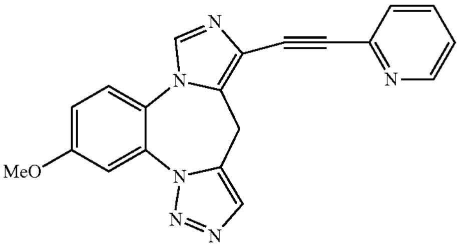 | 355 |

TABLE 5-continued
MS characterization of Compounds 180-471:
| Cmp No. | Structure | Observed MS (M + 1) |
|---|---|---|
| 409 | 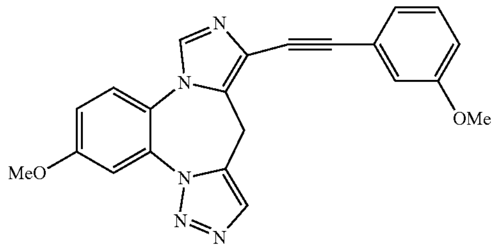 [SMILES: COc1cccc(C#Cc2ncn3c2Cc2cnnn2-c2cc(OC)ccc2-3)c1] | 384 |
| 410 | 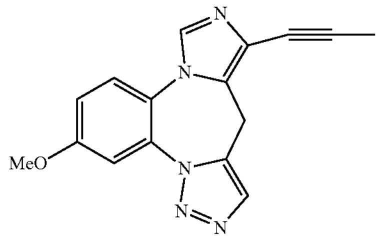 [SMILES: CC#Cc1ncn2c1Cc1cnnn1-c1cc(OC)ccc1-2] | 292 |
| 411 | 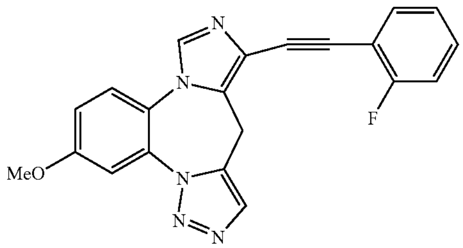 [SMILES: COc1ccc2c(c1)-n1nncc1Cc1c(C#Cc3ccccc3F)ncn1-2] | 372 |
| 412 | 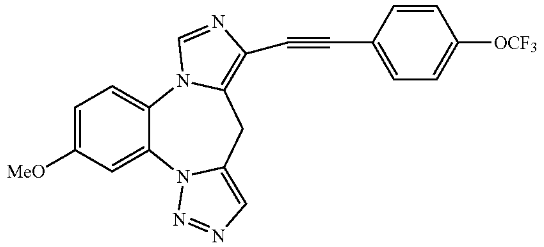 [SMILES: COc1ccc2c(c1)-n1nncc1Cc1c(C#Cc3ccc(OC(F)(F)F)cc3)ncn1-2] | 438 |
| 413 | 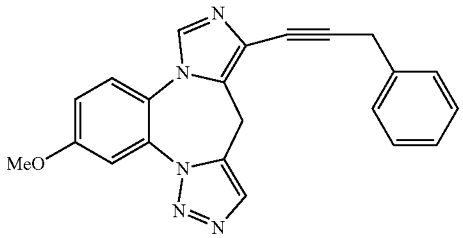 [SMILES: COc1ccc2c(c1)-n1nncc1Cc1c(C#CCc3ccccc3)ncn1-2] | 368 |
| 414 | 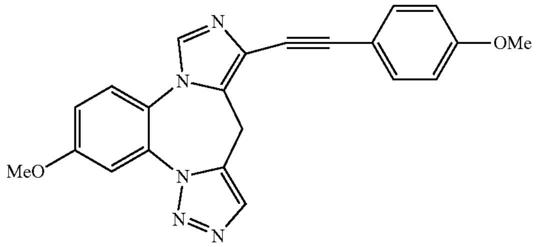 [SMILES: COc1ccc(C#Cc2ncn3c2Cc2cnnn2-c2cc(OC)ccc2-3)cc1] | 384 |

TABLE 5-continued
| Cmp No. | Structure | Observed MS (M + 1) |
|---|---|---|
| MS characterization of Compounds 180-471: | | |
| 415 | 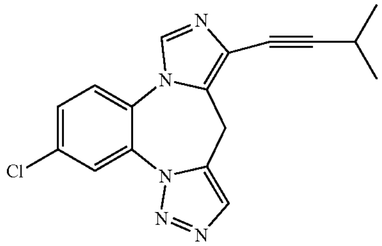 [SMILES: CC(C)C#Cc1ncn2c1Cc1cnnn1-c1cc(Cl)ccc1-2] | 324 |
| 416 | 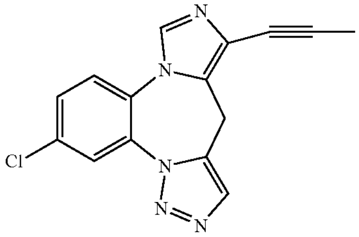 [SMILES: CC#Cc1ncn2c1Cc1cnnn1-c1cc(Cl)ccc1-2] | 296 |
| 417 | 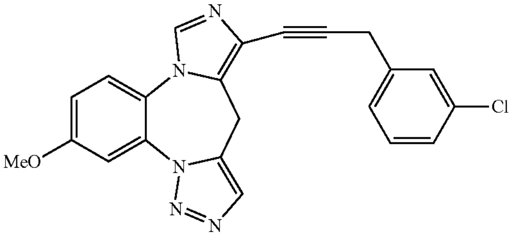 [SMILES: COc1ccc2c(c1)-n1nncc1Cc1c(C#CCc3cccc(Cl)c3)ncn1-2] | 402 |
| 418 | 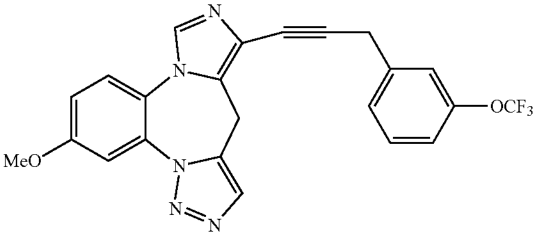 [SMILES: COc1ccc2c(c1)-n1nncc1Cc1c(C#CCc3cccc(OC(F)(F)F)c3)ncn1-2] | 452 |
| 419 | 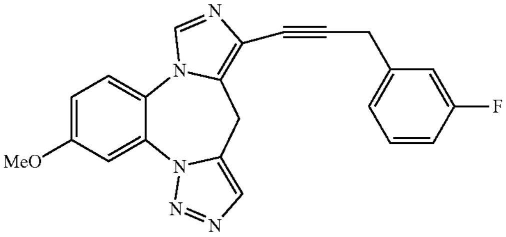 [SMILES: COc1ccc2c(c1)-n1nncc1Cc1c(C#CCc3cccc(F)c3)ncn1-2] | 386 |
| 420 | 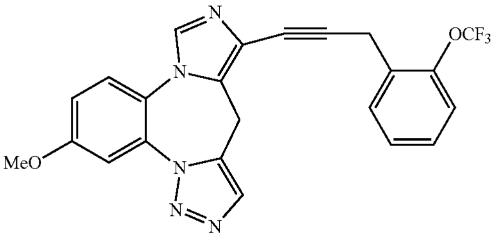 [SMILES: COc1ccc2c(c1)-n1nncc1Cc1c(C#CCc3ccccc3OC(F)(F)F)ncn1-2] | 452 |

TABLE 5-continued
| MS characterization of Compounds 180-471: | | |
|---|---|---|
| Cmp No. | Structure | Observed MS (M + 1) |
| 421 | 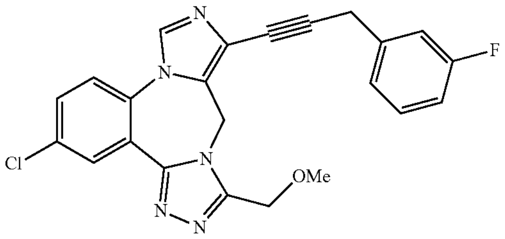 [SMILES: COCc1nnc2n1Cc1c(CCCc3cccc(F)c3)ncn1-c1ccc(Cl)cc1-2] | 434 |
| 422 | 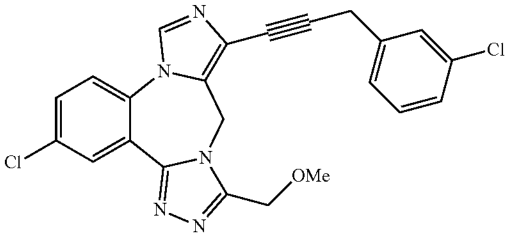 [SMILES: COCc1nnc2n1Cc1c(CCCc3cccc(Cl)c3)ncn1-c1ccc(Cl)cc1-2] | 451 |
| 423 | 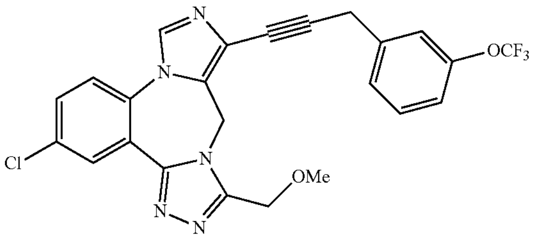 [SMILES: COCc1nnc2n1Cc1c(CCCc3cccc(OC(F)(F)F)c3)ncn1-c1ccc(Cl)cc1-2] | 500 |
| 424 | 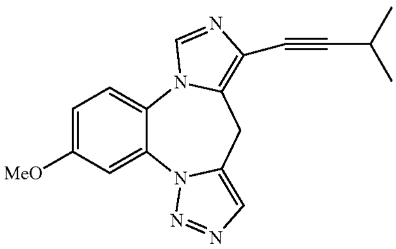 [SMILES: COc1ccc2c(c1)-n1nncc1Cc1c(C#CC(C)C)ncn1-2] | 320 |
| 425 | 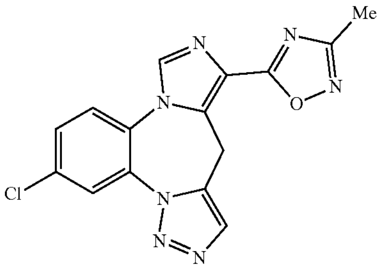 [SMILES: Cc1noc(-c2ncn3c2Cc2cnnn2-c2cc(Cl)ccc2-3)n1] | 340 |
| 426 | 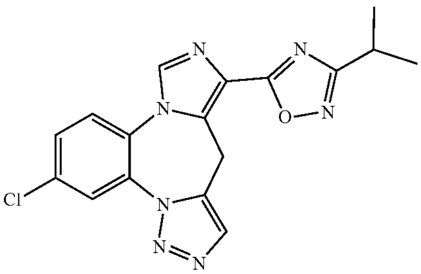 [SMILES: CC(C)c1noc(-c2ncn3c2Cc2cnnn2-c2cc(Cl)ccc2-3)n1] | 368 |

TABLE 5-continued
| MS characterization of Compounds 180-471: | | |
|---|---|---|
| Cmp No. | Structure | Observed MS (M + 1) |
| 427 | 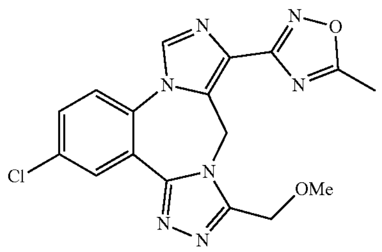 [SMILES: COCc1nnc2n1Cc1c(-c3noc(C)n3)ncn1-c1ccc(Cl)cc1-2] | 384 |
| 428 | 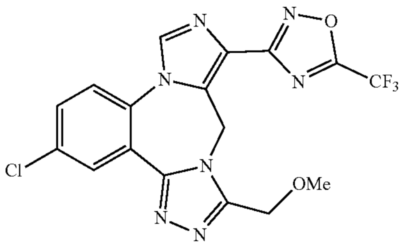 [SMILES: COCc1nnc2n1Cc1c(-c3noc(C(F)(F)F)n3)ncn1-c1ccc(Cl)cc1-2] | 438 |
| 429 | 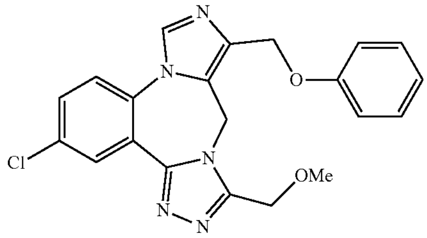 [SMILES: COCc1nnc2n1Cc1c(COc3ccccc3)ncn1-c1ccc(Cl)cc1-2] | 408 |
| 430 | 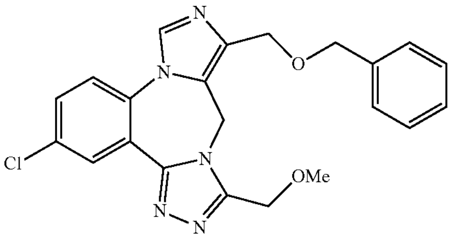 [SMILES: COCc1nnc2n1Cc1c(COCc3ccccc3)ncn1-c1ccc(Cl)cc1-2] | 422 |
| 431 | 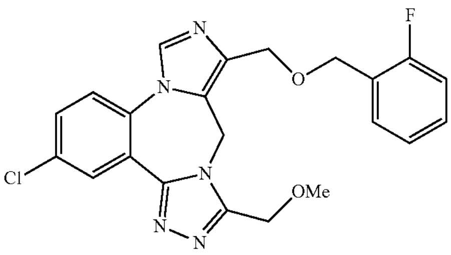 [SMILES: COCc1nnc2n1Cc1c(COCc3ccccc3F)ncn1-c1ccc(Cl)cc1-2] | 440 |
| 432 | 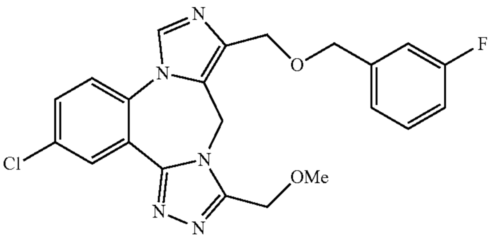 [SMILES: COCc1nnc2n1Cc1c(COCc3cccc(F)c3)ncn1-c1ccc(Cl)cc1-2] | 440 |

TABLE 5-continued
| MS characterization of Compounds 180-471: | | |
|---|---|---|
| Cmp No. | Structure | Observed MS (M + 1) |
| 433 | 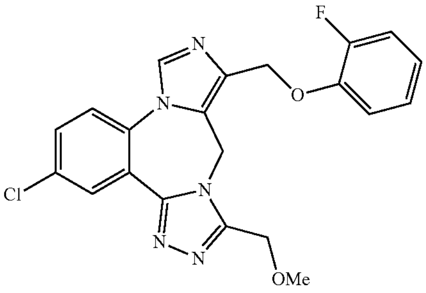 [SMILES: COCc1nnc2n1Cc1c(COc3ccccc3F)ncn1-c1ccc(Cl)cc1-2] | 426 |
| 434 | 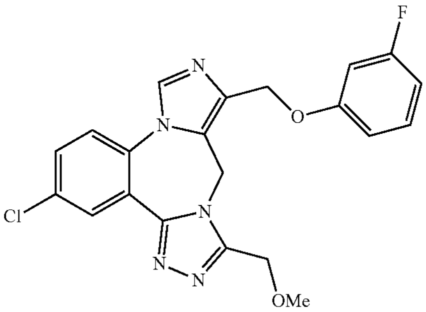 [SMILES: COCc1nnc2n1Cc1c(COc3cccc(F)c3)ncn1-c1ccc(Cl)cc1-2] | 426 |
| 435 | 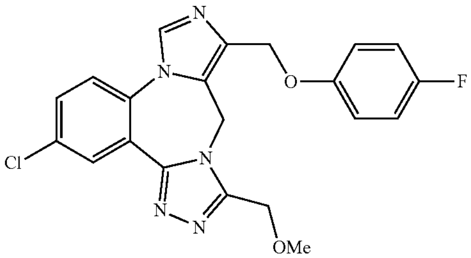 [SMILES: COCc1nnc2n1Cc1c(COc3ccc(F)cc3)ncn1-c1ccc(Cl)cc1-2] | 426 |
| 436 | 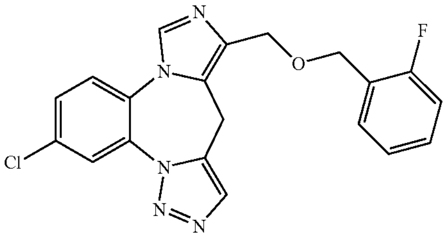 [SMILES: Fc1ccccc1COCc1ncn2c1Cc1cnnn1-c1cc(Cl)ccc1-2] | 396 |
| 437 | 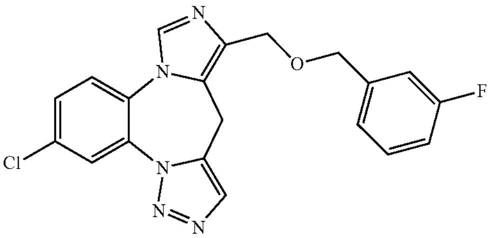 [SMILES: Fc1cccc(COCc2ncn3c2Cc2cnnn2-c2cc(Cl)ccc2-3)c1] | 396 |

TABLE 5-continued
MS characterization of Compounds 180-471:
| Cmp No. | Structure | Observed MS (M + 1) |
| --- | --- | --- |
| 438 | 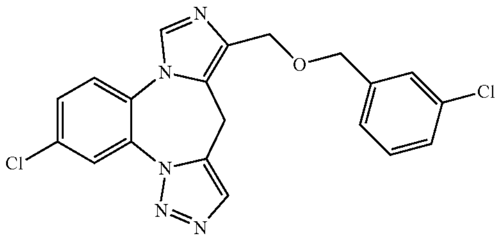 [SMILES: Clc1cccc(COCc2ncn3c2Cc2cnnn2-c2cc(Cl)ccc2-3)c1] | 413 |
| 439 | 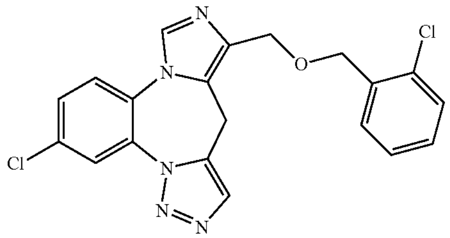 [SMILES: Clc1ccc2c(c1)-n1nncc1Cc1c(COCc3ccccc3Cl)ncn1-2] | 413 |
| 440 | 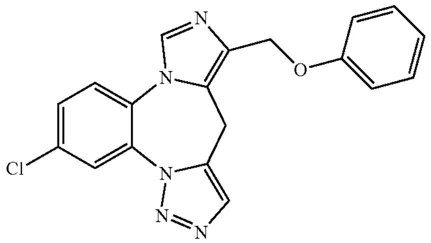 [SMILES: Clc1ccc2c(c1)-n1nncc1Cc1c(COc3ccccc3)ncn1-2] | 364 |
| 441 | 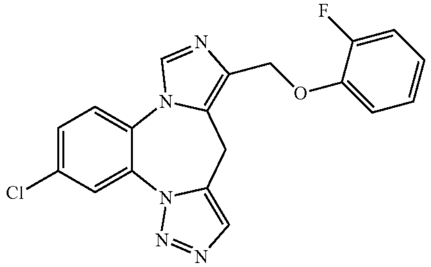 [SMILES: Fc1ccccc1OCc1ncn2c1Cc1cnnn1-c1cc(Cl)ccc1-2] | 382 |
| 442 | 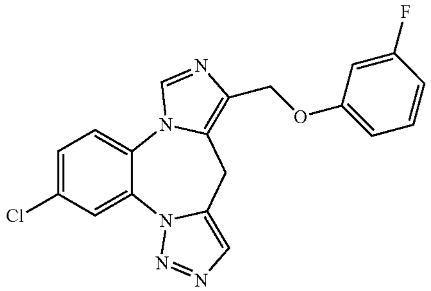 [SMILES: Fc1cccc(OCc2ncn3c2Cc2cnnn2-c2cc(Cl)ccc2-3)c1] | 382 |
| 443 | 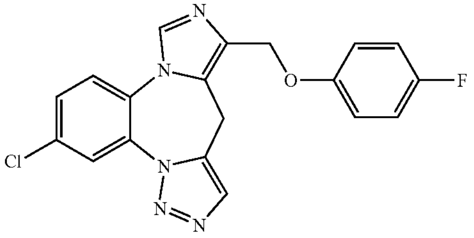 [SMILES: Fc1ccc(OCc2ncn3c2Cc2cnnn2-c2cc(Cl)ccc2-3)cc1] | 382 |

TABLE 5-continued
MS characterization of Compounds 180-471:
| Cmp No. | Structure | Observed MS (M + 1) |
|---|---|---|
| 444 | 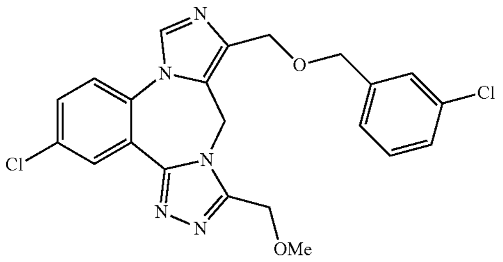 [SMILES: COCc1nnc2n1Cc1c(COCc3cccc(Cl)c3)ncn1-c1ccc(Cl)cc1-2] | 457 |
| 445 | 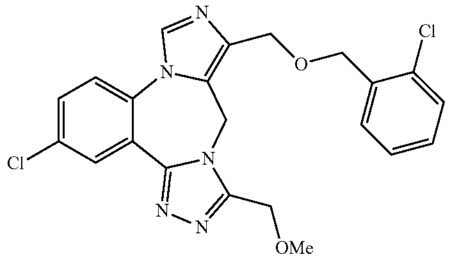 [SMILES: COCc1nnc2n1Cc1c(COCc3ccccc3Cl)ncn1-c1ccc(Cl)cc1-2] | 457 |
| 446 | 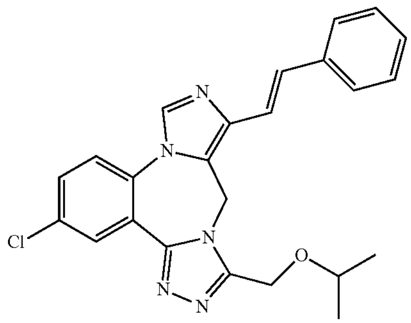 [SMILES: CC(C)OCc1nnc2n1Cc1c(/C=C/c3ccccc3)ncn1-c1ccc(Cl)cc1-2] | 432 |
| 447 | 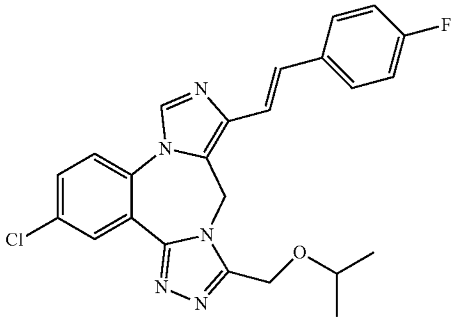 [SMILES: CC(C)OCc1nnc2n1Cc1c(/C=C/c3ccc(F)cc3)ncn1-c1ccc(Cl)cc1-2] | 450 |
| 448 | 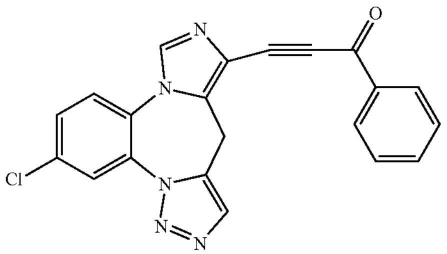 [SMILES: O=C(C#Cc1ncn2c1Cc1cnnn1-c1cc(Cl)ccc1-2)c1ccccc1] | 386 |

TABLE 5-continued
MS characterization of Compounds 180-471:
| Cmp No. | Structure | Observed MS (M + 1) |
|---|---|---|
| 449 | 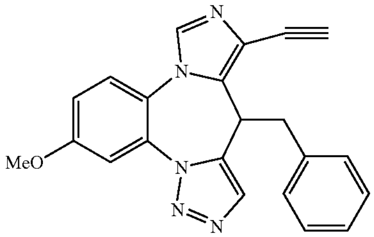 [SMILES: C#Cc1ncn2c1C(Cc1ccccc1)c1cnnn1-c1cc(OC)ccc1-2] | 368 |
| 450 | 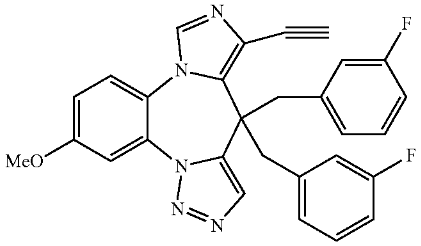 [SMILES: C#Cc1ncn2c1C(Cc1cccc(F)c1)(Cc1cccc(F)c1)c1cnnn1-c1cc(OC)ccc1-2] | 494 |
| 451 | 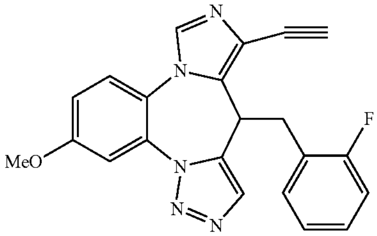 [SMILES: C#Cc1ncn2c1C(Cc1ccccc1F)c1cnnn1-c1cc(OC)ccc1-2] | 386 |
| 452 | 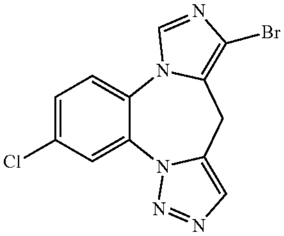 [SMILES: Clc1ccc2c(c1)-n1nncc1Cc1c(Br)ncn1-2] | 337 |
| 453 | 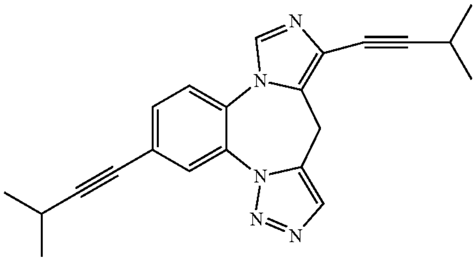 [SMILES: CC(C)C#Cc1ccc2c(c1)-n1nncc1Cc1c(C#CC(C)C)ncn1-2] | 356 |
| 454 | 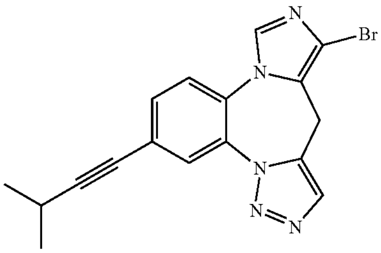 [SMILES: CC(C)C#Cc1ccc2c(c1)-n1nncc1Cc1c(Br)ncn1-2] | 369 |

TABLE 5-continued
| MS characterization of Compounds 180-471: | | |
|---|---|---|
| Cmp No. | Structure | Observed MS (M + 1) |
| 455 | 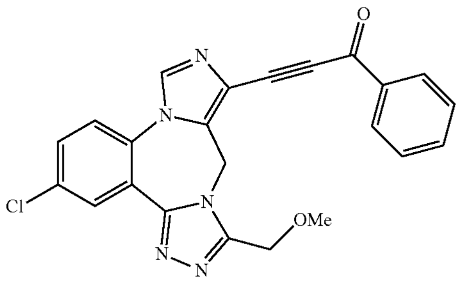 [SMILES: COCc1nnc2n1Cc1c(C#CC(=O)c3ccccc3)ncn1-c1ccc(Cl)cc1-2] | 430 |
| 456 | 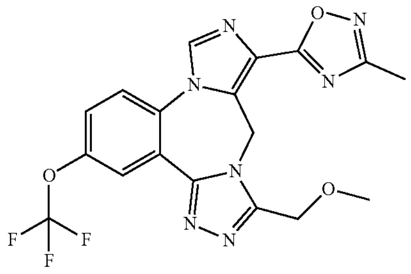 [SMILES: COCc1nnc2n1Cc1c(-c3nc(C)no3)ncn1-c1ccc(OC(F)(F)F)cc1-2] | 434 |
| 457 | 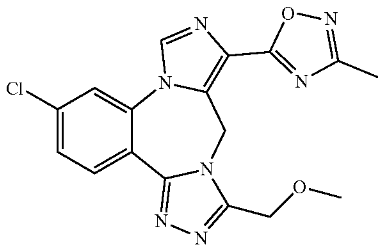 [SMILES: COCc1nnc2n1Cc1c(-c3nc(C)no3)ncn1-c1cc(Cl)ccc1-2] | 384 |
| 458 | 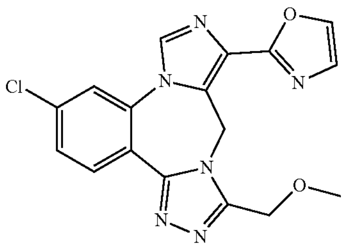 [SMILES: COCc1nnc2n1Cc1c(-c3ncco3)ncn1-c1cc(Cl)ccc1-2] | 369 |
| 459 | 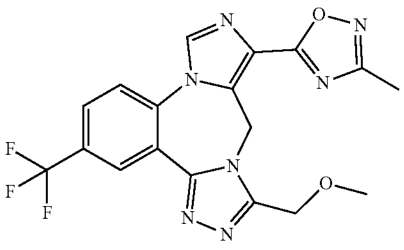 [SMILES: COCc1nnc2n1Cc1c(-c3nc(C)no3)ncn1-c1ccc(C(F)(F)F)cc1-2] | 418 |

TABLE 5-continued
MS characterization of Compounds 180-471:
| Cmp No. | Structure | Observed MS (M + 1) |
|---|---|---|
| 460 | 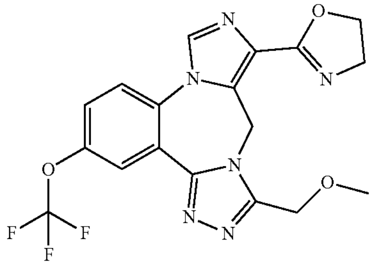 [SMILES: COCc1nnc2n1Cc1c(C3=NCCO3)ncn1-c1ccc(OC(F)(F)F)cc1-2] | 421 |
| 461 | 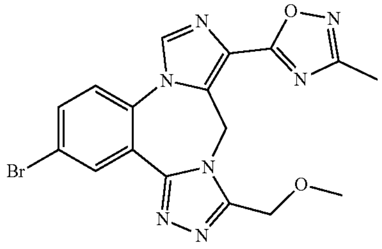 [SMILES: COCc1nnc2n1Cc1c(-c3nc(C)no3)ncn1-c1ccc(Br)cc1-2] | 428 |
| 462 | 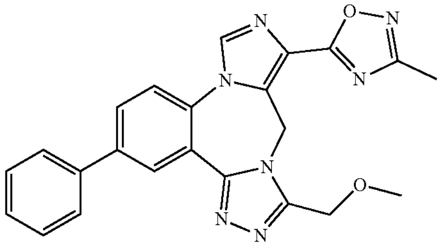 [SMILES: COCc1nnc2n1Cc1c(-c3nc(C)no3)ncn1-c1ccc(-c3ccccc3)cc1-2] | 426 |
| 463 | 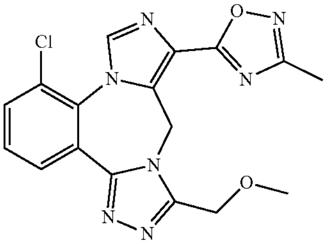 [SMILES: COCc1nnc2n1Cc1c(-c3nc(C)no3)ncn1-c1c(Cl)cccc1-2] | 384 |
| 464 | 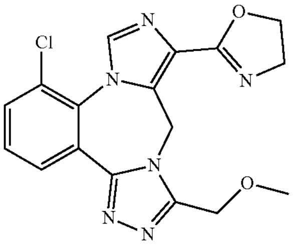 [SMILES: COCc1nnc2n1Cc1c(C3=NCCO3)ncn1-c1c(Cl)cccc1-2] | 371 |
| 465 | 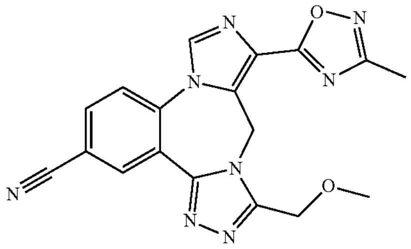 [SMILES: COCc1nnc2n1Cc1c(-c3nc(C)no3)ncn1-c1ccc(C#N)cc1-2] | 375 |

TABLE 5-continued
| MS characterization of Compounds 180-471: | | |
|---|---|---|
| Cmp No. | Structure | Observed MS (M + 1) |
| 466 | 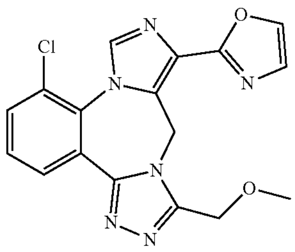 [SMILES: COCc1nnc2n1Cc1c(-c3ncco3)ncn1-c1c(Cl)cccc1-2] | 369 |
| 467 | 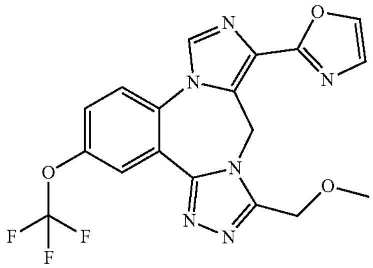 [SMILES: COCc1nnc2n1Cc1c(-c3ncco3)ncn1-c1ccc(OC(F)(F)F)cc1-2] | 419 |
| 468 | 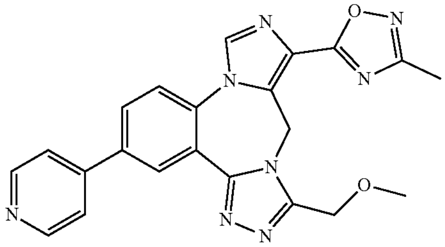 [SMILES: COCc1nnc2n1Cc1c(-c3nc(C)no3)ncn1-c1ccc(-c3ccncc3)cc1-2] | 427 |
| 469 | 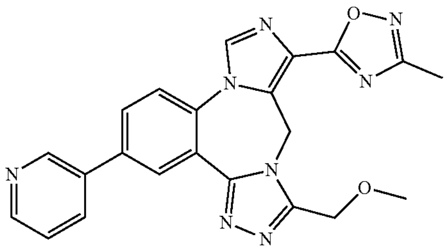 [SMILES: COCc1nnc2n1Cc1c(-c3nc(C)no3)ncn1-c1ccc(-c3cccnc3)cc1-2] | 427 |
| 470 | 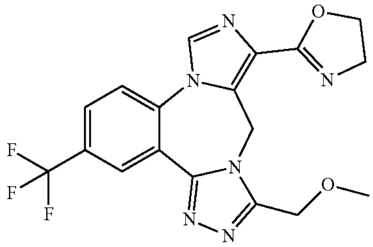 [SMILES: COCc1nnc2n1Cc1c(C3=NCCO3)ncn1-c1ccc(C(F)(F)F)cc1-2] | 405 |

TABLE 5-continued
| MS characterization of Compounds 180-471: | | |
|---|---|---|
| Cmp No. | Structure | Observed MS (M + 1) |
| 471 | 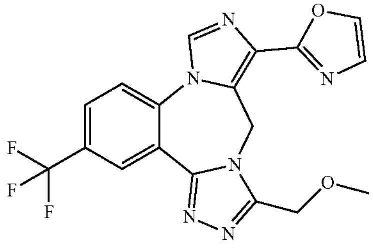 [SMILES: COCc1nnc2n1Cc1c(-c3ncco3)ncn1-c1ccc(C(F)(F)F)cc1-2] | 403 |
Implementing reactions similar and analogous to those shown in Schemes 1 through 37, the following compounds are also specifically contemplated in this application
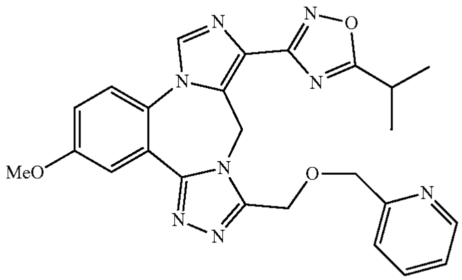
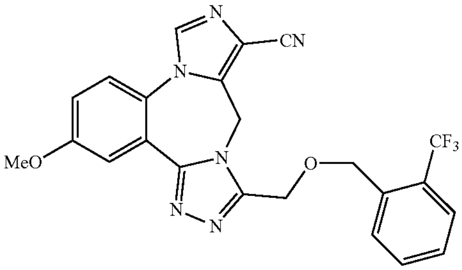
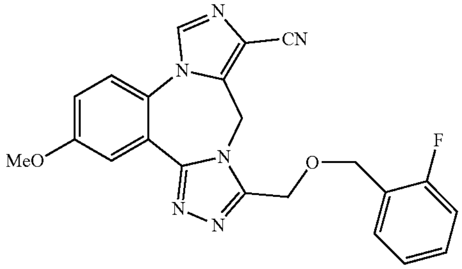
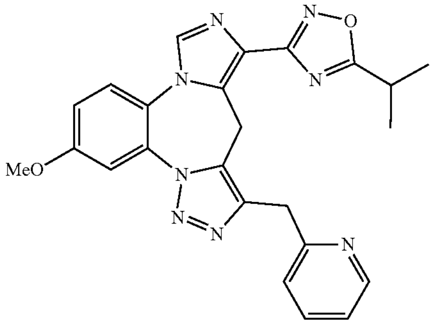
-continued
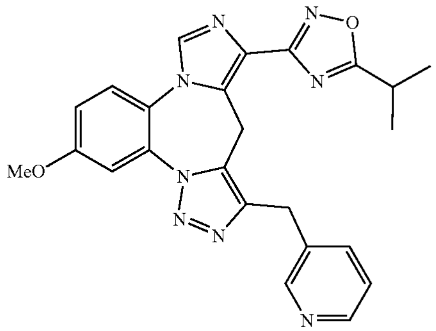
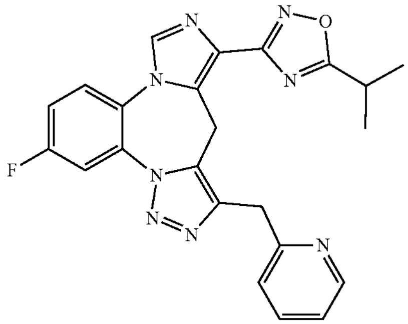
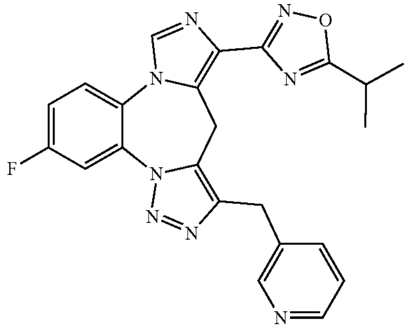
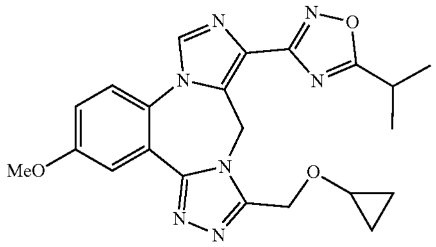

-continued
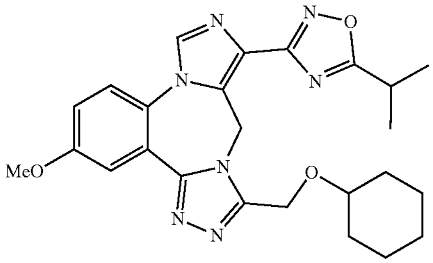
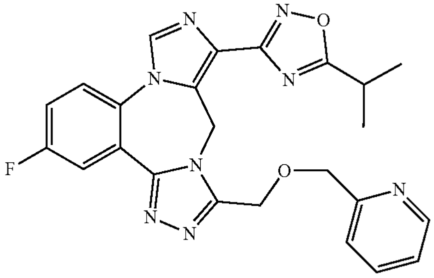
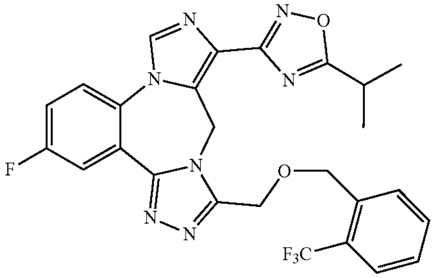
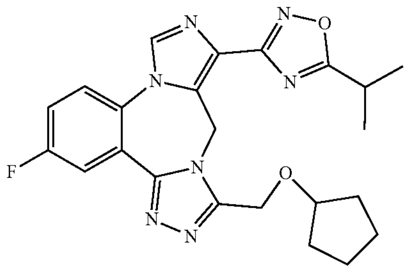
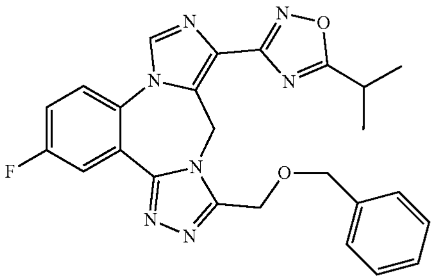
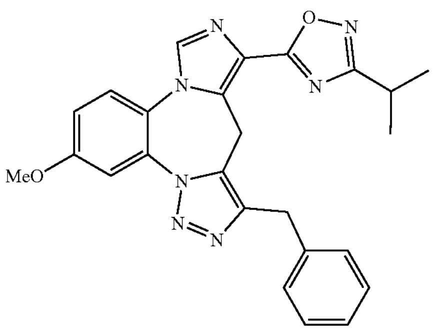
-continued
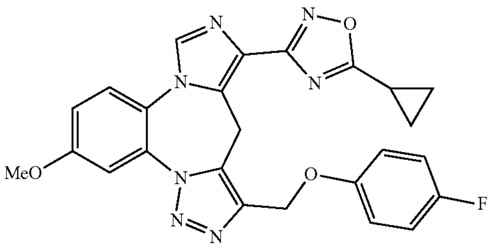
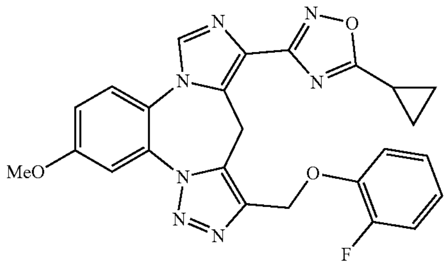
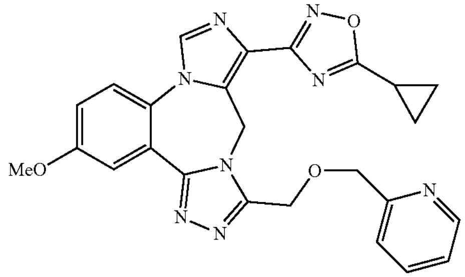
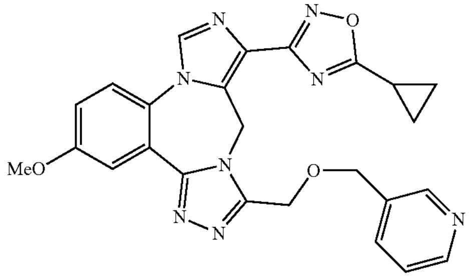
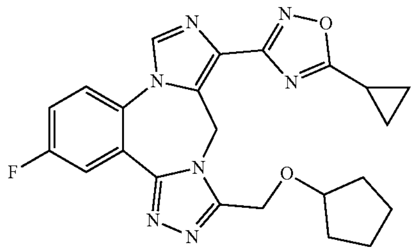
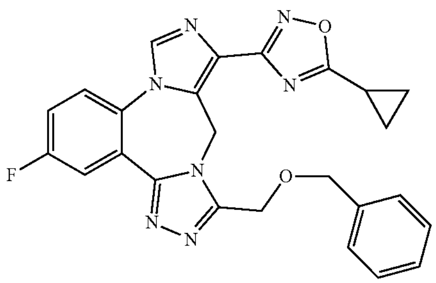

-continued
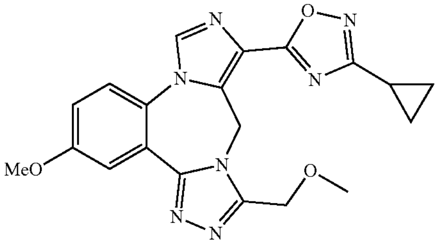
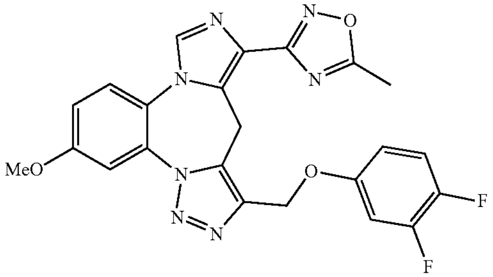
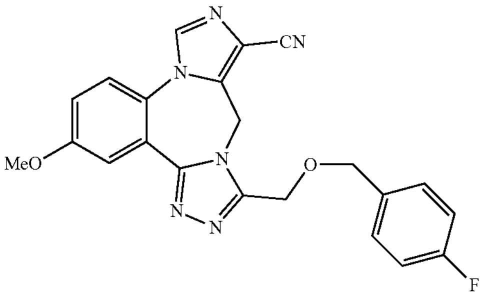
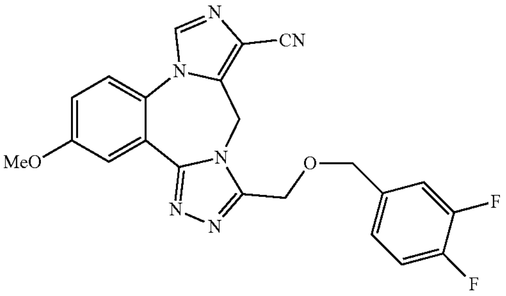
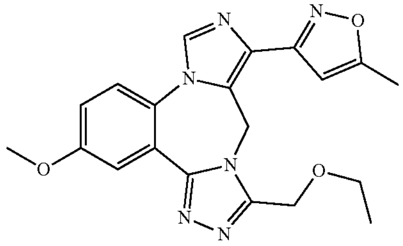
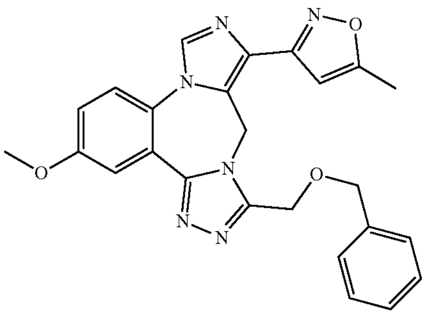
-continued
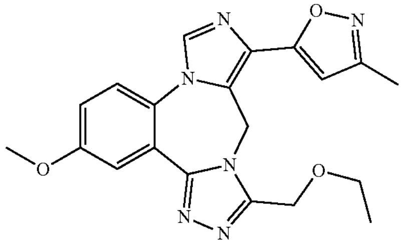
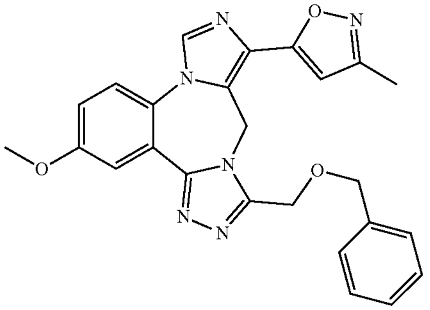
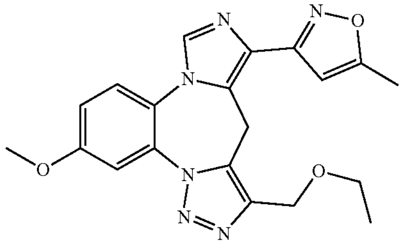
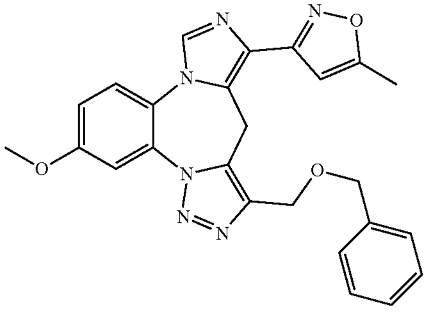
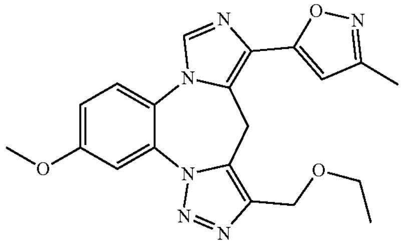
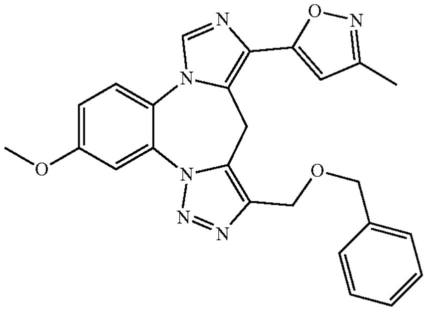

-continued
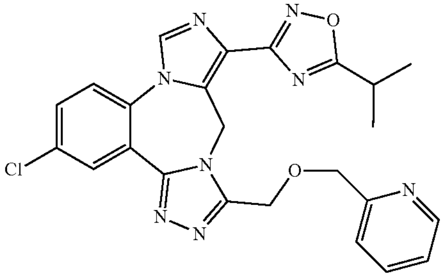
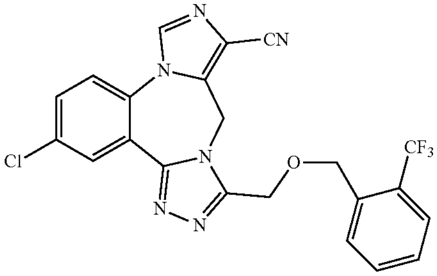
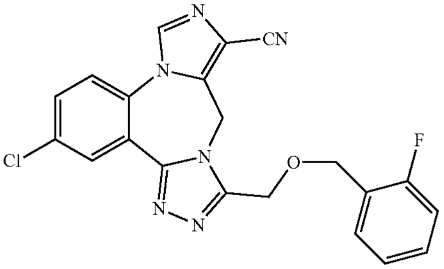
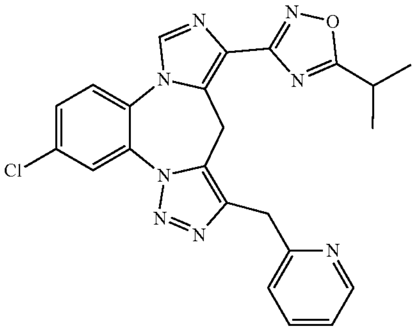
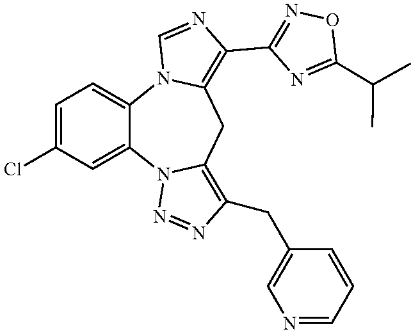
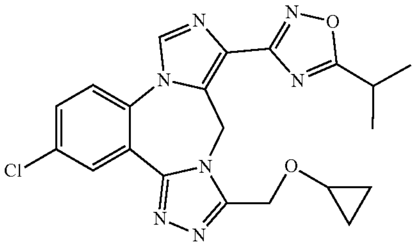
-continued
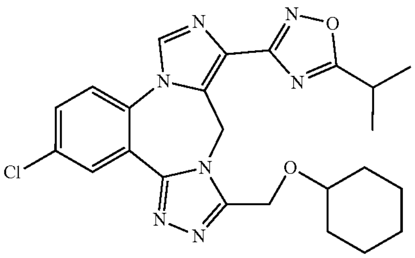
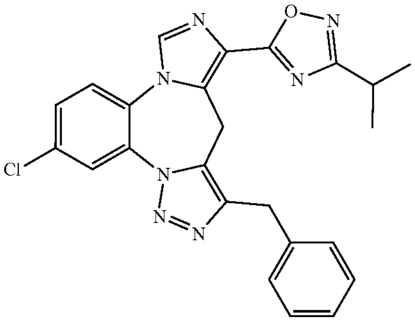
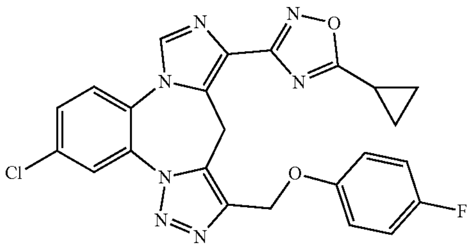
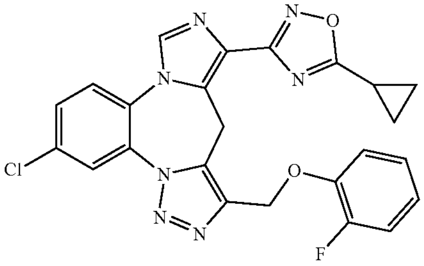
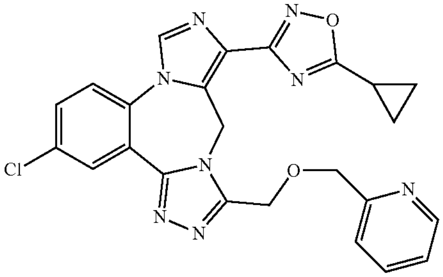
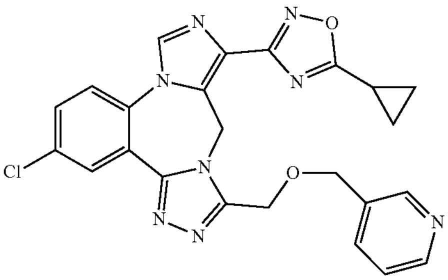

-continued
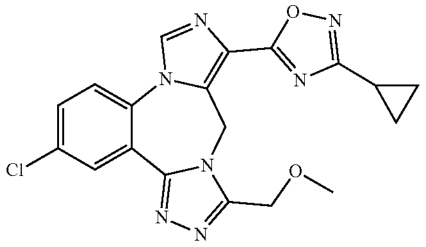
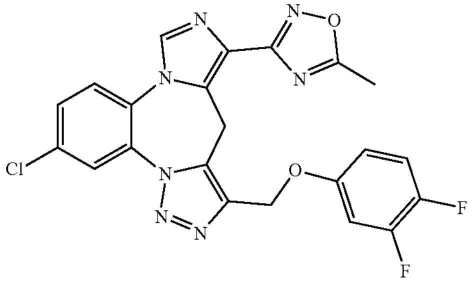
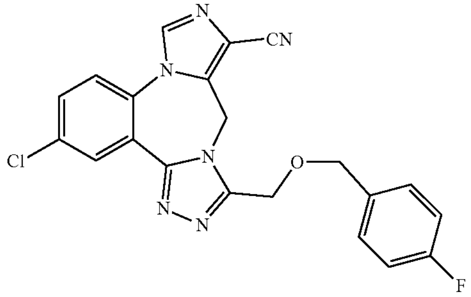
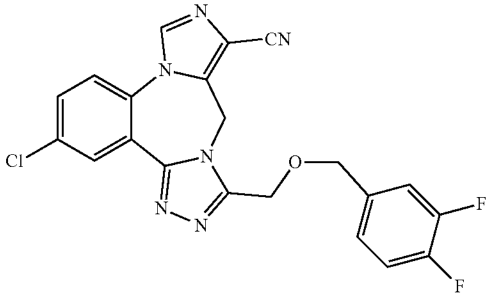
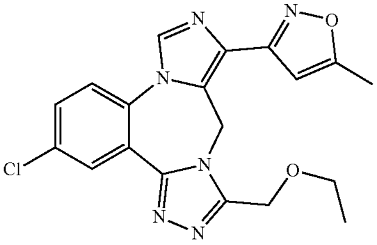
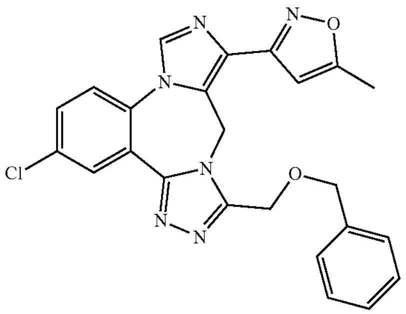
-continued
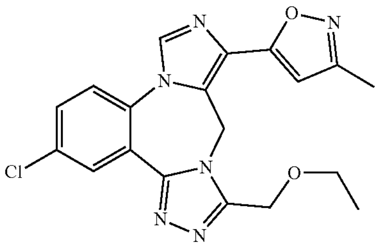
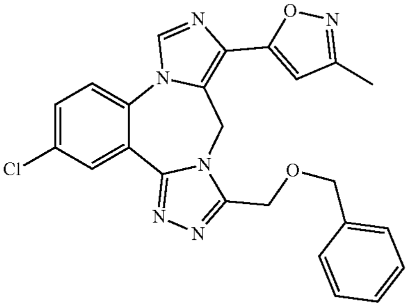
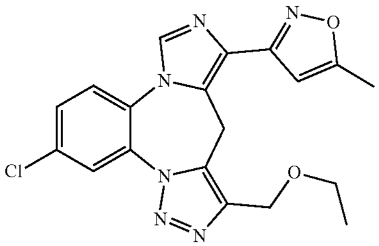
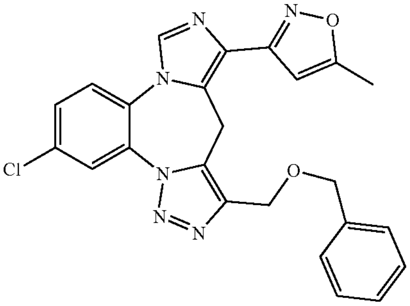
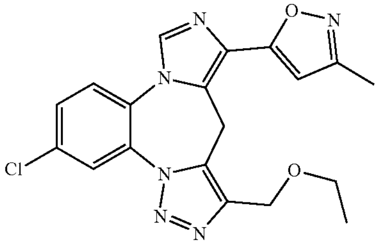
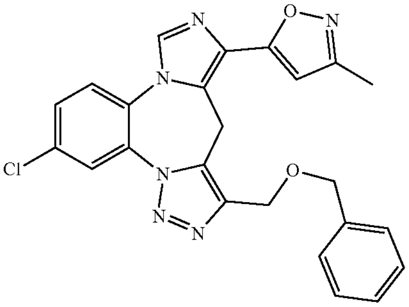

-continued
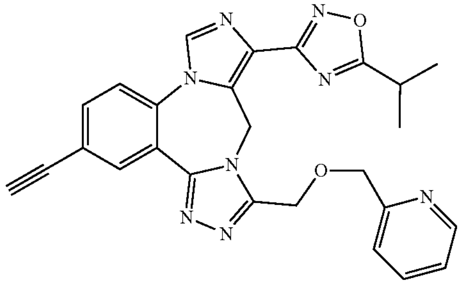
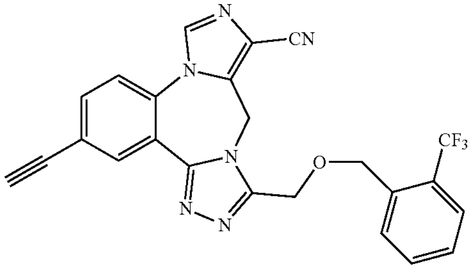
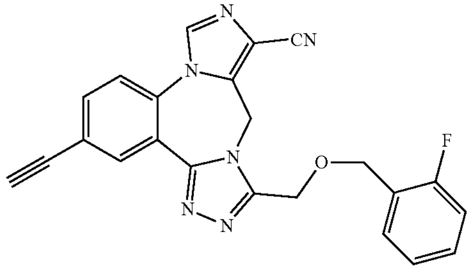
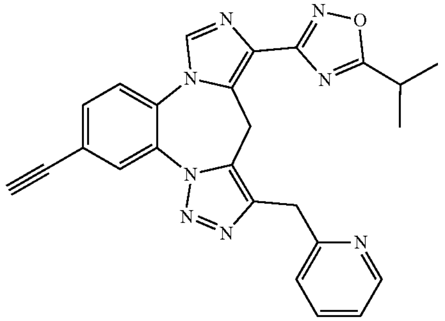
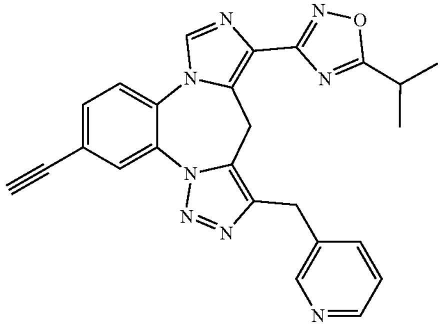
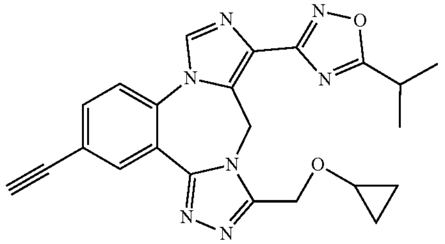
-continued
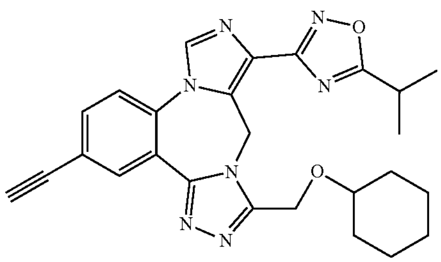
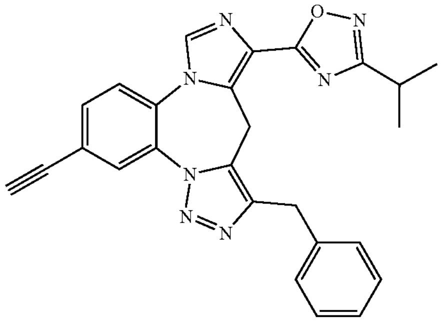
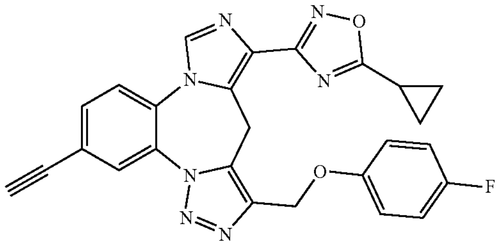
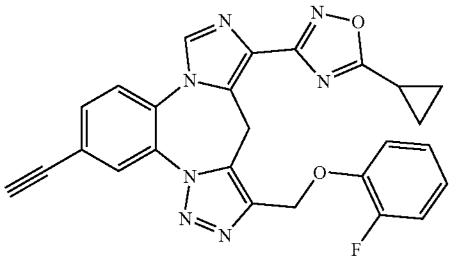
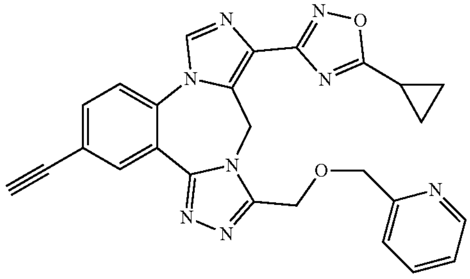
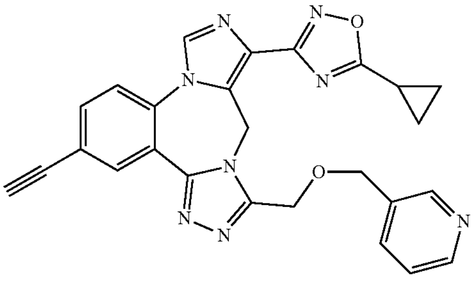

-continued
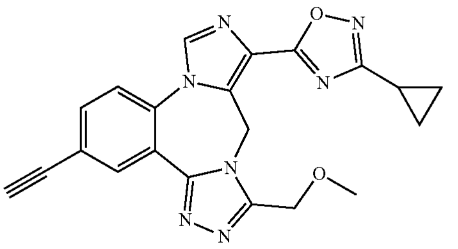
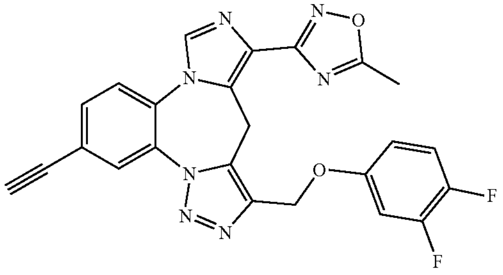
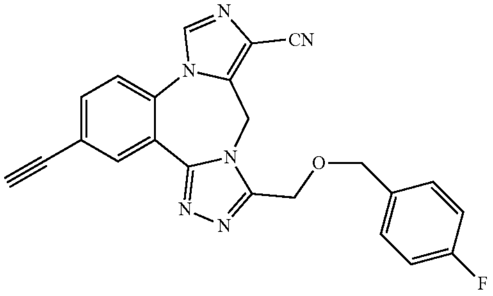
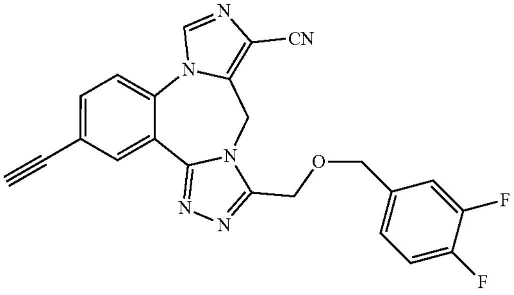
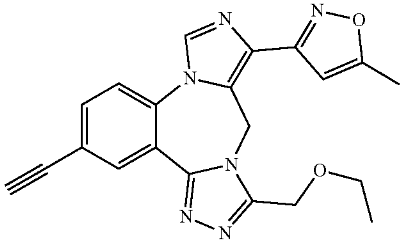
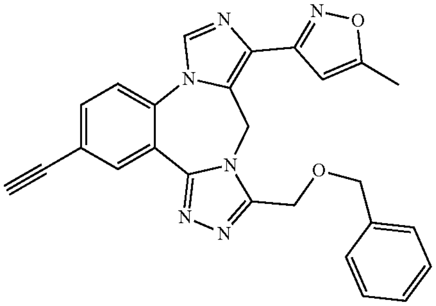
-continued
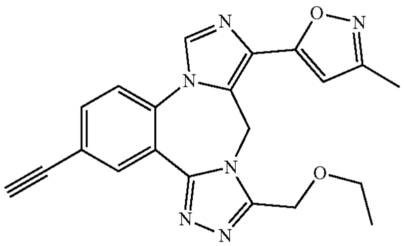
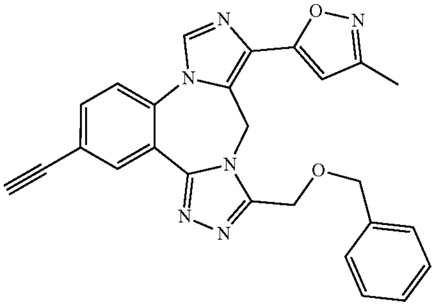
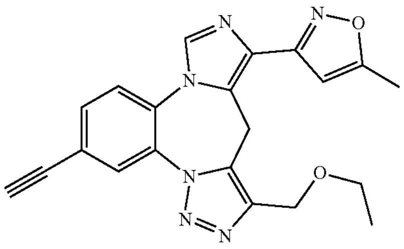
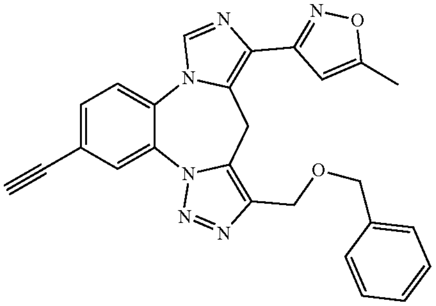
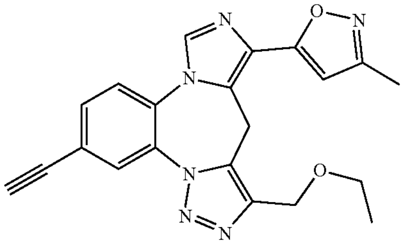
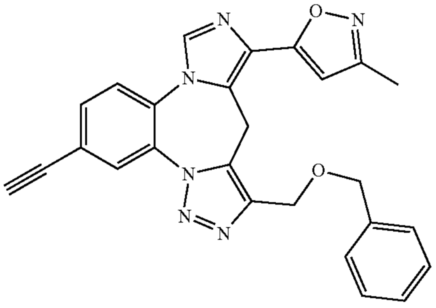

Example 105: Assessing α5-containing $GABA_A$ Receptor ($GABA_AR$) Positive Allosteric Modulator Activity Step 1: Establish clones of $GABA_AR$ subunits (α5, β3, γ2, α1, α2 and α3) and prepare the corresponding cRNAs: Human clones of $GABA_A$-R α5, 62 3, γ2, α1, α2 and α3 subunits are obtained from commercial resources (e.g., OriGene, http://www.origene.com and Genescript, http://www.genescript.com). These clones are engineered into pRC, pCDM, pcDNA, and pBluescript KSM vector (for oocyte expression) or other equivalent expression vectors. Conventional transfection agents (e.g., FuGene, Lipofectamine 2000, or others) are used to transiently transfect host cells.

Step 2-Functional $GABA_AR$ Assay of α5,β3γ2, α1β3γ2, α2β3γ2, and α3β3γ2, subtypes in *Xenopus* oocyte expression system: cRNAs encoding α5, β3, γ2, α1, α2 and α3 subunits are transcribed in vitro using T3 mMESSAGE mMACHINE Kit (Ambion) and injected (in a ratio of α:β:γ=2:2:1 or other optimized conditions) into oocytes freshly prepared from *Xenopus laevis*. After two days of culturing, GABA-gated Cl-currents from oocytes are performed using TEVC setups (Warner Instruments, Inc., Foster City, CA). GABA, benzodiazepine, and diazepam are used as reference compounds to validate the system.

Step 3—Evaluate test compounds for positive allosteric modulator activity on the α5β3γ2 subtype and test off target activity on the α1 to α3 coupled β3γ2 subtypes when the EC50=5 μM selectivity cut-off is reached: The GABA-gated Cl-current from oocytes are measured in the TEVC setup in the presence of the test compounds. The positive allosteric modulator activity of each the test compounds is tested in a 5-point dose-response assay. The test compounds include some reference compounds (literature EC50 values for the α5β3γ2 subtype are in the range of 3-10 μM). EC50s in the α5β3γ2 subtype are obtained for each compound. If the EC50 in α5β3γ2 is ≤5 μM, then the EC50 of the other three subtypes (α1β2γ2, α2β3γ2, and α3β3γ2) is further determined individually in order to test for selectivity of the compounds in the α5β3γ2 subtype over other subtypes.

Step 4—Evaluate further test compounds on the α5β3γ2 subtype and test off-target activities when the EC50-0.5 μM selectivity cut-off is reached: The second batch of test compounds are tested using the same strategy, but with a lower EC50 cutoff (0.5 μM). Again, the EC50s of the α5β3γ2 subtype for each of the compounds is determined. The α1 to α3 coupled β3γ2 subtypes are tested only if the EC50 for the α5-containing receptor is <0.5 μM.

Example 106: Evaluating Compounds for Binding and Positive Allosteric Modulator Activity on the $GABA_A$ α5 Receptors (A) Binding activity of test compounds on $GABA_AR$ Tissue culture and Membrane Preparation: The binding was performed on Ltk cells stably expressing $GABA_A$ receptors: α1β1γ2, α2β3γ2, α3β3γ2 and α5β3γ2 (provided by Merck Co., NJ, USA). Cells were seeded in 100 mm culture plates in DMEM/F12 medium containing 10% serum and antibiotics in 5% CO2 and allowed to grow for 1-2 days. $GABA_AR$ expression was then induced by dexamethasone as follows: 0.5 μM for 1 day for α5 containing and 2 μM for 3 days for α1, α2 and α3 containing $GABA_ARs$. After induction, cells were collected by scraping into Dulbecco's Phosphate buffered saline (DPBS, pH 7.4, Invitrogen, Carlsbad, CA, USA) and centrifuged at 150×g for 10 min. The pellet was washed twice by re-suspension and centrifugation. The cell pellets from at least 5 different preps were combined, suspended in the binding assay buffer (50 mM KH2PO4; 1 mM EDTA; 0.2 M KCl, pH 7.4) and membranes prepared by sonication (3-5 times, 30 sec) using Branson Sonifier 150 (G. Heinmann, Germany). Protein content was determined using BCA assay (Bio-Rad Labs, Reinach, Switzerland) with Bovine Serum Albumin (Sigma Aldrich, St. Louis, MO, USA) as the standard. Aliquots were prepared and stored at −20° C. for further use in binding assays.

Ligand Binding: Saturation binding curves were obtained by incubating membranes with increasing concentrations (0.01-8 nM) of [$^3$H]Rol5-1788 (Flumazepil, 75-85 Ci/mmol, PerkinElmer, MA, USA), with nonspecific binding measured in the presence of 10 μM diazepam. Inhibition of [$^3$H]Rol5-1788 binding of the test compounds was performed at concentrations of the radioligand at or lower than the $K_d$ values for α1, α2, α3 and α5 containing $GABA_ARs$ determined from the saturation curves.

All binding assays were performed for 1 h at 4° C. in assay buffer. The total assay volume was 0.5 ml containing 0.2 mg/ml protein for α5 and 0.4 mg/ml for α1, α2, and α3 containing $GABA_AR$ membranes. Incubations were terminated by filtration through GF/B filters using a 24-Cell Harvestor (Brandel, Gaithersburg, MD, USA) followed by 3 washes with ice-cold assay buffer. Filters were transferred to scintillation vials, 5 ml scintillation liquid added, vortex-mixed and kept in dark. Next day, radioactivity was obtained using a scintillation counter (Beckman Coulter, Brea, CA, USA). All assays were performed in triplicate.

Data Analyses: Saturation and inhibition curves were obtained using GraphPad Prism software (GraphPad Software, Inc., CA, USA). The equilibrium dissociation constants ($K_i$ values) of the unlabeled ligand were determined using Cheng-Prusoff equation $K_i$–$IC_{50}/(1+S/K_d)$, where $IC_{50}$ is the concentration of unlabeled ligand that inhibits 50% of [$^3$H] ligand binding, S is the concentration of radioligand and $K_d$ is the equilibrium dissociation constant of the radioactive ligand. A log range of the compounds (1 nM-10 μM) was used to determine the $K_i$ values which are presented as Mean±SD from triplicate assays.

(B) Positive Allosteric Modulator Activity of Test Compounds on α5β2γ2 Subtype $GABA_AR$ Compounds of the present invention were initially screened at 100 nM for their ability to potentiate an $EC_{20}$ concentration of GABA in oocytes containing $GABA_A$ receptors (α2β2γ2), using a protocol essentially similar to the one presented above.

On day 1, 1 ng/32 nL of $GABA_A$ α5β2γ2 cDNA was injected into one oocyte. Test starts on day 2. The cDNA injected to the oocytes was a mix of alpha, beta and gamma, their ratio is 1:1:10 (by weight) and the total weight of the mixed 3 subunits to be injected in one oocyte was 1 ng in 32 nl volume. The injected oocytes can also be tested on day 3. In such case, the cDNA amount injected to the oocytes should be reduced by 20%.

Compounds of the present invention were tested using the following procedures.

GABA Dose-Response

1). 8 oocytes were placed in 8 chambers of OpusXpress and superfused with Modified Barth's Saline (MBS) at 3 mL/min. Glass electrodes back-filled with 3M KCl (0.5-3 megaohms) were used. Membrane potential of oocytes was voltage-clamped at −60 mV.

2). Average EC20 GABA obtained from previous tests were applied for five-six times to stabilize oocytes. Oocytes were washed with MBS for 5-10 min between each GABA applications.

3). Run GABA dose-response to obtain $EC_{20}$ GABA value.

Control test (Diazepam or methyl 3,5-diphenylpyridazine-4-carboxylate)

1). New oocytes was used to run new test.

2). $EC_{20}$ GABA was applied for five-six times to stabilize oocytes. Oocytes were washed with MBS for 5-10 min between each GABA applications.

3). EC20 GABA was applied to obtain current ($I_{GABA}$). Oocytes were washed with MBS for 5-10 min.

4). 1 M diazepam or methyl 3,5-diphenylpyridazine-4-carboxylate was pre-applied for 40 see, followed by co-application of 1 μM diazepam or methyl 3,5-diphenylpyridazine-4-carboxylate and $EC_{20}$ GABA to obtain $I_{test}$. $I_{test}$ was divided by $I_{GABA}$ to obtain potentiation (%).

Test Compounds at Multiple Doses

1). Repeat the above steps 1), 2) and 3) in the control test.

2). The first concentration of a test compound was pre-applied for 40 see followed by co-application of the test compound of the same concentration and EC20 GABA to obtain $I_{test}$. Divide $I_{test}$ by $I_{GABA}$ to obtain potentiation (%).

3). Discard all tested oocytes, new oocytes were used and the above steps 1) and 2) were repeated to test second concentration of the same compound. Each oocyte was used for only one concentration test for a single test compound. The steps were repeated for other test compounds.

In some embodiments, the compounds of this application have a binding affinity (as represented by $K_i$) at α5-containing $GABA_ARs$ of less than 200 nM, less than 180 nM, less than 150 nM, or less than 100 nM. In some embodiments, the compounds of this application have a binding affinity (as represented by $K_i$) at α5-containing $GABA_ARs$ of less than 50 nM. In some embodiments, the compounds of this application have a binding affinity (as represented by $K_i$) at α5-containing $GABA_ARs$ of less than 10 nM.

In some embodiments, the compounds of this application are selective for α5-containing $GABA_ARs$ over α1-containing $GABA_ARs$. In some embodiments, the compounds of this application are more than 50-fold, more than 100-fold, more than 500-fold or more than 1000-fold selective for α5-containing $GABA_ARs$ over α1-containing $GABA_ARs$.

In some embodiments, the compounds of this application have an $EC_{50}$ at the α5-containing $GABA_ARs$ of less than 500 nM, less than 100 nM or less than 50 nM. In some embodiments, the compounds of this application have an $EC_{50}$ at the α5-containing $GABA_ARs$ of less than 25 nM.

In some embodiments, the compounds of this application potentiate α5-containing $GABA_ARs$ for more than 10%, more than 25%, more than 50%, or more than 75% at 100 nM. In some embodiments, the compounds of this application potentiate α5-containing $GABA_ARs$ for more than 10%, more than 25%, more than 50%, or more than 75% at 1000 nM.

Screening results of the binding and PAM functional activity tests are summarized in Tables 1 and 2 below.

The following Table 1 illustrates the ranges of GABA α5 binding $K_i$'s associated with compounds of this invention:

TABLE 1

| GABA α5 Binding Ki Values (nM) | | |
|---|---|---|
| <100 nM | 100-1000 nM | >1000 nM |
| Compounds 1, 2, 3, 4, 6, 7, 8, 9, 10, 11, 12, 44, 55, 101, 103, 105, 107, 108, 114, 128, 153, 158, 162, 163, 164, 166, 169, 171, 172, 173, 174, 175, 177, 179, 5, 47, 48, 49, 51, 52, 53, 54, 56, 102, 104, 106, 111, 112, 118, 120, 126, 127, 130, 133, 137, 145, 147, 148, 149, 155, 156, 157, 160, 165, 168, 178, 45, 46, 109, 122, 129, 132, 150, 151, 159, 161, 167, 176, 180-190, 194-199, 202, 203, 205-210, 216, 217, 218, 222, 223-227, 230, 232, 233, 235, 236, 238, 241-245, 249, 254-261, 263, 264, 268-271, 275-278, 280, 282, 285, 288-291, 293-296, 301, 302, 304, 307, 308, 310, 311, 313, 317, 319, 320, 322, 323, 324, 325, 326, 327, 328, 330, 331, 332, 333, 334, 335, 337, 338, 339, 340, 341, 342, 343, 344, 345, 346, 349-351, 353-62, 364, 366, 367-369, 372, 373, 375, 377, 383, 385, 387, 388, 393, 394-399, 401-427, 448, 451, 452, 454-456, 459, 461, 462, 465, 467, 471 | Compounds 50, 110, 113, 115, 119, 124, 125, 134, 136, 138, 139, 141, 143, 144, 146, 170, 191, 200, 201, 219, 220, 237, 240, 246, 247, 248, 265-267, 273, 274, 281, 283, 284, 286, 287, 292, 297-300, 303, 305, 309, 312, 314, 316, 318, 321, 336, 347, 348, 352, 363, 370, 371, 374, 376, 378, 379, 382, 384, 392, 453, 460, 469, 470 | Compounds 116, 117, 121, 123, 131, 135, 140, 142, 143, 152, 154, 192, 193, 204, 221, 229, 231, 234, 239, 250-253, 262, 272, 279, 306, 315, 329, 386, 389, 390, 429-435, 446, 447, 449, 450, 457, 458, 463, 466, 468, |

The following Table 2 illustrates the ranges of GABA α5 functional potentiation associated with compounds of this invention:

TABLE 2

| GABA α5 Functional Data | | |
|---|---|---|
| 5-20% @ 100 nM | 20-50% @ 100 nM | >50% @ 100 nM |
| 10, 50, 51, 104, 112, 118, 121, 122, 133, 164, 166, 168, 190, 200, 206, 211, 215, 217, 223, 227, 229, 232, 233, 236, 241, 242, 244, 245, 254-257, 268, 285, 301, 302, 304, 308, 310, 311, 328, 331-333, 335, 341, 349, 359, 367, 368, 385, 395, 396, 401, 404, 405, 407-409, 413, 417, 420, 423, 454 | Compounds 1, 2, 9, 11, 48, 45, 55, 109, 110, 111, 118, 120, 126, 127, 128, 130, 132, 137, 147, 148, 153, 155, 158, 162, 163, 175, 180-184, 187-189, 191, 195, 196, 198, 199, 202, 203, 205, 207, 210, 212, 213, 222, 224, 225, 226, 238, 243, 249, 254-257, 264, 290, 293, 313, 319, 320, 323-326, 330, 334, 337, 339, 340, 343, 345, 346, 351, 354, 355, 357, 358, 360, | Compounds 113, 114, 145, 149, 160, 171, 172, 173, 174, 176, 177, 178, 179, 185, 186, 194, 271, 350, 353, 356 |

TABLE 2-continued

| GABA α5 Functional Data | | |
|---|---|---|
| 5-20% @ 100 nM | 20-50% @ 100 nM | >50% @ 100 nM |
| | 361, 362, 397, 398, 400, 387, 402, 406, 414, 415, 418, 419, 421, 422 | |

Selected compounds of this invention demonstrate >10-fold binding selectivity for GABA α5 versus GABA α1, GABA α2, or GABA α3. Some compounds of this application demonstrate over 20-fold, 50-fold, or 100-fold binding selectivity for GABA α5 versus GABA α1, GABA α2, or GABA α3.

The following Table 6 illustrates the ranges of the binding selectivity of the compounds of the present application for GABA α5 versus GABA α1, GABA α2, or GABA α3:

TABLE 6

| Binding selectivity for GABA α5 versus GABA α1, GABA α2, or GABA α3 | | |
|---|---|---|
| 20- to 50-fold | 50- to 100-fold | >100-fold |
| 323, 324, 344, 127, 130, 148, 162, 169, 184, 206, 209, 222, 223, 254, 255, 261, 350, 353, 354, 403-405, 408, 409, 411, 459 | 147, 158, 164, 165, 171, 173, 176, 183, 198, 205, 242, 244, 245, 256-258, 293, 319, 320, 323, 326, 330, 339, 340, 343, 351, 354, 355, 366, 367, 373, 387, 388, 419, 426, 427, 448, 452, 455, 456 | 128, 163, 166, 168, 172, 174, 175, 177-182, 194, 195, 202, 203, 207, 210, 212, 217, 218, 232, 233, 236, 243, 249, 260, 264, 268, 270, 271, 275, 276, 285, 289, 290, 301, 302, 304, 313, 320, 324-326, 332, 334, 335, 337,, 340, 344-346, 357-362, 368, 372, 385, 393, 395-399, 401, 402, 414, 415, 417, 418, 420-425, 454 |

Example 107: Effect of Methyl 3,5-diphenylpyridazine-4-carboxylate in Aged-Impaired (AI) Rats Methyl 3,5-diphenylpyridazine-4-carboxylate, corresponding to compound number 6 in van Niel et al. *J. Med. Chem.* 48:6004-6011 (2005), is a selective α5-containing $GABA_A$ R agonist. It has an α5 in vitro efficacy of +27 (EC20). The effect of methyl 3,5-diphenylpyridazine-4-carboxylate in aged-impaired rats was studied using a RAM task. Moreover, receptor occupancy by methyl 3,5-diphenylpyridazine-4-carboxylate in α5-containing $GABA_A$ receptor was also studied.

(A) Effect of Methyl 3,5-diphenylpyridazine-4-carboxylate in Aged-Impaired Rats Using a Radial Arm Maze (RAM) Behavioral Task The effects of methyl 3,5-diphenylpyridazine-4-carboxylate on the in vivo spatial memory retention of aged-impaired (AI) rats were assessed in a Radial Arm Maze (RAM) behavioral task using vehicle control and four different dosage levels of methyl 3,5-diphenylpyridazine-4-carboxylate (0.1 mg/kg, 0.3 mg/kg, 1 mg/kg and 3 mg/kg, ip). RAM behavioral tasks were performed on eight AI rats. All five treatment conditions (vehicle and four dosage levels) were tested on all eight rats.

The RAM apparatus used consisted of eight equidistantly-spaced arms. An elevated maze arm (7 cm width×75 cm length) projected from each facet of an octagonal center platform (30 cm diameter, 51.5 cm height). Clear side walls on the arms were 10 cm high and were angled at 65° to form a trough. A food well (4 cm diameter, 2 cm deep) was located at the distal end of each arm. Froot Loops™ (Kellogg Company) were used as rewards. Blocks constructed of Plexiglas™ (30 cm height×12 cm width) could be positioned to prevent entry to any arm. Numerous extra maze cues surrounding the apparatus were also provided.

The AI rats were initially subjected to a pre-training test (Chappell et al. *Neuropharmacology* 37: 481-487, 1998). The pre-training test consisted of a habituation phase (4 days), a training phase on the standard win-shift task (18 days) and another training phase (14 days) in which a brief delay was imposed between presentation of a subset of arms designated by the experimenter (e.g., 5 arms available and 3 arms blocked) and completion of the eight-arm win-shift task (i.e., with all eight arms available).

In the habituation phase, rats were familiarized to the maze for an 8-minute session on four consecutive days. In each of these sessions, food rewards were scattered on the RAM, initially on the center platform and arms and then progressively confined to the arms. After this habituation phase, a standard training protocol was used, in which a food pellet was located at the end of each arm. Rats received one trial each day for 18 days. Each daily trial terminated when all eight food pellets had been obtained or when either 16 choices were made or 15 minutes had elapsed. After completion of this training phase, a second training phase was carried out in which the memory demand was increased by imposing a brief delay during the trial. At the beginning of each trial, three arms of the eight-arm maze were blocked. Rats were allowed to obtain food on the five arms to which access was permitted during this initial "information phase" of the trial. Rats were then removed from the maze for 60 seconds, during which time the barriers on the maze were removed, thus allowing access to all eight arms. Rats were then placed back onto the center platform and allowed to obtain the remaining food rewards during this "retention test" phase of the trial. The identity and configuration of the blocked arms varied across trials.

The number of "errors" the AI rats made during the retention test phase was tracked. An error occurred in the trial if the rats entered an arm from which food had already been retrieved in the pre-delay component of the trial, or if the rat re-visited an arm in the post-delay session that it had already visited.

After completion of the pre-training test, rats were subjected to trials with more extended delay intervals, i.e., a two-hour delay, between the information phase (presentation with some blocked arms) and the retention test (presentation of all arms). During the delay interval, rats remained off to the side of the maze in the testing room, on carts in their individual home cages. AI rats were pretreated 30-40 minutes before daily trials with a one-time shot of the following five conditions: 1) vehicle control—5% dimethyl sulfoxide, 25% polyethylene glycol 300 and 70% distilled water; 2) methyl 3,5-diphenylpyridazine-4-carboxylate at 0.1 mg/kg; 3) methyl 3,5-diphenylpyridazine-4-carboxylate at 0.3 mg/kg; 4) methyl 3,5-diphenylpyridazine-4-carboxylate at 1 mg/kg); and 5) methyl 3,5-diphenylpyridazine-4-carboxylate at 3 mg/kg; through intraperitoneal (i.p.) injection. Injections were given every other day with intervening washout days. Each AI rat was treated with all five conditions within the testing period. To counterbalance any potential bias, drug effect was assessed using ascending-descending dose series, i.e., the dose series was given first in an ascending order and then repeated in a descending order. Therefore, each dose had two determinations.

Parametric statistics (paired t-tests) was used to compare the retention test performance of the AI rats in the two-hour delay version of the RAM task in the context of different doses of methyl 3,5-diphenylpyridazine-4-carboxylate and vehicle control (see FIG. 1). The average numbers of errors that occurred in the trials were significantly fewer with methyl 3,5-diphenylpyridazine-4-carboxylate treatment of 3 mg/kg (average no. of errors±standard error of the mean (SEM)=1.31±0.40) than using vehicle control (average no. of errors±SEM=3.13±0.62). Relative to vehicle control treatment, methyl 3,5-diphenylpyridazine-4-carboxylate significantly improved memory performance at 3 mg/kg ($t(7)=4.233$, $p=0.004$).

The therapeutic dose of 3 mg/kg became ineffective when the AI rats were concurrently treated with 0.3 mg/kg of TB21007, a α5-containing $GABA_A$ R inverse agonist. The average numbers of errors made by rats with the combined TB21007/methyl 3,5-diphenylpyridazine-4-carboxylate treatment (0.3 mg/kg TB21007 with 3 mg/kg methyl 3,5-diphenylpyridazine-4-carboxylate) was 2.88±1.32, and was no different from rats treated with vehicle control (3.13±1.17 average errors). Thus, the effect of methyl 3,5-diphenylpyridazine-4-carboxylate on spatial memory is a $GABA_A$ α5 receptor-dependent effect (see FIG. 1).

(B) Effect of Methyl 3,5-diphenylpyridazine-4-carboxylate on α5-containing $GABA_A$ Receptor Occupancy Animals Adult male Long Evans rats (265-295 g, Charles River, Portage, MI, n=4/group) were used for $GABA_A$α5 receptor occupancy studies. Rats were individually housed in ventilated stainless-steel racks on a 12:12 light/dark cycle. Food and water were available ad libitum. In additional studies to evaluate compound exposures at behaviorally active doses, young or aged Long Evan rats (n=2-4/group) were used for these studies.

Compounds

Ro 15-4513 was used as a receptor occupancy (RO) tracer for $GABA_A$α5 receptor sites in the hippocampus and cerebellum. Ro 15-4513 was chosen as the tracer based on its selectivity for $GABA_A$α5 receptors relative to other alpha subunit containing $GABA_A$ receptors and because it has been successfully used for $GABA_A$α5 RO studies in animals and humans (see, e.g., Lingford-Hughes et al., *J. Cereb. Blood Flow Metab.* 22:878-89 (2002); Pym et al, *Br. J Pharmacol.* 146: 817-825 (2005); and Maeda et al., *Synapse* 47: 200-208 (2003)). Ro 15-4513 (1 μg/kg), was dissolved in 25% hydroxyl-propyl beta-cyclodextrin and administered i.v. 20' prior to the RO evaluations. Methyl 3,5-diphenylpyridazine-4-carboxylate (0.1-10 mg/kg) was synthesized by Nox Pharmaceuticals (India) and was dissolved in 25% hydroxyl-propyl beta-cyclodextrin and administered i.v. 15' prior to tracer injection. Compounds were administered in a volume of 0.5 ml/kg except for the highest dose of methyl 3,5-diphenylpyridazine-4-carboxylate (10 mg/kg) which was administered in a volume of 1 ml/kg due to solubility limitations.

Tissue Preparation and Analysis

The rats were sacrificed by cervical dislocation 20' post tracer injection. The whole brain was rapidly removed, and lightly rinsed with sterile water. Trunk blood was collected in EDTA coated eppendorf tubes and stored on wet ice until study completion. Hippocampus and cerebellum were dissected and stored in 1.5 ml eppendorf tubes, and placed on wet ice until tissue extraction. In a drug naïve rat, six cortical brain tissues samples were collected for use in generating blank and standard curve samples.

Acetonitrile containing 0.1% formic acid was added to each sample at a volume of four times the weight of the tissue sample. For the standard curve (0.1-30 ng/g) samples, a calculated volume of standard reduced the volume of acetonitrile. The sample was homogenized (FastPrep-24, Lysing Matrix D; 5.5 n/s, for 60 seconds or 7-8 watts power using sonic probe dismembrator; Fisher Scientific) and centrifuged for 16-minutes at 14,000 rpm. The (100 μl) supernatant solution was diluted by 300 μl of sterile water (pH 6.5). This solution was then mixed thoroughly and analyzed via LC/MS/MS for Ro 15-4513 (tracer) and methyl 3,5-diphenylpyridazine-4-carboxylate.

For plasma exposures, blood samples were centrifuged at 14000 rpm for 16 minutes. After centrifuging, 50 ul of supernatant (plasma) from each sample was added to 200 μl of acetonitrile plus 0.1% formic acid. For standard curve (1-1000 ng/ml) samples, a calculated volume of standard reduced the volume of acetonitrile. Samples were sonicated for 5 minutes in an ultrasonic water bath, followed by centrifugation for 30 minutes, at 16000 RPM. 100 ul of supernatant was removed from each sample vial and placed in a new glass auto sample vial, followed by the addition of 300 μl of sterile water (pH 6.5). This solution was then mixed thoroughly and analyzed via LC/MS/MS for methyl 3,5-diphenylpyridazine-4-carboxylate.

Receptor occupancy was determined by the ratio method which compared occupancy in the hippocampus (a region of high $GABA_A$α5 receptor density) with occupancy in the cerebellum (a region with low $GABA_A$α5 receptor density) and additionally by a high dose of the $GABA_A$α5 negative allosteric modulator L-655,708 (10 mg/kg, i.v.) to define full occupancy.

Vehicle administration followed by tracer administration of 1 μg/kg, i.v., of Ro 15-4513 resulted in >5-fold higher levels of Ro 15-4513 in hippocampus (1.93±0.05 ng/g) compared with cerebellum (0.36±0.02 ng/g). Methyl 3,5-diphenylpyridazine-4-carboxylate (0.01-10 mg/kg, i.v.) dose-dependently reduced Ro 15-4513 binding in hippocampus, without affecting cerebellum levels of Ro 15-4513 (FIG. 2) with a dose of 10 mg/kg, i.v., demonstrating >90% occupancy (FIG. 3). Both methods of calculating RO yielding very similar results with ED50 values for methyl 3,5-diphenylpyridazine-4-carboxylate as 1.8 mg/kg or 1.1 mg/kg based on the ratio method or using L-755,608 to define occupancy.

Methyl 3,5-diphenylpyridazine-4-carboxylate exposure was below the quantification limits (BQL) at 0.01 mg/kg, i.v., in both plasma and hippocampus and but was detectable at low levels in hippocampus at 0.1 mg/kg, i.v. (see Table 3). Hippocampal exposure was linear as a 10-fold increase in dose from 0.1 to 1 mg/kg, i.v., resulted in a 12-fold increase in exposure. Increasing the dose from 1 to 10 mg/kg, i.v., only increased the exposure by ~5-fold. Plasma exposure increased 12-fold as the dose increased from 1 to 10 mg/kg, i.v.

TABLE 3

% $GABA_A$ α5 Receptor Occupancy by methyl 3,5-diphenylpyridazine-4-carboxylate (0.01-10 mg/kg, i.v.). Hippocampus and Plasma Exposure of methyl 3,5-diphenylpyridazine-4-carboxylate by Treatment Group in young Long Evans rats.

| Dose (mg/kg, i.v.) | % RO (L-655, 708 Method) (SEM) | % RO (Ratio Method) (SEM) | Plasma ng/mL (SEM) | Hippocampus ng/g (SEM) |
|---|---|---|---|---|
| 0.01 | 19.2 (11.1) | 15.7 (9.1) | BQL | BQL |
| 0.1 | 16.4 (4.9) | 13.4 (4.0) | BQL | 14.6 (3.5) |
| 1 | 38.5 (11.2) | 31.5 (9.1) | 62.8 (6.1) | 180.0 (10.3) |
| 10 | 110.0 (6.6) | 90.2 (5.4) | 763.5 (85.7) | 947.2 (51.3) |

Additional studies were conducted in aged Long-Evans rats in order to determine the exposures at the behaviorally relevant doses in the cognition studies. Exposure in young Long-Evans rats was also determined to bridge with the receptor occupancy studies that were conducted in young Long-Evans rats. Exposures in young and aged Long-Evans rats were relatively similar (Table 4, FIG. 4). Increasing the dose 3-fold from 1 to 3 mg/kg, ip resulted in a greater than dose-proportional increase in exposure in young and aged rats in both hippocampus and plasma with increases ranging from 4.5 to 6.6-fold.

TABLE 4

Hippocampus and Plasma Exposure of methyl 3,5-diphenylpyridazine-4-carboxylate in Young Long Evans Rats by Treatment Group

| Dose (mg/kg, ip) | Young Hippocampus ng/g (SEM) | Young Plasma ng/mL (SEM) | Aged Hippocampus ng/g (SEM) | Aged Plasma ng/mL (SEM) |
|---|---|---|---|---|
| 1 | 25.9 (1.7) | 20.0 (1.4) | 38.8 (21.7) | 45.2 (29.6) |
| 3 | 129.1 (22.4) | 132.9 (19.5) | 177.5 (19.5) | 196 (18.2) |

In the RO studies, an exposure of 180 ng/g in hippocampus (1 mg/kg, i.v.) represented 32-39% receptor occupancy depending on method used to determine RO. This exposure is comparable to that observed in aged rats at 3 mg/kg, i.p., suggesting that 30-40% RO is required for cognitive efficacy in this model.

These studies demonstrated that methyl 3,5-diphenylpyridazine-4-carboxylate produced dose-dependent increase in $GABA_A$ α5 receptor occupancy. Methyl 3,5-diphenylpyridazine-4-carboxylate also demonstrated good brain exposure with brain/plasma ratios>1. The studies further demonstrated that methyl 3,5-diphenylpyridazine-4-carboxylate was producing its cognitive enhancing effects by positive allosteric modulation at the $GABA_A$ α5 subtype receptor.

Example 108: Effect of Ethyl 3-methoxy-7-methyl-9H-benzo[f]imidazo[1,5-a][1,2,4]triazolo[4,3-d][1,4]diazepine-10-carboxylate in Aged-Impaired (AI) Rats Ethyl 3-methoxy-7-methyl-9H-benzo[f]imidazo[1,5-a][1,2,4]triazolo[4,3-d][1,4]diazepine-10-carboxylate, corresponding to compound number 49 in Achermann et al. *Bioorg. Med. Chem. Lett.*, 19:5746-5752 (2009), is a selective α5-containing $GABA_AR$ agonist.

The effect of ethyl 3-methoxy-7-methyl-9H-benzo[f]imidazo[1,5-a][1,2,4]triazolo[4,3-d][1,4]diazepine-10-carboxylate on the in vivo spatial memory retention of aged-impaired (AI) rats was assessed in a Radial Arm Maze (RAM) behavioral task that is essentially similar to the task as described in Example 107 (A), using vehicle control (25% cyclodextrin, which was tested 3 times: at the beginning, middle and end of ascending/descending series) and six different doses levels (0.1 mg/kg, 0.3 mg/kg, 1 mg/kg, 3 mg/kg, 10 mg/kg and 30 mg/kg, each dose was tested twice) of ethyl 3-methoxy-7-methyl-9H-benzo[f]imidazo[1,5-a][1,2,4]triazolo[4,3-d][1,4]diazepine-10-carboxylate. The same experiment was repeated using the same vehicle control and doses of ethyl 3-methoxy-7-methyl-9H-benzo[f]imidazo[1,5-a][1,2,4]triazolo[4,3-d][1,4]diazepine-10-carboxylate, where the vehicle control was tested 5 times, the 3 mg/kg dose of ethyl 3-methoxy-7-methyl-9H-benzo[f]imidazo[1,5-a][1,2,4]triazolo[4,3-d][1,4]diazepine-10-carboxylate was tested 4 times, and the other doses of ethyl 3-methoxy-7-methyl-9H-benzo[f]imidazo[1,5-a][1,2,4]triazolo[4,3-d][1,4]diazepine-10-carboxylate were tested twice.

Parametric statistics (paired t-tests) was used to compare the retention test performance of the AI rats in the four-hour delay version of the RAM task in the context of different doses of ethyl 3-methoxy-7-methyl-9H-benzo[f]imidazo[1,5-a][1,2,4]triazolo[4,3-d][1,4]diazepine-10-carboxylate and vehicle control (see FIG. 5). Relative to vehicle control treatment, ethyl 3-methoxy-7-methyl-9H-benzo[f]imidazo[1,5-a][1,2,4]triazolo[4,3-d][1,4]diazepine-10-carboxylate significantly improved memory performance at 3 mg/kg ($t(7)=4.13$, $p=0.004$, or $t(7)=3.08$, $p=0.018$) and at 10 mg/kg ($t(7)$—2.82, p—0.026).

The effect of ethyl 3-methoxy-7-methyl-9H-benzo[f]imidazo[1,5-a][1,2,4]triazolo[4,3-d][1,4]diazepine-10-carboxylate on α5-containing $GABA_A$ receptor occupancy was also studied following a procedure that is essentially similar to the one as described in Example 107(B) (see above). This study demonstrated that ethyl 3-methoxy-7-methyl-9H-benzo[f]imidazo[1,5-a][1,2,4]triazolo[4,3-d][1,4]diazepine-10-carboxylate (0.01-10 mg/kg, i.v.) reduced Ro 15-4513 binding in hippocampus, without affecting cerebellum levels of Ro 15-4513 (FIG. 6) with a dose of 10 mg/kg, i.v., demonstrating >90% occupancy (FIG. 7).

Example 109: Effect of 6,6 dimethyl-3-(3-hydroxypropyl)thio-1-(thiazol-2-yl)-6,7-dihydro-2-benzothiophen-4(5H)-one in Aged-Impaired Rats Using a Morris Water Maze Behavioral Task 6,6 dimethyl-3-(3-hydroxypropyl)thio-1-(thiazol-2-yl)-6,7-dihydro-2-benzothiophen-4(5H)-one, corresponding to compound 44 in Chambers et al. *J. Med. Chem.* 46:2227-2240 (2003) is a selective α5-containing $GABA_A$ R agonist.

The effects of 6,6 dimethyl-3-(3-hydroxypropyl)thio-1-(thiazol-2-yl)-6,7-dihydro-2-benzothiophen-4(5H)-one on the in vivo spatial memory retention of aged-impaired (AI) rats were assessed in a Morris water maze behavioral task.

A water maze is a pool surrounded with a novel set of patterns relative to the maze. The training protocol for the water maze may be based on a modified water maze task that has been shown to be hippocampal-dependent (de Hoz et al., *Eur. J. Neurosci.*, 22:745-54, 2005; Steele and Morris, *Hippocampus* 9:118-36, 1999).

Cognitively impaired aged rats were implanted unilaterally with a cannula into the lateral ventricle. Stereotaxic coordinates were 1.0 mm posterior to bregma, 1.5 mm lateral to midline, and 3.5 mm ventral to the skull surface. After about a week of recovery, the rats were pre-trained in a water maze for 2 days (6 trials per day) to locate a submerged escape platform hidden underneath the surface of the pool, in which the escape platform location varied from day to day. No intracerebroventricular (ICV) infusion was given during pre-training.

After pre-training, rats received ICV infusion of either 100 μg 6,6 dimethyl-3-(3-hydroxypropyl)thio-1-(thiazol-2-yl)-6,7-dihydro-2-benzothiophen-4(5H)-one (n=6) in 5 μl DMSO or vehicle DMSO (n=5) 40 min prior to water maze training and testing. Training consisted of 8 trials per day for 2 days where the hidden escape platform remained in the same location. Rats were given 60 seconds to locate the platform with a 60 seconds inter-trial interval. The rats were given a probe test (120 seconds) 24 hr. after the end of training where the escape platform was removed. During the training, there were 4 blocks, where each block had 4 training trials.

Rats treated with vehicle and 6,6 dimethyl-3-(3-hydroxypropyl)thio-1-(thiazol-2-yl)-6,7-dihydro-2-benzothiophen-4 (5H)-one found the escape platform about the same time at the beginning of training (block 1). In this block of training, rats treated with vehicle and 6,6 dimethyl-3-(3-hydroxypropyl)thio-1-(thiazol-2-yl)-6,7-dihydro-2-benzothiophen-4 (5H)-one both spent about 24 seconds to find the escape platform. However, rats treated with 6,6 dimethyl-3-(3-hydroxypropyl)thio-1-(thiazol-2-yl)-6,7-dihydro-2-benzothiophen-4(5H)-one were able to find the platform more proficiently (i.e., quicker) at the end of training (block 4) than those treated with vehicle alone. In block 4, rats treated with 6,6 dimethyl-3-(3-hydroxypropyl)thio-1-(thiazol-2-yl)-6,7-dihydro-2-benzothiophen-4(5H)-one spent about 9.6 seconds to find the escape platform, while rats treated with vehicle spent about 19.69 seconds. These results suggest that 6,6 dimethyl-3-(3-hydroxypropyl)thio-1-(thiazol-2-yl)-6,7-dihydro-2-benzothiophen-4(5H)-one improved the learning of the water maze task in rats (see FIG. 8(A)).

During a test trial 24 hr. after training, the escape platform was removed. The search/swim pattern of the rats was used to measure whether the rats remember where the escape platform was located during pre-trial training in order to test for the long-term memory of the rats. In this trial, "target annulus" is a designated area 1.5 times the size of the escape platform around the area where the platform was located during pre-trial training. "Opposite annulus" is a control area of the same size as the size of the target annulus, which is located opposite to the target annulus in the pool. If the rats had good long term memory, they would tend to search in the area surrounding the location where the platform was during the pre-trial training (i.e., the "target" annulus; and not the "opposite" annulus). "Time in annulus" is the amount of time in seconds that the rat spent in the target or opposite annulus area. "Number (#) of crossings" in annulus is the number of times the rat swam across the target or opposite annulus area.

Rats received vehicle spent the same amount of time in the target annulus and opposite annulus, indicating that these rats did not seem to remember where the platform was during the pre-trial training. By contrast, rats treated with 6,6 dimethyl-3-(3-hydroxypropyl)thio-1-(thiazol-2-yl)-6,7-dihydro-2-benzothiophen-4(5H)-one spent significantly more time in the target annulus, and crossed the "target annulus" more often, as compared to the time they spent in, or the number of times they crossed the "opposite annulus". These results suggest that 6,6 dimethyl-3-(3-hydroxypropyl)thio-1-(thiazol-2-yl)-6,7-dihydro-2-benzothiophen-4(5H)-one improved the long-term memory of rats in the water maze task (see, FIGS. 8(B) and 8(C)).

Compounds of the present invention demonstrated positive allosteric modulatory effect on the $GABA_A$ α5 receptor (See, e.g., Example 106). These compounds will enhance the effects of GABA at the $GABA_A$ α5 receptor. Therefore, compounds of the present invention should produce cognitive enhancing effects in aged-impaired animals (such as rats), similar to the effects produced by other $GABA_A$ α5 receptor selective agonists, such as methyl 3,5-diphenylpyridazine-4-carboxylate, ethyl 3-methoxy-7-methyl-9H-benzo[f]imidazo[1,5-a][1,2,4]triazolo[4,3-d][1,4]diazepine-10-carboxylate, and 6,6 dimethyl-3-(3-hydroxypropyl)thio-1-(thiazol-2-yl)-6,7-dihydro-2-benzothiophen-4(5H)-one (See, e.g., Examples 28-30).

The invention claimed is:

1. A compound selected from the group consisting of:

318

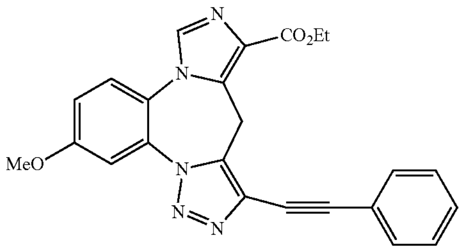

344

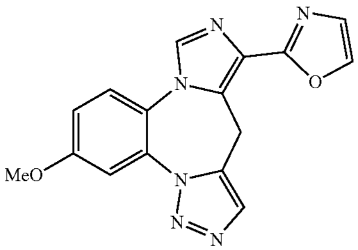 [SMILES: COc1ccc2c(c1)-n1nncc1Cc1c(-c3ncco3)ncn1-2]

347

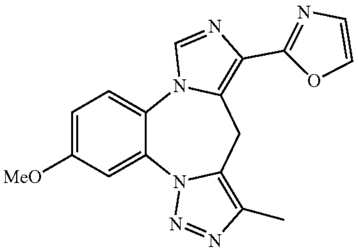 [SMILES: COc1ccc2c(c1)-n1nnc(C)c1Cc1c(-c3ncco3)ncn1-2]

356

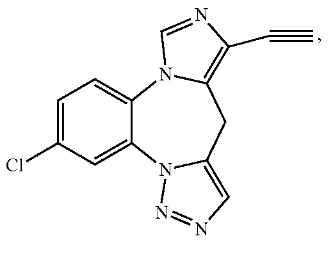 [SMILES: C#Cc1ncn2c1Cc1cnnn1-c1cc(Cl)ccc1-2]

-continued
357
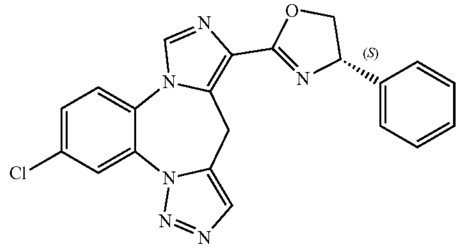
358
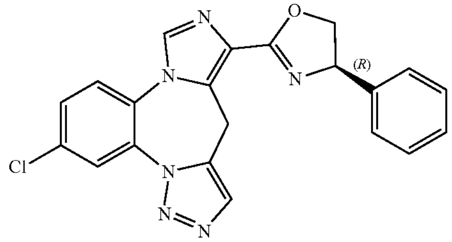
359
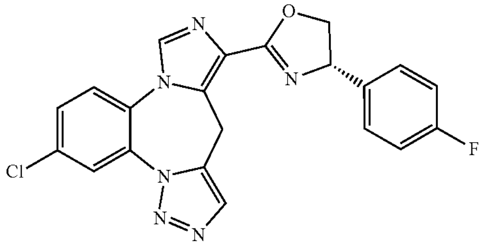 [SMILES: Fc1ccc([C@H]2COC(c3ncn4c3Cc3cnnn3-c3cc(Cl)ccc3-4)=N2)cc1]
360
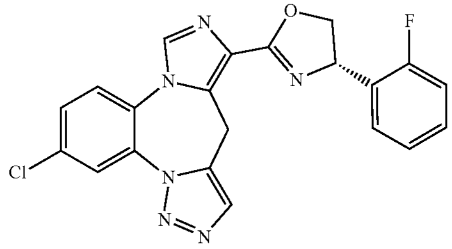 [SMILES: Fc1ccccc1[C@H]1COC(c2ncn3c2Cc2cnnn2-c2cc(Cl)ccc2-3)=N1]
361
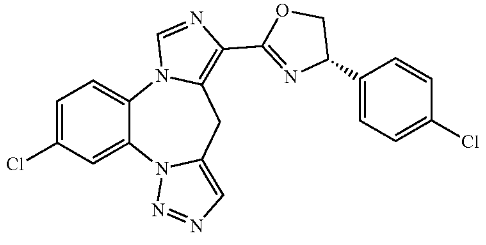 [SMILES: Clc1ccc([C@H]2COC(c3ncn4c3Cc3cnnn3-c3cc(Cl)ccc3-4)=N2)cc1]
362
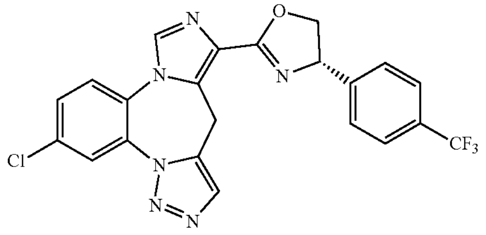 [SMILES: FC(F)(F)c1ccc([C@H]2COC(c3ncn4c3Cc3cnnn3-c3cc(Cl)ccc3-4)=N2)cc1]
-continued
363
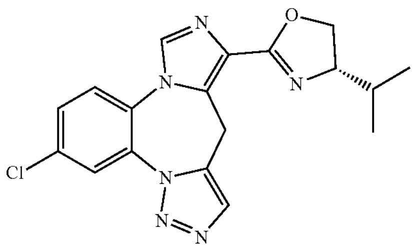 [SMILES: CC(C)[C@H]1COC(c2ncn3c2Cc2cnnn2-c2cc(Cl)ccc2-3)=N1]
364
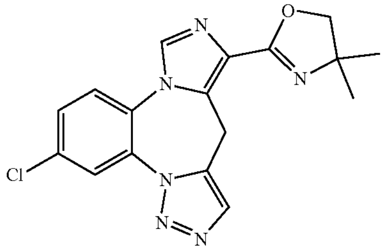 [SMILES: CC1(C)COC(c2ncn3c2Cc2cnnn2-c2cc(Cl)ccc2-3)=N1]
365
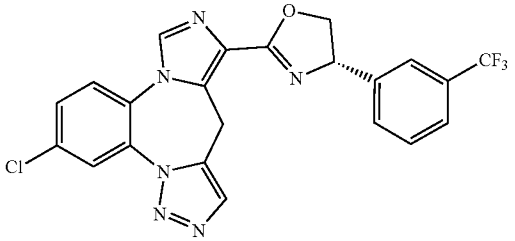 [SMILES: FC(F)(F)c1cccc([C@H]2COC(c3ncn4c3Cc3cnnn3-c3cc(Cl)ccc3-4)=N2)c1]
366
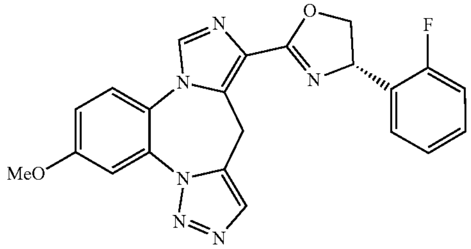 [SMILES: COc1ccc2c(c1)-n1nncc1Cc1c(C3=N[C@@H](c4ccccc4F)CO3)ncn1-2]
367
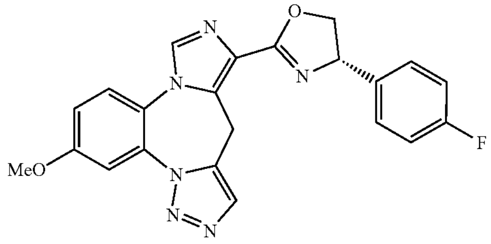 [SMILES: COc1ccc2c(c1)-n1nncc1Cc1c(C3=N[C@@H](c4ccc(F)cc4)CO3)ncn1-2]
368
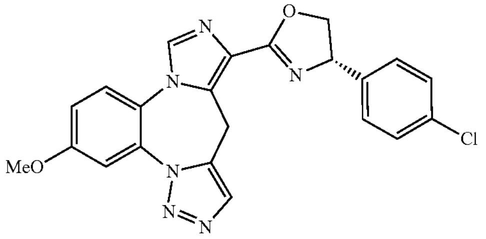 [SMILES: COc1ccc2c(c1)-n1nncc1Cc1c(C3=N[C@@H](c4ccc(Cl)cc4)CO3)ncn1-2]

-continued
369
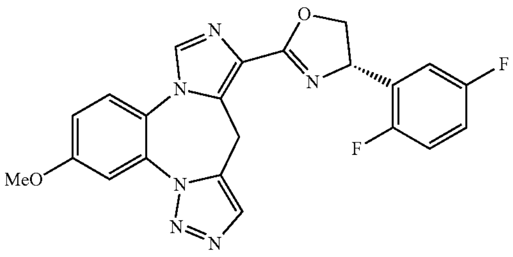 [SMILES: COc1ccc2c(c1)-n1nncc1Cc1c(C3=N[C@@H](c4cc(F)ccc4F)CO3)ncn1-2]
370
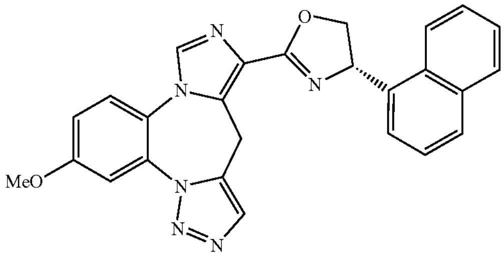 [SMILES: COc1ccc2c(c1)-n1nncc1Cc1c(C3=N[C@@H](c4cccc5ccccc45)CO3)ncn1-2]
371
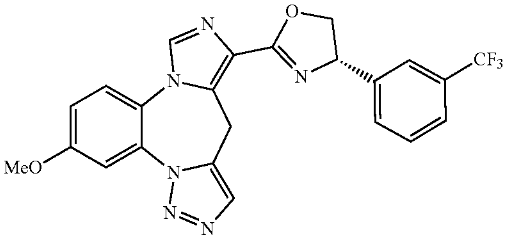 [SMILES: COc1ccc2c(c1)-n1nncc1Cc1c(C3=N[C@@H](c4cccc(C(F)(F)F)c4)CO3)ncn1-2]
372
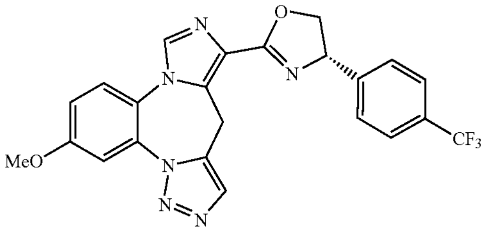 [SMILES: COc1ccc2c(c1)-n1nncc1Cc1c(C3=N[C@@H](c4ccc(C(F)(F)F)cc4)CO3)ncn1-2]
373
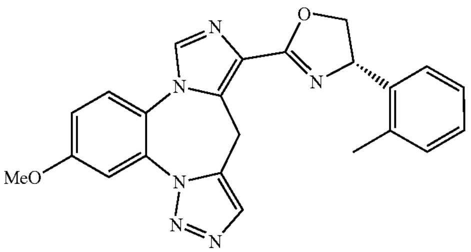 [SMILES: COc1ccc2c(c1)-n1nncc1Cc1c(C3=N[C@@H](c4ccccc4C)CO3)ncn1-2]
374
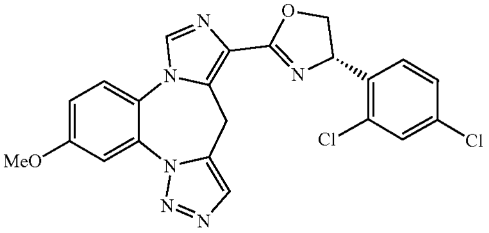 [SMILES: COc1ccc2c(c1)-n1nncc1Cc1c(C3=N[C@@H](c4ccc(Cl)cc4Cl)CO3)ncn1-2]
-continued
375
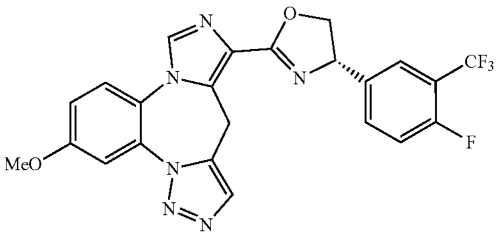 [SMILES: COc1ccc2c(c1)-n1nncc1Cc1c(C3=N[C@@H](c4ccc(F)c(C(F)(F)F)c4)CO3)ncn1-2]
376
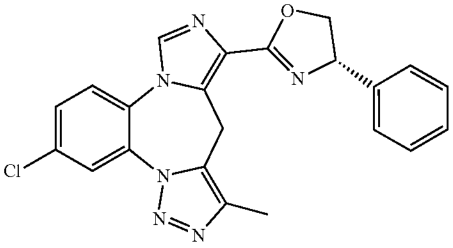 [SMILES: Cc1nnn2c1Cc1c(C3=N[C@@H](c4ccccc4)CO3)ncn1-c1ccc(Cl)cc1-2]
377
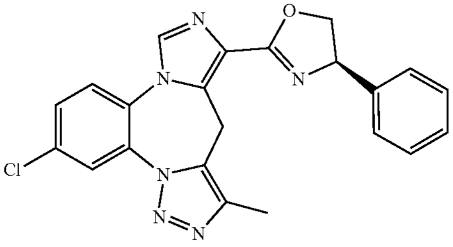 [SMILES: Cc1nnn2c1Cc1c(C3=N[C@H](c4ccccc4)CO3)ncn1-c1ccc(Cl)cc1-2]
378
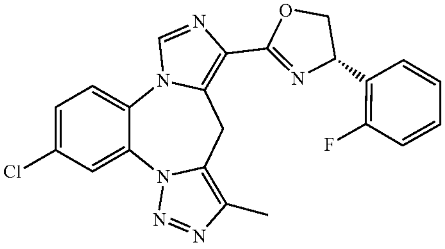 [SMILES: Cc1nnn2c1Cc1c(C3=N[C@@H](c4ccccc4F)CO3)ncn1-c1ccc(Cl)cc1-2]
379
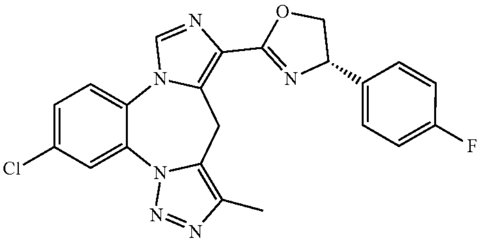 [SMILES: Cc1nnn2c1Cc1c(C3=N[C@@H](c4ccc(F)cc4)CO3)ncn1-c1ccc(Cl)cc1-2]
380
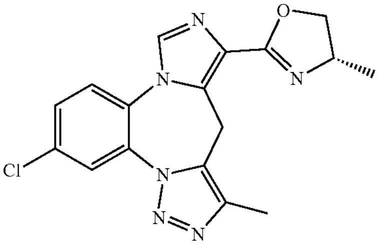 [SMILES: Cc1nnn2c1Cc1c(C3=N[C@@H](C)CO3)ncn1-c1ccc(Cl)cc1-2]

-continued
381
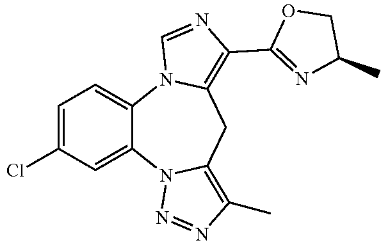 [SMILES: Cc1nnn2c1Cc1c(C3=N[C@H](C)CO3)ncn1-c1ccc(Cl)cc1-2]
382
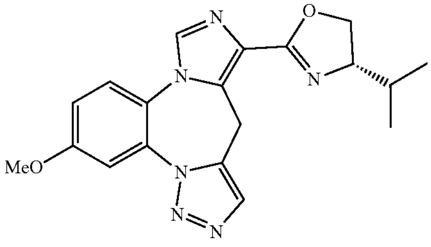 [SMILES: COc1ccc2c(c1)-n1nncc1Cc1c(C3=N[C@@H](C(C)C)CO3)ncn1-2]
383
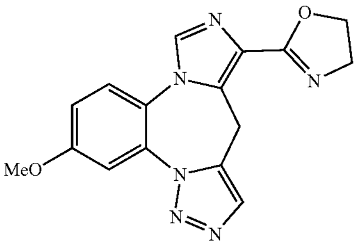 [SMILES: COc1ccc2c(c1)-n1nncc1Cc1c(C3=NCCO3)ncn1-2]
385
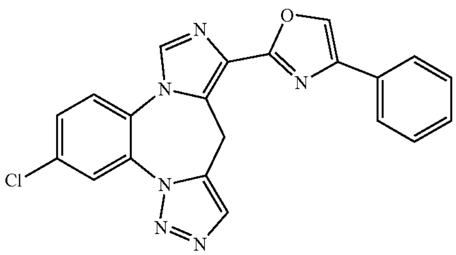 [SMILES: Clc1ccc2c(c1)-n1nncc1Cc1c(-c3nc(-c4ccccc4)co3)ncn1-2]
386
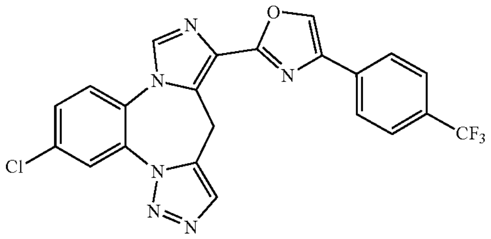 [SMILES: FC(F)(F)c1ccc(-c2coc(-c3ncn4c3Cc3cnnn3-c3cc(Cl)ccc3-4)n2)cc1]
387
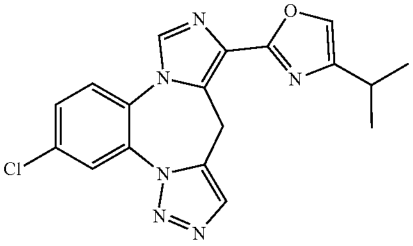 [SMILES: CC(C)c1coc(-c2ncn3c2Cc2cnnn2-c2cc(Cl)ccc2-3)n1]
-continued
388
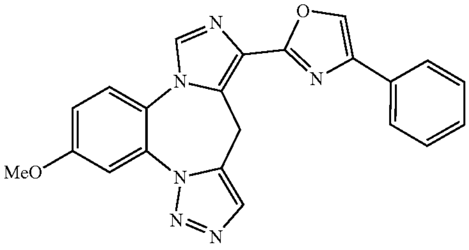 [SMILES: COc1ccc2c(c1)-n1nncc1Cc1c(-c3nc(-c4ccccc4)co3)ncn1-2]
389
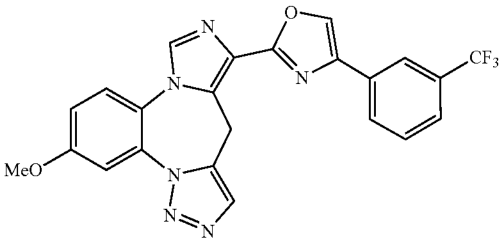 [SMILES: COc1ccc2c(c1)-n1nncc1Cc1c(-c3nc(-c4cccc(C(F)(F)F)c4)co3)ncn1-2]
390
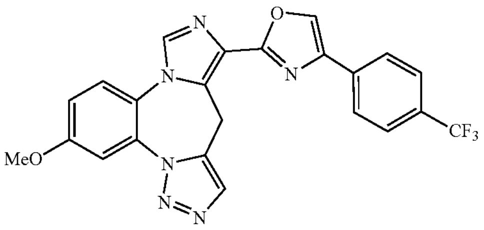 [SMILES: COc1ccc2c(c1)-n1nncc1Cc1c(-c3nc(-c4ccc(C(F)(F)F)cc4)co3)ncn1-2]
391
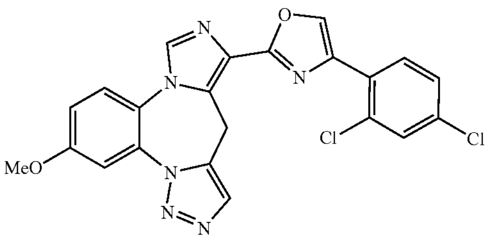 [SMILES: COc1ccc2c(c1)-n1nncc1Cc1c(-c3nc(-c4ccc(Cl)cc4Cl)co3)ncn1-2]
392
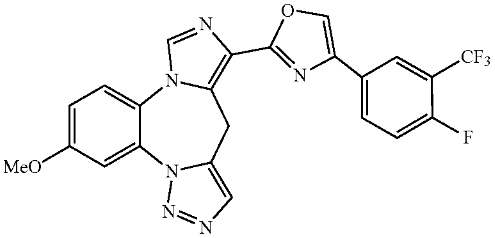 [SMILES: COc1ccc2c(c1)-n1nncc1Cc1c(-c3nc(-c4ccc(F)c(C(F)(F)F)c4)co3)ncn1-2]
393
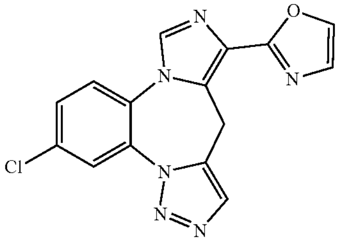 [SMILES: Clc1ccc2c(c1)-n1nncc1Cc1c(-c3ncco3)ncn1-2]

-continued
394
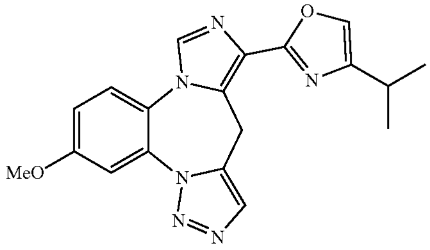 [SMILES: COc1ccc2c(c1)-n1nncc1Cc1c(-c3nc(C(C)C)co3)ncn1-2]
395
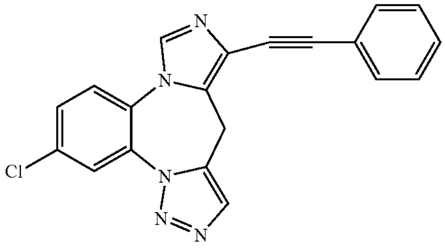
396
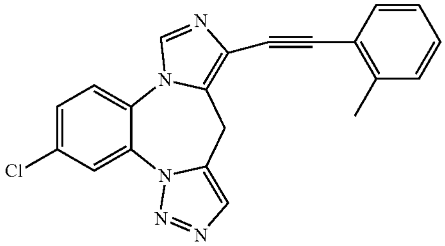 [SMILES: Cc1ccccc1C#Cc1ncn2c1Cc1cnnn1-c1cc(Cl)ccc1-2]
397
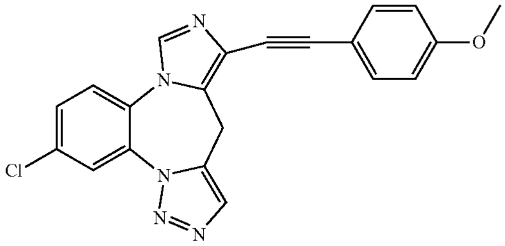 [SMILES: COc1ccc(C#Cc2ncn3c2Cc2cnnn2-c2cc(Cl)ccc2-3)cc1]
398
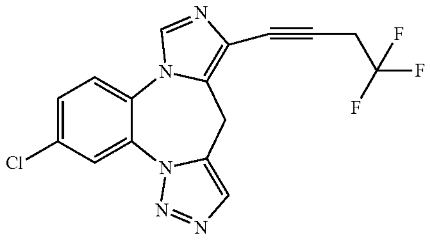 [SMILES: FC(F)(F)CC#Cc1ncn2c1Cc1cnnn1-c1cc(Cl)ccc1-2]
399
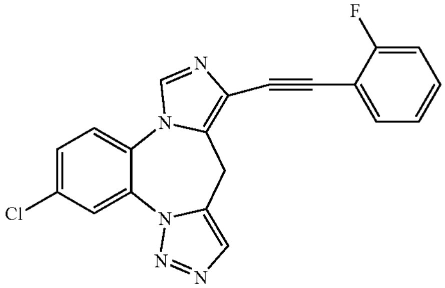 [SMILES: Fc1ccccc1C#Cc1ncn2c1Cc1cnnn1-c1cc(Cl)ccc1-2]
-continued
400
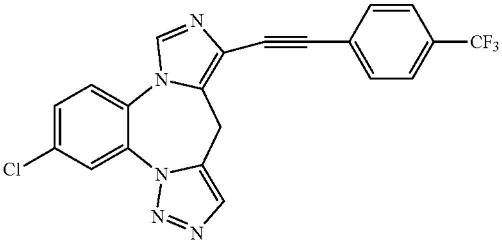 [SMILES: FC(F)(F)c1ccc(C#Cc2ncn3c2Cc2cnnn2-c2cc(Cl)ccc2-3)cc1]
403
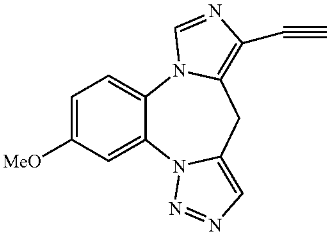 [SMILES: C#Cc1ncn2c1Cc1cnnn1-c1cc(OC)ccc1-2]
404
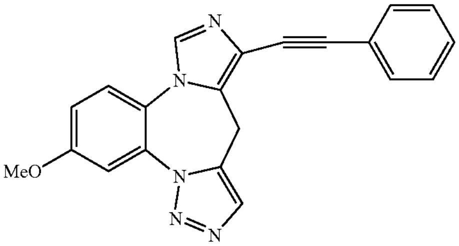
405
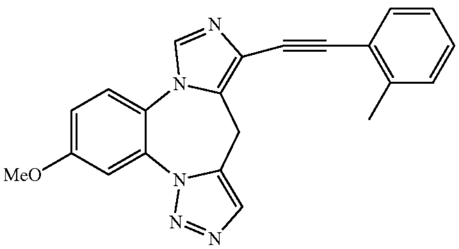 [SMILES: COc1ccc2c(c1)-n1nncc1Cc1c(C#Cc3ccccc3C)ncn1-2]
406
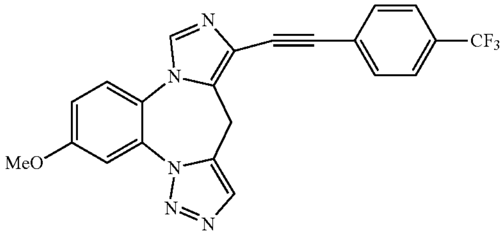 [SMILES: COc1ccc2c(c1)-n1nncc1Cc1c(C#Cc3ccc(C(F)(F)F)cc3)ncn1-2]
409
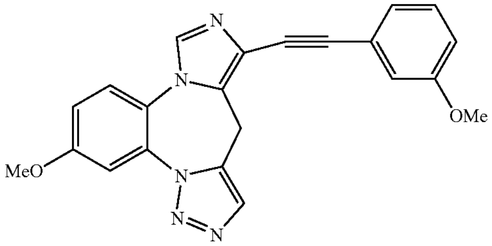 [SMILES: COc1cccc(C#Cc2ncn3c2Cc2cnnn2-c2cc(OC)ccc2-3)c1]

-continued
410
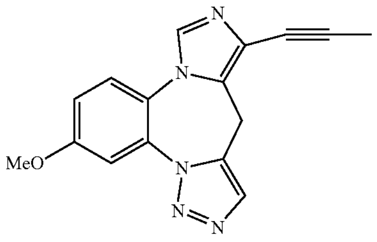 [SMILES: CC#Cc1ncn2c1Cc1cnnn1-c1cc(OC)ccc1-2]
411
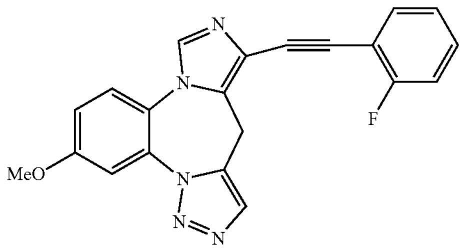 [SMILES: COc1ccc2c(c1)-n1nncc1Cc1c(C#Cc3ccccc3F)ncn1-2]
412
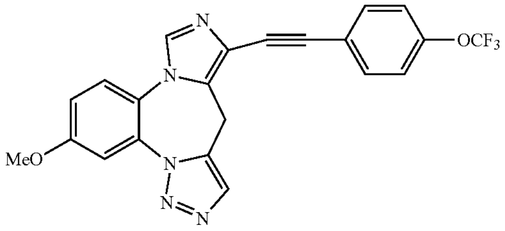
413
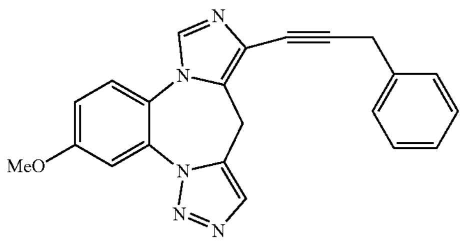 [SMILES: COc1ccc2c(c1)-n1nncc1Cc1c(C#CCc3ccccc3)ncn1-2]
414
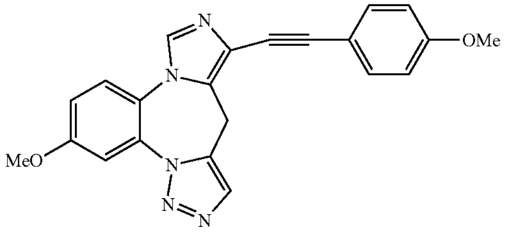 [SMILES: COc1ccc(C#Cc2ncn3c2Cc2cnnn2-c2cc(OC)ccc2-3)cc1]
415
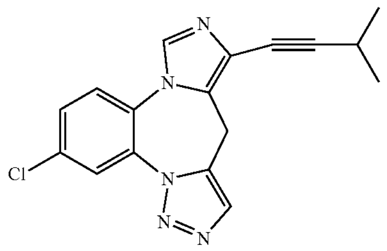 [SMILES: CC(C)C#Cc1ncn2c1Cc1cnnn1-c1cc(Cl)ccc1-2]
-continued
416
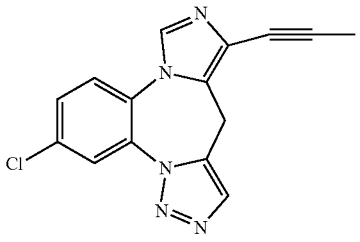 [SMILES: CC#Cc1ncn2c1Cc1cnnn1-c1cc(Cl)ccc1-2]
417
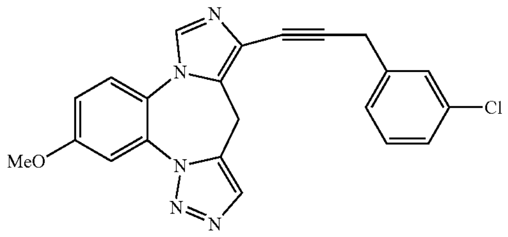 [SMILES: COc1ccc2c(c1)-n1nncc1Cc1c(C#CCc3cccc(Cl)c3)ncn1-2]
418
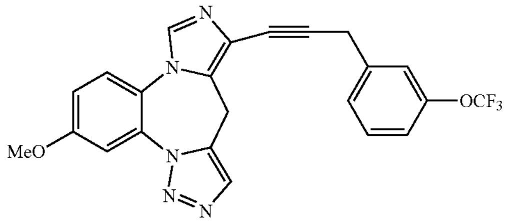 [SMILES: COc1ccc2c(c1)-n1nncc1Cc1c(C#CCc3cccc(OC(F)(F)F)c3)ncn1-2]
419
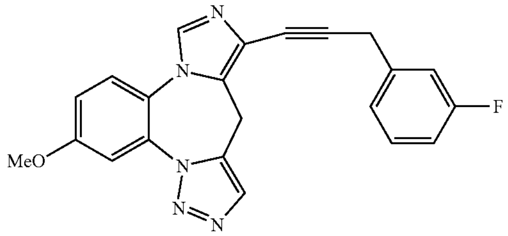 [SMILES: COc1ccc2c(c1)-n1nncc1Cc1c(C#CCc3cccc(F)c3)ncn1-2]
420
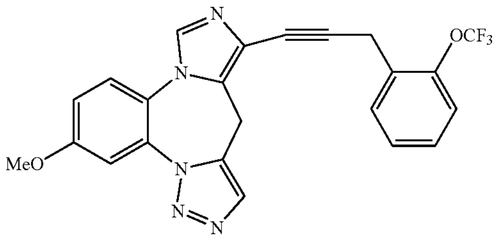 [SMILES: COc1ccc2c(c1)-n1nncc1Cc1c(C#CCc3ccccc3OC(F)(F)F)ncn1-2]
424
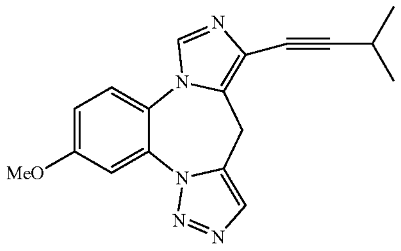 [SMILES: COc1ccc2c(c1)-n1nncc1Cc1c(C#CC(C)C)ncn1-2]

-continued
425
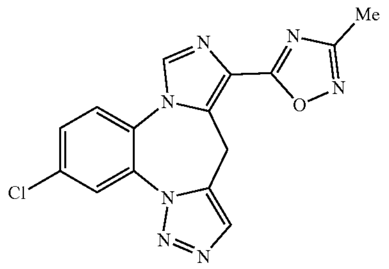 [SMILES: Cc1noc(-c2ncn3c2Cc2cnnn2-c2cc(Cl)ccc2-3)n1]
426
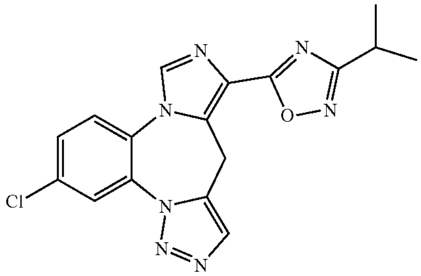 [SMILES: CC(C)c1noc(-c2ncn3c2Cc2cnnn2-c2cc(Cl)ccc2-3)n1]
436
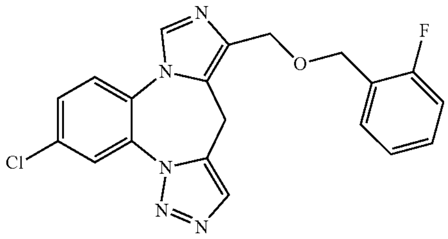 [SMILES: Fc1ccccc1COCc1ncn2c1Cc1cnnn1-c1cc(Cl)ccc1-2]
437
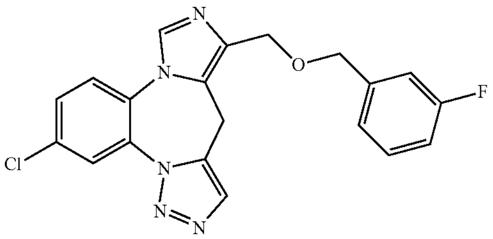 [SMILES: Fc1cccc(COCc2ncn3c2Cc2cnnn2-c2cc(Cl)ccc2-3)c1]
438
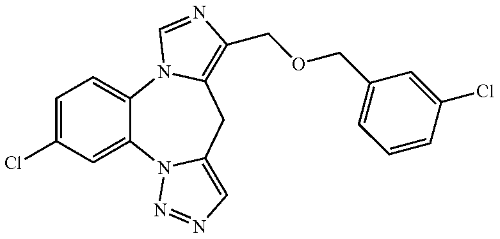 [SMILES: Clc1cccc(COCc2ncn3c2Cc2cnnn2-c2cc(Cl)ccc2-3)c1]
439
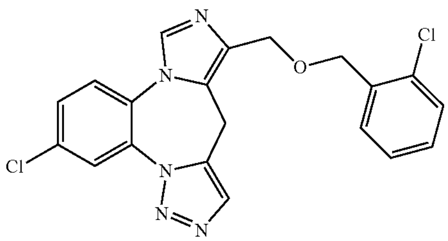 [SMILES: Clc1ccc2c(c1)-n1nncc1Cc1c(COCc3ccccc3Cl)ncn1-2]
-continued
440
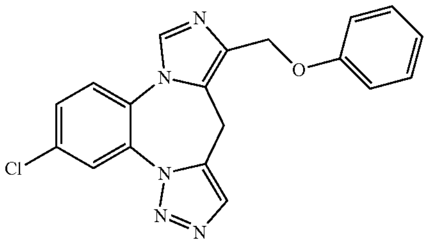 [SMILES: Clc1ccc2c(c1)-n1nncc1Cc1c(COc3ccccc3)ncn1-2]
441
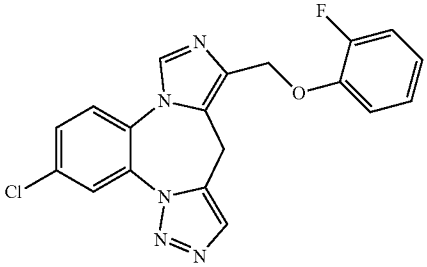 [SMILES: Fc1ccccc1OCc1ncn2c1Cc1cnnn1-c1cc(Cl)ccc1-2]
442
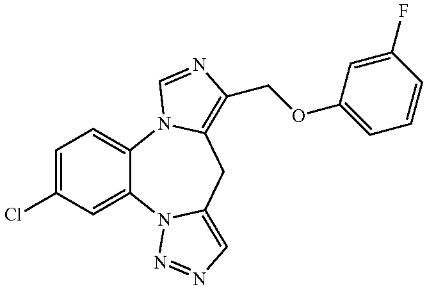 [SMILES: Fc1cccc(OCc2ncn3c2Cc2cnnn2-c2cc(Cl)ccc2-3)c1]
443
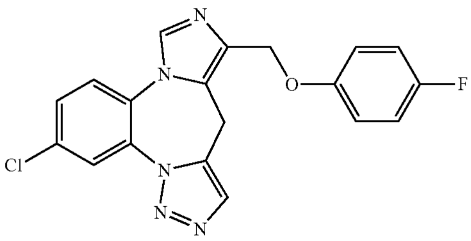 [SMILES: Fc1ccc(OCc2ncn3c2Cc2cnnn2-c2cc(Cl)ccc2-3)cc1]
448
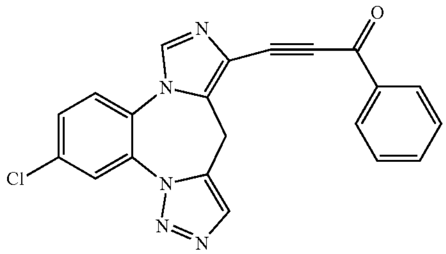 [SMILES: O=C(C#Cc1ncn2c1Cc1cnnn1-c1cc(Cl)ccc1-2)c1ccccc1]
449
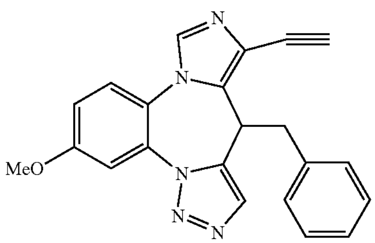 [SMILES: C#Cc1ncn2c1C(Cc1ccccc1)c1cnnn1-c1cc(OC)ccc1-2]

-continued

450

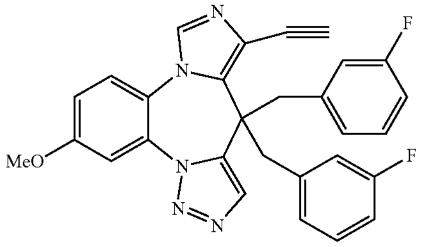 [SMILES: C#Cc1ncn2c1C(Cc1cccc(F)c1)(Cc1cccc(F)c1)c1cnnn1-c1cc(OC)ccc1-2]

451

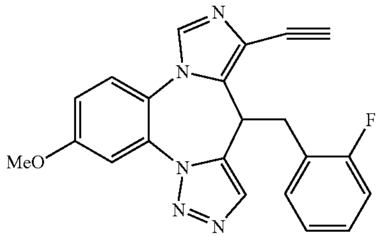 [SMILES: C#Cc1ncn2c1C(Cc1ccccc1F)c1cnnn1-c1cc(OC)ccc1-2]

452

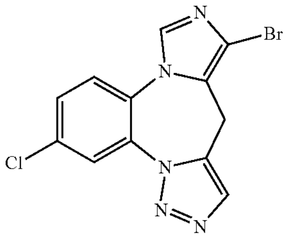 [SMILES: Clc1ccc2c(c1)-n1nncc1Cc1c(Br)ncn1-2]

453

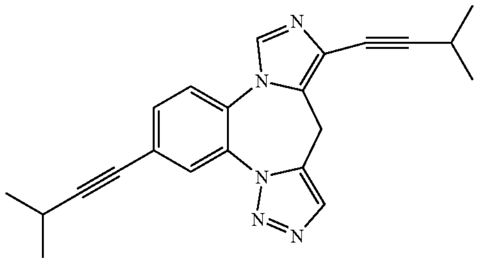 [SMILES: CC(C)C#Cc1ccc2c(c1)-n1nncc1Cc1c(C#CC(C)C)ncn1-2]

and

454

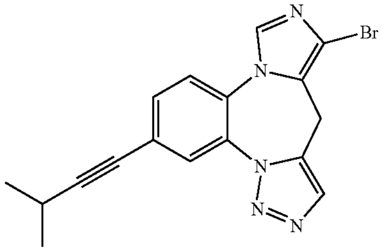 [SMILES: CC(C)C#Cc1ccc2c(c1)-n1nncc1Cc1c(Br)ncn1-2]

or a pharmaceutically acceptable salt, hydrate, solvate, polymorph, isomer, or combination thereof.

2. A pharmaceutical composition comprising a compound according to claim 1, or a pharmaceutically acceptable salt, hydrate, solvate, polymorph, isomer, or combination thereof, in a therapeutically effective amount; and an acceptable carrier, adjuvant or vehicle.

3. A method of treating cognitive impairment associated with a central nervous system (CNS) disorder in a subject in need thereof, comprising administering a compound according to claim 1, or a pharmaceutical composition according to claim 2.

4. The method according to claim 3, wherein the CNS disorder is:

a) age-related cognitive impairment, wherein the age-related cognitive impairment is Mild Cognitive Impairment (AMCI) or amnestic Mild Cognitive Impairment (aMCI); or b) dementia, Alzheimer's disease, schizophrenia, bipolar disorder, amyotrophic lateral sclerosis (ALS), post-traumatic stress disorder (PTSD), mental retardation, Parkinson's disease (PD), autism, compulsive behavior, substance addiction or a disorder associated with cancer therapy.

5. A method of slowing the progression of, alleviating, or ameliorating a brain cancer in a subject in need thereof, comprising administering a compound according to claim 1, or a pharmaceutical composition according to claim 2.

6. A method of treating cognitive impairment associated with a brain cancer in a subject in need thereof, comprising administering a compound according to claim 1, or a pharmaceutical composition according to claim 2.

7. The method according to claim 5, wherein said brain cancer is medulloblastoma.

8. The method according to claim 6, wherein said brain cancer is medulloblastoma.

9. A method of slowing the progression of, alleviating, or ameliorating a brain cancer or treating cognitive impairment associated with a brain cancer in a subject in need thereof, wherein the compound or the pharmaceutical composition comprising the compound is selected from:

1

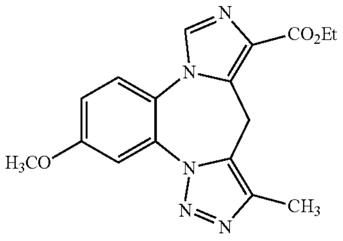 [SMILES: CCOC(=O)c1ncn2c1Cc1c(C)nnn1-c1cc(OC)ccc1-2]

2

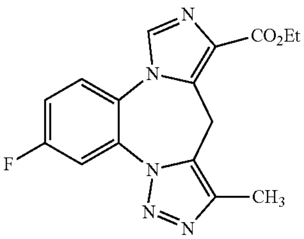 [SMILES: CCOC(=O)c1ncn2c1Cc1c(C)nnn1-c1cc(F)ccc1-2]

3

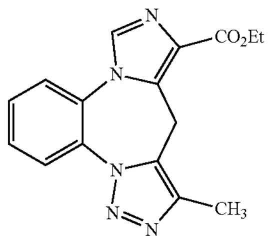 [SMILES: CCOC(=O)c1ncn2c1Cc1c(C)nnn1-c1ccccc1-2]

-continued
4
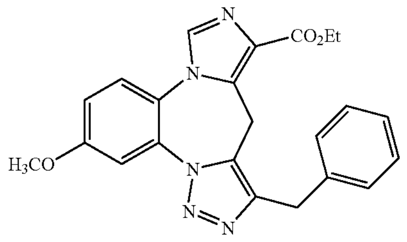 [SMILES: CCOC(=O)c1ncn2c1Cc1c(Cc3ccccc3)nnn1-c1cc(OC)ccc1-2]
5
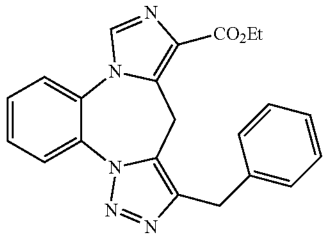 [SMILES: CCOC(=O)c1ncn2c1Cc1c(Cc3ccccc3)nnn1-c1ccccc1-2]
6
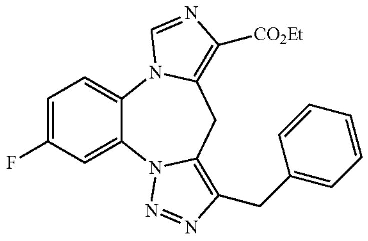 [SMILES: CCOC(=O)c1ncn2c1Cc1c(Cc3ccccc3)nnn1-c1cc(F)ccc1-2]
9
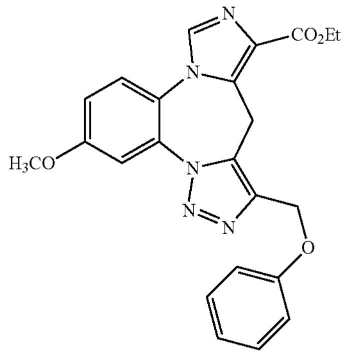 [SMILES: CCOC(=O)c1ncn2c1Cc1c(COc3ccccc3)nnn1-c1cc(OC)ccc1-2]
10
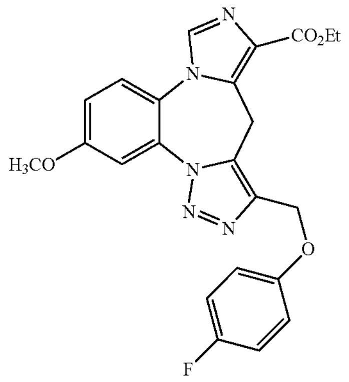 [SMILES: CCOC(=O)c1ncn2c1Cc1c(COc3ccc(F)cc3)nnn1-c1cc(OC)ccc1-2]
-continued
11
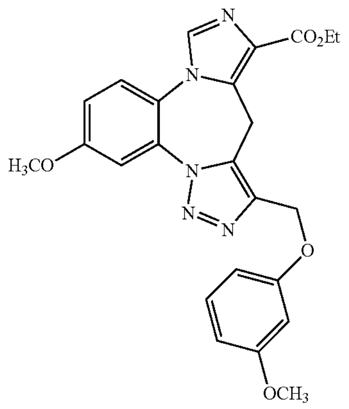 [SMILES: CCOC(=O)c1ncn2c1Cc1c(COc3cccc(OC)c3)nnn1-c1cc(OC)ccc1-2]
12
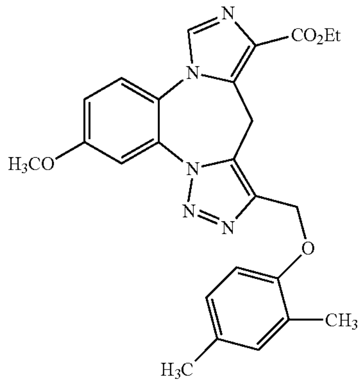 [SMILES: CCOC(=O)c1ncn2c1Cc1c(COc3ccc(C)cc3C)nnn1-c1cc(OC)ccc1-2]
44
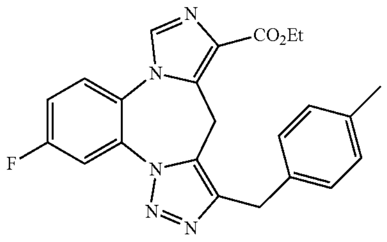 [SMILES: CCOC(=O)c1ncn2c1Cc1c(Cc3ccc(C)cc3)nnn1-c1cc(F)ccc1-2]
45
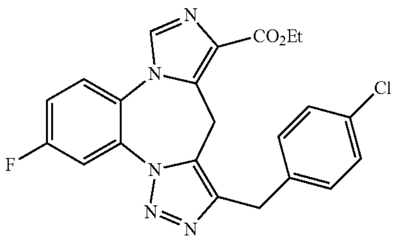 [SMILES: CCOC(=O)c1ncn2c1Cc1c(Cc3ccc(Cl)cc3)nnn1-c1cc(F)ccc1-2]
46
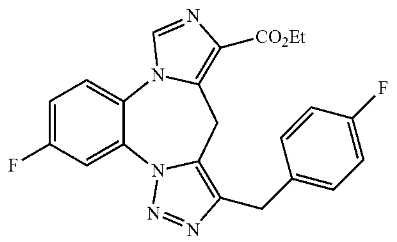 [SMILES: CCOC(=O)c1ncn2c1Cc1c(Cc3ccc(F)cc3)nnn1-c1cc(F)ccc1-2]

-continued
47
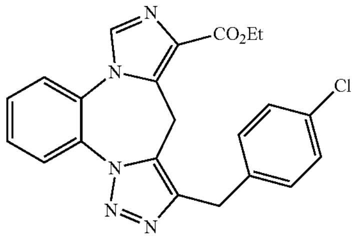 [SMILES: CCOC(=O)c1ncn2c1Cc1c(Cc3ccc(Cl)cc3)nnn1-c1ccccc1-2]
48
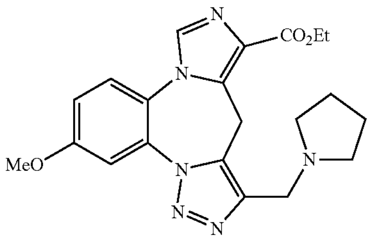 [SMILES: CCOC(=O)c1ncn2c1Cc1c(CN3CCCC3)nnn1-c1cc(OC)ccc1-2]
49
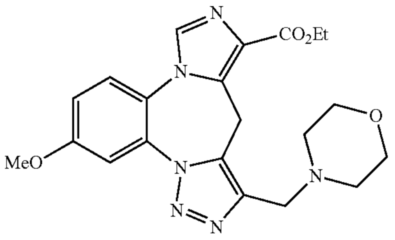 [SMILES: CCOC(=O)c1ncn2c1Cc1c(CN3CCOCC3)nnn1-c1cc(OC)ccc1-2]
50
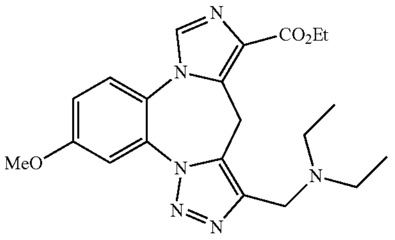 [SMILES: CCOC(=O)c1ncn2c1Cc1c(CN(CC)CC)nnn1-c1cc(OC)ccc1-2]
51
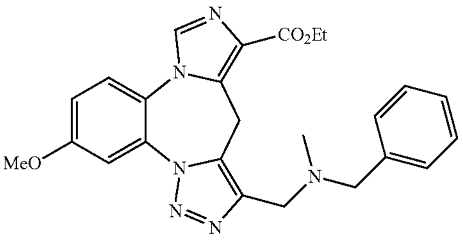 [SMILES: CCOC(=O)c1ncn2c1Cc1c(CN(C)Cc3ccccc3)nnn1-c1cc(OC)ccc1-2]
52
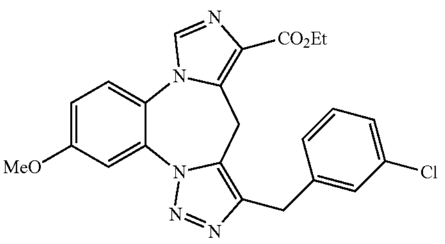 [SMILES: CCOC(=O)c1ncn2c1Cc1c(Cc3cccc(Cl)c3)nnn1-c1cc(OC)ccc1-2]
-continued
53
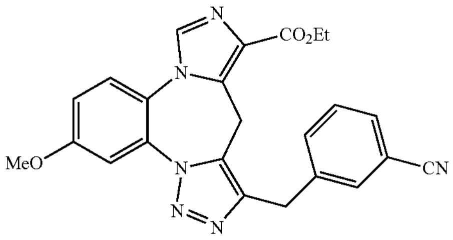 [SMILES: CCOC(=O)c1ncn2c1Cc1c(Cc3cccc(C#N)c3)nnn1-c1cc(OC)ccc1-2]
54
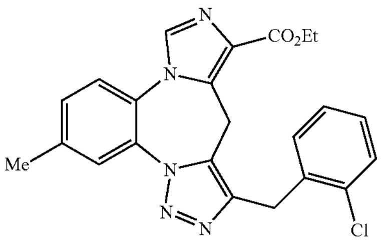 [SMILES: CCOC(=O)c1ncn2c1Cc1c(Cc3ccccc3Cl)nnn1-c1cc(C)ccc1-2]
101
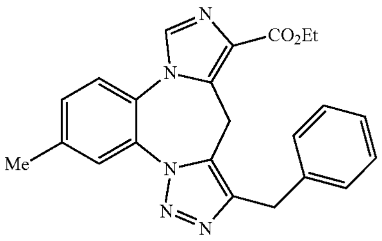 [SMILES: CCOC(=O)c1ncn2c1Cc1c(Cc3ccccc3)nnn1-c1cc(C)ccc1-2]
102
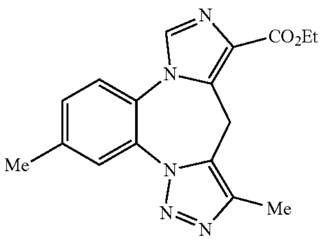 [SMILES: CCOC(=O)c1ncn2c1Cc1c(C)nnn1-c1cc(C)ccc1-2]
107
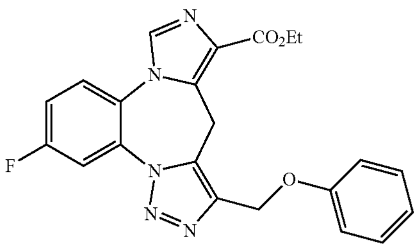 [SMILES: CCOC(=O)c1ncn2c1Cc1c(COc3ccccc3)nnn1-c1cc(F)ccc1-2]
108
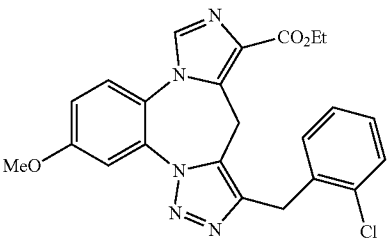 [SMILES: CCOC(=O)c1ncn2c1Cc1c(Cc3ccccc3Cl)nnn1-c1cc(OC)ccc1-2]

-continued
109
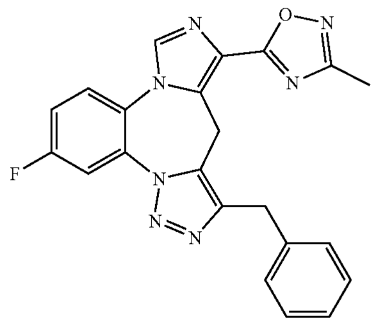 [SMILES: Cc1noc(-c2ncn3c2Cc2c(Cc4ccccc4)nnn2-c2cc(F)ccc2-3)n1]
110
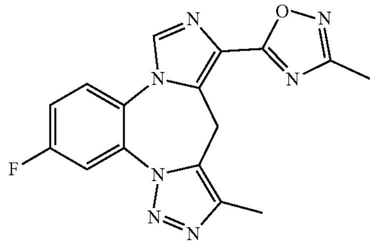 [SMILES: Cc1noc(-c2ncn3c2Cc2c(C)nnn2-c2cc(F)ccc2-3)n1]
111
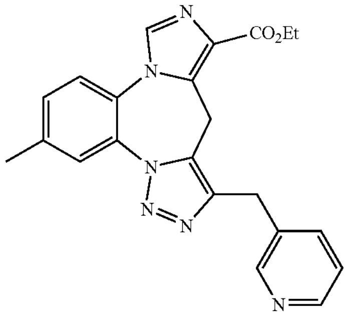 [SMILES: CCOC(=O)c1ncn2c1Cc1c(Cc3cccnc3)nnn1-c1cc(C)ccc1-2]
112
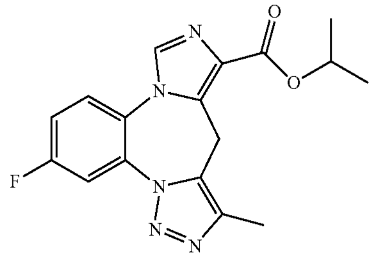 [SMILES: Cc1nnn2c1Cc1c(C(=O)OC(C)C)ncn1-c1ccc(F)cc1-2]
113
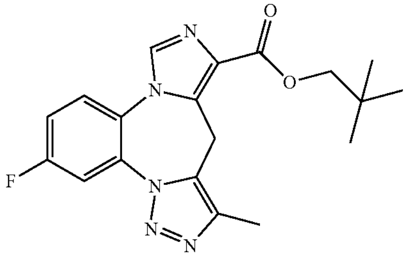 [SMILES: Cc1nnn2c1Cc1c(C(=O)OCC(C)(C)C)ncn1-c1ccc(F)cc1-2]
-continued
114
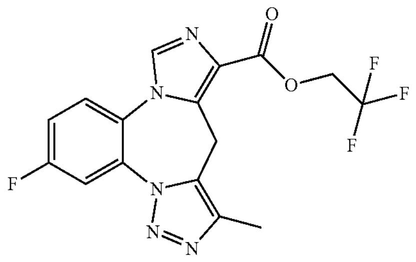 [SMILES: Cc1nnn2c1Cc1c(C(=O)OCC(F)(F)F)ncn1-c1ccc(F)cc1-2]
115
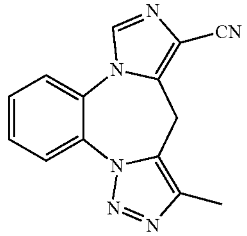 [SMILES: Cc1nnn2c1Cc1c(C#N)ncn1-c1ccccc1-2]
116
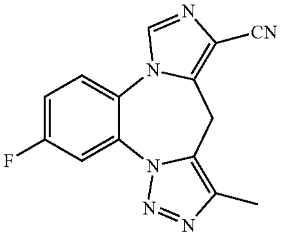 [SMILES: Cc1nnn2c1Cc1c(C#N)ncn1-c1ccc(F)cc1-2]
117
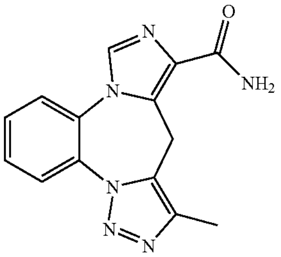 [SMILES: Cc1nnn2c1Cc1c(C(N)=O)ncn1-c1ccccc1-2]
121
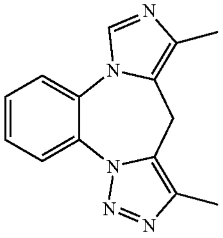 [SMILES: Cc1ncn2c1Cc1c(C)nnn1-c1ccccc1-2]
125
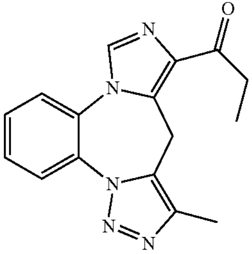 [SMILES: CCC(=O)c1ncn2c1Cc1c(C)nnn1-c1ccccc1-2]

-continued
126
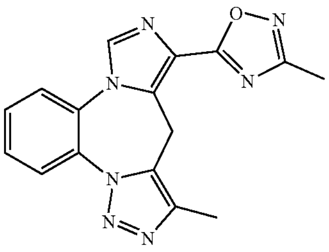 [SMILES: Cc1noc(-c2ncn3c2Cc2c(C)nnn2-c2ccccc2-3)n1]
127
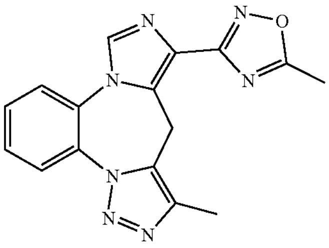 [SMILES: Cc1nc(-c2ncn3c2Cc2c(C)nnn2-c2ccccc2-3)no1]
132
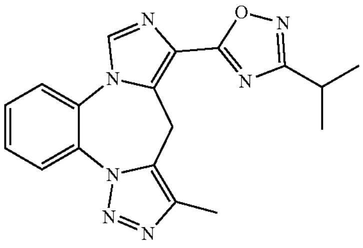 [SMILES: Cc1nnn2c1Cc1c(-c3nc(C(C)C)no3)ncn1-c1ccccc1-2]
133
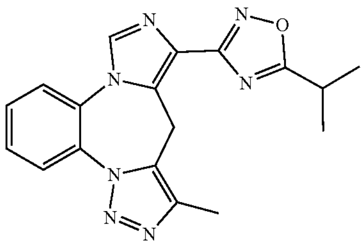 [SMILES: Cc1nnn2c1Cc1c(-c3noc(C(C)C)n3)ncn1-c1ccccc1-2]
134
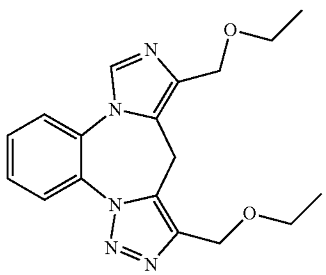 [SMILES: CCOCc1ncn2c1Cc1c(COCC)nnn1-c1ccccc1-2]
135
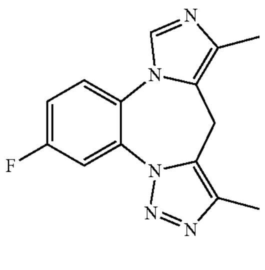 [SMILES: Cc1ncn2c1Cc1c(C)nnn1-c1cc(F)ccc1-2]
-continued
136
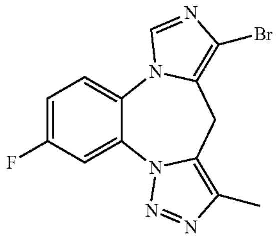 [SMILES: Cc1nnn2c1Cc1c(Br)ncn1-c1ccc(F)cc1-2]
139
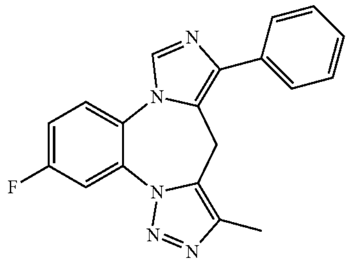 [SMILES: Cc1nnn2c1Cc1c(-c3ccccc3)ncn1-c1ccc(F)cc1-2]
140
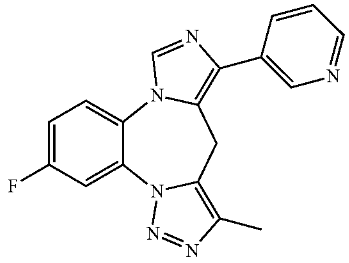 [SMILES: Cc1nnn2c1Cc1c(-c3cccnc3)ncn1-c1ccc(F)cc1-2]
143
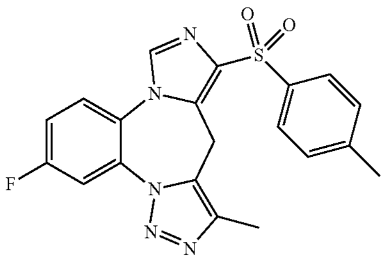 [SMILES: Cc1ccc(S(=O)(=O)c2ncn3c2Cc2c(C)nnn2-c2cc(F)ccc2-3)cc1]
144
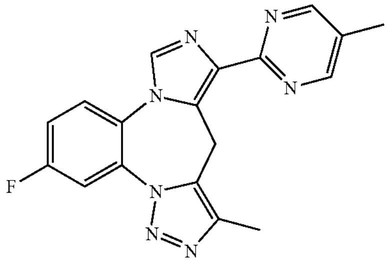 [SMILES: Cc1cnc(-c2ncn3c2Cc2c(C)nnn2-c2cc(F)ccc2-3)nc1]
145
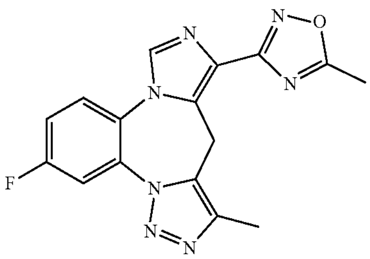 [SMILES: Cc1nc(-c2ncn3c2Cc2c(C)nnn2-c2cc(F)ccc2-3)no1]

-continued
146
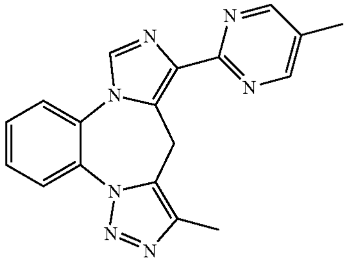 [SMILES: Cc1cnc(-c2ncn3c2Cc2c(C)nnn2-c2ccccc2-3)nc1]
149
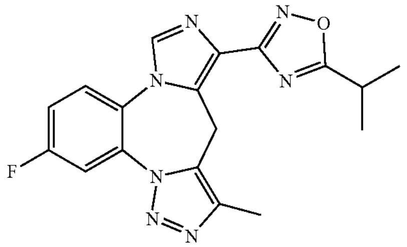 [SMILES: Cc1nnn2c1Cc1c(-c3noc(C(C)C)n3)ncn1-c1ccc(F)cc1-2]
150
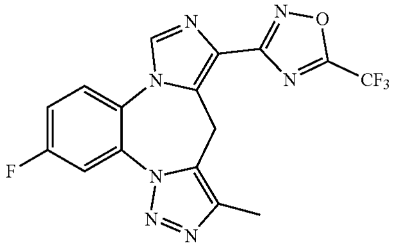 [SMILES: Cc1nnn2c1Cc1c(-c3noc(C(F)(F)F)n3)ncn1-c1ccc(F)cc1-2]
151
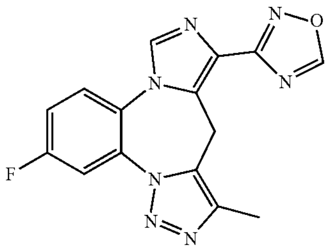 [SMILES: Cc1nnn2c1Cc1c(-c3ncon3)ncn1-c1ccc(F)cc1-2]
152
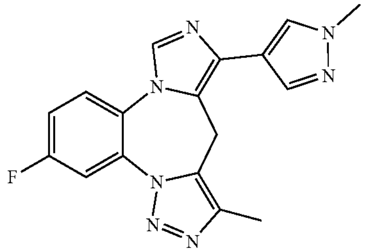 [SMILES: Cc1nnn2c1Cc1c(-c3cnn(C)c3)ncn1-c1ccc(F)cc1-2]
153
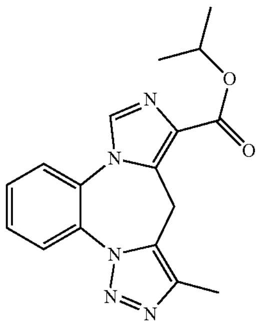 [SMILES: Cc1nnn2c1Cc1c(C(=O)OC(C)C)ncn1-c1ccccc1-2]
-continued
154
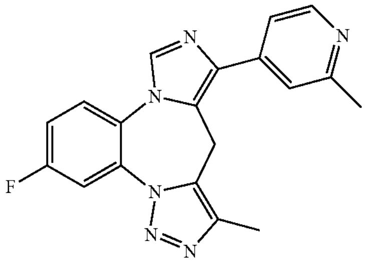 [SMILES: Cc1cc(-c2ncn3c2Cc2c(C)nnn2-c2cc(F)ccc2-3)ccn1]
155
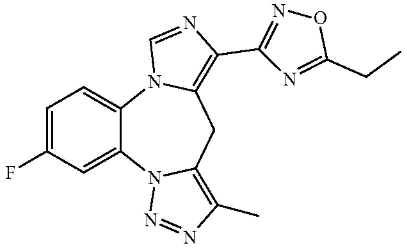 [SMILES: CCc1nc(-c2ncn3c2Cc2c(C)nnn2-c2cc(F)ccc2-3)no1]
160
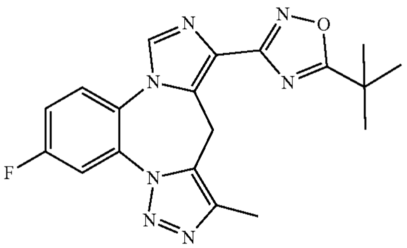 [SMILES: Cc1nnn2c1Cc1c(-c3noc(C(C)(C)C)n3)ncn1-c1ccc(F)cc1-2]
161
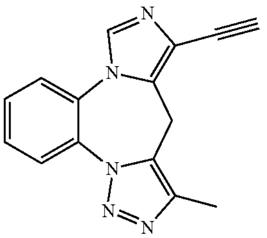 [SMILES: C#Cc1ncn2c1Cc1c(C)nnn1-c1ccccc1-2]
167
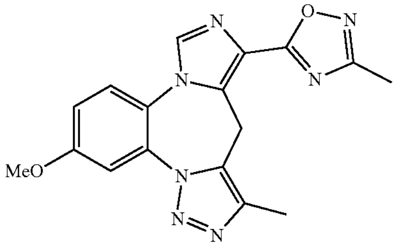 [SMILES: COc1ccc2c(c1)-n1nnc(C)c1Cc1c(-c3nc(C)no3)ncn1-2]
168
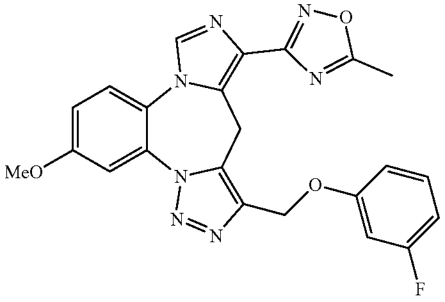 [SMILES: COc1ccc2c(c1)-n1nnc(COc3cccc(F)c3)c1Cc1c(-c3noc(C)n3)ncn1-2]

-continued
170
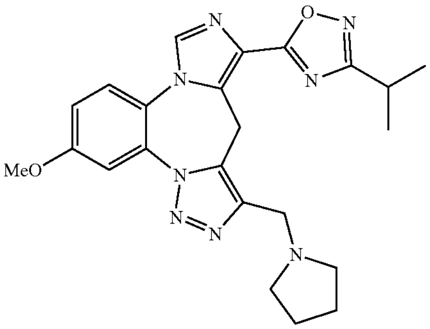 [SMILES: COc1ccc2c(c1)-n1nnc(CN3CCCC3)c1Cc1c(-c3nc(C(C)C)no3)ncn1-2]
180
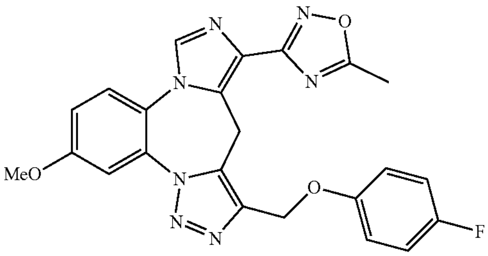 [SMILES: COc1ccc2c(c1)-n1nnc(COc3ccc(F)cc3)c1Cc1c(-c3noc(C)n3)ncn1-2]
181
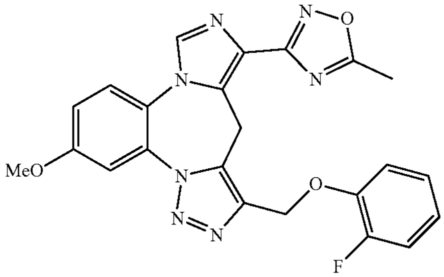 [SMILES: COc1ccc2c(c1)-n1nnc(COc3ccccc3F)c1Cc1c(-c3noc(C)n3)ncn1-2]
182
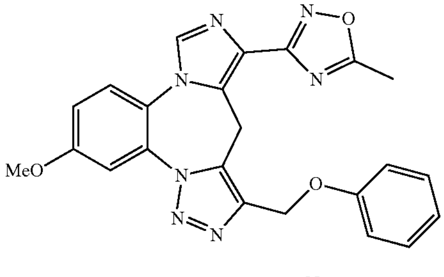 [SMILES: COc1ccc2c(c1)-n1nnc(COc3ccccc3)c1Cc1c(-c3noc(C)n3)ncn1-2]
194
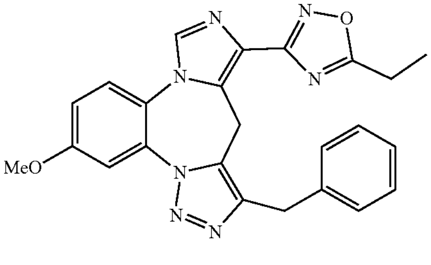 [SMILES: CCc1nc(-c2ncn3c2Cc2c(Cc4ccccc4)nnn2-c2cc(OC)ccc2-3)no1]
195
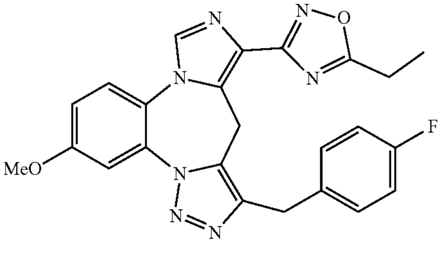 [SMILES: CCc1nc(-c2ncn3c2Cc2c(Cc4ccc(F)cc4)nnn2-c2cc(OC)ccc2-3)no1]
-continued
207
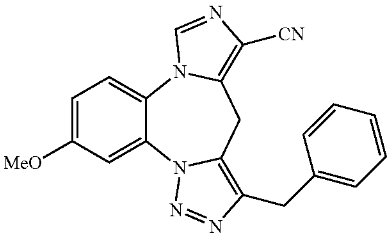 [SMILES: COc1ccc2c(c1)-n1nnc(Cc3ccccc3)c1Cc1c(C#N)ncn1-2]
208
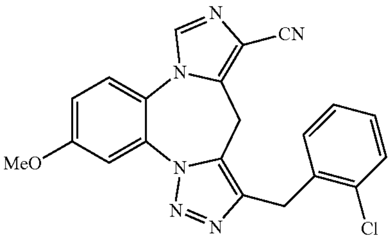 [SMILES: COc1ccc2c(c1)-n1nnc(Cc3ccccc3Cl)c1Cc1c(C#N)ncn1-2]
209
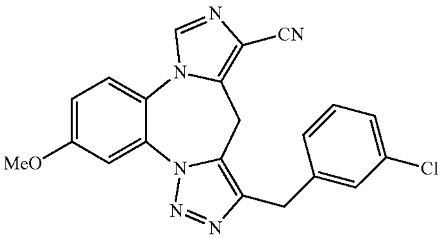 [SMILES: COc1ccc2c(c1)-n1nnc(Cc3cccc(Cl)c3)c1Cc1c(C#N)ncn1-2]
210
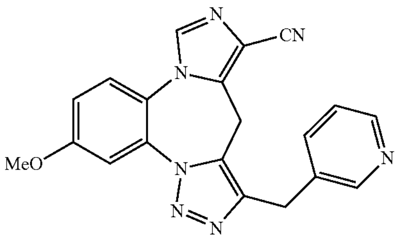 [SMILES: COc1ccc2c(c1)-n1nnc(Cc3cccnc3)c1Cc1c(C#N)ncn1-2]
211
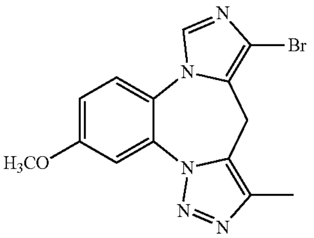 [SMILES: COc1ccc2c(c1)-n1nnc(C)c1Cc1c(Br)ncn1-2]
212
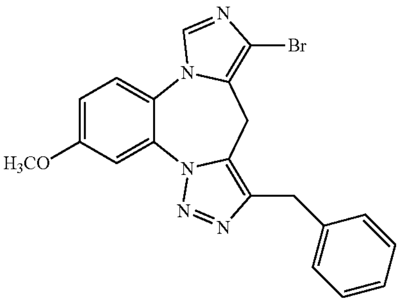 [SMILES: COc1ccc2c(c1)-n1nnc(Cc3ccccc3)c1Cc1c(Br)ncn1-2]

-continued
213
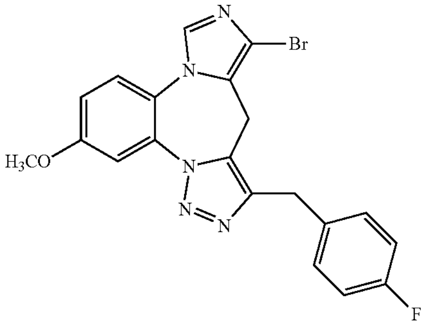 [SMILES: COc1ccc2c(c1)-n1nnc(Cc3ccc(F)cc3)c1Cc1c(Br)ncn1-2]
214
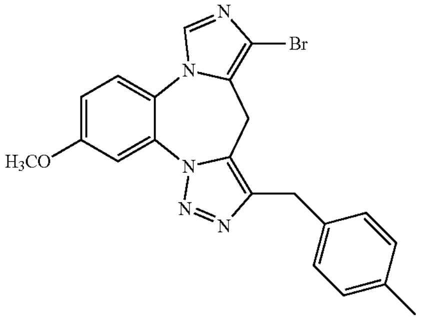 [SMILES: COc1ccc2c(c1)-n1nnc(Cc3ccc(C)cc3)c1Cc1c(Br)ncn1-2]
218
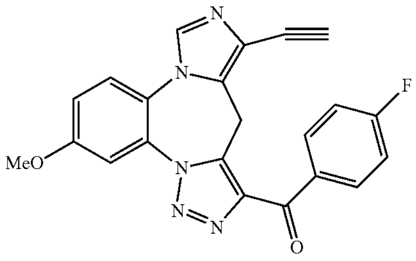 [SMILES: C#Cc1ncn2c1Cc1c(C(=O)c3ccc(F)cc3)nnn1-c1cc(OC)ccc1-2]
219
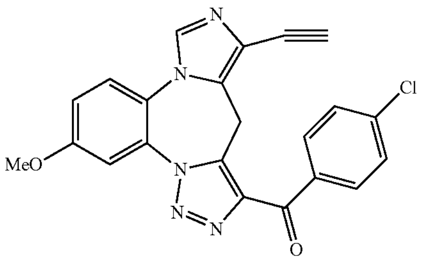 [SMILES: C#Cc1ncn2c1Cc1c(C(=O)c3ccc(Cl)cc3)nnn1-c1cc(OC)ccc1-2]
220
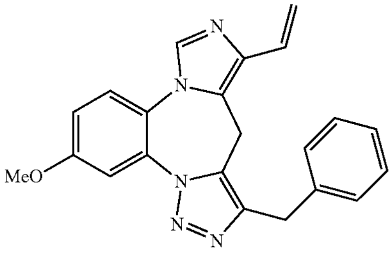 [SMILES: C=Cc1ncn2c1Cc1c(Cc3ccccc3)nnn1-c1cc(OC)ccc1-2]
-continued
221
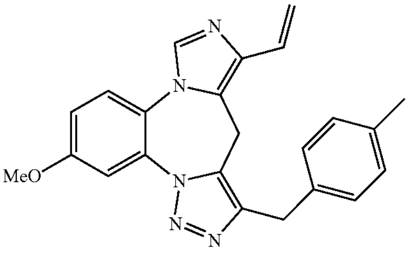 [SMILES: C=Cc1ncn2c1Cc1c(Cc3ccc(C)cc3)nnn1-c1cc(OC)ccc1-2]
222
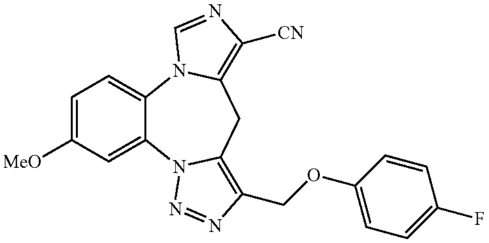 [SMILES: COc1ccc2c(c1)-n1nnc(COc3ccc(F)cc3)c1Cc1c(C#N)ncn1-2]
223
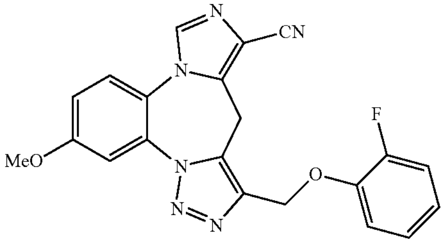 [SMILES: COc1ccc2c(c1)-n1nnc(COc3ccccc3F)c1Cc1c(C#N)ncn1-2]
224
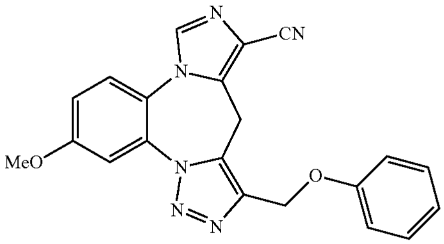 [SMILES: COc1ccc2c(c1)-n1nnc(COc3ccccc3)c1Cc1c(C#N)ncn1-2]
225
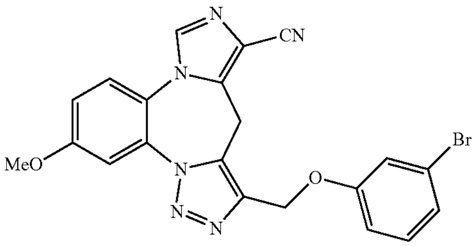 [SMILES: COc1ccc2c(c1)-n1nnc(COc3cccc(Br)c3)c1Cc1c(C#N)ncn1-2]
226
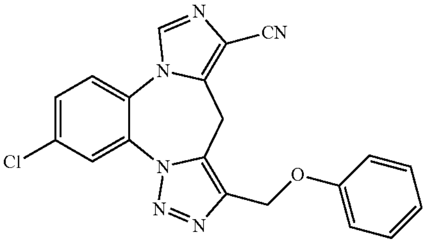 [SMILES: N#Cc1ncn2c1Cc1c(COc3ccccc3)nnn1-c1cc(Cl)ccc1-2]

-continued
227
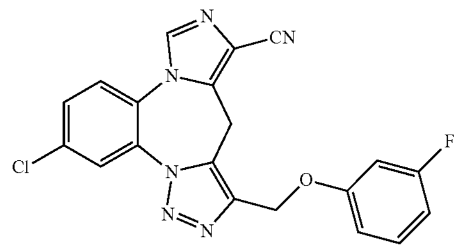 [SMILES: N#Cc1ncn2c1Cc1c(COc3cccc(F)c3)nnn1-c1cc(Cl)ccc1-2]
228
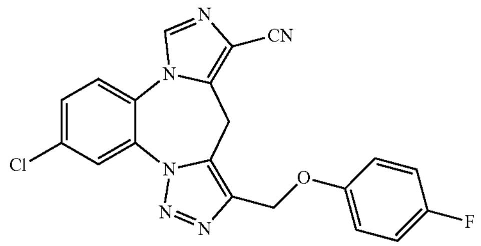 [SMILES: N#Cc1ncn2c1Cc1c(COc3ccc(F)cc3)nnn1-c1cc(Cl)ccc1-2]
229
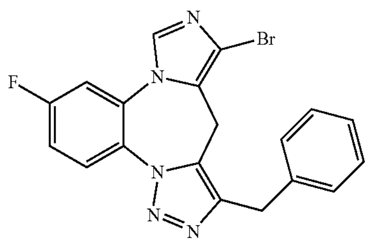 [SMILES: Fc1ccc2c(c1)-n1cnc(Br)c1Cc1c(Cc3ccccc3)nnn1-2]
230
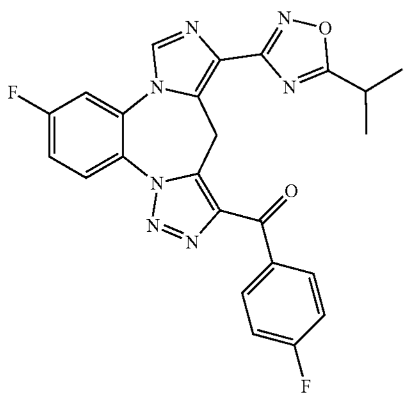 [SMILES: CC(C)c1nc(-c2ncn3c2Cc2c(C(=O)c4ccc(F)cc4)nnn2-c2ccc(F)cc2-3)no1]
231
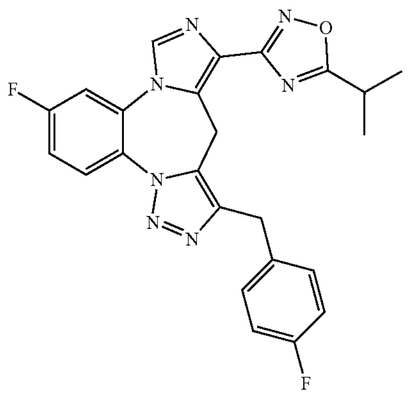 [SMILES: CC(C)c1nc(-c2ncn3c2Cc2c(Cc4ccc(F)cc4)nnn2-c2ccc(F)cc2-3)no1]
-continued
247
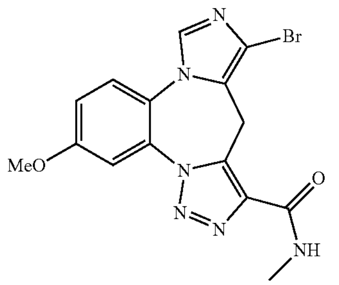 [SMILES: CNC(=O)c1nnn2c1Cc1c(Br)ncn1-c1ccc(OC)cc1-2]
248
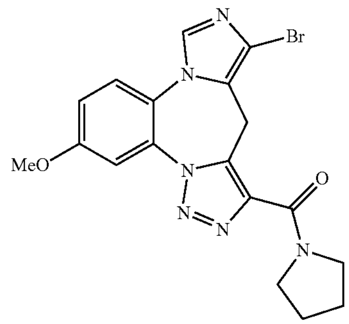 [SMILES: COc1ccc2c(c1)-n1nnc(C(=O)N3CCCC3)c1Cc1c(Br)ncn1-2]
250
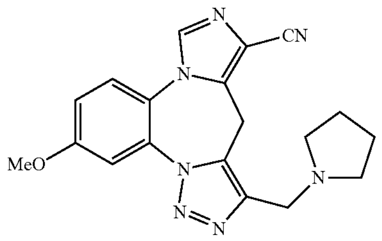 [SMILES: COc1ccc2c(c1)-n1nnc(CN3CCCC3)c1Cc1c(C#N)ncn1-2]
251
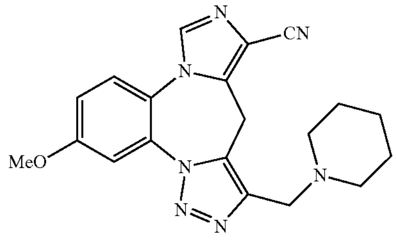 [SMILES: COc1ccc2c(c1)-n1nnc(CN3CCCCC3)c1Cc1c(C#N)ncn1-2]
252
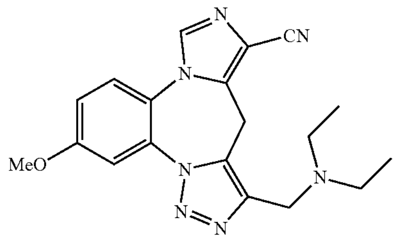 [SMILES: CCN(CC)Cc1nnn2c1Cc1c(C#N)ncn1-c1ccc(OC)cc1-2]
253
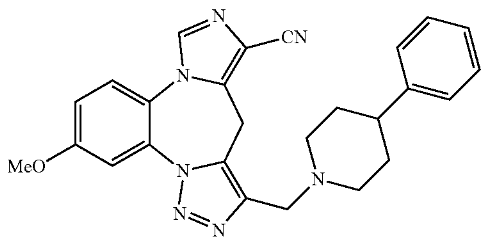 [SMILES: COc1ccc2c(c1)-n1nnc(CN3CCC(c4ccccc4)CC3)c1Cc1c(C#N)ncn1-2]

-continued
257
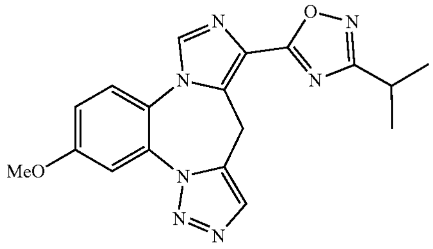 [SMILES: COc1ccc2c(c1)-n1nncc1Cc1c(-c3nc(C(C)C)no3)ncn1-2]
258
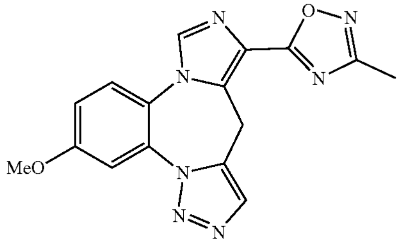 [SMILES: COc1ccc2c(c1)-n1nncc1Cc1c(-c3nc(C)no3)ncn1-2]
262
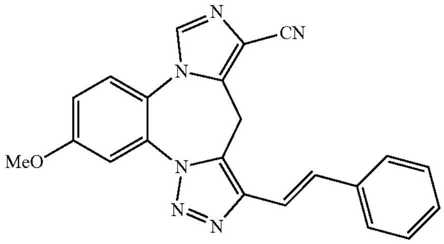 [SMILES: COc1ccc2c(c1)-n1nnc(/C=C/c3ccccc3)c1Cc1c(C#N)ncn1-2]
272
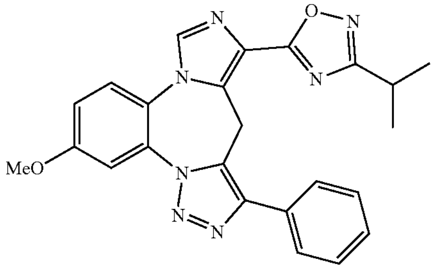 [SMILES: COc1ccc2c(c1)-n1nnc(-c3ccccc3)c1Cc1c(-c3nc(C(C)C)no3)ncn1-2]
273
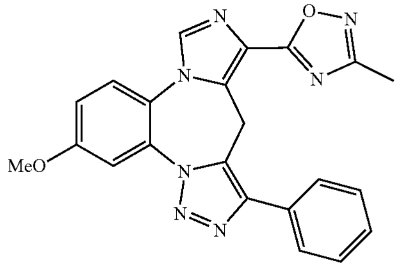 [SMILES: COc1ccc2c(c1)-n1nnc(-c3ccccc3)c1Cc1c(-c3nc(C)no3)ncn1-2]
277
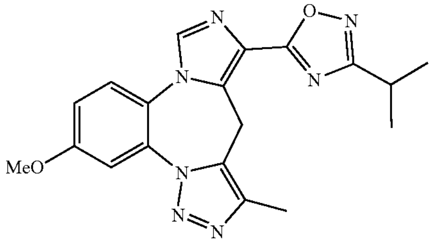 [SMILES: COc1ccc2c(c1)-n1nnc(C)c1Cc1c(-c3nc(C(C)C)no3)ncn1-2]
-continued
279
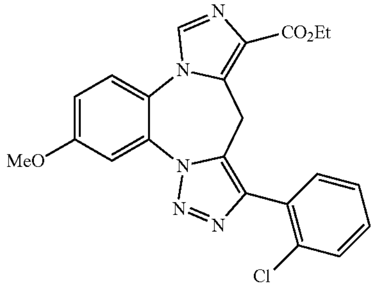 [SMILES: CCOC(=O)c1ncn2c1Cc1c(-c3ccccc3Cl)nnn1-c1cc(OC)ccc1-2]
289
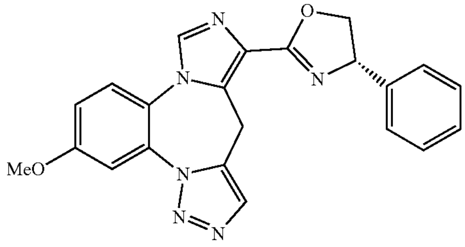 [SMILES: COc1ccc2c(c1)-n1nncc1Cc1c(C3=N[C@@H](c4ccccc4)CO3)ncn1-2]
290
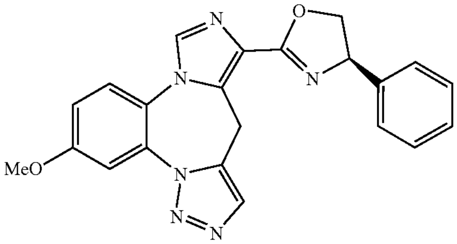 [SMILES: COc1ccc2c(c1)-n1nncc1Cc1c(C3=N[C@H](c4ccccc4)CO3)ncn1-2]
291
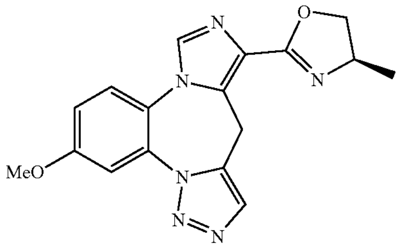 [SMILES: COc1ccc2c(c1)-n1nncc1Cc1c(C3=N[C@H](C)CO3)ncn1-2]
292
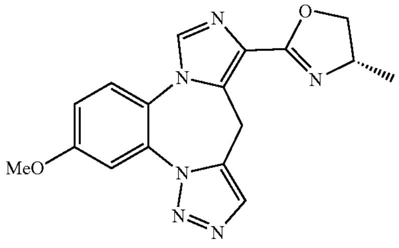 [SMILES: COc1ccc2c(c1)-n1nncc1Cc1c(C3=N[C@@H](C)CO3)ncn1-2]
298
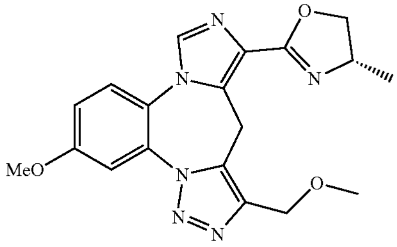 [SMILES: COCc1nnn2c1Cc1c(C3=N[C@@H](C)CO3)ncn1-c1ccc(OC)cc1-2]

-continued

299

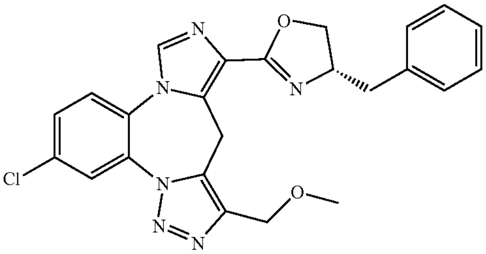 [SMILES: COCc1nnn2c1Cc1c(C3=N[C@@H](Cc4ccccc4)CO3)ncn1-c1ccc(Cl)cc1-2]

300

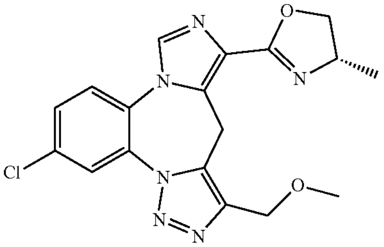 [SMILES: COCc1nnn2c1Cc1c(C3=N[C@@H](C)CO3)ncn1-c1ccc(Cl)cc1-2]

318

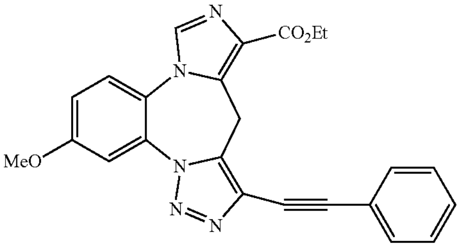 [SMILES: CCOC(=O)c1ncn2c1Cc1c(C#Cc3ccccc3)nnn1-c1cc(OC)ccc1-2]

344

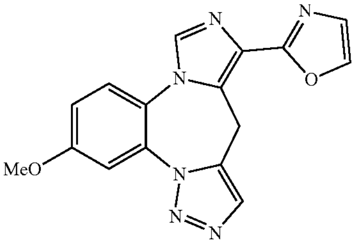 [SMILES: COc1ccc2c(c1)-n1nncc1Cc1c(-c3ncco3)ncn1-2]

347

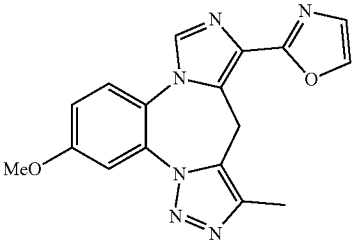 [SMILES: COc1ccc2c(c1)-n1nnc(C)c1Cc1c(-c3ncco3)ncn1-2]

and

356

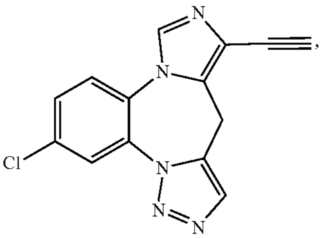 [SMILES: C#Cc1ncn2c1Cc1cnnn1-c1cc(Cl)ccc1-2]

or a pharmaceutically acceptable salt, hydrate, solvate, polymorph, isomer, or combination thereof.

10. A method of slowing the progression of, alleviating, or ameliorating a brain cancer or treating cognitive impairment associated with a brain cancer in a subject in need thereof, wherein the compound or the pharmaceutical composition comprising the compound is selected from:

357

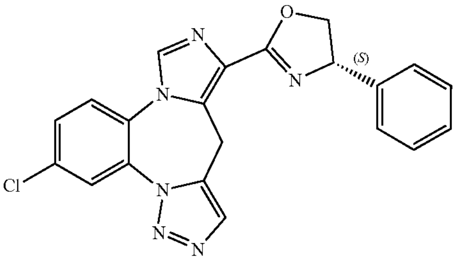

358

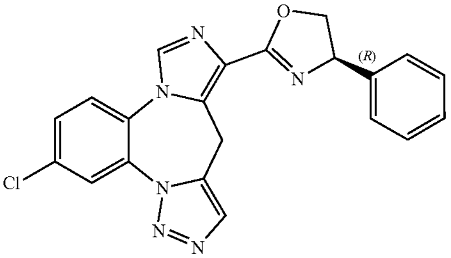

359

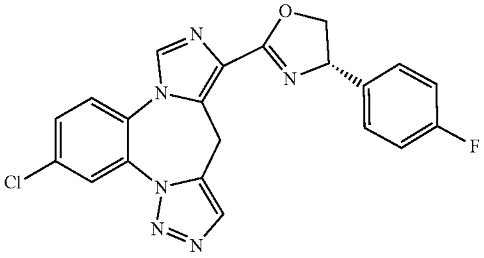 [SMILES: Fc1ccc([C@H]2COC(c3ncn4c3Cc3cnnn3-c3cc(Cl)ccc3-4)=N2)cc1]

360

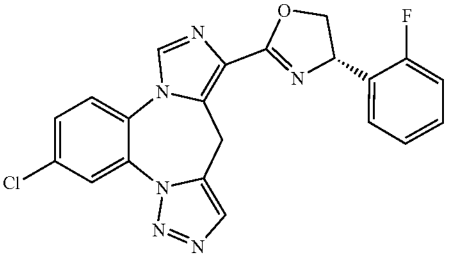 [SMILES: Fc1ccccc1[C@H]1COC(c2ncn3c2Cc2cnnn2-c2cc(Cl)ccc2-3)=N1]

361

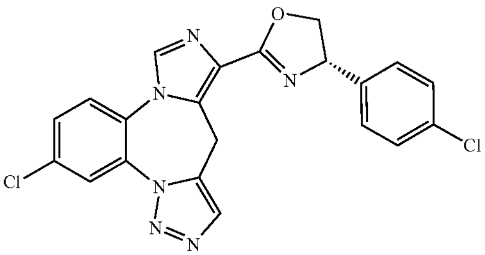 [SMILES: Clc1ccc([C@H]2COC(c3ncn4c3Cc3cnnn3-c3cc(Cl)ccc3-4)=N2)cc1]

-continued
362
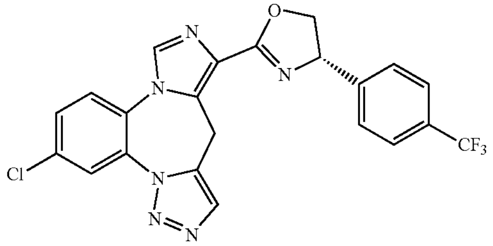 [SMILES: FC(F)(F)c1ccc([C@H]2COC(c3ncn4c3Cc3cnnn3-c3cc(Cl)ccc3-4)=N2)cc1]
363
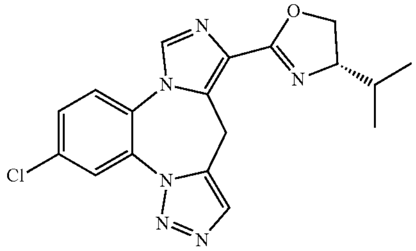 [SMILES: CC(C)[C@H]1COC(c2ncn3c2Cc2cnnn2-c2cc(Cl)ccc2-3)=N1]
364
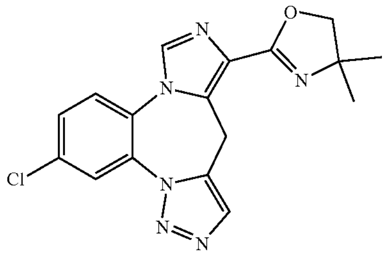 [SMILES: CC1(C)COC(c2ncn3c2Cc2cnnn2-c2cc(Cl)ccc2-3)=N1]
365
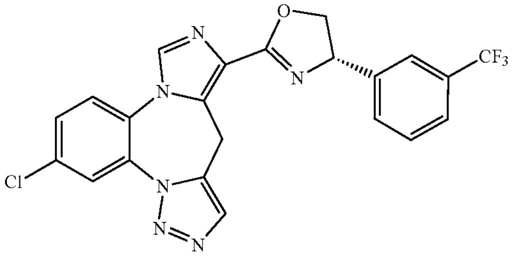 [SMILES: FC(F)(F)c1cccc([C@H]2COC(c3ncn4c3Cc3cnnn3-c3cc(Cl)ccc3-4)=N2)c1]
366
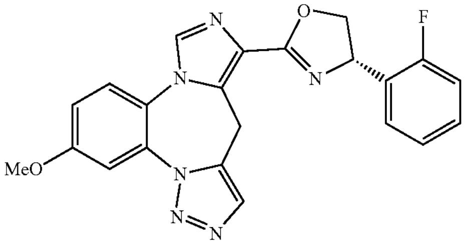 [SMILES: COc1ccc2c(c1)-n1nncc1Cc1c(C3=N[C@@H](c4ccccc4F)CO3)ncn1-2]
367
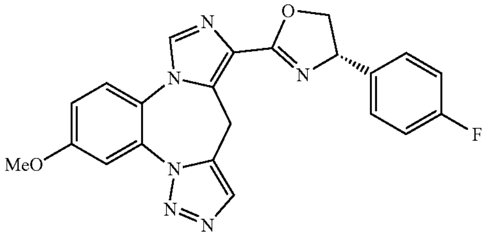 [SMILES: COc1ccc2c(c1)-n1nncc1Cc1c(C3=N[C@@H](c4ccc(F)cc4)CO3)ncn1-2]
-continued
368
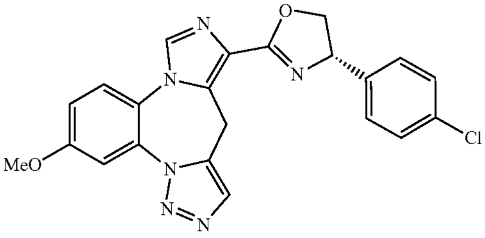 [SMILES: COc1ccc2c(c1)-n1nncc1Cc1c(C3=N[C@@H](c4ccc(Cl)cc4)CO3)ncn1-2]
369
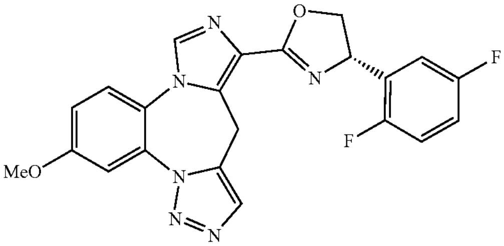 [SMILES: COc1ccc2c(c1)-n1nncc1Cc1c(C3=N[C@@H](c4cc(F)ccc4F)CO3)ncn1-2]
370
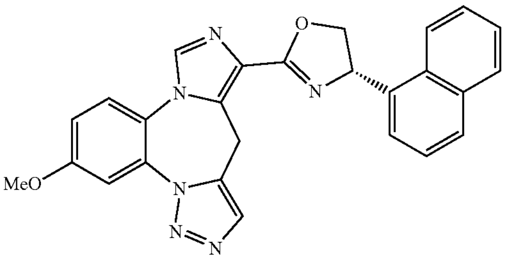 [SMILES: COc1ccc2c(c1)-n1nncc1Cc1c(C3=N[C@@H](c4cccc5ccccc45)CO3)ncn1-2]
371
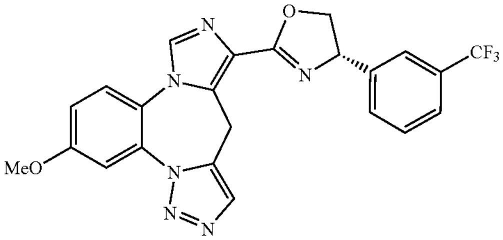 [SMILES: COc1ccc2c(c1)-n1nncc1Cc1c(C3=N[C@@H](c4cccc(C(F)(F)F)c4)CO3)ncn1-2]
372
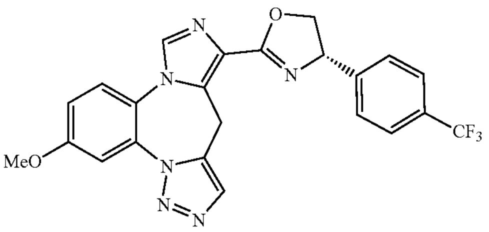 [SMILES: COc1ccc2c(c1)-n1nncc1Cc1c(C3=N[C@@H](c4ccc(C(F)(F)F)cc4)CO3)ncn1-2]
373
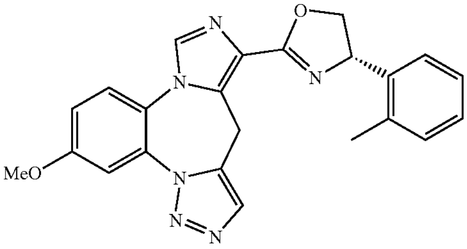 [SMILES: COc1ccc2c(c1)-n1nncc1Cc1c(C3=N[C@@H](c4ccccc4C)CO3)ncn1-2]

-continued
374
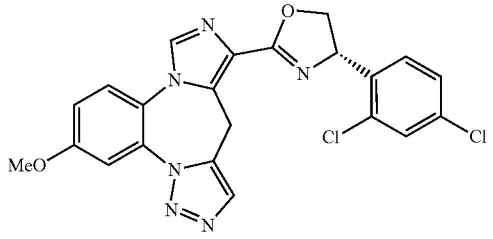 [SMILES: COc1ccc2c(c1)-n1nncc1Cc1c(C3=N[C@@H](c4ccc(Cl)cc4Cl)CO3)ncn1-2]
375
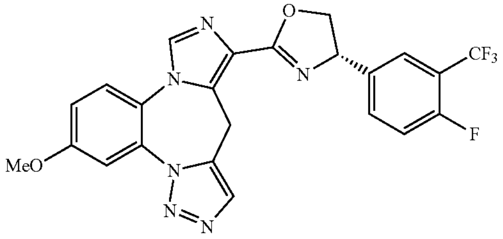 [SMILES: COc1ccc2c(c1)-n1nncc1Cc1c(C3=N[C@@H](c4ccc(F)c(C(F)(F)F)c4)CO3)ncn1-2]
376
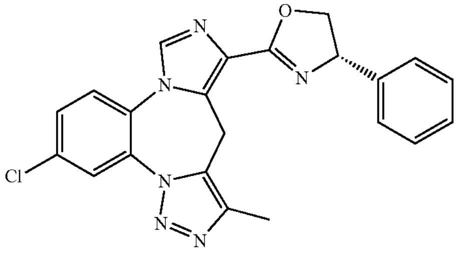 [SMILES: Cc1nnn2c1Cc1c(C3=N[C@@H](c4ccccc4)CO3)ncn1-c1ccc(Cl)cc1-2]
377
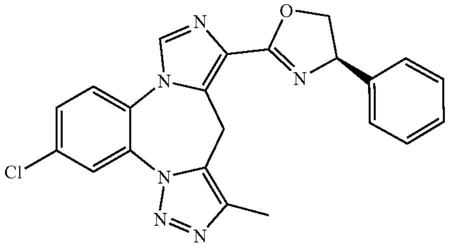 [SMILES: Cc1nnn2c1Cc1c(C3=N[C@H](c4ccccc4)CO3)ncn1-c1ccc(Cl)cc1-2]
378
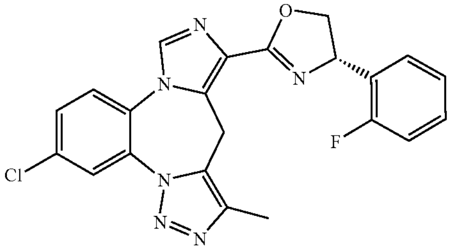 [SMILES: Cc1nnn2c1Cc1c(C3=N[C@@H](c4ccccc4F)CO3)ncn1-c1ccc(Cl)cc1-2]
379
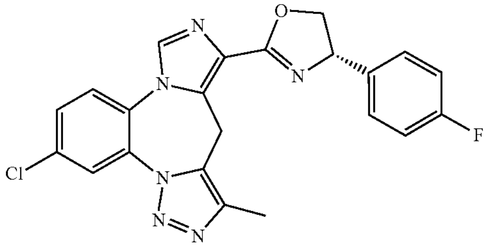 [SMILES: Cc1nnn2c1Cc1c(C3=N[C@@H](c4ccc(F)cc4)CO3)ncn1-c1ccc(Cl)cc1-2]
-continued
380
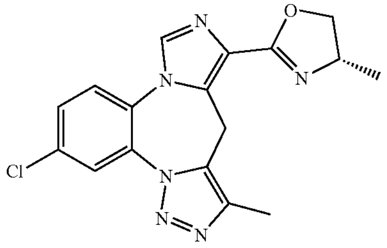 [SMILES: Cc1nnn2c1Cc1c(C3=N[C@@H](C)CO3)ncn1-c1ccc(Cl)cc1-2]
381
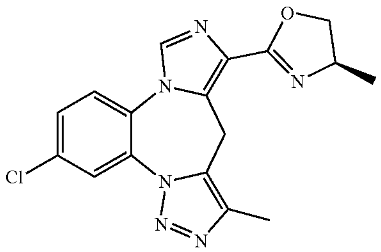 [SMILES: Cc1nnn2c1Cc1c(C3=N[C@H](C)CO3)ncn1-c1ccc(Cl)cc1-2]
382
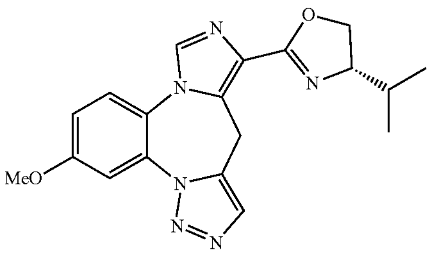 [SMILES: COc1ccc2c(c1)-n1nncc1Cc1c(C3=N[C@@H](C(C)C)CO3)ncn1-2]
383
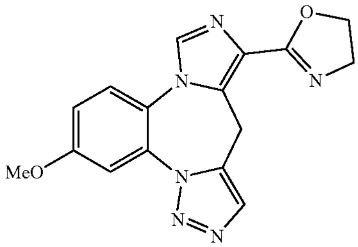 [SMILES: COc1ccc2c(c1)-n1nncc1Cc1c(C3=NCCO3)ncn1-2]
385
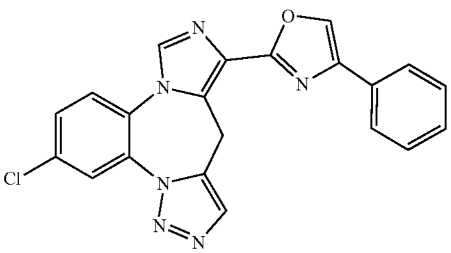 [SMILES: Clc1ccc2c(c1)-n1nncc1Cc1c(-c3nc(-c4ccccc4)co3)ncn1-2]
386
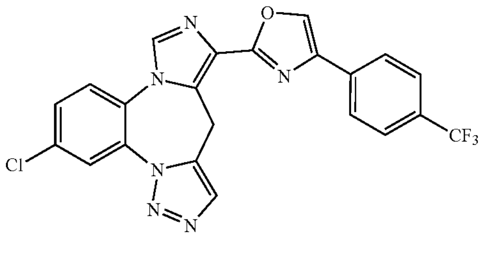 [SMILES: FC(F)(F)c1ccc(-c2coc(-c3ncn4c3Cc3cnnn3-c3cc(Cl)ccc3-4)n2)cc1]

387
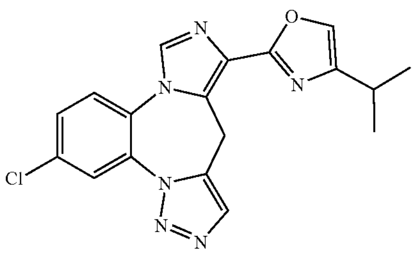 [SMILES: CC(C)c1coc(-c2ncn3c2Cc2cnnn2-c2cc(Cl)ccc2-3)n1]
388
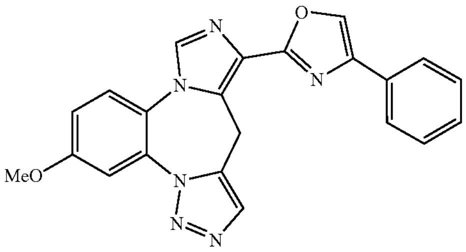 [SMILES: COc1ccc2c(c1)-n1nncc1Cc1c(-c3nc(-c4ccccc4)co3)ncn1-2]
389
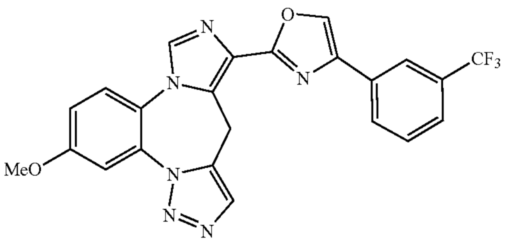 [SMILES: COc1ccc2c(c1)-n1nncc1Cc1c(-c3nc(-c4cccc(C(F)(F)F)c4)co3)ncn1-2]
390
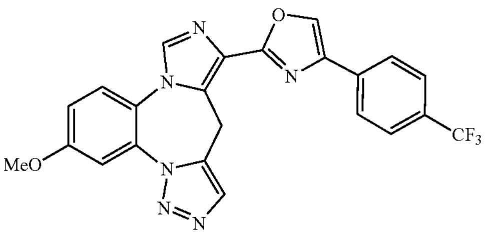 [SMILES: COc1ccc2c(c1)-n1nncc1Cc1c(-c3nc(-c4ccc(C(F)(F)F)cc4)co3)ncn1-2]
391
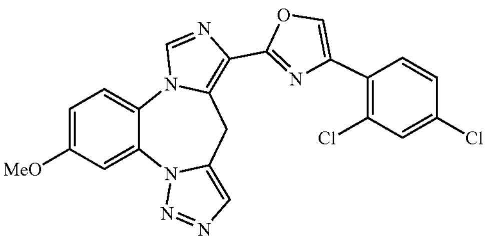 [SMILES: COc1ccc2c(c1)-n1nncc1Cc1c(-c3nc(-c4ccc(Cl)cc4Cl)co3)ncn1-2]
392
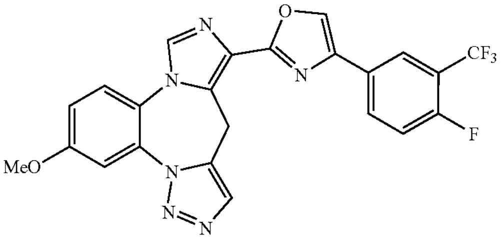 [SMILES: COc1ccc2c(c1)-n1nncc1Cc1c(-c3nc(-c4ccc(F)c(C(F)(F)F)c4)co3)ncn1-2]
393
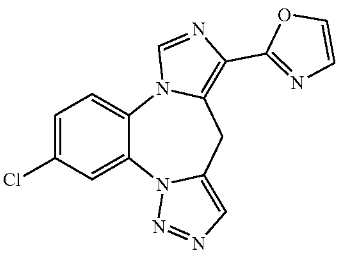 [SMILES: Clc1ccc2c(c1)-n1nncc1Cc1c(-c3ncco3)ncn1-2]
394
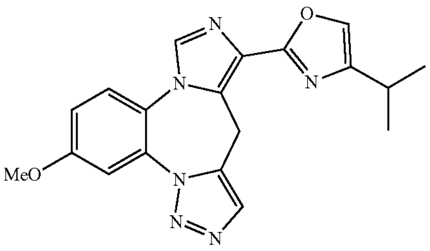 [SMILES: COc1ccc2c(c1)-n1nncc1Cc1c(-c3nc(C(C)C)co3)ncn1-2]
395
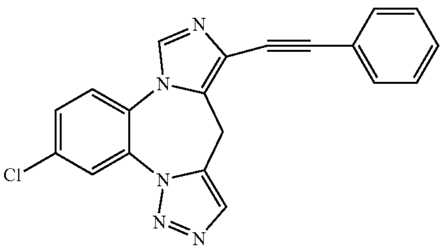
396
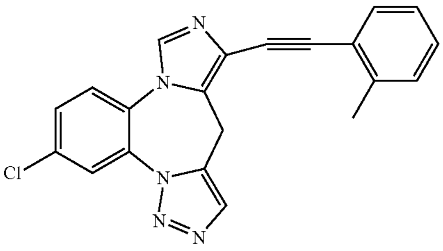 [SMILES: Cc1ccccc1C#Cc1ncn2c1Cc1cnnn1-c1cc(Cl)ccc1-2]
397
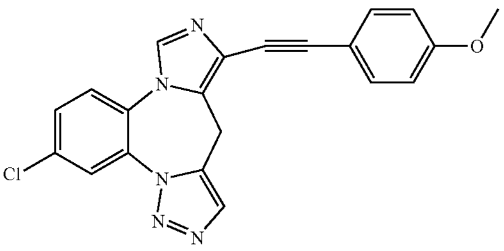 [SMILES: COc1ccc(C#Cc2ncn3c2Cc2cnnn2-c2cc(Cl)ccc2-3)cc1]
398
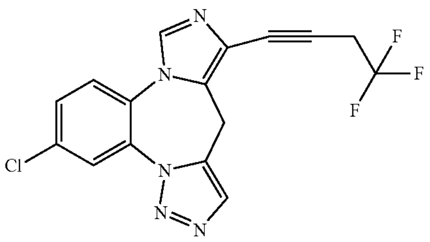 [SMILES: FC(F)(F)CC#Cc1ncn2c1Cc1cnnn1-c1cc(Cl)ccc1-2]

-continued
399
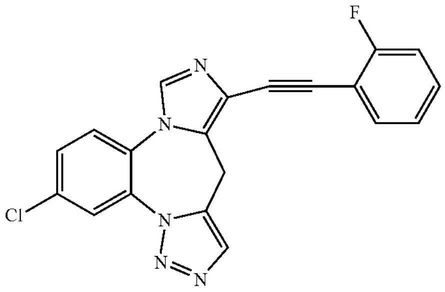 [SMILES: Fc1ccccc1C#Cc1ncn2c1Cc1cnnn1-c1cc(Cl)ccc1-2]
400
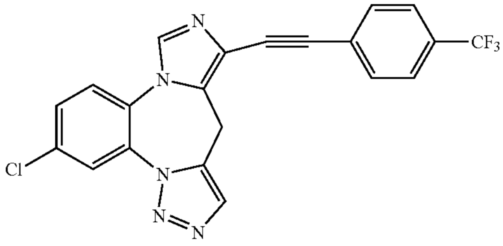 [SMILES: FC(F)(F)c1ccc(C#Cc2ncn3c2Cc2cnnn2-c2cc(Cl)ccc2-3)cc1]
403
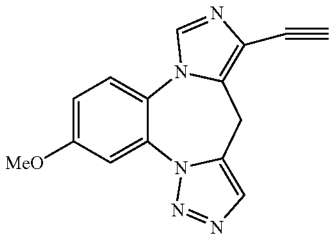 [SMILES: C#Cc1ncn2c1Cc1cnnn1-c1cc(OC)ccc1-2]
404
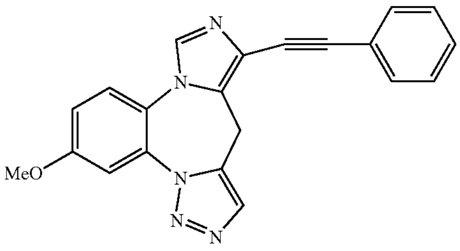
405
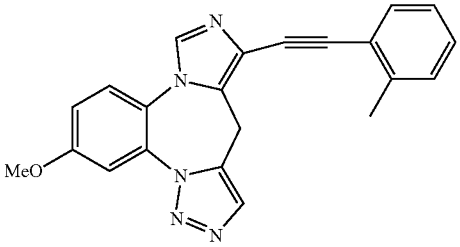 [SMILES: COc1ccc2c(c1)-n1nncc1Cc1c(C#Cc3ccccc3C)ncn1-2]
406
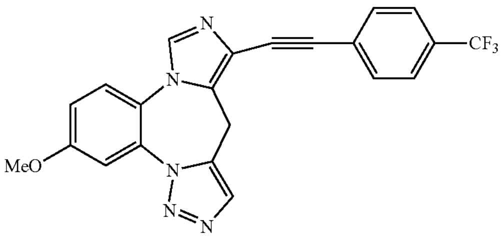 [SMILES: COc1ccc2c(c1)-n1nncc1Cc1c(C#Cc3ccc(C(F)(F)F)cc3)ncn1-2]
-continued
409
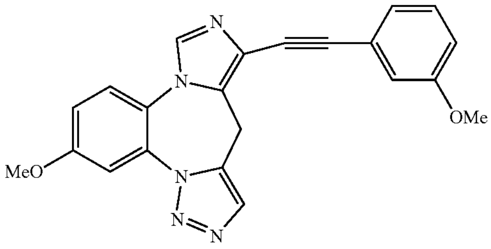 [SMILES: COc1cccc(C#Cc2ncn3c2Cc2cnnn2-c2cc(OC)ccc2-3)c1]
410
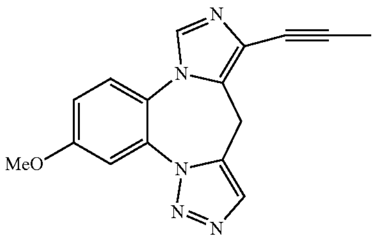 [SMILES: CC#Cc1ncn2c1Cc1cnnn1-c1cc(OC)ccc1-2]
411
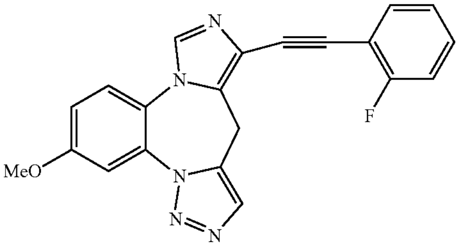 [SMILES: COc1ccc2c(c1)-n1nncc1Cc1c(C#Cc3ccccc3F)ncn1-2]
412
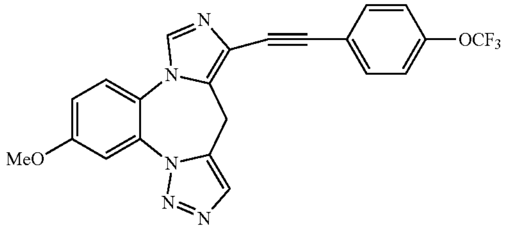 [SMILES: COc1ccc2c(c1)-n1nncc1Cc1c(C#Cc3ccc(OC(F)(F)F)cc3)ncn1-2]
413
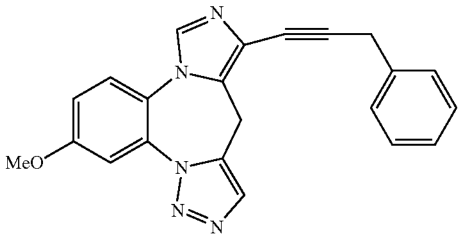 [SMILES: COc1ccc2c(c1)-n1nncc1Cc1c(C#CCc3ccccc3)ncn1-2]
414
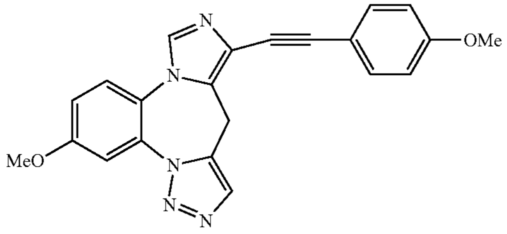 [SMILES: COc1ccc(C#Cc2ncn3c2Cc2cnnn2-c2cc(OC)ccc2-3)cc1]

-continued
415
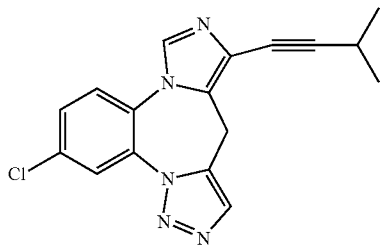 [SMILES: CC(C)C#Cc1ncn2c1Cc1cnnn1-c1cc(Cl)ccc1-2]
416
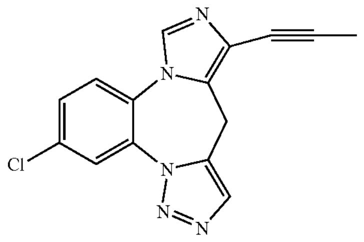 [SMILES: CC#Cc1ncn2c1Cc1cnnn1-c1cc(Cl)ccc1-2]
417
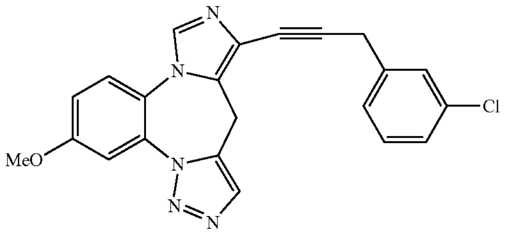 [SMILES: COc1ccc2c(c1)-n1nncc1Cc1c(C#CCc3cccc(Cl)c3)ncn1-2]
418
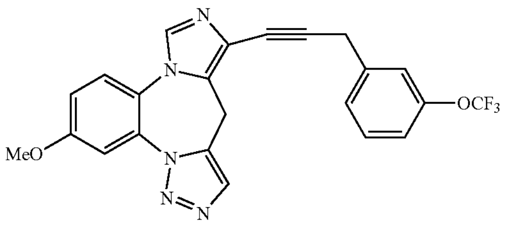 [SMILES: COc1ccc2c(c1)-n1nncc1Cc1c(C#CCc3cccc(OC(F)(F)F)c3)ncn1-2]
419
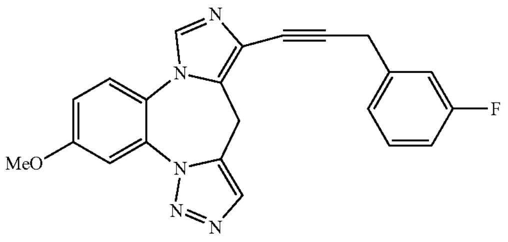 [SMILES: COc1ccc2c(c1)-n1nncc1Cc1c(C#CCc3cccc(F)c3)ncn1-2]
420
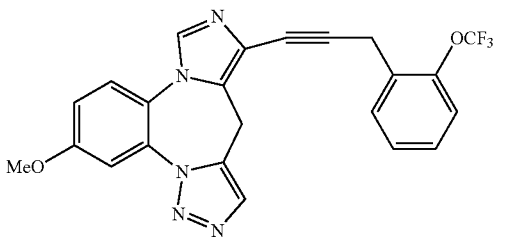 [SMILES: COc1ccc2c(c1)-n1nncc1Cc1c(C#CCc3ccccc3OC(F)(F)F)ncn1-2]
-continued
424
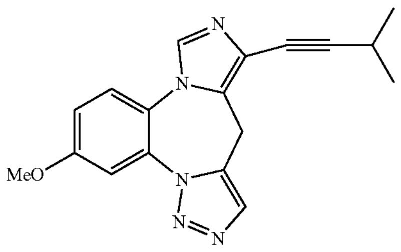
425
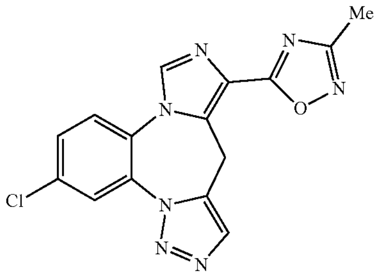 [SMILES: Cc1noc(-c2ncn3c2Cc2cnnn2-c2cc(Cl)ccc2-3)n1]
426
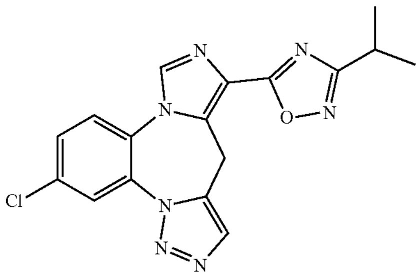 [SMILES: CC(C)c1noc(-c2ncn3c2Cc2cnnn2-c2cc(Cl)ccc2-3)n1]
436
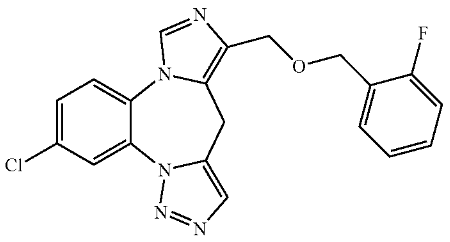 [SMILES: Fc1ccccc1COCc1ncn2c1Cc1cnnn1-c1cc(Cl)ccc1-2]
437
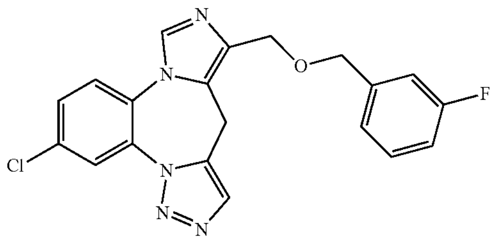 [SMILES: Fc1cccc(COCc2ncn3c2Cc2cnnn2-c2cc(Cl)ccc2-3)c1]
438
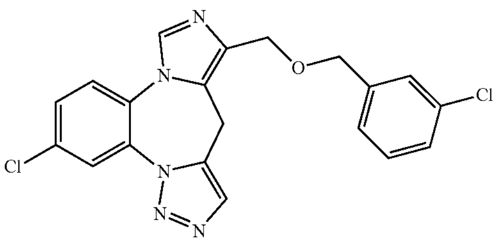 [SMILES: Clc1cccc(COCc2ncn3c2Cc2cnnn2-c2cc(Cl)ccc2-3)c1]

-continued
439
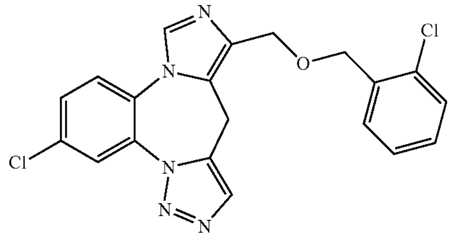 [SMILES: Clc1ccc2c(c1)-n1nncc1Cc1c(COCc3ccccc3Cl)ncn1-2]
440
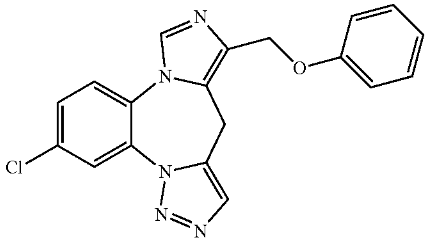 [SMILES: Clc1ccc2c(c1)-n1nncc1Cc1c(COc3ccccc3)ncn1-2]
441
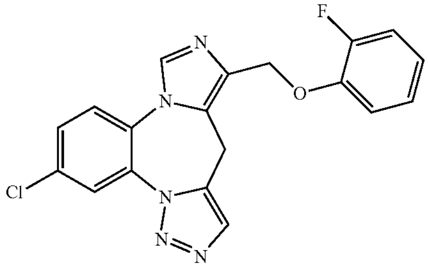 [SMILES: Fc1ccccc1OCc1ncn2c1Cc1cnnn1-c1cc(Cl)ccc1-2]
442
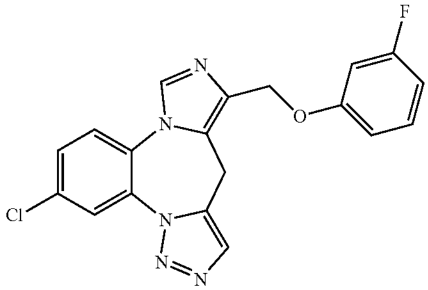 [SMILES: Fc1cccc(OCc2ncn3c2Cc2cnnn2-c2cc(Cl)ccc2-3)c1]
443
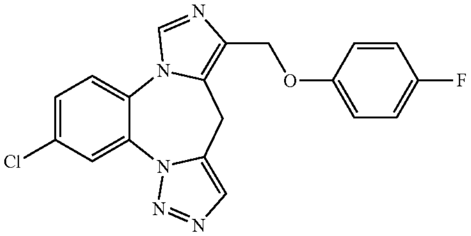 [SMILES: Fc1ccc(OCc2ncn3c2Cc2cnnn2-c2cc(Cl)ccc2-3)cc1]
448
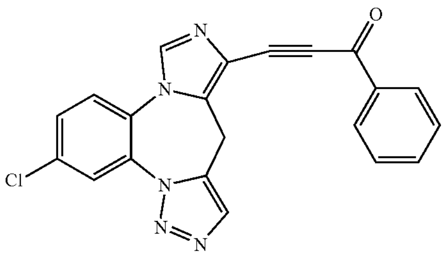 [SMILES: O=C(C#Cc1ncn2c1Cc1cnnn1-c1cc(Cl)ccc1-2)c1ccccc1]
-continued
449
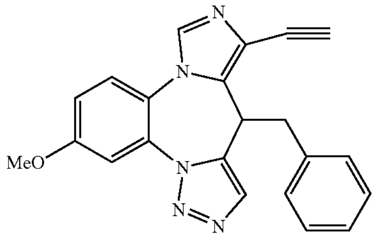 [SMILES: C#Cc1ncn2c1C(Cc1ccccc1)c1cnnn1-c1cc(OC)ccc1-2]
450
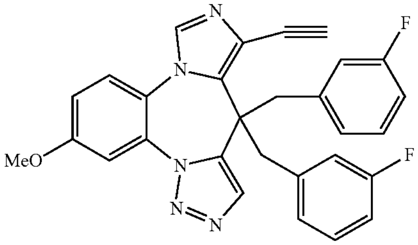 [SMILES: C#Cc1ncn2c1C(Cc1cccc(F)c1)(Cc1cccc(F)c1)c1cnnn1-c1cc(OC)ccc1-2]
451
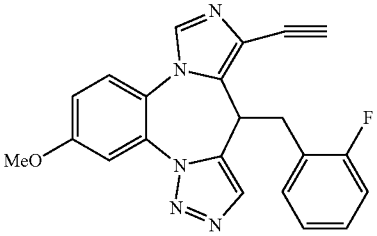 [SMILES: C#Cc1ncn2c1C(Cc1ccccc1F)c1cnnn1-c1cc(OC)ccc1-2]
452
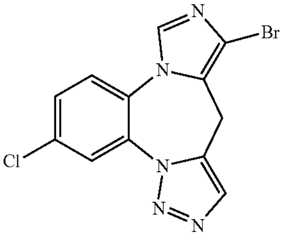 [SMILES: Clc1ccc2c(c1)-n1nncc1Cc1c(Br)ncn1-2]
453
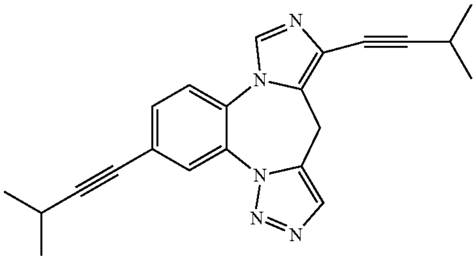 [SMILES: CC(C)C#Cc1ccc2c(c1)-n1nncc1Cc1c(C#CC(C)C)ncn1-2]
and
454
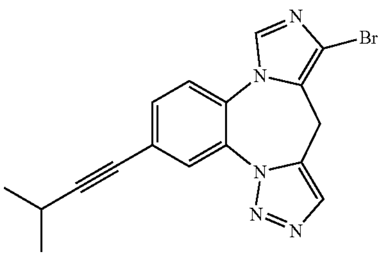 [SMILES: CC(C)C#Cc1ccc2c(c1)-n1nncc1Cc1c(Br)ncn1-2]
or a pharmaceutically acceptable salt, hydrate, solvate, polymorph, isomer, or combination thereof.

11. The method according to claim 9 or 10, wherein said brain cancer is medulloblastoma.

* * * * *